US012146238B2

(12) United States Patent
Wozniak-Knopp et al.

(10) Patent No.: US 12,146,238 B2
(45) Date of Patent: Nov. 19, 2024

(54) TARGET-SPECIFIC EXTRACELLULAR VESICLES

(71) Applicant: Evercyte GmbH, Vienna (AT)

(72) Inventors: Gordana Wozniak-Knopp, Vienna (AT); Stefan Vogt, Vienna (AT); Gerhard Stadlmayr, Vienna (AT); Florian Rueker, Vienna (AT); Johannes Grillari, Bisamberg (AT); Madhusudhan Reddy Bobbili, Vienna (AT)

(73) Assignee: EVERCYTE GMBH, Vienna (AT)

( * ) Notice: Subject to any disclaimer, the term of this patent is extended or adjusted under 35 U.S.C. 154(b) by 867 days.

(21) Appl. No.: 17/268,909

(22) PCT Filed: Aug. 14, 2019

(86) PCT No.: PCT/EP2019/071825

§ 371 (c)(1),
(2) Date: Feb. 16, 2021

(87) PCT Pub. No.: WO2020/035532

PCT Pub. Date: Feb. 20, 2020

(65) Prior Publication Data

US 2021/0395725 A1 Dec. 23, 2021

(30) Foreign Application Priority Data

Aug. 14, 2018 (EP) .................................... 18189014

(51) Int. Cl.
*C40B 30/04* (2006.01)
*A61K 9/127* (2006.01)
(Continued)

(52) U.S. Cl.
CPC ............ *C40B 30/04* (2013.01); *A61K 9/1271* (2013.01); *A61K 9/1278* (2013.01);
(Continued)

(58) Field of Classification Search
None
See application file for complete search history.

(56) References Cited

U.S. PATENT DOCUMENTS 5,705,161 A 1/1998 Van Der Ley et al.
7,252,958 B2 8/2007 Bolognesi et al.
(Continued)

FOREIGN PATENT DOCUMENTS

CN 106324244 A 1/2017
JP 5727361 B2 6/2015
(Continued)

OTHER PUBLICATIONS

Berditchevski et al., "Tetraspanins as Regulators of Protein Trafficking", Traffic 2007, 8: 89-96 (2006). (8 pages).
(Continued)

*Primary Examiner* — Christian C Boesen
(74) *Attorney, Agent, or Firm* — Loza & Loza, LLP; Michael Fedrick

(57) ABSTRACT

Provided herein is a method of producing a protein comprising a target-specific extravesicular domain (TED) of an extracellular vesicle (EV) surface protein comprising modifying a polynucleotide comprising a nucleotide sequence encoding the extravesicular domain (ED) of an EV surface protein by a mutagenesis method within at least one modified region within the ED amino acid sequence with a length of 3-20 contiguous amino acids flanked by regions of the wild-type ED sequence at its N-terminus and C-terminus, to incorporate a target binding site within the ED, thereby producing a repertoire of polynucleotides encoding a variety of TEDs, each comprising a different target binding site, and selecting a TED specifically recognizing a predetermined
(Continued)

Figure 2:
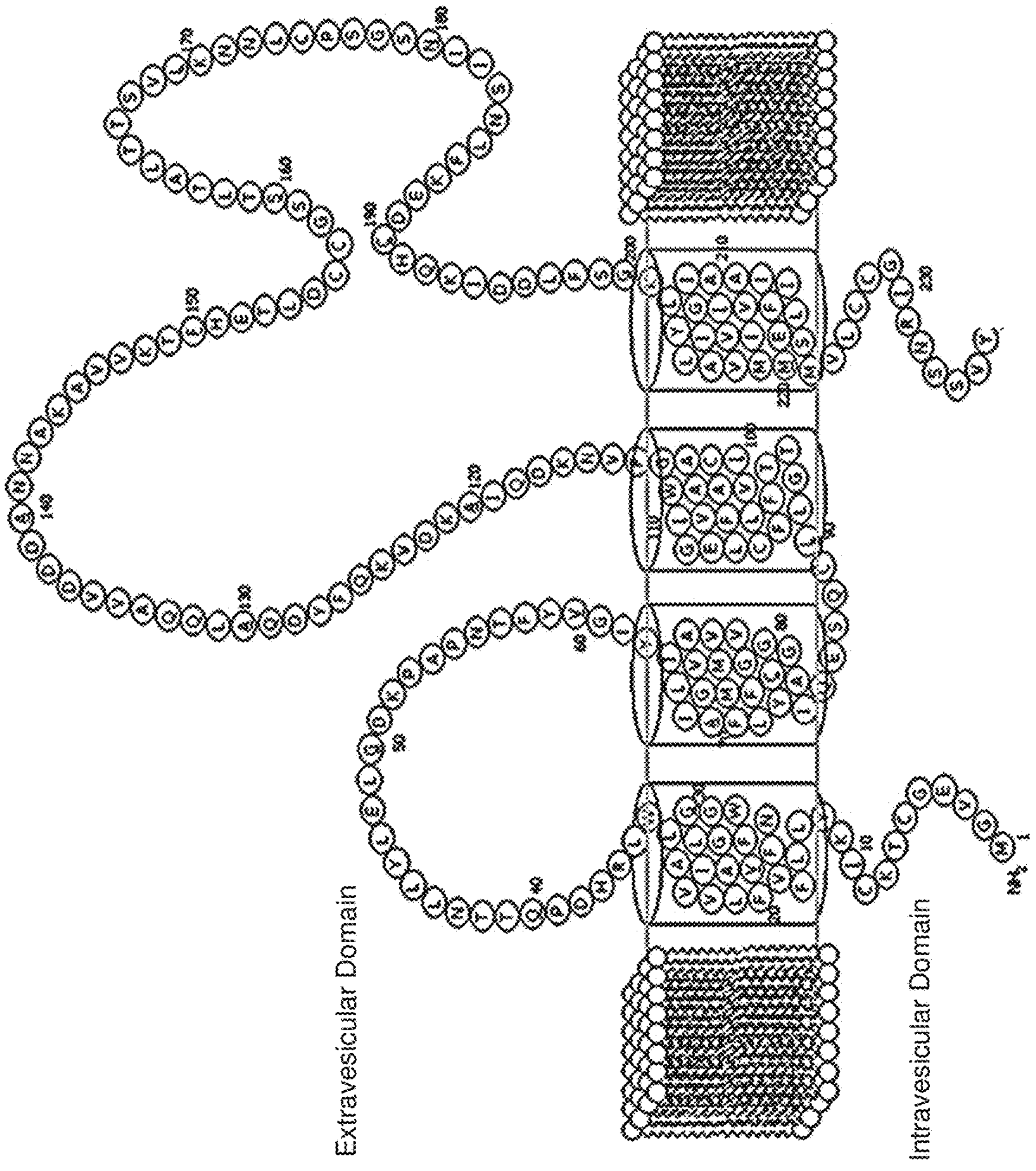

target, and producing the protein comprising the selected TED.

20 Claims, 38 Drawing Sheets

Specification includes a Sequence Listing.

(51) Int. Cl.
*A61K 31/7088* (2006.01)
*C07K 14/705* (2006.01)
*C12N 15/10* (2006.01)
*C12N 15/113* (2010.01)

(52) U.S. Cl.
CPC .... *A61K 31/7088* (2013.01); *C07K 14/70596* (2013.01); *C12N 15/1037* (2013.01); *C12N 15/113* (2013.01); *C07K 2319/03* (2013.01); *C12N 2310/14* (2013.01); *C12N 2320/32* (2013.01)

(56) References Cited

U.S. PATENT DOCUMENTS

| | | | |
|---|---|---|---|
| 9,546,371 | B2 | 1/2017 | Mamoun et al. |
| 2017/0087087 | A1 | 3/2017 | Leonard et al. |
| 2018/0015182 | A1 | 1/2018 | Lu et al. |
| 2019/0010211 | A1 | 1/2019 | Ivanusic |

FOREIGN PATENT DOCUMENTS

| | | | |
|---|---|---|---|
| JP | 2018508237 | A | 3/2018 |
| WO | 2008147816 | A2 | 12/2008 |
| WO | 2013084001 | A1 | 6/2013 |
| WO | 2014168548 | A2 | 10/2014 |
| WO | 2016073864 | A1 | 5/2016 |
| WO | 2017192743 | A1 | 11/2017 |
| WO | 2018011191 | A1 | 1/2018 |
| WO | 2018015535 | A1 | 1/2018 |
| WO | 2018075825 | A1 | 4/2018 |

OTHER PUBLICATIONS

Drummer et al., "Identification of the Hepatitis C Virus E2 Glycoprotein Binding Site on the Large Extracellular Loop of CD81", Journal of Virology, 2002, vol. 76, No. 21, p. 11143-11147. (5 pages).

Brown et al., "Snorkel: An Epitope Tagging System for Measuring the Surface Expression of Membrane Proteins", PLOS One, 2013, 8(9): e73255. (10 pages).

El Andaloussi et al., "Exosomes for targeted siRNA delivery across biological barriers", Advance Drug Delivery Reviews, 2013, 65:391-397. (Available online Aug. 18, 2012, 7 pages).

Escola et al., "Selective Enrichment of Tetraspan Proteins on the Internal Vesicles of Multivesicular Endosomes and on Exosomes Secreted by Human B-lymphocytes", The Journal of Biological Chemistry, vol. 273, No. 32, pp. 20121-20127, 1998. (7 pages).

Evans et al., "Analysis of the substrate recognition domain determinants of Botulinum Type B toxin using Phage Display", Toxicon, 2005, 46:446-453. (8 pages).

Higginbottom et al., "Identification of Amino Acid Residues in CD81 Critical for Interaction with Hepatitis C Virus Envelope Glycoprotein E2", Journal of Virology, 2000, vol. 74, No. 8, pp. 3642-3649. (8 pages).

Homsi et al., "The specificity of homomeric clustering of CD81 is mediated by its d-loop", FEBS Open Bio (2017), 7:274-283. (10 pages).

Homsi et al., "The Extracellular d-Domain is Essential for the Formation of CD81 Tetraspanin Webs", Biophysical Journal, 2014, vol. 107, pp. 100-113. (14 pages).

Iraci et al., "Focus on Extracellular Vesicles: Physiological Role and Signalling Properties of Extracellular Membrane Vesicles", Int. J. Mol. Sci., 2016, 17:171, doi: 10.3390/ijms17020171. (32 pages).

Kalra et al., "Focus on Extracellular Vesicles: Introducing the Next Small Big Thing", Int. J. Mol. Sci., 2016, 17: 170, doi: 10.3390/ijms17020170. (30 pages).

Kitadokoro et al., "Subunit Association and Conformational Flexibility in the Head Subdomain of Human CD81 arge Extracellular Loop", Biol. Chem., vol. 383, pp. 1447-1452, Sep. 2002. (6 pages).

Kitadokoro et al., "Crystallization and preliminary crystallographic studies on the large extracellular domain of human CD81, a tetraspanin receptor for hepatitis C virus", Acta Crysta. (2001) D57:156-158. (3 pages).

Kitadokoro et al., "CD81 extracellular domain 3D structure: insights into the tetraspanin superfamily structural motifs", The EMBO Journal, vol. 20, No. 1 & 2, pp. 12-18, 2001. (7 pages).

Levy et al., "Protein-Protein Interactions in the Tetraspanin Web", . Journal of Physiology, 20:218-224, 2005. (7 pages).

Li et al., "Structural basis for inhibition of the epidermal growth factor receptor by cetuximab", Cancer Cell, 2005, vol. 7, pp. 301-311. (11 pages).

Luan et al., "Engineering exosomes as refined biological nanoplatforms for drug delivery", Acta Pharmacologica Sinica (2017) 38:754-763. (10 pages).

Morelli et al., "Endocytosis, intracellular sorting, and processing of exosomes by dendritic cells", Blood, 2004, 104(10):3257-3266. (10 pages).

Pershad et al., "Generating thermal stable variants of protein domains through phage display", Methods (2013) 60:38-45. (8 pages).

Rajesh et al., "Structural Basis of Ligand Interactions of the Large Extracellular Domain of Tetraspanin CD81", Journal of Virology, 2012, vol. 86, No. 18, pp. 9606-9616. (11 pages).

Rana et al., "Exosome target cell selection and the importance of exosomal tetraspanins: a hypothesis", 4th European Conference on Tetraspanins. The Authors Journal compilation pp. 559-562, 2011, Biochemical Society. (4 pages).

Rubinstein et al., "CD9, CD63, CD81, and CD82 are components of a surface tetraspan network connected to HLA-DR and VLA integrins", Eur. J. Immunol., 1996, 26: 2657-2665. (9 pages).

Schmidt et al., "Oligomerization of the Tetraspanin CD81 via the Flexibility of Its d-Loop", Biophysical Journal, 2016, 110:2463-2474. (12 pages).

Schmiedel et al., "Matuzumab binding to EGFR prevents the conformational rearrangement required for dimerization", Cancer Cell, 2008, 13(4): 365-373. (19 pages).

Seigneuret et al., "Structure of the Tetraspanin Main Extracellular Domain A Partially Conserved Fold With a Structurally Variable Domain Insertion", 2001, vol. 276, No. 43, pp. 40055-40064. (10 pages).

Seigneuret, "Complete Predicted Three-Dimensional Structure of the Facilitator Transmembrane Protein and Hepatitis C Virus Receptor CD81: Conserved and Variable Structural Domains in the Tetraspanin Superfamily", Biophysical Journal, 2006, vol. 90, pp. 212-227. (16 pages).

Svensson et al., "Exosome Uptake Depends on ERK1/2-Heat Shock Protein 27 Signaling and Lipid Raft-mediated Endocytosis Negatively Regulated by Caveolin-1", The Journal of Biological Chemistry, vol. 288, No. 24, pp. 17713-17724, 2013. (12 pages).

Tian et al., "Exosome Uptake through Clathrin-mediated Endocytosis and Macropinocytosis and Mediating miR-21 Delivery", The Journal of Biological Chemistry, vol. 289, No. 32, pp. 22258-22267, 2014. (10 pages).

Vinayagam et al., "DSDBASE: a consortium of native and modelled disulphide bonds in proteins", Nucleic Acids Research, 2004, vol. 32, D200-D202. (3 pages).

Vogt et al., "Engineering of Surface Proteins in Extracellular Vesicles for Tissue-Specific Targeting", Current Topics in Biochemical Engineering, Naofumi Shiomi, IntechOpen, 2019, DOI: 10.5772/intechopen.83537. (21 pages).

Vogt et al., "Stabilization of the CD81 Large Extracellular Loop with De Novo Disulfide Bonds Improves Its Amenability for

(56) References Cited

OTHER PUBLICATIONS

Peptide Grafting", Pharmaceutics, 2018, 10:138, doi:10.3390/pharmaceutics 10030138. (14 pages).
Waterhouse et al., "Swiss-Model: homology modelling of protein structures and complexes", Nucleic Acids Research, 2018, vol. 46, pp. W296-W303, doi:10.1093/nar/gky427. (8 pages).
Corresponding International Patent Application No. PCT/EP2019/071825, Written Opinion of the International Searching Authority, Feb. 20, 2020. (10 pages).
Corresponding European Patent Application No. 18189014. European Search Report, Feb. 27, 2019. (10 pages).
Corresponding International Patent Application No. PCT/EP2019/071825. International Preliminary Report on Patentability, Feb. 16, 2021. (11 pages).
Corresponding International Patent Application No. PCT/EP2019/071825, International Search Report, Dec. 12, 2019. (8 Pages).
Imai T. and Yoshie O., J Immunol, 1993, vol. 151, No. 11, pp. 6470-6481.
Zhang et al., "The research progress of extracellular vesicles for drug delivery as natural nanocarriers," Chinese Pharmacological Bulletin, 2017, 33(6):757-760.

Fig. 1

Amino acid sequence of wildtype human CD81 LEL

SEQ ID NO:7

FVNKDQIAKDVKQFYDQALQQAVVDDDANNAKAVVKTFHETLDCCGSSTLTALTTSVLKNNLCP SGSNIISNLFKEDCHQKIDDLFSGK

Nucleotide sequence of wildtype human CD81 LEL

SEQ ID NO:8

TTTGTCAACAAGGACCAGATCGCCAAGGATGTGAAGCAGTTCTATGACCAGGCCCTACAGC AGGCCGTGGTGGATGATGACGCCAACAACGCCAAGGCTGTGGTGAAGACCTTCCACGAGACGCTT GACTGCTGTGGCTCCAGCACACTGACTGCTTTGACCACCTCAGTGCTCAAGAACAATTTGTGTCCCT CGGGCAGCAACATCATCAGCAACCTCTTCAAGGAGGACTGCCACCAGAAGATCGATGACCTCTTCT CCGGGAAG

Amino acid sequence of human CD81

SEQ ID NO:87

MGVEGCTKCIKYLLFVFNFVFWLAGGVILGVALWLRHDPQTTNLLYLELGDKAPNTFYVGIYILIAV GAVMMFVGFLGCYGAIQESQCLLGTFFTCLVILFACEVAAGIWGFVNKDQIAKDVKQFYDQALQQAVVDD DANNAKAVVKTFHETLDCCGSSTLTALTTSVLKNNLCPSGSNIISNLFKEDCHQKIDDLFSGKLYLIGIAAIV VAVIMIFEMILSMVLCCGIRNSSVY

Nucleotide sequence of human CD81

SEQ ID NO:88

ATGGGAGTGGAGGGCTGCACCAAGTGCATCAAGTACCTGCTCTTCGTCTTCAATTTCGTC

TTCTGGCTGGCTGGAGGCGTGATCCTGGGTGTGGCCCTGTGGCTCCGCCATGACCCGCAG ACCACCAACCTCCTGTATCTGGAGCTGGGAGACAAGCCCGCGCCCAACACCTTCTATGTAGGCATC TACATCCTCATCGCTGTGGGCGCTGTCATGATGTTCGTTGGCTTCCTGGGCTGCTACGGGGCCATC CAGGAATCCCAGTGCCTGCTGGGGACGTTCTTCACCTGCCTGGTCATCCTGTTTGCCTGTGAGGTG GCCGCCGGCATCTGGGGCTTTGTCAACAAGGACCAGATCGCCAAGGATGTGAAGCAGTTCTATGAC CAGGCCCTACAGCAGGCCGTGGTGGATGATGACGCCAACAACGCCAAGGCTGTGGTGAAGACCTT CCACGAGACGCTTGACTGCTGTGGCTCCAGCACACTGACTGCTTTGACCACCTCAGTGCTCAAGAA CAATTTGTGTCCCTCGGGCAGCAACATCATCAGCAACCTCTTCAAGGAGGACTGCCACCAGAAGATC GATGACCTCTTCTCCGGGAAGCTGTACCTCATCGGCATTGCTGCCATCGTGGTCGCTGTGATCATGA TCTTCGAGATGATCCTGAGCATGGTGCTGTGCTGTGGCATCCGGAACAGCTCCGTGTACTGA

Amino acid sequence of human CD9

SEQ ID NO:89

```
  1 mpvkggtkci kyllfgfnfi fwlagiavla iglwlrfdsq tksifeqetn nnnssfytgv
 61 yiligagalm mlvgflgccg avqesqcmlg lffgfllvif aieiaaaiwg yshkdevike
121 vqefykdtyn klktkdepqr etlkaihyal nccglaggve qfisdicpkk dvletftvks
181 cpdaikevfd nkfhiigavg igiavvmifg mifsmilcca irrnremv
```

Fig. 1 (continued)

Amino acid sequence of human CD53

SEQ ID NO:90

```
  1 mgmsslkllk yvlfffnllf wicgccilgf giyllihnnf gvlfhnlpsl tlgnvfvivg
 61 siimvvaflg cmgsikenkc llmsffilll iillaevtla illfvyeqkl neyvakgltd
121 sihryhsdns tkaawdsiqs flqccgingt sdwtsgppas cpsdrkvegc yakarlwfhs
181 nflyigiiti cvcvievlgm sfaltlncqi dktsqtigl
```

Amino acid sequence of human TSPAN32

SEQ ID NO:91

```
  1 mgpwsrvrva kcqmlvtcff illlglsvat mvtltyfgah favirrasle knpyqavhqw
 61 afsaglslvg lltlgavlsa aatvreaqgl maggflcfsl afcaqvqvvf wrlhsptqve
121 damldtydlv yeqamkgtsh vrrqelaaiq dvflccgkks pfsrlgstea dlcqgeeaar
181 edclqgirsf lrthqqvass ltsiglaltv sallfssflw faircgcsld rkgkytltpr
241 acgrqpqeps llrcsqggpt hclhseavai gprgcsgslr wlqesdaapl plschlaahr
301 alqgrsrggl sgcperglsd
```

Amino acid sequence of human CD82

SEQ ID NO:92

```
  1 mgsacikvtk yflflfnlif filgavilgf gvwiladkss fisvlqtsss slrmgayvfi
 61 gvgavtmlmg flgcigavne vrcllglyfa fllliliaqv tagalfyfnm gklkqemggi
121 vtelirdyns sredslqdaw dyvqaqvkcc gwvsfynwtd naelmnrpev typcscevkg
181 eednslsvrk gfceapgnrt qsgnhpedwp vyqegcmekv qawlqenlgi ilgvgvgvai
241 iellgmvlsi clcrhvhsed yskvpky
```

Amino acid sequence of human CD63

SEQ ID NO:93

```
  1 maveggmkcv kfllyvllla fcacavglia vgvgaqlvls qtiiqgatpg sllpvviiav
 61 gvflflvafv gccgackeny clmitfaifl slimlvevaa aiagyvfrdk vmsefnnnfr
121 qqmenypknn htasildrmq adfkccgaan ytdwekipsm sknrvpdscc invtvgcgin
181 fnekaihkeg cvekiggwlr knvlvvaaaa lgiafvevlg ivfacclvks irsgyevm
```

Amino acid sequence of human CD151

SEQ ID NO:94

```
  1 mgefnekktt cgtvclkyll ftynccfwla glavmavgiw tlalksdyis llasgtylat
 61 ayilvvagtv vmvtgvlgcc atfkerrnll rlyfilllii flleiiagil ayayyqqlnt
121 elkenlkdtm tkryhqpghe avtsavdqlq qefhccgsnn sqdwrdsewi rsqeaggrvv
181 pdscckttva lcgqrdhasn iykveggcit kletfiqehl rvigavgigi acvqvfgmif
241 tcclyrslkl ehy
```

Fig. 1 (continued)

Amino acid sequence of human CD37

SEQ ID NO:95

```
  1 msaqesclsl ikyflfvfnl fffvlgslif cfgiwilidk tsfvsfvgla fvplqiwskv
 61 laisgiftmg iallgcvgal kelrcllgly fgmllllfat qitlgilist qraqlerslr
121 dvvektiqky gtnpeetaae eswdyvqfql rccgwhypqd wfqvlilrgn gseahrvpcs
181 cynlsatnds tildkvilpq lsrlghlars rhsadicavp aeshiyregc aqglqkwlhn
241 nlisivgicl gvgllelgfm tlsiflcrnl dhvynrlary r
```

Amino acid sequence of human LAMP2

SEQ ID NO:96

```
  1 mvcfrlfpvp gsglvlvclv lgavrsyale lnltdsenat clyakwqmnf tvryettnkt
 61 yktvtisdhg tvtyngsicg ddqngpkiav qfgpgfswia nftkaastys idsvsfsynt
121 gdnttfpdae dkgiltvdel lairiplndl frcnslstle kndvvqhywd vlvqafvqng
181 tvstneflcd kdktstvapt ihttvpsptt tptpkekpea gtysvnngnd tcllatmglq
241 lnitqdkvas vininpntth stgscrshta llrlnsstik yldfvfavkn enrfylkevn
301 ismylvngsv fsiannnlsy wdaplgssym cnkeqtvsvs gafqintfdl rvqpfnvtqg
361 kystaqecsl dddtilipii vgaglsglii viviayvigr rksyagyqtl
```

Extravascular domains of CD81, CD9, CD53, TSPAN32, CD82, CD63, CD151, CD37, LAMP2

CD81:

EC1, SEQ ID NO:130: HDPQTTNLLYLELGDKAPNTFY

EC2, SEQ ID NO:131:

FVNKDQIAKDVKQFYDQALQQAVVDDDANNAKAVVKTFHETLDCCGSSTLTALTTSVLKNNLCPSGSNIISNLFKED
CHQKIDDLFSGK

CD9:

EC1, SEQ ID NO:132: FDSQTKSIFEQETNNNNSSFYT

EC1, SEQ ID NO:182: LRFDSQTKSIFEQETNNNNSSFYTG

EC2, , SEQ ID NO:133:

HKDEVIKEVQEFYKDTYNKLKTKDEPQRETLKAIHYALNCCGLAGGVEQFISDICPKKDVLETFTVKSCPDAIKEVF
DNK

CD53:

EC1, SEQ ID NO:134: LLIHNNFGVLFHNLPSLTLGN

EC2, SEQ ID NO:135:

FVYEQKLNEYVAKGLTDSIHRYHSDNSTKAAWDSIQSFLQCCGINGTSDWTSGPPASCPSDRKVEGCYAKARLWFHS
N

TSPAN32:

EC1, SEQ ID NO:136: TYFGAHFAVIRRASLEKNPYQAVHQ

EC2, SEQ ID NO:137:

FWRLHSPTQVEDAMLDTYDLVYEQAMKGTSHVRRQELAAIQDVFLCCGKKSPFSRLGSTEADLCQGEEAAREDCLQG
IRSFLRTHQQVASSLTS

CD82:

EC1, SEQ ID NO:138: GVWILADKSS FISVLQTSSS SLRM

EC2, SEQ ID NO:139:

FNMGKLKQEMGGIVTELIRDYNSSREDSLQDAWDYVQAQVKCCGWVSFYNWTDNAELMNRPEVTYPCSCEVKGEEDN
SLSVRKGFCEAPGNRTQSGNHPEDWPVYQEGCMEKVQAWLQEN

Fig. 1 (continued)

CD63:
EC1, SEQ ID NO:140: AQLVLSQTIIQGATPGSLLP
EC2, SEQ ID NO:141:
FRDKVMSEFNNNFRQQMENYPKNNHTASILDRMQADFKCCGAANYTDWEKIPSMSKNRVPDSCCINVTVGCGINFNE
KAIHKEGCVEKIGGWLRKN

CD151:
EC1, SEQ ID NO:142: TLALKSDYISLLASGTYLATA
EC2, SEQ ID NO:143:
YAYYQQLNTELKENLKDTMTKRYHQPGHEAVTSAVDQLQQEFHCCGSNNSQDWRDSEWIRSQEAGGRVVPDSCCKTV
VALCGQRDHASNIYKVEGGCITKLETFIQEHLR

CD37:
EC1, SEQ ID NO:144: GIWILIDKTSFVSFVGLAFVPLQIWSK
EC2, SEQ ID NO:145:
STQRAQLERSLRDVVEKTIQKYGTNPEETAAEESWDYVQFQLRCCGWHYPQDWFQVLILRGNGSEAHRVPCSCYNLS
ATNDSTILDKVILPQLSRLGHLARSRHSADICAVPAESHIYREGCAQGLQKWLHNN

LAMP2:
ED (EC): SEQ ID NO:146:
MVCFRLFPVPGSGLVLVCLVLGAVRSYALELNLTDSENATCLYAKWQMNFTVRYETTNKTYKTVTISDHGTVTYNGS
ICGDDQNGPKIAVQFGPGFSWIANFTKAASTYSIDSVSFSYNTGDNTTFPDAEDKGILTVDELLAIRIPLNDLFRCN
SLSTLEKNDVVQHYWDVLVQAFVQNGTVSTNEFLCDKDKTSTVAPTIHTTVPSPTTTPTPKEKPEAGTYSVNNGNDT
CLLATMGLQLNITQDKVASVININPNTTHSTGSCRSHTALLRLNSSTIKYLDFVFAVKNENRFYLKEVNISMYLVNG
SVFSIANNNLSYWDAPLGSSYMCNKEQTVSVSGAFQINTFDLRVQPFNVTQGKYSTAQECSLDDDTILIPI

Transmembrane domains: of CD81, CD9, CD53, TSPAN32, CD82, CD63, CD151, CD37, LAMP2

CD81:
TM1, SEQ ID NO:147: FVFNFVFWLAGGVILGVALWL,
TM2, SEQ ID NO:148: VGIYILIAVGAVMMFVGFL,
TM3, SEQ ID NO:149: FTCLVILFACEVAAGIWGFVN,
TM4, SEQ ID NO:150: LYLIGIAAIVVAVIMIFEMILSMVL

CD9:
TM1, SEQ ID NO:151: FNFIFWLAGIAVLAIGLWL,
TM2, SEQ ID NO:152: VYILIGAGALMMLVGFLGG,
TM3, SEQ ID NO:153: LFFGFLLVIFAIEIAAAI,
TM4, SEQ ID NO:154: IIGAVGIGIAVVMIFGMIFSMILCCAI

CD53:
TM1, SEQ ID NO:155: LFFFNLLFWICGCCILGFGIY,
TM2, SEQ ID NO:156: NVFVIVGSIIMVVAFLG,
TM3, SEQ ID NO:157: CLLMSFFILLLIILLAEVTLAILLFVY,
TM4, SEQ ID NO:158: FLYIGIITICVCVIEVLGMSF

TSPAN32:
TM1, SEQ ID NO:159: CQMLVTCFFILLLGLSVATMVTL,
TM2, SEQ ID NO:160: WAFSAGLSLVGLLTLGAVLSA,
TM3, SEQ ID NO:161: GLMAGGFLCFSLAFCAQVQVVF,
TM4, SEQ ID NO:162: IGLALTVSALLFSSFLWFAI

Fig. 1 (continued)

CD82:
TM1, SEQ ID NO:163: LFLFNLIFFILGAVILGF,
TM2, SEQ ID NO:164: MGAYVFIGVGAVTMLMGFL,
TM3, SEQ ID NO:165: CLLGLYFAFLLLILIAQVTAGALFYF,
TM4, SEQ ID NO:166: EKVQAWLQENLGIILGVGVGVAII

CD63:
TM1, SEQ ID NO:167: FLLYVLLLAFCACAVGLIAVGV,
TM2, SEQ ID NO:168: VIIAVGVFLFLVAFVGC,
TM3, SEQ ID NO:169: MITFAIFLSLIMLVEVAAAIAGYVF,
TM4, SEQ ID NO:170: VLVVAAAALGIAFVEVLGIVFACCLV

CD151:
TM1, SEQ ID NO:171: FTYNCCFWLAGLAVMAVGIW,
TM2, SEQ ID NO:172: YILVVAGTVVMVTGVLGCCA,
TM3, SEQ ID NO:173: LYFILLLIIFLLEIIAGILA,
TM4, SEQ ID NO:174: VIGAVGIGIACVQVFGMIFT

CD37:
TM1, SEQ ID NO:175: LFVFNLFFFVLGSLIFCF,
TM2, SEQ ID NO:176: LAISGIFTMGIALLGCVGAL,
TM3, SEQ ID NO:177: LLGLYFGMLLLLFATQITLGILI,
TM4, SEQ ID NO:178: LISIVGICLGVGLLELGFMTLSIF

LAMP2:
TM, SEQ ID NO:179: IVGAGLSGLIIVIVIAYVIG

EV surface proteins:

Further exemplary tetraspanins:

TSPAN8, NP_001356689, SEQ ID NO:184
magvsaciky smftfnflfw lcgililala iwvrvsndsq aifgsedvgs ssyvavdili
61 avgaiimilg flgccgaike srcmlllffi glllilllqv atgilgavfk sksdrivnet
121 lyentkllsa tgesekqfqe aiivfqeefk ccglvngaad wgnnfqhype lcacldkqrp
181 cqsyngkqvy ketcisfikd flaknliivi gisfglavie ilglvfsmvl ycqignk TSPAN14, NP_001121781, SEQ ID NO:185
mhyyrysnak vscwykyllf syniifwnqc cgaygpedwd lnvyfncsga sysrekcgvp
61 fsccvpdpaq kvvntqcgyd vriqlkskwd esiftkgciq aleswlprni yivagvfiai
121 sllqifgifl artlisdiea vkaghhf CD231 (TSPAN7), NP_004606, SEQ ID NO:186
masrrmetkp vitclktlli iysfvfwitg villavgvwg kltlgtyisl iaenstnapy
61 vligtgttiv vfglfgcfat crgspwmlkl yamflslvfl aelvagisgf vfrheikdtf
121 lrtytdamqt yngndersra vdhvqrslsc cgvqnytnws tspyflehgi ppsccmnetd
181 cnpqdlhnlt vaatkvnqkg cydlvtsfme tnmgiiagva fgiafsqlig mllacclsrf
241 itanqyemv

Fig. 1 (continued)

Integrin family of proteins

CD49d, NP_000876, SEQ ID NO:187

```
mawearrepg prraavretv mlllclgvpt grpynvdtes allyqgphnt lfgysvvlhs
      61 hganrwllvg aptanwlana svinpgaiyr crigknpgqt ceqlqlgspn gepcgktcle
     121 erdnqwlgvt lsrqpgengs ivtcghrwkn ifyiknenkl ptggcygvpp dlrtelskri
     181 apcyqdyvkk fgenfascqa gissfytkdl ivmgapgssy wtgslfvyni ttnkykafld
     241 kqnqvkfgsy lgysvgaghf rsqhttevvg gapqheqigk ayifsideke lnilhemkgk
     301 klgsyfgasv cavdlnadgf sdllvgapmq stireegrvf vyinsgsgav mnametnlvg
     361 sdkyaarfge sivnlgdidn dgfedvaiga pqeddlqgai yiyngradgi sstfsqrieg
     421 lqiskslsmf gqsisgqida dnngyvdvav gafrsdsavl lrtrpvvivd aslshpesvn
     481 rtkfdcveng wpsvcidltl cfsykgkevp gyivlfynms ldvnrkaesp prfyfssngt
     541 sdvitgsiqv ssreancrth qafmrkdvrd iltpiqieaa yhlgphvisk rsteefpplq
     601 pilqqkkekd imkktinfar fcahencsad lqvsakigfl kphenktyla vgsmktlmln
     661 vslfnagdda yettlhvklp vglyfikile leekqincev tdnsgvvqld csigyiyvdh
     721 lsridisfll dvsslsraee dlsitvhatc eneeemdnlk hsrvtvaipl kyevkltvhg
     781 fvnptsfvyg sndenepetc mvekmnltfh vintgnsmap nvsveimvpn sfspqtdklf
     841 nildvqtttg echfenyqrv caleqqksam qtlkgivrfl sktdkrllyc ikadphclnf
     901 lcnfgkmesg keasvhiqle grpsilemde tsalkfeira tgfpepnprv ielnkdenva
     961 hvlleglhhq rpkryftivi issslllgli vlllisyvmw kagffkrqyk silqeenrrd
    1021 swsyinsksn dd
```

ITGB5, NP_001341694.1, SEQ ID NO:188

```
1 mtpqeiavnl rpgdkttfql qvrqvedypv dlyylmdlsl smkddldnir slgtklaeem
      61 rkltsnfrlg fgsfvdkdis pfsytapryq tnpcigyklf pncvpsfgfr hllpltdrvd
     121 sfneevrkqr vsrnrdapeg gfdavlqaav ckekigwrkd alhllvfttd dvphialdgk
     181 lgglvqphdg qchlneaney tasnqmdyps lallgeklae nninlifavt knhymlyknf
     241 talipgttve ildgdsknii qliinaynsi rskvelsvwd qpedlnlfft atcqdgvsyp
     301 gqrkceglki gdtasfevsl earscpsrht ehvfalrpvg frdslevgvt ynctcgcsvg
     361 lepnsarcng sgtyvcglce cspgylgtrc ecqdgenqsv yqnlcreaeg kplcsgrgdc
     421 scnqcscfes efgkiygpfc ecdnfscarn kgvlcsghge chcgeckcha gyigdncncs
     481 tdistcrgrd gqicserghc lcgqcqctep gafgemcekc ptcpdacstk rdcveclllh
     541 sgkpdnqtch slcrdevitw vdtivkddqe avlcfyktak dcvmmftyve lpsgksnltv
     601 lrepecgntp namtillavv gsillvglal laiwkllvti hdrrefakfq sersraryem
     661 asnplyrkpi sthtvdftfn kfnksyngtv d
```

ITGB6, NP_000879.2, SEQ ID NO:189

```
1 mgiellclff lflgrndhvq ggcalggaet cedclligpq cawcaqenft hpsgvgercd
      61 tpanllakgc qlnfienpvs qveilknkpl svgrqknssd ivqiapqsli lklrpggaqt
     121 lqvhvrqted ypvdlyylmd lsasmdddln tikelgsrls kemskltsnf rlgfgsfvek
     181 pvspfvkttp eeianpcssi pyfclptfgf khilpltnda erfneivknq kisanidtpe
     241 ggfdaimqaa vckekigwrn dslhllvfvs dadshfgmds klagivipnd glchldskne
     301 ysmstvleyp tigqlidklv qnnvllifav tqeqvhlyen yaklipgatv gllqkdsgni
     361 lqliisayee lrsevelevl gdteglnlsf taicnngtlf qhqkkcshmk vgdtasfsvt
     421 vniphcerrs rhiiikpvgl gdalellvsp ecncdcqkev evnsskchhg ngsfqcgvca
     481 chpghmgprc ecgedmlstd sckeapdhps csgrgdcycg qcichlspyg niygpycqcd
     541 nfscvrhkgl lcggngdcdc gecvcrsgwt geycncttst dscvsedgvl csgrgdcvcg
     601 kcvctnpgas gptcercptc gdpcnskrsc iechlsaagq areecvdkck lagatiseee
     661 dfskdgsvsc slqgenecli tflittdneg ktiihsinek dcpkppnipm imlgvslail
     721 ligvvllciw kllvsfhdrk evakfeaers kakwqtgtnp lyrgststfk nvtykhrekq
     781 kvdlstdc
```

Fig. 1 (continued)

ITGB7, NP_000880.1, SEQ ID NO:190
1 mvalpmvlvl llvlsrgese ldakipstgd atewrnphls mlgscqpaps cqkcilshps
61 cawckqlnft asgeaearrc arreellarg cpleeleepr gqqevlqdqp lsqgargega
121 tqlapqrvrv tlrpgepqql qvrflraegy pvdlyylmdl sysmkddler vrqlghallv
181 rlqevthsvr igfgsfvdkt vlpfvstvps klrhpcptrl ercqspfsfh hvlsltgdaq
241 aferevgrqs vsgnldspeg gfdailqaal cqeqigwrnv srllvftsdd tfhtagdgkl
301 ggifmpsdgh chldsnglys rstefdypsv gqvaqalsaa niqpifavts aalpvyqels
361 klipksavge lsedssnvvq limdaynsls stvtlehssl ppgvhisyes qcegpekreg
421 kaedrgqcnh vrinqtvtfw vslqathclp ephllrlral gfseelivel htlcdcncsd
481 tqpqaphcsd gqghlqcgvc scapgrlgrl cecsvaelss pdlesgcrap ngtgplcsgk
541 ghcqcgrcsc sgqssghlce cddascerhe gilcggfgrc qcgvchchan rtgracecsg
601 dmdscispeg glcsghgrck cnrcqcldgy ygalcdqcpg cktpcerhrd caecgafrtg
661 platncstac ahtnvtlala pilddgwcke rtldnqlfff lveddargtv vlrvrpqekg
721 adhtqaivlg cvggivavgl glvlayrlsv eiydrreysr fekeqqqlnw kqdsnplyks
781 aitttinprf qeadsptl CD71, NP_003225, SEQ ID NO:191
1 mmdqarsafs nlfggeplsy trfslarqvd gdnshvemkl avdeeenadn ntkanvtkpk
61 rcsgsicygt iavivfflig fmigylgyck gvepktecer lagtespvre epgedfpaar
121 rlywddlkrk lsekldstdf tgtikllnen syvpreagsq kdenlalyve nqfrefklsk
181 vwrdqhfvki qvkdsaqnsv iivdkngrlv ylvenpggyv ayskaatvtg klvhanfgtk
241 kdfedlytpv ngsivivrag kitfaekvan aeslnaigvl iymdqtkfpi vnaelsffgh
301 ahlgtgdpyt pgfpsfnhtq fppsrssglp nipvqtisra aaeklfgnme gdcpsdwktd
361 stcrmvtses knvkltvsnv lkeikilnif gvikgfvepd hyvvvgaqrd awgpgaaksg
421 vgtalllkla qmfsdmvlkd gfqpsrsiif aswsagdfgs vgatewlegy lsslhlkaft
481 yinldkavlg tsnfkvsasp llytliektm qnvkhpvtgq flyqdsnwas kvekltldna
541 afpflaysgi pavsfcfced tdypylgttm dtykelieri pelnkvaraa aevagqfvik
601 lthdvelnld yerynsqlls fvrdlnqyra dikemglslq wlysargdff ratsrlttdf
661 gnaektdrfv mkklndrvmr veyhflspyv spkespfrhv fwgsgshtlp allenlklrk
721 qnngafnetl frnqlalatw tiqgaanals gdvwdidnef Proteoglycans CD138 (syndecan-1), NP_001006947, SEQ ID NO:192
mrraalwlwl calalslqpa lpqivatnlp pedqdgsgdd sdnfsgsgag alqditlsqq
61 tpstwkdtql ltaiptspep tgleataast stlpagegpk egeavvlpev epgltareqe
121 atprprettq lptthqastt tattaqepat shphrdmqpg hhetstpagp sqadlhtpht
181 edggpsater aaedgassql paaegsgeqd ftfetsgent avvavepdrr nqspvdqgat
241 gasqglldrk evlggviagg lvglifavcl vgfmlyrmkk kdegsyslee pkqanggayq
301 kptkqeefya syndecan-2, NP_002989, SEQ ID NO:193
mrrawilltl glvacvsaes raeltsdkdm yldnssieea sgvypidddd yasasgsgad
61 edvespeltt srplpkillt saapkvettt lniqnkipaq tkspeetdke kvhlsdserk
121 mdpaeedtnv ytekhsdslf krtevlaavi aggvigflfa iflilllvyr mrkkdegsyd
181 lgerkpssaa yqkaptkefy a syndecan-3, NP_055469, SEQ ID NO:194
mkpgpphrag aahgagagag aaagpgargl llpplllll agraagaqrw rsenferpvd
61 legsgdddsf pddelddlys gsgsgyfeqe sgietamrfs pdvalavstt pavlpttniq
121 pvgtpfeelp serptlepat splvvtevpe epsqrattvs ttmattaats tgdptvatvp
181 atvatatpst paappftatt avirttgvrr llplplttva tarattpeap sppttaavld
241 teaptprlvs tatsrpralp rpattqepdi perstlplgt tapgptevaq tptpetfltt
301 irdepevpvs ggpsgdfelp eeettqpdta nevvavggaa akassppgtl pkgarpgpgl
361 ldnaidsgss aaqlpqksil erkevlvavi vggvvgalfa aflvtlliyr mkkkdegsyt
421 leepkqasvt yqkpdkqeef ya

Fig. 1 (continued)

syndecan-4, NP_002990, SEQ ID NO:195

```
maparlfall lffvggvaes iretevidpq dllegryfsg alpddedvvg pgqesddfel
      61 sgsgdlddle dsmigpevvh plvpldnhip eragsgsqvp tepkkleene vipkrispve
     121 esedvsnkvs msstvqgsni fertevlaal ivggivgilf avflilllmy rmkkkdegsy
     181 dlgkkpiykk aptnefya
```

HSPG2, NP_001278789.1, SEQ ID NO:196

```
1 mgwraagall lalllhgrll avthglrayd glslpediet vtasqmrwth sylsddedml
      61 adsisgddlg sgdlgsgdfq mvyfralvnf trsieyspql edagsrefre vseavvdtle
     121 seylkipgdq vvsvvfikel dgwvfveldv gsegnadgaq iqemllrvis sgsvasyvts
     181 pqgfqfrrlg tvpqfpract eaefachsyn ecvaleyrcd rrpdcrdmsd elnceepvlg
     241 isptfsllve ttslpprpet timrqppvth apqpllpgsv rplpcgpqea acrnghcipr
     301 dylcdgqedc edgsdeldcg ppppcepnef pcgnghcalk lwrcdgdfdc edrtdeancp
     361 tkrpeevcgp tqfrcvstnm cipasfhcde esdcpdrsde fgcmppqvvt ppresiqasr
     421 gqtvtftcva igvptpiinw rlnwghipsh prvtvtsegg rgtliirdvk esdqgaytce
     481 amnargmvfg ipdgvlelvp qragpcpdgh fylehsaacl pcfcfgitsv cqstrrfrdq
     541 irlrfdqpdd fkgvnvtmpa qpgtpplsst qlqidpslhe fqlvdlsrrf lvhdsfwalp
     601 eqflgnkvds yggslrynvr yelargmlep vqrpdvvlmg agyrllsrgh tptqpgalnq
     661 rqvqfseehw vhesgrpvqr aellqvlqsl eavliqtvyn tkmasvglsd iamdttvtha
     721 tshgrahsve ecrcpigysg lscescdahf trvpggpylg tcsgcncngh asscdpvygh
     781 clncqhnteg pqcnkckagf fgdamkatat scrpcpcpyi dasrrfsdtc fldtdgqatc
     841 dacapgytgr rcescapgye gnpiqpggkc rpvnqeivrc dergsmgtsg eacrcknnvv
     901 grlcnecadg sfhlstrnpd gclkcfcmgv srhctsssws raqlhgasee pghfsltnaa
     961 sthttnegif sptpgelgfs sfhrllsgpy fwslpsrflg dkvtsyggel rftvtqrsqp
    1021 gstplhgqpl vvlqgnniil ehhvaqepsp gqpstfivpf reqawqrpdg qpatrehllm
    1081 alagidtlli rasyaqqpae srvsgismdv avpeetgqdp aleveqcscp pgyrgpscqd
    1141 cdtgytrtps glylgtcerc schghseace petgacqgcq hhtegprceq cqpgyygdaq
    1201 rgtpqdcqlc pcygdpaagq aahtcfldtd ghptcdacsp ghsgrhcerc apgyygnpsq
    1261 gqpcqrdsqv pgpigcncdp qgsvssqcda agqcqckaqv egltcshcrp hhfhlsasnp
    1321 dgclpcfcmg itqqcassay trhlisthfa pgdfqgfalv npqrnsrltg eftvepvpeg
    1381 aqlsfgnfaq lghesfywql petyqgdkva ayggklrytl sytagpqgsp lsdpdvqitg
    1441 nnimlvasqp alqgperrsy eimfreefwr rpdgqpatre hllmaladld elliratfss
    1501 vplaasisav slevaqpgps nrpralevee crcppgyigl scqdcapgyt rtgsglylgh
    1561 celcecnghs dlchpetgac sqcqhnaage fcelcapgyy gdatagtped cqpcacpltn
    1621 penmfsrtce slgaggyrct acepgytgqy ceqcgpgyvg npsvqggqcl petnqaplvv
    1681 evhparsivp qggshslrcq vsgspphyfy wsredgrpvp sgtqqrhqgs elhfpsvqps
    1741 dagvyictcr nlhqsntsra ellvteapsk pitvtveeqr sqsvrpgadv tfictaksks
    1801 paytlvwtrl hngklptram dfngiltirn vqlsdagtyv ctgsnmfamd qgtatlhvqa
    1861 sgtlsapvvs ihppqltvqp gqlaefrcsa tgsptptlew tggpggqlpa kaqihggilr
    1921 lpaveptdqa qylcrahssa gqqvaravlh vhggggprvq vspertqvha grtvrlycra
    1981 agvpsatitw rkeggslppq arsertdiat llipaittad agfylcvats pagtaqariq
    2041 vvvlsasdas pppvkiesss psvtegqtld lncvvagsah aqvtwyrrgg slpphtqvhg
    2101 srlrlpqvsp adsgeyvcrv engsgpkeas itvsvlhgth sgpsytpvpg strpirieps
    2161 sshvaegqtl dlncvvpgqa haqvtwhkrg gslparhqth gsllrlhqvt padsgeyvch
    2221 vvgtsgplea svlvtieasv ipgpippvri esssstvaeg qtldlscvva gqahaqvtwy
    2281 krggslparh qvrgsrlyif qaspadagqy vcrasngmea sitvtvtgtq ganlaypags
    2341 tqpiriepss sqvaegqtld lncvvpgqsh aqvtwhkrgg slpvrhqthg sllrlyqasp
    2401 adsgeyvcrv lgssvpleas vlvtiepags vpalgvtptv riessssqva egqtldlncl
    2461 vagqahaqvt whkrggslpa rhqvhgsrlr llqvtpadsg eyvcrvvgss gtqeasvlvt
    2521 iqqrlsgshs qgvaypvrie sssaslangh tldlnclvas qaphtitwyk rggslpsrhq
    2581 ivgsrlripq vtpadsgeyv chvsngagsr etslivtiqg sgsshvpsvs ppiriesssp
    2641 tvvegqtldl ncvvarqpqa iitwykrggs lpsrhqthgs hlrlhqmsva dsgeyvcran
    2701 nnidaleasi visvspsags psapgssmpi riesssshva egetldlncv vpgqahaqvt
    2761 whkrggslps hhqtrgsrlr lhhvspadsg eyvcrvmgss gpleasvlvt ieasgssavh
    2821 vpapggappi riepsssrva egqtldlkcv vpgqahaqvt whkrggnlpa rhqvhgpllr
    2881 lnqvspadsg eyscqvtgss gtleasvlvt iepsspgpip apglaqpiyi eassshvteg
    2941 qtldlncvvp gqahaqvtwy krggslparh qthgsqlrlh lvspadsgey vcraasgpgp
    3001 eqeasftvtv ppsegssyrl rspvisidpp sstvqqgqda sfkclihdga apislewktr
    3061 nqelednvhi spngsiitiv gtrpsnhgty rcvasnaygv aqsvvnlsvh gpptvsvlpe
```

Fig. 1 (continued)

```
3121 gpvwvkvgka vtlecvsage prssarwtri sstpakleqr tyglmdshav lqissakpsd
3181 agtyvclaqn algtaqkqve vivdtgamap gapqvqaeea eltveaghta tlrcsatgsp
3241 aptihwsklr splpwqhrle gdtliiprva qqdsgqyicn atspaghaea tiilhvespp
3301 yattvpehas vqagetvqlq clahgtpplt fqwsrvgssl pgratarnel lhferaaped
3361 sgryrcrvtn kvgsaeafaq llvqgppgsl patsipagst ptvqvtpqle tksigasvef
3421 hcavpsdrgt qlrwfkeggq lppghsvqdg vlriqnldqs cqgtyicqah gpwgkaqasa
3481 qlviqalpsv linirtsvqt vvvghavefe clalgdpkpq vtwskvgghl rpgivqsggv
3541 vriahvelad agqyrctatn aagttqshvl llvqalpqis mpqevrvpag saavfpcias
3601 gyptpdisws kldgslppds rlennmlmlp svrpqdagty vctatnrqgk vkafahlqvp
3661 ervvpyftqt pysflplpti kdayrkfeik itfrpdsadg mllyngqkrv pgsptnlanr
3721 qpdfisfglv ggrpefrfda gsgmatirhp tplalghfht vtllrsltqg slivgdlapv
3781 ngtsqgkfqg ldlneelylg gypdygaipk aglssgfigc vrelriqgee ivfhdlnlta
3841 hgishcptcr drpcqnggqc hdsesssyvc vcpagftgsr cehsqalhch peacgpdatc
3901 vnrpdgrgyt crchlgrsgl rceegvtvtt pslsgagsyl alpaltnthh elrldvefkp
3961 lapdgvllfs ggksgpvedf vslamvgghl efryelgsgl avlrsaepla lgrwhrvsae
4021 rlnkdgslrv nggrpvlrss pgksqglnlh tllylggvep svplspatnm sahfrgcvge
4081 vsvngkrldl tysflgsqgi gqcydsspce rqpcqhgatc mpageyefqc lcrdgfkgdl
4141 ceheenpcql repclhggtc qgtrclclpg fsgprcqqgs ghgiaesdwh legsggndap
4201 gqygayfhdd gflafpghvf srslpevpet ielevrtsta sglllwqgve vgeagqgkdf
4261 islglqdghl vfryqlgsge arlvsedpin dgewhrvtal regrrgsiqv dgeelvsgrs
4321 pgpnvavnak gsvyiggapd vatltggrfs sgitgcvknl vlhsarpgap ppqpldlqhr
4381 aqagantrpc ps
```

5 transmembrane domains protein family

CD133, XP_011512195, SEQ ID NO:262

```
malvlgslll lglcgnsfsg gqpsstdapk awnyelpatn yetqdshkag pigilfelvh
      61 iflyvvqprd fpedtlrkfl qkayeskidy dkpetvilgl kivyyeagii lccvlgllfi
     121 ilmplvgyff cmcrccnkcg gemhqrqken gpflrkcfai sllviciiis igifygfvan
     181 hqvrtrikrs rkladsnfkd lrtllnetpe qikyilaqyn ttkdkaftdl nsinsvlggg
     241 ildrlrpnii pvldeiksma taiketkeal enmnstlksl hqqstqlsss ltsvktslrs
     301 slndplclvh pssetcnsir lslsqlnsnp elrqlppvda eldnvnnvlr tdldglvqqg
     361 yqslndipdr vqrqtttvva gikrvlnsig sdidnvtqrl piqdilsafs vyvnntesyi
     421 hrnlptleey dsywwlgglv icslltlivi fyylgllcgv cgydrhatpt trgcvsntgg
     481 vflmvgvgls flfcwilmii vvltfvfgan veklicepyt skelfrvldt pyllnedwey
     541 ylsgklfnks kmkltfeqvy sdckknrgty gtlhlqnsfn isehlnineh tgsisseles
     601 lkvnlnifll gaagrknlqd faacgidrmn ydsylaqtgk spagvnllsf aydleakans
     661 lppgnlrnsl krdaqtikti hqqrvlpieq slstlyqsvk ilqrtgngll ervtrilasl
     721 dfaqnfitnn tssviieetk kygrtiigyf ehylqwiefs isekvasckp vataldtavd
     781 vflcsyiidp lnlfwfgigk atvfllpali favklakyyr rmdsedvydd vetipmknme
     841 ngnngyhkdh vygihnpvmt spsqh
```

Type I transmembrane proteins

CD50, NP_001307534, SEQ ID NO:263

```
matmvpsvlw pracwtllvc clltpgvqgq efllrvepqn pvlsaggslf vncstdcpss
      61 ekialetsls kelvasgmgw aafnlsnvtg nsrilcsvyc ngsqitgssn itvyrlperv
     121 elaplppwqp vgqnftlrcq vedgsprtsl tvvllrweee lsrqpaveep aevtatvlas
     181 rddhgapfsc rteldmqpqg lglfvntsap rqlrtfgflg pivnlsepta hegstvtvsc
     241 magarvqvtl dgvpaaapgq paqlqlnate sddgrsffcs atlevdgefl hrnssvqlrv
     301 lygpkidrat cpqhlkwkdk trhvlqcqar gnpypelrcl kegssrevpv gipffvnvth
     361 ngtyqcqass srgkytlvvv mdieagsshf vpvfvavllt lgvvtivlal myvfrehqrs
     421 gsyhvreest ylpltsmqpt eamgeepsra e
```

Fig. 1 (continued)

CD102, NP_001093259, SEQ ID NO:197
mssfgyrtlt valftliccp gsdekvfevh vrpkklavep kgslevncst tcnqpevggl
61 etsldkilld eqaqwkhylv snishdtvlq chftcsgkqe smnsnvsvyq pprqviltlq
121 ptlvavgksf tiecrvptve pldsltlflf rgnetlhyet fgkaapapqe atatfnstad
181 redghrnfsc lavldlmsrg gnifhkhsap kmleiyepvs dsqmviivtv vsvllslfvt
241 svllcfifgq hlrqqrmgty gvraawrrlp qafrp Notch family NOTCH1, NP_060087, SEQ ID NO:198
1 mppllapllc lallpalaar gprcsqpget clnggkceaa ngteacvcgg afvgprcqdp
61 npclstpckn agtchvvdrr gvadyacsca lgfsgplclt pldnacltnp crnggtcdll
121 tlteykcrcp pgwsgkscqq adpcasnpca nggqclpfea syichcppsf hgptcrqdvn
181 ecgqkpglcr hggtchnevg syrcvcrath tgpncerpyv pcspspcqng gtcrptgdvt
241 hecaclpgft gqnceenidd cpgnnckngg acvdgvntyn crcppewtgq yctedvdecq
301 lmpnacqngg tchnthggyn cvcvngwtge dcseniddca saacfhgatc hdrvasfyce
361 cphgrtgllc hlndacisnp cnegsncdtn pvngkaictc psgytgpacs qdvdecslga
421 npcehagkci ntlgsfecqc lqgytgprce idvnecvsnp cqndatcldq igefqcicmp
481 gyegvhcevn tdecasspcl hngrcldkin efqcecptgf tghlcqydvd ecastpckng
541 akcldgpnty tcvctegytg thcevdidec dpdpchygsc kdgvatftcl crpgytghhc
601 etninecssq pcrhggtcqd rdnaylcfcl kgttgpncei nlddcasspc dsgtcldkid
661 gyecacepgy tgsmcninid ecagnpchng gtcedgingf tcrcpegyhd ptclsevnec
721 nsnpcvhgac rdslngykcd cdpgwsgtnc dinnnecesn pcvnggtckd mtsgyvctcr
781 egfsgpncqt ninecasnpc lnqgtciddv agykcncllp ytgatcevvl apcapspcrn
841 ggecrqsedy esfscvcptg wqgqtcevdi necvlspcrh gascqnthgg yrchcqagys
901 grncetdidd crpnpchngg sctdgintaf cdclpgfrgt fceedineca sdpcrnganc
961 tdcvdsytct cpagfsgihc enntpdctes scfnggtcvd ginsftclcp pgftgsycqh
1021 dvnecdsqpc lhggtcqdgc gsyrctcpqg ytgpncqnlv hwcdsspckn ggkcwqthtq
1081 yrcecpsgwt glycdvpsvs cevaaqrqgv dvarlcqhgg lcvdagnthh crcqagytgs
1141 ycedlvdecs pspcqngatc tdylggysck cvagyhgvnc seeideclsh pcqnggtcld
1201 lpntykcscp rgtqgvhcei nvddcnppvd pvsrspkcfn ngtcvdqvgg ysctcppgfv
1261 gercegdvne clsnpcdarg tqncvqrvnd fhcecraght grrcesving ckgkpckngg
1321 tcavasntar gfickcpagf egatcendar tcgslrclng gtcisgprsp tclclgpftg
1381 pecqfpassp clggnpcynq gtceptsesp fyrclcpakf ngllchildy sfgggagrdi
1441 ppplieeace lpecqedagn kvcslqcnnh acgwdggdcs lnfndpwknc tqslqcwkyf
1501 sdghcdsqcn sagclfdgfd cqraegqcnp lydqyckdhf sdghcdqgcn saecewdgld
1561 caehvperla agtlvvvvlm ppeqlrnssf hflrelsrvl htnvvfkrda hgqqmifpyy
1621 greeelrkhp ikraaegwaa pdallgqvka sllpggsegg rrrreldpmd vrgsivylei
1681 dnrqcvqass qcfqsatdva aflgalaslg slnipykiea vqsetveppp paqlhfmyva
1741 aaafvllffv gcgvllsrkr rrqhgqlwfp egfkvseask kkrreplged svglkplkna
1801 sdgalmddnq newgdedlet kkfrfeepvv lpdlddqtdh rqwtqqhlda adlrmsamap
1861 tppqgevdad cmdvnvrgpd gftplmiasc sgggletgns eeeedapavi sdfiyqgasl
1921 hnqtdrtget alhlaarysr sdaakrllea sadaniqdnm grtplhaavs adaqgvfqil
1981 irnratdlda rmhdgttpli laarlavegm ledlinshad vnavddlgks alhwaaavnn
2041 vdaavvllkn gankdmqnnr eetplflaar egsyetakvl ldhfanrdit dhmdrlprdi
2101 aqermhhdiv rlldeynlvr spqlhgaplg gtptlspplc spngylgslk pgvqgkkvrk
2161 psskglacgs keakdlkarr kksqdgkgcl ldssgmlspv dslesphgyl sdvaspplp
2221 spfqqspsvp lnhlpgmpdt hlgighlnva akpemaalgg ggrlafetgp prlshlpvas
2281 gtstvlgsss ggalnftvgg stslngqcew lsrlqsgmvp nqynplrgsv apgplstqap
2341 slqhgmvgpl hsslaasals qmmsyqglps trlatqphlv qtqqvqpqnl qmqqqnlqpa
2401 niqqqqslqp pppppqphlg vssaasghlg rsflsgepsq advqplgpss lavhtilpqe
2461 spalptslps slvppvtaaq fltppsqhsy sspvdntpsh qlqvpehpfl tpspespdqw
2521 ssssphsnvs dwsegvsspp tsmqsqiari peafk

Fig. 1 (continued)

NOTCH2, NP_001186930, SEQ ID NO:199

```
   1 mpalrpallw allalwlcca apahalqcrd gyepcvnegm cvtyhngtgy ckcpegflge
  61 ycqhrdpcek nrcqnggtcv aqamlgkatc rcasgftged cqystshpcf vsrpclnggt
 121 chmlsrdtye ctcqvgftgk ecqwtdacls hpcangstct tvanqfsckc ltgftgqkce
 181 tdvnecdipg hcqhggtcln lpgsyqcqcp qgftgqycds lyvpcapspc vnggtcrqtg
 241 dftfecnclp gfegstcern iddcpnhrcq nggvcvdgvn tyncrcppqw tgqfctedvd
 301 ecllqpnacq nggtcanrng gygcvcvngw sgddcsenid dcafasctpg stcidrvasf
 361 scmcpegkag llchlddaci snpchkgalc dtnplngqyi ctcpqgykga dctedvdeca
 421 mansnpceha gkcvntdgaf hceclkgyag prcemdinec hsdpcqndat cldkiggftc
 481 lcmpgfkgvh celeinecqs npcvnngqcv dkvnrfqclc ppgftgpvcq ididdcsstp
 541 clngakcidh pngyecqcat gftgvlceen idncdpdpch hgqcqdgids ytcicnpgym
 601 gaicsdqide cysspclndg rcidlvngyq cncqpgtsgv nceinfddca snpcihgicm
 661 dginryscvc spgftgqrcn ididecasnp crkgatcing vngfrcicpe gphhpscysq
 721 vneclsnpci hgnctgglsg ykclcdagwv gincevdkne clsnpcqngg tcdnlvngyr
 781 ctckkgfkgy ncqvnideca snpclnqgtc fddisgytch cvlpytgknc qtvlapcspn
 841 pcenaavcke spnfesytcl capgwqgqrc tididecisk pcmnhglchn tqgsymcecp
 901 pgfsgmdcee diddclanpc qnggscmdgv ntfsclclpg ftgdkcqtdm neclsepckn
 961 ggtcsdyvns ytckcqagfd gvhcennine ctesscfngg tcvdginsfs clcpvgftgs
1021 fclheinecs shpclnegtc vdglgtyrcs cplgytgknc qtlvnlcsrs pcknkgtcvq
1081 kkaesqclcp sgwagaycdv pnvscdiaas rrgvlvehlc qhsgvcinag nthycqcplg
1141 ytgsyceeql decasnpcqh gatcsdfigg yrcecvpgyq gvnceyevde cqnqpcqngg
1201 tcidlvnhfk cscppgtrgm ksslsifhpg hclkl
```

NOTCH3, NP_000426, SEQ ID NO:200

```
   1 mgpgargrrr rrrpmspppp pppvralpll lllagpgaaa ppcldgspca nggrctqlps
  61 reaaclcppg wvgercqled pchsgpcagr gvcqssvvag tarfscrcpr gfrgpdcslp
 121 dpclsspcah garcsvgpdg rflcscppgy qgrscrsdvd ecrvgepcrh ggtclntpgs
 181 frcqcpagyt gplcenpavp capspcrngg tcrqsgdlty dcaclpgfeg qncevnvddc
 241 pghrclnggt cvdgvntync qcppewtgqf ctedvdecql qpnachnggt cfntlgghsc
 301 vcvngwtges csqniddcat avcfhgatch drvasfycac pmgktgllch lddacvsnpc
 361 hedaicdtnp vngraictcp pgftggacdq dvdecsigan pcehlgrcvn tqgsflcqcg
 421 rgytgprcet dvneclsgpc rnqatcldri gqftcicmag ftgtycevdi decqsspcvn
 481 ggvckdrvng fsctcpsgfs gstcqldvde castpcrnga kcvdqpdgye crcaegfegt
 541 lcdrnvddcs pdpchhgrcv dgiasfscac apgytgtrce sqvdecrsqp crhggkcldl
 601 vdkylcrcps gttgvncevn iddcasnpct fgvcrdginr ydcvcqpgft gplcnveine
 661 casspcgegg scvdgengfr clcppgslpp lclppshpca hepcshgicy dapggfrcvc
 721 epgwsgprcs qslardaces qpcraggtcs sdgmgfhctc ppgvqgrqce llspctpnpc
 781 ehggrcesap gqlpvcscpq gwqgprcqqd vdecagpapc gphgictnla gsfsctchgg
 841 ytgpscdqdi ndcdpnpcln ggscqdgvgs fscsclpgfa gprcardvde clsnpcgpgt
 901 ctdhvasftc tcppgyggfh ceqdlpdcsp sscfnggtcv dgvnsfsclc rpgytgahcq
 961 headpclsrp clhggvcsaa hpgfrctcle sftgpqcqtl vdwcsrqpcq nggrcvqtga
1021 yclcppgwsg rlcdirslpc reaaaqigvr leqlcqaggq cvdedsshyc vcpegrtgsh
1081 ceqevdpcla qpcqhggtcr gymggymcec lpgyngdnce ddvdecasqp cqhggscidl
1141 varylcscpp gtlgvlcein eddcgpgppl dsgprclhng tcvdlvggfr ctcppgytgl
1201 rceadinecr sgachaahtr dclqdpgggf rclchagfsg prcqtvlspc esqpcqhggq
1261 crpspgpggg ltftchcaqp fwgprcerva rscrelqcpv gvpcqqtprg prcacppgls
1321 gpscrsfpgs ppgasnasca aapclhggsc rpaplapffr cacaqgwtgp rceapaaape
1381 vseeprcpra acqakrgdqr cdrecnspgc gwdggdcsls vgdpwrqcea lqcwrlfnns
1441 rcdpacsspa clydnfdcha ggrertcnpv yekycadhfa dgrcdqgcnt eecgwdgldc
1501 asevpallar gvlvltvllp peellrssad flqrlsailr tslrfrldah gqamvfpyhr
1561 pspgseprar relapevigs vvmleidnrl clqspendhc fpdaqsaady lgalsaverl
1621 dfpyplrdvr gepleppeps vpllpllvag avlllvilvl gvmvarrkre hstlwfpegf
1681 slhkdvasgh kgrrepvgqd algmknmakg eslmgevatd wmdtecpeak rlkveepgmg
1741 aeeavdcrqw tqhhlvaadi rvapamaltp pqgdadadgm dvnvrgpdgf tplmlasfcg
1801 galepmptee deaddtsasi isdlicqgaq lgartdrtge talhlaarya radaakrlld
1861 agadtnaqdh sgrtplhtav tadaqgvfqi lirnrstdld armadgstal ilaarlaveg
1921 mveeliasha dvnavdelgk salhwaaavn nveatlallk ngankdmqds keetplflaa
1981 regsyeaakl lldhfanrei tdhldrlprd vaqerlhqdi vrlldqpsgp rsppgphglg
2041 pllcppgafl pglkaaqsgs kksrrppgka glgpqgprgr gkkltlacpg pladssvtls
```

Fig. 1 (continued)

2101 pvdsldsprp fggppaspgg fplegpyaaa tatavslaql ggpgraglgr qppggcvlsl
2161 gllnpvavpl dwarlpppap pgpsfllpla pgpqllnpgt pvspqerppp ylavpghgee
2221 ypaagahssp pkarflrvps ehpyltpspe spehwaspsp pslsdwsest pspatatgam
2281 atttgalpaq plplsvpssl aqaqtqlgpq pevtpkrqvl a NOTCH4, NP_004548, SEQ ID NO:201
1 mqppslllll llllllcvsv vrprgllcgs fpepcanggt clslslgqgt cqcapgflge
61 tcqfpdpcqn aqlcqnggsc qallpaplgl psspspltps flctclpgft gercqakled
121 pcppsfcskr grchiqasgr pqcscmpgwt geqcqlrdfc sanpcvnggv clatypqiqc
181 hcppgfegha cerdvnecfq dpgpcpkgts chntlgsfqc lcpvgqegpr celragpcpp
241 rgcsnggtcq lmpekdstfh lclcppgfig pdcevnpdnc vshqcqnggt cqdgldtytc
301 lcpetwtgwd csedvdecet qgpphcrngg tcqnsagsfh cvcvsgwggt sceenlddci
361 aatcapgstc idrvgsfscl cppgrtgllc hledmclsqp chgdaqcstn pltgstlclc
421 qpgysgptch qdldeclmaq qgpspcehgg sclntpgsfn clcppgytgs rceadhnecl
481 sqpchpgstc ldllatfhcl cppglegqlc evetnecasa pclnhadchd llngfqcicl
541 pgfsgtrcee didecrsspc anggqcqdqp gafhckclpg fegprcqtev declsdpcpv
601 gascldlpga ffclcpsgft gqlcevplca pnlcqpkqic kdqkdkancl cpdgspgcap
661 pednctchhg hcqrsscvcd vgwtgpecea elggcisapc ahggtcypqp sgynctcptg
721 ytgptcseem tachsgpcln ggscnpspgg yyctcppsht gpqcqtstdy cvsapcfngg
781 tcvnrpgtfs clcamgfqgp rcegklrpsc adspcrnrat cqdspqgprc lcptgytggs
841 cqtlmdlcaq kpcprnshcl qtgpsfhclc lqgwtgplcn lplsscqkaa lsqgidvssl
901 chngglcvds gpsyfchcpp gfqgslcqdh vnpcesrpcq ngatcmaqps gylcqcapgy
961 dgqncskeld acqsqpchnh gtctpkpggf hcacppgfvg lrcegdvdec ldqpchptgt
1021 aachslanaf ycqclpghtg qwceveidpc hsqpcfhggt ceatagsplg fichcpkgfe
1081 gptcshraps cgfhhchhgg lclpspkpgf pprcaclsgy ggpdcltppa pkgcgppspc
1141 lyngscsett glggpgfrcs cphsspgprc qkpgakgceg rsgdgacdag csgpggnwdg
1201 gdcslgvpdp wkgcpshsrc wllfrdgqch pqcdseeclf dgydcetppa ctpaydqych
1261 dhfhnghcek gcntaecgwd ggdcrpedgd pewgpslall vvlsppaldq qlfalarvls
1321 ltlrvglwvr kdrdgrdmvy pypgaraeek lggtrdptyq eraapqtqpl gketdslsag
1381 fvvvmgvdls rcgpdhpasr cpwdpglllr flaamaavga lepllpgpll avhphagtap
1441 panqlpwpvl cspvagvill algallvlql irrrrrehga lwlppgftrr prtqsaphrr
1501 rpplgedsig lkalkpkaev dedgvvmcsg peegeevgqa eetgppstcq lwslsggcga
1561 lpqaamltpp qesemeapdl dtrgpdgvtp lmsavccgev qsgtfqgawl gcpepwepll
1621 dggacpqaht vgtgetplhl aarfsrptaa rrlleaganp nqpdragrtp lhaavaadar
1681 evcqlllrsr qtavdarted gttplmlaar lavedlveel iaaqadvgar dkwgktalhw
1741 aaavnnaraa rsllqagadk daqdnreqtp lflaaregav evaqlllglg aarelrdqag
1801 lapadvahqr nhwdlltlle gagppearhk atpgreagpf prartvsvsv pphgggalpr
1861 crtlsagagp rgggaclqar twsvdlaarg ggayshcrsl sgvgagggpt prgrrfsagm
1921 rgprpnpaim rgrygvaagr ggrvstddwp cdwvalgacg sasnipippp cltpspergs
1981 pqldcgppal qempinqgge gkk DLL 1, NP_005609, SEQ ID NO:202
1 mgsrcalala vlsallcqvw ssgvfelklq efvnkkgllg nrnccrggag pppcacrtff
61 rvclkhyqas vspeppctyg savtpvlgvd sfslpdggga dsafsnpirf pfgftwpgtf
121 sliiealhtd spddlatenp erlisrlatq rhltvgeews qdlhssgrtd lkysyrfvcd
181 ehyygegcsv fcrprddafg hftcgergek vcnpgwkgpy ctepiclpgc deqhgfcdkp
241 geckcrvgwq grycdeciry pgclhgtcqq pwqcncqegw gglfcnqdln ycthhkpckn
301 gatctntgqg sytcscrpgy tgatcelgid ecdpspckng gsctdlensy sctcppgfyg
361 kicelsamtc adgpcfnggr csdspdggys crcpvgysgf ncekkidycs sspcsngakc
421 vdlgdaylcr cqagfsgrhc ddnvddcass pcanggtcrd gvndfsctcp pgytgrncsa
481 pvsrcehapc hngatcherg hryvcecarg yggpncqfll pelppgpavv dltekleggg
541 gpfpwvavca gvilvlmlll gcaavvvcvr lrlqkhrppa dpcrgetetm nnlancqrek
601 disvsiigat qikntnkkad fhgdhsadkn gfkarypavd ynlvqdlkgd dtavrdahsk
661 rdtkcqpqgs sgeekgtptt lrggeaserk rpdsgcstsk dtkyqsvyvi seekdecvia
721 tev

Fig. 1 (continued)

DLL4, NP_061947.1, SEQ ID NO:203

```
1 maaasrsasg walllllvalw qqraagsgvf qlqlqefine rgvlasgrpc epgcrtffrv
      61 clkhfqavvs pgpctfgtvs tpvlgtnsfa vrddssgggr nplqlpfnft wpgtfsliie
     121 awhapgddlr pealppdali skiaiqgsla vgqnwlldeq tstltrlrys yrvicsdnyy
     181 gdncsrlckk rndhfghyvc qpdgnlsclp gwtgeycqqp iclsgcheqn gycskpaecl
     241 crpgwqgrlc neciphngcr hgtcstpwqc tcdegwgglf cdqdlnycth hspckngatc
     301 snsgqrsytc tcrpgytgvd celelsecds npcrnggsck dqedgyhclc ppgyyglhce
     361 hstlscadsp cfnggscrer nqganyacec ppnftgsnce kkvdrctsnp canggqclnr
     421 gpsrmcrcrp gftgtycelh vsdcarnpca hggtchdlen glmctcpagf sgrrcevrts
     481 idacasspcf nratcytdls tdtfvcncpy gfvgsrcefp vglppsfpwv avslgvglav
     541 llvllgmvav avrqlrlrrp ddgsreamnn lsdfqkdnli paaqlkntnq kkelevdcgl
     601 dksncgkqqn htldynlapg plgrgtmpgk fphsdkslge kaplrlhsek pecrisaics
     661 prdsmyqsvc liseernecv iatev
```

JAG1, NP_000205.1, SEQ ID NO:204

```
1 mrsprtrgrs grplsllllal lcalrakvcg asgqfeleil smqnvngelq ngnccggarn
      61 pgdrkctrde cdtyfkvclk eyqsrvtagg pcsfgsgstp viggntfnlk asrgndrnri
     121 vlpfsfawpr sytllveawd ssndtvqpds iiekashsgm inpsrqwqtl kqntgvahfe
     181 yqirvtcddy yygfgcnkfc rprddffghy acdqngnktc megwmgpecn raicrqgcsp
     241 khgscklpgd crcqygwqgl ycdkciphpg cvhgicnepw qclcetnwgg qlcdkdlnyc
     301 gthqpclngg tcsntgpdky qcscpegysg pnceiaehac lsdpchnrgs cketslgfec
     361 ecspgwtgpt cstniddcsp nncshggtcq dlvngfkcvc ppqwtgktcq ldaneceakp
     421 cvnakscknl iasyycdclp gwmgqncdin indclgqcqn dascrdlvng yrcicppgya
     481 gdhcerdide casnpclngg hcqneinrfq clcptgfsgn lcqldidyce pnpcqngaqc
     541 ynrasdyfck cpedyegknc shlkdhcrtt pcevidsctv amasndtpeg vryissnvcg
     601 phgkcksqsg gkftcdcnkg ftgtycheni ndcesnpcrn ggtcidgvns ykcicsdgwe
     661 gaycetnind csqnpchngg tcrdlvndfy cdckngwkgk tchsrdsqcd eatcnnggtc
     721 ydegdafkcm cpggwegttc niarnssclp npchnggtcv vngesftcvc kegwegpica
     781 qntndcsphp cynsgtcvdg dnwyrcecap gfagpdcrin inecqsspca fgatcvdein
     841 gyrcvcppgh sgakcqevsg rpcitmgsvi pdgakwdddc ntcqclngri acskvwcgpr
     901 pcllhkghse cpsgqscipi lddqcfvhpc tgvgecrsss lqpvktkcts dsyyqdncan
     961 itftfnkemm spglttehic selrnlnilk nvsaeysiyi acepspsann eihvaisaed
    1021 irddgnpike itdkiidlvs krdgnsslia avaevrvqrr plknrtdflv pllssvltva
    1081 wicclvtafy wclrkrrkpg shthsasedn ttnnvreqln qiknpiekhg antvpikdye
    1141 nknskmskir thnseveedd mdkhqqkarf akqpaytlvd reekppngtp tkhpnwtnkq
    1201 dnrdlesaqs lnrmeyiv
```

JAG2, NP_002217.3, SEQ ID NO:205

```
1 mraqgrgrlp rrlllllalw vqaarpmgyf elqlsalrnv ngellsgacc dgdgrttrag
      61 gcghdecdty vrvclkeyqa kvtptgpcsy ghgatpvlgg nsfylppaga agdrararar
     121 aggdqdpglv vipfqfawpr sftliveawd wdndttpnee lliervshag minpedrwks
     181 lhfsghvahl elqirvrcde nyysatcnkf crprndffgh ytcdqygnka cmdgwmgkec
     241 keavckqgcn llhggctvpg ecrcsygwqg rfcdecvpyp gcvhgscvep wqcncetnwg
     301 gllcdkdlny cgshhpctng gtcinaepdq yrctcpdgys grncekaeha ctsnpcangg
     361 schevpsgfe chcpsgwsgp tcaldideca snpcaaggtc vdqvdgfeci cpeqwvgatc
     421 qldanecegk pclnafsckn liggyycdci pgwkginchi nvndcrgqcq hggtckdlvn
     481 gyqcvcprgf ggrhcelerd ecasspchsg glcedladgf hchcpqgfsg plcevdvdlc
     541 epspcrngar cynlegdyyc acpddfggkn csvprepcpg gacrvidgcg sdagpgmpgt
     601 aasgvcgphg rcvsqpggnf scicdsgftg tycheniddc lgqpcrnggt cidevdafrc
     661 fcpsgwegel cdtnpndclp dpchsrgrcy dlvndfycac ddgwkgktch srefqcdayt
     721 csnggtcyds gdtfrcacpp gwkgstcava knssclpnpc vnggtcvgsg asfscicrdg
     781 wegrtcthnt ndcnplpcyn ggicvdgvnw frcecapgfa gpdcrinide cqsspcayga
     841 tcvdeingyr cscppgragp rcqevigfgr scwsrgtpfp hgsswvedcn scrcldgrrd
     901 cskvwcgwkp cllagqpeal saqcplgqrc lekapgqclr ppceawgecg aeeppstpcl
     961 prsghldnnc arltlhfnrd hvpqgttvga icsgirslpa travardrll vllcdrassg
    1021 asavevavsf spardlpdss liqgaahaiv aaitqrgnss lllavtevkv etvvtggsst
    1081 gllvpvlcga fsvlwlacvv lcvwwtrkrr kerersrlpr eesannqwap lnpirnpier
    1141 pgghkdvlyq ckfntppprr adealpgpag haavredeed edlgrgeeds leaekflshk
    1201 ftkdpgrspg rpahwasgpk vdnravrsin earyagke
```

Fig. 1 (continued)

CD11a, XP_011544151.1, SEQ ID NO:206

```
   1 mtlatdptdg silacdpgls rtcdqntyls glcylfrqnl qgpmlqgrpg fqecikgnvd
  61 lvflfdgsms lqpdefqkil dfmkdvmkkl sntsyqfaav qfstsyktef dfsdyvkrkd
 121 pdallkhvkh mllltntfga inyvatevfr eelgarpdat kvliiitdge atdsgnidaa
 181 kdiiryiigi gkhfqtkesq etlhkfaskp asefvkildt feklkdlfte lqkkiyvieg
 241 tskqdltsfn melsssgisa dlsrghavvg avgakdwagg fldlkadlqd dtfigneplt
 301 pevragylgy tvtwlpsrqk tsllasgapr yqhmgrvllf qepqggghws qvqtihgtqi
 361 gsyfggelcg vdvdqdgete llligaplfy geqrggrvfi yqrrqlgfee vselqgdpgy
 421 plgrfgeait altdingdgl vdvavgaple eqgavyifng rhgglspqps qriegtqvls
 481 giqwfgrsih gvkdlegdgl advavgaesq mivlssrpvv dmvtlmsfsp aeipvhevec
 541 systsnkmke gvniticfqi kslipqfqgr lvanltytlq ldghrtrrrg lfpggrhelr
 601 rniavttsms ctdfsfhfpv cvqdlispin vslnfslwee egtprdqraq gkdippilrp
 661 slhsetweip fekncgedkk ceanlrvsfs parsralrlt afaslsvels lsnleedayw
 721 vqldlhfppg lsfrkvemlk phsqipvsce elpeesrlls ralscnvssp ifkaghsval
 781 qmmfntlvns swgdsvelha nvtcnnedsd llednsatti ipilypinil iqdqedstly
 841 vsftpkgpki hqvkhmyqvr iqpsihdhni ptleavvgvp qppsegpith qwsvqmeppv
 901 pchyedlerl pdaaepclpg alfrcpvvfr qeilvqvigt lelvgeieas smfslcssls
 961 isfnsskhfh lygsnaslaq vvmkvdvvye kqmlylyvls gigglllll ifivlykvgf
1021 fkrnlkekme agrgvpngip aedseqlasg qeagdpgclk plhekdsesg ggkd
```

CD11b, NP_001139280.1, SEQ ID NO:207

```
1 malrvlllta ltlchgfnld tenamtfqen argfgqsvvq lqgsrvvvga pqeivaanqr
  61 gslyqcdyst gscepirlqv pveavnmslg lslaattspp qllacgptvh qtcsentyvk
 121 glcflfgsnl rqqpqkfpea lrgcpqedsd iaflidgsgs iiphdfrrmk efvstvmeql
 181 kksktlfslm qyseefrihf tfkefqnnpn prslvkpitq llgrthtatg irkvvrelfn
 241 itngarknaf kilvvitdge kfgdplgyed vipeadregv iryvigvgda frseksrqel
 301 ntiaskpprd hvfqvnnfea lktiqnqlre kifaiegtqt gssssfehem sqegfsaait
 361 sngpllstvg sydwaggvfl ytskekstfi nmtrvdsdmn daylgyaaai ilrnrvqslv
 421 lgapryqhig lvamfrqntg mwesnanvkg tqigayfgas lcsvdvdsng stdlvligap
 481 hyyeqtrggq vsvcplprgq rarwqcdavl ygeqgqpwgr fgaaltvlgd vngdkltdva
 541 igapgeednr gavylfhgts gsgispshsq riagsklspr lqyfgqslsg gqdltmdglv
 601 dltvgaqghv lllrsqpvlr vkaimefnpr evarnvfecn dqvvkgkeag evrvclhvqk
 661 strdrlregq iqsvvtydla ldsgrphsra vfnetknstr rqtqvlgltq tcetlklqlp
 721 nciedpvspi vlrlnfslvg tplsafgnlr pvlaedaqrl ftalfpfekn cgndnicqdd
 781 lsitfsfmsl dclvvggpre fnvtvtvrnd gedsyrtqvt fffpldlsyr kvstlqnqrs
 841 qrswrlaces asstevsgal kstscsinhp ifpensevtf nitfdvdska slgnklllka
 901 nvtsennmpr tnktefqlel pvkyavymvv tshgvstkyl nftasentsr vmqhqyqvsn
 961 lgqrslpisl vflvpvrlnq tviwdrpqvt fsenlsstch tkerlpshsd flaelrkapv
1021 vncsiavcqr iqcdipffgi qeefnatlkg nlsfdwyikt shnhllivst aeilfndsvf
1081 tllpgqgafv rsqtetkvep fevpnplpli vgssvgglll lalitaalyk lgffkrqykd
1141 mmseggppga epq
```

CD11c, NP_001139280.1, SEQ ID NO:208

```
   1 malrvlllta ltlchgfnld tenamtfqen argfgqsvvq lqgsrvvvga pqeivaanqr
  61 gslyqcdyst gscepirlqv pveavnmslg lslaattspp qllacgptvh qtcsentyvk
 121 glcflfgsnl rqqpqkfpea lrgcpqedsd iaflidgsgs iiphdfrrmk efvstvmeql
 181 kksktlfslm qyseefrihf tfkefqnnpn prslvkpitq llgrthtatg irkvvrelfn
 241 itngarknaf kilvvitdge kfgdplgyed vipeadregv iryvigvgda frseksrqel
 301 ntiaskpprd hvfqvnnfea lktiqnqlre kifaiegtqt gssssfehem sqegfsaait
 361 sngpllstvg sydwaggvfl ytskekstfi nmtrvdsdmn daylgyaaai ilrnrvqslv
 421 lgapryqhig lvamfrqntg mwesnanvkg tqigayfgas lcsvdvdsng stdlvligap
 481 hyyeqtrggq vsvcplprgq rarwqcdavl ygeqgqpwgr fgaaltvlgd vngdkltdva
 541 igapgeednr gavylfhgts gsgispshsq riagsklspr lqyfgqslsg gqdltmdglv
 601 dltvgaqghv lllrsqpvlr vkaimefnpr evarnvfecn dqvvkgkeag evrvclhvqk
 661 strdrlregq iqsvvtydla ldsgrphsra vfnetknstr rqtqvlgltq tcetlklqlp
 721 nciedpvspi vlrlnfslvg tplsafgnlr pvlaedaqrl ftalfpfekn cgndnicqdd
 781 lsitfsfmsl dclvvggpre fnvtvtvrnd gedsyrtqvt fffpldlsyr kvstlqnqrs
 841 qrswrlaces asstevsgal kstscsinhp ifpensevtf nitfdvdska slgnklllka
 901 nvtsennmpr tnktefqlel pvkyavymvv tshgvstkyl nftasentsr vmqhqyqvsn
```

Fig. 1 (continued)

961 lgqrslpisl vflvpvrlnq tviwdrpqvt fsenlsstch tkerlpshsd flaelrkapv
1021 vncsiavcqr iqcdipffgi qeefnatlkg nlsfdwyikt shnhllivst aeilfndsvf
1081 tllpgqgafv rsqtetkvep fevpnplpli vgssvgglll lalitaalyk lgffkrqykd
1141 mmseggppga epq CD18/ITGB2, NP_001120963.2, SEQ ID NO:209
1 mlglrppl la lvgllslgcv lsqectkfkv sscreciesg pgctwcqkln ftgpgdpdsi
61 rcdtrpqllm rgcaaddimd ptslaetqed hnggqkqlsp qkvtlylrpg qaaafnvtfr
121 rakgypidly ylmdlsysml ddlrnvkklg gdllralnei tesgrigfgs fvdktvlpfv
181 nthpdklrnp cpnkekecqp pfafrhvlkl tnnsnqfqte vgkqlisgnl dapeggldam
241 mqvaacpeei gwrnvtrllv fatddgfhfa gdgklgailt pndgrchled nlykrsnefd
301 ypsvgqlahk laenniqpif avtsrmvkty eklteiipks avgelsedss nvvhliknay
361 nklssrvfld hnalpdtlkv tydsfcsngv thrnqprgdc dgvqinvpit fqvkvtatec
421 iqeqsfvira lgftdivtvq vlpqcecrcr dqsrdrslch gkgflecgic rcdtgyigkn
481 cecqtqgrss qelegscrkd nnsiicsglg dcvcgqclch tsdvpgkliy gqycecdtin
541 ceryngqvcg gpgrglcfcg kcrchpgfeg sacqcertte gclnprrvec sgrgrcrcnv
601 cechsgyqlp lcqecpgcps pcgkyiscae clkfekgpfg kncsaacpgl qlsnnpvkgr
661 tckerdsegc wvaytleqqd gmdryliyvd esrecvagpn iaaivggtva givligilll
721 viwkalihls dlreyrrfek eklksqwnnd nplfksattt vmnpkfaes CD41, NP_000410.2, SEQ ID NO:210
1 maralcplqa lwllewvlll lgpcaappaw alnldpvqlt fyagpngsqf gfsldfhkds
61 hgrvaivvga prtlgpsqee tggvflcpwr aeggqcpsll fdlrdetrnv gsqtlqtfka
121 rqglgasvvs wsdvivacap wqhwnvlekt eeaektpvgs cflaqpesgr raeyspcrgn
181 tlsriyvend fswdkrycea gfssvvtqag elvlgapggy yflgllaqap vadifssyrp
241 gillwhvssq slsfdssnpe yfdgywgysv avgefdgdln tteyvvgapt wswtlgavei
301 ldsyyqrlhr lrgeqmasyf ghsvavtdvn gdgrhdllvg aplymesrad rklaevgrvy
361 lflqprgpha lgapslllt g tqlygrfgsa iaplgdldrd gyndiavaap yggpsgrgqv
421 lvflgqsegl rsrpsqvlds pfptgsafgf slrgavdidd ngypdlivga yganqvavyr
481 aqpvvkasvq llvqdslnpa vkscvlpqtk tpvscfniqm cvgatghnip qklslnaelq
541 ldrqkprqgr rvlllgsqqa gttlnldlgg khspichttm aflrdeadfr dklspivlsl
601 nvslppteag mapavvlhgd thvqeqtriv ldcgeddvcv pqlqltasvt gspllvgadn
661 vlelqmdaan egegayeael avhlpqgahy mralsnvegf erlicnqkke netrvvlcel
721 gnpmkknaqi giamlvsvgn leeagesvsf qlqirsknsq npnskivlld vpvraeaqve
781 lrgnsfpasl vvaaeegere qnsldswgpk vehtyelhnn gpgtvnglhl sihlpgqsqp
841 sdllyildiq pqgglqcfpq ppvnplkvdw glpipspspi hpahhkrdrr qiflpepeqp
901 srlqdpvlvs cdsapctvvq cdlqemargq ramvtvlafl wlpslyqrpl dqfvlqshaw
961 fnvsslpyav pplslprgea qvwtqllral eeraipiwwv lvgvlgglll ltilvlamwk
1021 vgffkrnrpp leeddeege CD51, NP_001138472.1, SEQ ID NO:211
1 mafpprrrlr lgprglplll sglllplcra fnldvdspae ysgpegsyfg favdffvpsa
61 ssrmfllvga pkanttqpgi veggqvlkcd wsstrrcqpi efdatgnrdy akddplefks
121 hqwfgasvrs kqdkilacap lyhwrtemkq erepvgtcfl qdgtktveya pcrsrqlisd
181 qvaeivskyd pnvysikynn qlatrtaqai fddsylgysv avgdfngdgi ddfvsgvpra
241 artlgmvyiy dgknmsslyn ftgeqmaayf gfsvaatdin gddyadvfig aplfmdrgsd
301 gklqevgqvs vslqrasgdf qttklngfev farfgsaiap lgdldqdgfn diaiaapygg
361 edkkgivyif ngrstglnav psqilegqwa arsmppsfgy smkgatdidk ngypdlivga
421 fgvdrailyr arpvitvnag levypsilnq dnktcslpgt alkvscfnvr fclkadgkgv
481 lprklnfqve llldklkqkg airralflys rspshsknmt isrgglmqce eliaylrdes
541 efrdkltpit ifmeyrldyr taadttglqp ilnqftpani srqahilldc gednvckpkl
601 evsvdsdqkk iyigddnplt livkaqnqge gayeaelivs iplqadfigv vrnnealarl
661 scafktenqt rqvvcdlgnp mkagtqllag lrfsvhqqse mdtsvkfdlq iqssnlfdkv
721 spvvshkvdl avlaaveirg vsspdhiflp ipnwehkenp eteedvgpvv qhiyelrnng
781 pssfskamlh lqwpykynnn tllyilhydi dgpmnctsdm einplrikis slqttekndt
841 vagqgerdhl itkrdlalse gdihtlgcgv aqclkivcqv grldrgksai lyvksllwte
901 tfmnkenqnh syslkssasf nviefpyknl pieditnstl vttnvtwgiq papmpvpvwv
961 iilavlagll llavlvfvmy rmgffkrvrp pqeeqereql qphengegns et

Fig. 1 (continued)

CD61, NP_000203.2, SEQ ID NO:212

```
1 mrarprprpl watvlalgal agvgvggpni cttrgvsscq qclavspmca wcsdealplg
      61 sprcdlkenl lkdncapesi efpvsearvl edrplsdkgs gdssqvtqvs pqrialrlrp
     121 ddsknfsiqv rqvedypvdi yylmdlsysm kddlwsiqnl gtklatqmrk ltsnlrigfg
     181 afvdkpvspy myisppeale npcydmkttc lpmfgykhvl tltdqvtrfn eevkkqsvsr
     241 nrdapeggfd aimqatvcde kigwrndash llvfttdakt hialdgrlag ivqpndgqch
     301 vgsdnhysas ttmdypslgl mteklsqkni nlifavtenv vnlyqnysel ipgttvgvls
     361 mdssnvlqli vdaygkirsk velevrdlpe elslsfnatc lnnevipglk scmglkigdt
     421 vsfsieakvr gcpqekeksf tikpvgfkds livqvtfdcd cacqaqaepn shrcnngngt
     481 fecgvcrcgp gwlgsqcecs eedyrpsqqd ecspregqpv csqrgeclcg qcvchssdfg
     541 kitgkycecd dfscvrykge mcsghgqcsc gdclcdsdwt gyycncttrt dtcmssngll
     601 csgrgkcecg scvciqpgsy gdtcekcptc pdactfkkec veckkfdrga lhdentcnry
     661 crdeiesvke lkdtgkdavn ctykneddcv vrfqyyedss gksilyvvee pecpkgpdil
     721 vvllsvmgai lliglaalli wkllitihdr kefakfeeer arakwdtann plykeatstf
     781 tnityrgt
```

CD104, NP_001308052.1, SEQ ID NO:213

```
  1 magprpspwa rlllaalisv slsgtlanrc kkapvkscte cvrvdkdcay ctdemfrdrr
      61 cntqaellaa gcqresivvm essfqiteet qidttlrrsq mspqglrvrl rpgeerhfel
     121 evfeplespv dlyilmdfsn smsddldnlk kmgqnlarvl sqltsdytig fgkfvdkvsv
     181 pqtdmrpekl kepwpnsdpp fsfknvislt edvdefrnkl qgerisgnld apeggfdail
     241 qtavctrdig wrpdsthllv fstesafhye adganvlagi msrnderchl dttgtytqyr
     301 tqdypsvptl vrllakhnii pifavtnysy syyeklhtyf pvsslgvlqe dssnivelle
     361 eafnrirsnl diraldsprg lrtevtskmf qktrtgsfhi rrgevgiyqv qlralehvdg
     421 thvcqlpedq kgnihlkpsf sdglkmdagi icdvctcelq kevrsarcsf ngdfvcgqcv
     481 csegwsgqtc ncstgslsdi qpclregedk pcsgrgecqc ghcvcygegr yegqfceydn
     541 fqcprtsgfl cndrgrcsmg qcvcepgwtg pscdcplsna tcidsnggic ngrghcecgr
     601 chchqqslyt dticeinysa ihpglcedlr scvqcqawgt gekkgrtcee cnfkvkmvde
     661 lkraeevvvr csfrdedddc tysytmegdg apgpnstvlv hkkkdcppgs fwwlipllll
     721 llpllallll lcwkycacck aclallpccn rghmvgfked hymlrenlma sdhldtpmlr
     781 sgnlkgrdvv rwkvtnnmqr pgfathaasi nptelvpygl slrlarlcte nllkpdtrec
     841 aqlrqeveen lnevyrqisg vhklqqtkfr qqpnagkkqd htivdtvlma prsakpallk
     901 ltekqveqra fhdlkvapgy ytltadqdar gmvefqegve lvdvrvplfi rpedddekql
     961 lveaidvpag tatlgrrlvn itiikeqard vvsfeqpefs vsrgdqvari pvirrvldgg
    1021 ksqvsyrtqd gtaqgnrdyi pvegellfqp geawkelqvk llelqevdsl lrgrqvrrfh
    1081 vqlsnpkfga hlgqphstti iirdpdeldr sftsqmlssq ppphgdlgap qnpnakaags
    1141 rkihfnwlpp sgkpmgyrvk ywiqgdsese ahlldskvps veltnlypyc dyemkvcayg
    1201 aqgegpyssl vscrthqevp sepgrlafnv vsstvtqlsw aepaetngei tayevcyglv
    1261 nddnrpigpm kkvlvdnpkn rmllienlre sqpyrytvka rngagwgper eaiinlatqp
    1321 krpmsipiip dipivdaqsg edydsflmys ddvlrspsgs qrpsvsddte hlvngrmdfa
    1381 fpgstnslhr mtttsaaayg thlsphvphr vlstsstltr dynsltrseh shsttlprdy
    1441 stltsvsshd srltagvpdt ptrlvfsalg ptslrvswqe prcerplqgy sveyqllngg
    1501 elhrlnipnp aqtsvvvedl lpnhsyvfrv raqsqegwgr eregvities qvhpqsplcp
    1561 lpgsaftlst psapgplvft alspdslqls werprrpngd ivgylvtcem aqgggpataf
    1621 rvdgdspesr ltvpglsenv pykfkvqart tegfgpereg iitiesqdgg pfpqlgsrag
    1681 lfqhplqsey ssittthtsa tepflvdglt lgaqhleagg sltrhvtqef vsrtlttsgt
    1741 lsthmdqqff qt
```

Fig. 1 (continued)

Membrane proteins with enzymatic activity, misc.

CD13, NP_001141.2, SEQ ID NO:214

```
  1 makgfyisks lgilgillgv aavctiials vvysqeknkn ansspvastt psasattnpa
 61 sattldqska wnryrlpntl kpdsyrvtlr pyltpndrgl yvfkgsstvr ftckeatdvi
121 iihskklnyt lsqghrvvlr gvggsqppdi dktelvepte ylvvhlkgsl vkdsqyemds
181 efegeladdl agfyrseyme gnvrkvvatt qmqaadarks fpcfdepamk aefnitlihp
241 kdltalsnml pkgpstplpe dpnwnvtefh ttpkmstyll afivsefdyv ekqasngvli
301 riwarpsaia aghgdyalnv tgpilnffag hydtpyplpk sdqiglpdfn agamenwglv
361 tyrensllfd plsssssnke rvvtviahel ahqwfgnlvt iewwndlwln egfasyveyl
421 gadyaeptwn lkdlmvlndv yrvmavdala sshplstpas eintpaqise lfdaisyskg
481 asvlrmlssf lsedvfkqgl asylhtfayq ntiylnlwdh lqeavnnrsi qlpttvrdim
541 nrwtlqmgfp vitvdtstgt lsqehflldp dsnvtrpsef nyvwivpits irdgrqqqdy
601 wlidvraqnd lfstsgnewv llnlnvtgyy rvnydeenwr kiqtqlqrdh saipvinraq
661 iindafnlas ahkvpvtlal nntlflieer qympweaals slsyfklmfd rsevygpmkn
721 ylkkqvtplf ihfrnntnnw reipenlmdq ysevnaista csngvpecee mvsglfkqwm
781 enpnnnpihp nlrstvycna iaqggeeewd faweqfrnat lvneadklra alacskelwi
841 lnrylsytln pdlirkqdat stiisitnnv igqglvwdfv qsnwkklfnd ygggsfsfsn
901 liqavtrrfs teyelqqleq fkkdneetgf gsgtraleqa lektkanikw vkenkevvlq
961 wftensk
```

Immune regulatory surface proteins including Fc receptors, T-cell receptor, complement receptors, interleukin receptors, immunoglobulins, MHCI or MHC-II components

CD2, NP_001758.2, SEQ ID NO:215

```
  1 msfpckfvas fllifnvssk gavskeitna letwgalgqd inldipsfqm sddiddikwe
 61 ktsdkkkiaq frkeketfke kdtyklfkng tlkikhlktd dqdiykvsiy dtkgknvlek
121 ifdlkiqerv skpkiswtci nttltcevmn gtdpelnlyq dgkhlklsqr vithkwttsl
181 sakfkctagn kvskessvep vscpekgldi yliigicggg sllmvfvall vfyitkrkkq
241 rsrrndeele trahrvatee rgrkphqipa stpqnpatsq hppppphgrs qapshrpppp
301 ghrvqhqpqk rppapsgtqv hqqkgpplpr prvqpkpphg aaenslspss n
```

CD3 epsilon, NP_000724.1, SEQ ID NO:216

```
  1 mqsgthwrvl glcllsvgvw gqdgneemgg itqtpykvsi sgttviltcp qypgseilwq
 61 hndkniggde ddknigsded hlslkefsel eqsgyyvcyp rgskpedanf ylylrarvce
121 ncmemdvmsv ativivdici tggllllvyy wsknrkakak pvtrgagagg rqrgqnkerp
181 ppvpnpdyep irkgqrdlys glnqrri
```

CD3 zeta, NP_932170.1, SEQ ID NO:217

```
  1 mkwkalftaa ilqaqlpite aqsfglldpk lcylldgilf iygviltalf lrvkfsrsad
 61 apayqqgqnq lynelnlgrr eeydvldkrr grdpemggkp qrrknpqegl ynelqkdkma
121 eayseigmkg errrgkghdg lyqglstatk dtydalhmqa lppr
```

CD18, NP_001120963.2, SEQ ID NO:218

```
  1 mlglrppllа lvgllslgcv lsqectkfkv sscreciesg pgctwcqkln ftgpgdpdsi
 61 rcdtrpqllm rgcaaddimd ptslaetqed hnggqkqlsp qkvtlylrpg qaaafnvtfr
121 rakgypidly ylmdlsysml ddlrnvkklg gdllralnei tesgrigfgs fvdktvlpfv
181 nthpdklrnp cpnkekecqp pfafrhvlkl tnnsnqfqte vgkqlisgnl dapeggldam
241 mqvaacpeei gwrnvtrllv fatddgfhfa gdgklgailt pndgrchled nlykrsnefd
301 ypsvgqlahk laenniqpif avtsrmvkty eklteiipks avgelsedss nvvhliknay
361 nklssrvfld hnalpdtlkv tydsfcsngv thrnqprgdc dgvqinvpit fqvkvtatec
421 iqeqsfvira lgftdivtvq vlpqcecrcr dqsrdrslch gkgflecgic rcdtgyigkn
481 cecqtqgrss qelegscrkd nnsiicsglg dcvcgqclch tsdvpgkliy gqycecdtin
541 ceryngqvcg gpgrglcfcg kcrchpgfeg sacqcertte gclnprrvec sgrgrcrcnv
601 cechsgyqlp lcqecpgcps pcgkyiscae clkfekgpfg kncsaacpgl qlsnnpvkgr
661 tckerdsegc wvaytleqqd gmdryliyvd esrecvagpn iaaivggtva givligilll
721 viwkalihls dlreyrrfek eklksqwnnd nplfksattt vmnpkfaes
```

Fig. 1 (continued)

CD19, NP_001761.3, SEQ ID NO:219
1 mppprllffl lfltpmevrp eeplvvkvee gdnavlqclk gtsdgptqql twsresplkp
61 flklslglpg lgihmrplai wlfifnvsqq mggfylcqpg ppsekawqpg wtvnvegsge
121 lfrwnvsdlg glgcglknrs segpsspsgk lmspklyvwa kdrpeiwege ppclpprdsl
181 nqslsqdltm apgstlwlsc gvppdsvsrg plswthvhpk gpksllslel kddrpardmw
241 vmetglllpr ataqdagkyy chrgnltmsf hleitarpvl whwllrtggw kvsavtlayl
301 ifclcslvgi lhlqralvlr rkrkrmtdpt rrffkvtppp gsgpqnqygn vlslptptsg
361 lgraqrwaag lggtapsygn pssdvqadga lgsrsppgvg peeeegegye epdseedsef
421 yendsnlgqd qlsqdgsgye npedeplgpe dedsfsnaes yenedeeltq pvartmdfls
481 phgsawdpsr eatslgsqsy edmrgilyaa pqlrsirgqp gpnheedads yenmdnpdgp
541 dpawggggrm gtwstr CD30, NP_001268359.2, SEQ ID NO:220
1 mfcstsavns carcffhsvc pagmivkfpg taqkntvcep aspgvspaca spenckepss
61 gtipqakptp vspatssast mpvrggtrla qeaaskltra pdspssvgrp ssdpglsptq
121 pcpegsgdcr kqcepdyyld eagrctacvs csrddlvekt pcawnssrtc ecrpgmicat
181 satnscarcv pypicaaetv tkpqdmaekd ttfeapplgt qpdcnptpen geapastspt
241 qsllvdsqas ktlpiptsap valsstgkpv ldagpvlfwv ilvlvvvvgs safllchrra
301 crkrirqklh lcypvqtsqp klelvdsrpr rsstlrsgas vtepvaeerg lmsqplmetc
361 hsvgaayles lplqdaspag gpssprdlpe prvstehtnn kiekiyimka dtvivgtvka
421 elpegrglag paepeleeel eadhtphype qetepplgsc sdvmlsveee gkedplptaa
481 sgk CD34, NP_001764.1, SEQ ID NO:221
1 mlvrrgarag prmprgwtal cllsllpsgf msldnngtat pelptqgtfs nvstnvsyqe
61 tttpstlgst slhpvsqhgn eattnitett vkftstsvit svygntnssv qsqtsvistv
121 fttpanvstp ettlkpslsp gnvsdlstts tslatsptkp ytssspilsd ikaeikcsgi
181 revkltqgic leqnktssca efkkdrgegl arvlcgeeqa dadagaqvcs lllaqsevrp
241 qclllvlanr teissklqlm kkhqsdlkkl gildfteqdv ashqsysqkt lialvtsgal
301 lavlgitgyf lmnrrswspt gerlelep CD36, NP_001120915.1, SEQ ID NO:222
1 mgcdrncgli agavigavla vfggilmpvg dlliqktikk qvvleegtia fknwvktgte
61 vyrqfwifdv qnpqevmmns sniqvkqrgp ytyrvrflak envtqdaedn tvsflqpnga
121 ifepslsvgt eadnftvlnl avaaashiyq nqfvqmilns linksksssmf qvrtlrellw
181 gyrdpflslv pypvtttvgl fypynntadg vykvfngkdn iskvaiidty kgkrnlsywe
241 shcdmingtd aasfppfvek sqvlqffssd icrsiyavfe sdvnlkgipv yrfvlpskaf
301 aspvenpdny cfctekiisk nctsygvldi skckegrpvy islphflyas pdvsepidgl
361 npneeehrty ldiepitgft lqfakrlqvn llvkpsekiq vlknlkrnyi vpilwlnetg
421 tigdekanmf rsqvtgkinl lgliemills vgvvmfvafm isycacrskt ik CD40, NP_001289682.1, SEQ ID NO:223
1 mvrlplqcvl wgclltavhp epptacrekq ylinsqccsl cqpgqklvsd cteftetecl
61 pcgesefldt wnrethchqh kycdpnlglr vqqkgtsetd tictceegwh ctseacescv
121 lhrscspgfg vkqiatgvsd ticepcpvgf fsnvssafek chpwtscetk dlvvqqagtn
181 ktdvvcgesw tmgpgeslgr spgsaespgg dphhlrdpvc hplgaglyqk ggqeanq CD40L, NP_000065.1, SEQ ID NO:224
1 mietynqtsp rsaatglpis mkifmylltv flitqmigsa lfavylhrrl dkiedernlh
61 edfvfmktiq rcntgersls llnceeiksq fegfvkdiml nkeetkkens femqkgdqnp
121 qiaahvisea sskttsvlqw aekgyytmsn nlvtlengkq ltvkrqglyy iyaqvtfcsn
181 reassqapfi aslclkspgr ferillraan thssakpcgq qsihlggvfe lqpgasvfvn
241 vtdpsqvshg tgftsfgllk l

Fig. 1 (continued)

CD44, NP_001001391.1, SEQ ID NO:225

```
  1 mdkfwwhaaw glclvplsla qidlnitcrf agvfhvekng rysisrteaa dlckafnstl
 61 ptmaqmekal sigfetcryg fieghvvipr ihpnsicaan ntgvyiltsn tsqydtycfn
121 asappeedct svtdlpnafd gpititivnr dgtryvqkge yrtnpediyp snptdddvss
181 gsssersstS ggyifytfst vhpipdedsp witdstdrip atrdqdtfhp sggshtthgs
241 esdghshgsq egganttsgp irtpqipewl iilasllala lilavciavn srrrcgqkkk
301 lvinsgngav edrkpsglng easksqemvh lvnkessetp dqfmtadetr nlqnvdmkig
361 v
```

CD45, NP_001254727.1, SEQ ID NO:226

```
1 mtmylwlkll afgfafldte vfvtgqsptp sptghlqaee qgsqskspnl ksreadssaf
 61 swwpkarepl tnhwskskSp kaeelgv
```

CD47, NP_001768.1, SEQ ID NO:227

```
  1 mwplvaalll gsaccgsaql lfnktksvef tfcndtvvip cfvtnmeaqn ttevyvkwkf
 61 kgrdiytfdg alnkstvptd fssakievsq llkgdaslkm dksdavshtg nytcevtelt
121 regetiielk yrvvswfspn enilivifpi faillfwgqf giktlkyrsg gmdektiall
181 vaglvitviv ivgailfvpg eyslknatgl glivtstgil illhyyvfst aigltsfvia
241 ilviqviayi lavvglslci aacipmhgpl lisglsilal aqllglvymk fvasnqktiq
301 pprkaveepl nafkeskgmm nde
```

CD86, NP_787058, SEQ ID NO:228

```
  1 mdpqctmgls nilfvmafll sgaaplkiqa yfnetadlpc qfansqnqsl selvvfwqdq
 61 enlvlnevyl gkekfdsvhs kymgrtsfds dswtlrlhnl qikdkglyqc iihhkkptgm
121 irihqmnsel svlanfsqpe ivpisniten vyinltcssi hgypepkkms vllrtknsti
181 eydgvmqksq dnvtelydvs islsvsfpdv tsnmtifcil etdktrllss pfsieledpq
241 pppdhipwit avlptviicv mvfclilwkw kkkkrprnsy kcgtntmere eseqtkkrek
301 ihipersdea qrvfksskts scdksdtcf
```

CD110, NP_005364.1, SEQ ID NO:229

```
  1 mpswalfmvt sclllapqnl aqvssqdvsl lasdseplkc fsrtfedltc fwdeeeaaps
 61 gtyqllyayp rekpracpls sqsmphfgtr yvcqfpdqee vrlffplhlw vknvflnqtr
121 tqrvlfvdsv glpappsiik amggsqpgel qisweepape isdflryelr ygprdpknst
181 gptviqliat etccpalqrp hsasaldqsp caqptmpwqd gpkqtspsre asaltaeggs
241 clisglqpgn sywlqlrsep dgislggswg swslpvtvdl pgdavalglq cftldlknvt
301 cqwqqqdhas sqgffyhsra rccprdrypi wenceeeekt npglqtpqfs rchfksrnds
361 iihilvevtt apgtvhsylg spfwihqavr lptpnlhwre issghlelew qhpsswaaqe
421 tcyqlrytge ghqdwkvlep plgarggtle lrprsryrlq lrarlngpty qgpwsswsdp
481 trvetateta wislvtalhl vlglsavlgl lllrwqfpah yrrlrhalwp slpdlhrvlg
541 qylrdtaals ppkatvsdtc eevepsllei lpkssertpl plcssqaqmd yrrlqpsclg
601 tmplsvcppm aesgscctth ianhsylpls ywqqp
```

CD111, NP_976031.1, SEQ ID NO:230

```
  1 marmglagaa grwwglalgl tafflpgvhs qvvqvndsmy gfigtdvvlh csfanplpsv
 61 kitqvtwqks tngskqnvai ynpsmgvsvl apyrervefl rpsftdgtir lsrleledeg
121 vyicefatfp tgnresqlnl tvmakptnwi egtqavlrak kgqddkvlva tctsangkpp
181 svvswetrlk geaeyqeirn pngtvtvisr yrlvpsreah qqslacivny hmdrfkeslt
241 lnvqyepevt iegfdgnwyl qrmdvkltck adanppatey hwttlngslp kgveaqnrtl
301 ffkgpinysl agtyiceatn pigtrsgqve vnitafcqli ypgkgrtrar mf
```

Fig. 1 (continued)

CD115, NP_001336665.1, SEQ ID NO:231
```
1 mgpgvlllll vatawhgqgi pviepsvpel vvkpgatvtl rcvgngsvew dgppsphwtl
      61 ysdgsssils tnnatfqntg tyrctepgdp lggsaaihly vkdparpwnv laqevvvfed
     121 qdallpcllt dpvleagvsl vrvrgrplmr htnysfspwh gftihrakfi qsqdyqcsal
     181 mggrkvmsis irlkvqkvip gppaltlvpa elvrirgeaa qivcsassvd vnfdvflqhn
     241 ntklaipqqs dfhnnryqkv ltlnldqvdf qhagnyscva snvqgkhsts mffrvvesay
     301 lnlsseqnli qevtvgegln lkvmveaypg lqgfnwtylg pfsdhqpepk lanattkdty
     361 rhtftlslpr lkpseagrys flarnpggwr altfeltlry ppevsviwtf ingsgtllca
     421 asgypqpnvt wlqcsghtdr cdeaqvlqvw ddpypevlsq epfhkvtvqs lltvetlehn
     481 qtyecrahns vgsgswafip isagahthpp deflftpvvv acmsimalll llllllykyk
     541 kqkpkyqvrw kiiesyegns ytfidptqlp ynekwefprn nlqfgktlga gafgkvveat
     601 afglgkedav lkvavkmlks tahadekeal mselkimshl gqhenivnll gacthggpvl
     661 viteyccygd llnflrrkae amlgpslspg qdpeggvdyk nihlekkyvr rdsgfssqgv
     721 dtyvemrpvs tssndsfseq dldkedgrpl elrdllhfss qvaqgmafla skncihrdva
     781 arnvlltngh vakigdfgla rdimndsnyi vkgnarlpvk wmapesifdc vytvqsdvws
     841 ygillweifs lglnpypgil vnskfyklvk dgyqmaqpaf apkniysimq acwalepthr
     901 ptfqqicsfl qeqaqedrre rdytnlpsss rsggsgssss eleeessseh ltcceqgdia
     961 qpllqpnnyq fc
```

CD117, XP_016863667.1, SEQ ID NO:232
```
  1 mrgargawdf lcvllllllrv qtgssqpsvs pgepsppsih pgksdlivrv gdeirllctd
      61 pgfvkwtfei ldetnenkqn ewitekaeat ntgkytctnk hglsnsiyvf vrdpaklflv
     121 drslygkedn dtlvrcpltd pevtnyslkg cqgkplpkdl rfipdpkagi miksvkrayh
     181 rlclhcsvdq egksvlsekf ilkvrpafka vpvvsvskas yllregeeft vtctikdvss
     241 svystwkren sqtklqekyn swhhgdfnye rqatltissa rvndsgvfmc yanntfgsan
     301 vtttlevvdk gfinifpmin ttvfvndgen vdliveyeaf pkpehqqwiy mnrtftdkwe
     361 dypksenesn iryvselhlt rlkgteggty tflvsnsdvn aaiafnvyvn tkpeiltydr
     421 lvngmlqcva agfpeptidw yfcpgteqrc sasvlpvdvq tlnssgppfg klvvqssids
     481 safkhngtve ckayndvgkt sayfnfafkg nnkeqihpht lftplligfv ivagmmciiv
     541 miltykylqk pmyevqwkvv eeingnnyvy idptqlpydh kwefprnrls fgktlgagaf
     601 gkvveatayg liksdaamtv avkmlkpsah lterealmse lkvlsylgnh mnivnllgac
     661 tiggptlvit eyccygdlln flrrkrdsfi cskqedhaea alyknllhsk esscdstney
     721 mdmkpgvsyv vptkadkrrs vrigsyierd vtpaimedde laldledlls fsyqvakgma
     781 flaskncihr dlaarnillt hgritkicdf glardiknds nyvvkgnarl pvkwmapesi
     841 fncvytfesd vwsygiflwe lfslgsspyp gmpvdskfyk mikegfrmls pehapaemyd
     901 imktcwdadp lkrptfkqiv qliekqises tnhiysnlan cspnrqkpvv dhsvrinsvg
     961 stasssqpll vhddv
```

CD125, XP_011531979.1, SEQ ID NO:233
```
1 miivahvlli llgateilqa dllpdekisl lppvnftikv tglaqvllqw kpnpdqeqrn
      61 vnleyqvkin apkeddyetr iteskcvtil hkgfsasvrt ilqndhslla sswasaelha
     121 ppgspgtsiv nltcttntte dnysrlrsyq vslhctwlvg tdapedtqyf lyyrygswte
     181 ecqeyskdtl grniacwfpr tfilskgrdw lavlvngssk hsairpfdql falhaidqin
     241 pplnvtaeie gtrlsiqwek pvsafpihcf dyevkihntr ngylqieklm tnafisiidd
     301 lskydvqvra avssmcreag lwsewsqpiy vgndehkplr ewfvivimat icfillilsl
     361 ickichlwik lfppipapks nikdlfvttn yevlcifiyi ldsadnflqk kkagssetei
     421 evicyiekpg vetledsvf
```

Fig. 1 (continued)

CD135, XP_011533319.1, SEQ ID NO:234

```
  1 menqdalvci sesvpepive wvlcdsqges ckeespavvk keekvlhelf gtdirccarn
 61 elgrectrlf tidlnqtpqt tlpqlflkvg eplwirckav hvnhgfgltw elenkaleeg
121 nyfemstyst nrtmirilfa fvssvarndt gyytcssskh psqsalvtiv ekgfinatns
181 sedyeidqye efcfsvrfka ypqirctwtf srksfpceqk gldngysisk fcnhkhqpge
241 yifhaendda qftkmftlni rrkpqvlaea sasqascfsd gyplpswtwk kcsdkspnct
301 eeitegvwnr kanrkvfgqw vssstlnmse aikgflvkcc aynslgtsce tillnspgpf
361 pfiqdnisfy atigvcllfi vvltllichk ykkqfryesq lqmvqvtgss dneyfyvdfr
421 eyeydlkwef prenlefgkv lgsgafgkvm nataygiskt gvsiqvavkm lkekadsser
481 ealmselkmm tqlgsheniv nllgactlsg piylifeycc ygdllnylrs krekfhrtwt
541 eifkehnfsf yptfqshpns smpgsrevqi hpdsdqisgl hgnsfhsede ieyenqkrle
601 eeedlnvltf edllcfayqv akgmeflefk scvhrdlaar nvlvthgkvv kicdfglard
661 imsdsnyvvr gnarlpvkwm apeslfegiy tiksdvwsyg illweifslg vnpypgipvd
721 anfykliqng fkmdqpfyat eeiyiimqsc wafdsrkrps fpnltsflgc qladaeeamy
781 qnvdgrvsec phtyqnrrpf sremdlglls pqaqveds
```

CD184, NP_001334985.1, SEQ ID NO:235

```
  1 megisenapl pnvpnapsdk hedgkrpthr rsarlgeevp fvhfltlppn ipqapkglrf
 61 ktafslptts clkprmiyts dnyteemgsg dydsmkepcf reenanfnki flptiysiif
121 ltgivgnglv ilvmgyqkkl rsmtdkyrlh lsvadllfvi tlpfwavdav anwyfgnflc
181 kavhviytvn lyssvlilaf isldrylaiv hatnsqrprk llaekvvyvg vwipalllti
241 pdfifanvse addryicdrf ypndlwvvvf qfqhimvgli lpgivilscy ciiisklshs
301 kghqkrkalk ttvililaff acwlpyyigi sidsfillei ikqgcefent vhkwisitea
361 laffhcclnp ilyaflgakf ktsaqhalts vsrgsslkil skgkrgghss vstesesssf
421 hss
```

CD200, NP_001352780.1, SEQ ID NO:236

```
  1 merlvirmpf shlstyslvw vmaavvlcta qvqvvtqder eqlytpaslk cslqnaqeal
 61 ivtwqkkkav spenmvtfse nhgvviqpay kdkinitqlg lqnstitfwn itledegcym
121 clfntfgfgk isgtacltvy vqpivslhyk fsedhlnitc satarpapmv fwkvprsgie
181 nstvtlshpn gttsvtsilh ikdpknqvgk evicqvlhlg tvtdfkqtvn kgywfsvpll
241 lsivslvill vlisillywk rhrnqdrgel sqgvqkmt
```

CD279, NP_005009.2, SEQ ID NO:237

```
  1 mqipqapwpv vwavlqlgwr pgwfldspdr pwnpptfspa llvvtegdna tftcsfsnts
 61 esfvlnwyrm spsnqtdkla afpedrsqpg qdcrfrvtql pngrdfhmsv vrarrndsgt
121 ylcgaislap kaqikeslra elrvterrae vptahpspsp rpagqfqtlv vgvvggllgs
181 lvllvwvlav icsraargti garrtgqplk edpsavpvfs vdygeldfqw rektpeppvp
241 cvpeqteyat ivfpsgmgts sparrgsadg prsaqplrpe dghcswpl
```

CD273, NP_079515.2, SEQ ID NO:238

```
  1 miflllmlsl elqlhqiaal ftvtvpkely iiehgsnvtl ecnfdtgshv nlgaitaslq
 61 kvendtsphr eratlleeql plgkasfhip qvqvrdegqy qciiiygvaw dykyltlkvk
121 asyrkinthi lkvpetdeve ltcqatgypl aevswpnvsv pantshsrtp eglyqvtsvl
181 rlkpppgrnf scvfwnthvr eltlasidlq sqmeprthpt wllhifipfc iiafifiatv
241 ialrkqlcqk lysskdttkr pvtttkrevn sai
```

CD274, NP_054862.1, SEQ ID NO:239

```
  1 mrifavfifm tywhllnaft vtvpkdlyvv eygsnmtiec kfpvekqldl aalivyweme
 61 dkniiqfvhg eedlkvqhss yrqrarllkd qlslgnaalq itdvklqdag vyrcmisygg
121 adykritvkv napynkinqr ilvvdpvtse heltcqaegy pkaeviwtss dhqvlsgktt
181 ttnskreekl fnvtstlrin tttneifyct frrldpeenh taelvipelp lahppnerth
241 lvilgaillc lgvaltfifr lrkgrmmdvk kcgiqdtnsk kqsdthleet
```

CD362 = syndecan-2 (see SEQ ID NO:193)

Fig. 1 (continued)

EGFR, NP_958441.1, SEQ ID NO:240
1 mrpsgtagaa llallaalcp asraleekkv cqgtsnkltq lgtfedhfls lqrmfnncev
61 vlgnleityv qrnydlsflk tiqevagyvl ialntverip lenlqiirgn myyensyala
121 vlsnydankt glkelpmrnl qeilhgavrf snnpalcnve siqwrdivss dflsnmsmdf
181 qnhlgscqkc dpscpngscw gageencqkl tkiicaqqcs grcrgkspsd cchnqcaagc
241 tgpresdclv crkfrdeatc kdtcpplmly npttyqmdvn pegkysfgat cvkkcprnyv
301 vtdhgscvra cgadsyemee dgvrkckkce gpcrkvcngi gigefkdsls inatnikhfk
361 nctsisgdlh ilpvafrgds fthtppldpq eldilktvke itgflliqaw penrtdlhaf
421 enleiirgrt kqhgqfslav vslnitslgl rslkeisdgd viisgnknlc yantinwkkl
481 fgtsgqktki isnrgensck atgqvchalc spegcwgpep rdcvscrnvs rgrecvdkcn
541 llegeprefv enseciqchp eclpqamnit ctgrgpdnci qcahyidgph cvktcpagvm
601 genntlvwky adaghvchlc hpnctygpgn eslkamlfcl fklsscnqsn dgsvshqsgs
661 paaqesclgw ipsllpsefq lgwggcshlh awpsasviit assch L1CAM, NP_001137435.1, SEQ ID NO:241
1 mvvalryvwp lllcspclli qipeelmepp viteqsprrl vvfptddisl kceasgkpev
61 qfrwtrdgvh fkpkeelgvt vyqsphsgsf titgnnsnfa qrfqgiyrcf asnklgtams
121 heirlmaega pkwpketvkp veveegesvv lpcnpppsae plriywmnsk ilhikqderv
181 tmgqngnlyf anvltsdnhs dyichahfpg trtiiqkepi dlrvkatnsm idrkprllfp
241 tnssshlval qgqplvleci aegfptptik wlrpsgpmpa drvtyqnhnk tlqllkvgee
301 ddgeyrclae nslgsarhay yvtveaapyw lhkpqshlyg pgetarldcq vqgrpqpevt
361 wringipvee lakdqkyriq rgalilsnvq psdtmvtqce arnrhgllla nayiyvvqlp
421 akiltadnqt ymavqgstay llckafgapv psvqwldedg ttvlqderff pyangtlgir
481 dlqandtgry fclaandqnn vtimanlkvk datqitqgpr stiekkgsrv tftcqasfdp
541 slqpsitwrg dgrdlqelgd sdkyfiedgr lvihsldysd qgnyscvast eldvvesraq
601 llvvgspgpv prlvlsdlhl ltqsqvrvsw spaedhnapi ekydiefedk emapekwysl
661 gkvpgnqtst tlklspyvhy tfrvtainky gpgepspvse tvvtpeaape knpvdvkgeg
721 nettnmvitw kplrwmdwna pqvqyrvqwr pqgtrgpwqe qivsdpflvv sntstfvpye
781 ikvqavnsqg kgpepqvtig ysgedypqai pelegieiln ssavlvkwrp vdlaqvkghl
841 rgynvtywre gsqrkhskrh ihkdhvvvpa nttsvilsgl rpyssyhlev qafngrgsgp
901 aseftfstpe gvpghpealh lecqsntsll lrwqpplshn gvltgyvlsy hpldeggkgq
961 lsfnlrdpel rthnltdlsp hlryrfqlqa ttkegpgeai vreggtmals gisdfgnisa
1021 tagenysvvs wvpkegqcnf rfhilfkalg eekggaslsp qyvsynqssy tqwdlqpdtd
1081 yeihlfkerm frhqmavktn gtgrvrlppa gfategwfig fvsaiillll vllilcfikr
1141 skggkysvkd kedtqvdsea rpmkdetfge ysdneekafg ssqpslngdi kplgsddsla
1201 dyggsvdvqf nedgsfigqy sgkkekeaag gndssgatsp inpavale LFA-1, NP_001120963.2, SEQ ID NO:242
1 mlglrpplla lvgllslgcv lsqectkfkv sscreciesg pgctwcqkln ftgpgdpdsi
61 rcdtrpqllm rgcaaddimd ptslaetqed hnggqkqlsp qkvtlylrpg qaaafnvtfr
121 rakgypidly ylmdlsysml ddlrnvkklg gdllralnei tesgrigfgs fvdktvlpfv
181 nthpdklrnp cpnkekecqp pfafrhvlkl tnnsnqfqte vgkqlisgnl dapeggldam
241 mqvaacpeei gwrnvtrllv fatddgfhfa gdgklgailt pndgrchled nlykrsnefd
301 ypsvgqlahk laenniqpif avtsrmvkty eklteiipks avgelsedss nvvhliknay
361 nklssrvfld hnalpdtlkv tydsfcsngv thrnqprgdc dgvqinvpit fqvkvtatec
421 iqeqsfvira lgftdivtvq vlpqcecrcr dqsrdrslch gkgflecgic rcdtgyigkn
481 cecqtqgrss qelegscrkd nnsiicsglg dcvcgqclch tsdvpgkliy gqycecdtin
541 ceryngqvcg gpgrglcfcg kcrchpgfeg sacqcertte gclnprrvec sgrgrcrcnv
601 cechsgyqlp lcqecpgcps pcgkyiscae clkfekgpfg kncsaacpgl qlsnnpvkgr
661 tckerdsegc wvaytleqqd gmdryliyvd esrecvagpn iaaivggtva givligilll
721 viwkalihls dlreyrrfek eklksqwnnd nplfksattt vmnpkfaes

Fig. 1 (continued)

LGALS3BP, NP_005558.1, SEQ ID NO:243
```
  1 mtpprlfwvw llvagtqgvn dgdmrladgg atnqgrveif yrgqwgtvcd nlwdltdasv
 61 vcralgfena tqalgraafg qgsgpimlde vqctgteasl adckslgwlk sncrherdag
121 vvctnetrst htldlsrels ealgqifdsq rgcdlsisvn vqgedalgfc ghtviltanl
181 eaqalwkepg snvtmsvdae cvpmvrdllr yfysrridit lssvkcfhkl asaygarqlq
241 gycaslfail lpqdpsfqmp ldlyayavat gdalleklcl qflawnfeal tqaeawpsvp
301 tdllqlllpr sdlavpsela llkavdtwsw gerasheeve glvekirfpm mlpeelfelq
361 fnlslywshe alfqkktlqa lefhtvpfql larykglnlt edtykpriyt sptwsafvtd
421 sswsarksql vyqsrrgplv kyssdyfqap sdyryypyqs fqtpqhpsfl fqdkrvswsl
481 vylptiqscw nygfscssde lpvlgltksg gsdrtiayen kalmlceglf vadvtdfegw
541 kaaipsaldt nsskstssfp cpaghfngfr tvirpfyltn ssgvd
```

MFGE8, NP_001297248.1, SEQ ID NO:244
```
  1 mprprllaal cgallcapsl lvalecvepl glengnians qiaassvrvt flglqhwvpe
 61 larlnragmv nawtpssndd npwiqvnllr rmwvtgvvtq gasrlashey lkafkvaysl
121 nghefdfihd vnkkhkefvg nwnknavhvn lfetpveaqy vrlyptscht actlrfellg
181 celngcanpl glknnsipdk qitasssykt wglhlfswnp syarldkqgn fnawvagsyg
241 ndqwlqvdlg sskevtgiit qgarnfgsvq fvasykvays ndsanwteyq dprtgsskif
301 pgnwdnhshk knlfetpila ryvrilpvaw hnrialrlel lgc
```

SLIT2, NP_001276064.1, SEQ ID NO:245
```
   1 mrgvgwqmls lslglvlail nkvapqacpa qcscsgstvd chglalrsvp rniprnterl
  61 dlngnnitri tktdfaglrh lrvlqlmenk istiergafq dlkelerlrl nrnhlqlfpe
 121 llflgtakly rldlsenqiq aiprkafrga vdiknlqldy nqisciedga fralrdlevl
 181 tlnnnnitrl svasfnhmpk lrtfrlhsnn lycdchlawl sdwlrqrprv glytqcmgps
 241 hlrghnvaev qkrefvcsde eeghqsfmap scsvlhcpaa ctcsnnivdc rgkglteipt
 301 nlpetiteir leqntikvip pgafspykkl rridlsnnqi selapdafqg lrslnslvly
 361 gnkitelpks lfeglfslql lllnankinc lrvdafqdlh nlnllslydn klqtiakgtf
 421 splraiqtmh laqnpficdc hlkwladylh tnpietsgar ctsprrlank rigqikskkf
 481 rcsgtedyrs klsgdcfadl acpekcrceg ttvdcsnqkl nkipehipqy taelrlnnne
 541 ftvleatgif kklpqlrkin fsnnkitdie egafegasgv neilltsnrl envqhkmfkg
 601 leslktlmlr snritcvgnd sfiglssvrl lslydnqitt vapgafdtlh slstlnllan
 661 pfncncylaw lgewlrkkri vtgnprcqkp yflkeipiqd vaiqdftcdd gnddnscspl
 721 srcptectcl dtvvrcsnkg lkvlpkgipr dvtelyldgn qftlvpkels nykhltlidl
 781 snnristlsn qsfsnmtqll tlilsynrlr cipprtfdgl kslrllslhg ndisvvpega
 841 fndlsalshl aiganplycd cnmqwlsdwv kseykepgia rcagpgemad kllltkppskk
 901 ftcqgpvdvn ilakcnpcls npckndgtcn sdpvdfyrct cpygfkgqdc dvpihacisn
 961 pckhggtchl kegeedgfwc icadgfegen cevnvddced ndcennstcv dginnytclc
1021 ppeytgelce ekldfcaqdl npcqhdskci ltpkgfkcdc tpgyvgehcd idfddcqdnk
1081 ckngahctda vngytcicpe gysglfcefs ppmvlprtsp cdnfdcqnga qcivrinepi
1141 cqclpgyqge kceklvsvnf inkesylqip sakvrpqtni tlqiatdeds gillykgdkd
1201 hiavelyrgr vrasydtgsh pasaiysvet indgnfhive llaldqslsl svdggnpkii
1261 tnlskqstln fdsplyvggm pgksnvaslr qapgqngtsf hgcirnlyin selqdfqkvp
1321 mqtgilpgce pchkkvcahg tcqpssqagf tcecqegwmg plcdqrtndp clgnkcvhgt
1381 clpinafsys ckcleghggv lcdeeedlfn pcqaikckhg kcrlsglgqp ycecssgytg
1441 dscdreiscr gerirdyyqk qqgyaacqtt kkvsrlecrg gcaggqccgp lrskrrkysf
1501 ectdgssfvd evekvvkcgc trcvs
```

STX3, NP_004168.1, SEQ ID NO:246
```
  1 mkdrleqlka kqltqdddtd aveiaidnta fmdeffseie etrlnidkis ehveeakkly
 61 siilsapipe pktkddleql tteikkrann vrnklksmek hieedevrss adlrirksqh
121 svlsrkfvev mtkyneaqvd frerskgriq rqleitgkkt tdeeleemle sgnpaiftsg
181 iidsqiskqa lseiegrhkd ivrlessike lhdmfmdiam lvenqgemld nielnvmhtv
241 dhvekardet kkavkyqsqa rkkliiiivl vvvllgilal iiglsvgln
```

Fig. 1 (continued)

Surface markers of mesenchymal stem cells

CD44, CD45, CD71 (as above)

CD73 (also included in the group of enzymatic TM proteins), NP_001191742.1, SEQ ID NO:247

```
  1 mcpraarapa tlllalgavl wpaagawelt ilhtndvhsr leqtsedssk cvnasrcmgg
 61 varlftkvqq irraepnvll ldagdqyqgt iwftvykgae vahfmnalry damalgnhef
121 dngvegliep llkeakfpil sanikakgpl asqisglylp ykvlpvgdev vgivgytske
181 tpflsnpgtn lvfedeital qpevdklktl nvnkiialgh sgfemdklia qkvrgvdvvv
241 gghsntflyt gnppskevpa gkypfivtsd dgrkvpvvqa yafgkylgyl kiefdergnv
301 isshgnpill nssipedpsi kadinkwrik ldnystqelg ktivyldgss qscrfrecnm
361 gnlicdamin nnlrhtdemf wnhvsmciln gggirspide rnngihvvyd lsrkpgdrvv
421 kldvlctkcr vpsydplkmd evykvilpnf langgdgfqm ikdellrhds gdqdinvvst
481 yiskmkviyp avegrikfst gshchgsfsl iflslwavif vlyq
```

CD90, NP_001298091.1, SEQ ID NO:248

```
  1 mnlaisiall ltvlqvsrgq kvtsltaclv dqslrldcrh entssspiqy efsltretkk
 61 hvlfgtvgvp ehtyrsrtnf tskynmkvly lsaftskdeg tytcalhhsg hsppissqnv
121 tvlrdklvkc egisllaqnt swllllllsl sllqatdfms l
```

CD29 (also included in the group of the integrin family), NP_596867.1, SEQ ID NO:249

```
1 mnlqpifwig lissvccvfa qtdenrclka nakscgeciq agpncgwctn stflqegmpt
 61 sarcddleal kkkgcppddi enprgskdik knknvtnrsk gtaeklkped itqiqpqqlv
121 lrlrsgepqt ftlkfkraed ypidlyylmd lsysmkddle nvkslgtdlm nemrritsdf
181 rigfgsfvek tvmpyisttp aklrnpctse qnctspfsyk nvlsltnkge vfnelvgkqr
241 isgnldspeg gfdaimqvav cgsligwrnv trllvfstda gfhfagdgkl ggivlpndgq
301 chlennmytm shyydypsia hlvqklsenn iqtifavtee fqpvykelkn lipksavgtl
361 sanssnviql iidaynslss evilengkls egvtisyksy ckngvngtge ngrkcsnisi
421 gdevqfeisi tsnkcpkkds dsfkirplgf teevevilqy icececqseg ipespkcheg
481 ngtfecgacr cnegrvgrhc ecstdevnse dmdaycrken sseicsnnge cvcgqcvcrk
541 rdntneiysg kfcecdnfnc drsnglicgg ngvckcrvce cnpnytgsac dcsldtstce
601 asngqicngr gicecgvckc tdpkfqgqtc emcqtclgvc aehkecvqcr afnkgekkdt
661 ctqecsyfni tkvesrdklp qpvqpdpvsh ckekdvddcw fyftysvngn nevmvhvven
721 pecptgpdii pivagvvagi vliglallli wkllmiihdr refakfekek mnakwdtgen
781 piyksavttv vnpkyegk
```

CD105, NP_001265067.1, SEQ ID NO:250

```
1 mleasqdmgr tlewrprtpa lvrgchlegv aghkeahilr vlpghsagpr tvtvkvelsc
 61 apgdldavli lqgppyvswl idanhnmqiw ttgeysfkif peknirgfkl pdtpqgllge
121 armlnasiva sfvelplasi vslhasscgg rlqtspapiq ttppkdtcsp ellmsliqtk
181 caddamtlvl kkelvahlkc titgltfwdp sceaedrgdk fvlrsayssc gmqvsasmis
241 neavvnilss sspqrkkvhc lnmdslsfql glylsphflq asntiepgqq sfvqvrvsps
301 vsefllqlds chldlgpegg tveliqgraa kgncvsllsp spegdprfsf llhfytvpip
361 ktgtlsctva lrpktgsqdq evhrtvfmrl niispdlsgc tskglvlpav lgitfgafli
421 galltaalwy iyshtrspsk repvvavaap assessstnh sigstqstpc stssma
```

Fig. 1 (continued)

CD106 (also included in the group of the sialoglycoproteins), NP_001069.1, SEQ ID NO:251

```
  1 mpgkmvvilg asnilwimfa asqafkiett pesrylaqig dsvsltcstt gcespffswr
 61 tqidsplngk vtnegttstl tmnpvsfgne hsylctatce srklekgiqv eiysfpkdpe
121 ihlsgpleag kpitvkcsva dvypfdrlei dllkgdhlmk sqefledadr ksletkslev
181 tftpviedig kvlvcraklh idemdsvptv rqavkelqvy ispkntvisv npstklqegg
241 svtmtcsseg lpapeifwsk kldngnlqhl sgnatltlia mrmedsgiyv cegvnligkn
301 rkevelivqe kpftveispg priaaqigds vmltcsvmgc espsfswrtq idsplsgkvr
361 segtnstltl spvsfenehs ylctvtcghk klekgiqvel ysfprdpeie msgglvngss
421 vtvsckvpsv ypldrleiel lkgetileni efledtdmks lenkslemtf iptiedtgka
481 lvcqaklhid dmefepkqrq stqtlyvnva prdttvlvsp ssileegssv nmtclsqgfp
541 apkilwsrql pngelqplse natltlistk medsgvylce ginqagrsrk eveliiqvtp
601 kdikltafps esvkegdtvi isctcgnvpe twiilkkkae tgdtvlksid gaytirkaql
661 kdagvyeces knkvgsqlrs ltldvqgren nkdyfspell vlyfasslii paigmiiyfa
721 rkanmkgsys lveaqkskv
```

CD146, NP_006491.2, SEQ ID NO:252

```
  1 mglprlvcaf llaaccccpr vagvpgeaeq papelvevev gstallkcgl sqsqgnlshv
 61 dwfsvhkekr tlifrvrqgq gqsepgeyeq rlslqdrgat laltqvtpqd eriflcqgkr
121 prsqeyriql rvykapeepn iqvnplgipv nskepeevat cvgrngypip qviwykngrp
181 lkeeknrvhi qssqtvessg lytlqsilka qlvkedkdaq fycelnyrlp sgnhmkesre
241 vtvpvfypte kvwlevepvg mlkegdrvei rcladgnppp hfsiskqnps treaeeettn
301 dngvlvlepa rkehsgryec qgldldtmis llsepqellv nyvsdvrvsp aaperqegss
361 ltltceaess qdlefqwlre etgqvlergp vlqlhdlkre agggyrcvas vpsipglnrt
421 qlvnvaifgp pwmafkerkv wvkenmvlnl sceasghprp tiswnvngta seqdqdpqrv
481 lstlnvlvtp elletgvect asndlgknts ilflelvnlt tltpdsnttt glststasph
541 transtster klpepesrgv vivavivcil vlavlgavly flykkgklpc rrsgkqeitl
601 ppsrkselvv evksdklpee mgllqgssgd krapgdqgek yidlrh
```

CD164, NP_001135874.1, SEQ ID NO:253

```
  1 msrlsrsllw aatclgvlcv lsadknttqh pnvttlapis nvtsapvtsl plvttpapet
 61 cegrnscvsc fnvsvvnttc fwieckdesy cshnstvsdc qvgnttdfcs vstatpvpta
121 nstgttnntv tptsqpvrks tfdaasfigg ivlvlgvqav ifflykfcks kernyhtl
```

CD166, NP_001618.2, SEQ ID NO:254

```
  1 meskgasscr llfcllisat vfrpglgwyt vnsaygdtii ipcrldvpqn lmfgkwkyek
 61 pdgspvfiaf rsstkksvqy ddvpeykdrl nlsenytlsi snarisdekr fvcmlvtedn
121 vfeaptivkv fkqpskpeiv skalfleteq lkklgdcise dsypdgnitw yrngkvlhpl
181 egavviifkk emdpvtqlyt mtstleyktt kadiqmpftc svtyygpsgq ktihseqavf
241 diyypteqvt iqvlppknai kegdnitlkc lgngnpppee flfylpgqpe girssntytl
301 tdvrrnatgd ykcslidkks miastaitvh yldlslnpsg evtrqigdal pvsctisasr
361 natvvwmkdn irlrsspsfs slhyqdagny vcetalqeve glkkresltl ivegkpqikm
421 tkktdpsgls ktiichvegf pkpaiqwtit gsgsvinqte espyingryy skiiispeen
481 vtltctaenq lertvnslnv saisipehde adeisdenre kvndqakliv givvglllaa
541 lvagvvywly mkksktaskh vnkdlgnmee nkkleennhk tea
```

STRO-1, NP_004958.2, SEQ ID NO:255

```
  1 mktalillsi lgmacafsmk nlhrrvkied seengvfkyr pryylykhay fyphlkrfpv
 61 qgssdsseen gddsseeeee eeetsnegen neesnededs eaenttlsat tlgygedatp
121 gtgytglaai qlpkkagdit nkatkekesd eeeeeeeegn eneeseaevd eneqgingts
181 tnsteaengn gssggdngee geeesvtgan aedttetgrq gkgtskttts pnggfepttp
241 pqvyrttspp fgktttveye geyeytgane ydngyeiyes engeprgdny rayedeysyf
301 kgqgydgydg qnyyhhq
```

Fig. 1 (continued)

Glycoproteins

CD54, NP_000192.2, SEQ ID NO:256

```
mapssprpal pallvllgal fpgpgnaqts vspskvilpr ggsvlvtcst scdqpkllgi
       61 etplpkkell lpgnnrkvye lsnvqedsqp mcysncpdgq staktfltvy wtpervelap
      121 lpswqpvgkn ltlrcqvegg apranltvvl lrgekelkre pavgepaevt ttvlvrrdhh
      181 ganfscrtel dlrpqglelf entsapyqlq tfvlpatppq lvsprvlevd tqgtvvcsld
      241 glfpvseaqv hlalgdqrln ptvtygndsf sakasvsvta edegtqrltc avilgnqsqe
      301 tlqtvtiysf papnviltkp evsegtevtv kceahprakv tlngvpaqpl gpraqlllka
      361 tpedngrsfs csatlevagq lihknqtrel rvlygprlde rdcpgnwtwp ensqqtpmcq
      421 awgnplpelk clkdgtfplp igesvtvtrd legtylcrar stqgevtrkv tvnvlsprye
      481 iviitvvaaa vimgtaglst ylynrqrkik kyrlqqaqkg tpmkpntqat pp
```

Sialoglycoprotein CD235a, NP_001295116, SEQ ID NO:257

```
mygkiifvll lseivsisal sttevamhts tsssvtksyi ssqtndthkr dtyaatprah
       61 evseisvrtv yppeeeteit liifgvmagv igtillisyg irrlikksps dvkplpspdt
      121 dvplssveie npetsdq
```

Channelling proteins, including Ca-channel proteins

GLUR2, NP_000817.3, SEQ ID NO:258

```
    1 mqkimhisvl lspvlwglif gvssnsiqig glfprgadqe ysafrvgmvq fstsefrltp
       61 hidnlevans favtnafcsq fsrgvyaifg fydkksvnti tsfcgtlhvs fitpsfptdg
      121 thpfviqmrp dlkgallsli eyyqwdkfay lydsdrglst lqavldsaae kkwqvtainv
      181 gninndkkde myrslfqdle lkkerrvild cerdkvndiv dqvitigkhv kgyhyiianl
      241 gftdgdllki qfgganvsgf qivdyddslv skfierwstl eekeypgaht ttikytsalt
      301 ydavqvmtea frnlrkqrie isrrgnagdc lanpavpwgq gveieralkq vqveglsgni
      361 kfdqngkrin ytinimelkt ngprkigyws evdkmvvtlt elpsgndtsg lenktvvvtt
      421 ilespyvmmk knhemlegne ryegycvdla aeiakhcgfk ykltivgdgk ygardadtki
      481 wngmvgelvy gkadiaiapl titlvreevi dfskpfmslg isimikkpqk skpgvfsfld
      541 playeiwmci vfayigvsvv lflvsrfspy ewhteefedg retqssestn efgifnslwf
      601 slgafmqqgc disprslsgr ivggvwwfft liiissytan laafltverm vspiesaedl
      661 skqteiaygt ldsgstkeff rrskiavfdk mwtymrsaep svfvrttaeg varvrkskgk
      721 yayllestmn eyieqrkpcd tmkvggnlds kgygiatpkg sslrtpvnla vlklseqgvl
      781 dklknkwwyd kgecgakdsg skektsalsl snvagvfyil vgglglamlv aliefcyksr
      841 aeakrmkvak naqninpsss qnsqnfatyk egynvygies vki
```

GLUR3, NP_000819.3, SEQ ID NO:259

```
1 marqkkmgqs vlravfflvl gllghshggf pntisigglf mrntvqehsa frfavqlynt
       61 nqnttekpfh lnyhvdhlds snsfsvtnaf csqfsrgvya ifgfydqmsm ntltsfcgal
      121 htsfvtpsfp tdadvqfviq mrpalkgail sllghykwek fvylydterg fsilqaimea
      181 avqnnwqvta rsvgnikdvq efrriieemd rrqekrylid ceverintil eqvvilgkhs
      241 rgyhymlanl gftdillerv mhgganitgf qivnnenpmv qqfiqrwvrl derefpeakn
      301 aplkytsalt hdailviaea frylrrqrvd vsrrgsagdc lanpavpwsq gidieralkm
      361 vqvqgmtgni qfdtygrrtn ytidvyemkv sgsrkagywn eyerfvpfsd qqisndsass
      421 enrtivvtti lespyvmykk nheqlegner yegycvdlay eiakhvriky klsivgdgky
      481 gardpetkiw ngmvgelvyg radiavaplt itlvreevid fskpfmslgi simikkpqks
      541 kpgvfsfldp layeiwmciv fayigvsvvl flvsrfspye whlednneep rdpqsppdpp
      601 nefgifnslw fslgafmqqg cdisprslsg rivggvwwff tliiissyta nlaafltver
      661 mvspiesaed lakqteiayg tldsgstkef frrskiavye kmwsymksae psvftkttad
      721 gvarvrkskg kfafllestm neyieqrkpc dtmkvggnld skgygvatpk gsalgnavnl
      781 avlklneqgl ldklknkwwy dkgecgsggg dskdktsals lsnvagvfyi lvgglglamm
      841 valiefcyks raeskrmklt kntqnfkpap atntqnyaty regynvygte svki
```

Fig. 1 (continued)

HLA-DM, NP_006111.2, SEQ ID NO:260

```
1 mgheqnqgaa llqmlpllwl lphswavpea ptpmwpddlq nhtflhtvyc qdgspsvgls
       61 eaydedqlff fdfsqntrvp rlpefadwaq eqgdapailf dkefcewmiq qigpkldgki
      121 pvsrgfpiae vftlkplefg kpntlvcfvs nlfppmltvn wqhhsvpveg fgptfvsavd
      181 glsfqafsyl nftpepsdif scivtheidr ytaiaywvpr nalpsdllen vlcgvafglg
      241 vlgiivgivl iiyfrkpcsg d
```

Miscellaneous:

FLOT2, NP_004466, SEQ ID NO:261

```
mgnchtvgpn ealvvsggcc gsdykqyvfg gwawawwcis dtqrisleim tlqprcedve
       61 taegvaltvt gvaqvkimte kellavaceq flgknvqdik nvvlqtlegh lrsilgtltv
      121 eqiyqdrdqf aklvrevaap dvgrmgieil sftikdvydk vdylsslgkt qtavvqrdad
      181 igvaeaerda gireaeckke mldvkfmadt kiadskrafe lqksafseev niktaeaqla
      241 yelqgareqq kirqeeieie vvqrkkqiav eaqeilrtdk eliatvrrpa eaeahriqqi
      301 aegekvkqvl laqaeaekir kigeaeaavi eamgkaeaer mklkaeayqk ygdaakmalv
      361 lealpqiaak iaapltkvde ivvlsgdnsk vtsevnrlla elpasvhalt gvdlskipli
      421 kkatgvqv
```

A

Figure 5:
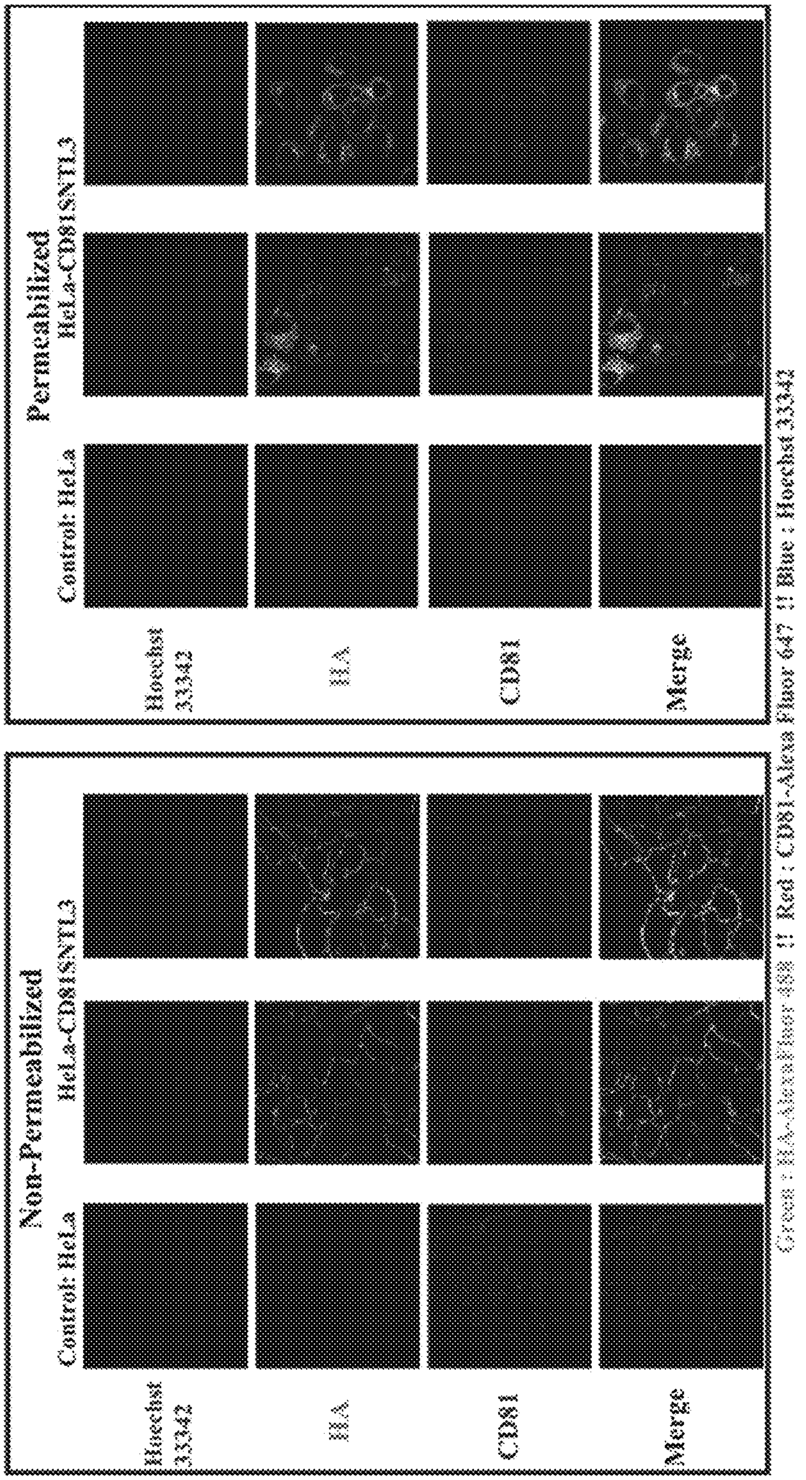

Fig. 5 (continued)
B
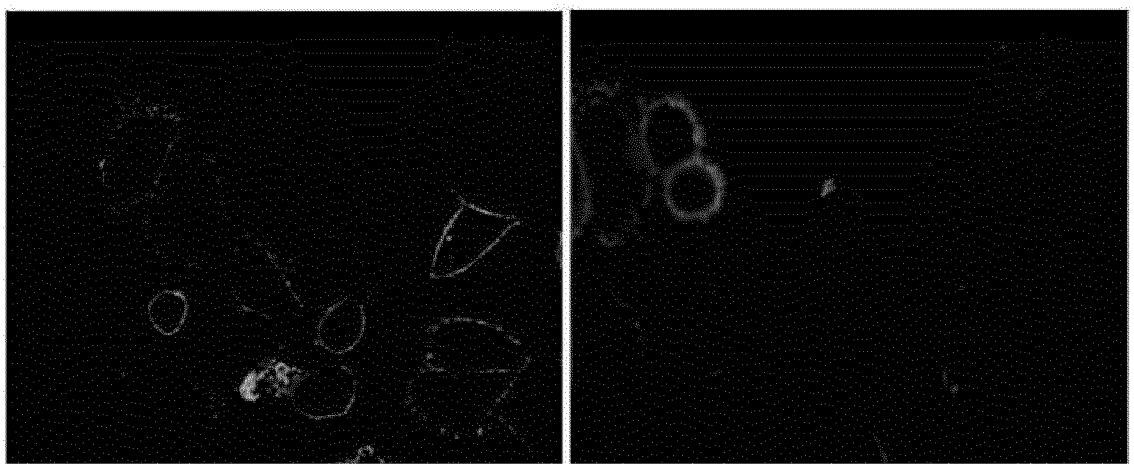
C
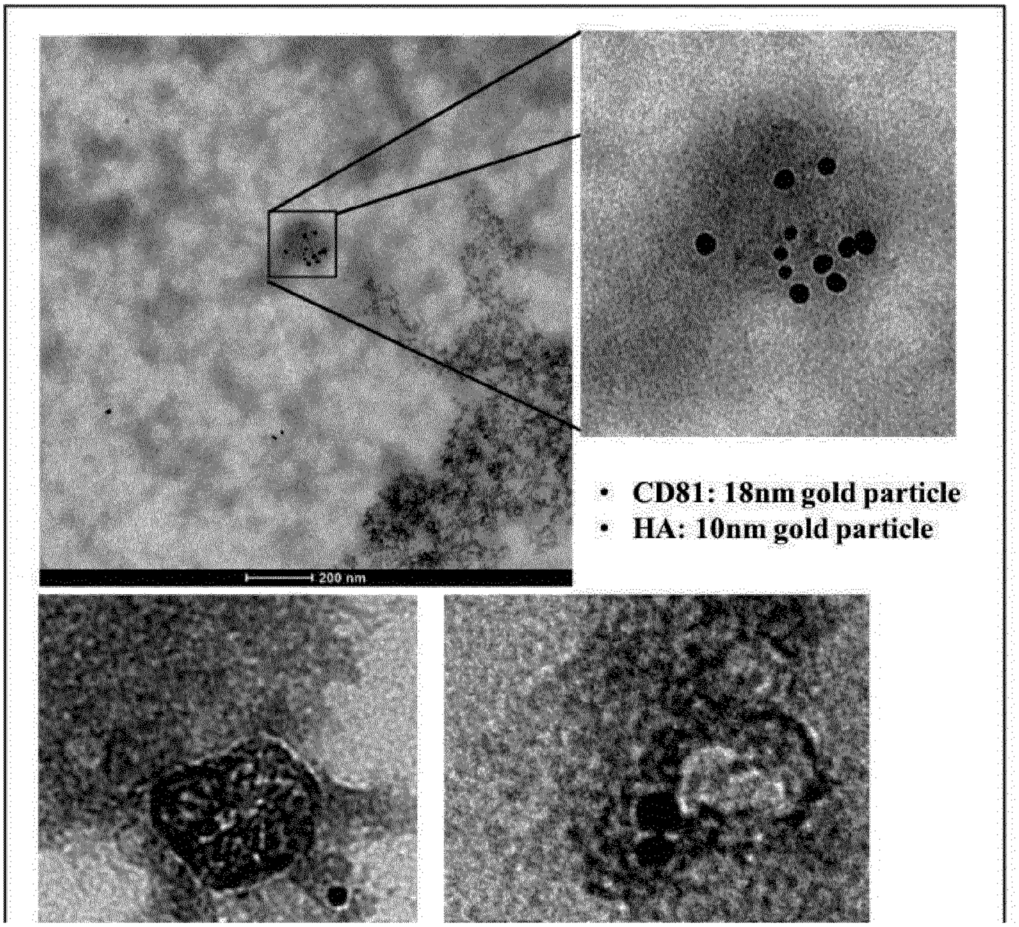

H: HeLa
SNTL: CD81 SNTL3
ON: overnight digestion
FT: Flow through

| EV isolation batch #1 | Number of total particles (x10^11 per mL) | Number of fluorescent (recombinant) particles (x10^11 per mL) | Percentage of recombinant particles (in %) |
|---|---|---|---|
| EVs from CD81-wt-eGFP | 8.3 | 2 | 24.1 |
| EVs from CD81-CP4-eGFP | 11.3 | 3.5 | 31.0 |
| EVs from CD81-Tfr1-eGFP | 9.9 | 4.7 | 47.5 |
| EVs from CD81-Tfr2-eGFP | 10.5 | 4.9 | 46.7 |
| EVs from CD81-Tfr2CP4-eGFP | 9.6 | 4.5 | 47.4 |

Figure 7:
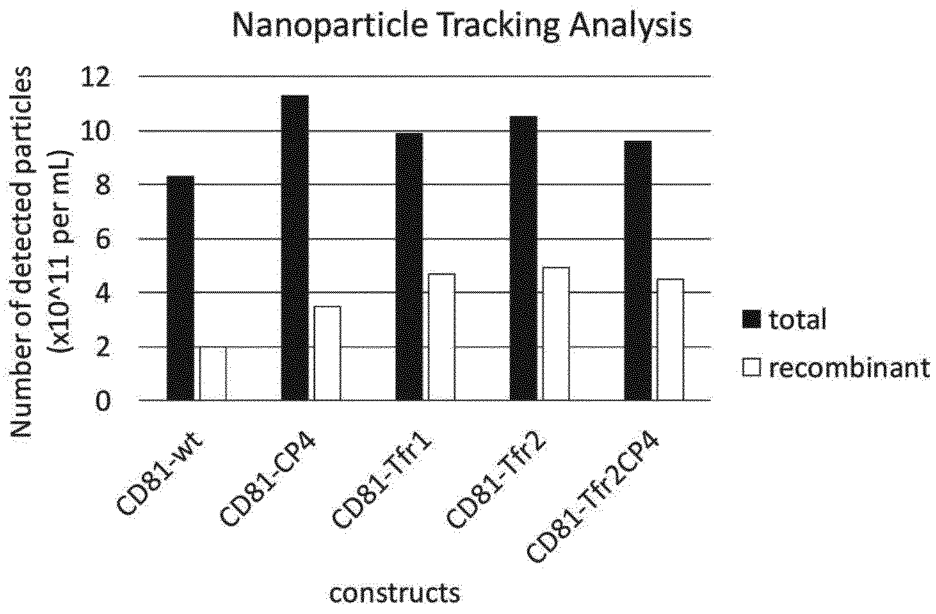

Fig. 7 continued
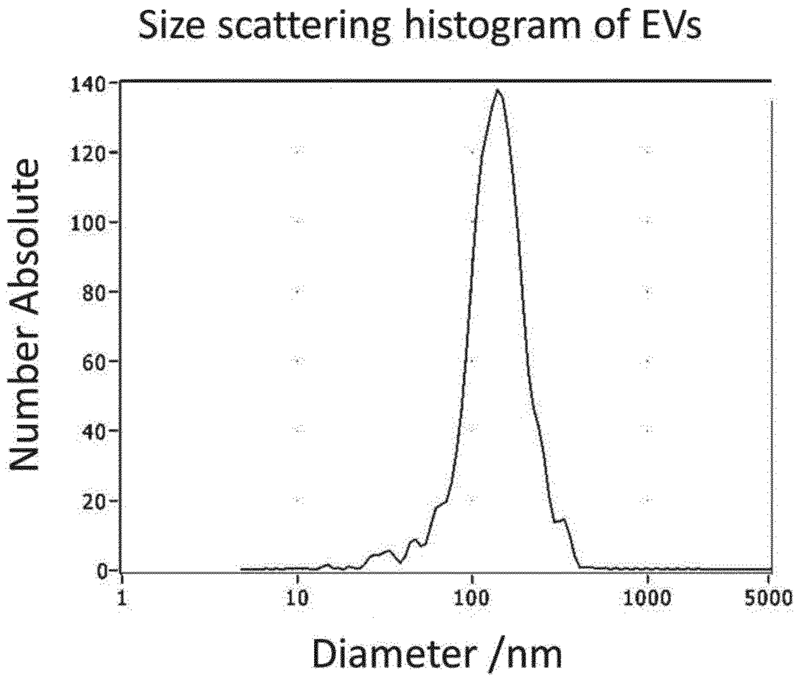
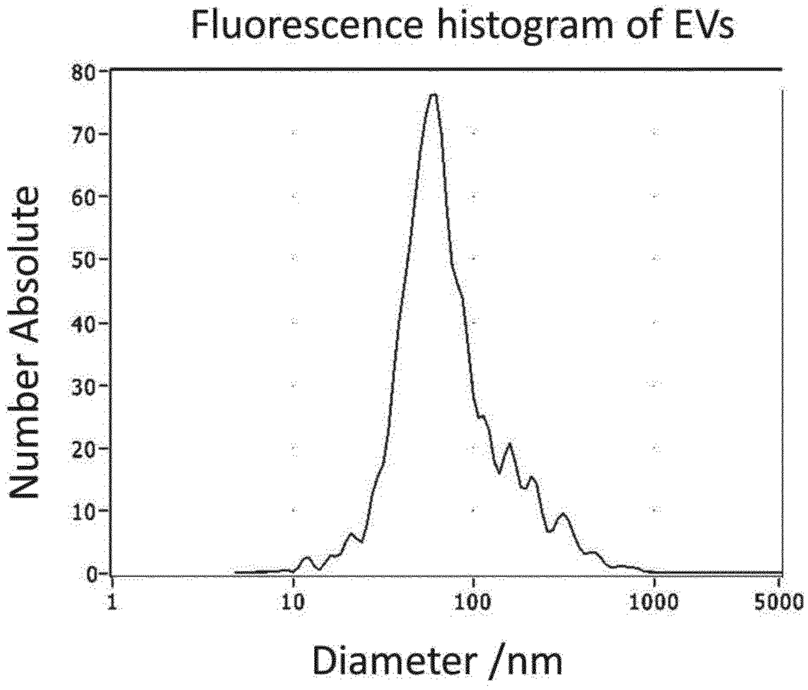

A

B

TARGET-SPECIFIC EXTRACELLULAR VESICLES

CROSS-REFERENCE TO RELATED APPLICATIONS

This application is the U.S. national stage of International Patent Application No. PCT/EP2019/071825, filed on Aug. 14, 2019 and entitled TARGET-SPECIFIC EXTRACELLULAR VESICLES, which claims the benefit of priority under § 35 U.S.C. § 119 from European Patent Application No. 18189014.6, filed Aug. 14, 2018. The disclosures of the foregoing applications are incorporated herein by reference in their entirety.

SEQUENCE LISTING

The entire content of a Sequence Listing titled "Sequence_ Listing.txt," created on Jan. 26, 2021 and having a size of 569 kilobytes, which has been submitted in electronic form in connection with the present application, is hereby incorporated by reference herein in its entirety.

FIELD OF THE INVENTION

The invention relates to the field of engineering target-specific extracellular vesicles. The invention further relates to methods of production of said target-specific extracellular vesicles.

BACKGROUND OF THE INVENTION

In the last decade, the research into exosomes has intensified as they have been recognized as significant mediators of cell-to-cell communication [1]. Exosomes are released from multivesicular bodies upon their fusion with the plasma membrane, and released vesicles function as delivery vehicles transferring functional RNAs, exosomal DNA and transmembrane proteins including receptors to cells in the surrounding environment [2]. Regarding their advantages as a potential therapeutic moiety, including favorable properties such as low immunogenicity and low cytotoxicity, the interest in their application has triggered further development, such as new methods for encapsulation, improved cytosolic release of exosomal contents, enhanced cellular uptake and more specific cellular targeting [3].

Vesicular uptake of exosomes is cell type-specific and can involve membrane fusion or endocytosis, and can even be induced by stimulation of oncogenic cancer receptors [4]. To achieve tissue specific delivery, targeting of exosomes can be optimized by engineering the source cells to overexpress exosomal membrane proteins, such as tetraspanins, harboring receptor-specific ligand peptides as recognition units [5]. Tetraspanins are known as molecular facilitators, associating in large cell-signaling complexes known as the tetraspan web, which also involves members of other protein families, such as integrins and coreceptor molecules. Furthermore, such large membrane protein assemblies may be associated with lipid rafts [6-7]. The function of tetraspanins CD9, CD63 and CD81 ligands for endocytosis of exosomes has been reported [8-10], however the mechanism of uptake has not yet been clarified.

In spite of its almost ubiquitous distribution, the tetraspan protein CD81 is the major protein enriched in the exosomal fraction of multivesicular bodies [11]. The large extracellular loop (LEL) of CD81, topologically located between transmembrane domains 3 and 4, is characterized by five helical elements forming a mushroom-like structure [12-13], stabilized by two pairs of cysteines. This motif is conserved among the protein members of tetraspanin family [14] and the oxidation of cysteine bonds is a prerequisite for high-affinity binding of the E2 envelope protein of hepatitis C virus (HCV), the natural ligand of CD81 [15]. Correct pairing of the cysteines is described for the recognition by the antibody M38 [16], which does not bind to denatured or reduced proteins, but can react with the membrane-bound hCD81 as well as a native form of purified soluble hCD81.

The crystal structure of hCD81 LEL, solved at 1.6 Å, revealed a new type of protein fold [12], and a subsequent sequence analysis of 160 tetraspanin family members indicated that their fold and key structural features are conserved [17]. Apart from cysteine bridges, the hCD81 LEL is stabilized by the invariant residues Gly157 and Pro176, which are located to accommodate cysteine connections, as well as Tyr127, which is fully buried and contributes to the hydrogen bonding network together with His151 and Cys190. Soluble hCD81 LEL assembles into dimers around a 2-fold axis, and the contact between the protomers is a low-polarity region between helices of each interacting partner and between helix B and C-terminal residues of the opposite protomer. The N- and C-termini of the protomers fall in the central region on opposite faces of the assembled dimer, similar to the dimeric assembly at the cell surface, where transmembrane segments are also present. A second low-polarity region comprises the solvent-exposed surface of helices C and D, which is energetically unfavorable. According to the solution studies, helix D is fairly unstructured and attains helical conformation only upon binding with certain antigens [18]. The sequence alignments of the tetraspanin family members indeed show an increased variability in this region, including insertions and deletions [19]. It has been suggested that this surface area might be involved in a species- or tetraspanin-specific recognition process, [20] which could hint to the possibility of heterodimeric tetraspanin species assembly [21]. In particular, segment D of CD81 should be able to guide specific homomeric clustering [22].

WO2014/168548 discloses a therapeutic delivery vesicle, which can for example be an exosome or microvesicle, which has attached to its membrane a polypeptide construct comprising a carrier polypeptide fused to a decoy receptor which is signaling-incompetent.

WO2016/073864 discloses a B cell targeting agent comprising a CD19 or CD21 targeting antibody coupled to a nanoparticle, lipid-based carrier molecule or extracellular vesicle.

WO2018/075825 discloses bioengineered exosomes comprising a fusion protein which comprises a segment of an exosome protein fused to a cancer stem cell targeting peptide.

WO2018/015535A1 discloses EVs coated with proteins containing Fc binding domains. Exemplary EVs carry fusion constructs comprising exosomal proteins fused to Fc binders such as Protein A/G, the Z domain or ZZ domain of Protein A.

US2018/0015182A1 discloses exosomes delivering bioactive cargo by engineering tetraspanins comprising fusions to proteins, or including a terminal or loop peptide attachment site to attach proteins to the exosomes.

El Andaloussi et al. (Advanced Drug Delivery Reviews 2013, 65:391-397) describe exosomes for targeted siRNA delivery. Exemplary targeting exosomes comprise a Lamp2b-brain specific peptide (RVG, a 29-mer peptide) fusion protein.

Drummer et al. (Journal of Virology 2002, 76(21):11143-11147) describe a binding site on the LEL of CD81 binding to hepatitis C virus E2 glycoprotein.

To enhance their potential as the next-generation therapeutic carriers, exosome-mediated delivery systems need to be further developed, especially to improve their inherently low efficiency of cellular uptake. There is a specific need for exosome-mediated delivery systems comprising exosomal membrane proteins with increased stability and improved target-specificity.

SUMMARY OF THE INVENTION

It is the objective of the present invention, to provide target-specific extracellular vesicles with improved target binding characteristics. It is a further objective to provide target-specific EV surface proteins and binding domains thereof with improved target binding characteristics.

The problem is solved by the present invention.

According to the invention, there is provided a method of producing a protein comprising a target-specific extravesicular domain (TED) of an extracellular vesicle (EV) surface protein comprising modifying a polynucleotide comprising a nucleotide sequence encoding the extravesicular domain (ED) of an EV surface protein by a mutagenesis method within at least one modified region within the ED amino acid sequence with a length of 3-20 contiguous amino acids flanked by regions of the wild-type ED sequence at its N-terminus and C-terminus, to incorporate a target binding site within the ED, thereby producing a repertoire of polynucleotides encoding a variety of TEDs, each comprising a different target binding site, and selecting a TED specifically recognizing a predetermined target, and producing the protein comprising the selected TED.

It is specifically understood that all features of the proteins, in particular the target binding molecules (“binders”, “target-specific molecules”) described herein are features characterizing the method of the invention, and vice versa.

Specifically, the protein comprising the TED may consist of the TED, or a protein comprising the TED any one or more further regions e.g., another ED and/or a transmembrane domain, or a recombinant fusion protein in particular comprising a heterologous sequence.

Specifically, the repertoire of polynucleotides is comprised in genetic packages displaying the variety of TEDs on the outer surface, preferably employing a display system selected from the group consisting of a yeast, phage, bacterium, ribosome, mRNA or mammalian cell display.

Specifically, the modified region has a lower target binding affinity when isolated from the TED.

Specifically, the target binding site comprises at least one further binding region which is within a further modified region distant at least 2 amino acids, or within the wild-type ED sequence. Said at least one further binding region is preferably of the same ED and/or positioned within the same TED at a certain distance further described herein.

Specifically, the TED comprises at least 70% sequence identity to the wild-type ED.

Specifically, the wild-type ED originates from (or is of) an EV surface protein selected from the group consisting of tetraspan-like proteins, proteins of the integrin family, proteoglycans, five-transmembrane domains proteins, type I transmembrane proteins, Notch family proteins, enzymatic membrane proteins, immune regulatory surface proteins, surface markers of mesenchymal stem cells, glycoproteins, or channeling proteins.

Specifically, the tetraspan-like protein is a tetraspanin, preferably selected from the group consisting of:

a) CD81 comprising or consisting of the amino acid sequence identified as SEQ ID NO:87;
b) CD9 comprising or consisting of the amino acid sequence identified as SEQ ID NO:89;
c) CD53 comprising or consisting of the amino acid sequence identified as SEQ ID NO:90;
d) TSPAN32 comprising or consisting of the amino acid sequence identified as SEQ ID NO:91;
e) CD82 comprising or consisting of the amino acid sequence identified as SEQ ID NO:92,
f) CD63 comprising or consisting of the amino acid sequence identified as SEQ ID NO:93;
g) CD151 comprising or consisting of the amino acid sequence identified as SEQ ID NO:94; and
h) CD37 comprising or consisting of the amino acid sequence identified as SEQ ID NO:95 or wherein the tetraspan-like protein is a lysosome-associated membrane protein, preferably LAMP2 comprising or consisting of the amino acid sequence identified as SEQ ID NO:96.

Specifically, the wild-type ED is of any one of:

a) CD81, wherein the ED comprises or consists of any one of the amino acid sequences identified as SEQ ID NO:130 or SEQ ID NO:131;
b) CD9, wherein the ED comprises or consists of any one of the amino acid sequences identified as SEQ ID NO:132, SEQ ID NO:182 or SEQ ID NO:133;
c) CD53, wherein the ED comprises or consists of any one of the amino acid sequences identified as SEQ ID NO:134 or SEQ ID NO:135;
d) TSPAN32, wherein the ED comprises or consists of any one of the amino acid sequences identified as SEQ ID NO:136 or SEQ ID NO:137;
e) CD82, wherein the ED comprises or consists of any one of the amino acid sequences identified as SEQ ID NO:138 or SEQ ID NO:139;
f) CD63, wherein the ED comprises or consists of any one of the amino acid sequences identified as SEQ ID NO:140 or SEQ ID NO:141;
g) CD151, wherein the ED comprises or consists of any one of the amino acid sequences identified as SEQ ID NO:142 or SEQ ID NO:143;
h) CD37, wherein the ED comprises or consists of any one of the amino acid sequences identified as SEQ ID NO:144 or SEQ ID NO:145;

or i) LAMP2, wherein the ED comprises or consists of the amino acid sequence identified as SEQ ID NO:146:

Specifically, the protein comprises a loop structure in the ED amino acid sequence which is stabilized by one or more cysteine(s) at position(s) to allow the formation of one or more disulfide bonds.

Specifically, the modified region is positioned within a loop region of the ED.

Specifically, the ED is a) of CD81 and the amino acid sequence is modified to introduce cysteines to allow formation of one or more disulfide bonds not naturally-occurring in the wild-type ED sequence, preferably between positions 134 and 144 and/or 130 and 146 and/or 135 and 168, wherein numbering is of human CD81 identified as SEQ ID NO:87, or
b) of CD9 and the amino acid sequence is modified to introduce cysteines to allow formation of one or more disulfide bonds not naturally-occurring in the wild-type ED sequence, preferably between positions 20 and 28, wherein numbering of the positions is of the CD9 large extracellular loop (LEL, SEQ ID NO:118).

Specifically, the ED is of CD81, and the modified region is positioned within positions 160 and 172, wherein numbering is of human CD81 identified as SEQ ID NO:87.

Specifically, the TED comprises at least one further binding region positioned between positions 132 and 141, or between positions 180 and 189, wherein numbering is of human CD81 identified as SEQ ID NO:87.

Specifically, the ED is of CD9 and the modified region is positioned within any one of positions 155-166, positions 128-142, positions 130-140, or positions 169-180, wherein numbering is of human CD9 identified as SEQ ID NO:89.

Specifically, the target is selected from the group consisting of cellular targets, preferably mitogenic receptors, cytokine receptors, asyaloglycoprotein receptors, membrane transporters, lipoproteins, liposaccharides, glycoproteins, proteoglycans, or acellular targets, preferably cytokines, artificial proteins or artificial surface structures.

Specifically, the protein comprising the TED is a target-specific EV surface protein (TSP) comprising said TED and at least one transmembrane domain.

Specifically, the transmembrane domain comprises at least 70% sequence identity to a transmembrane domain originating from a mammalian EV surface protein.

Specifically, the transmembrane domain is of any one of:

a) CD81, wherein the transmembrane domain comprises or consists of any one of the amino acid sequences identified as SEQ ID NO:147, SEQ ID NO:148, SEQ ID NO:149 or SEQ ID NO:150;

b) CD9, wherein the transmembrane domain comprises or consists of any one of the amino acid sequences identified as SEQ ID NO:151, SEQ ID NO:152, SEQ ID NO:153 or SEQ ID NO:154;

c) CD53, wherein the transmembrane domain comprises or consists of any one of the amino acid sequences identified as SEQ ID NO:155, SEQ ID NO:156, SEQ ID NO:157 or SEQ ID NO:158;

d) TSPAN32, wherein the transmembrane domain comprises or consists of any one of the amino acid sequences identified as SEQ ID NO:159, SEQ ID NO:160, SEQ ID NO:161 or SEQ ID NO:162;

e) CD82, wherein the transmembrane domain comprises or consists of any one of the amino acid sequences identified as SEQ ID NO:163, SEQ ID NO:164, SEQ ID NO:165 or SEQ ID NO:166;

f) CD63, wherein the transmembrane domain comprises or consists of any one of the amino acid sequences identified as SEQ ID NO:167, SEQ ID NO:168, SEQ ID NO:169 or SEQ ID NO:170;

g) CD151, wherein the transmembrane domain comprises or consists of any one of the amino acid sequences identified as SEQ ID NO:171, SEQ ID NO:172, SEQ ID NO:173 or SEQ ID NO:174;

h) CD37, wherein the transmembrane domain comprises or consists of any one of the amino acid sequences identified as SEQ ID NO:175, SEQ ID NO:176, SEQ ID NO:177 or SEQ ID NO:178;

or i) LAMP2, wherein the transmembrane domain comprises or consists of the amino acid sequence identified as SEQ ID NO:179.

Specifically, both, the ED and the transmembrane domain, originate from (or are of) the same EV surface protein, preferably wherein the EV surface protein is selected from the group consisting of:

a) CD81 comprising or consisting of the amino acid sequence identified as SEQ ID NO:87;

b) CD9 comprising or consisting of the amino acid sequence identified as SEQ ID NO:89;

c) CD53 comprising or consisting of the amino acid sequence identified as SEQ ID NO:90;

d) TSPAN32 comprising or consisting of the amino acid sequence identified as SEQ ID NO:91;

e) CD82 comprising or consisting of the amino acid sequence identified as SEQ ID NO:92, f) CD63 comprising or consisting of the amino acid sequence identified as SEQ ID NO:93;

g) CD151 comprising or consisting of the amino acid sequence identified as SEQ ID NO:94;

h) CD37 comprising or consisting of the amino acid sequence identified as SEQ ID NO:95; and i) LAMP2 comprising or consisting of the amino acid sequence identified as SEQ ID NO:96.

The invention further provides for a method of producing a target-specific extracellular vesicle (TEV) preparation by a) providing a polynucleotide encoding a protein comprising the TED obtainable by a method described herein;

b) introducing said polynucleotide into a source cell or source cell mixture;

b) culturing said cell(s) under conditions producing extracellular vesicles;

c) isolating a fraction comprising a TEV comprising the target binding site of the TED; and d) producing a preparation of the TEV comprised in said fraction.

Specifically, the protein comprising the TED is a target-specific EV surface protein (TSP) comprising said TED and at least one transmembrane domain, and the TEV is displaying the target binding site on the outer surface of its membrane.

Specifically, the method described herein further comprises loading the TEV with an intravesicular load, wherein the load comprises any one or more of peptides, polypeptides, protein domains, proteins, lipids, genes, nucleic acids such as mRNAs, miRNAs, RNAi mediating molecules in particular locked nucleic acids or phosphorothioates, DNA, DNA fragments, plasmids such as minicircle DNA, drugs such as small molecules, in particular chemotherapeutics or senolytics.

Specifically, the source cell or source cell mixture is originating from (or is of) a eukaryotic or prokaryotic source, preferably of body tissue, body fluid, or a cell culture.

Specifically, the source cell or source cell mixture is obtained from a subject and the TEV preparation is formulated for autologous use.

According to a specific aspect, the invention provides for a TEV preparation obtainable or obtained by the method described herein.

According to a specific aspect, the invention provides for an autologous TEV preparation obtainable or obtained by the method described herein, wherein the source cell or source cell mixture is obtained from a subject and the TEV preparation is administered to the same subject.

The invention further provides for the medical use of such autologous TEV preparation, in particular for use in treating a subject in need thereof, wherein the source cell or source cell mixture is obtained from said subject.

Specifically, the subject is a patient, in particular a human patient suffering from a disorder or a disease.

According to a specific aspect, the invention provides for a protein comprising a target-specific extravesicular domain (TED) of an extracellular vesicle (EV) surface protein obtainable or obtained by a method described herein.

According to a specific aspect, the invention provides for a target-specific extravesicular domain (TED) of an extracellular vesicle (EV) surface protein comprising at least 70% sequence identity to a wild-type extravesicular domain (ED) of a mammalian EV surface protein sequence and at least one modified region with a length of 3-20 contiguous amino acids flanked by regions of the wild-type ED sequence at its N-terminus and C-terminus, which modified region is at least part of a target binding site not naturally-occurring in the wild-type ED, wherein the modified region has a lower target binding affinity when isolated from the TED and/or wherein the target binding site comprises at least one further binding region within a further modified region distant at least 2 amino acids, or within the wild-type ED sequence.

According to a specific aspect, the invention provides for a target-specific EV surface protein (TSP) comprising at least one transmembrane domain and an extravesicular domain (ED) comprising at least 70% sequence identity to a wild-type ED of a mammalian EV surface protein sequence and at least one modified region with a length of 3-20 contiguous amino acids flanked by regions of the wild-type ED sequence at its N-terminus and C-terminus, which modified region is at least part of a target binding site not naturally-occurring in the wild-type ED, wherein the modified region has a lower target binding affinity when isolated from the TSP and/or wherein the target binding site comprises at least one further binding region within a further modified region distant at least 2 amino acids, or within the wild-type ED sequence.

According to a specific aspect, the invention provides for a polynucleotide encoding any of the target-specific molecules described herein, in particular any one of the protein comprising the TED described herein, the TED described herein, or the TSP described herein. Specifically, the polynucleotide is a cDNA molecule.

According to a specific aspect, the invention provides for a target-specific extracellular vesicle (TEV) comprising a membrane and a displaying a target-specific molecule on the outer surface of the membrane, wherein the target-specific molecule is any of the target-specific molecules described herein, in particular any one of the protein comprising the TED described herein, the TED described herein, or the TSP described herein.

According to a specific aspect, the invention provides for a pharmaceutical preparation comprising any one of the target-specific molecules described herein, in particular any one of the protein comprising the TED described herein, the TED described herein, or the TSP described herein, or which comprises a TEV described herein, and a pharmaceutically acceptable carrier, preferably in a formulation for intradermal, subcutaneous, intravenous, topical, or oral use.

According to a specific aspect, the invention provides for a target-specific extracellular vesicle (TEV) library comprising a variety of at least $10^2$ TEVs described herein, wherein the variety comprises or consists of TEVs with a different modified region flanked by the same regions of the same wild-type extravesicular domain (ED) at its N-terminus and C-terminus.

Specifically, the TEV library comprises a repertoire of TEVs that include target-specific molecules described herein, wherein the repertoire covers at least $10^2$ different modified regions or target binding sites.

According to a specific aspect, the invention provides for a method of producing a library of target-specific extracellular vesicles (TEVs), comprising:

a) providing a repertoire of polynucleotides encoding a variety of target-specific EV surface proteins (TSPs), each comprising a different target binding site;
b) introducing said repertoire into said source cell(s); and
b) isolating a fraction comprising a repertoire of target-specific extracellular vesicles (TEVs), with a different target binding specificity, to produce a library of TEVs, wherein the repertoire of polynucleotides is produced by mutagenizing a polynucleotide encoding an EV surface protein by a mutagenesis method to obtain mutations of the extravesicular domain (ED) of said EV surface protein within at least one modified region with a length of 3-20 contiguous amino acids flanked by regions of the wild-type ED sequence at its N-terminus and C-terminus, to incorporate a target binding site within the ED.

According to a specific aspect, the invention provides for a TEV library obtainable or obtained by the method described herein, preferably comprising at least $10^2$ TEVs with different target specificity.

According to a specific aspect, the invention provides for a target-specific extravesicular domain (TED) of an extracellular vesicle (EV) surface protein comprising at least 70% sequence identity to a wild-type extravesicular domain (ED) of a mammalian EV surface protein sequence and at least one modified region with a length of 3-20 contiguous amino acids flanked by regions of the wild-type ED sequence at its N-terminus and C-terminus, which modified region is at least part of a target binding site not naturally-occurring in the wild-type ED, wherein the TED is characterized as further described herein.

Specifically, the modified region has a lower target binding affinity when isolated from the TED.

Specifically, the TED comprises at least any one of 70%, 80%, 85%, 90%, or 95% sequence identity to the respective wild-type ED sequence.

Specifically, the wild-type ED originates from an EV surface protein as further described herein.

Specific EV surface proteins are any one of (or combinations of):

a) tetraspan-like proteins,
b) proteins of the integrin family, proteoglycans,
d) five-transmembrane domains proteins,
e) type I transmembrane proteins,
f) Notch family proteins,
g) membrane proteins, in particular those with enzymatic activity (enzymatic TM proteins),
h) immune regulatory surface proteins,
i) surface markers of mesenchymal stem cells,
j) glycoproteins,
k) channeling proteins, or
l) miscellaneous exosomal (vesicular) surface proteins.

According to a specific embodiment, the EV surface protein is a tetraspan-like protein, in particular a tetraspanin or a lysosome-associated membrane protein.

Specifically, the tetraspan-like protein is of the tetraspan junctional complex superfamily, such as a tetraspanin of class I or II, preferably selected from the group consisting of:

a) CD81 comprising or consisting of the amino acid sequence identified as SEQ ID NO:87;
b) CD9 comprising or consisting of the amino acid sequence identified as SEQ ID NO:89;

c) CD53 comprising or consisting of the amino acid sequence identified as SEQ ID NO:90;
d) TSPAN32 comprising or consisting of the amino acid sequence identified as SEQ ID NO:91;
e) CD82 comprising or consisting of the amino acid sequence identified as SEQ ID NO:92;
f) CD63 comprising or consisting of the amino acid sequence identified as SEQ ID NO:93;
g) CD151 comprising or consisting of the amino acid sequence identified as SEQ ID NO:94; and
h) CD37 comprising or consisting of the amino acid sequence identified as SEQ ID NO:9.

Specifically, the lysosome-associated membrane protein is LAMP2 comprising or consisting of the amino acid sequence identified as SEQ ID NO:96.

Specifically, the originating protein is a human wild-type EV surface protein or an artificial protein (or a wild-type protein of a non-human animal) comprising at least 90% sequence identity thereto.

Specifically, the originating ED is a wild-type ED which is originating from a human wild-type EV surface protein or an artificial protein (or a wild-type protein of a non-human animal) comprising at least 90% sequence identity thereto.

Specifically, the wild-type ED is of a mammalian EV surface protein, such as comprising or consisting of a human or non-human animal amino acid sequence.

Specifically, the wild-type ED comprises at least any one of 90, 95, 98, 99% sequence identity, or comprises 100% sequence identity, to any one of the ED amino acid sequences comprised in or composed of the wild-type EC sequences, in particular of a human EV surface protein, which is any one:

a) of CD81, wherein the ED comprises or consists of any one of the amino acid sequences identified as SEQ ID NO:130 or SEQ ID NO:131;
b) of CD9, wherein the ED comprises or consists of any one of the amino acid sequences identified as SEQ ID NO:132, SEQ ID NO:182 or SEQ ID NO:133;
c) of CD53, wherein the ED comprises or consists of any one of the amino acid sequences identified as SEQ ID NO:134 or SEQ ID NO:135;
d) of TSPAN32, wherein the ED comprises or consists of any one of the amino acid sequences identified as SEQ ID NO:136 or SEQ ID NO:137;
e) of CD82, wherein the ED comprises or consists of any one of the amino acid sequences identified as SEQ ID NO:138 or SEQ ID NO:139;
f) of CD63, wherein the ED comprises or consists of any one of the amino acid sequences identified as SEQ ID NO:140 or SEQ ID NO:141;
g) of CD151, wherein the ED comprises or consists of any one of the amino acid sequences identified as SEQ ID NO:142 or SEQ ID NO:143;
h) of CD37, wherein the ED comprises or consists of any one of the amino acid sequences identified as SEQ ID NO:144 or SEQ ID NO:145;

or i) of LAMP2, wherein the ED comprises or consists of the amino acid sequence identified as SEQ ID NO:146:

Specifically, the sequence of an ED may vary at one or at both ends, such that the ED is prolonged or shortened by a number of amino acids, e.g., by 1, 2, 3, 4, or 5 amino acids, depending on the EV displaying the EV surface protein or the method of determining the regions of an ED.

Specifically, the ED may be of any non-human mammalian origin, such as comprising or consisting of the respective EC or extravascular loop sequences of the respective non-human homologs.

Specifically, the mammalian wild-type tetraspan-like protein comprises at least any one of 90, 95, 98, or 99% sequence identity, or comprises 100% sequence identity, to a mammalian wild-type tetraspan-like protein.

According to a specific example, the EV surface protein is CD81, and the modified region is positioned within positions 160 and 172, wherein numbering is of human CD81 identified as SEQ ID NO:87. Preferably, such TED comprising said modified region comprises at least one further binding region positioned between positions 132 and 141, or between positions 180 and 189, wherein numbering is of human CD81 identified as SEQ ID NO:87.

According to another specific example, the EV surface protein is CD9, and the modified region is positioned within any one of positions 155-166, positions 128-142, positions 130-140, or positions 169-180, wherein numbering is of human CD9 identified as SEQ ID NO:89.

According to a specific embodiment, said at least one modified region within the TED (in particular within at least two distant regions or EDs comprised in the target binding site) comprises solvent exposed residues, preferably wherein said at least one modified region is located in a loop and/or helical region of the ED. Solvent exposure of a position is typically indicative of favorable accessibility for target binding. Test methods to determine exposure to solvents are solvent accessible surface area and relative accessible surface area. Specifically, solvent exposed residues are those with relative accessible surface area of more than 20%.

According to a further specific embodiment, said at least one modified region is located in an alpha-helical region of the ED comprising solvent exposed residues. Specifically, an alpha-helical region comprises a series of coils e.g., coil amino acid sequences, in particular coil repeat sequences, comprising a repeated pattern of hydrophobic and charged amino acid residues, thereby forming a peptidic alpha-helix. Specifically, the helical region of the ED has a length ranging between 5 and 30, preferably 7 to 18 amino acids. Specifically, at least one of the helical regions is part of the target binding site. Since helical regions typically tend to dimerize or multimerize, said target binding site suitably prevents dimerization and multimerization, respectively, if the target binding site is comprised in the ED monomer.

Specifically, the ED is of a tetraspanin such as CD81 or CD9, and the target binding site comprises or involves at least one helical and/or loop structure of the tetraspanin, in particular within the LEL of CD81 and CD9, respectively. Specifically, the EV surface protein is CD81 or CD9, in particular human CD81 or CD9. Specifically, the surface protein is monomeric CD81 or monomeric CD9.

Yet, in some cases, the ED or the EV surface protein incorporates the target binding site only when present as a dimer or multimer. In such cases, it is preferred to engineer the target binding site within non-helical regions, to ensure dimerization and multimerization, respectively, and effective target binding.

Specifically, the location of the target binding site varies in different types of EDs or EV surface proteins. Certain motifs are conserved, whereas others can vary within a protein family or in analogous sequences of different species. For example, helix D in the tetraspanin protein family is fairly unstructured and attains helical conformation only upon binding with certain antigens. Sequence alignment of the tetraspanin family members shows an increased natural variability in this region, including insertions and deletions. Specifically, such natural variability indicates good tolerability of site-directed mutagenesis.

Specifically, the modified region of the TED described herein is positioned within a loop region of the wild-type ED sequence, in particular a large extracellular loop region. EV surface proteins may have tertiary structure when attached to the EV including a loop structure, and exposing the loop to the vesicle surrounding. Such loop region is particularly suitable for engineering a target binding site within the ED.

For example, tetraspan-like molecules may have one or more small extravesicular loops and/or one or more large extravesicular loops (LEL). Exemplary LEL sequences of CD81 and CD9 are further disclosed herein. In the case of human CD81 the LEL sequence is identified as SEQ ID NO:7, and in the case of human CD9 the LEL sequence is identified as SEQ ID NO:118.

Specifically, the TED or EV surface protein as described herein comprises a loop structure in the amino acid sequence which is stabilized by one or more cysteine(s) at position(s) to allow the formation of one or more disulfide bonds. Specifically, the TED or EV surface protein comprising said TED as described herein comprises at least one loop region which is stabilized by at least one intramolecular bond connecting at least two amino acid side chains e.g., disulfide bonds.

The loop length of an ED or an EV surface protein can vary. Specifically, the ED or the EV surface protein comprises at least one large extravesicular loop, and a loop of a smaller size. The large extravesicular loop typically has a length ranging between 75 and 140 amino acids, preferably, between 78 and 132 amino acids. Specifically, a small loop has a length ranging between 25 and 35 amino acids, preferably between 26 and 32 amino acids.

Specifically, the ED or an EV surface protein comprises at least one helical region or domain, e.g., 1, 2, 3, or 4 helical regions. Specifically, a helical region is within a loop region, or within the terminal region of the surface protein.

Specifically, the TED or an EV surface protein comprising a TED described herein is present on the surface of an EV as a monomer. Though extracellular or extravesicular surface proteins tend to dimerize or oligomerize for biological function, the surface protein is engineered to be target binding as a monomer.

Specifically, at least one of the loop and/or helical regions is mutagenized for producing the modified region within the ED to become at least part of the target-binding site.

Specifically, the TED described herein is comprised in a target-specific EV (TEV) surface protein which comprises at least one loop and/or helical structure anchored to the EV, typically a transmembrane domain.

Specifically, the modified region within the TED described herein has a length of 3-20 contiguous amino acids, preferably at least 3, 4, 5, 6, 7, 8, 9, 10, 11, or 12, up to e.g., 20, 19, 18, 17, 16, 15, 14, 13, or 12. Modifications typically result in at least 1, 2, 3, 4, 5, 6, 7, 8, 9, 10, 11, 12, 13, 14, 15, 16, 17, 18, 19, or up to 20 point mutations within any such modified region.

Specifically, said modification introduces a number of point mutations, including substitution, insertion or deletion of one amino acid at one position, preferably an amino acid substitution, e.g., at least (or not more than) any one of 3, 4, 5, 6, 7, 8, 9. 10, 11, 12, 13, 14, 15, 16, 17, 18, 19, or 20.

Specifically preferred are a number of point mutations at contiguous positions within a first modified region e.g., a number ranging from 3 to 20, in particular 3, 4, 5, 6, 7, 8, 9, or 10; and optionally a number of point mutations within a second modified region at contiguous positions distant said first modified region e.g., a number ranging from 3 to 20, in particular 3, 4, 5, 6, 7, 8, 9, or 10, wherein both, said first and second modified regions are comprised in the target binding site. The distance between said first and second modified region is typically composed of flanking sequences originating from a wild-type ED.

Specifically, the modified region is flanked by regions of the wild-type ED sequence at its N-terminus and C-terminus, such that the flanking regions are adjacent to the respective terminus of the modified region. Typically, the flanking regions are characterized by the wild-type amino acid sequence of the wild-type ED spanning, wherein the wild-type flanking sequences have a length of at least 2, 3, 4, 5, 6, 7, 8, 9, or 10 contiguous amino acids that are identical to the respective (unmodified) sequence of the wild-type ED.

Yet, according to a specific embodiment, one (but not both) of the flanking regions may be absent. For example, the modified region can be a terminal region including the C-terminus of the ED. In such case, the modified region is flanked by regions of the wild-type ED sequence only at its N-terminus, and the modified region is a C-terminal region of the ED.

Specifically, the modified region is binding to the target when positioned within the TED, thus, involving the surrounding secondary or tertiary structure of the TED to specifically recognize the target.

According to a specific embodiment, the target binding site comprises at least said modified region and a wild-type region of the TED, and/or another modified region within the TED, within the TSP, or on the surface of an EV comprising the TED and/or TSP.

When isolated from the TED, or when produced as a separate peptide consisting of the same amino acid sequence as the modified region, typically, such isolated modified region has a lower target binding affinity or even lacks specificity or selectivity to bind the target. Compared to the target binding of the modified region within the TED, the isolated modified region specifically, has less affinity or less selective binding, with a binding constant or binding dynamics which is at least 10 fold, or at least 100 fold, at least 1000 fold different, as determined with the same assay or in a comparable setting.

Suitable assays to compare the target binding property of a TED described herein and of the modified region isolated from said TED, may employ any of the following assays: ELISA, affinity determination e.g., using Biacore, biolayer interferometry, fluorescence measurement of cells displaying the TED incubated with cognate antigen, isothermal titration microcalorimetry, fluorescence correlation spectroscopy.

Specifically, the target binding site comprises at least two regions (wherein at least one or two of them is the modified region as further described herein), which are within at least two different EDs of the same EV surface protein, such as EDs separated by at least one transmembrane domain of the EV surface protein.

Such target binding site incorporated within the TED and comprising or otherwise involving said at least one modified region within the same ED or within at least two EDs has the particular advantage of improved binding properties. Such improved binding properties are typically obtained when mutagenizing a predetermined region within the ED to become a modified region with binding properties embedded within the ED, and selecting the suitable binders according to their target binding specificity and/or affinity.

The binding properties are specifically improved over comparable fusions of specific (peptide) binders to an ED thereby producing fusion proteins. This is because upon fusion, the binding properties typically are changed such that comparable fusion proteins have less affinity or less selective binding upon fusion of a binder to the ED as compared to the isolated binders.

Specifically, the modified region is at least part of a target binding site or consists of the target binding site. According to a specific embodiment, the modified region includes all contact amino acid residues of the binding site.

According to a specific embodiment, the target binding site comprises more than one modified binding region, wherein at least a first modified region is positioned at a certain distance from a second modified region.

Specifically, the target binding site comprises at least one further binding region within a further modified region distant at least any one of 2, 3, 4, 5, 6, 7, 8, 9, or 10 contiguous amino acids, or within the wild-type ED sequence. Specifically, the region between said at least two distant modified regions includes one of the regions flanking the modified region described herein at its N-terminus or C-terminus, which is a region of the wild-type ED sequence.

Specifically, the target binding site comprises binding residues within at least two distant regions of said TED. Specifically, the TED is modified or mutagenized within said at least two distant regions to incorporate said target binding site.

According to a specific embodiment, the target binding site comprises contact amino acid residues within the ED, but outside the modified region. Such further contact amino acids may be positioned in one or more further regions of the ED, which one or more further regions may comprise a modified (mutated) amino acid sequence e.g. comprising one or more point mutations, or may comprise the wild-type sequence of the ED.

According to a specific embodiment, the ED or the target binding site comprises said at least one modified region, and one or more further point mutations, or a series of at least 2, 3, 4, 5, 6, 7, 8, 9, or 10 contiguous point mutations within the amino acid sequence, specifically at a certain distance e.g., distant at least 2, 3, 4, 5, 6, 7, 8, 9, or 10 amino acids.

According to a specific embodiment, the ED or the target binding site comprises at least two or three of said modified regions.

In specifically preferred embodiments, the target binding site is a conformational binding site comprising two or more non-contiguous regions within the same ED or at least two different EDs, such as involving a binding surface stretching over at least two regions, each at a certain distance e.g., distant at least 2, 3, 4, 5, 6, 7, 8, 9, 10 11, 12, 13, 14, 15, 16, 17, 18, 19, or 20, typically up to 100 or 80 amino acids. Specifically, the distant binding regions are not adjacent to each other. Specifically, the distant binding regions are not contiguous in the sequence of the respective EV surface protein.

Specifically, the binding site comprises each of the distant binding regions and optionally one or more further contact points or regions of the TED. Specifically, the target binding site comprises contact points within at least two modified (e.g., synthetic or mutagenized) regions and optionally at least one further region which is neither synthetic nor mutagenized, but a native (wild-type) region of the ED.

Specifically, a target is bound by a conformational paratope of a binding site that is incorporated within the extravesicular part of an EV surface protein (in particular the part comprising the TED described herein), which paratope comprises contact areas in distant regions of the TED e.g., loop and/or helical region(s). Suitable TEDs and respective EV surface proteins are conveniently produced by mutagenizing selected areas within the distinct regions. For example, a TED as described herein is mutagenized within one, two, or three distant regions.

Specifically, the target binding site is a novel binding site recognizing a specific predetermined target, not naturally-occurring in the wild-type ED or wild-type EV surface protein, herein also referred to as "artificial" binding site.

According to a specific embodiment, the target binding site may be a new or additional binding site within one or more EDs, such that the ED(s) has/have a novel or an additional specificity to bind a target. Such new target binding site may have a specificity to bind the same target as any naturally-occurring binding site of the ED(s), or may have a different specificity e.g. recognizing a different target.

According to another specific embodiment, the target binding site may be a modified naturally-occurring binding site of the ED(s), such that the ED(s) has/have a specificity to bind the same target as the naturally-occurring binding site (though fine specificity or affinity may be changed).

According to a specific aspect, the TED provided as a separate molecule or a protein comprising such TED (such as an EV surface protein or a TSP) may comprise at least one or two different target binding sites specifically recognizing the same target or different targets.

The TED described herein is specifically used for medical purposes e.g. to deliver therapeutically effective amounts of proteins comprising a TED described herein, or target-specific EV surface proteins (TSPs) comprising such TED, in particular when attached to an EV, thereby providing a target-specific extracellular vesicle (TEV) as further described herein.

Specifically, the target is selected from the group consisting of cellular targets, preferably mitogenic receptors, cytokine receptors, asyaloglycoprotein receptors, membrane transporters, lipoproteins, liposaccharides, glycoproteins, proteoglycans, or acellular targets, preferably cytokines, artificial proteins or artificial surface structures.

According to a specific aspect, the target is a human cell, e.g., a cell originating from a healthy or diseased subject, or the respective cell lysate. Human cells of the diseased phenotype are preferably used as a target.

According to a certain aspect, the target binding site specifically recognizes a novel target, i.e., a target which would otherwise not be bound by the naturally-occurring ED or EV surface protein.

According to another aspect, the target binding site specifically recognizes a target which is the natural ligand of the ED or EV surface protein, yet with modified binding properties, such as selectivity, fine specificity, affinity and/or avidity e.g., for improved target binding. For example, natural ligands of tetraspanins are e.g., antigens of pathogens or pathogens such as cellular pathogens or viruses. By modifying the tertiary structure of a tetraspanin presented as a surface protein by an TED, TSP or TEV as described herein, binding properties can be improved e.g., to attain increased selectivity and/or affinity of binding to target the respective pathogens.

Specifically, the target consists of an antigen or antigenic structure of an antigen, in particular an epitope which is otherwise recognized by a target-specific antibody.

Specifically, the target is a cellular receptor. According to a specific example, an EV comprising the TED or TSP described herein, which is targeting a cellular receptor can directly fuse with the recipient cell membrane, thus incorporating its membrane proteins to the plasma membrane and delivering their cargo to the cytoplasm of the recipient cell.

Specifically, the target is an antigen e.g., naturally-occurring antigens or synthetic antigens. In certain embodiments, the target antigens are present in a diseased patient's blood, which antigens are bound by the surface protein of the EV and thus removed from the patient's cardiovascular and/or lymphatic system. Specific examples are undesired natural agents such as pathogens, toxins, diseased or cancer cells, cytokines, or metabolites. In certain further embodiments, the target antigens are synthetic antigens e.g., of solid surfaces such as grafts or implants, or soluble compounds such as chemicals or synthetic compounds, which can be removed upon effective binding by a specific binder (e.g., a TED, TSP or TEV) described herein.

Specific targets may be natural targets which are typically recognized by wild-type EVs. However, the target binding site comprised in the binders described herein may specifically recognize novel targets, which are otherwise not recognized by a wild-type EV. Among natural targets there are pathogens, such as viral antigens. Specific binders (e.g., a TED, TSP or TEV) described herein may bind such natural targets through a novel binding site, which may have improved binding characteristics, such as binding affinity, avidity or specificity.

According to a specific aspect, the invention provides for a target-specific EV surface protein (TSP) comprising at least one transmembrane domain and at least one extravesicular domain (ED) comprising at least 70% sequence identity to a wild-type ED of a mammalian EV surface protein sequence and at least one modified region with a length of 3-20 contiguous amino acids flanked by regions of the wild-type ED sequence at its N-terminus and C-terminus, which modified region is at least part of a target binding site not naturally-occurring in the wild-type ED, wherein the TSP is characterized as further described herein.

Specifically, the modified region has a lower target binding affinity when isolated from the TSP.

Specifically, the TSP described herein is characterized by one or more extravesicular domains, wherein at least one of them is target binding ("target-specific"). Specifically, the ED of the TSP described is a TED described herein.

Specifically, said at least one transmembrane domain is of a vesicular membrane protein, or an artificial transmembrane domain e.g., produced by mutagenesis of wild-type transmembrane domains or by de novo synthesis of suitable amino acid sequences.

Specifically, the transmembrane domain (TM) comprises at least any one of 70%, 80%, 85%, 90%, 95%, 96%, 977%, 98%, 99% sequence identity, or 100% sequence identity to the respective wild-type transmembrane domain sequence originating from a mammalian EV surface protein, e.g. any of the EV surface proteins as further described herein.

Specifically, the wild-type TM is of a mammalian EV surface protein, such as comprising or consisting of a human or non-human animal amino acid sequence.

Specifically, the TM is of a vesicular membrane protein which is of exosomal, microvesicular, or apoptotic body origin, in particular a wild-type exosomal, microvesicular, apoptotic body protein, or such wild-type protein which includes modifications e.g., in the extravesicular region.

Specifically, the wild-type TM comprises at least any one of 90, 95, 98, 99% sequence identity, or comprises 100% sequence identity, to any one of the TM amino acid sequences comprised in or composed of the wild-type sequence of an EV surface protein that is capable of being integrated within a cellular or vesicular membrane when binding the EV surface protein to a respective cell or vesicle, in particular of a human EV surface protein.

Specifically, the transmembrane domain is of any one of:

a) CD81, wherein the transmembrane domain comprises or consists of any one of the amino acid sequences identified as SEQ ID NO:147, SEQ ID NO:148, SEQ ID NO:149 or SEQ ID NO:150;
b) CD9, wherein the transmembrane domain comprises or consists of any one of the amino acid sequences identified as SEQ ID NO:151, SEQ ID NO:152, SEQ ID NO:153 or SEQ ID NO:154;
c) CD53, wherein the transmembrane domain comprises or consists of any one of the amino acid sequences identified as SEQ ID NO:155, SEQ ID NO:156, SEQ ID NO:157 or SEQ ID NO:158;
d) TSPAN32, wherein the transmembrane domain comprises or consists of any one of the amino acid sequences identified as SEQ ID NO:159, SEQ ID NO:160, SEQ ID NO:161 or SEQ ID NO:162;
e) CD82, wherein the transmembrane domain comprises or consists of any one of the amino acid sequences identified as SEQ ID NO:163, SEQ ID NO:164, SEQ ID NO:165 or SEQ ID NO:166;
f) CD63, wherein the transmembrane domain comprises or consists of any one of the amino acid sequences identified as SEQ ID NO:167, SEQ ID NO:168, SEQ ID NO:169 or SEQ ID NO:170;
g) CD151, wherein the transmembrane domain comprises or consists of any one of the amino acid sequences identified as SEQ ID NO:171, SEQ ID NO:172, SEQ ID NO:173 or SEQ ID NO:174;
h) CD37, wherein the transmembrane domain comprises or consists of any one of the amino acid sequences identified as SEQ ID NO:175, SEQ ID NO:176, SEQ ID NO:177 or SEQ ID NO:178;

or i) LAMP2, wherein the transmembrane domain comprises or consists of the amino acid sequence identified as SEQ ID NO:179.

Specifically, the sequence of a TM may vary at one or at both ends, such that the TM is prolonged or shortened by a number of amino acids, e.g., by 1, 2, 3, 4, or 5 amino acids, depending on the EV displaying the EV surface protein or the method of determining the regions of a transmembrane domain.

According to a specific embodiment, both, the wild-type ED and said at least one transmembrane domain, originate from the same mammalian EV surface protein, preferably selected from the group consisting of:

a) CD81 comprising or consisting of the amino acid sequence identified as SEQ ID NO:87;
b) CD9 comprising or consisting of the amino acid sequence identified as SEQ ID NO:89;
c) CD53 comprising or consisting of the amino acid sequence identified as SEQ ID NO:90;
d) TSPAN32 comprising or consisting of the amino acid sequence identified as SEQ ID NO:91;
e) CD82 comprising or consisting of or consisting of the amino acid sequence identified as SEQ ID NO:92;
f) CD63 comprising or consisting of the amino acid sequence identified as SEQ ID NO:93;
g) CD151 comprising or consisting of the amino acid sequence identified as SEQ ID NO:94;
h) CD37 comprising or consisting of the amino acid sequence identified as SEQ ID NO:95, and
i) LAMP2 comprising or consisting of the amino acid sequence identified as SEQ ID NO:96.

Specifically, the EV surface protein is a vesicular membrane protein which is of exosomal, microvesicular, or apoptotic body origin, in particular a wild-type exosomal, microvesicular, apoptotic body protein, or such wild-type protein which includes modifications e.g., in the extravesicular region.

Specifically, the EV surface protein is a protein originating from a cellular exosome i.e., an exosomal protein.

Specifically, the EV surface protein is a protein originating from a cellular microvesicle i.e., a microvesicular protein.

Specifically, the EV surface protein is a protein originating from an apoptotic body i.e., an apoptotic body protein.

It is well-understood that an exosomal protein, microvesicular, or apoptotic body protein as used herein for modification purposes is of cellular origin, i.e., which can be produced by a respective cell or which can be artificial and produced by de novo synthesis.

Specifically, said EV surface protein is a polypeptide, protein domain or protein which has a structure to incorporate an artificial target binding site. Such polypeptide, protein domain or protein may be naturally-occurring, or partially or fully synthetic.

Specifically, one or two of the transmembrane domains is/are fused to the ED of the surface protein, and capable of attaching the ED to the membrane of an EV.

According to a specific aspect, the invention provides for a target-specific extracellular vesicle (TEV) comprising a lipid bilayer membrane and the TED described herein, or the TSP described herein, displaying the target binding site on the outer surface of the lipid bilayer membrane.

Specifically, the TED described herein can be bound to an EV through a TSP described herein or any other suitable means, e.g., by conjugation, fusion, or affinity binding.

Specifically, the TSP described herein can be bound to an EV through said at least one transmembrane domain comprised in the TSP, in particular wherein said transmembrane domain(s) is/are within the vesicle membrane, such that the TSP is presenting the TED and optionally at least one further ED (which may be target binding or not) to the outer surface of the EV.

Specifically, said at least one transmembrane domain serves as an anchor which can be fused to any kind of target binding molecule incorporating the TED described herein e.g., a TSP described herein.

Specifically, the TSP comprises at least two, three, or four transmembrane domains, preferably all transmembrane membranes of the same wild-type EV surface protein.

Specifically, a series of more than one transmembrane domains of one or more (e.g., the same type or different) proteins or artificial transmembrane domains can be used, thereby creating extravesicular loop regions i.e., loop structures outside the EV. Specifically, the number of transmembrane domains used to anchor at least one loop structure is 2, 3, or 4. Specifically, the surface protein comprises one or more loops e.g., at least 1, 2, 3, or 4 loops. Yet, in certain case, the surface protein comprises a tertiary structure without loops.

Specifically, two transmembrane domains are used to present one extravesicular loop structure on the surface of an EV comprising the TSP described herein. According to specific embodiments, three or four transmembrane domains are used to present two extravesicular loop structures, and four or five transmembrane domains are used to present three extravesicular loop structures. Specifically, within one TSP described herein, one transmembrane domain is followed by a loop structure, such as an amino acid sequence spanning said transmembrane domain to another transmembrane domain, or connecting a loop structure including one or more intramolecular bonds, such as those stabilizing the loop or stem structure, to the vesicular surface. It is understood that the loop structure can be flanked by at least one transmembrane domain, in order to be bound to a vesicular membrane e.g., by either N-terminal or C-terminal fusion of a peptide loop sequence. If flanked by only one transmembrane domain, the opposite end (the N- or C-terminus of the loop sequence which is opposite to the fusion with the transmembrane domain) is typically not anchored to the membrane, e.g., a loose end. If flanked by two transmembrane domains e.g., by both, N-terminal and C-terminal fusion of a peptide loop sequence to a transmembrane domain, the loop structure is anchored to the EV membrane on both sides.

Specifically, the TSP is a tetraspan-like protein comprising a number of transmembrane domains spanning one or more loop sequences, in particular four transmembrane domains capable of presenting the wild-type loop structure of a tetraspanin protein on the surface of an EV, in particular two extravascular loops anchored by the four transmembrane domains.

Specifically, the TEV is originating from eukaryotic or prokaryotic source cells of body tissue, body fluid, or a cell culture.

According to a specific embodiment, the TEV is carrying an intravesicular load, e.g., wherein the load comprises any one or more of peptides, polypeptides, protein domains, proteins, lipids, genes, nucleic acids such as mRNAs, miRNAs, RNAi mediating molecules in particular locked nucleic acids or phosphorothioates, DNA, DNA fragments, plasmids such as minicircle DNA, drugs such as small molecules, in particular chemotherapeutics or senolytics.

The EV can be a membrane vesicle, which is a submicroscopical vesicle comprising a lipid bilayer membrane, such as the membrane of an exosome, microvesicle or apoptotic body. Specifically, the EV is produced by cells or synthetically produced. When produced by a cell, the EV can be released by the cell into the extracellular space by biological processes, and the surface protein is engineered prior to or after the cell release. The EV may be surface decorated e.g., with carbohydrate structures and/or by fusion with amino acids or amino acid sequences and/or by coupling with chemical compounds, such as drugs, labels or tags.

Specifically, the lipid bilayer membrane is anchoring the TED or the EV surface protein (the TSP) through said at least one transmembrane domain of a membrane surface protein, fusion of a respective coding sequence, or alternatively by chemical and/or affinity binding. In certain cases, a surface protein is anchored to the lipid bilayer membrane of the extracellular vesicle by means other as a transmembrane domain. Such anchors may involve an affinity-based interaction such as e.g. streptavidin-biotin, or protein A-Fc interaction, or covalent-based interaction such as e.g. maleimide-free cysteine. The anchorage may be achieved e.g. over click-chemistry coupling.

Exemplary techniques for binding a surface protein to the membrane comprises linking atoms of amino acid side chains, such as S—S linkage (disulfide bridges), binding by bioconjugation e.g., by click-chemistry, or otherwise covalently bonding. Alternative techniques employ affinity binders such as biotin and avidin to link the surface protein to the membrane.

In certain cases, one or more (artificial) target binding sites are comprised in one or two surface proteins (the same proteins or different) of the TEV described herein. Specifically, two different surface proteins may be used to produce at least two different binding sites e.g., to recognize different epitopes of the same of different antigens. Specifically, TEVs described herein can be mono- or bispecific, or even oligospecific.

In certain cases, additional target binding sites of a TEV described herein may originate from any binding structure, such as derived from proteins, polypeptides or peptides, including antibodies and antibody fragments or composite molecules with a binding part. Specifically, the binding site may be of an antigen-binding portion of an antibody, or the binding site of any one of an enzyme, an adhesion protein, a ligand or a ligand binding portion of a receptor, which binding site is capable of binding a cognate structure of a binding partner. The EV surface protein particularly may comprise one or more binding sites of protein domains of antibodies or antibody fragments, or the respective antibody domains or fragments, such as those comprising one, two or more variable antibody domains e.g., Fab, Fv, VH/VL dimer, scFv, dAb, F(ab)2, or other biological binders, such as soluble T-cell receptor, Darpins, etc.

Specifically described herein are modified tetraspanin proteins comprising a novel target binding site characterized by at least any one of 75, 80, 85, or 90% sequence identity, preferably ranging between 80 and 90% sequence identity, to the amino acid sequence of a wild-type human tetraspanin protein LEL, such as in the case of CD81 the LEL identified as SEQ ID NO:7, or in the case of CD9 the LEL identified as SEQ ID NO:118.

Specific examples of a modified tetraspanin protein comprising a novel target binding site are characterized by at least any one of 75, 80, 85, 90, 95, 96, 97, or 98% sequence identity, preferably ranging between 90 and 98% sequence identity, to the amino acid sequence of a full-length wild-type human tetraspanin protein, such as in the case of CD81 the amino acid sequence identified as SEQ ID NO:87, or in the case of CD9 the amino acid sequence identified as SEQ ID NO:89.

According to a specific example, the novel target binding site comprises a modified region (a binding region) within the LEL of CD81, identified as SEQ ID NO:7, in particular within the region aa113-201 of the full-length protein identified as SEQ ID NO:87. Specific embodiments refer to a novel target binding site within aa130-201.

Specific examples refer to modifications in the amino acid sequence of CD81 (SEQ ID NO:87) to substitute at least one amino acid at positions 160-162, and 181-189.

According to a further specific embodiment, the EV surface protein is CD9 and the binding residues are located within at least one or two different regions selected from the following regions: 155-166; 128-142; 130-140; 169-180. Specifically, the CD9 is human CD9 identified by SEQ ID NO:89. Preferred Cys residues for disulfide bridging are 132 and 140, wherein numbering is according to SEQ ID NO: 89.

According to a further specific embodiment, the EV surface protein is CD53 and the binding residues are located within at least two different regions selected from the following regions: 147-160; 121-134; 123-129; 164-169. Specifically, the CD53 is human CD53 identified by SEQ ID NO:90.

According to a further specific embodiment, the EV surface protein is TSPAN32 and the binding residues are located within at least two different regions selected from the following regions: 158-171; 130-144; 132-139; 174-183. Specifically, the TSPAN32 is human TSPAN32 identified by SEQ ID NO:91.

According to a further specific embodiment, the EV surface protein is CD82 and the binding residues are located within at least two different regions selected from the following regions: 153-172; 178-188; 128-137; 194-215. Specifically, the CD82 is human CD82 identified by SEQ ID NO:92.

According to a further specific embodiment, the EV surface protein is CD63 and the binding residues are located within at least two different regions selected from the following regions: 149-165; 171-176; 127-135; 179-189. Specifically, the CD63 is human CD63 identified by SEQ ID NO:93.

According to a further specific embodiment, the EV surface protein is CD151 and the binding residues are located within at least two different regions selected from the following regions: 159-177; 186-191; 135-145; 194-206. Specifically, the CD151 is human CD151 identified by SEQ ID NO:94.

According to a further specific embodiment, the EV surface protein is CD37 and the binding residues are located within at least two different regions selected from the following regions: 156-177; 183-206; 131-141; 218-229. Specifically, the CD37 is human CD37 identified by SEQ ID NO:95.

The EV surface proteins or the respective EDs (or any domain other than the transmembrane domain comprised in the EV surface protein) can be used for mutagenesis in the predetermined regions to introduce one or more novel target binding sites as described herein.

Further EV surface proteins comprising a novel target binding site may be produced by mutagenizing respective regions. For identifying the suitable regions, sequences of large extracellular loop of tetraspanins Class I (e.g., CD9, CD53, and TSPAN32) have been analysed using Swiss-model modeling server with a template such as CD81. The sequence of large extracellular loop of CD82, a representative of tetraspanin Class II, has been modeled using a program for protein structure and function prediction (i-Tasser modeling server). Sequences of tetraspanins Class II (CD63, CD151, and CD37) have been modeled using the CD82 model coordinates.

According to a specific embodiment, the EV surface protein (e.g., CD81 or any other tetraspanin) is stabilized or thermostabilized by introducing one or more cysteine(s) at position(s) to allow the formation of one or more additional disulfide bonds stabilizing the extravesicular loop structure of the protein. Specifically, at least one additional cysteine is introduced in at least one region of an extravesicular domain of the surface protein. Specifically, a cysteine is introduced in at least two different regions of the surface protein. Introducing novel cysteine(s) allows connection of the regions via a novel (artificial) disulfide bond, which are usually formed from the oxidation of sulfhydryl (—SH) groups of the cysteines.

In particular, the tertiary structure of the surface protein can be modified by one or more additional small loop(s) resulting from one or more additional intramolecular bonds. Such additional small loop(s) can be used to create further contact points of the artificial binding site.

One or more additional intramolecular disulfide bond(s) successfully increased the stability of a surface protein, as measured by methods determining thermostability of the protein by standard methods. A stabilized EV surface protein can be conveniently used as a scaffold to produce a repertoire of EV surface proteins by mutagenesis of pre-determined regions within the EV surface protein each with different target binding or different target binding properties. Such repertoire is suitably used as a library to select binders to a target of interest.

Specifically, as the number of endorsed residues is theoretically decisive of the free energy change in respect to an unmutated protein, candidate positions for mutagenesis into pairs of cysteines and subsequent formation of a cysteine bond can be pre-selected in a first step by visual inspection of the crystal structure. Specifically, at least one novel cysteine bond is introduced in pre-selected candidates, preferably, new cysteine bonds are created by introduction of at least one or one pair of cysteines via mutagenesis.

Specifically preferred examples refer to a modified tetraspanin comprising novel disulfide bonds that connect Cys residues when reduced, which Cys residues are introduced by mutating the tetraspanin sequence (e.g., one of the ECs, in particular the LEL of the tatraspanin) at two distant sites which are e.g., at the N- and C-terminus of a loop, thereby stabilizing the loop structure. Any such loop structure stabilized by at least one disulfide bond is preferably used to mutagenize the tetraspanin for engineering a novel target binding site within such loop structure.

Specifically, at least two cysteines are introduced by any of insertion or substitution. According to a specific example, additional cysteines are introduced in CD81 to stabilize and/or modify the tertiary structure of the LEL.

According to a specific embodiment, the EV surface protein is CD81 and the amino acid sequence is modified to introduce cysteines to allow formation of one or more disulfide bonds not naturally-occurring in the wild-type ED sequence, preferably between positions 134 and 144 and/or between positions 130 and 146 and/or between positions 135 and 168.

Specifically, the CD81 is human CD81 and a first cysteine is introduced at a position within amino acid 120 and 200 and at least a second cysteine is introduced at a position within amino acid 143 and 201, wherein numbering is of human CD81 identified as SEQ ID NO:87.

Specifically, a first cysteine is introduced at a position within amino acid 130 and 140 and a second cysteine is introduced at a position within amino acid 144 and 170.

Specifically, cysteines are introduced into the human CD81 sequence (in particular an ED of CD81, such as the LEL) at positions 134 and 144, substituting A134C and L144C, respectively, thereby connecting helix A and helix B of the LEL of CD81 by an additional intramolecular disulfide bond. Alternatively, additional cysteines are introduced at positions 135 and 168, respectively, substituting V134C and S144C, respectively, thereby connecting helix A and helix C of the large extracellular loop of CD81 by an additional intramolecular disulfide bond.

According to a specific embodiment, Cys residues are introduced in the CD81 sequence identified as SEQ ID NO:87 (in particular an ED of CD81, such as the LEL), e.g., by the mutation Ala134Cys and Lys144Cys, thereby introducing a novel disulfide bond spanning the cysteines at positions 134 and 144, According to a further embodiment (additional or alternative) Cys residues are introduced in the CD81 sequence identified as SEQ ID NO:87, by the mutation Val135Cys and Ser168Cys, thereby introducing a novel disulfide bond spanning the cysteines at positions 135 and 168. According to a further embodiment (additional or alternative) Cys residues are introduced in the CD81 sequence identified as SEQ ID NO:87, by the mutation Ala130Cys and Ala146Cys, thereby introducing a novel disulfide bond spanning the cysteines at positions 130 and 146.

According to a further embodiment (additional or alternative) Cys residues are introduced in the CD81 sequence identified as SEQ ID NO:87, by the mutation Val135Cys and Ser168Cys, thereby introducing a novel disulfide bond spanning the cysteines at positions 135 and 168.

Specifically, at least one of the EDs of human CD81, in particular the LEL, is modified to introduce additional cysteines at positions 134 and 144, and at positions 135 and 168, thereby connecting helix A to helix B, and helix A to helix C. Such CD81 mutant with a combination of potently stabilizing novel disulfide bonds Ala134Cys/Lys144Cys and Val135Cys/Ser168Cys in its LEL shows an increased positive shift in melting temperature of at least 20° C.

Specifically, at least one of the EDs of human CD9, in particular the LEL, is modified to introduce additional cysteines, thereby obtaining one or more new (additional) disulfide bridges. Preferably, a disulfide bridge is linking positions 20 and 28, such as obtainable by mutating Lys20Cys and Arg28Cys, wherein numbering of the positions is of the CD9 LEL (SEQ ID NO:118). The resulting sequence of the stabilized variant specifically comprises or consists of SEQ ID NO:125.

Specifically, an increase in thermostability of mutated pre-selected candidates is indicated by an increase in the temperature at which thermal unfolding occurs by at least 5, 10, 15, 20, 25, 30, 35, 40, 45, 50 or 55° C. compared to wild-type protein.

Specifically, any one of the TED, TSP or TEV described herein has an affinity to bind said target with a $K_D$ of less than $10^{-5}$ M, preferably less than $10^{-6}$M, $10^{-7}$M, or $10^{-8}$M, or even less than $10^{-9}$M.

Usually, a binder is considered a high affinity binder with a $K_D$<10 nM, in some cases, e.g., for therapeutic purposes EVs with higher affinities are provided, e.g., with a $K_D$<1 nM, or a $K_D$<0.1 nM, or a $K_D$<0.01 nM or a $K_D$<pM (picomolar=$10^{-12}$M).

Once a selected TED, TSP or TEV has proven to bind a target of interest, the selected binding ED or EV surface protein may undergo affinity maturation by standard methods of affinity maturation, e.g., those methods typically used for producing affinity matured antibodies. For this purpose, only a few point mutations e.g., 1, 2, 3, 4, or 5, up to 10 point mutations may be introduced within one region of the molecule, or within the whole molecule, to produce a new repertoire of target binders that can be selected to isolate a binder with an increased binding affinity. Such affinity matured binders may exhibit an increased binding affinity with a $K_D$ difference of at least 1 or 2 logs.

The specific binding may be determined in a suitable binding assay, such as conventional immunoassays. There are numerous methods known in the art for detecting binding in an immunoassay. Various immunoassays known in the art can be used including competitive and non-competitive assay systems using techniques such as radioimmunoassays, ELISA (enzyme linked immunosorbent assay), immunoradiometric assays, gel diffusion precipitation reactions, immunodiffusion assays, western blot, BIAcore etc.

According to a preferred embodiment, the TEV described herein is originating from eukaryotic or prokaryotic source cells. Source cells are herein understood as donor cells capable of producing the EVs described herein. However, source cells may also just serve as a template to produce the respective synthetic EVs in vitro, e.g., using one or more components (such as a transmembrane domain and/or a surface protein) that would otherwise be produced by the source cell, and constructing the TEV with features described herein without relying on cellular transport mechanisms.

Exemplary eukaryotes are mammalian, plant, insect, fungi or yeast. Specific examples are cells of human or non-human animal origin, in particular mammals including Chinese hamster derived cells such as CHO cells, plants, in particular *Arabidopsis thaliana* or *Zea mays*, or fungi, in particular *Saccharomyces cerevisiae* or *Pichia pastoris*.

Exemplary prokaryotes are bacteria. EVs from Gram-negative bacteria are known as outer-membrane vesicles (OMVs). Specific examples are EVs of *Lactobacillus* or Mycobacteria pathogens, or *Salmonella enterica, M. tuberculosis, Moraxella catarrhalis* or *Haemophilus influenzae*.

Specifically, the source cell is of a body tissue, body fluid, or a cell culture, preferably of animal or plant cells; or of a mammalian body fluid or tissue, preferably of blood, urine, amniotic fluid, ascites, cerebrospinal fluid, saliva, synovial fluid, or bone marrow. Specifically, the EV described herein is produced by a cell culture of a source cell.

Specifically, the tissue is of an organ, such as a kidney, brain, or of placenta. Specifically, the tissue is a tumor or metastasis tissue, or a benign tissue.

Specifically, the source cell is a stem cell, such as a mesenchymal stem cell (MSC), amniotic stem cell, or induced pluripotent stem (iPS) cell, a dendritic cell, a hematopoietic cell, epithelial cell, endothelial cell, nerve cell, blood cell or immune cell. Specifically, the source cells of EVs can be amnion-derived multipotent progenitor cell, chorion derived mesenchymal stem cell, induced pluripotent stem cell, keratinocyte, fibroblast, embryonic stem cell, ectodermal stromal cell, endodermal stromal cell, olfactory ensheathing cell, dental pulp stem cell, or immortalized mesenchymal stem cell.

Specifically, the source cell is selected from the group consisting of normal or immortalized human cells, such as induced pluripotent or adult stem cells, epithelial cells and cancer cells.

Specifically, the source cell is a cell line of a recombinant host cell, such as mammalian host cells e.g., cell lines used as cell factories such as for example human primary cells, telomerase immortalized cell lines, or cell lines immortalized by viral oncogenes including adenoviral E1A, HPV derived E6, EBV derived oncogenes, SV40, or combinations of transcription factors. Specifically, cell lines including telomerase immortalized endothelial or mesenchymal stem cells, HEK293, CHO, Vero, HEK, or CAP.

Cells suitably employed in large-scale EV production include mesenchymal stem cells, dendritic cells, and HEK cells or 293T cells.

Specifically, the source cell is a mammalian stem cell or dendritic cell, preferably of human origin.

According to a specific embodiment, the EV surface protein is endogenous to the source cell. Yet, the endogenous EV surface protein is typically presented as a modified surface protein by the TEV described herein.

According to a further specific embodiment, the EV surface protein is heterologous to the source cell. The heterologous EV surface protein can originate from a source cell of a different type, or be a synthetic surface protein which is not naturally occurring. When using a synthetic surface protein, the novel target binding site can be synthesized within the molecule without any further modification. Unlike modified native surface proteins, synthetic surface proteins typically do not have a sequence identity (e.g., less than 50% sequence identity) to a native (wild-type) surface protein.

Specifically, the TEV described herein has a size ranging from 10 to 1000 nm, preferably from 30 to 150 nm.

Specifically, the TEV described herein has a buoyant density ranging from 1.0 to 1.4, preferably between 1.1 and 1.2 (g/$cm^3$), such as measured by density-gradient ultracentrifugation.

According to a specific embodiment, the TEV described herein is carrying an intravesicular load. Specifically, the load is within a volume of $10^{-14}$ to $10^{-10}$ μl (volume per one EV). Specifically, the load comprises an active substance or a mixture of active substances e.g., at loading efficiencies between 5 and 90%.

According to a specific embodiment, the binders described herein (in particular the TED, TSP, or TEV described herein) are provided for medical use in treating a subject in need thereof. Medical use encompasses treatment for therapy of a disease condition, either by administering a TEV described herein, or by ex vivo use e.g., as reagent or affinity matrix such as for purging undesired substances from body fluids. Further medical uses are for triggering an immune response e.g., to present an antigen to a subject's immune system, such as for active immunotherapy.

EVs can be used as a therapeutic agent by themselves or as delivery systems to deliver a specific load. According to a specific example, the intravesicular load is an active substance or a drug encapsulated within the vesicular membrane. Specifically, an active substance is used which acts in collaboration with elements naturally present in the EVs. According to another specific example, EVs serve only as vehicles to reach a specific target, sometimes highly protected from conventional administration routes.

Specifically, the binders described herein are provided for any cosmetic, food or industrial purpose. Specific embodiments refer to such TEVs which are provided in a lipid or oily composition, or encapsulated e.g., for cosmetic or food purposes. Industrial purposes encompass analytical or preparatory purposes, such as to analyse or prepare specific binders (on an industrial scale), respectively.

Specifically, the TEV is carrying a load comprising an autologous or heterologous active substance, in particular a heterologous compound, for medical use as a targeting vector in treating a subject in need of targeted therapy with said compound.

According to a specific aspect, the invention provides for a method of treating a subject in need thereof, by administering an effective amount of a binder described herein, in particular a TEV or a TEV preparation described herein to said subject for therapeutic or diagnostic purposes, such as to improve or detect a certain condition, in particular a disease condition.

Specifically, an effective amount of the TEV is used, wherein dosing is measured according to the administered intravesicular load.

Specifically, the load comprises at least one autologous or heterologous compound. Specifically, the load comprises any one or more of peptides, polypeptides, protein domains, proteins, lipids, genes, nucleic acids such as mRNAs, miRNAs, RNAi mediating molecules in particular locked nucleic acids or phosphorothioates, DNA, DNA fragments, plasmids such as minicircle DNA, drugs such as small molecules, in particular chemotherapeutics or senolytics.

Small molecule drugs are herein understood to as low molecular weight (<900 D) organic compounds that may regulate a biological process. Small molecules can have a variety of biological functions or applications, serving as cell signaling molecules, drugs in medicine, pesticides in farming, and in many other roles. These compounds can be natural (such as secondary metabolites) or artificial (such as antiviral or chemotherapeutic drugs); they may have a beneficial effect against a disease (such as drugs) or may be detrimental (such as teratogens and carcinogens).

According to a specific aspect, the TEV is originating from a source cell which is autologous to said subject. Specifically, a TEV of autologous origin is used, which is modified and/or loaded in vitro (outside the subject's body) for administration in vivo, according to the subject's needs.

According to a specific aspect, the invention provides for a TEV preparation comprising isolated TEVs. The TEV preparation specifically is characterized by a homogenous EV population, which consists of at least 50% EVs with the same target specificity, preferably at least any one of 30%, 40%, 50%, 60%, 70%, 80%, 90%, or 95%.

According to a specific aspect, the TEV preparation is a homogeneous preparation with a median size between 100 and 150 nm, or between 120 and 140 nm. The specific yield is preferably at least 1000 EVs per source cell, more preferably at least 1500, or at least 1600 EVs per source cell.

Specifically, the TEV preparation is provided in a storage-stable aqueous solution or as a lyophilized preparation.

The invention further provides for a pharmaceutical preparation comprising any of the TED, or the TSP, or the TEV described herein, and a pharmaceutically acceptable carrier, preferably in a formulation for intradermal, subcutaneous, intravenous, topical, or oral use.

According to a specific aspect, the invention provides for a method of producing a protein comprising a target-specific extravesicular domain (TED) of an extracellular vesicle (EV) surface protein comprising modifying a polynucleotide comprising a coding sequence encoding the extravesicular domain (ED) of an EV surface protein by a mutagenesis method to obtain mutations of the ED amino acid sequence within at least one modified region with a length of 3-20 contiguous amino acids flanked by regions of the wild-type ED sequence at its N-terminus and C-terminus, to incorporate a target binding site within the ED, thereby producing a repertoire of polynucleotides encoding a variety of TEDs, each comprising a different target binding site, and selecting a protein comprising the TED specifically recognizing a predetermined target, and producing the selected protein.

Specifically, the repertoire of polynucleotides is comprised in genetic packages displaying the variety of TEDs on the outer surface, preferably employing a display system selected from the group consisting of a yeast, phage, bacterium, ribosome, mRNA or mammalian cell display.

Specifically, the protein comprising the selected TED is the TSP described herein.

Specifically, the selected TED is characterized as further described herein.

The invention further provides for a method of producing the TEV preparation described herein, comprising:

a) introducing a polynucleotide encoding the TSP described herein into a source cell or source cell mixture;
b) culturing said cell(s) under conditions producing extracellular vesicles;
c) isolating a fraction comprising a TEV comprising the target binding site of the TSP, and
d) producing a preparation of the TEV comprised in said fraction.

Specifically, the source cell or source cell mixture is obtained from a biological sample of a subject.

Specifically, the biological sample of said subject is selected from the group consisting of blood, urine, amniotic fluid, ascites, cerebrospinal fluid, saliva, synovial fluid, or bone marrow.

Specifically, the source cell is isolated before culturing in a cell culture, or cultured within the biological sample.

Specifically, the subject is an animal, such as a mammal, including a human being or non-human animals.

According to a further specific embodiment, there is provided a method of producing a preparation of the TEV described herein, which is originating from a stem cell of a subject, comprising:

a) introducing a polynucleotide or gene encoding the TEV surface protein into a stem cell;
b) culturing said stem cell under conditions producing extracellular vesicles;
c) isolating a fraction comprising the TEV e.g. according to the target binding specificity; and
d) producing a TEV preparation.

Specifically, the stem cell is isolated before culturing in a cell culture, or cultured within the biological sample.

According to a specific embodiment, the EVs are obtained from mesenchymal stem cells (MSCs). MSCs can be prepared by an in vitro proliferation of cell culture, for example, by dispersing an embryonic stem cell colony. Isolation of the EVs, in particular exosomes, from MSCs may be done in a mesenchymal stem cell conditioned medium. The medium may be obtained by culturing MSCs, descendent thereof or a cell line derived therefrom in a cell culture medium and isolating the cell culture medium.

Specifically, the source cell or source cell mixture is obtained from a subject, and the TEV preparation is formulated for autologous use.

Specifically provided herein is an autologous TEV preparation produced by the method described herein, wherein the source cell or source cell mixture is obtained from a subject and the TEV preparation is administered to the same subject.

According to a specific embodiment, TEVs can be targeted to a tumor, and loaded TEVs can be produced upon loading with antigens directly obtained from said tumor.

Specifically, the polynucleotide or gene, which is introduced into a source cell or source cell mixture, encodes a TSP, and the ED of the TSP is bound to the surface of the EV via at least one of the transmembrane domains of the TSP.

According to a specific embodiment, introduction of the polynucleotide or gene encoding the TSP into the source cell can be achieved via transfection. Specifically, the cell(s) is/are transfected with said gene prior to culturing. Specifically, the coding gene is introduced into the cell by any of commonly used transfection methods, such as electroporation, or transfection with apoptosis-inducing agents, such as siRNA, in particular liposome-based transfection.

According to a specific embodiment, the source cell or source cell mixture is cultured in a cell culture under conditions to produce membrane vesicles and to release the TEVs, thereby obtaining the TEVs in a culture supernatant.

Specifically, the cell culture conditions are adapted to the different source cells, or the different biological samples comprising the source cells. According to a specific aspect, the biological samples consist of a biological fluid from a subject (bone marrow, peripheral blood, etc.), a culture supernatant, a cell lysate, a pre-purified solution or any other composition comprising membrane vesicles. Specific cell culture methods for the production of TEVs may further involve inducing oxidative stress. The oxidative stress may be induced by an externally added cytokine or by an oxidant such as hydrogen peroxide.

Exosomes may also be synthesized or manufactured artificially, i.e., not isolated from a human or non-human cell. Instead of being isolated, exosomes could be synthesized by various lipid formation technologies.

Specifically, the source cell or source cell mixture is cultured in a cell culture comprising an active substance e.g., a heterologous compound under conditions to produce extracellular vesicles carrying said compound, preferably by intravesicular loading said vesicles.

Specifically, said intravesicular loading is by incubation, optionally disrupting the membrane, or by binding the load to a component of the membrane. In particular the TEV is loaded by any suitable transfection technique, including reagent-based methods (Calcium phosphate, polyethylenimine, cationic polymers, DEAE-dextran, activated dendrimers, magnetic beads), or instrument-based methods (electroporation, sonication, bolistic technology, microinjection, laserfection, optoinjection). Alternatively, TEVs can be loaded by binding or fusing a compound to the membrane e.g., by binding to or fusion with membrane lipoproteins.

Loading the TEVs can be carried out in vitro, in vivo or ex vivo.

TEVs can be loaded prior to or after producing the extracellular vesicles.

Specifically, a source cell can be further surface decorated by any suitable method employing biological, enzymatic and/or chemical reactions, such as to produce TEVs comprising modifications e.g., modifying the surface protein glycosylation (e.g., by sialylation, fucosylation, or aglycosylation), post-translational modifications, and/or coupling chemical compounds, drugs, labels, tags, or enzymatic (e.g., enzyme substrate) or chemical reaction groups.

For isolation of TEVs, in particular microvesicles or exosomes, medium of a cell culture of source cells is collected, pre-cleared of cells and debris, and subjected to a series of (ultra)centrifugation steps. Subsequently, the resulting TEV pellet is usually subjected to sucrose density gradient centrifugation, to separate a homogeneous EV population. Specifically, a culture supernatant is treated so as to be enriched with membrane vesicles. In particular, a pre-purified solution obtained from a culture supernatant of a population of membrane vesicle-producing cells or from a biological sample, is subjected to treatments such as centrifugation, clarification, ultrafiltration, nanofiltration and/or affinity chromatography.

A cell culture medium or supernatant can be filtered e.g., through a membrane which has a particular porous size or a particular molecular weight cut-off, particularly employing tangential force filtration or ultrafiltration.

Specifically, the TEV containing fraction is isolated and optionally concentrated by any one or more of binding to affinity ligands, centrifugation, chromatography, clarification, ultrafiltration, or nanofiltration.

According to a specific aspect, the method of preparing the TEVs, particularly of purifying from a biological sample, includes at least one anion exchange chromatography step. Different types of anion exchange materials may be used to perform the anion exchange chromatography, such as including cellulose, poly(styrene-divinylbenzene), agarose, dextran, acrylamide, silica, ethylene glycol-methacrylate co-polymer, or mixtures thereof, e.g., agarose-dextran mixtures. The EVs retained on the column may be eluted in different ways, particularly using the passage of a saline solution gradient of increasing concentration. Typically, different fractions purified in this way are detected by measuring their optical density at the column outlet using a continuous spectrophotometric reading.

As an alternative, or in addition to anion exchange chromatography step, gel permeation chromatography can be used. Typically, a material selected from silica, acrylamide, agarose, dextran, ethylene glycol-methacrylate co-polymer or mixtures thereof, e.g., agarose-dextran mixtures, is used to perform a gel permeation chromatography step.

The invention further provides for a TED library comprising a variety of at least at least any of $10^2$, $10^3$, $10^4$, $10^5$, or $10^6$ TEDs described herein, each with a different modified region flanked by the same regions of the same wild-type extravesicular domain (ED) at its N-terminus and C-terminus.

Preferably, the library of TEDs comprises at least any of $10^2$, $10^3$, $10^4$, $10^5$, or $10^6$ TEDs, each with different modified region and/or target specificity. Specifically, the repertoire of a library of TEDs comprises at least $2\times10^6$, $10^7$, $2\times10^7$, $10^8$ or $2\times10^8$ TEDs with different target specificity.

The invention further provides for a TSP library comprising a variety of at least at least any of $10^2$, $10^3$, $10^4$, $10^5$, or $10^6$ TSDs described herein, each with a different modified region flanked by the same regions of the same wild-type extravesicular domain (ED) at its N-terminus and C-terminus.

Preferably, the library of TSDs comprises at least any of $10^2$, $10^3$, $10^4$, $10^5$, or $10^6$ TSDs, each with different modified region and/or target specificity. Specifically, the repertoire of a library of TSDs comprises at least $2\times10^6$, $10^7$, $2\times10^7$, $10^8$ or $2\times10^8$ TSDs with different target specificity.

The invention further provides for a TEV library comprising a variety of at least at least any of $10^2$, $10^3$, $10^4$, $10^5$, or $10^6$ TEVs described herein, each with a different modified region flanked by the same regions of the same wild-type extravesicular domain (ED) at its N-terminus and C-terminus.

Preferably, the library of TEVs comprises at least any of $10^2$, $10^3$, $10^4$, $10^5$, or $10^6$ TEVs, each with different modified region and/or target specificity. Specifically, the repertoire of a library of TEVs comprises at least $2\times10^6$, $10^7$, $2\times10^7$, $10^8$ or $2\times10^8$ TEVs with different target specificity.

According to a specific aspect, the invention further provides for a library of binders, such as TEDs, TSPs, or TEVs described herein, produced by a method further described herein. Specifically, the method of producing any such library comprises mutagenizing a nucleic acid sequence comprising a polynucleotide encoding an ED of a EV surface protein by a mutagenesis method to obtain mutations of said ED within at least one predetermined modified region with a length of 3-20 contiguous amino acids flanked by regions of the wild-type ED sequence at its N-terminus and C-terminus, to incorporate a novel target binding site within the ED or the EV surface protein.

The invention further provides for a method of producing a library of target-specific extracellular vesicles (TEVs), comprising:

a) providing a repertoire of polynucleotides encoding a variety of target-specific EV surface proteins (TSPs), each comprising a different target binding site;
b) introducing said repertoire into said source cell(s); and
b) isolating a fraction comprising a repertoire of target-specific extracellular vesicles (TEVs), with a different target binding specificity, to produce a library of TEVs, wherein the repertoire of polynucleotides is produced by mutagenizing a polynucleotide encoding an EV surface protein by a mutagenesis method to obtain mutations of the extravesicular domain (ED) of said EV surface protein within at least one modified region with a length of 3-20 contiguous amino acids flanked by regions of the wild-type ED sequence at its N-terminus and C-terminus, to incorporate a target binding site within the ED.

Specifically, the repertoire can be produced by a mutagenesis method to modify said polynucleotide or gene within at least a predetermined region of the ED to produce the modified region described herein. Specifically, said mutagenesis method is applied to obtain a randomized amino acid sequence within the modified region. Specifically, said mutagenesis method employs mutagenesis of at least one or two distant regions of said ED or EV surface protein as described herein, thereby producing a repertoire of polynucleotides encoding a variety of EDs or EV surface proteins, each with a different binding specificity, and selecting a polynucleotide encoding the TED or TEV which specifically recognizes the target. Specifically, the repertoire of polynucleotides is comprised in genetic packages displaying the variety of surface proteins on the outer surface of extracellular vesicles.

Specifically, the display package further described herein is used e.g., a replicable genetic package encoding the surface protein described herein, wherein the display package is displayed on extracellular vesicles of natural or artificial origin, preferably selected from the group consisting of exosomes, microvesicles, nanoparticles and liposomes.

Optionally, a polynucleotide encoding the TED or the TSP is selected for producing the respective TED or TSP in a cell culture and/or for producing the respective TEV comprising said TED or TSP.

Mutagenesis of the surface protein or the respective coding sequence may be performed with or without using an EV, such as to introduce one or more point mutation(s) within predetermined regions of the EV surface protein, in particular within those regions which can be presented on the outer surface of an EV or a cell (i.e., the extravesicular or extracellular part of the surface protein).

Specifically, a repertoire of polynucleotides is produced which is comprised in genetic packages displaying the variety of surface proteins on the outer surface.

Specifically, the display package is a replicable genetic package encoding the surface protein described herein, such as selected from the group consisting of a bacteriophage, phagemid, and a cellular display package, preferably a bacterial, mammalian, or insect cell, or yeast, or an in vitro display system, such as a ribosome display system. Such in vitro display systems specifically translate nucleic acid information into the corresponding protein sequence that exhibits the associated binding specificity and affinity. Specifically preferred methods employ a display system selected from the group consisting of a phage, yeast, bacterium, ribosome, mRNA or mammalian cell display.

According to a specific example, the ED or EV surface protein described herein can be displayed by a bacteriophage or phagemid via an anchor protein selected from the group consisting of the protein product of gene III, gene VI, gene VII, gene VIII or gene IX, where gene III is often favored as it is located at the N-terminus of the phagemid or phage.

According to another specific example, the ED or EV surface protein described herein can be displayed by yeast which routinely displays proteins, e.g., by fusion to the Aga2 yeast surface protein. This is routinely used for yeast display libraries. Anchoring to the yeast cells can also be achieved via coexpression of an anchoring protein such as for example, Protein A. Alternatively, the soluble surface proteins can be secreted from the yeast cells and captured following derivatization of the yeast cell surface by an external addition of protein A or antibodies specifically recognizing a desired target sequence.

A series of display packages displaying different surface proteins, e.g., with different binding properties, may be provided. In particular, a series of display packages displaying different modifications of the same surface protein, e.g., different modifications within the artificial binding site of the surface protein, may be provided to display those proteins with different binding properties.

In the method as described herein, the display library is specifically contacted with a target, such that a series of members of the display library are selected according to their target binding properties. Amongst the members of the display library recognizing the target, one or more library members may be identified as having high target specificity and/or affinity. Such identification may be specifically understood as a step of selecting binders of any kind, i.e. a selection according to binding specificity.

Specific methods allow the simultaneous selection according to both binding and functionality, using any of the following methods and means: Fluorescence activated cell sorting (FACS) is routinely utilized for these studies, with any appropriate target cell, coupled with any detecting antibody, binder protein, or dye such as Annexin V that registers binding or phenotypic changes such as apoptosis. Any similarly sensitive system can track and characterize binding events to target cells by advanced imaging or photodetection systems of microscopic sensitivity. FACS is also a primary technique for fractionating the binders and characterizing their corresponding phenotypic changes in cells.

Additionally, there is a spectrum of technologies that are also used in high throughput proteomics and cell biology, of which highly automated microscopic analysis is one of the most useful for the present purposes. Improvements may be achieved with automated high-information content digital microscopy that robotically analyzes individual cells in samples.

Once a suitable binder is selected its coding sequence can be used to produce the surface protein or to engineer fusion proteins comprising said TSP e.g., a fusion of a transmembrane domain and said TED, and to produce recombinant cells expressing such proteins on the surface of vesicular and/or cellular membranes, or to otherwise produce the TEVs described herein comprising the TSP and/or presenting the TED on its outer surface.

Further provided herein is a method of selecting a candidate binder specifically recognizing a predetermined target from a library described herein, by contacting the repertoire with the target under conditions to allow specific target binding, selecting and isolating a candidate binder with proven target binding specificity.

In the method as described herein, the library is specifically contacted with a target e.g., a target antigen or a target cell, such that the target is bound by members of the library. Amongst the members of the library recognizing the target, one or more library members may be identified as having high target specificity and/or affinity. Such identification may be specifically understood as a step of selecting binders of any kind, i.e. a selection according to binding specificity.

FIGURES

FIG. 1: Sequences used herein.

SEQ ID NO:7, amino acid sequence of wildtype human CD81 LEL

SEQ ID NO:8, nucleotide sequence of wildtype human CD81 LEL

SEQ ID NO:87, amino acid sequence of human CD81

SEQ ID NO:88, nucleotide sequence of human CD81

SEQ ID NO:89, amino acid sequence of human CD9

SEQ ID NO:90, amino acid sequence of human CD53

SEQ ID NO:91, amino acid sequence of human TSPAN32

SEQ ID NO:92, amino acid sequence of human CD82

SEQ ID NO:93, amino acid sequence of human CD63

SEQ ID NO:94, amino acid sequence of human CD151

SEQ ID NO:95, amino acid sequence of human CD37

SEQ ID NO:96, amino acid sequence of human LAMP2

Extravascular Domains of CD81, CD9, CD53, TSPAN32, CD82, CD63, CD151, CD37, LAMP2:

SEQ ID NO:130, EC1 of human CD81

SEQ ID NO:131, EC2 of human CD81

SEQ ID NO:132: EC1 of human CD9

SEQ ID NO:182: EC1 of human CD9

SEQ ID NO:133: EC2 of human CD9

SEQ ID NO:134: EC1 of human CD53

SEQ ID NO:135 EC2 of human CD53

SEQ ID NO:136: EC1 of human TSPAN32

SEQ ID NO:137: EC2 of human TSPAN32

SEQ ID NO:138: EC1 of human CD82

SEQ ID NO:139: EC2 of human CD82

SEQ ID NO:140: EC1 of human CD63

SEQ ID NO:141: EC2 of human CD63

SEQ ID NO:142: EC1 of human CD151

SEQ ID NO:143: EC2 of human CD151

SEQ ID NO:144: EC1 of human CD37

SEQ ID NO:145: EC2 of human CD37

SEQ ID NO:146: ED (EC) of human LAMP2

Four Transmembrane Domains (TM1-4) of CD81, CD9, CD53, TSPAN32, CD82, CD63, CD151, CD37; One TM of LAMP2:

SEQ ID NO:147: TM1 of human CD81

SEQ ID NO:148: TM2 of human CD81

SEQ ID NO:149: TM3 of human CD81

SEQ ID NO:150: TM4 of human CD81

SEQ ID NO:151: TM1 of human CD9

SEQ ID NO:152: TM2 of human CD9

SEQ ID NO:153: TM3 of human CD9

SEQ ID NO:154: TM4 of human CD9

SEQ ID NO:155: TM1 of human CD53

SEQ ID NO:156: TM2 of human CD53

SEQ ID NO:157: TM3 of human CD53

SEQ ID NO:158: TM4 of human CD53

SEQ ID NO:159: TM1 of human TSPAN32

SEQ ID NO:160: TM2 of human TSPAN32

SEQ ID NO:161: TM3 of human TSPAN32

SEQ ID NO:162: TM4 of human TSPAN32

SEQ ID NO:163: TM1 of human CD82

SEQ ID NO:164: TM2 of human CD82

SEQ ID NO:165: TM3 of human CD82

SEQ ID NO:166: TM4 of human CD82

SEQ ID NO:167: TM1 of human CD63

SEQ ID NO:168: TM2 of human CD63

SEQ ID NO:169: TM3 of human CD63

SEQ ID NO:170: TM4 of human CD63

SEQ ID NO:171: TM1 of human CD151

SEQ ID NO:172: TM2 of human CD151

SEQ ID NO:173: TM3 of human CD151

SEQ ID NO:174: TM4 of human CD151

SEQ ID NO:175: TM1 of human CD37

SEQ ID NO:176: TM2 of human CD37

SEQ ID NO:177: TM3 of human CD37

SEQ ID NO:178: TM4 of human CD37

SEQ ID NO:179: TM of human LAMP2

Further Exemplary Tetraspanins:

TSPAN8, NP_001356689, SEQ ID NO:184

TSPAN14, NP_001121781, SEQ ID NO:185

CD231 (TSPAN7), NP_004606, SEQ ID NO:186

Integrin Family of Proteins

CD49d, NP_000876, SEQ ID NO:187

ITGB5, NP_001341694.1, SEQ ID NO:188

ITGB6, NP_000879.2, SEQ ID NO:189

ITGB7, NP_000880.1, SEQ ID NO:190

CD71, NP_003225, SEQ ID NO:191

Proteoglycans

CD138 (syndecan-1), NP_001006947, SEQ ID NO:192 syndecan-2, NP_002989, SEQ ID NO:193 syndecan-3, NP_055469, SEQ ID NO:194 syndecan-4, NP_002990, SEQ ID NO:195

HSPG2, NP_001278789.1, SEQ ID NO:196

5 Transmembrane Domains Protein Family

CD133, XP_011512195, SEQ ID NO:195

Type I Transmembrane Proteins

LD50, NP_001307534, SEQ ID NO:196

CD102, NP_001093259, SEQ ID NO:197

Notch Family

NOTCH1, NP_060087, SEQ ID NO:198

NOTCH2, NP_001186930, SEQ ID NO:199

NOTCH3, NP_000426, SEQ ID NO:200

NOTCH4, NP_004548, SEQ ID NO:201

DLL 1, NP_005609, SEQ ID NO:202

DLL4, NP_061947.1, SEQ ID NO:203

JAG1, NP_000205.1, SEQ ID NO:204

JAG2, NP_002217.3, SEQ ID NO:205

CD11a, XP_011544151.1, SEQ ID NO:206

CD11b, NP_001139280.1, SEQ ID NO:207

CD11c, NP_001139280.1, SEQ ID NO:208

CD18/ITGB2, NP_001120963.2, SEQ ID NO:209

CD41, NP_000410.2, SEQ ID NO:210

CD51, NP_001138472.1, SEQ ID NO:211

CD61, NP_000203.2, SEQ ID NO:212

CD104, NP_001308052.1, SEQ ID NO:213

Membrane Proteins with Enzymatic Activity (Enzymatic TM Proteins)

CD13, NP_001141.2, SEQ ID NO:214

Immune Regulatory Surface Proteins Including Fc Receptors, T-Cell Receptor, Complement Receptors, Interleukin Receptors, Immunoglobulins, MHCI or MHC-II Components

CD2, NP_001758.2, SEQ ID NO:215

CD3 epsilon, NP_000724.1, SEQ ID NO:216

CD3 zeta, NP_932170.1, SEQ ID NO:217

CD18, NP_001120963.2, SEQ ID NO:218

CD19, NP_001761.3, SEQ ID NO:219

CD30, NP_001268359.2, SEQ ID NO:220

CD34, NP_001764.1, SEQ ID NO:221

CD36, NP_001120915.1, SEQ ID NO:222

CD40, NP_001289682.1, SEQ ID NO:223

CD40L, NP_000065.1, SEQ ID NO:224

CD44, NP_001001391.1, SEQ ID NO:225

CD45, NP_001254727.1, SEQ ID NO:226

CD47, NP_001768.1, SEQ ID NO:227

CD86, NP_787058, SEQ ID NO:228

CD110, NP_005364.1, SEQ ID NO:229

CD111, NP_976031.1, SEQ ID NO:230

CD115, NP_001336665.1, SEQ ID NO:231
CD117, XP_016863667.1, SEQ ID NO:232
CD125, XP_011531979.1, SEQ ID NO:233
CD135, XP_011533319.1, SEQ ID NO:234
CD184, NP_001334985.1, SEQ ID NO:235
CD200, NP_001352780.1, SEQ ID NO:236
CD279, NP_005009.2, SEQ ID NO:237
CD273, NP_079515.2, SEQ ID NO:238
CD274, NP_054862.1, SEQ ID NO:239
CD362=syndecan-2 (see SEQ ID NO:193)
EGFR, NP_958441.1, SEQ ID NO:240
L1CAM, NP_001137435.1, SEQ ID NO:241
LFA-1, NP_001120963.2, SEQ ID NO:242
LGALS3BP, NP_005558.1, SEQ ID NO:243
MFGE8, NP_001297248.1, SEQ ID NO:244
SLIT2, NP_001276064.1, SEQ ID NO:245
STX3, NP_004168.1, SEQ ID NO:246

Surface Markers of Mesenchymal Stem Cells

CD44 (SEQ ID NO:225, as above)
CD45 (SEQ ID NO:226, as above)
CD71 (SEQ ID NO:191, as above)
CD73 (also included in the group of enzymatic TM proteins), NP_001191742.1, SEQ ID NO:247
CD90, NP_001298091.1, SEQ ID NO:248
CD29 (also included in the group of the integrin family), NP_596867.1, SEQ ID NO:249
CD105, NP_001265067.1, SEQ ID NO:250
CD106 (also included in the group of the sialoglycoproteins), NP_001069.1, SEQ ID NO:251
CD146, NP_006491.2, SEQ ID NO:252
CD164, NP_001135874.1, SEQ ID NO:253
CD166, NP_001618.2, SEQ ID NO:254
STRO-1, NP_004958.2, SEQ ID NO:255

Glycoproteins

CD54, NP_000192.2, SEQ ID NO:256
Sialoglycoprotein CD235a, NP_001295116, SEQ ID NO:257

Channeling Proteins, Including Ca-Channel Proteins

GLUR2, NP_000817.3, SEQ ID NO:258
GLUR3, NP_000819.3, SEQ ID NO:259
HLA-DM, NP_006111.2, SEQ ID NO:260

Miscellaneous:

FLOT2, NP_004466, SEQ ID NO:261

EV surface protein sequences are herein provided as amino acid sequences which may or may not include a signal sequence. It is herein understood that the EV protein sequences as used for the purpose of engineering binders such as TED, TSP, or TEV described herein, are those without the signal sequence of the respective sequence information, if any. The skilled person can easily identify which is a signal sequence included as the N-terminal part of a sequence identified herein.

Protein reference numbers referred to herein are respective NCBI References (National Center for Biotechnology Information, U.S. National Library of Medicine 8600 Rockville Pike, Bethesda MD, 20894 USA).

FIG. 2: Schematic illustration of a two-dimensional model of human CD81 (SEQ ID NO:87). The extracellular domain contains two loops, the small extravesicular loop (SEL) from amino acid Trp34 to Tyr63 and the large extravesicular loop (LEL) from Phe113 to Lys201. It comprises four transmembrane domains (TM), TM1 spanning Val12 to Leu33, TM2 spanning Tyr64 to Gln85, TM3 spanning Leu90 to Gly112 and TM4 spanning Leu202 to Met228.

Figure 3:
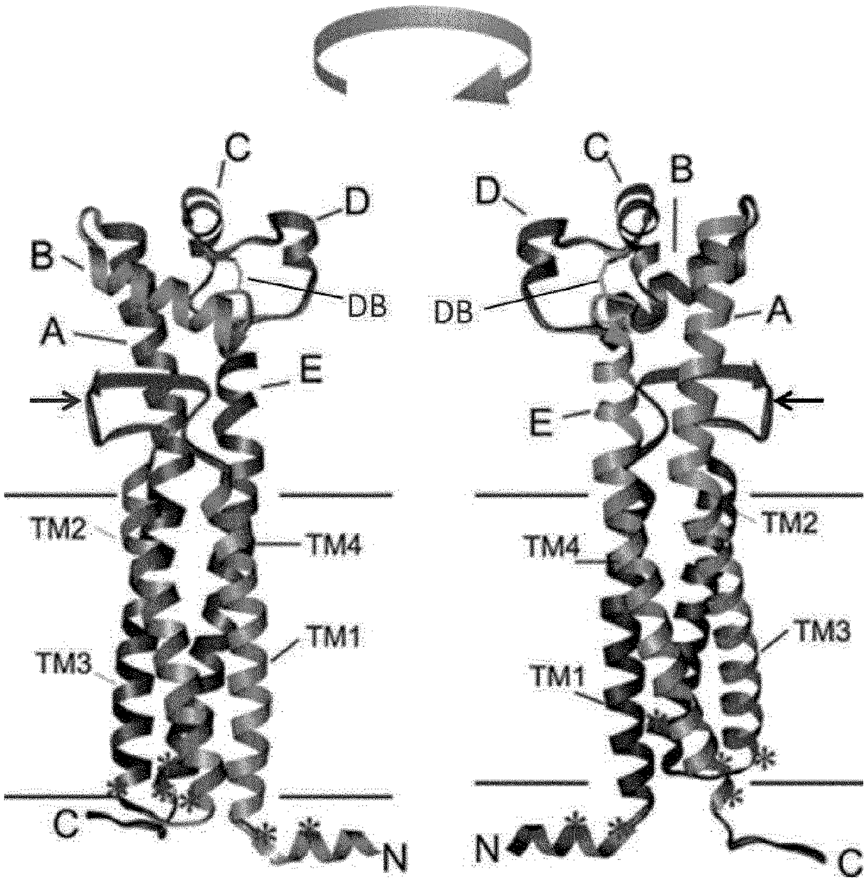

FIG. 3: Two different views of the structure of the wildtype tetraspanin CD81. The transmembrane regions TM1-TM4, the small extravesicular loop (indicated by arrows), the structurally conserved domain of the large extravesicular loop (helices A, B and E), and the variable region of this domain (helices C and D) is shown. The disulfide bridges (DB) of the LEL are indicated, and the intravesicular cysteine residues that are probable sites of palmitate attachment are marked by asterisks. The variable region of the LEL contains two (as for wildtype CD81 as shown here), three or four segments separated by cysteine residues.

Figure 4:
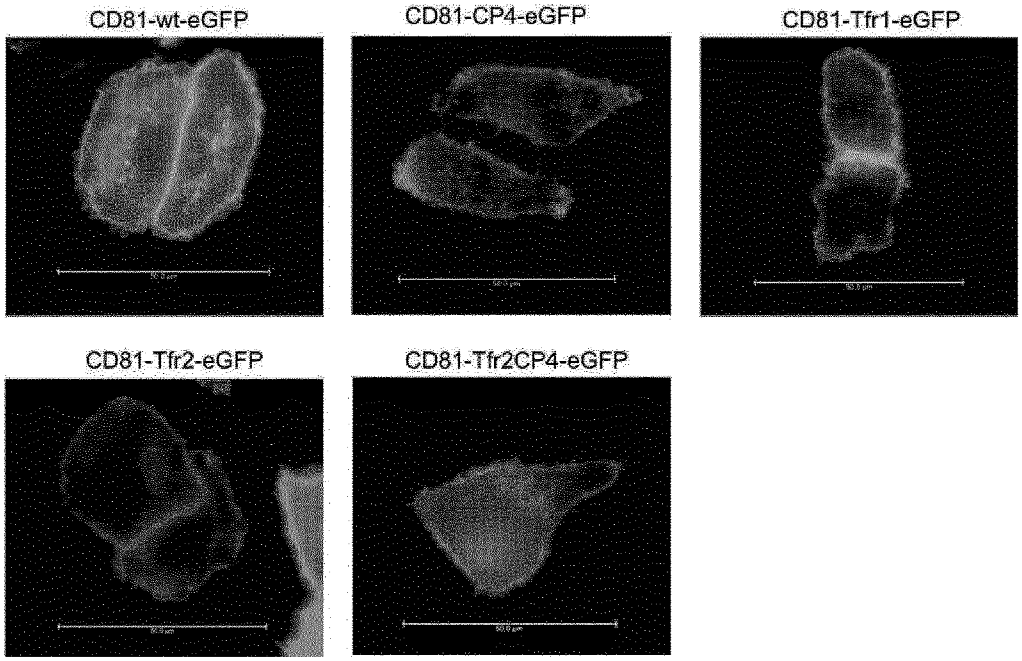

FIG. 4: Localization of recombinant CD81 at HeLa cell membranes.

FIG. 5: Recombinant Snorkel tag at the membrane. (A): snorkel-tagged CD81 (B): snorkel-tagged CD63 as visualized using anti HA antibodies in transiently transfected HeLa cells. (C) Immunogold-labelling in electron microscopy to confirm CD81 and HA positivity of recombinant EVs.

Figure 6:
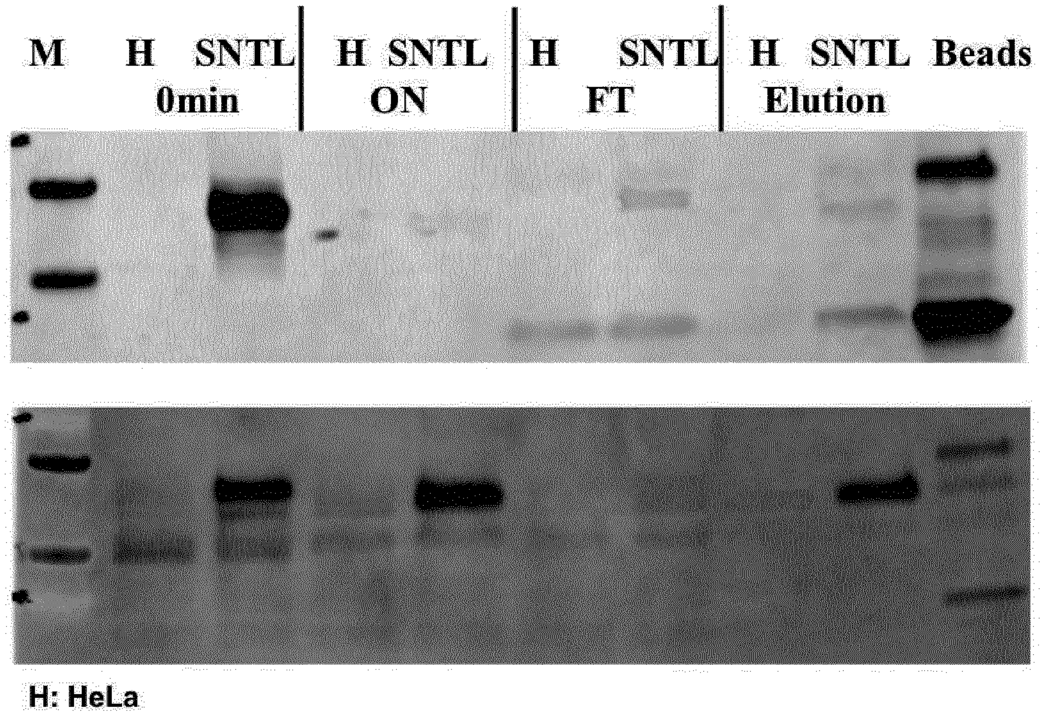

FIG. 6: Elution of recombinant EVs carrying a Snorkel Tag using PreScission protease.

FIG. 7: Characterization of recombinant EVs by size, amount and ratio of EVs carrying the recombinant CD81-GFP fusion protein.

Figure 8:
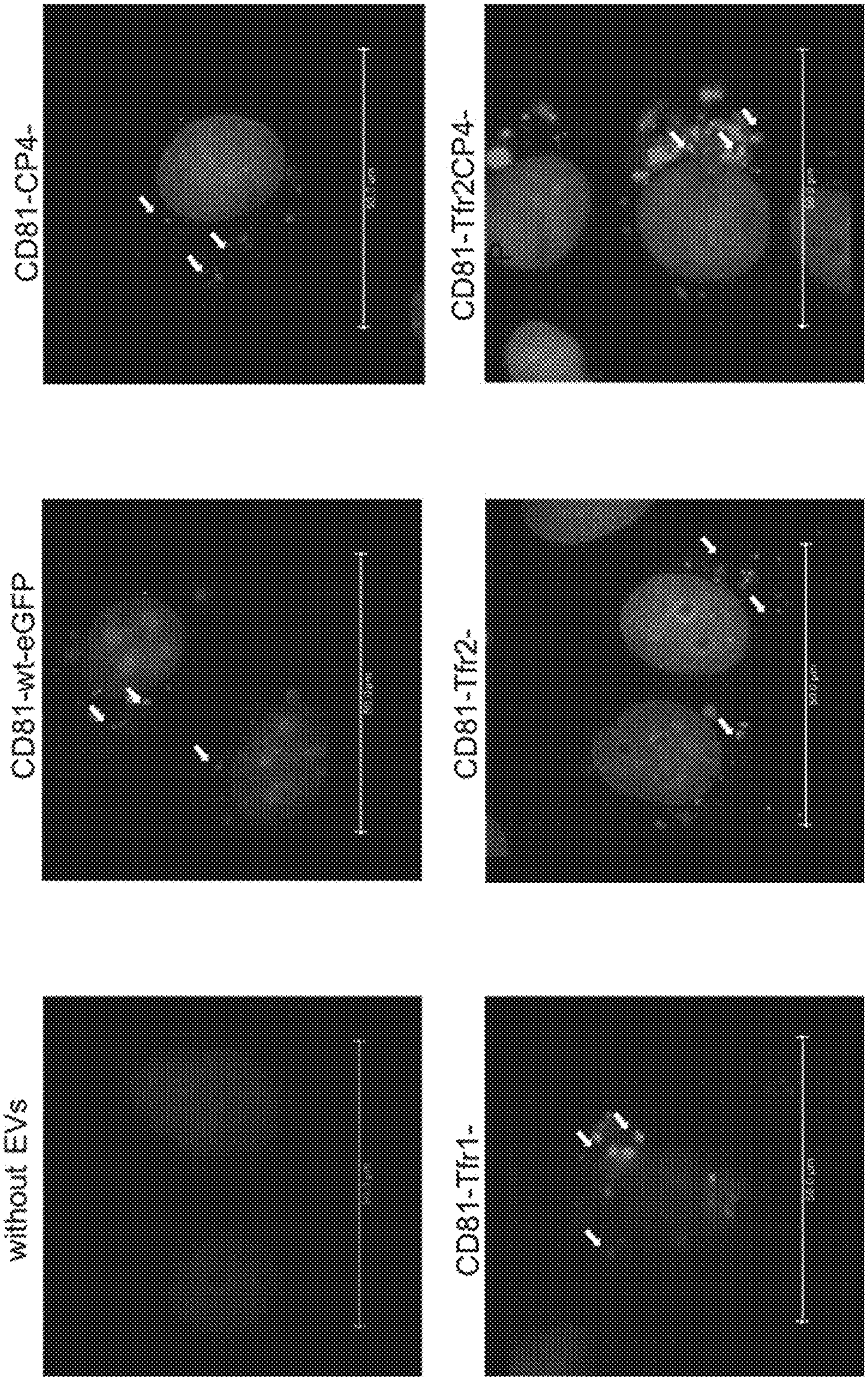
Figure 8:
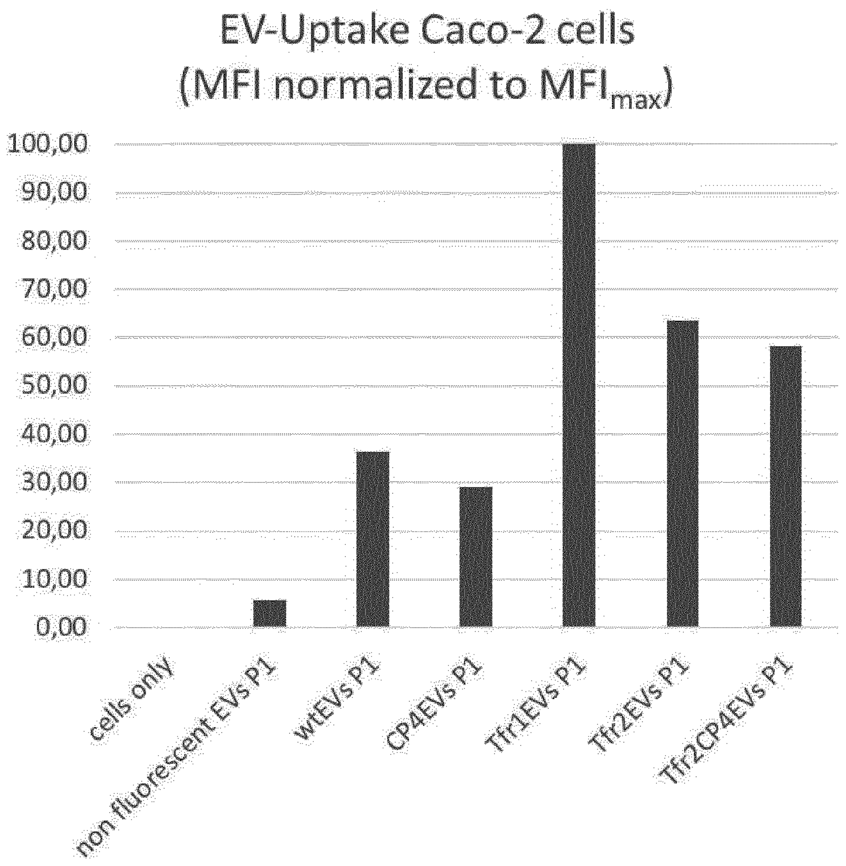

FIG. 8: EV uptake in CaCo-2 (A) Uptake visualized by fluorescence microscopy (B) quantitation of uptake positive cells by flow cytometry.

Figure 9:
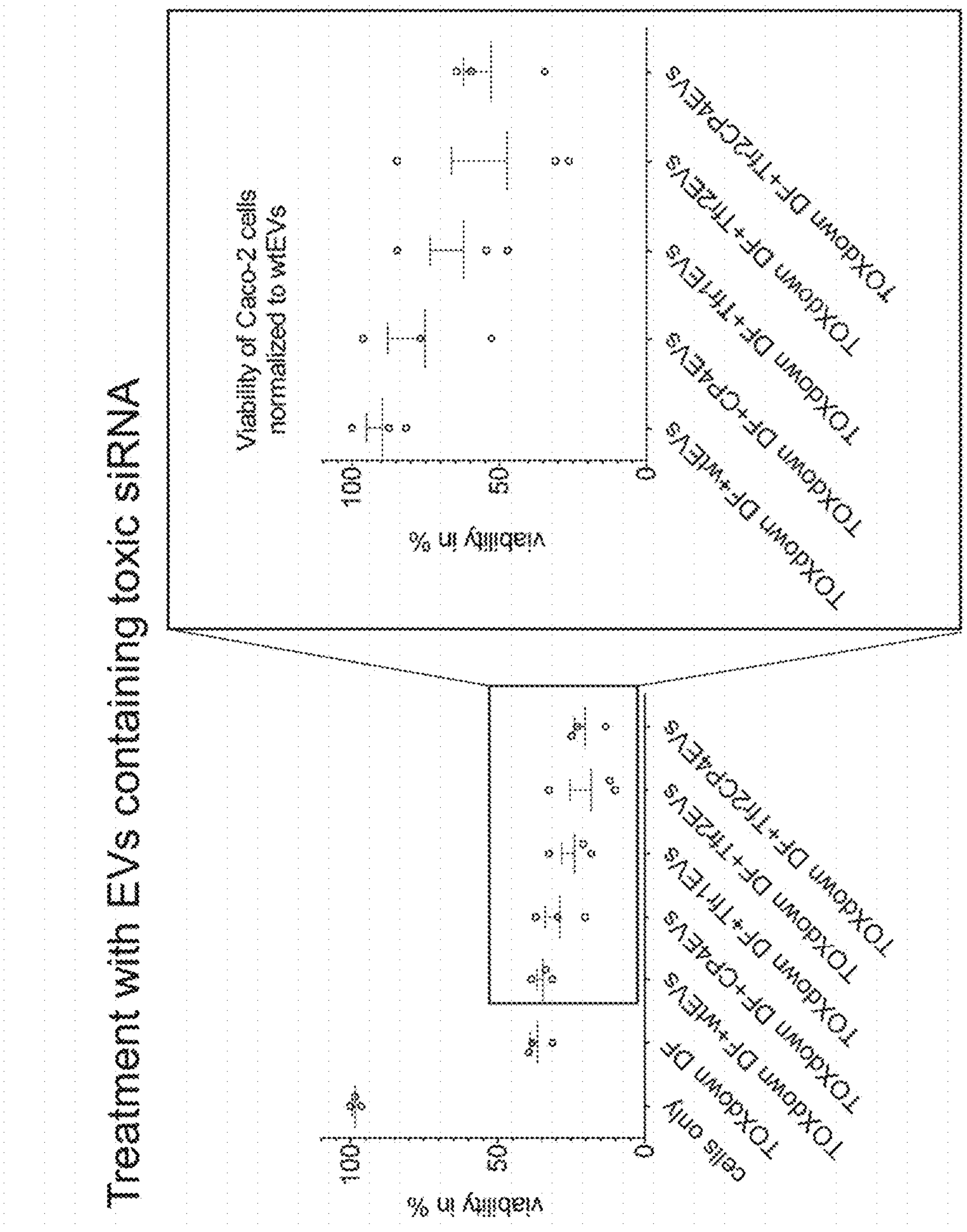
Figure 9:
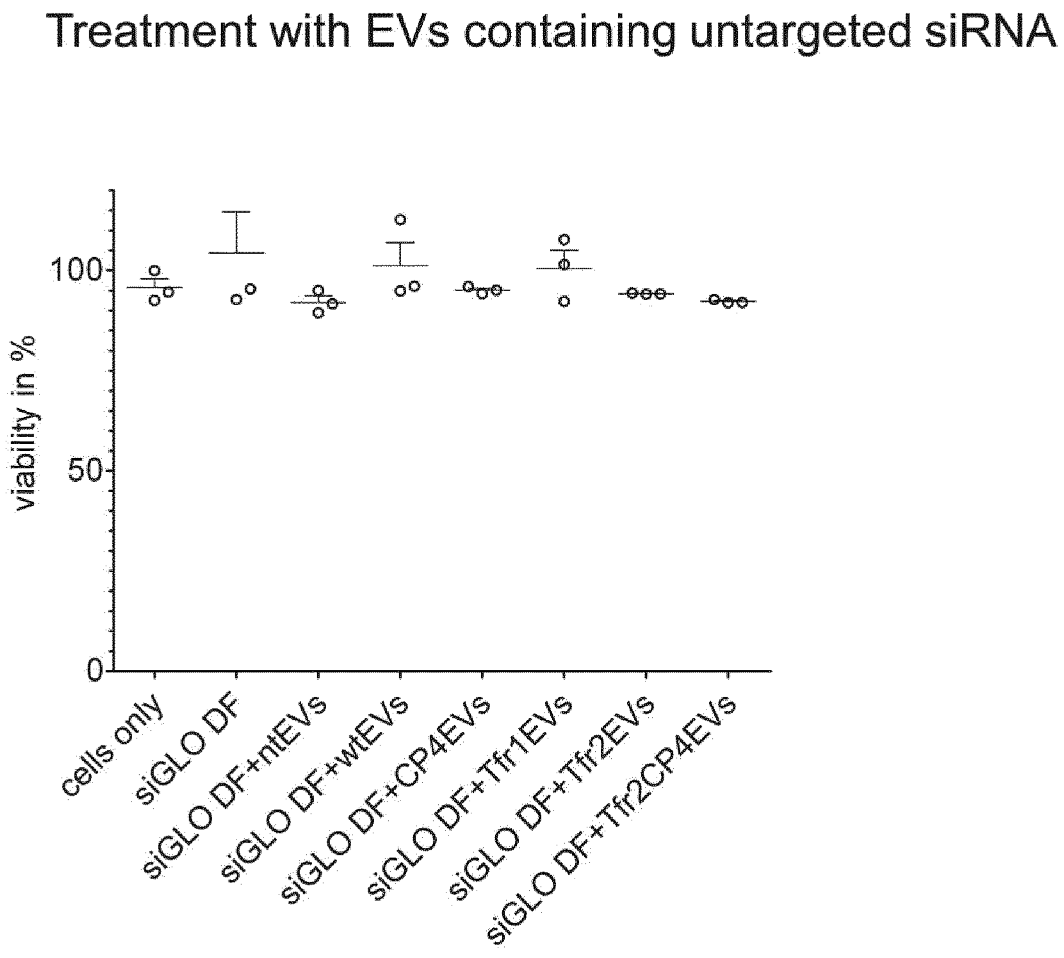

FIG. 9: Treatment of Caco-2 cells with recombinant EVs containing toxic siRNA.

DETAILED DESCRIPTION

Unless indicated or defined otherwise, all terms used herein have their usual meaning in the art, which will be clear to the skilled person. Reference is for example made to the standard handbooks, such as Sambrook et al, "Molecular Cloning: A Laboratory Manual" (2nd Ed.), Vols. 1-3, Cold Spring Harbor Laboratory Press (1989); Lewin, "Genes IV", Oxford University Press, New York, (1990), and Janeway et al, "Immunobiology" (5th Ed., or more recent editions), Garland Science, New York, 2001.

The subject matter of the claims specifically refers to artificial products or methods employing or producing such artificial products, which may be variants of native (wildtype) products. Though there can be a certain degree of sequence identity to the native structure, it is well understood that the materials, methods and uses of the invention, e.g., specifically referring to isolated nucleic acid sequences, amino acid sequences, expression constructs, transformed host cells and recombinant proteins, are "man-made" or synthetic, and are therefore not considered as a result of "laws of nature".

The term "domain" with respect to a protein domain such as an ED or a transmembrane domain is herein understood as a polypeptide or protein of a contiguous amino acid sequence which is at least a certain part (or the full length) of a polypeptide or protein. The domain can be comprised in a larger protein. Yet, a protein domain is also called domain while being isolated from a protein that is larger than the domain.

The term "expression" is understood in the following way. Nucleic acid molecules containing a desired coding sequence of an expression product such as e.g., an antibody as described herein, and control sequences such as e.g., a promoter in operable linkage, may be used for expression purposes. Hosts transformed or transfected with these sequences are capable of producing the encoded proteins. In order to effect transformation, the expression system may be included in a vector; however, the relevant DNA may also be integrated into the host chromosome. Specifically the term refers to a host cell and compatible vector under suitable conditions, e.g., for the expression of a protein coded for by foreign DNA carried by the vector and introduced to the host cell.

Coding DNA is a DNA sequence that encodes a particular amino acid sequence for a particular polypeptide or protein such as e.g., an antibody. Promoter DNA is a DNA sequence which initiates, regulates, or otherwise mediates or controls the expression of the coding DNA. Promoter DNA and coding DNA may be from the same gene or from different genes, and may be from the same or different organisms. Recombinant cloning vectors often include one or more replication systems for cloning or expression, one or more markers for selection in the host, e.g., antibiotic resistance, and one or more expression cassettes.

"Expression vectors" or "vectors" as used herein are defined as DNA sequences that are required for the transcription of cloned recombinant nucleotide sequences, i.e. of recombinant genes and the translation of their mRNA in a suitable host organism.

An "expression cassette" refers to a DNA coding sequence or segment of DNA that codes for an expression product that can be inserted into a vector at defined restriction sites. The cassette restriction sites are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct".

Expression vectors comprise the expression cassette and additionally usually comprise an origin for autonomous replication in the host cells or a genome integration site, one or more selectable markers (e.g., an amino acid synthesis gene or a gene conferring resistance to antibiotics such as zeocin, kanamycin, G418 or hygromycin), a number of restriction enzyme cleavage sites, a suitable promoter sequence and a transcription terminator, which components are operably linked together. The term "vector" as used herein includes autonomously replicating nucleotide sequences as well as genome integrating nucleotide sequences. A common type of vector is a "plasmid", which generally is a self-contained molecule of double-stranded DNA that can readily accept additional (foreign) DNA and which can readily be introduced into a suitable host cell. A plasmid vector often contains coding DNA and promoter DNA and has one or more restriction sites suitable for inserting foreign DNA. Specifically, the term "vector" or "plasmid" refers to a vehicle by which a DNA or RNA sequence (e.g., a foreign gene) can be introduced into a host cell, so as to transform the host and promote expression (e.g., transcription and translation) of the introduced sequence.

The term "extracellular vesicles", abbreviated as "EVs", including those EVs with target binding specificity such as TEVs described herein, is herein understood as cellular vesicles, or those vesicles originating from a cell, which are provided outside a cell. EVs can not only be produced in vivo or ex vivo by respective source or donor cells, but can also be artificially produced without using a cell, e.g., by in vitro methods of engineering liposomes or nanoparticles to produce synthetic EVs comprising the EV features as described herein.

EVs are typically membrane-packed vesicles that are secreted by a variety of cell types, including T cells, B cells, dendritic cells, platelets, mast cells, epithelial cells, endothelial cells, neuronal cells, cancerous cells, oligodendrocytes, Schwann cells, embryonic cells, and MSCs. EVs are also naturally occurring in physiological fluids such as normal urine, blood, bronchial lavage fluid, breast milk, saliva, cerebrospinal fluid, amniotic fluid, synovial fluid, and malignant ascites. It has been demonstrated that EVs perform an important role in cell-to-cell communication. They mediate intercellular communication, enabling the transfer of functional nucleic acids from the cell of origin to the recipient cells. They have been implicated in processes such as immune responses, homeostasis maintenance, coagulation, inflammation, cancer progression, angiogenesis, and antigen presentation. Thus, EVs participate in many physiological and pathological conditions.

EVs may contain biomolecular or synthetic cargo herein referred to as "load". Thus, they make an attractive delivery vehicle for targeted therapeutics or diagnostics owing to their stability in circulation, biocompatibility, low immunogenicity and toxicity profiles. EVs are specifically able to transport compounds between cells, including neurons. Advantageously, they are able to cross the blood brain barrier. This natural trafficking ability gives extracellular vesicles the potential to be used as delivery vehicles for various autologous or heterologous compounds.

Exemplary EVs described herein are exosomes or microvesicles.

Exosomes are a type of extracellular membrane-enclosed vesicle, which contains molecular constituents of the cell in which it was secreted from.

Exosomes constitute one of the main subclasses of EVs and have an endosomal origin. Exosomal EVs are nanometer-sized vesicles of endocytic origin that form by inward budding of the limiting membrane of multivesicular endosomes (MVEs). Thus, their size is equivalent to that of the intraluminal vesicle within MVEs, which generally ranges between 30 nm and 120 nm, preferably 50 to 100 nm.

The biogenesis of exosomal EVs occurs via the endocytosis-exocytosis pathway when cells absorb small amounts of intracellular fluid in a specific membrane region and form early endosomes. The early endosome begins to mature and expands into a late endosome; then intraluminal vesicles or multivesicular bodies (MVBs) are formed by internal budding of the endosomal membrane. The MVBs then fuse to the cell membrane and are released into the extracellular environment. At this point the vesicles are named exosomes, which are released via exocytosis that is regulated by p53 and under the control of the cytoskeleton activation pathway but not affected by calcium. Exosomal EVs may have a diameter of 30-100 nm and a density of 1.13 to 1.19 g/mL in a sucrose gradient; they can be collected by centrifugation e.g., at 100,000 g. After isolation, they can be stored as a lyophilisate, or in an aqueous solution e.g., at room temperature, or at refrigerator temperature (2°-8° C.), or frozen, e.g., without any toxic cryoprotectant agents (at −80° C., or higher up to −18° C.) for more than 6 months while maintaining their functions.

Exosomal EVs may contain large amounts of surface proteins such as annexins, tetraspanins e.g., CD63, CD81, and CD9, and heat-shock proteins, including Hsp60, Hsp70, and Hsp90. They also express Alix, tumor susceptibility gene 101 (Tsg101), and clathrin. Exosomal EVs specifically comprise a lipid bilayer membrane that protects their contents and enables them to move long distances in tissues. The membrane typically possesses small amounts of phosphatidylserine and large amounts of cholesterol, ceramide, and sphingolipids.

Microvesicles are a type of membrane-enclosed vesicle, derived from fragments of plasma membrane. Microvesicular EVs typically bud from the cell surface and their size may vary between 50 nm to 1000 nm. Artificial microvesicular vesicles, such as semi-synthetic EVs and fully-synthetic EVs, can have a size ranging from 10 to 1000 nm, preferably 10 to 500 nm, even more preferably 10 to 100 nm.

Microvesicular EVs are typically isolated by ultracentrifugation with a density of 1.04 to 1.07 g/mL in a sucrose gradient. Microvesicular EVs typically contain high amounts of phosphatidylserine-containing proteins associated with lipid rafts and are rich in the surface marker CD40 as well as cholesterol, sphingomyelin, and ceramide. Specifically, they are also encapsulated in a lipid bilayer membrane and comprise transmembrane proteins, such as tetraspanins.

Typically, apoptotic body EVs are released through outward blebbing and fragmentation of the cell membrane of apoptotic cells, and have a broad size range of 50-2,000 nm in diameter.

EVs typically interact with targets via surface ligand and adhesion molecules e.g., with target cells. In some cases, they may enter cells via endocytic uptake or by direct fusion of the vesicles to the cell membrane. They may also transmit their contents through adhesion to the cell surface mediated by the interaction of a lipid-ligand receptor. These interactions indicate that EVs may possess pivotal roles in cell-to-cell communication and immune modulation in different physiologic and pathologic conditions.

Nano-sized EVs represent an excellent alternative for drug delivery. As the composition of EV's membrane is typically from a source or donor cell (e.g., stem cells), these particles are non-immunogenic in nature allowing them to resist to fast clearance from circulation and thereby increasing the drug delivery efficiency to target tissues. They are known to naturally possess specific cell tropism or homing ability by cell type specific proteins (with their surface ligand and adhesion molecules), one of the key requirements for targeted drug delivery. However, natural targets are limited and problems with affinity and specificity are common. By engineering EVs comprising a surface protein as described herein, the target-specific EVs are provided which can be targeted to any desired target or cell type with great specificity and affinity.

EVs described herein are particularly useful for medical purposes e.g., to diagnose or treat diseases or disease conditions, in particular those diseases where targeted therapy has proven to ameliorate disease conditions.

Mesenchymal stem cell-derived EVs, especially exosomal EVs, may be particularly useful with regard to their use as regenerative therapies. EVs originating from mesenchymal stem cells (MSCs) can carry biologically active molecules which can be transferred to target cells to exert their therapeutic effects like regenerating tissue injuries suppressing inflammatory responses modulating the immune system and many other beneficial effects. Accordingly, EVs can be an effective safe and cheap therapeutic approach in cell-free regenerative medicine.

EVs can be a suitable drug delivery system, in particular to cross biological barriers (e.g., the blood brain barrier) and deliver their load to otherwise unaccessible sites.

EVs can be formulated to exhibit intended drug carrying activity through various approaches including biological, chemical and physical means. Encapsulation of active substances or drugs (e.g., chemicals, RNAs, DNA, proteins or lipids) into EVs can greatly increase their bioavailability by preserving their integrity and biological activity in vivo. Lipid membranes from donor cells are suited to avoid phagocytosis, degradation and modification in host circulation. In particular, autologous but also heterologous EVs typically avoid entrapment in the reticuloendothelial system (also known as mononuclear phagocytic system) and are non-immunogenic in most, if not all, parameters.

Various approaches can be utilized for loading active substances agents into EVs. These include (1) loading to purified EVs ex vivo, or (2) pre-loading to donor (source) cells prior to EV production, each followed by isolation and optionally purification.

Ex vivo loading strategies mostly utilize passive packaging of therapeutic molecules, ranging from simple incubation to more sophisticated chemical and/or physical methods. Hydrophobic (i.e., lipophilic) molecules, such as antioxidants, anti-cancer drugs, lipophilic dyes, can be spontaneously packaged into EV under ambient conditions. Indeed, successful loading of curcumin, doxorubicin and paclitaxel into EVs has been demonstrated. Compared to standard liposomes composed of phosphatidylcholine and cholesterol, EVs exhibit higher loading efficiency and loading capacity to hydrophobic chemical drugs.

Many active substances cannot penetrate the membrane of EVs freely, therefore loading of EVs is typically effected e.g., by means of electroporation, sonication, permeabilization, fusogenic liposomes, polymeric carriers and/or other physical insults. Sonication and extrusion, or permeabilization with saponin, have been shown to result in stable EV reformation with high loading efficiency.

Electroporation specifically applies an electrical field to create pores in the membrane of EVs temporally, thereby allowing the movement of active substances into the lumen of EVs. Electroporation is also known to induce vesicular aggregation thereby affecting the integrity of the vesicles. The skilled person may choose several parameters including EV sources and concentrations, the cargo molecules (the load) and the applying voltage with time for optimal loading of the cargo.

EVs are conveniently loaded upon electroporation. Studies demonstrated the enhanced efficacy with decreased adverse effects typically associated with chemotherapeutic drugs when compared to either EV-free drugs or drug-loaded liposomes.

EVs are natural carriers of various nucleic acid molecules e.g., mRNA, miRNA and various noncoding RNAs, or DNA molecules, and thus represent suitable vehicles for nucleic acid transfer. Although nucleic acid molecules are effective means for the regulation of genes of interests, their low stability and transducibility in circulation dictates the necessity of vehicles that can protect and deliver these therapeutic molecules to target cells and tissues. Again, electroporation can be performed to load the material into EVs.

Sonication can be a suitable alternative for active loading of molecules with minimal aggregation and degradation.

Different methods of pre-loading of drugs to donor (source) cells prior to the release of EVs exist in the field. For example, active substances can be incorporated to EVs from host cells, in particular recombinant host cells overexpressing a protein of interest or a cellular metabolite. As described herein, EVs can be isolated from donor cells transfected with heterologous genes in addition to the gene encoding the surface protein incorporating the target binding site. Since the load may comprise proteins, loading of recombinant proteins expressed by host cells can be an attractive mode of protein delivery by loaded EVs. A number of model proteins, including ovalbumin, catalase, glial cell-line derived neurotropic factor (GDNF) have already been successfully loaded into EVs from gene-modified host cells.

The use of target-specific EVs as described herein represents a next generation drug delivery system with ability to transverse complex biological barriers such as the blood brain barrier, while avoiding or overcoming a number of safety concerns related to drugs or vehicles, such as cytotoxicity, short biodistribution and low efficiency of targeted delivery. Chemical drugs and biological molecules with low stability in circulation and/or low transducibility to target cells can be efficiently transferred to cytoplasm of target cells without undergoing endosomal and lysosomal degradation.

As is described herein, EVs may be produced to target certain tissues, cells, artificial surfaces or soluble compounds by the artificial target binding site. EVs can be engineered for the purpose of expressing suitable surface proteins and structures incorporating the binding site. For example, surface proteins can be overexpressed in source cells to be expressed on the surface of the EVs employing suitable recombinant expression systems in the source cells.

The artificial target binding site is either engineered prior to or after vesicle formation. For example, the binding site may be incorporated within the surface protein as described herein at pre-determined regions to comprise e.g., loop, helical, and/or linear (peptide) structures. Specific target contact surfaces or binding residues within said at least two distant regions of said surface protein may be produced in situ, i.e. when producing the EV e.g., by methods of recombining nucleic acid molecules such as employing methods of mutagenizing a source cells producing point mutations in the respective surface proteins, and/or by further modifications of EVs involving biologic, enzymatic and/or chemical reactions.

The EVs described herein are suitably provided in an EV preparation comprising isolated EVs. EVs may be characterized by certain features which can be determined by suitable quality control measures, such as determining the size, density, the amount and composition of the load, the target binding affinity and/or selectivity, purity, etc.

Exemplary methods of quality control are further described in the Examples section.

The term "extravesicular domain", abbreviated ED, as used herein is understood to encompass a protein domain which is positioned at the outer surface (the extravesicular surface) of an EV when attached or bound to the EV. Yet, a protein domain is also called an ED while being isolated from an EV or isolated from an EV surface protein.

The term "flanking" or "flanked" as used herein with respect to elements of an amino acid sequence or nucleotide sequence is herein understood as follows: A first sequence element is said to be "flanked" by a second sequence element when the first sequence element is located immediately adjacent to the second sequence element, thereby providing a contiguous sequence of said first and second sequences. The linear first sequence element may be flanked by another element at only one of its termini or at both termini, i.e. on one or both sides.

In a TED described herein, the modified region is specifically flanked by two flanking sequences, one at its N-terminus, and one at its C-terminus. Thus, such modified region is positioned between the flanking sequences, also called "embedded"

The term "host cell" as used herein shall refer to primary subject cells transformed to produce a particular recombinant protein, such as a surface protein as described herein, or to produce the EV described herein, and any progeny thereof. It should be understood that not all progeny are exactly identical to the parental cell (due to deliberate or inadvertent mutations or differences in environment), however, such altered progeny are included in these terms, so long as the progeny retain the same functionality as that of the originally transformed cell. The term "host cell line" refers to a cell line of host cells as used for expressing a recombinant gene to produce recombinant polypeptides or proteins. The term "cell line" as used herein refers to an established clone of a particular cell type that has acquired the ability to proliferate over a prolonged period of time. Such host cell or host cell line may be maintained in cell culture and/or cultured to produce a recombinant polypeptide.

The term "isolated" or "isolation" as used herein with respect to a modified region of an ED shall refer to a peptide consisting of the amino acid sequence of the modified region that has been sufficiently separated from the flanking sequences of the ED, so as to exist in "substantially pure" form. "Isolated" does not necessarily mean the exclusion of artificial or synthetic peptides, or mixtures of such peptides with other compounds or materials, or the presence of impurities that do not interfere with the fundamental binding activity, and that may be present, for example, due to incomplete purification. The term "isolated" is also meant to include those chemically synthesized.

In particular, an modified region can be isolated from the TED as described herein, or isolated from the TSP described herein, or provided as a respective isolated peptide for the purpose of comparing its binding properties, such as target binding affinity and/or specificity as compared to the same modified region that is comprised in (not isolated from) the TED and TSP, respectively.

The term "isolated" or "isolation" as used herein with respect to an EV described herein shall refer to such vesicle that has been sufficiently separated from the environment with which it would naturally be associated, so as to exist in "substantially pure" form. "Isolated" does not necessarily mean the exclusion of artificial or synthetic mixtures with other compounds or materials, or the presence of impurities that do not interfere with the fundamental activity, and that may be present, for example, due to incomplete purification. In particular, isolated EVs as described herein are also meant to include those chemically synthesized.

With reference to polypeptides or proteins, such as EV surface proteins described herein, the term "isolated" shall specifically refer to compounds that are free or substantially free of material with which they are naturally associated such as other compounds with which they are found in their natural environment, or the environment in which they are prepared (eg. cell culture) when such preparation is by recombinant DNA technology practiced in vitro or in vivo.

A "library" as described herein with respect to a binder described herein, in particular a TED, TSP, or TEV described herein, is understood to comprise a repertoire of binders that includes a number of different target binding species (library members) that covers a certain variety of binders. The library typically comprises library members which can be distinguished by their functional binding and thus be selected according to the desired binding properties.

A TED library described herein specifically includes a set or a collection of TEDs, in particular TEVs described herein, each with a different modified region embedded in the same wild-type sequences of the same wild-type ED.

A TSP library described herein specifically includes a set or a collection of TSPs, in particular TSPs described herein, each with a different TED embedded in the same wild-type sequences of the same wild-type EV surface protein. The TSP library may comprise a library of EDs, such as a TED library. A TED library is suitably produced by mutagenizing the ED or an EV surface protein thereby producing a repertoire of ED and EV surface protein mutants, respectively, either as soluble proteins or on the surface of an EV.

A TEV library described herein specifically includes a set or a collection of TEVs, in particular TEVs described herein, each with a different TED embedded in the same wild-type sequences of the same wild-type EV surface protein bound to the membrane of the vesicle. The TEV library may comprise a library of surface proteins, such as a TSP library.

Libraries can be constructed by well-known techniques, involving suitable methods of mutagenesis, e.g., site-directed mutagenesis of extravesicular domains of a surface protein.

Libraries as described herein preferably comprise at least $10^2$ library members, more preferred at least $10^3$, more preferred at least $10^4$, more preferred at least $10^5$, more preferred at least $10^6$ library members, more preferred at least $10^7$, more preferred at least $10^8$, more preferred at least $10^9$, more preferred at least $10^{10}$, more preferred at least $10^{11}$, up to $10^{12}$ members of a library.

Specifically, the library comprises at least $10^2$, $10^3$, $10^4$, $10^5$, or $10^6$ library members, wherein each library member differs in at least one nucleotide in the sequence of the modified surface protein. Specifically, the library comprises at least $10^6$ library members, wherein each library member has a different target binding site or specificity.

Any protein or gene diversity library may be used for the purpose described herein, which, e.g., includes a high number of individual library members, to create a diversity of sequences, or employing preselected libraries, which are e.g., enriched in stabilized or functionally active library members.

For example, a display system can couple a given protein, herein the surface protein described herein, with its encoding nucleic acid, e.g., its encoding mRNA, cDNA or genes. Thus, each member of a library comprises a nucleic acid encoding the modified surface protein which is displayed thereon. Display systems encompass, without being limited to, cells, virus such as phages, ribosomes, eukaryotic cells such as yeast, DNAs including plasmids, and mRNA display.

As is well-known in the art, there is a variety of display and selection technologies that may be used for the identification and isolation of proteins with certain binding characteristics and affinities, including, for example, display technologies such as cellular and non-cellular methods, in particular mobilized display systems. Among the cellular systems the phage display, virus display, yeast or other eukaryotic cell display, such as mammalian or insect cell display, may be used. Mobilized systems are relating to display systems in the soluble form, such as in vitro display systems, among them ribosome display, mRNA display or nucleic acid display.

Specific libraries are provided for herein to display a diversity of surface proteins, and/or a diversity of the surface proteins anchored to an EV or cell. Preferably, the libraries are phage display or yeast libraries. Specifically, the yeast host cell exhibits surface protein described herein at the surface of the yeast cell. Phage and phagemid display systems are well-known for their versatility and potential ability to streamline the selection process. Yeast display offers a number of attractive features: The eukaryotic transcription and translation machinery is very well suited for expression of proteins, and the use of flow cytometry allows high-throughput quantitative analysis of individual clones in real-time, using scaffold ligands.

The yeast host cell is preferably selected from the genera *Saccharomyces, Pichia, Hansenula, Schizisaccharomyces, Kluyveromyces, Yarrowia* and *Candida*. Most preferred the host cell is *Saccharomyces cerevisiae.*

In certain cases, a repertoire of surface proteins described herein is displayed such that entity comprising DNA, RNA or cDNA encoding a surface protein described herein may be directly connected to the surface protein that it encodes, as in RNA or DNA display libraries. In such case, the surface protein variants are generated by modifications of the methods of cell-free protein synthesis.

Screening for binding activity (or any other desired activity) in the library is conducted according to methods well-known in the art, for instance from phage display technology. For example, targets immobilized to a solid phase can be used to identify and isolate binding members of a repertoire. Screening allows selection of members of a repertoire according to desired characteristics.

In a method of selecting suitable binders of a target, it is advantageous to provide a large multiplicity of each binder in the repertoire of library members, e.g., of at least 10 copies, to increase the chance of selecting one or more candidate binding sequences, which can be further characterized for the suitability to engineer a target-specific extracellular vesicle construct.

Screening the library for library members comprising a target-binding structure may be done by any suitable selection method. The screening step may comprise one or several rounds of selection (also referred to as panning).

One or several rounds of selection encompass e.g., 1, 2, or preferably 3, and may encompass 4, 5, 6, 7, 8, 9, or 10 rounds of selection. In particular, the rounds of selection may comprise incubating the library in the presence of said target, so as to select the proteins which bind said target, or an epitope thereof.

The term “mutagenesis” as used herein refers to any art recognized technique for altering a polynucleotide or polypeptide sequence. Preferred types of mutagenesis include error prone PCR mutagenesis, saturation mutagenesis, or other site directed mutagenesis. Any of the known mutagenesis methods may be employed, to introduce point mutations at desired positions, e.g., by randomisation techniques. In some cases positions are chosen randomly, e.g., with either any of the possible amino acids or a selection of preferred amino acids to randomise the antibody sequences.

The term “recombinant” as used herein shall mean “being prepared by or the result of genetic engineering”. Alternatively, the term “engineered” is used. For example, a surface protein may be mutated to produce a variant by engineering the respective parent sequence to produce a variant of the parent sequence. A recombinant host specifically comprises a recombinant expression vector or cloning vector, or it has been genetically engineered to contain a recombinant nucleic acid sequence, in particular employing nucleotide sequence foreign to the host. A recombinant protein is produced by expressing a respective recombinant nucleic acid in a host.

A “point mutation” is herein particularly understood as the engineering of a polynucleotide that results in the expression of an amino acid sequence that differs from the non-engineered amino acid sequence in the substitution or exchange, deletion or insertion of one or more amino acids for different amino acids, at a certain position (at one position) of the amino acid sequence. Specifically, one or more single (non-consecutive) or doublets of amino acid residues may be subject to a point mutation. Specifically preferred methods of mutagenesis provide of point mutations at selected positions, preferably the substitution of one amino acid by another one at one (predetermined) amino acid position or more amino acids at only a predetermined amino acid position. One or more point mutations can be within a modified region, in particular point mutations at non-consecutive or consecutive positions within the region.

The term "repertoire" as used herein shall refer to a collection of variants, such as variants of the modified surface protein with a variety of specificities to bind the target with high affinity. Typically, the structure of the surface protein, which comprises the extracellular domain with helix and loop regions, is the same in such repertoire. The variety will specifically reflect the diversity of the binding site comprising binding residues within one or more predetermined positions or regions to be modified e.g., at least two distant regions which are part of the same target binding site to specifically recognize and bind the target.

The repertoire as described herein is specifically provided within a library, which is a mixture of heterogeneous surface proteins, target-specific extracellular vesicle constructs or targets. The library may take the form of a simple mixture of the proteins or EVs, or may be in the form of respective binding regions such modified surface proteins, either as isolated polypeptides or proteins, or as nucleic acids encoding such polypeptides or proteins, or even organisms or cells expressing the nucleic acids, e.g., for example bacteria, viruses, animal or plant cells and the like, transformed with a library of nucleic acids, reflecting the variety of target-specific binders of said repertoire.

The term "subject" as used herein shall refer to a warm-blooded mammalian, particularly a human being or a non-human animal. Thus, the term "subject" may also particularly refer to animals including dogs, cats, rabbits, horses, cattle, pigs and poultry. In particular, the antibody as described herein is provided for medical use to treat a subject or patient in need of prophylaxis or treatment of a disease condition. The term "patient" includes human and other mammalian subjects that receive either prophylactic or therapeutic treatment. The term "treatment" is thus meant to include both prophylactic and therapeutic treatment.

The term "surface protein" including "EV surface proteins" as used herein refers to a protein located on or at the surface of an EV, which is anchored within in the lipid bilayer membrane of the EV. To this end "anchoring" is herein understood to bind to the cellular surface by fusion to a protein domain which is located within the membrane. A surface protein is herein understood to comprise at least one ED and at least one transmembrane domain. Such surface protein can be bound to an EV through integration of said at least one transmembrane protein domain to the membrane of an EV. The transmembrane domain(s) may be part of the surface protein, or fused to a surface protein, e.g., for the purpose of anchoring the surface protein to the EV.

The term "EV surface protein" specifically includes "exosomal proteins" and those proteins of an EV that can be utilized to transport a polypeptide or protein construct to a suitable vesicular structure or EV. Specifically, the term includes any protzein that enables transporting, trafficking or shuttling of a polypeptide or protein construct to a vesicular structure, such as an EV. Examples of such EV surface protein are for instance isolated, synthetic and or recombinant amino acid sequence, comprising in whole or in part (as fragments) one or more types of the EV surface proteins described herein, such as identified by the sequences provided herein (in particular in FIG. 1) (excluding signal sequences, if any), or isoforms thereof, including cloned isoforms.

Exemplary EV surface proteins are a) tetraspan-like proteins including
  i) tetraspanins e.g., any one of the group consisting of CD81 (such as human CD81, SEQ ID NO:87), CD9 (such as human CD9, SEQ ID NO:89), CD53 (such as human CD53, SEQ ID NO:90), TSPAN32 (such as human TSPAN32, SEQ ID NO:91), CD82 (such as human CD82, SEQ ID NO:92), CD63 (such as human CD63, SEQ ID NO:93), CD151 (such as human CD151, SEQ ID NO:94), CD37 (such as human CD37, SEQ ID NO:95), TSPAN8 (such as human TSPAN8, SEQ ID NO:184), TSPAN14 (such as human TSPAN14, SEQ ID NO:185), or CD231 (TSPAN7) (such as human CD231 (TSPAN7), SEQ ID NO:186; or
  ii) lysosome-associated membrane proteins, e.g., LAMP2 (such as human LAMP2, SEQ ID NO:96);
b) proteins of the integrin family e.g., CD49d (such as human CD49d, SEQ ID NO:187), ITGB5 (such as human ITGB5, SEQ ID NO:188), ITGB6 (such as human ITGB6, SEQ ID NO:189), ITGB7 (such as human ITGB7, SEQ ID NO:190), CD71 (such as human CD71, SEQ ID NO:191), CD29 (such as human CD29, SEQ ID NO:249);
c) proteoglycans e.g., CD138 (syndecan-1) (such as human CD138 (syndecan-1), SEQ ID NO:192), syndecan-2 (such as human syndecan-2, SEQ ID NO:193), syndecan-3 (such as human syndecan-3, SEQ ID NO:194), syndecan-4 (such as human syndecan-4, SEQ ID NO:195), HSPG2 (such as human HSPG2, SEQ ID NO:196);
d) family of five-transmembrane domains proteins e.g., CD133 (such as human CD133, SEQ ID NO:195);
e) type I transmembrane proteins e.g., (such as human LD50, SEQ ID NO:196), CD102 (such as human CD102, SEQ ID NO:197);
f) Notch family e.g., NOTCH1 (such as human NOTCH1, SEQ ID NO:198), NOTCH2 (such as human NOTCH2, SEQ ID NO:199), NOTCH3 (such as human NOTCH3, SEQ ID NO:200), NOTCH4 (such as human NOTCH4, SEQ ID NO:201), DLL1 (such as human DLL1, SEQ ID NO:202), DLL4 (such as human DLL4, SEQ ID NO:203), JAG1 (such as human JAG1, SEQ ID NO:204), JAG2 (such as human JAG2, SEQ ID NO:205), CD11a (such as human CD11a, SEQ ID NO:206), CD11 b (such as human CD11b, SEQ ID NO:207), CD11c (such as human CD11c, SEQ ID NO:208), CD18/ITGB2 (such as human CD18/ITGB2, SEQ ID NO:209), CD41 (such as human CD41, SEQ ID NO:210), CD51 (such as human CD51, SEQ ID NO:211), CD61 (such as human CD61, SEQ ID NO:212), CD104 (such as human CD104, SEQ ID NO:213);
g) membrane proteins with enzymatic activity (enzymatic TM proteins) e.g., CD13 (such as human CD13, SEQ ID NO:214), CD73 (such as human CD73, SEQ ID NO:247);
h) immune regulatory surface proteins, including e.g., Fc receptors, T-cell receptors, complement receptors, interleukin receptors, immunoglobulins, MHCI or MHC-II components; exemplary proteins are CD2 (such as human CD2, SEQ ID NO:215), CD3 epsilon (such as human CD3 epsilon, SEQ ID NO:216), CD3 zeta (such as human CD3 zeta, SEQ ID NO:217), CD18 (such as human CD18, SEQ ID NO:218), CD19 (such as human CD19, SEQ ID NO:219), CD30 (such as human CD30, SEQ ID NO:220), CD34 (such as human CD34, SEQ ID NO:221), CD36 (such as human CD36, SEQ ID NO:222), CD40 (such as human CD40, SEQ ID NO:223), CD40L (such as human CD40L, SEQ ID NO:224), CD44 (such as human CD44, SEQ ID NO:225), CD45 (such as human CD45, SEQ ID NO:226), CD47 (such as human CD47, SEQ ID NO:227), CD86 (such as human CD86, SEQ ID NO:228), CD110 (such as human CD110, SEQ ID NO:229), CD111 (such as human CD111, SEQ ID NO:230), CD115 (such as human CD115, SEQ ID NO:231), CD117 (such as human CD117, SEQ ID NO:232), CD125 (such as human CD125, SEQ ID NO:233), CD135 (such as human CD135, SEQ ID NO:234), CD184 (such as human CD184, SEQ ID NO:235), CD200 (such as human CD200, SEQ ID NO:236), CD279 (such as human CD279, SEQ ID NO:237), CD273 (such as human CD273, SEQ ID NO:238), CD274 (such as human CD274, SEQ ID NO:239), CD362=syndecan-2 (such as human, SEQ ID NO:193), EGFR (such as human EGFR, SEQ ID NO:240), L1CAM (such as human L1CAM, SEQ ID NO:241), LFA-1 (such as human LFA-1, SEQ ID NO:242), LGALS3BP (such as human LGALS3BP, SEQ ID NO:243), MFGE8 (such as human MFGE8, SEQ ID NO:244), SLIT2 (such as human SLIT2, SEQ ID NO:245), STX3 (such as human STX3, SEQ ID NO:246);

i) surface markers of mesenchymal stem cells e.g., CD44 (such as human CD44, SEQ ID NO:225), CD45 (such as human CD45, SEQ ID NO:226), CD71 (such as human CD71, SEQ ID NO:191), CD73 (such as human CD73, SEQ ID NO:247), CD90 (such as human CD90, SEQ ID NO:248), CD29 (such as human CD29, SEQ ID NO:249), CD105 (such as human CD105, SEQ ID NO:250), CD106 (such as human CD106, SEQ ID NO:251), CD146 (such as human CD146, SEQ ID NO:252), CD164 (such as human CD164, SEQ ID NO:253), CD166 (such as human CD166, SEQ ID NO:254), STRO-1 (such as human STRO-1, SEQ ID NO:255);

j) glycoproteins e.g., CD54 (such as human CD54, SEQ ID NO:256), CD235a (such as human CD235a, SEQ ID NO:257), CD106 (such as human CD106, SEQ ID NO:251);

k) channeling proteins, including Ca-channel proteins e.g., GLUR2 (such as human GLUR2, SEQ ID NO:258), GLUR3 (such as human GLUR3, SEQ ID NO:259), HLA-DM (such as human HLA-DM, SEQ ID NO:260); or l) miscellaneous exosomal (vesicular) surface proteins e.g., FLOT2 (such as human FLOT2, SEQ ID NO:261).

Further miscellaneous EV surface proteins are selected from TCRA, TCRB, TCRD, TCRG, and T-cell receptors (T cell receptor loci), which have variable amono acid sequences, The skilled person may easily identify the suitable EV surface proteins based on the information provided herein, or from respective databases e.g., databases providing genomic loci and amino acid sequences of the human EV surface proteins (including fragments comprising at least one ED or TM, or isoforms of such EV surface proteins), or homologues or analogs from non-human animals.

Specifically, the EV surface protein comprises a tertiary structure comprising regions with loop, helical, and/or linear (peptide) structures, in particular a tetraspan-like tertiary structure such as described for CD81, which includes at least one large loop, and one or more helical regions. Such tertiary structure can be suitably engineered to incorporate an artificial binding site comprising contact points in distant regions of the tertiary structure.

In certain cases, the surface protein is anchored to the lipid bilayer membrane of the extracellular vesicle via a linker. Such linker may for example be an amino acid linker, linker based on hydrophilic and non-charged polymers, such as polyethylene glycol (PEG) and polysaccharide, or composed of zwitterionic polymers, containing both cationic and anionic groups.

Specific surface proteins are of mammalian origin, particularly those naturally occurring in species including human beings or non-human mammalian animals, such as warm-blooded animals, particularly dogs, cats, rabbits, horses, cattle, pigs and poultry.

The term "transmembrane domain" as used herein refers to a lipid membrane-spanning protein domain, which is typically hydrophobic. Specifically, the surface protein comprises at least two transmembrane domains anchoring an extravesicular loop to the EV. Tetraspanin proteins typically comprise four membrane-spanning domains. A transmembrane domain is typically positioned within the membrane of an EV when attached or bound to the EV. Yet, a protein domain is also called transmembrane domain while being isolated from an EV or isolated from an EV surface protein.

"Tetraspanins" also referred to as "tetraspans" or "tetraspan proteins" are herein understood as proteins of the transmembrane 4 superfamily, a protein superfamily that organize membrane microdomains termed tetraspanin-enriched microdomains by forming clusters and interacting with a large variety of transmembrane and cytosolic signaling proteins (also referred to as "tetraspanin superfamily"). Tetraspanins are typically cell-surface proteins that are characterized by the presence of four hydrophobic transmembrane domains. Naturally-occurring tetraspanin proteins mediate signal transduction events that play a role in the regulation of cell development, activation, growth and motility.

Tetraspanins as understood herein typically are comprised of extravascular domains (also referred to as extravesicular domains, ED), transmembrane domains and intravascular domains. For example, the N- and C-terminus of a tetraspanin is typically located within the EV, whereas the transmembrane domains are located within the lipid bilayer membrane, and the extravascular domains are placed on the outer surface of an EV. Specific examples of tetraspanins are glycosylated.

Extracellular (extravascular) domains, also referred to as extravesicular domains, ED, are the most variable regions in tetraspanins, which can be involved in binding a target. EC1 (first extracellular loop) is also referred to as small extracellular loop (SEL). EC2 ("large extracellular loop", LEL) of tetraspanins has been studied using the CD81LEL as a model protein for all tetraspanins. The LEL domain is divided into a constant region with conserved A, B, and E helices, suggested to mediate homodimerization through a hydrophobic surface, and a variable region with helices C and D flanking those sequences responsible for protein-protein interactions. Specifically, EC2 comprises at least two conserved cysteine residues forming disulfide bonds, for EC2 folding (the CCG motif), one cysteine residue proximal to transmembrane four present in all tetraspanins, and a Pro-Xaa-Xaa-Cys (PXXC, SEQ ID NO:183, wherein X can be any amino acid) motif in the majority of tetraspanins.

Among tetraspanins, CD9, CD63, CD81, CD82, and CD151 have a broad tissue distribution, while others are restricted to particular tissues, such as Tssc6, CD37, and CD53 in hematopoietic cells. Immunoelectron microscopy studies have shown that tetraspanins are abundant on various types of endocytic membranes and have been widely used as exosomal markers.

The tetraspan protein CD81 is the major protein enriched in the exosomal fraction of multivesicular bodies. Human CD81 comprises or consists of the amino acid sequence identified as SEQ ID NO:87 (coding sequence identified as SEQ ID NO:88).

The large extracellular loop of CD81, topologically located between transmembrane domains 3 and 4, is characterized by five helical elements forming a mushroom-like structure, stabilized by two pairs of cysteines. This motif is conserved among the protein members of tetraspanin family, and the oxidation of cysteine bonds is e.g., involved in high-affinity binding of the E2 envelope protein of hepatitis C virus (HCV), a natural ligand of CD81.

Tetraspan proteins may be expressed as soluble proteins or be displayed on the surface of tetraspanin expressing cells or the respective EVs.

The crystal structure of hCD81 LEL, solved at 1.6 Å, revealed a new type of protein fold, and a subsequent sequence analysis of 160 tetraspanin family members indicated that their fold and key structural features are conserved. Apart from cysteine bridges, the hCD81 LEL can be stabilized by the invariant residues Gly157 and Pro176, which are located to accommodate cysteine connections, as well as Tyr127, which is fully buried and contributes to the hydrogen bonding network together with His151 and Cys190. Soluble hCD81 LEL can assemble into dimers around a 2-fold axis, and the contact between the protomers is a low-polarity region between helices of each interacting partner and between helix B and C-terminal residues of the opposite protomer. The N- and C-termini of the protomers fall in the central region on opposite faces of the assembled dimer, similar to the dimeric assembly at the cell surface, where transmembrane segments are also present. A second low-polarity region comprises the solvent-exposed surface of helices C and D. According to solution studies, helix D is fairly unstructured and attains helical conformation only upon binding with certain antigens. The sequence alignments of the tetraspanin family members indeed show an increased variability in this region, including insertions and deletions. It has been suggested that this surface area might be involved in a species- or tetraspanin-specific recognition process, which could hint to the possibility of heterodimeric tetraspanin species assembly. In particular, segment D of CD81 may guide specific homomeric clustering.

According to a specific embodiment, biophysical properties of tetraspanins like CD81 are improved by introduction of de novo pairs of cysteine residues to form novel disulfide bridges stabilizing the protein. Specifically, formation of novel disulfide bridges increases the stability of tetraspanins like CD81, which allows production of mutants with higher stability e.g., mutants that incorporate one or more modified regions or a novel target-specific binding site comprising binding residues within said one or more modified regions. Specifically, the amino acid sequence can be modified by targeted or random mutagenesis to incorporate (in particular by substitution of) binding residues at predetermined positions or region(s) which make up a binding site, or to generate a library comprising a diversity of binding sites comprising binding residues.

Alike CD81, the tetraspanin CD9 is a cell-surface protein containing four hydrophobic transmembrane domains and two extracellular domains, EDs (such as comprising or consisting of EC1 and EC2).

Naturally-occurring CD9 consists of 228 amino acids and weighs 24-27 kDa. The four small and highly conserved hydrophobic transmembrane domains each comprise 24-27 amino acids. It has a small N-terminal (11 amino acids) and a C-terminal cytoplasmic (7 amino acids) tail as well as a very small intracellular domain (4 amino acids). The remaining part of the protein is composed of two extracellular domains (a small one, EC1, of 20 amino acids and a large one, EC2, of 83 amino acids). Two disulfide bonds, generated by four well-conserved cysteine residues (C), stabilize the large extracellular domain (EC2). CD9 also contains a tetraspanin signature (amino acids 65-89) and a CCG motif (amino acids 152 to 154). CD9 is one of the most ubiquitously expressed proteins on the surface of exosomes and therefore considered an exosome marker. Although there are variations in the amino acid sequence in the extracellular loops, the CD9 protein sequence is very well conserved between species (90% between human, mice and rat). CD9 share also some homologies with other tetraspanins, particularly in the transmembrane domains.

Wild-type CD9 can interact or form complexes with many other proteins, including other tetraspanins, integrins, EWI molecules, TGF-a, diphtheria toxin receptor, or tyrosine kinase, pregnancy specific glycoproteins, and proteins of the immune system such as MHC class II molecules and members of the Ig superfamily. Moreover, CD9 is involved in platelet activation and aggregation, as well as in cell adhesion, spreading, cell motility and tumor metastasis. CD9 also regulates paranodal junction formation, and is required for gamete fusion. Furthermore, CD9 promotes muscle cell fusion and supports myotube maintenance.

As described herein, tetraspanin CD63 is a highly glycosylated protein cell-surface protein containing four transmembrane domains and three putative N-glycosylation sites.

Wild-type CD63 typically resides in late endosomes, lysosomes, secretory vesicles, and at the plasma membrane, and it moves among these compartments. CD63 is extensively and variably glycosylated and its EC2 region contains three potential N-linked glycosylation sites (N130, N150, and N172. It is often used as a marker for multivesicular bodies, which are enriched with CD63. It has numerous natural interaction partners, including other tetraspanins, such as CD82; the MHC class II molecules HLA-DR, HLA-DM, and HLA-DO; several integrins; and phosphatidylinositol 4-kinase. CD63 also contains a tyrosine-based motif on its extreme C terminus. Tyrosine-based motifs in the cytoplasmic domains of membrane proteins are recognized by clathrin adaptor complexes and play important roles in endocytosis, lysosomal targeting, and basolateral targeting. The tyrosine-based motif in CD63 mediates its interaction with the μ-subunits of adaptor protein complexes 2 and 3 (AP-2 and AP-3).

As described herein, tetraspanin CD151 has the characteristic structure of a tetraspanin. It is a 253-amino acid protein with a single N-glycosylation site in its LEL and is palmitoylated on several cysteine residues. Immunoblotting reveals a doublet of bands of apparent kDa 28 and 32, representing unglycosylated and glycosylated forms of CD151. Human CD151 comprises or consists of the amino acid sequence identified as SEQ ID NO:94.

Wild-type CD151 has a wide cell and tissue distribution, including epithelium, endothelium, muscle, renal glomeruli and proximal and distal tubules, Schwann cells, and dendritic cells, with a single RNA species observed in most human adult tissues. CD151 is expressed at high levels on platelets and megakaryocytes. As with other tetraspanins, CD151 is associated in cell membranes with several integrins.

While all immune cells express tetraspanins, most of these are present in a variety of other cell types. There are a few, such as CD37, CD53, TSPAN32 (Tssc6) and TSPAN33, which are found in hematopoietic lineages.

As described herein, tetraspanin CD37 is a cell surface glycoprotein with the typical structure of a tetraspanin that is known to complex with integrins and other transmembrane 4 superfamily proteins. Alternate splicing results in multiple transcript variants encoding different isoforms. Human CD37 comprises or consists of the amino acid sequence identified as SEQ ID NO:95.

CD37 is known to be expressed by cells of the immune system, with highest abundance on mature B cells, and lower expression is found on T cells and myeloid cells. Wild-type CD37 controls both humoral and cellular immune responses. CD37-deficiency in mice leads to spontaneous development on B cell lymphoma, and patients with CD37-negative lymphomas have a worse clinical outcome.

As described herein, tetraspanin CD53 is a pan-leukocyte surface glycoprotein which spans the plasma membrane four times and is a member of the transmembrane 4 superfamily. The protein sequence and gene structure of mouse CD53 (Cd53) were determined by isolation of both genomic and cDNA clones. CD53 is highly conserved in evolution, as mouse Cd53 was 91% identical to rat CD53 and 82% identical to human CD53. The tetraspanin CD53 has four transmembrane domains and it is glycosylated twice in its second extracellular loop. It has a length of 219 amino acids and is located in the cell membrane, endosomes and in the lipid bilayer membrane of exosomes. Human CD53 comprises or consists of the amino acid sequence identified as SEQ ID NO:90.

Wild-type CD53 is expressed by virtually all immune cells, a subset of hematopoietic stem cells, and in a variety of haematological malignancies.

There are several tetraspanins present in platelets including CD9, CD151, Tssc6, and CD63. Recent studies in knockout mouse models have revealed that CD151 and Tssc6 are physically and functionally involved in regulation of the 'outside-in' signalling properties of the major platelet integrin, integrin alpha(IIb)beta(3) and thrombus stability in vivo.

As used herein, tetraspanin Tssc6, also called TSPAN32, is a member of the tetraspanin superfamily. The protein has a size of 320 amino acids and is expressed ubiquitously at low levels. High levels of TSPAN32 expression are typically confined to hematopoietic tissues including peripheral blood leukocytes, thymus and spleen.

Human TSPAN32 comprises or consists of the amino acid sequence identified as SEQ ID NO:91.

As used herein, lysosomal associated membrane protein 2 (LAMP2), is a lysosome-associated membrane glycoprotein. LAMP2 is an integral membrane protein with two conserved luminal domains (constituting 90% of the entire protein), a single transmembrane (TM) domain (about 20 amino acids), and a short (10-12-amino acid) C-terminal cytosolic tail. Glycosylation is found in its luminal domains. Human LAMP2 comprises or consists of the amino acid sequence identified as SEQ ID NO:96. LAMP2, as used herein, preferably comprises modification in the extravesicular loop regions to incorporate the artificial binding site.

Wild-type LAMP2 plays an important role in chaperone-mediated autophagy, a process that mediates lysosomal degradation of proteins in response to various stresses and as part of the normal turnover of proteins with a long biological half-live.

The term "tetraspan-like proteins" (sometimes called tetraspanin-like) as used herein shall refer to EV surface proteins which comprise at least two transmembrane domains and at least one ED positioned between said at least two transmembrane domains, preferably wherein the region between said at least two transmembrane domains comprises or consists of one ED.

Specific examples of tetraspan-like proteins are naturally-occurring or modified tetraspanin proteins and others, such as lysosome-associated membrane glycoproteins (LAMPs), or recombinant or synthetic proteins e.g. chimeric proteins comprising one or more transmembrane domains of one protein and one or more EDs of another protein, thereby obtaining a recombinant tetraspan-like protein.

"Sequence identity" or "percent (%) amino acid sequence identity" with respect to protein sequences and mutants thereof is defined as the percentage of amino acid residues in a candidate sequence that are identical with the amino acid residues in the specific polypeptide sequence to be compared (the "parent sequence"), after aligning the sequence and introducing gaps, if necessary, to achieve the maximum percent sequence identity, and not considering any conservative substitutions as part of the sequence identity. Those skilled in the art can determine appropriate parameters for measuring alignment, including any algorithms needed to achieve maximal alignment over the full length of the sequences being compared.

As used herein, the term "specificity", "target-specific" or "specific binding" refers to a binding reaction which is determinative of the cognate ligand of interest in a heterogeneous population of molecules. Thus, under designated conditions (e.g., immunoassay conditions), the modified surface protein binds to its particular target and does not bind in a significant amount to other molecules present in a sample. The specific binding means that binding is selective in terms of target identity, high, medium or low binding affinity or avidity, as selected. Selective binding is usually achieved if the binding constant or binding dynamics is at least 10 fold different, preferably the difference is at least 100 fold, and more preferred at least 1000 fold.

A specific binding does not exclude certain cross-reactivity with similar antigens, or the same antigens of a different species (analogues). For example, a binding entity may also preferably cross-react with rodent targets analogous to human targets, to facilitate preclinical animal studies.

The term "target" as used herein shall in particular include all antigens and target molecules capable of being recognised by a binding site of an antibody. Surface proteins described herein are engineered to comprise an artificial target binding site, which is specifically recognizing antigenic structures or epitopes alike an antibody.

Specific targets are cellular targets or soluble targets. In many cases, targets are self-antigens such as receptors located on the surface of tumor cells or cytokines or growth factors that can be present in the circulation of subjects or patients. Further targets may be of pathogen origin, e.g., microbial or viral pathogens.

The target antigen is either recognized as a whole target molecule or as a fragment of such molecule, especially substructures, e.g., a polypeptide or carbohydrate structure of targets, generally referred to as "epitopes", e.g., B-cell epitopes, T-cell epitope), which are immunologically relevant, i.e. are also recognisable by natural or monoclonal antibodies.

Specifically, a target antigen is selected from cell surface antigens, including receptors, in particular from the group consisting of erbB receptor tyrosine kinases (such as EGFR, HER2 including Her2neu, HER3 and HER4, in particular those epitopes of the extracellular domains of such receptors, e.g., the 4D5 epitope). In addition further antigens may be targeted, e.g., molecules of the TNF-receptor superfamily, such as Apo-1 receptor, TNFR1, TNFR2, nerve growth factor receptor NGFR, CD40, CD40-Ligand, OX40, TACI, BCMA, BAFF-receptor, T-cell surface molecules, T-cell receptors, T-cell antigen, Apo-3, DR4, DR5, DR6, decoy receptors, such as DcR1, DcR2, CAR1, HVEM, GITR, ZTNFR-5, NTR-1, TNFL1, IGFR-1, c-Met, but not limited to these molecules, B-cell surface antigens, such as CD10, CD19, CD20, CD21, CD22, DC-SIGN, antigens or markers of solid tumors or hematologic cancer cells, cells of lymphoma or leukaemia, other blood cells including blood platelets, but not limited to these molecules.

The term "therapeutically effective amount", used herein interchangeably with any of the terms "effective amount" or "sufficient amount" of a compound, e.g., a binder as described herein, particularly a TEV as described herein, is a quantity or activity sufficient to, when administered to the subject effect beneficial or desired results, including clinical results, and, as such, an effective amount or synonym thereof depends upon the context in which it is being applied.

An effective amount is intended to mean that amount of a compound that is sufficient to treat, prevent or inhibit a disease or disorder. In the context of disease, therapeutically effective amounts of a binder or TEV as described herein are specifically used to treat, modulate, attenuate, reverse, or affect a disease or condition that benefits from the interaction of the binder or TEV with its target antigen, e.g. a tumor cell.

The amount of the compound that will correspond to such an effective amount will vary depending on various factors, such as the given drug or compound, the pharmaceutical formulation, the route of administration, the type of disease or disorder, the identity of the subject or host being treated, and the like, but can nevertheless be routinely determined by one skilled in the art.

A binder as described herein may specifically be used in a pharmaceutical composition. Therefore, a pharmaceutical composition is provided which comprise a binder as described herein and a pharmaceutically acceptable carrier or excipient. These pharmaceutical compositions can suitably be administered s a bolus injection or infusion or by continuous infusion. Besides parenteral administration, topic or oral administration may be preferred. Pharmaceutical carriers suitable for facilitating such means of administration are well-known in the art.

Pharmaceutically acceptable carriers generally include any and all suitable solvents, adjuvants, dispersion media, coatings, isotonic and absorption delaying agents, and the like that are physiologically compatible with a binder provided herein. Further examples of pharmaceutically acceptable carriers include sterile water, saline, phosphate buffered saline, dextrose, glycerol, ethanol, and the like, as well as combinations of any thereof.

Suitable pharmaceutically acceptable carriers or excipients specifically include one or more of any and all conventional solvents, dispersion media, fillers, solid carriers, aqueous solutions, coatings, vehicles suitable for topical administration, other antimicrobial agents, isotonic and absorption enhancing or delaying agents, or activity enhancing or delaying agents for pharmaceutically active substances. Common pharmaceutically acceptable additives are disclosed, by way of example, in Remington: the Science & Practice of Pharmacy by Alfonso Gennaro, 20th ed., Lippencott Williams & Wilkins, (2000).

In one embodiment, suitable pharmaceutically acceptable carriers include, but are not limited to, inert solid fillers or diluents and sterile aqueous or organic solutions (e.g., polyethylene glycol, propylene glycol, polyvinyl pyrrolidone, ethanol, benzyl alcohol, etc.). In certain such embodiments, suitable pharmaceutically acceptable excipients include, but are not limited to, water, salt solutions, alcohol, polyethylene glycols, gelatin, lactose, amylase, magnesium stearate, talc, silicic acid, viscous paraffin, hydroxymethylcellulose, polyvinylpyrrolidone, fillers, such as sugars (e.g., lactose, sucrose, mannitol, or sorbitol), and cellulose preparations (e.g., maize starch, wheat starch, rice starch, potato starch, gelatin, gum tragacanth, methyl cellulose, hydroxypropylmethylcellulose, sodium carboxymethylcellulose, and/or polyvinylpyrrolidone, PVP).

In one such aspect, a binder can be combined with one or more carriers appropriate for a desired route of administration, e.g., admixed with any of lactose, sucrose, starch, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, polyvinyl alcohol, and optionally further tableted or encapsulated for conventional administration. Other carriers, adjuvants, and modes of administration are well known in the pharmaceutical arts. A carrier may include a controlled release material or time delay material, such as glyceryl monostearate or glyceryl distearate alone or with a wax, or other materials well known in the art.

Additional pharmaceutically acceptable carriers are known in the art and described in, e.g., REMINGTON'S PHARMACEUTICAL SCIENCES. Liquid formulations can be solutions, emulsions or suspensions and can include excipients such as suspending agents, solubilizers, surfactants, preservatives, and chelating agents.

Pharmaceutical compositions are contemplated wherein a binder as described herein and one or more therapeutically active agents are formulated. Stable formulations of the binder described herein are prepared for storage by mixing said construct having the desired degree of purity with optional pharmaceutically acceptable carriers, excipients or stabilizers, in the form of lyophilized formulations or aqueous solutions. Formulations for in vivo administration are preferably sterile, e.g., in the form of a sterile aqueous solution. This is readily accomplished by filtration through sterile filtration membranes or other suitable sterilization methods.

Administration of the pharmaceutical composition comprising a binder described herein, may be done in a variety of ways, including orally, subcutaneously, intravenously, intranasally, intraotically, transdermally, mucosal, topically, e.g., tablets, gels, ointments, salves, suppositories, patches, lotions, creams, etc., intraperitoneally, intramuscularly, intrapulmonary, vaginally, parenterally, rectally, or intraocularly.

In one embodiment, the pharmaceutical composition is administered orally, intravenously, or inhalationally. In a specific embodiment, the binder is administered in a dosage form selected from the group consisting of solid dosage form, a cream, an aqueous mixture, a lyophilized aqueous mixture and an aerosol.

Exemplary formulations as used for parenteral administration include those suitable for subcutaneous, intramuscular or intravenous injection as, for example, a sterile solution, emulsion or suspension.

The binder described herein may specifically be used in a diagnostic composition e.g., for in vitro or in vivo use. Therefore, a diagnostic composition is provided which comprises a binder as described herein, and optionally a diagnostic reagent in a composition or a kit of parts.

The diagnostic kit preferably comprises all essential components to qualitatively or quantitatively determine the target in a biological sample, optionally without common or unspecific substances or components, such as water, buffer or excipients. A storage stable kit can be provided with a shelf-life of preferably at least 6 months, more preferably at least 1 or 2 years. It may be composed of dry (e.g., lyophilized) components, and/or include preservatives.

The preferred diagnostic kit is provided as a packaged or prepackaged unit e.g., wherein the components are contained in only one package, which facilitates routine experiments. Such package may include the reagents necessary for one or more tests e.g., suitable to perform the tests of a series of biological samples. The kit may further suitably contain a standard or reference control.

The diagnostic composition may be a reagent ready-to-use in a reaction mixture with the biological sample, or a conserved form of such reagent e.g., a storage-stable form such as lyophilized; snap-frozen (e.g., in liquid nitrogen), ultra-low-temperature storage (−70° C. and −80° C.), cold-storage (−20° C. and 5° C.) and controlled room temperature (15° C.-27° C.); standard sample storage as e.g., glycerol-stocks, tissue paraffin-blocks, (buccal) swabs and other standard biological sample storage methods, which conserved form of a reagent can be reconstituted or prepared to obtain a ready-to-use reagent. Such ready-to-use reagent is typically in the form of an aqueous solution, specifically (physiological) buffer conditions (e.g., EDTA buffered, phosphate buffer, HBSS, citrate buffer etc.).

Specifically, the further diagnostic reagent is a reagent specifically reacting with the binder and/or a reaction product of the binder binding to its target. The appropriate diagnostic reagent can be a solvent, a buffer, a dye, an anticoagulant, a ligand that specifically binds to the binder described herein and/or the binder-target complex.

Specifically, the invention provides for a diagnostic preparation of a binder described herein, optionally containing the binder with a label and/or a further diagnostic reagent with a label, such as a reagent specifically recognizing the binder or a complex of the binder with the respective target, and/or a solid phase to immobilize at least one of the binder and the diagnostic reagent.

Specifically, the further diagnostic reagent is a diagnostic label or a reagent specifically reacting with the binder and/or the reaction product of the binder binding to its target.

The EV or the diagnostic reagent can be directly labeled or indirectly labeled. The indirect label may comprise a labeled binding agent that forms a complex with the binder or diagnostic reagent to the target.

The label is typically a molecule or part of a molecule that can be detected in an assay. Exemplary labels are chromophores, fluorochromes, or radioactive molecules. In some embodiments the EV or diagnostic reagent is conjugated to a detectable label which may include molecules that are themselves detectable (e.g., fluorescent moieties, electrochemical labels, metal chelates, etc.) as well as molecules that may be indirectly detected by production of a detectable reaction product (e.g., enzymes such as horseradish peroxidase, alkaline phosphatase, etc.) or by a specific binding molecule which itself may be detectable (e.g., biotin, digoxigenin, maltose, oligohistidine, 2,4-dintrobenzene, phenylarsenate, ssDNA, dsDNA, etc.).

Preferred diagnostic preparations or assays comprise the EV described herein immobilized on a solid phase e.g., latex beads, gold particles, etc.

The following items are considered specific embodiments of the invention:

1. A target-specific extracellular vesicle (EV) comprising a lipid bilayer membrane anchoring a surface protein which comprises an artificial binding site specifically recognizing a target, wherein said binding site comprises binding residues within at least two distant regions of said surface protein.
2. The EV of item 1, wherein said surface protein comprises a transmembrane domain of a vesicular membrane protein, which transmembrane domain is anchoring the surface protein to the EV.
3. The EV of item 2, wherein the membrane protein is a tetraspan protein, preferably selected from the group consisting of CD81, CD9, CD37, CD53, CD63, and CD82, or LAMP2.
4. The EV of any of items 1 to 3, wherein the surface protein is CD81 and the binding residues are located within a first region between positions 160 and 172, and within at least one further region located between positions 132 and 139, or between positions 180 and 189, wherein numbering is of CD81 identified as SEQ ID NO:87.
5. The EV of item 4, wherein the surface protein is CD81 which is stabilized by introducing one or more cysteine(s) at position(s) to allow the formation of one or more additional disulfide bonds stabilizing the extravesicular loop structure of the protein.
6. The EV of any one items 1 to 5, which is originating from eukaryotic or prokaryotic source cells of body tissue, body fluid, or a cell culture.
7. The EV of any one of items 1 to 6, which is carrying an intravesicular load, wherein the load comprises any one or more of peptides, polypeptides, protein domains, proteins, lipids, genes, nucleic acids such as mRNAs, miRNAs, RNAi mediating molecules in particular locked nucleic acids or phosphorothioates, DNA, DNA fragments, plasmids such as minicircle DNA, drugs such as small molecules, in particular chemotherapeutics or senolytics.
8. The EV of any one of items 1 to 7, wherein the target is selected from the group consisting of cellular targets such as mitogenic receptors, cytokine receptors, asyaloglycoprotein receptors, membrane transporters, lipoproteins, liposaccharides, glycoproteins, proteoglycans, or acellular targets such as cytokines, artificial proteins or artificial surface structures.
9. A pharmaceutical preparation comprising the EV of any one items 1 to 8, and a pharmaceutically acceptable carrier, preferably in a formulation for intradermal, subcutaneous, intravenous, topical, or oral use.
10. A method of producing a preparation of EV of any one of items 1 to 8, comprising:
    a) introducing a gene encoding the surface protein into a source cell or source cell mixture;
    b) culturing said cell(s) under conditions producing extracellular vesicles;
    c) isolating a fraction comprising the EV with the target binding specificity; and
    d) producing an EV preparation.

11. The method of item 10, wherein the gene is modified by a mutagenesis method to incorporate an artificial binding site specifically recognizing a target, wherein said mutagenesis method employs mutagenesis of at least two distant regions of said surface protein, thereby producing a repertoire of polynucleotides encoding a variety of surface proteins, each with a different binding specificity, and selecting a polynucleotide encoding the surface protein which specifically recognizes the target.
12. The method of item 11, wherein the repertoire of polynucleotides is comprised in genetic packages displaying the variety of surface proteins on the outer surface, preferably employing a display system selected from the group consisting of a phage, yeast, bacterium, ribosome, mRNA or mammalian cell display.
13. The EV preparation produced according to any one of items 10 to 12, for autologous use, wherein the source cell or source cell mixture is obtained from a subject and the EV preparation is administered to the same subject.
14. The method of any one of items 10 to 12, to produce a library of EVs, wherein
    a) a repertoire of a gene encoding a variety of surface proteins is introduced into said source cell(s); and
    b) a repertoire of EVs is isolated, each with a different target binding specificity, to produce a library of EVs comprising a repertoire of target binding EVs with a variety of target binding specificity, wherein the repertoire is produced by mutagenizing said gene within at least two predetermined distant regions of said gene.
15. A library of EVs produced by a method of item 14, preferably wherein the repertoire comprises at least $10^2$ EVs with different target specificity.

The examples described herein are illustrative of the present invention and are not intended to be limitations thereon. Different embodiments of the present invention have been described according to the present invention. Many modifications and variations may be made to the techniques described and illustrated herein without departing from the spirit and scope of the invention. Accordingly, it should be understood that the examples are illustrative only and are not limiting upon the scope of the invention.

EXAMPLES

Example 1: Yeast Display of CD81 LEL

Wild-type human CD81 LEL sequence was cloned as a C-terminal fusion protein with Aga2, preceded by an Xpress-tag and with a C-terminally appended his-tag and V5-tag.

The amino acid sequence of CD81 LEL was

```
(SEQ ID NO: 7):
FVNKDQIAKDVKQFYDQALQQAVVDDDANNAKAVVKTFHETLDCCGSSTL

TALTTSVLKNNLCPSGSNIISNLFKEDCHQKIDDLFSGK.
```

The coding nucleotide sequence was

```
(SEQ ID NO: 8):
TTTGTCAACAAGGACCAGATCGCCAAGGATGTGAAGCAGTTCTATGACCA
```

-continued

```
GGCCCTACAGCAGGCCGTGGTGGATGATGACGCCAACAACGCCAAGGCTG

TGGTGAAGACCTTCCACGAGACGCTTGACTGCTGTGGCTCCAGCACACTG

ACTGCTTTGACCACCTCAGTGCTCAAGAACAATTTGTGTCCCTCGGGCAG

CAACATCATCAGCAACCTCTTCAAGGAGGACTGCCACCAGAAGATCGATG

ACCTCTTCTCCGGGAAG.
```

Primers for amplification of human CD81 LEL were

```
(SEQ ID NO: 9):
ACGTGGATCCTTTGTCAACAAGGACCAGATC

(SEQ ID NO: 10):
ACGTGCGGCCGCGCCTTCCCGGAGAAGAGGTC.
```

PCR product was cut with BamHI and NotI and ligated with correspondingly cut vector pYD1 (Thermo Fisher Scientific). Ligation mixture was transformed into electrocompetent *E. coli* TOP10 and transformants were selected on ampicilline plates. Plasmid was isolated with minipreparation and transformed into *S. cerevisiae* EBY100 using chemical transformation. A starter culture of EBY100 (Thermo Fisher Scientific) in 20 ml YPD medium (2% peptone, 1% yeast extract, 2% glucose) (Merck) was incubated overnight at 30° C. and 180 rpm. The culture was then diluted to an $OD_{600}$ of 0.4 and incubated for about 5 hours at 30° C. and 180 rpm. Aliquots of 50 ml cell culture were then pelleted at 1000 g for 5 min at room temperature, then washed with 25 ml AD and pelleted again. The cells were resuspended in 3 ml 100 mM Li-acetate and incubated for 15 min at 30° C. in a shaking incubator. 0.3 ml of cell suspension was then pelleted and supernatant removed. Components of the transformation mix were added as follows: 240 µl 50% PEG 3350, 36 µl 1.0 M Li-acetate, 50 µl 2 mg/ml ssDNA (salmon sperm carrier DNA, previously heated up to 95° C. for 5 minutes and then placed on ice) (Sigma Aldrich) and 1 µg of pYD1-CD81 LEL plasmid. The cell pellets were resuspended in the transformation mix, incubated for 30 min at 30° C. in a shaking incubator and then heat-shocked at 42° C. for 45 min. Yeast cells were pelleted at 1000 g, 5 min at RT, resuspended in AD and transformants were selected on MDL medium at 30° C. for three days.

Transformants were inoculated into SD-CAA (1% Casamino acids (Becton Dickinson), 100 mM K-phosphate buffer, pH 6.0 (Merck), 1×YNB (Becton Dickinson), 2% glucose (Merck)) and cultured overnight at 30° C. Induction was with SG/R-CAA medium (1% Casamino acids (Becton Dickinson), 100 mM K-phosphate buffer, pH 6.0 (Merck), 1×YNB (Becton Dickinson), 2% galactose (Merck), 1% raffinose (Merck)) overnight at 37° C. or for 2 days at 20° C. Yeast cultures were then examined for the expression of the recombinant proteins. FACS analysis revealed display levels similar to yeast transformed with the unmodified expression vector encoding only the reporter tags. Further, the wild-type CD81 LEL displaying yeast culture was stained with structure-reporting antibodies M38 and 1.3.3.22 (Thermo Fisher Scientific), and the results have shown the same expression level as for the tags examined. FACS analysis revealed similar display levels for cultures induced at 20° C. or under stress conditions of 37° C. The expression of tags was at a similar level as found for the yeast transformed with the vector encoding the tags only. Further, the yeast cells expressing wild-type CD81 were stained with the anti-CD81 antibodies similarly to the cells induced at 20° C.

Example 2: Phage Display of CD81 LEL

The sequence encoding wild-type CD81 LEL was cloned into the multiple cloning site of the expression vector fdmyc that allows the expression of phage particles with the recombinant protein N-terminally positioned from the c-myc tag and the g3p protein. The primers for amplifications were

```
(SEQ ID NO: 11):
ACGAGTGCACAGTTTGTCAACAAGGACCAGATC

(SEQ ID NO: 12):
ACGTGCGGCCGCCTTCCCGGAGAAGAGGTC.
```

PCR product was cut with restriction enzymes ApaLI and NotI and ligated into the correspondingly cut vector fdmyc. Ligation mixture was transformed into *E. coli* TG1 cells (Thermo Fisher Scientific) and selected on tetracycline-containing TYE-plates (1.5% agar, 1.6% peptone, 1% yeast extract (Merck)). After overnight cultivation in tetracycline-containing medium at 30° C., high titers of $10^{11}$-$10^{12}$ phage particles/L culture could be obtained, indicating that the expressed proteins are not detrimental to phage multiplication. The expression level of the fusion protein was tested using analysis of phage particles with SDS-PAGE and Western blotting. Detection of displayed protein was performed with an anti-g3p antibody (New England Biolabs) and found to be 50% fused with wild-type CD81 LEL. Phage-borne CD81 LEL could be detected with both CD81-specific antibodies, M38 and 1.3.3.22, indicating the correct folding of the phage-displayed molecule.

Example 3: Expression of Soluble CD81 LEL

CD81 LEL sequence was amplified with primers

```
(SEQ ID NO: 13):
ACGTGCTAGCTTTGTCAACAAGGACCAGATC

(SEQ ID NO: 14):
ACGTGGATCCTCATCACTTCCCGGAGAAGAGGTC.
```

PCR fragment was cut with restriction enzymes NheI and BamHI and ligated to vector pTT22SSP4 (CNRC) that was cut with the same enzymes. Ligation mixture was transformed into electrocompetent *E. coli* TOP10 (Thermo Fisher Scientific) and transformants were selected on ampicilline plates. Plasmid was isolated with minipreparation and transfected into HEK-293-6E cells (CNRC), exactly according to manufacturer's instructions. Protein expression proceeded for 5 days with addition of TN-20 to an end concentration of 0.5%. hCD81 LEL was then purified via Ni-NTA chromatography using standard protocols. Supernatant was buffered with PBS and 20 mM imidazole and pH adjusted to 7.5. Excel Ni-NTA column (GE Healthcare) was equilibrated with PBS and 20 mM imidazole, pH 7.5, and loaded with the buffered supernatant. Elution was in 5 column volumes with a linear gradient from 20 to 500 mM imidazol in PBS, pH 7.5. Protein-containing fractions were pooled and dialysed against 100-times volume of PBS at 4° C. overnight.

SEC analysis in native conditions revealed a monodisperse elution profile corresponding to a dimeric form of the protein, analogously to the soluble wild-type CD81 LEL.

Alternatively, protein was expressed in ExpiCHO expression system (Thermo Fisher Scientific) following MaxTiter protocol exactly according to manufacturer's instructions. hCD81 LEL was then purified via Ni-NTA chromatography using standard protocols. Supernatant was diluted with an equal volume of AD and buffered with PBS and 20 mM imidazole and pH adjusted to 7.5. Excel Ni-NTA column (GE Healthcare) was equilibrated with PBS and 20 mM imidazole, pH 7.5, and loaded with the buffered supernatant. Elution was in 5 column volumes with a linear gradient from 20 to 500 mM imidazol in PBS, pH 7.5. Protein-containing fractions were pooled and dialysed against 100-times volume of PBS at 4° C. overnight.

Example 4: Construction of CD81 Library 1

A yeast-display library of CD81 LEL mutants randomized in the total of 12 amino acid residues in C- and D-segment of the CD81 LEL was constructed. Randomized were the amino acid residues: 160-162 and 181-189 (numbering as in 1G8Q). Yeast display library was prepared at a size of $7\times10^7$ independent members. PCR fragment for recombination was prepared using oligonucleotides

```
(SEQ ID NO: 15):
CTTCCACGAGACGCTTGACTGCTGTGGATCCNNKNNKNNKACTGCTTTGA

CCACCTC,
wherein N is any one of A, C, G, or T

(SEQ ID NO: 16):
CCGCGCCTTCCCGGAGAAGAGGTCATCGATCTTCTGGTGGCAAKMMNNMN

NMNNMMNNMNNMNNMNNMNNGTTGCTGCCCGAGGGAC,
wherein N is any one of A, C, G, or T;
and M is any one of A or C.
```

using Q5 HiFi polymerase (New England Biolans) and purified after gel electrophoresis. Recipient vector was modified to facilitate the recombination of PCR fragment. All mutagenesis steps were performed using QuikChange Lightning Mutagenesis kit (Agilent), exactly according to manufacturer's instructions.

A BamHI site was introduced into pYD1_CD81 LEL with oligonucleotides

```
(SEQ ID NO: 17):
GCTTGACTGCTGTGGATCCAGCACACTGACTG

(SEQ ID NO: 18):
CAGTCAGTGTGCTGGATCCACAGCAGTCAAGC,
```

and then the naturally occurring BamHI site was removed using oligonucleotides

```
(SEQ ID NO: 19):
CGATAAGGTACCAGGTTCCTTTGTCAACAAG

(SEQ ID NO: 20):
CTTGTTGACAAAGGAACCTGGTACCTTATCG.
```

Vector was linearized with BamHI and ClaI and vector backbone was purified from the agarose gel. Chemical transformation was used to introduce PCR fragment and vector backbone into *S. cerevisiae* EBY100. A starter culture of EBY100 in 20 ml YPD medium was incubated overnight at 30° C. and 180 rpm. The culture was then diluted to an $OD_{600}$=0.4 and incubated for about 5 hours at 30° C. and 180 rpm. Aliquots of 50 ml cell culture were then pelleted at 1000 g for 5 min at room temperature, then washed with 25 ml AD and pelleted again. The cells were resuspended in 3 ml 100 mM Li-acetate and incubated for 15 min at 30° C. in a shaking incubator. Cells were pelleted and supernatant removed. Components of the transformation mix were added as follows: 2400 µl 50% PEG 3350, 360 µl 1.0 M Li-acetate, 500 µl 2 mg/ml ssDNA (salmon sperm carrier DNA, previously heated up to 95° C. for 5 minutes and then placed on ice), 10 µg linearized recipient vector and 7 µg DNA fragment. The cell pellets were resuspended in the transformation mix and incubated for 30 min at 30° C. in a shaking incubator and heat-shocked at 42° C. for 45 min.

After collecting the cells by centrifugation at 1000 g for 5 min at room temperature and removing the supernatant, the pellets were resuspended in 10 ml SD-CAA medium (1% Casamino acids (Becton Dickinson), 100 mM K-phosphate buffer, pH 6.0 (Merck), 1×YNB (Becton Dickinson), 2% glucose (Merck). Aliquots were removed for dilution plating to determine the library size: 10 µl of cell suspension were diluted in 990 µl SD-CAA medium of which 100 µl were plated on an MDL plate (1.5% agar (Merck), 1×YNB (Becton Dickinson), 2% glucose (Merck) and 0.01% leucin (Sigma-Aldrich) and incubated at 30° C. for 3 days. Yeast cells were diluted in 50 ml SD-CAA medium and incubated at 30° C. at 180 rpm for 24 h, passaged into fresh SD-CAA medium at 1:20 dilution and cultured for another 24 h under the same conditions. Cells were harvested at 1000 g, 5 min, at 4° C. and pellets were resuspended in an equal volume of 30% glycerol before freezing at −80° C.

Example 5: Selection of CD81 LEL Library 1 with Mouse EGFR-Fc

Mouse EGFR-Fc was purchased from Sino Biological. For biotinylation, EZ-Link™ Sulfo-NHS-LC-LC-Biotin reagent was used in a 3:1 molar ratio. The antigen was reconstituted exactly according to manufacturer's instructions to a concentration of 0.25 µg/µl. Incubation with biotinylation reagent proceeded for 1 h at room temperature with shaking. Unbound biotin was removed with dialysis against 100× volume of PBS, using Snakeskin dialysis tubing (Thermo Fisher Scientific) with 10.000 Da MWCO, at 4° C. overnight with stirring.

For selection, library was inoculated into SD-CAA and cultured overnight at 30° C. Induction was with SG/R-CAA medium overnight at 37° C. The induced cell suspensions were diluted to $10^8$ cells per 1 ml 10% BSA-PBS and centrifuged at 1000 g for 5 min at 20° C. To block the cells, the pellets were resuspended in 1 ml 10% BSA-PBS and incubated for 30 min at 20° C. on a rotating platform. The cells were centrifuged at 3000 rpm for 5 min at 20° C. and resuspended in 250 µl 10% BSA-PBS containing 1 µM biotinylated EGFR-Fc. After incubation for 30 min at room temperature on a rotating platform the cells were centrifuged at 3000 rpm for 5 min at 4° C. To wash the cells, the pellets were resuspended in 1 ml ice-cold PBS and centrifuged at 1000 g for 5 min at 4° C. Then, the cells were resuspended in 250 µl 10% BSA-PBS with streptavidin-Alexafluor 647 (1:800) and anti-V5-FITC antibody (1:100) (Thermo Fisher Scientific) and incubated for 30 min on ice. The cells were centrifuged at 3000 rpm for 5 min at 4° C. before they were resuspended in 1 ml ice-cold PBS and centrifuged again. Lastly, the cells were resuspended in 250 µl ice-cold PBS and were kept on ice until sorting with FACS Aria™. 1st sort covered 2.5× library size and 1% false positive yeast cells were collected and in the $2^{nd}$ sort 20× output of $1^{st}$ sort was processed and 0.1% false positive yeast cells were propagated. In the following two sorting rounds at least 100× output of previous sort was processed, again 0.1% of yeast cells were collected and after the $4^{th}$ sort plated out to characterize single yeast display clones. 23 selected clones were screened using staining with mouse EGFR-Fc and all except clones 9, 10 and 23 stained significantly with the antigen, but not with the secondary reagent streptavidin-Alexafluor 647.

Table 1 showing median fluorescence of yeast clones displaying selected CD81 LEL variants with antigen mouse EGFR-Fc and secondary reagent streptavidin-Alexafluor 647 or only with secondary reagent streptavidin-Alexafluor 647.

| Yeast clone | 2nd only | Antigen + 2nd |
|---|---|---|
| 1 | 15.69 | 33.12 |
| 2 | 12.81 | 22.36 |
| 3 | 12.49 | 23.39 |
| 4 | 12.42 | 16.48 |
| 5 | 16.96 | 34.12 |
| 6 | 11.39 | 24.6 |
| 7 | 8.84 | 18.65 |
| 8 | 16.14 | 51.32 |
| 9 | 14.59 | 11.76 |
| 10 | 13.96 | 16.18 |
| 11 | 19.67 | 36.52 |
| 12 | 25.87 | 56.93 |
| 13 | 21.36 | 47.54 |
| 14 | 19.85 | 26.23 |
| 15 | 16.93 | 43.68 |
| 16 | 14.61 | 26.19 |
| 17 | 18.56 | 21.22 |
| 18 | 16.67 | 57.94 |
| 19 | 16.72 | 20.57 |
| 20 | 15.67 | 13.24 |
| 21 | 10.08 | 33.69 |
| 22 | 14.03 | 18.58 |
| 23 | 20.27 | 15.97 |
| wild-type CD81 LEL | 28.27 | 9.1 |

Upon sequencing, 6 different sequences were identified (Table 2).

Table 2 showing identified sequences.

| clone | Helix C (AA 160-162) | Segment D (AA 181-189) |
|---|---|---|
| 1 | VRR | RRPRKRTRS (SEQ ID NO: 1) |
| 2 | ERL | RRSRRRVHD (SEQ ID NO: 2) |
| 3 | RAN | IWRARRRRS (SEQ ID NO: 3) |
| 4 | ERL | RRSRRRVHD (SEQ ID NO: 2) |
| 5 | SFS | RRFRKRPGD (SEQ ID NO: 4) |
| 6 | SSS | SRRWRHRIA (SEQ ID NO: 5) |
| 7 | ERL | RRSRRRVHD (SEQ ID NO: 2) |
| 8 | VRR | RRPRKRTRS (SEQ ID NO: 1) |
| 9 | MGN | WWGRRFRVS (SEQ ID NO: 6) |
| 10 | ERL | RRSRRRVHD (SEQ ID NO: 2) |
| 11 | ERL | RRSRRRVHD (SEQ ID NO: 2) |
| 12 | ERL | RRSRRRVHD (SEQ ID NO: 2) |
| 13 | RAN | IWRARRRRS (SEQ ID NO: 3) |

-continued

| clone | Helix C (AA 160-162) | Segment D (AA 181-189) |
|---|---|---|
| 14 | ERL | RRSRRRVHD (SEQ ID NO: 2) |
| 15 | VRR | RRPRKRTRS (SEQ ID NO: 1) |
| 16 | ERL | RRSRRRVHD (SEQ ID NO: 2) |
| 17 | ERL | RRSRRRVHD (SEQ ID NO: 2) |
| 18 | SSS | SRRWRHRIA (SEQ ID NO: 5) |
| 19 | SFS | RRFRKRPGD (SEQ ID NO: 4) |
| 20 | ERL | RRSRRRVHD (SEQ ID NO: 2) |
| 21 | RAN | IWRARRRRS (SEQ ID NO: 3) |
| 22 | ERL | RRSRRRVHD (SEQ ID NO: 2) |
| 23 | ERL | RRSRRRVHD (SEQ ID NO: 2) |

Example 6: Selections of CD81 Library 1 with Human EGFR-Fc

Human EGFR-Fc was purchased from Sino Biological. For biotinylation, EZ-Link™ Sulfo-NHS-LC-LC-Biotin reagent was used in a 3:1 molar ratio. The antigen was reconstituted exactly according to manufacturer's instructions to a concentration of 0.25 μg/μl. Incubation with biotinylation reagent proceeded for 1 h at room temperature with shaking. Unbound biotin was removed with dialysis against 100× volume of PBS, using Snakeskin dialysis tubing (Thermo Fisher Scientific) with 10.000 Da MWCO, at 4° C. overnight with stirring.

For sorting, libraries were first cultured in SD-CAA medium supplemented with penicillin-streptomycin at 30° C. with shaking overnight and then the expression of recombinant protein was induced by resuspending the yeast cells in SG/R-CAA medium with penicillin-streptomycin and incubating them with shaking overnight at 37° C.

For MACS, $10^9$ induced yeast cells were pelleted for 5 min at 2500 g and washed by resuspending the pellet in 50 ml wash buffer (PBS, pH 7.2, 0.25% BSA, 2 mM EDTA) and pelleted again for 5 min at 2500 g. Washed cells were resuspended in 25 ml wash buffer containing 0.25 μM biotinylated antigen and incubated for 30 min at room temperature with gentle agitation and 10 min in an ice bath. Then, the cells and antigen solution was pelleted for 5 min at 2500 g and 4° C., washed twice with 50 ml wash buffer and pelleted after each washing step. The cells were resuspended in 5 ml wash buffer plus 25 μl streptavidin microbeads (μMACS streptavidin kit, MACS Miltenyi) and incubated on ice for 10 min. Finally, 15 ml wash buffer were added.

The LS column was placed in the separator and 3 ml of wash buffer were applied to precondition the column. Then, the cell solution was loaded in 7 ml batches. Once the column stopped dripping it was briefly removed from the magnet and placed back in the magnet to reorient the beads in the column to allow trapped cells to flow through. Before loading the next 7 ml cell suspension 1 ml of wash buffer was applied to the column. These steps were repeated until all cells were loaded. Then, the column was washed with 3 ml wash buffer, briefly removed from the magnet and washed again with 3 ml wash buffer. To elute the binding cells, the column was removed from the magnet and 5 ml wash buffer were added. Using the supplied plunger, the cells were pushed through the column into a new tube. The binding cell fraction was pelleted for 5 min at 2,500 g. The pellet was resuspended in 10 ml SD-CAA medium and incubated at 30° C. and 180 rpm overnight. 10 μl of eluted cells were diluted in 990 μl SD-CAA and 100 μl were plated onto an MDL plate and incubated at 30° C. for three days to estimate the output of MACS procedure.

In the FACS selection rounds that followed, the induced cell suspensions were diluted to $10^8$ cells per 1 ml 10% BSA-PBS and centrifuged at 3000 rpm for 5 min at 20° C. To block the cells, the pellets were resuspended in 1 ml 10% BSA-PBS and incubated for 30 min at 20° C. on a rotating platform. The cells were centrifuged at 3000 rpm for 5 min at 20° C. and resuspended in 250 μl 10% BSA-PBS containing 1 μM biotinylated EGFR-Fc. After incubation for 30 min at 20° C. on a rotating platform the cells were centrifuged at 3000 rpm for 5 min at 4° C. To wash the cells, the pellets were resuspended in 1 ml ice-cold PBS and centrifuged at 3000 rpm for 5 min at 4° C. Then, the cells were resuspended in 250 μl 10% BSA-PBS with streptavidin-Alexafluor 647 (1:800) and anti-V5-FITC antibody (1:100) (Thermo Fisher Scientific) and incubated for 30 min on ice. The cells were centrifuged at 3000 rpm for 5 min at 4° C. before they were resuspended in 1 ml ice-cold PBS and centrifuged again. Finally, the cells were resuspended in 250 μl ice-cold PBS and were kept on ice until sorting with FACS Aria™. At least 20× output of the previous sorting round was processed and 0.1% top anti-V5-antibody positive yeast cells were collected. The $5^{th}$ sort was plated out to characterize single yeast display clones.

Following sequences of binders were identified (Table 3): Table 3 depicts the identified sequences of binders

| clone | Helix C (AA 160-162) | Segment D (AA 181-189) |
|---|---|---|
| 1 | ILG | PHHWRFPKA (SEQ ID NO: 181) |

Example 7: Construction of CD81 LEL Library 2

To expand the possible repertoire of antigen-specific CD81 LEL binders it was aimed to design libraries where amino acid residues different those randomized in CD81 LEL library 1 could form a potential antigen recognition site. This design involves randomization of 11 amino acid residues: in helix A amino acid residues 132-133, in AB loop 136-139 and in helix C 162-165, 167 and 171-172. The scaffold here is a CD81 LEL mutant that harbors two novel disulfide bonds: one connects helices A and B (C4) and one connects helices A and C (C9). This CD81LEL mutant with a combination of novel disulfide bonds Ala134Cys/Lys144Cys and Val135Cys/Ser168Cys was then produced in HEK293-6E cells (CNRC) and tested for its thermostability. Thermal unfolding was recorded up to 130° C. and proceeded in a single event at a Tm of 109.40±0.25° C., higher from the wild-type hCD81LEL for 43° C. This protein termed C4C9 migrated in SEC in native conditions as a single sharp peak at a time characteristic for the wild-type protein. Importantly, the stabilized mutant was able to bind to the structure-reporter antibody M38 (Thermo Fisher Scientific) to the same extent as to the wild-type hCD81 LEL. Far-UV CD spectrum for this mutant was examined and found to be identical to one obtained for the wild-type hCD81 LEL, which was typical of a protein with high α-helix content with two characteristic minima at 208 and 222 nm, similarly to previously published results.

First, a series of mutagenesis steps the recipient vector for yeast display pyd1_CD81 LEL was modified with deletion of inherent BamHI and HindIII restriction sites. All mutagenesis steps were performed using Quickchange Lightning Mutagenesis Kit (Agilent) using oligonucleotides: BamHI site was deleted using oligonucleotides

```
(SEQ ID NO: 21):
CGATAAGGTACCAGGTTCCTTTGTCAACAAG

(SEQ ID NO: 22):
CTTGTTGACAAAGGAACCTGGTACCTTATCG,
```

and HindIII site was deleted using oligonucleotides

```
(SEQ ID NO: 23):
GTATGTTTTTAAGCTCCTGCAGGCTAGTGGTG

(SEQ ID NO: 24):
CACCACTAGCCTGCAGGAGCTTAAAAACATAC.
```

To facilitate the recombination of library fragment after linearization, novel BamHI restriction site was introduced using oligonucleotides

```
(SEQ ID NO: 25):
TTTGTGTCCCTCGGGATCCAACATCATCAGCAA

(SEQ ID NO: 26):
TTGCTGATGATGTTGGATCCCGAGGGACACAAA,
```

and a novel HindIII restriction site was introduced using oligonucleotides

```
(SEQ ID NO: 27):
GCAGTTCTATGACCAAGCTTTACAGCAGGCCGTGG

(SEQ ID NO: 28):
CCACGGCCTGCTGTAAAGCTTGGTCATAGAACTGC.
```

Recipient vector DNA was isolated with midipreparation using Nucleobond (Macherey-Nagel) and the vector was linearized using restriction with BamHI and HindIII. Vector backbone was isolated using purification after preparative gel electrophoresis.

Further, the template insert of CD81 with mutations Ala134Cys and Lys144Cys, which form the novel disulfide bond, and Val135Cys and Ser168Cys, which form another novel disulfide bond, was modified to introduce sequences with restriction sites to facilitate the correct recombination of the library encoding fragment. Template for modifications was pTT22SSP4_CD81 LEL C4C9 mutant. HindIII site was introduced using oligonucleotides

```
(SEQ ID NO: 29):
GCAGTTCTATGACCAAGCTTTACAGCAGTGCTGTG

(SEQ ID NO: 30):
CACAGCACTGCTGTAAAGCTTGGTCATAGAACTGC
```

and BamHI site was introduced using oligonucleotides

```
(SEQ ID NO: 31):
TTTGTGTCCCTCGGGATCCAACATCATCAGCAA
```

-continued

```
(SEQ ID NO: 32):
TTGCTGATGATGTTGGATCCCGAGGGACACAAA.
```

PCR fragment with randomized nucleotide sequences was produced with oligonucleotides

```
(SEQ ID NO: 33):
AAGGATGTGAAGCAGTTCTATGACCAAGCTTTANNKNNKTGCTGTNNKNN

KNNKNNKGCCAACAACGCCTGTGCTGTG,
wherein N is any one of A, C, G, or T
and

(SEQ ID NO: 34):
CTTGAAGAGGTTGCTGATGATGTTGGATCCCGAGGGACACAAATTMNNMN

NGAGCACACAMNNGGTMNNMNNMNNMNNTGTGCTGGAGCCACAGCA,
wherein N is any one of A, C, G, or T;
and M is any one of A or C.
```

(according to IUPAC nucleotide code).

In a PCR reaction using Q5 HiFi Polymerase (New England Biolabs) and library fragment was purified after gel electrophoresis.

For transformation, a starter culture of EBY100 (Thermo Fisher Scientific) in 20 ml YPD medium (2% peptone, 1% yeast extract, 2% glucose) (Merck) was incubated overnight at 30° C. and 180 rpm. The culture was then diluted to an $OD_{600}$ of 0.4 and incubated for about 5 hours at 30° C. and 180 rpm. Aliquots of 50 ml cell culture were then pelleted at 1000 g for 5 min at room temperature, then washed with 25 ml AD and pelleted again. The cells were resuspended in 3 ml 100 mM Li-acetate and incubated for 15 min at 30° C. in a shaking incubator. Cells were pelleted and supernatant removed. Components of the transformation mix were added as follows: 2400 µl 50% PEG 3350, 360 µl 1.0 M Li-acetate, 500 µl 2 mg/ml ssDNA (salmon sperm carrier DNA, previously heated up to 95° C. for 5 minutes and then placed on ice)(Sigma-Aldrich), 10 µg linearized recipient vector and 7 µg DNA fragment. The cell pellets were resuspended in the transformation mix and incubated for 30 min at 30° C. in a shaking incubator and heat-shocked at 42° C. for 45 min.

After collecting the cells by centrifugation at 1000 g for 5 min at room temperature and removing the supernatant, the pellets were resuspended in 10 ml SD-CAA medium. Aliquots were removed for dilution plating to determine the library size: 10 µl of cell suspension were diluted in 990 µl SD-CAA medium of which 100 µl were plated on an MDL plate and incubated at 30° C. for 3 days. Yeast cells were diluted in 50 ml SD-CAA medium and incubated at 30° C. at 180 rpm for 24 h, passaged into fresh SD-CAA medium at 1:20 dilution and cultured for another 24 h under the same conditions. Cells were harvested at 1000 g, 5 min, at 4° C. and pellets were resuspended in an equal volume of 30% glycerol before freezing at −80° C.

Yeast display transformations of the CD81_LEL Library 2 resulted in:

Library 2_4: $9.5\times10^{6}$ independent members,

Library 2_5: $2.1\times10^{7}$ independent members, and

Library 2_6: $1.7\times10^{7}$ independent members.

Example 7: Selections of CD81 LEL Library 2 with Human EGFR-Fc

For sorting, libraries were first cultured in SD-CAA medium supplemented with penicillin-streptomycin at 30° C. with shaking overnight and then the expression of recombinant protein was induced by resuspending the yeast cells in SG/R-CAA medium with penicillin-streptomycin and incubating them with shaking overnight at 37° C.

Next, $10^9$ cells were pelleted for 5 min at 2500 g, then they were washed by resuspending the pellet in 50 ml wash buffer (1×D-PBS (Thermo Fisher Scientific), 0.25% BSA (Sigma Aldrich), 2 mM EDTA (Sigma Aldrich) and pelleted again for 5 min at 2500 g. The washed cells were resuspended in 25 ml wash buffer containing 0.25 μM biotinylated antigen and incubated for 30 min at room temperature with gentle agitation and 10 min in an ice bath. Then, the cells and antigen solution was pelleted for 5 min at 2,500 g and 4° C., washed twice with 50 ml wash buffer and pelleted after each washing step. The cells were resuspended in 5 ml wash buffer plus 25 μl streptavidin microbeads and incubated on ice for 10 min. Lastly, 15 ml wash buffer were added.

The LS column (Milteny Biotec) was placed in the separator and 3 ml of wash buffer were applied to precondition the column. Then, the cell solution was loaded in 7 ml batches. Once the column stopped dripping it was briefly removed from the magnet and placed back in the magnet to reorient the beads in the column to allow trapped cells to flow through. Before loading the next 7 ml cell suspension 1 ml of wash buffer was applied to the column. These steps were repeated until all cells were loaded. Then, the column was washed with 3 ml wash buffer, briefly removed from the magnet and washed again with 3 ml wash buffer. To elute the binding cells the column was removed from the magnet and 5 ml wash buffer were added. Using the supplied plunger, the cells were pushed through the column into a new tube. The binding cell fraction was pelleted for 5 min at 2500 g. The pellet was resuspended in 10 ml SD-CAA medium and incubated at 30° C. and 180 rpm overnight. Additionally, 100 μl of a $10^{-2}$ dilution were plated onto an MDL plate and incubated at 30° C.

The induced cell suspensions were diluted to $10^8$ cells per 1 ml 10% BSA-PBS and centrifuged at 3000 rpm for 5 min at 20° C. To block the cells, the pellets were resuspended in 1 ml 10% BSA-PBS and incubated for 30 min at 20° C. on a rotating platform. The cells were centrifuged at 3000 rpm for 5 min at 20° C. and resuspended in 250 μl 10% BSA-PBS containing 1 μM biotinylated EGFR-Fc (Sino Biological). After incubation for 30 min at 20° C. on a rotating platform the cells were centrifuged at 3000 rpm for 5 min at 4° C. To wash the cells, the pellets were resuspended in 1 ml ice-cold PBS and centrifuged at 3000 rpm for 5 min at 4° C. Then, the cells were resuspended in 250 μl 10% BSA-PBS with streptavidin-Alexafluor 647 (1:800) and anti-V5-FITC antibody (1:100) (Thermo Fisher Scientific) and incubated for 30 min on ice. The cells were centrifuged at 3000 rpm for 5 min at 4° C. before they were resuspended in 1 ml ice-cold PBS and centrifuged again. Lastly, the cells were resuspended in 250 μl ice-cold PBS and were kept on ice until sorting with FACS Aria™.

After sorting the cells were resuspended in an appropriate amount of SD-CAA and incubated at 30° C. and 180 rpm before induction as described above.

TABLE 4

| Library | AB1 (AA 132-133) | AB2 (AA 136-139) | CD1 (AA 162-165) | CD2 (AA167) | CD3 (AA171-172) |
|---|---|---|---|---|---|
| 81_2_4 | VI | GASA (SEQ ID NO: 35) | DAGP (SEQ ID NO: 36) | H | VE |
| 81_2_4 | KW | SFLV (SEQ ID NO: 37) | PLTM (SEQ ID NO: 38) | T | LK |
| 81_2_6 | WR | AKMY (SEQ ID NO: 39) | SARF (SEQ ID NO: 40) | E | TW |

Example 8: Expression of Modified CD81 LEL in Soluble Form

Sequences encoding CD81 were amplified from yeast display clones using oligonucleotides

```
(SEQ ID NO: 41):
ACGTGCTAGCTTTGTCAACAAGGACCAGATC

(SEQ ID NO: 42):
ACGTGGTGACCGGTGCTGGAACCCTTCCCGGAGAAGAGGTC.
```

PCR fragment was cut with restriction enzymes NheI and BstEII and ligated to vector pTT28 (CNRC) that was cut with the same enzymes. Ligation mixture was transformed into electrocompetent *E. coli* TOP10 (Thermo Fisher Scientific) and transformats were selected on ampicilline plates. Plasmid was isolated with minipreparation and transfected into ExpiCHO cells (Thermo Fisher Scientific). Expression in ExpiCHO expression system (Thermo Fisher Scientific) was according to MaxTiter protocol exactly following the manufacturer's instructions. hCD81 LEL variants were then purified via Ni-NTA chromatography using standard protocols. Supernatant was diluted with an equal volume of AD and buffered with PBS and 20 mM imidazole and pH adjusted to 7.5. Excel Ni-NTA column (GE Healthcare) was equilibrated with PBS and 20 mM imidazole, pH 7.5, and loaded with the buffered supernatant. Elution was in 5 column volumes with a linear gradient from 20 to 500 mM imidazol in PBS, pH 7.5. Protein-containing fractions were pooled and dialysed against 100-times volume of PBS at 4° C. overnight.

SEC analysis in native conditions revealed a monodisperse elution profile corresponding to a dimeric form of the protein, analogously to the soluble wild-type CD81 LEL.

Alternatively, protein was expressed in ExpiCHO expression system (Thermo Fisher Scientific) following MaxTiter protocol exactly according to manufacturer's instructions. hCD81 LEL was then purified via Ni-NTA chromatography using standard protocols. Supernatant was diluted with an equal volume of AD and buffered with PBS and 20 mM imidazole and pH adjusted to 7.5. Excel Ni-NTA column (GE Healthcare) was equilibrated with PBS and 20 mM imidazole, pH 7.5, and loaded with the buffered supernatant. Elution was in 5 column volumes with a linear gradient from 20 to 500 mM imidazol in PBS, pH 7.5. Protein-containing fractions were pooled and dialysed against 100-times volume of PBS at 4° C. overnight.

Example 9: Thermal Stabilization of the CD81 LEL

The fragment encoding hCD81 LEL (fragment Phe113-Lys201) (numbering according to SEQ ID NO:87) was amplified from a synthetic construct with a full length CD81 sequence (Geneart). DSDBASE (Vinayagam et al. 2004, Nucleic Acids Research, Volume 32, Issue suppl_1, Pages D200-D202, https://doi.org/10.1093/nar/gkh026) was used as a prediction tool for the identification of positions with the potential to harbor cysteine residues suitable for the creation of intradomain disulfide bonds. The algorithm was used to analyze hCD81 LEL crystal structure 1G8Q for the distances between Cα and Cβ atoms of neighboring amino acid residues as well as for torsion angles and resulting S—S bond lengths. Out of 36 predicted possible disulfide bonds 11 with the highest likelihood of success as judged by visual examination of the crystal structure were selected. Five of those were predicted by the DSDBASE program both in protomer A and protomer B of hCD81 LEL.

Mutagenesis of single chosen amino acid residues to cysteine was performed using QuikChange Lightning Mutagenesis kit (Agilent), exactly according to manufacturer's instructions with oligonucleotides listed in Table 5.

Table 5 showing oligonucleotides used for mutagenesis

| hCD81 LEL variant | Substitution | Oligonucleotide sequence | SEQ ID NO: |
|---|---|---|---|
| C1 | A134C | CAGGCCCTACAGCAGTGCGTGGTGGATGATGAC | 43 |
| | | GTCATCATCCACCACGCACTGCTGTAGGGCCTG | 44 |
| | A143C | GATGATGCCAACAACTGCAAGGCTGTGGTGAAG | 45 |
| | | CTTCACCACAGCCTTGCAGTTGTTGGCATCATC | 46 |
| C2 | A130C | CAGTTCTATGACCAGTGTCTACAGCAGGCCGTG | 47 |
| | | CACGGCCTGCTGTAGACACTGGTCATAGAACTG | 48 |
| | V146C | AACAACGCCAAGGCTTGTGTGAAGACCTTCCAC | 49 |
| | | GTGGAAGGTCTTCACACAAGCCTTGGCGTTGTT | 50 |
| C3 | Q133C | GACCAGGCCCTACAGTGCGCCGTGGTGGATGATG | 51 |
| | | CATCATCCACCACGGCGCACTGTAGGGCCTGGTC | 52 |
| | A143C | GATGATGCCAACAACTGCAAGGCTGTGGTGAAG | 53 |
| | | CTTCACCACAGCCTTGCAGTTGTTGGCATCATC | 54 |
| C4 | A134C | CAGGCCCTACAGCAGTGCGTGGTGGATGATGAC | 55 |
| | | GTCATCATCCACCACGCACTGCTGTAGGGCCTG | 56 |
| | K144C | GACGCCAACAACGCCTGTGCTGTGGTGAAGACC | 57 |
| | | GGTCTTCACCACAGCACAGGCGTTGTTGGCGTC | 58 |
| C5 | L154C | GACCTTCCACGAGACGTGTGACTGCTGTGGCTC | 59 |
| | | GAGCCACAGCAGTCACACGTCTCGTGGAAGGTC | 60 |
| | K193C | GAGGACTGCCACCAGTGTATCGATGACCTCTTC | 61 |
| | | GAAGAGGTCATCGATACACTGGTGGCAGTCCTC | 62 |
| C6 | A120C | CAACAAGGACCAGATCTGTAAGGATGTGAAGCAG | 63 |
| | | CTGCTTCACATCCTTACAGATCTGGTCCTTGTTG | 64 |
| | F198C | AAGATCGATGACCTCTGTTCCGGGAAGTGATGAG | 65 |
| | | CTCATCACTTCCCGGAACAGAGGTCATCGATCTT | 66 |
| C7 | A130C | CAGTTCTATGACCAGTGTCTACAGCAGGCCGTG | 67 |
| | | CACGGCCTGCTGTAGACACTGGTCATAGAACTG | 68 |
| | A143C | GATGATGCCAACAACTGCAAGGCTGTGGTGAAG | 69 |
| | | CTTCACCACAGCCTTGCAGTTGTTGGCATCATC | 70 |
| C8 | L131C | TTCTATGACCAGGCCTGCCAGCAGGCCGTGGTG | 71 |
| | | CACCACGGCCTGCTGGCAGGCCTGGTCATAGAA | 72 |
| | L165C | AGCACACTGACTGCTTGTACCACCTCAGTGCTC | 73 |
| | | GAGCACTGAGGTGGTACAAGCAGTCAGTGTGCT | 74 |
| C9 | V135C | GCCCTACAGCAGGCCTGTGTGGATGATGACGCC | 75 |
| | | GGCGTCATCATCCACACAGGCCTGCTGTAGGGC | 76 |
| | S168C | GCTTTGACCACCTGTGTGCTCAAGAACAAT | 77 |
| | | ATTGTTCTTGAGCACACAGGTGGTCAAAGC | 78 |
| C10 | V169C | TTGACCACCTCAGTGTGCAAGAACAATTTGTGTC | 79 |
| | | GACACAAATTGTTCTTGCACACTGAGGTGGTCAA | 80 |
| | L174C | GTGCTCAAGAACAATTGTTGTCCCTCGGGCAGC | 81 |
| | | GCTGCCCGAGGGACAACAATTGTTCTTGAGCAC | 82 |
| C11 | S160C | GACTGCTGTGGCTCCTGTACACTGACTGCTTTG | 83 |
| | | CAAAGCAGTCAGTGTACAGGAGCCACAGCAGTC | 84 |
| | D189C | AACCTCTTCAAGGAGTGTTGCCACCAGAAGATC | 85 |
| | | GATCTTCTGGTGGCAACACTCCTTGAAGAGGTT | 86 |

hCD81 LEL variants were cloned into the pTT22SSP4 mammalian expression vector (CNRC) and expressed in two different expression systems. For prescreening, the constructs were expressed in HEK293-6E cells (CNRC) at a 2-mL-scale in F17 medium supplemented with 4 mM glutamine and 50 μg/mL G-418 (Thermo Fisher Scientific) on an orbital shaker at 180 rpm, at 37° C. under 5% $CO_2$ for 4 days, with feeding of TN-20 to an end concentration of 0.8% on the second day after transfection. Mutant C5 did not express, C6 expressed poorly and 010 formed a conspicuous dimer, therefore they were omitted from further analysis. Mutants selected for further characterization (C1, C2, C3, C4, C7, C8, C9 and C11) were transfected into ExpiCHO cells (Thermo Fisher Scientific) exactly according to manufacturer's instructions. Cultivation of the cells proceeded according to MaxTiter protocol (Thermo Fisher Scientific). Supernatants were harvested after 14 days and purified using Ni-NTA affinity chromatography. After clarification, the samples were buffered with phosphate buffered saline (PBS) with 20 mM imidazole, pH 7.5, and passed over Excel Ni-NTA column (GE Healthcare) equilibrated with the same buffer. His-tagged hCD81 LEL was eluted with a gradient from 20 to 500 mM imidazole in 5 column volumes. Fractions containing the target protein were pooled and dialyzed twice against 100-times volume of PBS overnight at 4° C. The proteins were stored at −80° C. until use.

Shimadzu LC-20A Prominence system equipped with a diode array detector and a refractive index detector was used to perform SEC-HPLC with a Superdex 200 Increase 10/300 GL column (GE Healthcare). The mobile-phase buffer used was PBS with 200 mM NaCl. Chromatography was conducted with a constant flow rate of 0.75 mL/min. A total of 200 μg protein at about 2 mg/mL were loaded on the column for analysis. Column calibration was performed with a set of molecular weight standards ranging from 10 to 500 kDa (Bio-Rad). Mutants C1 and C8 did not show well resolved peaks and all other mutants were similar to the wild-type protein.

DSC experiments were performed using an automated MicroCal PEAQ-DSC Automated system (Malvern), using 80 μM protein solution, diluted in PBS at pH 7.4. The heating was performed from 20° C. to 110° C. at a rate of 1° C./min. Protein solution was then cooled in situ and an identical thermal scan was run to obtain the baseline for subtraction from the first scan. All measurements were taken in duplicates. Fitting was performed with MicroCal PEAQ-DSC Software using the non-2-state transition mechanism.

Measurement of thermal stability of wild-type CD81 LEL revealed a single melting point at 66.15° C., however a low enthalpy of $2.4\times10^4$ kcal/mol.

Table 6 showing Tm of hCD81 LEL variants

| | Mutated position 1 | | Mutated position 2 | | |
|---|---|---|---|---|---|
| hCD81 LEL variant | Located on segment | Amino acid | Located on segment | Amino acid | Tm (° C.) |
| wild-type | | | | | 66.15 ± 0.25 |
| C1 | Helix A | Ala134 | Helix B | Ala143 | n.d.[1] |
| C2 | Helix A | Ala130 | Helix B | Val146 | 67.35 ± 0.05 |
| C3 | Helix A | Gln133 | Helix B | Ala143 | 82.15 ± 0.05 |
| C4 | Helix A | Ala134 | Helix B | Lys144 | 88.95 ± 0.05 |
| C5 | Helix B | Leu154 | Helix E | Lys193 | n.d. |
| C6 | Helix A | Ala120 | Helix E | Phe198 | n.d. |
| C7 | Helix A | Ala130 | Helix B | Ala143 | 76.90 ± 0.00 |
| C8 | Helix A | Leu131 | Helix C | Leu165 | n.d. |
| C9 | Helix A | Val135 | Helix C | Ser168 | 90.45 ± 0.15 |
| C10 | Helix C | Val169 | Unstructured part of segment C | Leu174 | n.d. |
| C11 | Loop preceding helix C | Ser160 | Start of helix D | Asp189 | 70.25 ± 0.15 |

Differential thermal calorimetry scans were run with a re-scan of the denatured protein solution to be subtracted as background. Here it was discovered that the mutant C2 in contrast with wild-type CD81 LEL and other stabilized variants surprisingly exhibited reversible unfolding up to 110° C.

A hCD81LEL mutant with a combination of potently stabilizing novel disulfide bonds Ala134Cys/Lys144Cys and Val135Cys/Ser168Cys was then produced and tested for its thermostability. Thermal unfolding was recorded up to 130° C. and proceeded in a single event at a Tm of 109.40±0.25° C., higher from the wild-type CD81LEL for 43° C. This protein termed C4C9 migrated in SEC in native conditions as a single sharp peak at a time characteristic for the wild-type protein.

Importantly, the stabilized mutant was able to bind to the structure-reporter antibody M38 to the same extent as to the wild-type CD81 LEL. ELISA plate (Maxisorp, NUNC) was coated with an anti-hCD81 M38 antibody (Thermo Fisher Scientific) at 5 μg/mL in PBS for 1 h at room temperature. After blocking with 5% bovine serum albumin (BSA)-PBS for 1 h at RT, supernatants of HEK293-6E cells transfected with hCD81 LEL variants or purified variants of hCD81 LEL diluted in 2.5% BSA-PBS were allowed to bind for 1 h at RT. After extensive washing, the binding of mutant proteins was detected with an anti-his-horseradish peroxidase (HRP) conjugated antibody (QIAgen), diluted 1:2000 in 2.5% BSA-PBS. Antibody binding was revealed with 3,3',5,5'-tetramethylbenzidine (TMB) (Sigma Aldrich), the reaction was stopped by adding an equal volume of 30% $H_2SO_4$ and absorbance was read at 450/620 nm.

Table 7 showing absorbance values of wildtype and mutant CD81 LEL

| CD LEL variant concentration (μg/ml) | A 450/620 (wild-type CD81 LEL) | SE (wild-type CD81 LEL) | A 450/620 (C4C9) | SE (C4C9) |
|---|---|---|---|---|
| 5 | 3.9684 | 0.0316 | 3.82795 | 0.01235 |
| 1.666667 | 3.694 | 0.077 | 3.82425 | 0.08275 |
| 0.555556 | 3.6268 | 0.1979 | 3.73145 | 0.02185 |
| 0.185185 | 3.67715 | 0.06925 | 3.69125 | 0.05935 |
| 0.061728 | 3.53355 | 0.09535 | 3.45675 | 0.04415 |
| 0.020576 | 1.8876 | 0.0352 | 1.97565 | 0.00285 |
| 0.006859 | 0.61595 | 0.01845 | 0.7503 | 0.0542 |
| 0.002286 | 0.17665 | 0.01115 | 0.187 | 0.0405 |
| 0 (2nd only) | 0.02185 | 0.00125 | | |

Far-UV CD spectrum for the mutant C4C9 and wild-type CD81 was examined. The CD spectra were measured on a Chirascan spectropolarimeter (Applied Photophysics). A 1 mm quartz cuvette was used Protein preparations were diluted in PBS to 1 mg/mL. Spectra were found to be identical for the wild-type hCD81 LEL and C4C9. Spectrum observed was typical of a protein with high α-helix content with two characteristic minima at 208 and 222 nm, similarly to previously published results.

Table 8 showing Far-UV CD spectrum for wildtype and mutant CD81

| Wavelength (nm) | Raw ellipticity (millideg) Wild-type CD81 LEL | Raw ellipticity (millideg) C4C9 |
|---|---|---|
| 260 | 0.206785 | 0.145295 |
| 259 | 0.19977 | 0.177317 |
| 258 | 0.265558 | 0.205747 |
| 257 | 0.206915 | 0.148188 |
| 256 | 0.221795 | 0.159402 |
| 255 | 0.257513 | 0.183345 |
| 254 | 0.223584 | 0.140538 |
| 253 | 0.231864 | 0.120346 |
| 252 | 0.157287 | 0.072734 |
| 251 | 0.0663846 | −0.0527117 |
| 250 | −0.157381 | −0.263102 |
| 249 | −0.325095 | −0.453448 |
| 248 | −0.617804 | −0.716791 |
| 247 | −1.118 | −1.19926 |
| 246 | −1.6976 | −1.79587 |
| 245 | −2.4624 | −2.56849 |
| 244 | −3.50611 | −3.55678 |
| 243 | −4.72366 | −4.74579 |
| 242 | −6.31973 | −6.25803 |
| 241 | −8.27745 | −8.2164 |
| 240 | −10.556 | −10.3732 |
| 239 | −13.4046 | −13.1298 |
| 238 | −16.736 | −16.3624 |
| 237 | −20.6866 | −20.1611 |
| 236 | −25.1074 | −24.5011 |
| 235 | −30.1779 | −29.403 |
| 234 | −35.8887 | −35.0253 |
| 233 | −42.0612 | −40.9566 |
| 232 | −48.5922 | −47.4025 |
| 231 | −55.3904 | −53.9963 |
| 230 | −61.9441 | −60.4902 |
| 229 | −68.2922 | −66.5214 |
| 228 | −74.0251 | −72.2262 |
| 227 | −79.1404 | −77.2646 |
| 226 | −83.4069 | −81.4188 |
| 225 | −86.7399 | −84.7366 |
| 224 | −88.9684 | −86.9499 |
| 223 | −90.4185 | −88.2177 |
| 222 | −90.8311 | −88.7247 |
| 221 | −90.4246 | −88.2572 |
| 220 | −89.1682 | −87.186 |
| 219 | −87.7019 | −85.7441 |
| 218 | −86.3482 | −84.3822 |
| 217 | −85.2084 | −83.4309 |
| 216 | −84.2489 | −82.4846 |
| 215 | −83.359 | −81.8334 |
| 214 | −82.945 | −81.2163 |
| 213 | −83.4676 | −81.9112 |
| 212 | −85.7387 | −83.7029 |
| 211 | −88.655 | −87.0087 |
| 210 | −92.3376 | −90.7764 |
| 209 | −95.7168 | −93.9584 |
| 208 | −97.4284 | −95.5125 |
| 207 | −93.7432 | −93.6295 |
| 206 | −84.8028 | −86.8648 |
| 205 | −63.0458 | −70.4512 |
| 204 | −45.8841 | −52.7578 |
| 203 | −17.4302 | −33.2052 |
| 202 | 16.0949 | 13.3243 |
| 201 | 791.06 | −95.0327 |
| 200 | −113.547 | −58.5575 |
| 199 | −93.1264 | −40.4351 |
| 198 | −69.128 | −23.4953 |
| 197 | −58.7217 | −17.9316 |
| 196 | −65.7443 | −35.5883 |
| 195 | −50.8545 | −23.3845 |

Example 10: Production of Target-Specific EVs in Cell Culture 10.1 Transient Transfection of Target-Specific EV Donor Cell Line Using HeLa Cells HeLa cells expressing C-terminal GFP-fused recombinant CD81 to secrete target-specific CD81-GFP-containing exosomes (CD81-GFP-exosomes) were transiently transfected using electroporation. HeLa cells ($5\times10^6$ cells) were plated on a T175 cell culture flask (Sigma, Kremsmünster, Germany) 2-3 days prior to transfection. Complete RPMI-1640 medium (Merck, Darmstadt, Germany), containing 10% FCS, 4 mM L-Glutamine, was used for the regular culturing of donor HeLa cells. On the day of transfection (Day 0), HeLa cells (optimally at 70-85% of confluency) were harvested using 0.1% Trypsin solution (5 minutes treatment, neutralization with complete RPMI-1640). Detached HeLa cells in RPMI-1640 were quantified using the ViCell Cell Counter. $3\times10^6$ cells were transfected with CD81-GFP plasmid (pTT5, NRC Canada, Ottawa, Canada, 4 μg) to fill one T175 flask. Electroporation was performed using an Amaxa Nucleofector I device (Lonza, Basel, Switzerland) according to the manufacturers brochure (program 1-013 for HeLa cells) using an in-house prepared electroporation buffer (5 mM KCl, 15 mM MgCl2, 120 mM Na2HPO4/NaH2PO4 pH7.2, 50 mM Mannitol, 0.005% Pluronic F-68). Electroporated cells were recovered in complete RPMI-1640 and cultured for a time period of 24 hours allowing the cells to attach to culture flask surface. Indeed, various forms of human transferrin receptor targeting recombinant CD81 localized to the plasma membrane suggesting functional integration of the recombinant tetraspanin (FIG. 4).

10.2 Isolation and Purification of Target-Specific EVs

On Day 1 (24 hours after transfection), the culturing medium was removed and replaced by a respective volume (45 mL for 1× T175) of EV-depleted secretion medium (RPMI-1640). EV-depleted RPMI-1640 was prepared by collecting the supernatant fraction from ultracentrifuged (14-18 h, 4° C., 100,000 g) complete RPMI-1640 (containing 20% FCS) and diluting the medium to 10% FCS with RPMI-1640 and adding of L-Glutamine to a final concentration of 4 mM. HeLa cells were incubated with EV-depleted medium for 72 hours (37° C., 5% CO2 atmosphere) to secrete target-specific EVs.

Isolation of EVs was performed after 72 h of collection time by using ultracentrifugation. The conditioned cell culture medium was collected and centrifuged (3,100×g) for 30 min at 4° C. to remove cells and cell debris. The supernatant was passed through a 450 nm syringe filter unit (Merck, Darmstadt, Germany) and transferred to 100 mL sealable ultracentrifuge tubes. The supernatant was then centrifuged (100,000×g) for 90 min at 4° C. using an ultracentrifuge (Optima L-60, Beckman Coulter, Brea, USA). The supernatant was removed and the pellet was collected in 1 mL the remaining medium. A second step of ultracentrifugation was performed (100,000×g, 90 min, 4° C.) to collect EVs in a smaller volume. The supernatant was again removed and the remaining EV pellet was resuspended in 200 to 400 μl of HEPES-based 1× Live Cell Imaging Solution (ThermoFisher Scientific, Waltham, USA). Using this method, around $10^{11}$ EVs/ml were purified from HeLa supernatants.

Example 11: Production of EVs Carrying a Traceable and Purifiable Tag 11.1 Sequence and Cloning of CD81-Snorkel Tag in Retroviral System Wild-type human CD81 sequence amino acid sequence SEQ ID NO:87; nucleic acid sequence SEQ ID NO:88) was cloned into pBMN vector with C-terminally fused SNORKEL tag (Brown et al. 2013, PLoS ONE 8(9): e73255. doi:10.1371/journal.pone.0073255). SNORKEL tag enables tags displayed on the surface of vesicular membrane. The PCR product of CD81 was cut with NcoI and AgeI and PCR product of SNORKEL tag was cut with AgeI and NotI. pBMN plasmid was cut with NcoI and NotI. Digested PCR products where ligated with NcoI and NotI digested pBMN plasmid. The ligation mixture was transformed into competent *E. coli* cells and transformants were selected on ampicillin plates. Plasmids were isolated by endotoxin free plasmid preparation (Qiagen Maxiprep).

11.2 Stable Expression of CD81-Snorkel Tag in EV Donor Cells Using Retroviral Transfection Phoenix cells ($5\times10^6$ cells) were plated in a T75 plate (Sigma, Kremsmünster, Germany) 1 day prior (day 0) to transfection. Cells were cultured in complete growth media with DMEM 4.5 g glucose with 10% FCS and 4 mM L-Glutamine. Once cells were 60-70% confluent, culture media was removed and replaced with DMEM 4.5 g glucose with 4 mM L-Glutamine without FCS. Cells are transfected with 10 µg of pBMN-CD81-SNORKEL tag (SNORKEL tag fused to CD81 C-termini) plasmid using jetPRIME transfection reagent (Polyplus, France). 24 hrs post transfection (day 1), media was changed to complete growth media of 7 ml. Target cells (HeLa) were plated in 6 well plate (Sigma, Kremsmünster, Germany) with $1\times10^5$ cells/well in RPMI-1640 medium containing 10% FCS and 4 mM L-Glutamine. 24 hrs post seeding (day 2), HeLa cells (50-80% confluency) can be infected. 7 mL supernatant from Phoenix cells (containing virus particles) was filtered using 0.45 µm filter (Merck, Darmstadt, Germany) and polybrene (final conc 8 µg/mL) to this filtrate and mixed. Fresh growth media was added onto Phoenix cells. Supernatant from target cells was removed and up to 2 mL of virus-containing supernatant were added. The entire plate was wrapped in parafilm and centrifuge at 800×g for 60 min at room temperature. Then, virus supernatant was discarded and fresh growth media was added onto Hela cells. Viral infection was carried out for next 3 more days until the cells reach 95-100% expressing CD81-SNORKEL tag. The tagged CD81 was localized to cell membranes indicating correct folding and localization (FIG. 5A). Along with SNORKEL tag fused to C-termini of CD81 the method was also successfully performed with CD63 fusion protein in Hela cells (FIG. 5B). Similar results were observed in human mesenchymal stem cells (ASCs). The EVs are simultaneously positive for the HA tag as well as the CD81 when subjected to electron microscopy after immunogold labelling by anti HA antibodies coupled to 10 nm gold particles and anti-CD81 antibodies coupled to 18 nm gold particles (FIG. 5C).

11.3 Characterization of EVs for Size, Number and Incorporation of CD81-SNORKEL Tag HeLa cells stably expressing CD81-SNORKEL tag were plated in 3 T75 plates ($5\times10^6$ cells/flask) in culture medium. 24 hrs of post seeding (day 1) the culturing medium was removed and replaced by a respective volume (12 mL for 1× T75) of EV-depleted secretion medium (RPM1-1640). EV-depleted RPM1-1640 was prepared by collecting the supernatant fraction from ultracentrifuged (14-18 h, 4° C., 100,000 g) complete RPMI-1640 (containing 20% FCS) and diluting the medium to 10% FCS with RPMI-1640 and adding of L-Glutamine to a final concentration of 4 mM. HeLa cells were incubated with EV-depleted medium for 48 hours (37° C., 5% CO2 atmosphere) to secret EVs carrying SNORKEL tag.

Isolation of EVs carrying SNORKEL tag was performed after culturing cells in EV depleted media for 48 hrs. The conditioned media was collected and centrifuged at 700 g for 5 min at 4° C. to remove cell debris. The supernatant was passed for $2^{nd}$ round of centrifugation at 2000 g for 10 min at 4° C. to remove apoptotic bodies and larger particles. Next the supernatant is passed through 0.22 µm filter (Merck, Darmstadt, Germany) to remove larger particles like microvesicles. The processed supernatant was concentrated to $1/20^{th}$ times of initial volume using tangential flow filtration columns with 300 kDa pore size hollow fibers (SpectrumLabs, Netherlands). The concentrated conditioned media used for further characterizing EVs. 10 µl of concentrated conditioned media was diluted to 1000 times in filtered DPBS (Merck, Darmstadt, Germany) and used for nanoparticle tracking analysis (NTA) in a scatter mode with nanosight NS500. All of the acquisition parameters were identical to those of the size and concentration measurements. All experiments were measured in experimental triplicates. The size of the EVs from different isolations are around 110-140 nm.

The incorporation of CD81-SNORKEL tag into EVs was confirmed by western blot analysis. 1E10 EVs quantified by nanosight were loaded per well along with 50 µg of cell lysate quantified by BCA kit (Thermo fisher scientific) in NuPAGE 4-12% Bis-Tris protein gels and SDS-PAGE was performed. Proteins on gel were transferred to PVDF membrane using Trans-Blot turbo transfer system (Bio-Rad). Specific antibodies against EV specific markers along with SNORKEL tag for quantification. Indeed, EVs showed markers of typical EV proteins in Western blots including CD63, CD81, and TSG101 as well as absence of the intracellular protein calnexin.

11.4 Isolation of EVs Exclusively Carrying SNORKEL Tag Using Anti-HA Matrix and PreScission Protease The conditioned media from HeLa cells expressing CD81-SNORKEL tag was processed by differential centrifugation (700 g & 2000 g), filtered using 0.22 µm filter (Merck, Darmstadt, Germany) and concentrated to 1 ml using tangential flow filtration columns with 300 kDa pore size hollow fibers (SpectrumLabs, Netherlands). 350 µl of concentrated conditioned media was mixed with 200 µl of anti-HA antibody conjugated to agarose beads (Sigma) and incubated overnight at 4° C. on test tube rotator. After 16-18 hrs of incubation, the agarose beads were spun down at 500 g for 5 min at 4° C. and flowthrough (unbound EVs) were collected and beads were washed with 1 ml of filtered DPBS by spinning down the agarose beads at 500 g for 5 min at 4° C. Next the anti-HA antibody conjugated agarose beads bound to SNORKEL tag on EVs were subjected to PreScission protease treatment (sigma) 4 µl with 8 units in 50 mM Tris (Sigma), 150 mM NacI (Sigma) with pH 7-7.4 for 16-18 hrs at 4° C. on test tube rotator. After PreScission protease treatment for 16-18 hrs agarose beads were spun down at 500 g and supernatant was collected. All the samples (input, flowthrough, wash and elute) were used for NTA analysis with 1 to 1000 times dilution to quantify the number of EVs carrying SNORKEL tag were purified. Purification using PreScission protease yielded around 80-90% of vesicles mildly eluted from the affinity matrix, as no bands are detectable in the elution fraction after PreScission digest using the cleaved off HA tag, while the remaining CLIP tag is well visible in the elution fraction. Comparing elution fraction to the fraction not eluted and remaining on the beads, a yield of about 80-90% is observed (FIG. 6).

Insertion of antigen specific ligands such as Gas6 for AXL-specific targeting before the PreScission protease site in SNORKEL tag enables purification of specific EVs carrying SNORKEL tag and targeting EVs after purification is performed.

Example 12: Characterization of the Target-Specific Extracellular EVs 12.1 Characterization of EV Size and Recombinant Protein Incorporation Ratio 10 μl of EV isolates were diluted with 6 mL of filtered DPBS (Merck, Darmstadt, Germany) and used for nanoparticle tracking analysis (NTA) in scattering and fluorescence mode with a ZetaView (Particle Metrix, Inning, Germany), followed by evaluation using the NTA software (Particle Metrix, Inning, Germany). All of the acquisition parameters were identical to those of the size and concentration measurements. All experiments were measured in experimental triplicates.

The ratio of the particle numbers measured in scattering and fluorescence mode equals the ratio between recombinant EVs, harboring the target-specific CD81-LEL portion and the fluorescent GFP, and non-recombinant and non-fluorescent native EVs. Through different batches of recombinant EV production the ratio obtained from NTA measurements showed that approximately 30-50% of all isolated EVs are recombinant. The common median size of isolated EVs with the above-mentioned isolation method is around 120-140 nm and the typical yield of target-specific fluorescent EV amounts to 1600 to 5000 recombinant EVs per HeLa cell in a size range of 60-400 nm, peaking at 130 nm in diameter of particle size (FIG. 7).

12.2 Qualification and Quantification of Specific EV Uptake In Vitro (a) Qualification of EV Uptake in Target-Antigen Positive Cells Via Fluorescence Microscopy Recipient cells (e.g. Caco-2 cells) were seeded in an 8-well ibidi glass bottom plate ($2.5\times10^4$ cells per well) and allowed to attach for 24 h in complete culture medium (37° C., 5% CO2 atmosphere). After the incubation time, the $10^9$ recombinant EVs were added to each well. Cells were cultivated for another 24 h allowing recombinant particles to be taken up by the recipient cells. Cells were eventually washed PBS and treated with acidic glycine buffer (100 mM NaCl, 100 mM Glycine, pH 3.5) on ice to remove surface bound EVs. Cells were then imaged at 40× magnification using fluorescence microscopy (DMI3000B, Leica Microsystems, Wetzlar, Germany). Microscopic imaging parameters (exposure time, contrast, and gain) were the same for all experiments. Indeed, recombinant EVs were readily taken up by recipient cells (FIG. 8A).

(b) Quantification of EV Uptake in Target-Antigen Positive Cells Via Flow Cytometry Recipient cells (e.g. Caco-2 cells) were seeded in a 24-well plastic bottom plate ($0.25\times10^6$ cells per well) and allowed to attach for 24 h in complete culture medium (37° C., 5% CO2 atmosphere). After the incubation time, a fixed number of $5\times10^9$ recombinant EVs were added to each well. Cells were cultivated for another 24 h allowing recombinant particles to be taken up by the recipient cells. Cells were eventually washed DPBS and treated with 0.1% Trypsin (5 minutes, 37° C.) and neutralized with complete medium containing 10% FBS. Cells were then centrifuged at 300 g and the pellet was resuspended in ice-cold DPBS.

Samples were kept on ice and measured with the Cytoflex S flow cytometer (Beckman Coulter, Brea, USA). Data was analyzed with the Cytoflex software. Mean fluorescence intensity was normalized over the control/untreated cell sample (ΔMFI). Here an increased uptake of recombinant EVs targeting the transferrin receptor by about 30-60% was observed depending on the recombinant CD81 construct (Tfr1EVsP1, Tfr2EVs P1, Tfr2CP4EVs P1) as compared to EVs of cells overexpressing non-Tfr1 targeting CD81 (CP4EVs) or wild type EVs (wtEVs) (FIG. 8B).

Example 13: Production of Therapeutic Loaded Target-Specific EVs Using Apoptosis-Inducing siRNA 13.1 Transfection of Recombinant EVs with siRNAs Purified EVs carrying either non-recombinant or recombinant CD81 targeting the human transferrin receptor were transfected either with apoptosis-inducing siRNA (TOX transfection control, Dharmacon) or with untargeted control siRNA (ON-TARGETplus Non-targeting siRNA, Dharmacon) by using the liposome-based transfection reagent Dharmafect (Dharmacon, Lafyette, USA). EVs were transfected with respective targeted or untargeted siRNA (to a final concentration of 25 nM siRNA) according to the manufacturer's brochure. Loading of siRNA was controlled for using qPCR.

13.2 Cell-Based Assay for the Determination of Target-Specific Cytotoxicity

Target-antigen expressing cells were seeded at a density of $7.5\times10^3$ cells/well in 96-well plates in complete medium followed by incubation with $5\times10^8$ recombinant/siRNA-transfected EVs per well for 72 h. Experiments were performed in six replicates per EV dose or EV control. Following medium removal and PBS washing, cells were incubated with 1×WST-1 (Sigma, St. Louis, USA) for 1 h, 2 h and 4 h or 1× AlamarBlue (ThermoFisher Scientific, Waltham, USA) overnight in complete medium. Assays readouts were performed at the microplate reader Infinite 200 Pro (Tecan, Männedorf, Switzerland) according to the respective manufacturer's brochures. Indeed, an about 30% higher cytotoxicity of EVs targeting the transferrin receptor as compared to controls was observed, especially using the Tfr1CP4 recombinant CD81 construct (FIG. 10).

Example 14: Design of the Library CD81 LEL_L3

CD81 LEL_L3 library design was based on the reversibly refolding CD81 LEL stabilized mutant (SEQ ID NO:180)

```
SEQ ID NO: 180:
FVNKDQIAKDVKQFYDQCLQQACVDDDANNAKACVKTFHETLDCCGSSTL

TALTTCVLKNNLCPSGSNIISNLFKEDCHQKIDDLFSGK
```

In this library, the stabilizing mutations Ala130Cys/Ala146Cys and Val135Cys/Ser168Cys work additively to increase the midpoint of thermal transition of CD81 LEL to 93.4° C., and this combined mutant can reversibly refold when heated up to 110° C. In the library, the amino acid residues at the positions 132-133, 136-141, 162-165, 167, and 171-172 were randomized to form a composite surface available for antigen binding (X in SEQ ID NO:1) (SEQ ID NO:97).

SEQ ID NO: 97:
FVNKDQIAKDVKQFYDQCLXXACXXXXXXNAKACVKTFHETLDCCGSSTX

XXXTXCVLXXNLCPSGSNIISNLFKEDCHQKIDDLFSGK
wherein X is any amino acid.

Example 15: Construction of Yeast Display Libraries CD81 LEL_L2 and L3

For the yeast display library CD81 LEL_L2, PCR recombination products encoding the randomized inserts were produced in 100 μl aliquots using Q5 HiFi Polymerase MasterMix (New England Biolabs), 10 ng/μl template (pTT22SSP4_C4C9), and 50 pmol of oligonucleotides LIB2FWD (SEQ 1D98) and EFrev (SEQ ID NO:99). The initial denaturation for 30 sec at 98° C. was followed by 35 cycles of each 20 sec denaturation at 98° C., 20 sec annealing at 55° C. and 20 sec extension at 72° C., and completed with an incubation step at 72° C. for 5 min. PCR products were purified with Illustra GFX purification kit and eluted in AD.

SEQ ID NO: 98:
AAGGATGTGAAGCAGTTCTATGACCAAGCTTTANNKNNKTGCTGTNNKNN

KNNKNNKGCCAACAACGCCTGTGCTGTG
wherein N is anyone of A, C, G, or T.

SEQ ID NO: 99:
CTTGAAGAGGTTGCTGATGATGTTGGATCCCGAGGGACACAAATTMNNMN

NGAGCACACAMNNGGTMNNMNNMNNMNNTGTGCTGGAGCCACAGCA
wherein N is anyone of A, C, G, or T; and M is anyone of A or C.

For the yeast display library CD81 LEL_L3, PCR recombination products encoding the randomized inserts were produced in 100 μl aliquots using Q5 HiFi Polymerase MasterMix (New England Biolabs), 10 ng/μl template (pTT22SSP4_C2C9), and 50 pmol of oligonucleotides LIB3FWD (SEQ ID 100) and LIB2REV2 (SEQ ID 99). The initial denaturation for 30 sec at 98° C. was followed by 35 cycles of each 20 sec denaturation at 98° C., 20 sec annealing at 55° C. and 20 sec extension at 72° C., and completed with an incubation step at 72° C. for 5 min. PCR products were purified with Illustra GFX purification kit (GE Healthcare) and eluted in AD.

SEQ ID NO: 100:
AAGGATGTGAAGCAGTTCTATGACCAGTGTCTANNKNNKGCCTGTNNKNN

KNNKNNKNNKNNKAACGCCAAGGCTTGTGTG
wherein N is anyone of A, C, G, or T.

The recipient vector pYD1 delbamdelhind_bamhind was linearized using BamHI and HindIII and purified using preparative agarose gel electrophoresis and Illustra GFX purification kit (GE Healthcare), and eluted in AD.

Yeast *Saccharomyces cerevisiae* EBY100 was transformed with linearized recipient vector and PCR recombination product using chemical PEG3350/Li-acetate/ssDNA transformation method. 2 libraries, L2A and L2B, and L3A and L3B, were produced with each of the recombination fragments. For each library, 250 ml YPD medium were inoculated with an overnight culture to $OD_{600}$ of 0.4. After 5 h incubation on shaking incubator at 30° C., the yeast cells were harvested in 50-ml-aliquots. Supernatant was removed and yeast cells were washed with 25 ml AD per aliquot at 3000 rpm, 5 min at RT. Cell pellet was resuspended in 3 ml per aliquot of 100 mM Li-acetate and shaken at 200 rpm, 15 min at 30° C. Cells were collected at 3000 rpm, 5 min at RT. To each yeast cell aliquot a mix of 2750 μl 50% PEG3350 solution, 360 μl 1 M Li-acetate, 500 μl heat-shocked ssDNA, and 10 μg linearized recipient vector and 10 μg of recombination PCR fragment was added. The incubation was performed at 200 rpm, 30 min at 30° C., and was followed by a heat shock for 45 min at 42° C. Yeast cells were collected at 3000 rpm, 5 min at RT and diluted into 250 ml SD-CAA medium with penicillin and streptomycin. Cultivation proceeded at 200 rpm for 24 h at 30° C. and 12.5 ml of the culture were transferred into 250 ml of fresh SD-CAA medium with penicillin and streptomycin for 24 h at 30° C., pelleted at 3000 rpm, 10 min at 4° C. and frozen after mixing with an equal volume of 30% glycerol. The size of the libraries was determined using dilution plating and was determined to be $1.1\times10^8$ independent members for L2 and in $1.2\times10^8$ independent members for L3.

To determine the level of correctness of the libraries, plasmid DNA was isolated from 10 μl of pelleted yeast cells and transformed to *E. coli* TOP10 using electroporation. The expression cassette of CD81 LEL mutant was amplified using primers pydfwd (SEQ ID NO:101) and pydrev (SEQ ID NO:102) and sequenced using one of these primers. The correctness of the library L2A was found to be 62.5%, L2B 87.5%, L3A 62.5% and L3B 100%.

SEQ ID NO: 101:
AGTAACGTTTGTCAGTAATTGC

SEQ ID NO: 102:
GTCGATTTTGTTACATCTACAC

For quality control, the yeast cells were induced in SG/RCAA medium with penicillin and streptomycin either for 48 h at 20° C. or 24 h at 37° C. For staining, the yeast cells were blocked in a 2% BSA-PBS solution for 30 min at RT at an $OD_{600}$ of 1. Then they were resuspended into 100 μl-aliquots and stained with anti-Xpress antibody (Thermo Scientific) (1:1000) reactive with the N-terminally positioned Xpress tag, and M38 antibody (Thermo Scientific) (1 μg/ml), which detects the properly folded CD81 LEL, in 2% BSA-PBS for 1 h at RT. Cells were pelleted at 3000 rpm, for 5 min at 4° C. and resuspended in 2% BSA-PBS with goat anti-mouse $(Fab')_2$-FITC conjugate (Sigma Aldrich), diluted 1:200 in 2% BSA-PBS. Other stainings were: anti-his-tag-Alexa Fluor 488 (QIAgen), diluted 1:200 in 2% BSA-PBS and anti-V5-tag-FITC (Thermo Scientific), diluted 1:100 in 2% BSA-PBS, used to detect C-terminal his tag and C-terminal V-tag to determine the correct read-through of the clones. The incubation with fluorescent antibodies was for 30 min on ice. Finally, the cells were collected at 3000 rpm, 5 min at 4° C., and resuspended in 200 μl ice-cold PBS. The fluorescence of stained samples and unstained controls was determined using Guava EasyCyte flow cytometer. The percentage of positive cells was determined and is presented in Table 9.

TABLE 9

| staining | | Sample L2A | L2A | L2B | L2B | L3A | L3A | L3B | L3B |
|---|---|---|---|---|---|---|---|---|---|
| | | Induction temperature (° C.) | | | | | | | |
| 1st step | 2nd step | 20 | 37 | 20 | 37 | 20 | 37 | 20 | 37 |
| unstained | unstained | 0.57 | 0.43 | 0.29 | 0.34 | 0.06 | 1.25 | 0.09 | 1.21 |
| Anti-Xpress | goat anti-mouse (Fab')$_2$-FITC | 75.4 | 68.65 | 77.13 | 65.79 | 78.04 | 77.89 | 80.15 | 70.84 |
| M38 | goat anti-mouse (Fab')$_2$-FITC | 1.73 | 1.99 | 0.66 | 1.81 | 1.94 | 1.65 | 1.19 | 0.81 |
| unstained | goat anti-mouse (Fab')$_2$-FITC | 0.48 | 1.31 | 0.43 | 1.26 | 0.45 | 0.44 | 0.60 | 1.12 |
| unstained | anti-his-tag-Alexa Fluor 488 | 57.73 | 49.16 | 61.29 | 50.21 | 59.52 | 48.44 | 65.13 | 46.45 |
| unstained | anti-V5-tag-FITC | 61.05 | 51.81 | 60.92 | 51.95 | 62.27 | 55.67 | 66.85 | 51.60 |

Example 16: CD81 LEL-Based EGFR-Specific Binders

16.1 Selections of CD81 LEL Libraries L2 and L3 with Human EGFR-Fc

Human EGFR-Fc was purchased from Sino Biological. For biotinylation, EZ-Link™ Sulfo-NHS-LC-LC-Biotin reagent (Thermo Scientific) was used in a 3:1 biotin to protein molar ratio. The antigen was reconstituted exactly according to manufacturer's instructions to a concentration of 0.25 μg/μl. Incubation with biotinylation reagent proceeded for 1 h at room temperature with shaking. Unbound biotin was removed with dialysis against 100× volume of PBS, using Snakeskin dialysis tubing (Thermo Scientific) with 10.000 Da MWCO, at 4° C. overnight with stirring.

For sorting, libraries 2A, 2B, 3A and 3B were first cultured in SD-CAA medium supplemented with penicillin-streptomycin at 30° C. with shaking overnight and then the expression of recombinant protein was induced by resuspending the yeast cells in SG/R-CAA medium with penicillin-streptomycin and incubating them with shaking overnight at 37° C.

For MACS, $10^9$ induced yeast cells were pelleted for 5 min at 1000 g and washed by resuspending the pellet in 50 ml wash buffer (PBS, pH 7.2, 0.25% BSA, 2 mM EDTA) and pelleted again for 5 min at 2500 g. Washed cells were resuspended in 5 ml wash buffer containing 0.5 μM biotinylated antigen and incubated for 30 min at room temperature with gentle agitation. Antigen binding was quenched with the addition of 10 ml ice-cold wash buffer and the cells and antigen solution was pelleted for 5 min at 1000 g and 4° C. The cells were resuspended in 5 ml wash buffer plus 25 μl streptavidin microbeads (μMACS streptavidin kit, MACS Miltenyi) and incubated on ice for 10 min. Finally, 15 ml wash buffer were added and the cells were passed through a 40 μl-cell strainer.

The LS column (MACS Miltenyi) was placed in the separator and 3 ml of wash buffer were applied to precondition the column. Then, the cell solution was loaded in 7 ml batches. Once the column stopped dripping, it was briefly removed from the magnet and placed back in the magnet to reorient the beads in the column to allow trapped cells to flow through. Before loading the next 7 ml cell suspension, 1 ml of wash buffer was applied to the column. These steps were repeated until all cells were loaded. Then, the column was washed with 3 ml wash buffer, briefly removed from the magnet and washed again with 3 ml wash buffer. To elute the binding cells, the column was removed from the magnet and 5 ml wash buffer were added. Using the supplied plunger, the cells were pushed through the column into a new tube. The binding cell fraction was pelleted for 10 min at 2500 g. The pellet was re-suspended in 10 ml SD-CAA medium and 10 μl of eluted cells were diluted in 990 μl SD-CAA and 100 μl were plated onto an MDL plate and incubated at 30° C. for three days to estimate the output of MACS procedure, and the rest of the cells were incubated at 30° C. and 180 rpm overnight.

In the FACS selection rounds that followed, the induced cell suspensions were diluted to $10^8$ cells per 1 ml 10% BSA-PBS and centrifuged at 3000 rpm for 5 min at 20° C. To block the cells, the pellets were resuspended in 1 ml 10% BSA-PBS and incubated for 30 min at 20° C. on a rotating platform. The cells were centrifuged at 3000 rpm for 5 min at 20° C. and resuspended in 250 μl 10% BSA-PBS containing 0.5 μM biotinylated EGFR-Fc. After incubation for 1 h at 20° C. on a rotating platform the cells were centrifuged at 3000 rpm for 5 min at 4° C. To wash the cells, the pellets were resuspended in 1 ml ice-cold PBS and centrifuged at 3000 rpm for 5 min at 4° C. Then, the cells were resuspended in 250 μl 10% BSA-PBS with streptavidin-Alexa Fluor 647 (1:800) and anti-V5-FITC antibody (1:100) and incubated for 30 min on ice. The cells were centrifuged at 3000 rpm for 5 min at 4° C., resuspended in 250 μl ice-cold PBS and kept on ice until sorting with Sony cell sorter SH8000. At least 20× output of the previous sorting round was processed and 0.1% top anti-V5-antibody-positive yeast cells were collected. After visible enrichment, the sorts were plated out to characterize single yeast display clones. For some enriched sorts, an additional selection round using 100 nM antigen concentration was performed.

For screening, induced yeast cells were blocked with 2% BSA-PBS at $OD_{600}$ of 1, for 30 min at RT. Then they were incubated with a 2-fold serial dilution of biotinylated human EGFR-Fc, starting at 100 nM, in 2% BSA-PBS, for 30 min at RT. Binding was detected with streptavidin-Alexa Fluor 647 at 1:1000 dilution in 2% BSA-PBS, for 30 min on ice. Finally, cells were resuspended in 200 μl ice-cold PBS and fluorescence of the sample was recorded on a Guava EasyCyte flow cytometer. Percent of antigen-binding cells was evaluated (Table 10) and an EGFR-specific binder L2B_EU1_1 was identified with the amino acid sequence with SEQ ID 103. Residues different from the parental clone are in bold print.

TABLE 10

| Concentration EGFR-Fc (nM) | % of antigen-binding cells |
|---|---|
| 100 | 12.34 |
| 50 | 8.17 |
| 25 | 2.95 |
| 12.5 | 1.65 |
| 0 | 1.13 |

SEQ ID NO: 103:
FVNKDQIAKDVKQFYDQALWWCCVLYKANNACAVVKTFHETLDCCGSSTG

RSHTACVLKGNLCPSGSNIISNLFKEDCHQKIDDLFSGK 16.2 Mammalian Display System for Confirmation of Antigen Binding for the EGFR-Specific Clone The sequences of wild-type CD81 LEL and EGFR-specific clone L2BEU1_1 were cloned between the SfiI and SalI restriction sites of the pDisplay vector (Thermo Scientific). This display system allows the expression of C-terminal anchored protein of interest between N-terminal HA-tag and C-terminal c-myc-tag. Constructs were transfected into HEK293-6E cells (CNRC). Cells were harvested after 48 or 72 h, blocked for 30 min in 4% BSA-PBS on ice and stained with antibodies against CD81 (M38, Thermo Scientific) at 10 μg/ml in 4% BSA-PBS and anti-c-myc (A-14, sc789, Santa Cruz) at 10 μg/ml in 4% BSA-PBS, for 30 min on ice. Their binding was detected after incubation with secondary reagents anti-mouse F(ab)2-Alexa Fluor 555 (Thermo Scientific), diluted 1:1000 in 4% BSA-PBS, and anti-rabbit (H+L) antibody conjugated with Alexa Fluor 488 (Thermo Scientific), diluted 1:100 in 4% BSA-PBS, for 30 min on ice. Cells were then resuspended in PBS and kept on ice until analysis with Guava EasyCyte flow cytometer (Merck Millipore). Antigen reactivity was determined after incubation with biotinylated human EGFR-Fc at 300 nM and detection with streptavidin-Alexa Fluor 647 at 1:1000 in 4% BSA-PBS. Both wild-type CD81 LEL and EGFR-binding mutant showed a good level of display on the mammalian cell surface judging from the reactivity with the anti-c-myc antibody (Table 11). Wild-type CD81 LEL reacted well with the anti-CD81 antibody while the mutant did not display any reactivity, presumably due to the modifications of the relevant epitope due to library mutagenesis (Table 11). Antigen binding in mammalian cell-display format could be confirmed for the antigen-binding CD81 LEL mutant (Table 11).

TABLE 11

| staining 1$^{st}$ step | 2$^{nd}$ step | MFI construct | wild-type CD81 LEL | L2B_EU1_1 |
|---|---|---|---|---|
| anti-c-myc antibody | anti-rabbit(H + L)-Alexa Fluor 488 | | 69.60 | 55.57 |
| unstained | anti-rabbit (H + L)-Alexa Fluor 488 | | 13.50 | 13.57 |
| M38 | anti-mouse F(ab)$_2$-Alexa Fluor 555 | | 83.81 | 50.55 |
| unstained | anti-mouse F(ab)$_2$-Alexa Fluor 555 | | 8.52 | 8.58 |
| EGFR-Fc-biotin | streptavidin-Alexa Fluor 647 | | 156.41 | 1825.91 |
| unstained | streptavidin-Alexa Fluor 647 | | 156.36 | 167.80 |

16.3 Characterization of Specificity, Species Cross-Reactivity and Epitope Mapping of EGFR Binder HEK293-6E cells have been transfected with pDisplay construct encoding wild-type CD81 LEL and anti-EGFR mutant CD81 LEL L2B_EU1_1. 1×10$^5$ cells have been blocked in 2% BSA-PBS for 30 min on ice and then stained with each 500 nM biotinylated human EGFR-Fc, biotinylated human Her2/neu-Fc and biotinylated mouse EGFR-Fc for 30 min on ice in 2% BSA-PBS. After the centrifugation at 300 g, 5 min at 4° C., binding of the antigens has been detected with streptavidin-Alexa Fluor 647 (Thermo Scientific), diluted 1:1000 for 30 min on ice. Cells were then centrifuged at 300 g, 5 min at 4° C. and resuspended in 200 μl ice-cold PBS. The display was measured by staining the induced cultures with anti-c-myc antibody (A-14, sc789, Santa Cruz) at 10 μg/ml in 2% BSA-PBS and anti-rabbit (H+L) antibody conjugated with Alexa Fluor 488 (Thermo Scientific), diluted 1:1000 in 2% BSA-PBS, for 30 min on ice. The fluorescence has been determined with Guava EasyCyte flow cytometer. The anti-EGFR clone has shown binding only to its cognate antigen, but not to human Fc and Her2/neu Fc protein (Table 12). The EGFR-reactive clone was shown to be cross-reactive with mouse EGFR (Table 12).

TABLE 12

| staining 1$^{st}$ step | 2$^{nd}$ step | construct MFI | wild-type CD81 LEL | L2BEU1_1 |
|---|---|---|---|---|
| anti-c-myc antibody | anti-rabbit(H + L)-Alexa Fluor 488 | % antigen | 176.45 | 117.88 |
| unstained | anti-rabbit (H + L)-Alexa Fluor 488 | binding | 16.10 | 17.09 |
| Human EGFR-Fc-biotin | streptavidin-Alexa Fluor 647 | cells | 10.36 | 71.11 |
| Human Her2/neu-Fc-biotin | streptavidin-Alexa Fluor 647 | | 10.49 | 8.17 |
| Mouse EGFR-Fc-biotin | streptavidin-Alexa Fluor 647 | | 12.80 | 89.34 |
| unstained | streptavidin-Alexa Fluor 647 | | 14.11 | 5.82 |

In the epitope mapping experiment, 300 nM antigen solution was incubated with 3-fold molar excess of the validated anti-EGFR antibodies cetuximab (Li et al., Cancer Cell 7 (4), 301-311 (2005). DOI: 10.1016/j.ccr.2005.03.003) and matuzumab (Schmiedel et al., Cancer Cell 13 (4), 365-373 (2008). doi: 10.1016/j.ccr.2008.02.019.2005) or commercially available human IgG-kappa isotype antibody (Sigma-Aldrich) and then used for staining of the mutant CD81 LEL-displaying cells. The binding of validated antibodies to the antigen proceeded for 30 minutes in 2% BSA-PBS at room temperature and the solution was then used to stain CD81 LEL mutant-displaying cells. Detection proceeded with streptavidin-Alexa Fluor 647, diluted 1:1000 in 2% BSA-PBS for 30 min on ice. MFI values of displaying cells were recorded. The data indicates that the binding site of the L2B_EU1_1 clone overlaps with the binding site for the cetuximab antibody (Table 13). L2B_EU1_1 could still bind to the antigen in the presence of the excess of matuzumab antibody.

TABLE 13

| staining 1st step | 2nd step | MFI |
|---|---|---|
| Human EGFR-Fc-biotin | streptavidin-Alexa Fluor 647 | 5332 |
| Human EGFR-Fc-biotin + human IgG-kappa isotype | streptavidin-Alexa Fluor 647 | 5546 |
| Human EGFR-Fc-biotin + cetuximab | streptavidin-Alexa Fluor 647 | 1324 |
| Human EGFR-Fc-biotin + matuzumab | streptavidin-Alexa Fluor 647 | 2141 |
| unstained | streptavidin-Alexa Fluor 647 | 1080 |

16.4 Rerandomization of Modified Loops of CD81 LEL-Based EGFR-Binder

The aim of this experiment was to re-randomize the mutated stretches of residues in the EGFR-binding mutant and show that the binding of the clone is dependent on amino acid residues on both stretches of the polypeptide chain that were randomized in the parental clone to introduce an antigen binding site.

PCR fragments for recombination were produced by using once the mutagenic primer LIB2FWD (SEQ ID NO:98) and that randomizes the mutated residues in helix A and the AB-loop in Library L2BE1_A, and once the mutagenic primer LIB2REV2 (SEQ ID NO:99) that randomized the mutated residues in helix C in Library L2BE1_B. PCR fragments were produced using Q5 High-Fidelity Polymerase (New England Biolabs). For recombination fragment for library L2BE1_A primer LIB2FWD was used together with primer AP2 (SEQ ID NO:104) and for library L2BE1_B primer LIB2REV2 (SEQ ID 99) was used together with primer AP1 (SEQ ID NO:105).

```
SEQ ID NO: 104:
CTTGAAGAGGTTGCTGAT

SEQ ID NO: 105:
AAGGATGTGAAGCAGTTC
```

Each recombination fragment was transformed together with BamHI/HindIII linearized recipient vector pYD1 with cloned CD81 LEL_dellbamdelhind_bamhind sequence using chemical transformation into *S. cerevisiae* EBY100. 35 μg of linearized vector and 25 μg of the PCR fragment were used for library construction. The size of the libraries were $8.4\times10^6$ independent members for library L2BE1_A and $1.18\times10^7$ independent members for Library L2BE1_B. Quality control of the libraries included induction of library members as a stress temperature and subsequent measurement of yeast-surface displayed protein via the N-terminal tag, detected with an anti-Xpress tag antibody, followed by incubation with a goat anti-mouse (Fab')2-FITC (Sigma Aldrich) and the determination of the correct reading frame of the displayed proteins via detection of the C-terminal V5-tag with an anti-V5-FITC antibody (Thermo Scientific). The percentage of antigen-binding cells for each library was determined after staining with human EGFR-Fc at 500 nM and the detection with goat anti-human gamma chain—PE conjugate (Sigma Aldrich). The percentages of positive cells for the libraries are presented along with the values characteristic for the parental clone in Table 14. Rerandomization of the mutated residues in both targeted regions caused a reduction in the number of antigen-positive clones, implicating that amino acid residues in both randomized stretches contribute to antigen binding.

TABLE 14

| staining | Percentage of positive cells (%) | Sample | | |
|---|---|---|---|---|
| 1st step | 2nd step | L2BE1_1 | L2BE1_A | L2BE1_B |
| Human EGFR-Fc | Goat anti-human gamma -PE | 61.77 | 15.77 | 15.55 |
| unstained | Goat anti-human gamma -PE | 6.16 | 6.70 | 6.91 |
| Anti-Xpress | goat anti-mouse $(Fab')_2$-FITC | 75.17 | 65.84 | 60.67 |
| unstained | goat anti-mouse $(Fab')_2$-FITC | 1.53 | 0.84 | 0.48 |
| unstained | anti-V5-tag-FITC | 83.64 | 73.37 | 62.73 |
| unstained | unstained | 2.30 | 1.10 | 1.20 |

Example 17: CD81 LEL-Based Binders to Human Placental Laminin 17.1 Selections of CD81 LEL Libraries L2 and L3 with Human Laminin Human laminin was purchased from Sigma-Aldrich. For biotinylation, EZ-Link™ Sulfo-NHS-LC-LC-Biotin reagent (Thermo Scientific) was used in a 3:1 molar ratio, after dialysis of the antigen against 100-fold volume of PBS overnight at 4° C. Incubation with biotinylation reagent proceeded for 1 h at room temperature with shaking. Unbound biotin was removed with dialysis against 100-fold volume of PBS, using Snakeskin dialysis tubing (Thermo Scientific) with 10.000 Da MWCO, at 4° C. overnight with stirring.

For sorting, libraries 2A, 2B, 3A and 3B were first cultured in SD-CAA medium supplemented with penicillin-streptomycin at 30° C. with shaking overnight and then the expression of recombinant protein was induced by resuspending the yeast cells in SG/R-CAA medium with penicillin-streptomycin and incubating them with shaking overnight at 37° C.

For MACS, $10^9$ induced yeast cells were pelleted for 5 min at 1000 g and washed by resuspending the pellet in 50 ml wash buffer (PBS, pH 7.2, 0.25% BSA, 2 mM EDTA)

and pelleted again for 5 min at 1000 g. Washed cells were resuspended in 5 ml wash buffer containing 1 µM biotinylated antigen and incubated for 30 min at room temperature with gentle agitation. Antigen binding was quenched with the addition of 10 ml ice-cold wash buffer and the cells and antigen solution was pelleted for 5 min at 1000 g and 4° C. The cells were resuspended in 5 ml wash buffer plus 25 µl streptavidin microbeads (µMACS streptavidin kit, MACS Miltenyi) and incubated on ice for 10 min. Finally, 15 ml wash buffer were added and cell suspension was filtered through a 40-µm strainer.

The LS column (MACS Miltenyi) was placed in the separator and 3 ml of wash buffer were applied to precondition the column. Then, the cell solution was loaded in 7 ml batches. Once the column stopped dripping it was briefly removed from the magnet and placed back in the magnet to reorient the beads in the column to allow trapped cells to flow through. Before loading the next 7 ml cell suspension, 1 ml of wash buffer was applied to the column. These steps were repeated until all cells were loaded. Then, the column was washed with 3 ml wash buffer, briefly removed from the magnet and washed again with 3 ml wash buffer. To elute the binding cells, the column was removed from the magnet and 5 ml wash buffer were added. Using the supplied plunger, the cells were pushed through the column into a new tube. The binding cell fraction was pelleted for 10 min at 2500 g. The pellet was resuspended in 10 ml SD-CAA medium and 10 µl of eluted cells were diluted in 990 µl SD-CAA and 100 µl were plated onto an MDL plate and incubated at 30° C. for three days to estimate the output of MACS procedure, and the rest of the cells were incubated at 30° C. and 180 rpm overnight.

In the FACS selection rounds that followed, the induced cell suspensions were diluted to $10^8$ cells per 1 ml 10% BSA-PBS and centrifuged at 3000 rpm for 5 min at 20° C. To block the cells, the pellets were resuspended in 1 ml 10% BSA-PBS and incubated for 30 min at 20° C. on a rotating platform. The cells were centrifuged at 3000 rpm for 5 min at 20° C. and resuspended in 250 µl 10% BSA-PBS containing 1 µM biotinylated laminin. After incubation for 1 h at 20° C. on a rotating platform the cells were centrifuged at 3000 rpm for 5 min at 4° C. To wash the cells, the pellets were resuspended in 1 ml ice-cold PBS and centrifuged at 3000 rpm for 5 min at 4° C. Then, the cells were resuspended in 250 µl 10% BSA-PBS with streptavidin-Alexa Fluor 647 (1:800) and anti-V5-FITC antibody (1:100) and incubated for 30 min on ice. The cells were centrifuged at 3000 rpm for 5 min at 4° C., resuspended in 250 µl ice-cold PBS and kept on ice until sorting with Sony cell sorter. At least 20× output of the previous sorting round was processed and 0.1% top anti-V5-antibody positive yeast cells were collected. After visible enrichment, the sorts were plated out to characterize single yeast display clones. For some enriched sorts, an additional selection round using 100 nM antigen was performed.

17.2 Expression in Mammalian Cells

Unique binder sequences amplified using oligonucleotide sequences CD81hnhe1 (SEQ ID NO:106) and LELp28_bste2 (SEQ ID NO:107) and cloned between the NheI and BstEII sites of the mammalian expression vector pTT28 and the sequences of the constructs were verified using Sanger sequencing.

SEQ ID NO: 106:
ACGTGCTAGCTTTGTCAACAAGGACCAGATC

-continued

SEQ ID NO: 107:
ACGTGGTGACCGGTGCTGGAACCCTTCCCGGAGAAGAGGTC

Recombinant proteins were expressed in HEK293-6E exactly after manufacturer's instructions. The supernatant of 25-ml-cultures was harvested with centrifugation at 3500 rpm, 15 min at 4° C., buffered with PBS and 20 mM imidazole and filtered through an 0.45-µm-filter before loading to a 1-ml-His Excel column (GE Healthcare), equilibrated with PBS/20 mM imidazole, pH 7.5. Column was then washed with the same buffer and his-tagged protein was eluted with a gradient from 20-500 mM imidazole in PBS, pH 7.5, in 5 column volumes. Fractions 4-6 were analyzed for the presence of the eluted protein with SDS-PAGE followed with Coomassie staining. Expression could be confirmed for following mutants: L2A_LU1 (SEQ ID 108), L2A_LU1_1 (SEQ ID 109), L2B_LU1 (SEQ ID 110), L3B_LU1_2 (SEQ ID 111). Residues different from the parental clone are in bold print.

SEQ ID NO: 108: L2A_LU1:
FVNKDQIAKDVKQFYDQALRECCNTFDANNACAVVKTFHETLDCCGSSTT

HSSTGCVLFFNLCPSGSNIISNLFKEDCHQKIDDLFSGK

SEQ ID NO: 109: L2A_LU1_1:
FVNKDQIAKDVKQFYDQALMICCHRHYANNACAVVKTFHETLDCCGSSTP

SSTTPCVLQNNLCPSGSNIISNLFKEDCHQKIDDLFSGK

SEQ ID NO: 110: L2B_LU1:
FVNKDQIAKDVKQFYDQALVFCCFGGHANNACAVVKTFHETLDCCGSSTH

PYKTKCVLQRNLCPSGSNIISNLFKEDCHQKIDDLFSGK

SEQ ID NO: 111: L3B_LU1_2:
FVNKDQIAKDVKQFYDQCLKYACKQGDWENAKACVKTFHETLDCCGSSTV

ANMTRCVLPANLCPSGSNIISNLFKEDCHQKIDDLFSGK 17.3 Antigen Binding in Soluble Format Neat eluted proteins were tested for binding to their cognate antigen and BSA as a control antigen. Streptavidin-activated plates (Immobilizer, NUNC) were coated with biotinylated laminin at 5 µg/ml in PBS for 30 min at RT and blocked with 4% BSA-PBS for 1 h at RT. Eluted proteins were added in 2% BSA-PBS and allowed to bind for 1 h at RT. After three wash steps with PBS, binding was detected with a 1:3000 dilution of anti-pentaHis antibody-HRP conjugate (QIAgen) in 2% BSA-PBS for 30 min and revealed upon addition of TMB (Sigma-Aldrich). The reaction was stopped with the addition of $H_2SO_4$ and the absorbance read at 450/620 nm (Table 15). Specific reactivity with the target protein could be confirmed for 3 laminin-specific clones: L2A_LU1, L2B_LU1 and L3B_LU1_2.

TABLE 15

| Clone | Antigen | $A_{450/620}$ (average) | St. dev. |
|---|---|---|---|
| L2A_LU1 | laminin | 0.156 | 0.00745937 |
| L2A_LU1 | BSA | 0.045 | 0.00511881 |
| L3A_LU1 | laminin | 1.702 | 0.27844276 |
| L3A_LU1 | BSA | 0.016 | 0.00171464 |
| L3B_LU1_2 | laminin | 1.316 | 0.16702341 |
| L3B_LU1_2 | BSA | 0.021 | 0.00283314 |

17.4 Expression of Laminin Binders in Mammalian Cell Display System

The sequences of laminin binding clones were cloned between the SfiI and SalI restriction sites of the pDisplay vector (Thermo Scientific). This display system allows the expression of C-terminal anchored protein of interest between N-terminal HA-tag and C-terminal c-myc-tag. Constructs were transfected into HEK293-6E cells (CNRC). Cells were harvested after 48 or 72 h, blocked for 30 min in 4% BSA-PBS on ice and stained with an anti-c-myc antibody (A-14, sc789, Santa Cruz) at 10 μg/ml in 4% BSA-PBS, for 30 min on ice. Their binding was detected after incubation with secondary anti-rabbit (H+L) antibody conjugated with Alexa Fluor 488 (Thermo Scientific A11034), diluted 1:1000 in 4% BSA-PBS, for 30 min on ice. Antigen reactivity was determined after incubation with biotinylated human laminin at 500 nM and detection with streptavidin-Alexa Fluor 647 at 1:1000 in 4% BSA-PBS. Cells were then resuspended in PBS and kept on ice until analysis with Guava EasyCyte flow cytometer (Merck Millipore). For all tested clones, display on mammalian cell surface could be detected (Table 16). For nine clones, reactivity with the recombinant antigen could be established (Table 16).

-continued

SEQ ID NO: 115:
FVNKDQIAKDVKQFYDQCLRHACSGLSGRNAKACVKTFHETLDCCGSSTI

KHKTLCVLIKNLCPSGSNIISNLFKEDCHQKIDDLFSGK

SEQ ID NO: 116:
FVNKDQIAKDVKQFYDQALFICCFRRYANNACAVVKTFHETLDCCGSSTR

NNETACVLAKNLCPSGSNIISNLFKEDCHQKIDDLFSGK

Example 18: Anti-Laminin CD81 Mutants Expressed on the Surface of EVs 18.1 EV Preparation HeLA cells were transduced with wild-type CD81 or C081 with modified LEL corresponding to the sequence of L2A_LU1 (SEQ ID NO:12) or L3B_LU1_2 (SEQ ID NO:15), cloned into pBMN expression vector in frame with eGFP. Extracellular vesicles (EVs) were prepared from transduced HeLa cells cultured to a confluence of 80% in RPMI (10% FOS, 4 mM L-Glutamine). Afterwards medium was changed and EV collection was performed for 72-96 hours in OptiPRO SFM. Cell culture supernatants were centrifuged at 3000 g for 30 min in order to remove cells and cell debris. Larger particles were excluded by filtering supernatants through a 0.45 μm cellulose acetate filter. Ultimately. EVs were pelleted by ultracentrifugation at 120000 g for 90 min and resuspended in Live Cell imaging solution (Thermo Scientific). Recombinant EVs, harboring CD81-eGFP fusion, were verified using human COG capture beads for flow cytometry based detection (ImmunoStep).

TABLE 16

| | | MFI | | | |
|---|---|---|---|---|---|
| | | Anti-c-myc | unstained | % antigen-positive cells | |
| clone | Staining 1st step 2nd step | anti-rabbit (H + L)-Alexa Fluor 488 | anti-rabbit (H + L)-Alexa Fluor 488 | laminin-biotin streptavidin-Alexa Fluor 647 | unstained streptavidin-Alexa Fluor 647 |
| L2A_LU1 | | 37.68 | 16.77 | 28.98 | 5.92 |
| L3B_LU1_2 | | 71.30 | 17.90 | 29.35 | 2.75 |
| L3A_LU1* | | 74.45 | 14.04 | 28.60 | 8.08 |
| L2A_LU1_1 | | 74.79 | 15.19 | 37.93 | 5.57 |
| L2B_LU1_1 | | 103.85 | 10.96 | 20.08 | 1.77 |
| 81_L1 | | 41.04 | 15.68 | 54.17 | 6.09 |
| 81_L13 | | 46.47 | 13.42 | 30.78 | 4.17 |
| 81_L17 | | 80.52 | 12.05 | 28.11 | 4.11 |
| 81_L21 | | 55.83 | 12.48 | 37.14 | 3.28 |

*For L3A_LU1 clone, neutravidin-PE (Thermo Scientific) was used as a secondary reagent.

The sequences of the discovered clones were determined for: L3A_LU1 (SEQ ID NO:112), L2B_LU1_1 (SEQ ID NO:113), 81 L1 (SEQ ID NO:110, same as L2B_LU1), 81L_13 (SEQ ID NO:114), 81L_17 (SEQ ID NO:115), 81L_21 (SEQ ID NO:116). Residues different from the parental clone are in bold print.

SEQ ID NO: 112:
FVNKDQIAKDVKQFYDQCLLWACSKRYKYNAKACVKTFHETLDCCGSSTM

GNLTECVLIENLCPSGSNIISNLFKEDCHQKIDDLFSGK

SEQ ID NO: 113:
FVNKDQIAKDVKQFYDQALWKCCNLSQANNACAVVKTFHETLDCCGSSTY

LCATYCVLWPNLCPSGSNIISNLFKEDCHQKIDDLFSGK

81L_1 (SEQ ID NO: 110):
FVNKDQIAKDVKQFYDQALVFCCFGGHANNACAVVKTFHETLDCCGSSTH

PYKTKCVLQRNLCPSGSNIISNLFKEDCHQKIDDLFSGK

SEQ ID NO: 114:
FVNKDQIAKDVKQFYDQCLSWACNRKYEPNAKACVKTFHETLDCCGSSTK

ANYTHCVLEMNLCPSGSNIISNLFKEDCHQKIDDLFSGK 18.2 Competition Assay Showing Specific Antigen Binding of Anti-Laminin CD81 Mutants Expressed on the Surface of EVs $5\times10^9$ recombinant EVs harboring wild-type CD81-eGFP and respective Laminin targeting variants L2A_LU1 and L3B_LU1_2 were incubated overnight with $6\times10^3$ CD9+ capture beads. 5 μg/mL of biotinylated human placental laminin were added to the beads, and in some parallel samples 15 μg/mL of unlabeled laminin for competition. Neutravidin-PE (1:800) was used to detect EV-bound laminin. Background (BG) fluorescence was determined by staining with neutravidin-PE only. Fluorescence of eGFP was measured at 488 nm and PE-fluorescence at 561 nm. For both laminin-binding CD81 mutants, specific binding to the target antigen was shown, while this was not observed for the wild-type CD81. In addition, outcompeting of labelled by unlabeled laminin resulted in reduction of signals indicating specific binding (Table 17).

TABLE 17

| | construct | Mean 488 | Mean 561 | Mean 561 - BG | ratio 488/561 |
|---|---|---|---|---|---|
| without competition | Wild-type-eGFP-EVs | 96203.4 | 20191.9 | 14762.2 | 0.209888 |
| | L2A_LU1-eGFP-EVs | 150790.6 | 31526.3 | 26096.6 | 0.209073 |
| | L3B_LU1-2-eGFP-EVs | 187387.7 | 36420.4 | 30990.7 | 0.194359 |
| with competition of 3-fold molar excess of unlabelled laminin | Wild-type-eGFP-EVs | 96391 | 23944.7 | 18665.1 | 0.248412 |
| | L2A_LU1-eGFP-EVs | 126038.4 | 23397.8 | 18118.2 | 0.18564 |
| | L3B_LU1_2-eGFP-EVs | 139326.7 | 16024.8 | 10745.2 | 0.115016 |

18.3 the Uptake of Laminin-Targeting EVs into Model Hepatocarcinoma Cell Line Huh7

2.4×, 1.6× and 0.8×$10^{10}$ recombinant EVs harboring CD81-eGFP and its targeting variants were incubated with 0.4×$10^6$ Huh7 cells for 3 hours. Cells were trypsinized, neutralized and resuspended in 100 μl of PBS. Flow cytometry was used to measure uptake levels of cells with incorporated eGFP-positive EVs and the MFI values of the main population (gated through FSC/SSC) were determined. In Table 18, biological triplicates of results obtained of a single batch of EVs, normalized to $MFI_{max}$ of CD81wild-type-eGFP, are presented showing a 2 to 3-fold increased uptake of the laminin targeting EVs.

TABLE 18

| | construct | Mean 488 | Mean 561 | Mean 561 - BG | ratio 488/561 |
|---|---|---|---|---|---|
| without competition | Wild-type-eGFP-EVs | 96203.4 | 20191.9 | 14762.2 | 0.209888 |
| | L2A_LU1-eGFP-EVs | 150790.6 | 31526.3 | 26096.6 | 0.209073 |
| | L3B_LU1-2-eGFP-EVs | 187387.7 | 36420.4 | 30990.7 | 0.194359 |
| with competition of 3-fold molar excess of unlabelled laminin | Wild-type-eGFP-EVs | 96391 | 23944.7 | 18665.1 | 0.248412 |
| | L2A_LU1-eGFP-EVs | 126038.4 | 23397.8 | 18118.2 | 0.18564 |
| | L3B_LU1_2-eGFP-EVs | 139326.7 | 16024.8 | 10745.2 | 0.115016 |

In another experiment, replicates of uptake of different batches of laminin-targeting EVs into hepatocarcinoma cell line Huh7 were performed. 3 independent EV batches were tested in duplicates and normalized to $MFI_{max}$. 2.4×$10^{10}$ recombinant EVs harboring CD81-eGFP or respective targeting variants were incubated with 0.4×$10^6$ Huh7 cells for 3 hours. Cells were trypsinized, neutralized and resuspended in 120 μl of PBS. Flow cytometry was used to measure uptake levels of cells with incorporated eGFP-positive EVs and the MFI values of the main population (gated through FSC/SSC) were determined. The values were normalized to MFI max. Means and standard deviations of duplicates are presented in Table 19. The EVs with overexpressed laminin-binding CD81 have shown a higher uptake into the Huh7-cells.

TABLE 19

| EV batch | construct | Mean % MFI max | St. dev. % MFI max |
|---|---|---|---|
| Batch I | CD81 wild-type-eGFP | 29.0997817 | 0.38828317 |
| | L2A_LU1-eGFP | 95.0826781 | 4.91732192 |
| | L3B_LU1-2-eGFP | 75.5668285 | 1.66717452 |

TABLE 19-continued

| EV batch | construct | Mean % MFI max | St. dev. % MFI max |
|---|---|---|---|
| Batch II | CD81 wild-type-eGFP | 40.8614463 | 0.03708697 |
| | L2A_LU1-eGFP | 96.583803 | 3.41619699 |
| | L3B_LU1-2-eGFP | 71.1655595 | 1.82037455 |
| Batch III | CD81 wild-type-eGFP | 57.5887719 | 0.6223537 |
| | L2A_LU1-eGFP | 99.3962027 | 0.60379729 |
| | L3B_LU1-2-eGFP | 93.5651161 | 2.95038121 |

Example 19: CD81 LEL-Based Binders to Human Her2/Neu 19.1 Selections of CD81 LEL Libraries L2A and L2B with Human Her2/Neu Human Her2/neu-Fc was purchased from SinoBiological. For biotinylation, EZ-Link™ Sulfo-NHS-LC-LC-Biotin reagent (Thermo Scientific) was used in a 3:1 molar ratio of biotin to protein. Incubation with biotinylation reagent proceeded for 1 h at room temperature with shaking. Unbound biotin was removed with dialysis against 100× volume of PBS, using Snakeskin dialysis tubing (Thermo Scientific) with 10,000 Da MWCO, at 4° C. overnight with stirring and aliquots of labelled antigen were stored at −80° C. until further use.

For sorting, libraries 2A and 2B were first cultured in SD-CAA medium supplemented with penicillin-streptomycin at 30° C. with shaking overnight and then the expression of recombinant protein was induced by resuspending the yeast cells in SG/R-CAA medium with penicillin-streptomycin and incubating them with shaking overnight at 37° C.

For MACS, 4×$10^9$ induced yeast cells were pelleted for 5 min at 1000 g and blocked in 10% BSA-PBS, on a rotating wheel for 30 min at room temperature. Cells were pelleted and resuspended in 10% BSA-PBS with 0.5 μM biotinylated antigen and incubated for 30 min at room temperature on a rotating wheel. Antigen binding was quenched with the addition of 10-fold volume of ice-cold PBS and the cells were pelleted for 5 min at 1000 g and 4° C. The cells were resuspended in 5 ml wash buffer plus 200 µl streptavidin microbeads (MACS Miltenyi) and incubated on ice for 15 min. Finally, 15 ml MACS wash buffer (0.5% BSA, 2 mM EDTA in PBS; pH 7.4) were added. Cell suspension was strained through a 40-µm cell strainer.

The LS column (MACS Miltenyi) was placed in the separator and 3 ml of wash buffer were applied to precondition the column. Then, the cell solution was loaded in 7 ml batches. Once the column stopped dripping it was briefly removed from the magnet and placed back in the magnet to reorient the beads in the column to allow trapped cells to flow through. Before loading the next 7 ml cell suspension, 1 ml of wash buffer was applied to the column. These steps were repeated until all cells were loaded. Then, the column was washed three times with 5 ml wash buffer. To elute the binding cells, the column was removed from the magnet and 5 ml wash buffer were added. Using the supplied plunger, the cells were pushed through the column into a new tube. The binding cell fraction was pelleted for 10 min at 2500 g. The pellet was re-suspended in 10 ml SD-CAA medium and 10 µl of eluted cells were diluted in 990 µl SD-CAA and 100 µl were plated onto an MDL plate and incubated at 30° C. for three days to estimate the output of MACS procedure, and the rest of the cells were incubated at 30° C. and 180 rpm overnight.

In the FACS selection rounds that followed, the induced cell suspensions were diluted to $10^8$ cells per 1 ml 10% BSA-PBS and centrifuged at 3000 rpm for 5 min at 20° C. To block the cells, the pellets were resuspended in 1 ml 10% BSA-PBS and incubated for 30 min at 20° C. on a rotating platform. The cells were centrifuged at 3000 rpm for 5 min at 20° C. and resuspended in 150 µl 10% BSA-PBS containing 0.5 µM biotinylated Her2/neu-Fc. After incubation for 1 h at room temperature on a rotating platform, antigen binding was quenched by adding 1 ml ice-cold PBS. The cells were centrifuged at 3000 rpm for 5 min at 4° C. and resuspended in 800 µl 10% BSA-PBS with streptavidin-Alexa Fluor 647 (Thermo Fisher Scientific) (1:800) and anti-V5-FITC antibody (Thermo Scientific) (1:100) and incubated for 30 min on ice. The cells were centrifuged at 3000 rpm for 5 min at 4° C., resuspended in 250 µl ice-cold PBS and kept on ice until sorting with Sony SH8000 sorting apparatus. At least 20× output of the previous sorting round was processed and 0.1% top anti-V5-antibody positive yeast cells were collected. Enriched pools were subjected to five sorting rounds and single yeast clones were plated out for screening. 5 identified sequences were cloned to pDisplay expression vector, expressed in HEK293-6E cells and tested for binding to human Her2/neu. Cells were harvested after 48 or 72 h, blocked for 30 min in 4% BSA-PBS on ice and stained with an anti-c-myc antibody (A-14, sc789, Santa Cruz) at 10 µg/ml in 4% BSA-PBS, for 30 min on ice. Their binding was detected after incubation with secondary anti-rabbit (H+L) antibody conjugated with Alexa Fluor 488 (Thermo Scientific A11034), diluted 1:1000 in 4% BSA-PBS, for 30 min on ice. Antigen reactivity was determined after incubation with biotinylated human Her2/neu/Fc in 2-fold dilution series starting from 300 nM and detection with streptavidin-Alexa Fluor 647 at 1:1000 in 4% BSA-PBS. Cells were then resuspended in PBS and kept on ice until analysis with Guava EasyCyte flow cytometer (Merck Millipore).

Clone 81_H2_11 (SEQ ID NO:117) could specifically bind to human Her2/neu protein (Table 20). Residues different from the parental clone are in bold print.

SEQ ID NO: 117:
FVNKDQIAKDVKQFYDQALVNCCYTRAANNACAVVKTFHETLDCCGSSTH

YVDTHCVLNRNLCPSGSNIISNLFKEDCHQKIDDLFSGK

TABLE 20

| EV batch | construct | Mean % MFI max | St. dev. % MFI max |
|---|---|---|---|
| Batch I | CD81 wild-type-eGFP | 29.0997817 | 0.38828317 |
| | L2A_LU1-eGFP | 95.0826781 | 4.91732192 |
| | L3B_LU1-2-eGFP | 75.5668285 | 1.66717452 |
| Batch II | CD81 wild-type-eGFP | 40.8614463 | 0.03708697 |
| | L2A_LU1-eGFP | 96.583803 | 3.41619699 |
| | L3B_LU1-2-eGFP | 71.1655595 | 1.82037455 |
| Batch III | CD81 wild-type-eGFP | 57.5887719 | 0.6223537 |
| | L2A_LU1-eGFP | 99.3962027 | 0.60379729 |
| | L3B_LU1-2-eGFP | 93.5651161 | 2.95038121 |

19.2 Characterization of Specificity of the CD81 LEL-Based Her2/Neu Binder

HEK293-6E cells have been transfected with pDisplay construct encoding wild-type CD81 LEL and anti-Her2/neu directed CD81 LEL 81H2-11. $1\times10^5$ cells have been blocked in 2% BSA-PBS for 30 min on ice and then stained with each 500 nM biotinylated human EGFR-Fc, biotinylated human Her2/neu-Fc and biotinylated mouse EGFR-Fc for 30 min on ice in 2% BSA-PBS. After the centrifugation at 300 g, 5 min at 4° C., binding of the antigens has been detected with streptavidin-Alexa Fluor 647, diluted 1:1000 for 30 min on ice. Cells were then centrifuged at 300 g, 5 min at 4° C. and re-suspended in 200 µl ice-cold PBS. The display was measured by staining the induced cultures with anti-c-myc antibody (A-14, sc789, Santa Cruz) at 10 µg/ml in 2% BSA-PBS and anti-rabbit (H+L) antibody conjugated with Alexa Fluor 488 (Thermo Scientific A11034), diluted 1:1000 in 2% BSA-PBS, for 30 min on ice. The fluorescence has been determined with Guava EasyCyte flow cytometer. The anti-Her2/neu clone has shown binding only to its cognate antigen (Table 21).

TABLE 21

| staining $1^{st}$ step | $2^{nd}$ step | construct MFI | wild-type CD81 LEL | 81_H2_11 |
|---|---|---|---|---|
| anti-c-myc antibody | anti-rabbit(H + L)-Alexa Fluor 488 | % antigen | 176.45 | 75.06 |
| unstained | anti-rabbit (H + L)-Alexa Fluor 488 | binding | 16.10 | 13.07 |
| Human EGFR-Fc-biotin | streptavidin-Alexa Fluor 647 | cells | 10.36 | 5.16 |
| Human Her2/neu-Fc-biotin | streptavidin-Alexa Fluor 647 | | 10.49 | 44.22 |
| Mouse EGFR-Fc-biotin | streptavidin-Alexa Fluor 647 | | 12.80 | 5.68 |
| unstained | streptavidin-Alexa Fluor 647 | | 14.11 | 2.67 |

Example 20: Stabilization of Human CD9 LEL 20.1 Design and Construction of Stabilized CD9 LEL Mutants The Genbank entries with the full-length human CD9 sequence were identified and BLAST comparison was performed to delineate the borders of the LEL region. Homology modelling of the CD9 LEL region, as defined in Seigneuret, 2006, was performed using Swissmodel (Waterhouse et al., 2018) with CD81 LEL PDB:1iv5 as the closest model proposed. The resulting structure could be aligned with the CD81 LEL crystal structure 1g8q with an RMSD of 0.413 Å. The sequence of CD9 LEL (SEQ ID NO:118) was cloned using oligonucleotides CD9hnhe1 (SEQ ID NO:119) and CD9p28_bste2 (SEQ ID NO:120) between the NheI and BstEII cloning sites of the pTT28 vector (CNRC).

```
SEQ ID NO: 118:
HKDEVIKEVQEFYKDTYNKLKTKDEPQRETLKAIHYALNCCGLAGGVEQF

ISDICPKKDVLETFTVKSCPDAIKEVFDNK

SEQ ID NO: 119:
ACGTGCTAGCCACAAGGATGAGGTGATTAAG

SEQ ID NO: 120:
ACGTGGTGACCGGTGCTGGAACCTTTATTGTCGAAGACCTC
```

Mutagenesis reaction was performed to replace the amino acids at positions 20 and 28 for cysteine residues with QuickChange Lightning Mutagenesis Kit (Agilent) according to manufacturer's instructions using oligonucleotides CD9_L20C (SEQ ID NO:121) and CD9_20 Ca (SEQ ID NO:122), and CD9_280 (SEQ ID NO:123) and CD9_28Ca (SEQ ID NO:124), to produce a stabilized variant CD9_LEL_20_28 with amino acid sequence as in (SEQ ID NO:125).

```
SEQ ID NO: 121:
GACACCTACAACAAGTGCAAAACCAAGGATGAG

SEQ ID NO: 122:
CTCATCCTTGGTTTTGCACTTGTTGTAGGTGTC

SEQ ID NO: 123:
AAGGATGAGCCCCAGTGTGAAACGCTGAAAGCC

SEQ ID NO: 124:
GGCTTTCAGCGTTTCACACTGGGGCTCATCCTT

SEQ ID NO: 125:
HKDEVIKEVQEFYKDTYNKCKTKDEPQCETLKAIHYALNCCGLAGGVEQF

ISDICPKKDVLETFTVKSCPDAIKEVFDNK
```

CD9 LEL and CD9 LEL_20_28 were expressed in ExpiCHO system according to MaxTiter protocol exactly according to manufacturer's instructions and purified with one-step Ni-NTA affinity chromatography at 35 and 70 mg/L supernatant, respectively. Purified proteins were analysed with SDS-PAGE and both were monomeric. Thermostability was determined using differential scanning calorimetry (DSC). The melting point of the wild-type protein was determined to be at 52.7° C. and of the stabilized variant 20-28 at 81.9° C., indicating successful stabilization.

20.2 CD9 LEL-Based Yeast Display Library Construction for Binder Selection 20.2.1 Yeast Display of Wild-Type CD9 LEL The sequence of CD9 LEL was cloned using oligonucleotides CD9YDbam1 (SEQ ID NO:126) and CD9YDnot2 (SEQ ID NO:127) between the BamHI and NotI cloning sites of the pYD1 vector and the construct was transformed to *S. cerevisiae* using chemical transformation.

```
SEQ ID NO: 126:
ACGTGGATCCCACAAGGATGAGGTGATTAAG

SEQ ID NO: 127:
ACGTGCGGCCGCGCTTTATTGTCGAAGACCTC
```

Transformants were selected on MDL-plates, cultured at 30° C. in SD-CAA and induced for 48 h at 20° C. and for 24 h at 37° C. Subsequent measurement of yeast-surface displayed protein via the N-terminal tag was performed via detection with an 1:2000 dilution of anti-Xpress tag antibody (Thermo Scientific), followed by incubation with a goat anti-mouse $(Fab')_2$-Alexa Fluor 555 (Thermo Scientific) at 1:1000 and the determination of the correct reading frame of the displayed proteins was via detection of the C-terminal his-tag with an anti-his-Alexa Fluor 488 antibody (QIAgen) at 1:200 and C-terminal V5-tag with an anti-V5-FITC antibody at 1:100 (Thermo Scientific), all in 2% BSA-PBS. Additionally, reactivity with an anti-CD9 specific antibody MEM-61 (Thermo Scientific) was determined after incubating the yeast cells first with the 10 μg/ml antibody in 2% BSA-PBS and detecting the binding with goat anti-mouse (Fab')2-Alexa Fluor 555 (Thermo Scientific) at 1:1000 dilution in 2% BSA-PBS. After resuspending in 200 μl ice-cold PBS, the percentage of positive yeast cells was determined with Guava EasyFlow Cytometer (Table 22).

TABLE 22

| staining | | Sample: wild-type CD9 LEL | Sample: wild-type CD9 LEL |
|---|---|---|---|
| | | Induction temperature (° C.) | |
| 1st step | 2nd step | 20 | 37 |
| unstained | unstained | 0.38 | 4.90 |
| Anti-Xpress | goat anti-mouse-Alexa Fluor 555 | 72.98 | 67.47 |
| MEM-61 | goat anti-mouse-Alexa Fluor 555 | 46.38 | 26.21 |
| unstained | goat anti-mouse-Alexa Fluor 555 | 1.14 | 4.21 |
| unstained | anti-his-tag-Alexa Fluor 488 | 83.87 | 84.65 |
| unstained | anti-V5-tag-FITC | 83.11 | 85.20 |

20.2.2 Mutagenesis of CD9 LEL for Design of Binding Clones

Residues 18-19, 21-25 and 27 of the CD9 LEL_20_28 sequence were mutagenized using oligonucleotide CD9PFOREC1 (SEQ ID NO:128) that was combined with oligonucleotide CD9NOTREC2 (SEQ ID NO:129) to produce a PCR recombination fragment.

```
SEQ ID NO: 128:
CACAAGGATGAGGTGATTAAGGAAGTCCAGGAGTTTTACAAGGACACCTA

CNNKNNKTGCNNKNNKNNKNNKNNKCCCNNKTGTGAAACGCTGAAAGCC
wherein N is anyone of A, C, G, or T.

SEQ ID NO: 129:
CTTCGAAGGGCCCTCTAGACTCGAGCGGCCGCGCTTTATTGTCGAAGACC

TC
```

This fragment is used together with vector pYD1CD9, linearized with enzymes PfoI and NotI, to transform *S. cerevisiae* EBY100. The resulting library of $1\times10^8$ independent members in size is selected for binders with human EGFR-Fc with one MACS-based selection and several FACS-based selection rounds, until an enrichment of binding clones is achieved. The sequences of binders are recloned to mammalian pDisplay vector and resulting plasmids used to transfect HEK293-6E cells. After 48-72 h, cells are harvested and stained with antigen and a secondary reagent to detect specifically binding clones.

REFERENCES

1. Kalra, H.; Drummen, G. P.; Mathivanan, S. Focus on Extracellular Vesicles: Introducing the Next Small Big Thing. *Int J Mol Sci* 2016, 17 (2), 170, 10.3390/ijms17020170.
2. Iraci, N.; Leonardi, T.; Gessler, F.; Vega, B.; Pluchino, S. Focus on Extracellular Vesicles: Physiological Role and Signalling Properties of Extracellular Membrane Vesicles. *Int J Mol Sci* 2016, 17 (2), 171, 10.3390/ijms17020171.
3. Luan, X.; Sansanaphongpricha, K.; Myers, I.; Chen, H.; Yuan, H.; Sun, D. Engineering exosomes as refined biological nanoplatforms for drug delivery. *Acta Pharmacol Sin* 2017, 38 (6), 754-763, 10.1038/aps.2017.12.
4. Tian, T.; Zhu, Y. L.; Zhou, Y. Y.; Liang, G. F.; Wang, Y. Y.; Hu, F. H.; Xiao, Z. D. Exosome uptake through clathrin-mediated endocytosis and macropinocytosis and mediating miR-21 delivery. *J Biol Chem* 2014, 289 (32), 22258-67, 10.1074/jbc.M114.588046.
5. El Andaloussi, S.; Lakhal, S.; Mager, I.; Wood, M. J. Exosomes for targeted siRNA delivery across biological barriers. *Adv Drug Deliv Rev* 2013, 65 (3), 391-7, 10.1016/j.addr.2012.08.008.
6. Rubinstein, E.; Le Naour, F.; Lagaudriere-Gesbert, C.; Billard, M.; Conjeaud, H.; Boucheix, C. CD9, CD63, CD81, and CD82 are components of a surface tetraspan network connected to HLA-DR and VLA integrins. *Eur J Immunol* 1996, 26 (11), 2657-65, 10.1002/eji.1830261117.
7. Levy, S.; Shoham, T. Protein-protein interactions in the tetraspanin web. *Physiology* (*Bethesda*) 2005, 20, 218-24, 10.1152/physiol.00015.2005.
8. Morelli, A. E.; Larregina, A. T.; Shufesky, W. J.; Sullivan, M. L.; Stolz, D. B.; Papworth, G. D.; Zahorchak, A. F.; Logar, A. J.; Wang, Z.; Watkins, S. C.; Falo, L. D., Jr.; Thomson, A. W. Endocytosis, intracellular sorting, and processing of exosomes by dendritic cells. *Blood* 2004, 104 (10), 3257-66, 10.1182/blood-2004-03-0824.
9. Svensson, K. J.; Christianson, H. C.; Wittrup, A.; Bourseau-Guilmain, E.; Lindqvist, E.; Svensson, L. M.; Morgelin, M.; Belting, M. Exosome uptake depends on ERK1/2-heat shock protein 27 signaling and lipid Raft-mediated endocytosis negatively regulated by caveolin-1. *J Biol Chem* 2013, 288 (24), 17713-24, 10.1074/jbc.M112.445403.
10. Berditchevski, F.; Odintsova, E. Tetraspanins as regulators of protein trafficking. *Traffic* 2007, 8 (2), 89-96, 10.1111/j.1600-0854.2006.00515.x.
11. Escola, J. M.; Kleijmeer, M. J.; Stoorvogel, W.; Griffith, J. M.; Yoshie, O.; Geuze, H. J. Selective enrichment of tetraspan proteins on the internal vesicles of multivesicular endosomes and on exosomes secreted by human B-lymphocytes. *J Biol Chem* 1998, 273 (32), 20121-7,
12. Kitadokoro, K.; Galli, G.; Petracca, R.; Falugi, F.; Grandi, G.; Bolognesi, M. Crystallization and preliminary crystallographic studies on the large extracellular domain of human CD81, a tetraspanin receptor for hepatitis C virus. *Acta Crystallogr D Biol Crystallogr* 2001, 57 (Pt 1), 156-8,
13. Kitadokoro, K.; Ponassi, M.; Galli, G.; Petracca, R.; Falugi, F.; Grandi, G.; Bolognesi, M. Subunit association and conformational flexibility in the head subdomain of human CD81 large extracellular loop. *Biol Chem* 2002, 383 (9), 1447-52, 10.1515/BC.2002.164.
14. Kitadokoro, K.; Bordo, D.; Galli, G.; Petracca, R.; Falugi, F.; Abrignani, S.; Grandi, G.; Bolognesi, M. CD81 extracellular domain 3D structure: insight into the tetraspanin superfamily structural motifs. *EMBO J* 2001, 20 (1-2), 12-8, 10.1093/emboj/20.1.12.
15. Higginbottom, A.; Quinn, E. R.; Kuo, C. C.; Flint, M.; Wilson, L. H.; Bianchi, E.; Nicosia, A.; Monk, P. N.; McKeating, J. A.; Levy, S. Identification of amino acid residues in CD81 critical for interaction with hepatitis C virus envelope glycoprotein E2. *J Virol* 2000, 74 (8), 3642-9,
16. Imai, T.; Yoshie, O. C33 antigen and M38 antigen recognized by monoclonal antibodies inhibitory to syncytium formation by human T cell leukemia virus type 1 are both members of the transmembrane 4 superfamily and associate with each other and with CD4 or CD8 in T cells. *J Immunol* 1993, 151 (11), 6470-81,
17. Seigneuret, M. Complete predicted three-dimensional structure of the facilitator transmembrane protein and hepatitis C virus receptor CD81: conserved and variable structural domains in the tetraspanin superfamily. *Biophys J* 2006, 90 (1), 212-27, 10.1529/biophysj.105.069666.
18. Rajesh, S.; Sridhar, P.; Tews, B. A.; Feneant, L.; Cocquerel, L.; Ward, D. G.; Berditchevski, F.; Overduin, M. Structural basis of ligand interactions of the large extracellular domain of tetraspanin CD81. *J Virol* 2012, 86 (18), 9606-16, 10.1128/JVI.00559-12.
19. Seigneuret, M.; Delaguillaumie, A.; Lagaudriere-Gesbert, C.; Conjeaud, H. Structure of the tetraspanin main extracellular domain. A partially conserved fold with a structurally variable domain insertion. *J Biol Chem* 2001, 276 (43), 40055-64, 10.1074/jbc. M105557200.
20. Homsi, Y.; Schloetel, J. G.; Scheffer, K. D.; Schmidt, T. H.; Destainville, N.; Florin, L.; Lang, T. The extracellular delta-domain is essential for the formation of CD81 tetraspanin webs. *Biophys J* 2014, 107 (1), 100-13, 10.1016/j.bpj.2014.05.028.
21. Schmidt, T. H.; Homsi, Y.; Lang, T. Oligomerization of the Tetraspanin CD81 via the Flexibility of Its delta-Loop. *Biophys J* 2016, 110 (11), 2463-74, 10.1016/j.bpj.2016.05.003.
22. Homsi, Y.; Lang, T. The specificity of homomeric clustering of CD81 is mediated by its delta-loop. *FEBS Open Bio* 2017, 7 (2), 274-283, 10.1002/2211-5463.12187.
23. Michel Seigneuret: Complete Predicted Three-Dimensional Structure of the Facilitator Transmembrane Protein and Hepatitis C Virus Receptor CD81: Conserved and Variable Structural Domains in the Tetraspanin Superfamily. Biophys J. 2006 Jan. 1; 90(1): 212-227. doi: 10.1529/biophysj.105.069666
24. Andrew Waterhouse, Martino Bertoni, Stefan Bienert, Gabriel Studer, Gerardo Tauriello, Rafal Gumienny, Florian T Heer, Tjaart A P de Beer, Christine Rempfer, Lorenza Bordoli, Rosalba Lepore, Torsten Schwede: SWISS-MODEL: homology modelling of protein structures and complexes. Nucleic Acids Res. 2018 Jul. 2; 46 (Web Server issue): W296-W303. Published online 2018 May 21. doi: 10.1093/nar/gky427

The invention claimed is:

1. A method of producing a protein comprising a target-specific extravesicular domain (TED) of an extracellular vesicle (EV) surface protein, wherein the EV surface protein is a tetraspanin, comprising:

modifying a polynucleotide comprising a nucleotide sequence encoding an amino acid sequence of an extravesicular domain (ED) of the EV surface protein by a mutagenesis method to engineer a target binding site comprising at least two modified regions within the ED amino acid sequence, wherein each modified region has a length of 3-20 contiguous amino acids flanked by regions of wild-type ED amino acid sequences at its N-terminus and C-terminus, thereby producing a repertoire of modified polynucleotides encoding a variety of TEDs, wherein each TED comprises a different target binding site, wherein the tetraspanin selected from the group consisting of: a) CD81 comprising the amino acid sequence identified as SEQ ID NO:87; b) CD9 comprising the amino acid sequence identified as SEQ ID NO:89; c) CD53 comprising the amino acid sequence identified as SEQ ID NO: 90; d) TSPAN32 comprising the amino acid sequence identified as SEQ ID NO:91; e) CD82 comprising the amino acid sequence identified as SEQ ID NO:92; f) CD63 comprising the amino acid sequence identified as SEQ ID NO:93; g) CD151 comprising the amino acid sequence identified as SEQ ID NO:94; and h) CD37 comprising the amino acid sequence identified as SEQ ID NO:95, selecting a TED specifically recognizing a predetermined target, and producing the protein comprising the selected TED.

2. The method of claim 1, wherein the repertoire of modified polynucleotides comprises genetic packages displaying the variety of TEDs on their outer surfaces, preferably employing a display system selected from the group consisting of a yeast, phage, bacterium, ribosome, mRNA or mammalian cell display.

3. The method of claim 1, wherein the target binding site comprises at least one further binding region which is within a further modified region distant at least 2 amino acids, or within the wild-type ED sequence.

4. The method of claim 1, wherein the TED comprises at least 70% sequence identity to the wild-type ED.

5. The method of claim 1, wherein the wild-type ED is selected from the group consisting of:

a) the ED of CD81 comprising any one of the amino acid sequences identified as SEQ ID NO: 130 or SEQ ID NO: 131;

b) the ED of CD9 comprising any one of the amino acid sequences identified as SEQ ID NO:132, SEQ ID NO:182 or SEQ ID NO:133;

c) the ED of CD53 comprising any one of the amino acid sequences identified as SEQ ID NO:134 or SEQ ID NO:135;

d) the ED of TSPAN32 comprising any one of the amino acid sequences identified as SEQ ID NO:136 or SEQ ID NO:137;

e) the ED of CD82 comprising any one of the amino acid sequences identified as SEQ ID NO:138 or SEQ ID NO: 139;

f) the ED of CD63 comprising any one of the amino acid sequences identified as SEQ ID NO:140 or SEQ ID NO:141;

g) the ED of CD151 comprising any one of the amino acid sequences identified as SEQ ID NO: 142 or SEQ ID NO: 143; and h) the ED of CD37 comprising any one of the amino acid sequences identified as SEQ ID NO: 144 or SEQ ID NO: 145.

6. The method of claim 1, wherein the protein comprises a loop structure in the ED amino acid sequence which is stabilized by one or more cysteine(s) at position(s) to allow the formation of one or more disulfide bonds.

7. The method of claim 1, wherein the modified regions are positioned within a loop region of the ED.

8. The method of claim 1, wherein the ED is:

a) of CD81 and the amino acid sequence is modified to introduce cysteines to allow formation of one or more disulfide bonds not naturally-occurring in the wild-type ED sequence, preferably between positions 134 and 144 and/or 130 and 146 and/or 135 and 168, wherein numbering is of human CD81 identified as SEQ ID NO:87, or b) of CD9 and the amino acid sequence is modified to introduce cysteines to allow formation of one or more disulfide bonds not naturally-occurring in the wild-type ED sequence, preferably between positions 20 and 28, wherein numbering of the positions is of the CD9 large extracellular loop (LEL, SEQ ID NO:118);

c) of CD81, and one of the modified regions is positioned within positions 160 and 172, wherein numbering is of human CD81 identified as SEQ ID NO:87;

d) of CD9 and the modified regions are positioned within positions 155-166, positions 128-142, positions 130-140, or positions 169-180, wherein numbering is of human CD9 identified as SEQ ID NO:89.

9. The method of claim 1, wherein:

a) the ED is of CD81, and one of the modified regions is positioned within positions 160 and 172; and b) the TED comprises at least one further binding region positioned between positions 132 and 141, or between positions 180 and 189, wherein numbering is of human CD81 identified as SEQ ID NO:87.

10. The method of claim 1, wherein the target is a cellular target or acellular target.

11. The method of claim 1, wherein the protein comprising the TED is a target-specific EV surface protein (TSP) comprising said TED and at least one transmembrane domain.

12. The method of claim 11, wherein the transmembrane domain comprises at least 70% sequence identity to a transmembrane domain originating from a mammalian EV surface protein.

13. The method of claim 11, wherein the transmembrane domain is selected from the group consisting of:

a) the transmembrane domain of CD81 comprising any one of the amino acid sequences identified as SEQ ID NO:147, SEQ ID NO:148, SEQ ID NO:149 or SEQ ID NO: 150;

b) the transmembrane domain of CD9 comprising any one of the amino acid sequences identified as SEQ ID NO: 151, SEQ ID NO:152, SEQ ID NO: 153 or SEQ ID NO: 154;

c) the transmembrane domain of CD53 comprising any one of the amino acid sequences identified as SEQ ID NO:155, SEQ ID NO:156, SEQ ID NO: 157 or SEQ ID NO: 158;

d) the transmembrane domain of TSPAN32 comprising any one of the amino acid sequences identified as SEQ ID NO: 159, SEQ ID NO: 160, SEQ ID NO: 161 or SEQ ID NO: 162;

e) the transmembrane domain of CD82 comprising any one of the amino acid sequences identified as SEQ ID NO: 163, SEQ ID NO:164, SEQ ID NO: 165 or SEQ ID NO: 166;

f) the transmembrane domain of CD63 comprising any one of the amino acid sequences identified as SEQ ID NO: 167, SEQ ID NO: 168, SEQ ID NO: 169 or SEQ ID NO: 170;

g) the transmembrane domain of CD151 comprising any one of the amino acid sequences identified as SEQ ID NO:171, SEQ ID NO:172, SEQ ID NO: 173 or SEQ ID NO: 174; and h) the transmembrane domain of CD37 comprising any one of the amino acid sequences identified as SEQ ID NO:175, SEQ ID NO: 176, SEQ ID NO: 177 or SEQ ID NO: 178.

14. The method of claim 11, wherein both the ED and the transmembrane domain originate from the same EV surface protein, and wherein the EV surface protein is selected from the group consisting of:

a) CD81 comprising the amino acid sequence identified as SEQ ID NO:87;

b) CD9 comprising the amino acid sequence identified as SEQ ID NO:89;

c) CD53 comprising the amino acid sequence identified as SEQ ID NO:90;

d) TSPAN32 comprising the amino acid sequence identified as SEQ ID NO:91;

e) CD82 comprising the amino acid sequence identified as SEQ ID NO:92;

f) CD63 comprising the amino acid sequence identified as SEQ ID NO:93;

g) CD151 comprising the amino acid sequence identified as SEQ ID NO:94; and h) CD37 comprising the amino acid sequence identified as SEQ ID NO:95.

15. The method of claim 1, further comprising the steps of:

a) providing a polynucleotide encoding the protein comprising the selected TED;

b) introducing said polynucleotide into a source cell or source cell mixture;

b) culturing said cell(s) under conditions producing extracellular vesicles;

c) isolating a fraction comprising a TEV comprising the target binding site of the TED; and d) producing a preparation of the TEV comprised in said fraction.

16. The method of claim 15, wherein in method step a) the polynucleotide encodes a protein which is a target-specific EV surface protein (TSP) comprising said TED and at least one transmembrane domain, and in method step c) a fraction is isolated comprising such TEV displaying the target binding site on the outer surface of the vesicular membrane.

17. The method of claim 15, further comprising loading the TEV with an intravesicular load, wherein the load comprises any one or more of peptides, polypeptides, protein domains, proteins, lipids, genes, nucleic small molecule drugs, chemotherapeutics, and/or senolytics, wherein the nucleic acids are mRNAs, miRNAs, RNAi mediating molecules, locked nucleic acids phosphorothioates, DNA, DNA fragments, plasmids, and/or minicircle DNA.

18. The method of any one of claim 15, wherein the source cell or source cell mixture is originates from a body tissue, a body fluid, or a cell culture.

19. The method of claim 10, wherein the cellular targets are selected from the group consisting of mitogenic receptors, cytokine receptors, asyaloglycoprotein receptors, membrane transporters, lipoproteins, liposaccharides, glycoproteins, and proteoglycans.

20. The method of claim 10, wherein the acellular targets are selected from the group consisting of cytokines and artificial proteins, and artificial surface structures.

* * * * *

SEQUENCE LISTING

<160> NUMBER OF SEQ ID NOS: 263

<210> SEQ ID NO 1
<211> LENGTH: 9
<212> TYPE: PRT
<213> ORGANISM: Artificial Sequence
<220> FEATURE:
<223> OTHER INFORMATION: Binding Sequence

<400> SEQUENCE: 1

Arg Arg Pro Arg Lys Arg Thr Arg Ser
1 5

<210> SEQ ID NO 2
<211> LENGTH: 9
<212> TYPE: PRT
<213> ORGANISM: Artificial Sequence
<220> FEATURE:
<223> OTHER INFORMATION: Binding Sequence

<400> SEQUENCE: 2

Arg Arg Ser Arg Arg Arg Val His Asp
1 5

<210> SEQ ID NO 3
<211> LENGTH: 9
<212> TYPE: PRT
<213> ORGANISM: Artificial Sequence
<220> FEATURE:
<223> OTHER INFORMATION: Binding Sequence

<400> SEQUENCE: 3

Ile Trp Arg Ala Arg Arg Arg Arg Ser
1 5

<210> SEQ ID NO 4
<211> LENGTH: 9
<212> TYPE: PRT
<213> ORGANISM: Artificial Sequence
<220> FEATURE:
<223> OTHER INFORMATION: Binding Sequence

<400> SEQUENCE: 4

Arg Arg Phe Arg Lys Arg Pro Gly Asp
1 5

<210> SEQ ID NO 5
<211> LENGTH: 9
<212> TYPE: PRT
<213> ORGANISM: Artificial Sequence
<220> FEATURE:
<223> OTHER INFORMATION: Binding Sequence

<400> SEQUENCE: 5

Ser Arg Arg Trp Arg His Arg Ile Ala
1 5

<210> SEQ ID NO 6
<211> LENGTH: 9
<212> TYPE: PRT
<213> ORGANISM: Artificial Sequence
<220> FEATURE:
<223> OTHER INFORMATION: Binding Sequence

<400> SEQUENCE: 6

Trp Trp Gly Arg Arg Phe Arg Val Ser
1 5

<210> SEQ ID NO 7
<211> LENGTH: 89
<212> TYPE: PRT
<213> ORGANISM: Homo sapiens

<400> SEQUENCE: 7

```
Phe Val Asn Lys Asp Gln Ile Ala Lys Asp Val Lys Gln Phe Tyr Asp
1               5                   10                  15

Gln Ala Leu Gln Gln Ala Val Val Asp Asp Asp Ala Asn Asn Ala Lys
            20                  25                  30

Ala Val Val Lys Thr Phe His Glu Thr Leu Asp Cys Cys Gly Ser Ser
        35                  40                  45

Thr Leu Thr Ala Leu Thr Thr Ser Val Leu Lys Asn Asn Leu Cys Pro
    50                  55                  60

Ser Gly Ser Asn Ile Ile Ser Asn Leu Phe Lys Glu Asp Cys His Gln
65                  70                  75                  80

Lys Ile Asp Asp Leu Phe Ser Gly Lys
                85
```

<210> SEQ ID NO 8
<211> LENGTH: 267
<212> TYPE: DNA
<213> ORGANISM: Homo sapiens

<400> SEQUENCE: 8

```
tttgtcaaca aggaccagat cgccaaggat gtgaagcagt tctatgacca ggccctacag     60

caggccgtgg tggatgatga cgccaacaac gccaaggctg tggtgaagac cttccacgag    120

acgcttgact gctgtggctc cagcacactg actgctttga ccacctcagt gctcaagaac    180

aatttgtgtc cctcgggcag caacatcatc agcaacctct tcaaggagga ctgccaccag    240

aagatcgatg acctcttctc cgggaag                                        267
```

<210> SEQ ID NO 9
<211> LENGTH: 31
<212> TYPE: DNA
<213> ORGANISM: Artificial Sequence
<220> FEATURE:
<223> OTHER INFORMATION: Primer

<400> SEQUENCE: 9

```
acgtggatcc tttgtcaaca aggaccagat c                                    31
```

<210> SEQ ID NO 10
<211> LENGTH: 32
<212> TYPE: DNA
<213> ORGANISM: Artificial Sequence
<220> FEATURE:
<223> OTHER INFORMATION: Primer

<400> SEQUENCE: 10

```
acgtgcggcc gcgccttccc ggagaagagg tc                                   32
```

<210> SEQ ID NO 11
<211> LENGTH: 33
<212> TYPE: DNA
<213> ORGANISM: Artificial Sequence
<220> FEATURE:
<223> OTHER INFORMATION: Primer

<400> SEQUENCE: 11

-continued acgagtgcac agtttgtcaa caaggaccag atc 33

<210> SEQ ID NO 12
<211> LENGTH: 30
<212> TYPE: DNA
<213> ORGANISM: Artificial Sequence
<220> FEATURE:
<223> OTHER INFORMATION: Primer

<400> SEQUENCE: 12
acgtgcggcc gccttcccgg agaagaggtc 30

<210> SEQ ID NO 13
<211> LENGTH: 31
<212> TYPE: DNA
<213> ORGANISM: Artificial Sequence
<220> FEATURE:
<223> OTHER INFORMATION: Primer

<400> SEQUENCE: 13
acgtgctagc tttgtcaaca aggaccagat c 31

<210> SEQ ID NO 14
<211> LENGTH: 34
<212> TYPE: DNA
<213> ORGANISM: Artificial Sequence
<220> FEATURE:
<223> OTHER INFORMATION: Primer

<400> SEQUENCE: 14
acgtggatcc tcatcacttc ccggagaaga ggtc 34

<210> SEQ ID NO 15
<211> LENGTH: 57
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (32)..(33)
<223> OTHER INFORMATION: n is any of A, C, G or T
<220> FEATURE:
<221> NAME/KEY: misc_feature
<222> LOCATION: (35)..(36)
<223> OTHER INFORMATION: n is any of A, C, G or T
<220> FEATURE:
<221> NAME/KEY: misc_feature
<222> LOCATION: (38)..(39)
<223> OTHER INFORMATION: n is any of A, C, G or T

<400> SEQUENCE: 15
cttccacgag acgcttgact gctgtggatc cnnknnknnk actgctttga ccacctc 57

<210> SEQ ID NO 16
<211> LENGTH: 86
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (45)..(46)
<223> OTHER INFORMATION: n is any one of A or C
<220> FEATURE:
<221> NAME/KEY: misc_feature
<222> LOCATION: (47)..(48)
<223> OTHER INFORMATION: n is any one of A, C, G or T
<220> FEATURE:
<221> NAME/KEY: misc_feature
<222> LOCATION: (49)..(49)
<223> OTHER INFORMATION: n is any one of A or C
<220> FEATURE:
<221> NAME/KEY: misc_feature
<222> LOCATION: (50)..(51)
<223> OTHER INFORMATION: n is any one of A, C, G or T
<220> FEATURE:
<221> NAME/KEY: misc_feature
<222> LOCATION: (52)..(52)
<223> OTHER INFORMATION: n is any one of A or C
<220> FEATURE:
<221> NAME/KEY: misc_feature
<222> LOCATION: (53)..(54)
<223> OTHER INFORMATION: n is any one of A, C, G or T
<220> FEATURE:
<221> NAME/KEY: misc_feature
<222> LOCATION: (55)..(55)
<223> OTHER INFORMATION: n is any one of A or C
<220> FEATURE:
<221> NAME/KEY: misc_feature
<222> LOCATION: (56)..(57)
<223> OTHER INFORMATION: n is any one of A, C, G or T
<220> FEATURE:
<221> NAME/KEY: misc_feature
<222> LOCATION: (58)..(58)
<223> OTHER INFORMATION: n is any one of A or C
<220> FEATURE:
<221> NAME/KEY: misc_feature
<222> LOCATION: (59)..(60)
<223> OTHER INFORMATION: n is any one of A, C, G or T
<220> FEATURE:
<221> NAME/KEY: misc_feature
<222> LOCATION: (61)..(61)
<223> OTHER INFORMATION: n is any one of A or C
<220> FEATURE:
<221> NAME/KEY: misc_feature
<222> LOCATION: (62)..(63)
<223> OTHER INFORMATION: n is any one of A, C, G or T
<220> FEATURE:
<221> NAME/KEY: misc_feature
<222> LOCATION: (64)..(64)
<223> OTHER INFORMATION: n is any one of A or C
<220> FEATURE:
<221> NAME/KEY: misc_feature
<222> LOCATION: (65)..(66)
<223> OTHER INFORMATION: n is any one of A, C, G or T
<220> FEATURE:
<221> NAME/KEY: misc_feature
<222> LOCATION: (67)..(67)
<223> OTHER INFORMATION: n is any one of A or C
<220> FEATURE:
<221> NAME/KEY: misc_feature
<222> LOCATION: (68)..(69)
<223> OTHER INFORMATION: n is any one of A, C, G or T

<400> SEQUENCE: 16
ccgcgccttc ccggagaaga ggtcatcgat cttctggtgg caaknnnnnn nnnnnnnnnn 60
nnnnnnnnng ttgctgcccg agggac 86

<210> SEQ ID NO 17
<211> LENGTH: 32
<212> TYPE: DNA
<213> ORGANISM: Artificial Sequence
<220> FEATURE:
<223> OTHER INFORMATION: Oligonucleotide

<400> SEQUENCE: 17
gcttgactgc tgtggatcca gcacactgac tg 32

<210> SEQ ID NO 18
<211> LENGTH: 32
<212> TYPE: DNA
<213> ORGANISM: Artificial Sequence
<220> FEATURE:

<223> OTHER INFORMATION: Oligonucleotide

<400> SEQUENCE: 18
cagtcagtgt gctggatcca cagcagtcaa gc 32

<210> SEQ ID NO 19
<211> LENGTH: 31
<212> TYPE: DNA
<213> ORGANISM: Artificial Sequence
<220> FEATURE:
<223> OTHER INFORMATION: Oligonucleotide

<400> SEQUENCE: 19
cgataaggta ccaggttcct ttgtcaacaa g 31

<210> SEQ ID NO 20
<211> LENGTH: 31
<212> TYPE: DNA
<213> ORGANISM: Artificial Sequence
<220> FEATURE:
<223> OTHER INFORMATION: Oligonucleotide

<400> SEQUENCE: 20
cttgttgaca aaggaacctg gtaccttatc g 31

<210> SEQ ID NO 21
<211> LENGTH: 31
<212> TYPE: DNA
<213> ORGANISM: Artificial Sequence
<220> FEATURE:
<223> OTHER INFORMATION: Oligonucleotide

<400> SEQUENCE: 21
cgataaggta ccaggttcct ttgtcaacaa g 31

<210> SEQ ID NO 22
<211> LENGTH: 31
<212> TYPE: DNA
<213> ORGANISM: Artificial Sequence
<220> FEATURE:
<223> OTHER INFORMATION: Oligonucleotide

<400> SEQUENCE: 22
cttgttgaca aaggaacctg gtaccttatc g 31

<210> SEQ ID NO 23
<211> LENGTH: 32
<212> TYPE: DNA
<213> ORGANISM: Artificial Sequence
<220> FEATURE:
<223> OTHER INFORMATION: Oligonucleotide

<400> SEQUENCE: 23
gtatgttttt aagctcctgc aggctagtgg tg 32

<210> SEQ ID NO 24
<211> LENGTH: 32
<212> TYPE: DNA
<213> ORGANISM: Artificial Sequence
<220> FEATURE:
<223> OTHER INFORMATION: Oligonucleotide

<400> SEQUENCE: 24
caccactagc ctgcaggagc ttaaaaacat ac 32

<210> SEQ ID NO 25
<211> LENGTH: 33
<212> TYPE: DNA
<213> ORGANISM: Artificial Sequence
<220> FEATURE:
<223> OTHER INFORMATION: Oligonucleotide

<400> SEQUENCE: 25
tttgtgtccc tcgggatcca acatcatcag caa 33

<210> SEQ ID NO 26
<211> LENGTH: 33
<212> TYPE: DNA
<213> ORGANISM: Artificial Sequence
<220> FEATURE:
<223> OTHER INFORMATION: Oligonucleotide

<400> SEQUENCE: 26
ttgctgatga tgttggatcc cgagggacac aaa 33

<210> SEQ ID NO 27
<211> LENGTH: 35
<212> TYPE: DNA
<213> ORGANISM: Artificial Sequence
<220> FEATURE:
<223> OTHER INFORMATION: Oligonucleotide

<400> SEQUENCE: 27
gcagttctat gaccaagctt tacagcaggc cgtgg 35

<210> SEQ ID NO 28
<211> LENGTH: 35
<212> TYPE: DNA
<213> ORGANISM: Artificial Sequence
<220> FEATURE:
<223> OTHER INFORMATION: Oligonucleotide

<400> SEQUENCE: 28
ccacggcctg ctgtaaagct tggtcataga actgc 35

<210> SEQ ID NO 29
<211> LENGTH: 35
<212> TYPE: DNA
<213> ORGANISM: Artificial Sequence
<220> FEATURE:
<223> OTHER INFORMATION: Oligonucleotide

<400> SEQUENCE: 29
gcagttctat gaccaagctt tacagcagtg ctgtg 35

<210> SEQ ID NO 30
<211> LENGTH: 35
<212> TYPE: DNA
<213> ORGANISM: Artificial Sequence
<220> FEATURE:
<223> OTHER INFORMATION: Oligonucleotide

<400> SEQUENCE: 30
cacagcactg ctgtaaagct tggtcataga actgc 35

<210> SEQ ID NO 31
<211> LENGTH: 33
<212> TYPE: DNA
<213> ORGANISM: Artificial Sequence
<220> FEATURE:
<223> OTHER INFORMATION: Oligonucleotide

<400> SEQUENCE: 31
tttgtgtccc tcgggatcca acatcatcag caa 33

<210> SEQ ID NO 32
<211> LENGTH: 33
<212> TYPE: DNA
<213> ORGANISM: Artificial Sequence
<220> FEATURE:
<223> OTHER INFORMATION: Oligonucleotide

<400> SEQUENCE: 32
ttgctgatga tgttggatcc cgagggacac aaa 33

<210> SEQ ID NO 33
<211> LENGTH: 78
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (34)..(35)
<223> OTHER INFORMATION: n is any one of A, C, G or T
<220> FEATURE:
<221> NAME/KEY: misc_feature
<222> LOCATION: (37)..(38)
<223> OTHER INFORMATION: n is any one of A, C, G or T
<220> FEATURE:
<221> NAME/KEY: misc_feature
<222> LOCATION: (46)..(47)
<223> OTHER INFORMATION: n is any one of A, C, G or T
<220> FEATURE:
<221> NAME/KEY: misc_feature
<222> LOCATION: (49)..(50)
<223> OTHER INFORMATION: n is any one of A, C, G or T
<220> FEATURE:
<221> NAME/KEY: misc_feature
<222> LOCATION: (52)..(53)
<223> OTHER INFORMATION: n is any one of A, C, G or T
<220> FEATURE:
<221> NAME/KEY: misc_feature
<222> LOCATION: (55)..(56)
<223> OTHER INFORMATION: n is any one of A, C, G or T

<400> SEQUENCE: 33
aaggatgtga agcagttcta tgaccaagct ttannknnkt gctgtnnknn knnknnkgcc 60
aacaacgcct gtgctgtg 78

<210> SEQ ID NO 34
<211> LENGTH: 96
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (46)..(46)
<223> OTHER INFORMATION: n is any one of A or C
<220> FEATURE:
<221> NAME/KEY: misc_feature
<222> LOCATION: (47)..(48)
<223> OTHER INFORMATION: n is any one of A, C, G or T
<220> FEATURE:
<221> NAME/KEY: misc_feature
<222> LOCATION: (49)..(49)
<223> OTHER INFORMATION: n is any one of A or C
<220> FEATURE:
<221> NAME/KEY: misc_feature
<222> LOCATION: (50)..(51)
<223> OTHER INFORMATION: n is any one of A, C, G or T
<220> FEATURE:
<221> NAME/KEY: misc_feature
<222> LOCATION: (61)..(61)
<223> OTHER INFORMATION: n is any one of A or C
<220> FEATURE:
<221> NAME/KEY: misc_feature
<222> LOCATION: (62)..(63)
<223> OTHER INFORMATION: n is any one of A, C, G or T
<220> FEATURE:
<221> NAME/KEY: misc_feature
<222> LOCATION: (67)..(67)
<223> OTHER INFORMATION: n is any one of A or C
<220> FEATURE:
<221> NAME/KEY: misc_feature
<222> LOCATION: (68)..(69)
<223> OTHER INFORMATION: n is any one of A, C, G or T
<220> FEATURE:
<221> NAME/KEY: misc_feature
<222> LOCATION: (70)..(70)
<223> OTHER INFORMATION: n is any one of A or C
<220> FEATURE:
<221> NAME/KEY: misc_feature
<222> LOCATION: (71)..(72)
<223> OTHER INFORMATION: n is any one of A, C, G or T
<220> FEATURE:
<221> NAME/KEY: misc_feature
<222> LOCATION: (73)..(73)
<223> OTHER INFORMATION: n is any one of A or C
<220> FEATURE:
<221> NAME/KEY: misc_feature
<222> LOCATION: (74)..(75)
<223> OTHER INFORMATION: n is any one of A, C, G or T
<220> FEATURE:
<221> NAME/KEY: misc_feature
<222> LOCATION: (76)..(76)
<223> OTHER INFORMATION: n is any one of A or C
<220> FEATURE:
<221> NAME/KEY: misc_feature
<222> LOCATION: (77)..(78)
<223> OTHER INFORMATION: n is any one of A, C, G or T

<400> SEQUENCE: 34
cttgaagagg ttgctgatga tgttggatcc cgagggacac aaattnnnnn ngagcacaca 60
nnnggtnnnn nnnnnnnntg tgctggagcc acagca 96

<210> SEQ ID NO 35
<211> LENGTH: 4
<212> TYPE: PRT
<213> ORGANISM: Artificial Sequence
<220> FEATURE:
<223> OTHER INFORMATION: Binding Sequence

<400> SEQUENCE: 35

Gly Ala Ser Ala
1

<210> SEQ ID NO 36
<211> LENGTH: 4
<212> TYPE: PRT
<213> ORGANISM: Artificial Sequence
<220> FEATURE:
<223> OTHER INFORMATION: Binding Sequence

<400> SEQUENCE: 36

Asp Ala Gly Pro
1

<210> SEQ ID NO 37
<211> LENGTH: 4
<212> TYPE: PRT
<213> ORGANISM: Artificial Sequence
<220> FEATURE:
<223> OTHER INFORMATION: Binding Sequence

<400> SEQUENCE: 37

Ser Phe Leu Val
1

<210> SEQ ID NO 38
<211> LENGTH: 4
<212> TYPE: PRT
<213> ORGANISM: Artificial Sequence
<220> FEATURE:
<223> OTHER INFORMATION: Binding Sequence

<400> SEQUENCE: 38

Pro Leu Thr Met
1

<210> SEQ ID NO 39
<211> LENGTH: 4
<212> TYPE: PRT
<213> ORGANISM: Artificial Sequence
<220> FEATURE:
<223> OTHER INFORMATION: Binding Sequence

<400> SEQUENCE: 39

Ala Lys Met Tyr
1

<210> SEQ ID NO 40
<211> LENGTH: 4
<212> TYPE: PRT
<213> ORGANISM: Artificial Sequence
<220> FEATURE:
<223> OTHER INFORMATION: Binding Sequence

<400> SEQUENCE: 40

Ser Ala Arg Phe
1

<210> SEQ ID NO 41
<211> LENGTH: 31
<212> TYPE: DNA
<213> ORGANISM: Artificial Sequence
<220> FEATURE:
<223> OTHER INFORMATION: Oligonucleotide

<400> SEQUENCE: 41
acgtgctagc tttgtcaaca aggaccagat c 31

<210> SEQ ID NO 42
<211> LENGTH: 41
<212> TYPE: DNA
<213> ORGANISM: Artificial Sequence
<220> FEATURE:
<223> OTHER INFORMATION: Oligonucleotide

<400> SEQUENCE: 42
acgtggtgac cggtgctgga acccttcccg gagaagaggt c 41

<210> SEQ ID NO 43
<211> LENGTH: 33
<212> TYPE: DNA
<213> ORGANISM: Artificial Sequence
<220> FEATURE:
<223> OTHER INFORMATION: Oligonucleotide

<400> SEQUENCE: 43
caggccctac agcagtgcgt ggtggatgat gac 33

<210> SEQ ID NO 44
<211> LENGTH: 33
<212> TYPE: DNA
<213> ORGANISM: Artificial Sequence
<220> FEATURE:
<223> OTHER INFORMATION: Oligonucleotide

<400> SEQUENCE: 44
gtcatcatcc accacgcact gctgtagggc ctg 33

<210> SEQ ID NO 45
<211> LENGTH: 33
<212> TYPE: DNA
<213> ORGANISM: Artificial Sequence
<220> FEATURE:
<223> OTHER INFORMATION: Oligonucleotide

<400> SEQUENCE: 45
gatgatgcca acaactgcaa ggctgtggtg aag 33

<210> SEQ ID NO 46
<211> LENGTH: 33
<212> TYPE: DNA
<213> ORGANISM: Artificial Sequence
<220> FEATURE:
<223> OTHER INFORMATION: Oligonucleotide

<400> SEQUENCE: 46
cttcaccaca gccttgcagt tgttggcatc atc 33

<210> SEQ ID NO 47
<211> LENGTH: 33
<212> TYPE: DNA
<213> ORGANISM: Artificial Sequence
<220> FEATURE:
<223> OTHER INFORMATION: Oligonucleotide

<400> SEQUENCE: 47
cagttctatg accagtgtct acagcaggcc gtg 33

<210> SEQ ID NO 48
<211> LENGTH: 33
<212> TYPE: DNA
<213> ORGANISM: Artificial Sequence
<220> FEATURE:
<223> OTHER INFORMATION: Oligonucleotide

<400> SEQUENCE: 48
cacggcctgc tgtagacact ggtcatagaa ctg 33

<210> SEQ ID NO 49
<211> LENGTH: 33
<212> TYPE: DNA
<213> ORGANISM: Artificial Sequence
<220> FEATURE:
<223> OTHER INFORMATION: Oligonucleotide

<400> SEQUENCE: 49
aacaacgcca aggcttgtgt gaagaccttc cac 33

<210> SEQ ID NO 50
<211> LENGTH: 33
<212> TYPE: DNA
<213> ORGANISM: Artificial Sequence
<220> FEATURE:

<223> OTHER INFORMATION: Oligonucleotide

<400> SEQUENCE: 50
gtggaaggtc ttcacacaag ccttggcgtt gtt 33

<210> SEQ ID NO 51
<211> LENGTH: 34
<212> TYPE: DNA
<213> ORGANISM: Artificial Sequence
<220> FEATURE:
<223> OTHER INFORMATION: Oligonucleotide

<400> SEQUENCE: 51
gaccaggccc tacagtgcgc cgtggtggat gatg 34

<210> SEQ ID NO 52
<211> LENGTH: 34
<212> TYPE: DNA
<213> ORGANISM: Artificial Sequence
<220> FEATURE:
<223> OTHER INFORMATION: Oligonucleotide

<400> SEQUENCE: 52
catcatccac cacggcgcac tgtagggcct ggtc 34

<210> SEQ ID NO 53
<211> LENGTH: 33
<212> TYPE: DNA
<213> ORGANISM: Artificial Sequence
<220> FEATURE:
<223> OTHER INFORMATION: Oligonucleotide

<400> SEQUENCE: 53
gatgatgcca acaactgcaa ggctgtggtg aag 33

<210> SEQ ID NO 54
<211> LENGTH: 33
<212> TYPE: DNA
<213> ORGANISM: Artificial Sequence
<220> FEATURE:
<223> OTHER INFORMATION: Oligonucleotide

<400> SEQUENCE: 54
cttcaccaca gccttgcagt tgttggcatc atc 33

<210> SEQ ID NO 55
<211> LENGTH: 33
<212> TYPE: DNA
<213> ORGANISM: Artificial Sequence
<220> FEATURE:
<223> OTHER INFORMATION: Oligonucleotide

<400> SEQUENCE: 55
caggccctac agcagtgcgt ggtggatgat gac 33

<210> SEQ ID NO 56
<211> LENGTH: 33
<212> TYPE: DNA
<213> ORGANISM: Artificial Sequence
<220> FEATURE:
<223> OTHER INFORMATION: Oligonucleotide

<400> SEQUENCE: 56
gtcatcatcc accacgcact gctgtagggc ctg 33

<210> SEQ ID NO 57
<211> LENGTH: 33
<212> TYPE: DNA
<213> ORGANISM: Artificial Sequence
<220> FEATURE:
<223> OTHER INFORMATION: Oligonucleotide

<400> SEQUENCE: 57
gacgccaaca acgcctgtgc tgtggtgaag acc 33

<210> SEQ ID NO 58
<211> LENGTH: 33
<212> TYPE: DNA
<213> ORGANISM: Artificial Sequence
<220> FEATURE:
<223> OTHER INFORMATION: Oligonucleotide

<400> SEQUENCE: 58
ggtcttcacc acagcacagg cgttgttggc gtc 33

<210> SEQ ID NO 59
<211> LENGTH: 33
<212> TYPE: DNA
<213> ORGANISM: Artificial Sequence
<220> FEATURE:
<223> OTHER INFORMATION: Oligonucleotide

<400> SEQUENCE: 59
gaccttccac gagacgtgtg actgctgtgg ctc 33

<210> SEQ ID NO 60
<211> LENGTH: 33
<212> TYPE: DNA
<213> ORGANISM: Artificial Sequence
<220> FEATURE:
<223> OTHER INFORMATION: Oligonucleotide

<400> SEQUENCE: 60
gagccacagc agtcacacgt ctcgtggaag gtc 33

<210> SEQ ID NO 61
<211> LENGTH: 33
<212> TYPE: DNA
<213> ORGANISM: Artificial Sequence
<220> FEATURE:
<223> OTHER INFORMATION: Oligonucleotide

<400> SEQUENCE: 61
gaggactgcc accagtgtat cgatgacctc ttc 33

<210> SEQ ID NO 62
<211> LENGTH: 33
<212> TYPE: DNA
<213> ORGANISM: Artificial Sequence
<220> FEATURE:
<223> OTHER INFORMATION: Oligonucleotide

<400> SEQUENCE: 62
gaagaggtca tcgatacact ggtggcagtc ctc 33

<210> SEQ ID NO 63
<211> LENGTH: 34
<212> TYPE: DNA
<213> ORGANISM: Artificial Sequence
<220> FEATURE:
<223> OTHER INFORMATION: Oligonucleotide

<400> SEQUENCE: 63
caacaaggac cagatctgta aggatgtgaa gcag 34

<210> SEQ ID NO 64
<211> LENGTH: 34
<212> TYPE: DNA
<213> ORGANISM: Artificial Sequence
<220> FEATURE:
<223> OTHER INFORMATION: Oligonucleotide

<400> SEQUENCE: 64
ctgcttcaca tccttacaga tctggtcctt gttg 34

<210> SEQ ID NO 65
<211> LENGTH: 34
<212> TYPE: DNA
<213> ORGANISM: Artificial Sequence
<220> FEATURE:
<223> OTHER INFORMATION: Oligonucleotide

<400> SEQUENCE: 65
aagatcgatg acctctgttc cgggaagtga tgag 34

<210> SEQ ID NO 66
<211> LENGTH: 34
<212> TYPE: DNA
<213> ORGANISM: Artificial Sequence
<220> FEATURE:
<223> OTHER INFORMATION: Oligonucleotide

<400> SEQUENCE: 66
ctcatcactt cccggaacag aggtcatcga tctt 34

<210> SEQ ID NO 67
<211> LENGTH: 33
<212> TYPE: DNA
<213> ORGANISM: Artificial Sequence
<220> FEATURE:
<223> OTHER INFORMATION: Oligonucleotide

<400> SEQUENCE: 67
cagttctatg accagtgtct acagcaggcc gtg 33

<210> SEQ ID NO 68
<211> LENGTH: 33
<212> TYPE: DNA
<213> ORGANISM: Artificial Sequence
<220> FEATURE:
<223> OTHER INFORMATION: Oligonucleotide

<400> SEQUENCE: 68
cacggcctgc tgtagacact ggtcatagaa ctg 33

<210> SEQ ID NO 69
<211> LENGTH: 33
<212> TYPE: DNA
<213> ORGANISM: Artificial Sequence
<220> FEATURE:
<223> OTHER INFORMATION: Oligonucleotide

<400> SEQUENCE: 69
gatgatgcca acaactgcaa ggctgtggtg aag 33

<210> SEQ ID NO 70
<211> LENGTH: 33

<212> TYPE: DNA
<213> ORGANISM: Artificial Sequence
<220> FEATURE:
<223> OTHER INFORMATION: Oligonucleotide

<400> SEQUENCE: 70
cttcaccaca gccttgcagt tgttggcatc atc 33

<210> SEQ ID NO 71
<211> LENGTH: 33
<212> TYPE: DNA
<213> ORGANISM: Artificial Sequence
<220> FEATURE:
<223> OTHER INFORMATION: Oligonucleotide

<400> SEQUENCE: 71
ttctatgacc aggcctgcca gcaggccgtg gtg 33

<210> SEQ ID NO 72
<211> LENGTH: 33
<212> TYPE: DNA
<213> ORGANISM: Artificial Sequence
<220> FEATURE:
<223> OTHER INFORMATION: Oligonucleotide

<400> SEQUENCE: 72
caccacggcc tgctggcagg cctggtcata gaa 33

<210> SEQ ID NO 73
<211> LENGTH: 33
<212> TYPE: DNA
<213> ORGANISM: Artificial Sequence
<220> FEATURE:
<223> OTHER INFORMATION: Oligonucleotide

<400> SEQUENCE: 73
agcacactga ctgcttgtac cacctcagtg ctc 33

<210> SEQ ID NO 74
<211> LENGTH: 33
<212> TYPE: DNA
<213> ORGANISM: Artificial Sequence
<220> FEATURE:
<223> OTHER INFORMATION: Oligonucleotide

<400> SEQUENCE: 74
gagcactgag gtggtacaag cagtcagtgt gct 33

<210> SEQ ID NO 75
<211> LENGTH: 33
<212> TYPE: DNA
<213> ORGANISM: Artificial Sequence
<220> FEATURE:
<223> OTHER INFORMATION: Oligonucleotide

<400> SEQUENCE: 75
gccctacagc aggcctgtgt ggatgatgac gcc 33

<210> SEQ ID NO 76
<211> LENGTH: 33
<212> TYPE: DNA
<213> ORGANISM: Artificial Sequence
<220> FEATURE:
<223> OTHER INFORMATION: Oligonucleotide

<400> SEQUENCE: 76

-continued ggcgtcatca tccacacagg cctgctgtag ggc 33

<210> SEQ ID NO 77
<211> LENGTH: 30
<212> TYPE: DNA
<213> ORGANISM: Artificial Sequence
<220> FEATURE:
<223> OTHER INFORMATION: Oligonucleotide

<400> SEQUENCE: 77
gctttgacca cctgtgtgct caagaacaat 30

<210> SEQ ID NO 78
<211> LENGTH: 30
<212> TYPE: DNA
<213> ORGANISM: Artificial Sequence
<220> FEATURE:
<223> OTHER INFORMATION: Oligonucleotide

<400> SEQUENCE: 78
attgttcttg agcacacagg tggtcaaagc 30

<210> SEQ ID NO 79
<211> LENGTH: 34
<212> TYPE: DNA
<213> ORGANISM: Artificial Sequence
<220> FEATURE:
<223> OTHER INFORMATION: Oligonucleotide

<400> SEQUENCE: 79
ttgaccacct cagtgtgcaa gaacaatttg tgtc 34

<210> SEQ ID NO 80
<211> LENGTH: 34
<212> TYPE: DNA
<213> ORGANISM: Artificial Sequence
<220> FEATURE:
<223> OTHER INFORMATION: Oligonucleotide

<400> SEQUENCE: 80
gacacaaatt gttcttgcac actgaggtgg tcaa 34

<210> SEQ ID NO 81
<211> LENGTH: 33
<212> TYPE: DNA
<213> ORGANISM: Artificial Sequence
<220> FEATURE:
<223> OTHER INFORMATION: Oligonucleotide

<400> SEQUENCE: 81
gtgctcaaga acaattgttg tccctcgggc agc 33

<210> SEQ ID NO 82
<211> LENGTH: 33
<212> TYPE: DNA
<213> ORGANISM: Artificial Sequence
<220> FEATURE:
<223> OTHER INFORMATION: Oligonucleotide

<400> SEQUENCE: 82
gctgcccgag ggacaacaat tgttcttgag cac 33

<210> SEQ ID NO 83
<211> LENGTH: 33
<212> TYPE: DNA
<213> ORGANISM: Artificial Sequence
<220> FEATURE:
<223> OTHER INFORMATION: Oligonucleotide

<400> SEQUENCE: 83
gactgctgtg gctcctgtac actgactgct ttg 33

<210> SEQ ID NO 84
<211> LENGTH: 33
<212> TYPE: DNA
<213> ORGANISM: Artificial Sequence
<220> FEATURE:
<223> OTHER INFORMATION: Oligonucleotide

<400> SEQUENCE: 84
caaagcagtc agtgtacagg agccacagca gtc 33

<210> SEQ ID NO 85
<211> LENGTH: 33
<212> TYPE: DNA
<213> ORGANISM: Artificial Sequence
<220> FEATURE:
<223> OTHER INFORMATION: Oligonucleotide

<400> SEQUENCE: 85
aacctcttca aggagtgttg ccaccagaag atc 33

<210> SEQ ID NO 86
<211> LENGTH: 33
<212> TYPE: DNA
<213> ORGANISM: Artificial Sequence
<220> FEATURE:
<223> OTHER INFORMATION: Oligonucleotide

<400> SEQUENCE: 86
gatcttctgg tggcaacact ccttgaagag gtt 33

<210> SEQ ID NO 87
<211> LENGTH: 235
<212> TYPE: PRT
<213> ORGANISM: Homo sapiens

<400> SEQUENCE: 87

```
Met Gly Val Glu Gly Cys Thr Lys Cys Ile Lys Tyr Leu Leu Phe Val
1               5                   10                  15

Phe Asn Phe Val Phe Trp Leu Ala Gly Gly Val Ile Leu Gly Val Ala
            20                  25                  30

Leu Trp Leu Arg His Asp Pro Gln Thr Thr Asn Leu Leu Tyr Leu Glu
        35                  40                  45

Leu Gly Asp Lys Ala Pro Asn Thr Phe Tyr Val Gly Ile Tyr Ile Leu
    50                  55                  60

Ile Ala Val Gly Ala Val Met Met Phe Val Gly Phe Leu Gly Cys Tyr
65                  70                  75                  80

Gly Ala Ile Gln Glu Ser Gln Cys Leu Leu Gly Thr Phe Phe Thr Cys
                85                  90                  95

Leu Val Ile Leu Phe Ala Cys Glu Val Ala Ala Gly Ile Trp Gly Phe
            100                 105                 110

Val Asn Lys Asp Gln Ile Ala Lys Asp Val Lys Gln Phe Tyr Asp Gln
        115                 120                 125

Ala Leu Gln Gln Ala Val Val Asp Asp Asp Ala Asn Asn Ala Lys Ala
    130                 135                 140

Val Val Lys Thr Phe His Glu Thr Leu Asp Cys Cys Gly Ser Ser Thr
```

```
145                 150                 155                 160

Leu Thr Ala Leu Thr Thr Ser Val Leu Lys Asn Asn Leu Cys Pro Ser
                165                 170                 175

Gly Ser Asn Ile Ile Ser Asn Leu Phe Lys Glu Asp Cys His Gln Lys
            180                 185                 190

Ile Asp Asp Leu Phe Ser Gly Lys Leu Tyr Leu Ile Gly Ile Ala Ala
        195                 200                 205

Ile Val Val Ala Val Ile Met Ile Phe Glu Met Ile Leu Ser Met Val
    210                 215                 220

Leu Cys Cys Gly Ile Arg Asn Ser Ser Val Tyr
225                 230                 235


<210> SEQ ID NO 88
<211> LENGTH: 711
<212> TYPE: DNA
<213> ORGANISM: Homo sapiens

<400> SEQUENCE: 88

atgggagtgg agggctgcac caagtgcatc aagtacctgc tcttcgtctt caatttcgtc     60

ttctggctgg ctggaggcgt gatcctgggt gtggccctgt ggctccgcca tgacccgcag    120

accaccaacc tcctgtatct ggagctggga gacaagcccg cgcccaacac cttctatgta    180

ggcatctaca tcctcatcgc tgtgggcgct gtcatgatgt tcgttggctt cctgggctgc    240

tacggggcca tccaggaatc ccagtgcctg ctggggacgt tcttcacctg cctggtcatc    300

ctgtttgcct gtgaggtggc cgccggcatc tggggctttg tcaacaagga ccagatcgcc    360

aaggatgtga agcagttcta tgaccaggcc ctacagcagg ccgtggtgga tgatgacgcc    420

aacaacgcca aggctgtggt gaagaccttc cacgagacgc ttgactgctg tggctccagc    480

acactgactg ctttgaccac ctcagtgctc aagaacaatt tgtgtccctc gggcagcaac    540

atcatcagca acctcttcaa ggaggactgc caccagaaga tcgatgacct cttctccggg    600

aagctgtacc tcatcggcat tgctgccatc gtggtcgctg tgatcatgat cttcgagatg    660

atcctgagca tggtgctgtg ctgtggcatc cggaacagct ccgtgtactg a             711


<210> SEQ ID NO 89
<211> LENGTH: 228
<212> TYPE: PRT
<213> ORGANISM: Homo sapiens

<400> SEQUENCE: 89

Met Pro Val Lys Gly Gly Thr Lys Cys Ile Lys Tyr Leu Leu Phe Gly
1               5                   10                  15

Phe Asn Phe Ile Phe Trp Leu Ala Gly Ile Ala Val Leu Ala Ile Gly
            20                  25                  30

Leu Trp Leu Arg Phe Asp Ser Gln Thr Lys Ser Ile Phe Glu Gln Glu
        35                  40                  45

Thr Asn Asn Asn Asn Ser Ser Phe Tyr Thr Gly Val Tyr Ile Leu Ile
    50                  55                  60

Gly Ala Gly Ala Leu Met Met Leu Val Gly Phe Leu Gly Cys Cys Gly
65                  70                  75                  80

Ala Val Gln Glu Ser Gln Cys Met Leu Gly Leu Phe Phe Gly Phe Leu
                85                  90                  95

Leu Val Ile Phe Ala Ile Glu Ile Ala Ala Ala Ile Trp Gly Tyr Ser
            100                 105                 110

His Lys Asp Glu Val Ile Lys Glu Val Gln Glu Phe Tyr Lys Asp Thr
```

-continued

```
        115                 120                 125

Tyr Asn Lys Leu Lys Thr Lys Asp Glu Pro Gln Arg Glu Thr Leu Lys
    130                 135                 140

Ala Ile His Tyr Ala Leu Asn Cys Cys Gly Leu Ala Gly Gly Val Glu
145                 150                 155                 160

Gln Phe Ile Ser Asp Ile Cys Pro Lys Lys Asp Val Leu Glu Thr Phe
                165                 170                 175

Thr Val Lys Ser Cys Pro Asp Ala Ile Lys Glu Val Phe Asp Asn Lys
            180                 185                 190

Phe His Ile Ile Gly Ala Val Gly Ile Gly Ile Ala Val Val Met Ile
        195                 200                 205

Phe Gly Met Ile Phe Ser Met Ile Leu Cys Cys Ala Ile Arg Arg Asn
    210                 215                 220

Arg Glu Met Val
225


<210> SEQ ID NO 90
<211> LENGTH: 219
<212> TYPE: PRT
<213> ORGANISM: Homo sapiens

<400> SEQUENCE: 90

Met Gly Met Ser Ser Leu Lys Leu Leu Lys Tyr Val Leu Phe Phe Phe
1               5                   10                  15

Asn Leu Leu Phe Trp Ile Cys Gly Cys Cys Ile Leu Gly Phe Gly Ile
            20                  25                  30

Tyr Leu Leu Ile His Asn Asn Phe Gly Val Leu Phe His Asn Leu Pro
        35                  40                  45

Ser Leu Thr Leu Gly Asn Val Phe Val Ile Val Gly Ser Ile Ile Met
    50                  55                  60

Val Val Ala Phe Leu Gly Cys Met Gly Ser Ile Lys Glu Asn Lys Cys
65                  70                  75                  80

Leu Leu Met Ser Phe Phe Ile Leu Leu Leu Ile Ile Leu Leu Ala Glu
                85                  90                  95

Val Thr Leu Ala Ile Leu Leu Phe Val Tyr Glu Gln Lys Leu Asn Glu
            100                 105                 110

Tyr Val Ala Lys Gly Leu Thr Asp Ser Ile His Arg Tyr His Ser Asp
        115                 120                 125

Asn Ser Thr Lys Ala Ala Trp Asp Ser Ile Gln Ser Phe Leu Gln Cys
    130                 135                 140

Cys Gly Ile Asn Gly Thr Ser Asp Trp Thr Ser Gly Pro Pro Ala Ser
145                 150                 155                 160

Cys Pro Ser Asp Arg Lys Val Glu Gly Cys Tyr Ala Lys Ala Arg Leu
                165                 170                 175

Trp Phe His Ser Asn Phe Leu Tyr Ile Gly Ile Ile Thr Ile Cys Val
            180                 185                 190

Cys Val Ile Glu Val Leu Gly Met Ser Phe Ala Leu Thr Leu Asn Cys
        195                 200                 205

Gln Ile Asp Lys Thr Ser Gln Thr Ile Gly Leu
    210                 215


<210> SEQ ID NO 91
<211> LENGTH: 320
<212> TYPE: PRT
<213> ORGANISM: Homo sapiens
```

<400> SEQUENCE: 91

Met Gly Pro Trp Ser Arg Val Arg Val Ala Lys Cys Gln Met Leu Val
1 5 10 15

Thr Cys Phe Phe Ile Leu Leu Leu Gly Leu Ser Val Ala Thr Met Val
20 25 30

Thr Leu Thr Tyr Phe Gly Ala His Phe Ala Val Ile Arg Arg Ala Ser
35 40 45

Leu Glu Lys Asn Pro Tyr Gln Ala Val His Gln Trp Ala Phe Ser Ala
50 55 60

Gly Leu Ser Leu Val Gly Leu Leu Thr Leu Gly Ala Val Leu Ser Ala
65 70 75 80

Ala Ala Thr Val Arg Glu Ala Gln Gly Leu Met Ala Gly Gly Phe Leu
85 90 95

Cys Phe Ser Leu Ala Phe Cys Ala Gln Val Gln Val Val Phe Trp Arg
100 105 110

Leu His Ser Pro Thr Gln Val Glu Asp Ala Met Leu Asp Thr Tyr Asp
115 120 125

Leu Val Tyr Glu Gln Ala Met Lys Gly Thr Ser His Val Arg Arg Gln
130 135 140

Glu Leu Ala Ala Ile Gln Asp Val Phe Leu Cys Cys Gly Lys Lys Ser
145 150 155 160

Pro Phe Ser Arg Leu Gly Ser Thr Glu Ala Asp Leu Cys Gln Gly Glu
165 170 175

Glu Ala Ala Arg Glu Asp Cys Leu Gln Gly Ile Arg Ser Phe Leu Arg
180 185 190

Thr His Gln Gln Val Ala Ser Ser Leu Thr Ser Ile Gly Leu Ala Leu
195 200 205

Thr Val Ser Ala Leu Leu Phe Ser Ser Phe Leu Trp Phe Ala Ile Arg
210 215 220

Cys Gly Cys Ser Leu Asp Arg Lys Gly Lys Tyr Thr Leu Thr Pro Arg
225 230 235 240

Ala Cys Gly Arg Gln Pro Gln Glu Pro Ser Leu Leu Arg Cys Ser Gln
245 250 255

Gly Gly Pro Thr His Cys Leu His Ser Glu Ala Val Ala Ile Gly Pro
260 265 270

Arg Gly Cys Ser Gly Ser Leu Arg Trp Leu Gln Glu Ser Asp Ala Ala
275 280 285

Pro Leu Pro Leu Ser Cys His Leu Ala Ala His Arg Ala Leu Gln Gly
290 295 300

Arg Ser Arg Gly Gly Leu Ser Gly Cys Pro Glu Arg Gly Leu Ser Asp
305 310 315 320

<210> SEQ ID NO 92
<211> LENGTH: 267
<212> TYPE: PRT
<213> ORGANISM: Homo sapiens

<400> SEQUENCE: 92

Met Gly Ser Ala Cys Ile Lys Val Thr Lys Tyr Phe Leu Phe Leu Phe
1 5 10 15

Asn Leu Ile Phe Phe Ile Leu Gly Ala Val Ile Leu Gly Phe Gly Val
20 25 30

Trp Ile Leu Ala Asp Lys Ser Ser Phe Ile Ser Val Leu Gln Thr Ser
35 40 45

-continued

```
Ser Ser Ser Leu Arg Met Gly Ala Tyr Val Phe Ile Gly Val Gly Ala
    50                  55                  60

Val Thr Met Leu Met Gly Phe Leu Gly Cys Ile Gly Ala Val Asn Glu
65                  70                  75                  80

Val Arg Cys Leu Leu Gly Leu Tyr Phe Ala Phe Leu Leu Leu Ile Leu
                85                  90                  95

Ile Ala Gln Val Thr Ala Gly Ala Leu Phe Tyr Phe Asn Met Gly Lys
            100                 105                 110

Leu Lys Gln Glu Met Gly Gly Ile Val Thr Glu Leu Ile Arg Asp Tyr
        115                 120                 125

Asn Ser Ser Arg Glu Asp Ser Leu Gln Asp Ala Trp Asp Tyr Val Gln
    130                 135                 140

Ala Gln Val Lys Cys Cys Gly Trp Val Ser Phe Tyr Asn Trp Thr Asp
145                 150                 155                 160

Asn Ala Glu Leu Met Asn Arg Pro Glu Val Thr Tyr Pro Cys Ser Cys
                165                 170                 175

Glu Val Lys Gly Glu Glu Asp Asn Ser Leu Ser Val Arg Lys Gly Phe
            180                 185                 190

Cys Glu Ala Pro Gly Asn Arg Thr Gln Ser Gly Asn His Pro Glu Asp
        195                 200                 205

Trp Pro Val Tyr Gln Glu Gly Cys Met Glu Lys Val Gln Ala Trp Leu
    210                 215                 220

Gln Glu Asn Leu Gly Ile Ile Leu Gly Val Gly Val Gly Val Ala Ile
225                 230                 235                 240

Ile Glu Leu Leu Gly Met Val Leu Ser Ile Cys Leu Cys Arg His Val
                245                 250                 255

His Ser Glu Asp Tyr Ser Lys Val Pro Lys Tyr
            260                 265


<210> SEQ ID NO 93
<211> LENGTH: 238
<212> TYPE: PRT
<213> ORGANISM: Homo sapiens

<400> SEQUENCE: 93

Met Ala Val Glu Gly Gly Met Lys Cys Val Lys Phe Leu Leu Tyr Val
1               5                   10                  15

Leu Leu Leu Ala Phe Cys Ala Cys Ala Val Gly Leu Ile Ala Val Gly
            20                  25                  30

Val Gly Ala Gln Leu Val Leu Ser Gln Thr Ile Ile Gln Gly Ala Thr
        35                  40                  45

Pro Gly Ser Leu Leu Pro Val Val Ile Ile Ala Val Gly Val Phe Leu
    50                  55                  60

Phe Leu Val Ala Phe Val Gly Cys Cys Gly Ala Cys Lys Glu Asn Tyr
65                  70                  75                  80

Cys Leu Met Ile Thr Phe Ala Ile Phe Leu Ser Leu Ile Met Leu Val
                85                  90                  95

Glu Val Ala Ala Ala Ile Ala Gly Tyr Val Phe Arg Asp Lys Val Met
            100                 105                 110

Ser Glu Phe Asn Asn Asn Phe Arg Gln Gln Met Glu Asn Tyr Pro Lys
        115                 120                 125

Asn Asn His Thr Ala Ser Ile Leu Asp Arg Met Gln Ala Asp Phe Lys
    130                 135                 140

Cys Cys Gly Ala Ala Asn Tyr Thr Asp Trp Glu Lys Ile Pro Ser Met
145                 150                 155                 160
```

-continued

```
Ser Lys Asn Arg Val Pro Asp Ser Cys Cys Ile Asn Val Thr Val Gly
                165                 170                 175

Cys Gly Ile Asn Phe Asn Glu Lys Ala Ile His Lys Glu Gly Cys Val
            180                 185                 190

Glu Lys Ile Gly Gly Trp Leu Arg Lys Asn Val Leu Val Val Ala Ala
        195                 200                 205

Ala Ala Leu Gly Ile Ala Phe Val Glu Val Leu Gly Ile Val Phe Ala
    210                 215                 220

Cys Cys Leu Val Lys Ser Ile Arg Ser Gly Tyr Glu Val Met
225                 230                 235
```

<210> SEQ ID NO 94
<211> LENGTH: 253
<212> TYPE: PRT
<213> ORGANISM: Homo sapiens

<400> SEQUENCE: 94

```
Met Gly Glu Phe Asn Glu Lys Lys Thr Thr Cys Gly Thr Val Cys Leu
1               5                   10                  15

Lys Tyr Leu Leu Phe Thr Tyr Asn Cys Cys Phe Trp Leu Ala Gly Leu
            20                  25                  30

Ala Val Met Ala Val Gly Ile Trp Thr Leu Ala Leu Lys Ser Asp Tyr
        35                  40                  45

Ile Ser Leu Leu Ala Ser Gly Thr Tyr Leu Ala Thr Ala Tyr Ile Leu
    50                  55                  60

Val Val Ala Gly Thr Val Val Met Val Thr Gly Val Leu Gly Cys Cys
65                  70                  75                  80

Ala Thr Phe Lys Glu Arg Arg Asn Leu Leu Arg Leu Tyr Phe Ile Leu
                85                  90                  95

Leu Leu Ile Ile Phe Leu Leu Glu Ile Ile Ala Gly Ile Leu Ala Tyr
            100                 105                 110

Ala Tyr Tyr Gln Gln Leu Asn Thr Glu Leu Lys Glu Asn Leu Lys Asp
        115                 120                 125

Thr Met Thr Lys Arg Tyr His Gln Pro Gly His Glu Ala Val Thr Ser
    130                 135                 140

Ala Val Asp Gln Leu Gln Gln Glu Phe His Cys Cys Gly Ser Asn Asn
145                 150                 155                 160

Ser Gln Asp Trp Arg Asp Ser Glu Trp Ile Arg Ser Gln Glu Ala Gly
                165                 170                 175

Gly Arg Val Val Pro Asp Ser Cys Cys Lys Thr Val Val Ala Leu Cys
            180                 185                 190

Gly Gln Arg Asp His Ala Ser Asn Ile Tyr Lys Val Glu Gly Gly Cys
        195                 200                 205

Ile Thr Lys Leu Glu Thr Phe Ile Gln Glu His Leu Arg Val Ile Gly
    210                 215                 220

Ala Val Gly Ile Gly Ile Ala Cys Val Gln Val Phe Gly Met Ile Phe
225                 230                 235                 240

Thr Cys Cys Leu Tyr Arg Ser Leu Lys Leu Glu His Tyr
                245                 250
```

<210> SEQ ID NO 95
<211> LENGTH: 281
<212> TYPE: PRT
<213> ORGANISM: Homo sapiens

<400> SEQUENCE: 95

Met Ser Ala Gln Glu Ser Cys Leu Ser Leu Ile Lys Tyr Phe Leu Phe
1 5 10 15

Val Phe Asn Leu Phe Phe Phe Val Leu Gly Ser Leu Ile Phe Cys Phe
20 25 30

Gly Ile Trp Ile Leu Ile Asp Lys Thr Ser Phe Val Ser Phe Val Gly
35 40 45

Leu Ala Phe Val Pro Leu Gln Ile Trp Ser Lys Val Leu Ala Ile Ser
50 55 60

Gly Ile Phe Thr Met Gly Ile Ala Leu Leu Gly Cys Val Gly Ala Leu
65 70 75 80

Lys Glu Leu Arg Cys Leu Leu Gly Leu Tyr Phe Gly Met Leu Leu Leu
85 90 95

Leu Phe Ala Thr Gln Ile Thr Leu Gly Ile Leu Ile Ser Thr Gln Arg
100 105 110

Ala Gln Leu Glu Arg Ser Leu Arg Asp Val Val Glu Lys Thr Ile Gln
115 120 125

Lys Tyr Gly Thr Asn Pro Glu Glu Thr Ala Ala Glu Glu Ser Trp Asp
130 135 140

Tyr Val Gln Phe Gln Leu Arg Cys Cys Gly Trp His Tyr Pro Gln Asp
145 150 155 160

Trp Phe Gln Val Leu Ile Leu Arg Gly Asn Gly Ser Glu Ala His Arg
165 170 175

Val Pro Cys Ser Cys Tyr Asn Leu Ser Ala Thr Asn Asp Ser Thr Ile
180 185 190

Leu Asp Lys Val Ile Leu Pro Gln Leu Ser Arg Leu Gly His Leu Ala
195 200 205

Arg Ser Arg His Ser Ala Asp Ile Cys Ala Val Pro Ala Glu Ser His
210 215 220

Ile Tyr Arg Glu Gly Cys Ala Gln Gly Leu Gln Lys Trp Leu His Asn
225 230 235 240

Asn Leu Ile Ser Ile Val Gly Ile Cys Leu Gly Val Gly Leu Leu Glu
245 250 255

Leu Gly Phe Met Thr Leu Ser Ile Phe Leu Cys Arg Asn Leu Asp His
260 265 270

Val Tyr Asn Arg Leu Ala Arg Tyr Arg
275 280

<210> SEQ ID NO 96
<211> LENGTH: 410
<212> TYPE: PRT
<213> ORGANISM: Homo sapiens

<400> SEQUENCE: 96

Met Val Cys Phe Arg Leu Phe Pro Val Pro Gly Ser Gly Leu Val Leu
1 5 10 15

Val Cys Leu Val Leu Gly Ala Val Arg Ser Tyr Ala Leu Glu Leu Asn
20 25 30

Leu Thr Asp Ser Glu Asn Ala Thr Cys Leu Tyr Ala Lys Trp Gln Met
35 40 45

Asn Phe Thr Val Arg Tyr Glu Thr Thr Asn Lys Thr Tyr Lys Thr Val
50 55 60

Thr Ile Ser Asp His Gly Thr Val Thr Tyr Asn Gly Ser Ile Cys Gly
65 70 75 80

Asp Asp Gln Asn Gly Pro Lys Ile Ala Val Gln Phe Gly Pro Gly Phe

```
                85                  90                  95

Ser Trp Ile Ala Asn Phe Thr Lys Ala Ala Ser Thr Tyr Ser Ile Asp
            100                 105                 110

Ser Val Ser Phe Ser Tyr Asn Thr Gly Asp Asn Thr Thr Phe Pro Asp
        115                 120                 125

Ala Glu Asp Lys Gly Ile Leu Thr Val Asp Glu Leu Leu Ala Ile Arg
    130                 135                 140

Ile Pro Leu Asn Asp Leu Phe Arg Cys Asn Ser Leu Ser Thr Leu Glu
145                 150                 155                 160

Lys Asn Asp Val Val Gln His Tyr Trp Asp Val Leu Val Gln Ala Phe
                165                 170                 175

Val Gln Asn Gly Thr Val Ser Thr Asn Glu Phe Leu Cys Asp Lys Asp
            180                 185                 190

Lys Thr Ser Thr Val Ala Pro Thr Ile His Thr Thr Val Pro Ser Pro
        195                 200                 205

Thr Thr Thr Pro Thr Pro Lys Glu Lys Pro Glu Ala Gly Thr Tyr Ser
    210                 215                 220

Val Asn Asn Gly Asn Asp Thr Cys Leu Leu Ala Thr Met Gly Leu Gln
225                 230                 235                 240

Leu Asn Ile Thr Gln Asp Lys Val Ala Ser Val Ile Asn Ile Asn Pro
                245                 250                 255

Asn Thr Thr His Ser Thr Gly Ser Cys Arg Ser His Thr Ala Leu Leu
            260                 265                 270

Arg Leu Asn Ser Ser Thr Ile Lys Tyr Leu Asp Phe Val Phe Ala Val
        275                 280                 285

Lys Asn Glu Asn Arg Phe Tyr Leu Lys Glu Val Asn Ile Ser Met Tyr
    290                 295                 300

Leu Val Asn Gly Ser Val Phe Ser Ile Ala Asn Asn Asn Leu Ser Tyr
305                 310                 315                 320

Trp Asp Ala Pro Leu Gly Ser Ser Tyr Met Cys Asn Lys Glu Gln Thr
                325                 330                 335

Val Ser Val Ser Gly Ala Phe Gln Ile Asn Thr Phe Asp Leu Arg Val
            340                 345                 350

Gln Pro Phe Asn Val Thr Gln Gly Lys Tyr Ser Thr Ala Gln Glu Cys
        355                 360                 365

Ser Leu Asp Asp Asp Thr Ile Leu Ile Pro Ile Ile Val Gly Ala Gly
    370                 375                 380

Leu Ser Gly Leu Ile Ile Val Ile Val Ile Ala Tyr Val Ile Gly Arg
385                 390                 395                 400

Arg Lys Ser Tyr Ala Gly Tyr Gln Thr Leu
                405                 410
```

<210> SEQ ID NO 97
<211> LENGTH: 89
<212> TYPE: PRT
<213> ORGANISM: Artificial Sequence
<220> FEATURE:
<223> OTHER INFORMATION: CD81 LEL mutant
<220> FEATURE:
<221> NAME/KEY: MISC_FEATURE
<222> LOCATION: (20)..(21)
<223> OTHER INFORMATION: X can be any amino acid
<220> FEATURE:
<221> NAME/KEY: MISC_FEATURE
<222> LOCATION: (24)..(29)
<223> OTHER INFORMATION: X can be any amino acid
<220> FEATURE:
<221> NAME/KEY: MISC_FEATURE
<222> LOCATION: (50)..(53)
<223> OTHER INFORMATION: X can be any amino acid
<220> FEATURE:
<221> NAME/KEY: MISC_FEATURE
<222> LOCATION: (55)..(55)
<223> OTHER INFORMATION: X can be any amino acid
<220> FEATURE:
<221> NAME/KEY: MISC_FEATURE
<222> LOCATION: (59)..(60)
<223> OTHER INFORMATION: X can be any amino acid

<400> SEQUENCE: 97

```
Phe Val Asn Lys Asp Gln Ile Ala Lys Asp Val Lys Gln Phe Tyr Asp
1               5                   10                  15

Gln Cys Leu Xaa Xaa Ala Cys Xaa Xaa Xaa Xaa Xaa Xaa Asn Ala Lys
            20                  25                  30

Ala Cys Val Lys Thr Phe His Glu Thr Leu Asp Cys Cys Gly Ser Ser
        35                  40                  45

Thr Xaa Xaa Xaa Xaa Thr Xaa Cys Val Leu Xaa Xaa Asn Leu Cys Pro
    50                  55                  60

Ser Gly Ser Asn Ile Ile Ser Asn Leu Phe Lys Glu Asp Cys His Gln
65                  70                  75                  80

Lys Ile Asp Asp Leu Phe Ser Gly Lys
                85
```

<210> SEQ ID NO 98
<211> LENGTH: 78
<212> TYPE: DNA
<213> ORGANISM: Artificial Sequence
<220> FEATURE:
<223> OTHER INFORMATION: CD81 LEL mutant
<220> FEATURE:
<221> NAME/KEY: misc_feature
<222> LOCATION: (34)..(35)
<223> OTHER INFORMATION: N is any one of A, C, G, or T
<220> FEATURE:
<221> NAME/KEY: misc_feature
<222> LOCATION: (37)..(38)
<223> OTHER INFORMATION: N is any one of A, C, G, or T
<220> FEATURE:
<221> NAME/KEY: misc_feature
<222> LOCATION: (46)..(47)
<223> OTHER INFORMATION: N is any one of A, C, G, or T
<220> FEATURE:
<221> NAME/KEY: misc_feature
<222> LOCATION: (49)..(50)
<223> OTHER INFORMATION: N is any one of A, C, G, or T
<220> FEATURE:
<221> NAME/KEY: misc_feature
<222> LOCATION: (52)..(53)
<223> OTHER INFORMATION: N is any one of A, C, G, or T
<220> FEATURE:
<221> NAME/KEY: misc_feature
<222> LOCATION: (55)..(56)
<223> OTHER INFORMATION: N is any one of A, C, G, or T

<400> SEQUENCE: 98

```
aaggatgtga agcagttcta tgaccaagct ttannknnkt gctgtnnknn knnknnkgcc     60

aacaacgcct gtgctgtg                                                   78
```

<210> SEQ ID NO 99
<211> LENGTH: 96
<212> TYPE: DNA
<213> ORGANISM: Artificial Sequence
<220> FEATURE:
<223> OTHER INFORMATION: CD81 LEL mutant
<220> FEATURE:
<221> NAME/KEY: misc_feature
<222> LOCATION: (46)..(46)

<223> OTHER INFORMATION: M is any one of A or C
<220> FEATURE:
<221> NAME/KEY: misc_feature
<222> LOCATION: (47)..(48)
<223> OTHER INFORMATION: N is any one of A, C, G, or T
<220> FEATURE:
<221> NAME/KEY: misc_feature
<222> LOCATION: (49)..(49)
<223> OTHER INFORMATION: M is any one of A or C
<220> FEATURE:
<221> NAME/KEY: misc_feature
<222> LOCATION: (50)..(51)
<223> OTHER INFORMATION: N is any one of A, C, G, or T
<220> FEATURE:
<221> NAME/KEY: misc_feature
<222> LOCATION: (61)..(61)
<223> OTHER INFORMATION: M is any one of A or C
<220> FEATURE:
<221> NAME/KEY: misc_feature
<222> LOCATION: (62)..(63)
<223> OTHER INFORMATION: N is any one of A, C, G, or T
<220> FEATURE:
<221> NAME/KEY: misc_feature
<222> LOCATION: (67)..(67)
<223> OTHER INFORMATION: M is any one of A or C
<220> FEATURE:
<221> NAME/KEY: misc_feature
<222> LOCATION: (68)..(69)
<223> OTHER INFORMATION: N is any one of A, C, G, or T
<220> FEATURE:
<221> NAME/KEY: misc_feature
<222> LOCATION: (70)..(70)
<223> OTHER INFORMATION: M is any one of A or C
<220> FEATURE:
<221> NAME/KEY: misc_feature
<222> LOCATION: (71)..(72)
<223> OTHER INFORMATION: N is any one of A, C, G, or T
<220> FEATURE:
<221> NAME/KEY: misc_feature
<222> LOCATION: (73)..(73)
<223> OTHER INFORMATION: M is any one of A or C
<220> FEATURE:
<221> NAME/KEY: misc_feature
<222> LOCATION: (74)..(75)
<223> OTHER INFORMATION: N is any one of A, C, G, or T
<220> FEATURE:
<221> NAME/KEY: misc_feature
<222> LOCATION: (76)..(76)
<223> OTHER INFORMATION: M is any one of A or C
<220> FEATURE:
<221> NAME/KEY: misc_feature
<222> LOCATION: (77)..(78)
<223> OTHER INFORMATION: N is any one of A, C, G, or T

<400> SEQUENCE: 99
cttgaagagg ttgctgatga tgttggatcc cgagggacac aaattmnnmn ngagcacaca 60
mnnggtmnnm nnmnnmnntg tgctggagcc acagca 96

<210> SEQ ID NO 100
<211> LENGTH: 81
<212> TYPE: DNA
<213> ORGANISM: Artificial Sequence
<220> FEATURE:
<223> OTHER INFORMATION: CD81 LEL mutant
<220> FEATURE:
<221> NAME/KEY: misc_feature
<222> LOCATION: (34)..(35)
<223> OTHER INFORMATION: N is any one of A, C, G, or T
<220> FEATURE:
<221> NAME/KEY: misc_feature
<222> LOCATION: (37)..(38)
<223> OTHER INFORMATION: N is any one of A, C, G, or T
<220> FEATURE:
<221> NAME/KEY: misc_feature
<222> LOCATION: (46)..(47)
<223> OTHER INFORMATION: N is any one of A, C, G, or T -continued
<220> FEATURE:
<221> NAME/KEY: misc_feature
<222> LOCATION: (49)..(50)
<223> OTHER INFORMATION: N is any one of A, C, G, or T
<220> FEATURE:
<221> NAME/KEY: misc_feature
<222> LOCATION: (52)..(53)
<223> OTHER INFORMATION: N is any one of A, C, G, or T
<220> FEATURE:
<221> NAME/KEY: misc_feature
<222> LOCATION: (55)..(56)
<223> OTHER INFORMATION: N is any one of A, C, G, or T
<220> FEATURE:
<221> NAME/KEY: misc_feature
<222> LOCATION: (58)..(59)
<223> OTHER INFORMATION: N is any one of A, C, G, or T
<220> FEATURE:
<221> NAME/KEY: misc_feature
<222> LOCATION: (61)..(62)
<223> OTHER INFORMATION: N is any one of A, C, G, or T

<400> SEQUENCE: 100
aaggatgtga agcagttcta tgaccagtgt ctannknnkg cctgtnnknn knnknnknnk 60
nnkaacgcca aggcttgtgt g 81

<210> SEQ ID NO 101
<211> LENGTH: 22
<212> TYPE: DNA
<213> ORGANISM: Artificial Sequence
<220> FEATURE:
<223> OTHER INFORMATION: primer

<400> SEQUENCE: 101
agtaacgttt gtcagtaatt gc 22

<210> SEQ ID NO 102
<211> LENGTH: 22
<212> TYPE: DNA
<213> ORGANISM: Artificial Sequence
<220> FEATURE:
<223> OTHER INFORMATION: primer

<400> SEQUENCE: 102
gtcgattttg ttacatctac ac 22

<210> SEQ ID NO 103
<211> LENGTH: 89
<212> TYPE: PRT
<213> ORGANISM: Artificial Sequence
<220> FEATURE:
<223> OTHER INFORMATION: CD81 LEL mutant

<400> SEQUENCE: 103

```
Phe Val Asn Lys Asp Gln Ile Ala Lys Asp Val Lys Gln Phe Tyr Asp
1               5                   10                  15

Gln Ala Leu Trp Trp Cys Cys Val Leu Tyr Lys Ala Asn Asn Ala Cys
            20                  25                  30

Ala Val Val Lys Thr Phe His Glu Thr Leu Asp Cys Cys Gly Ser Ser
        35                  40                  45

Thr Gly Arg Ser His Thr Ala Cys Val Leu Lys Gly Asn Leu Cys Pro
    50                  55                  60

Ser Gly Ser Asn Ile Ile Ser Asn Leu Phe Lys Glu Asp Cys His Gln
65                  70                  75                  80

Lys Ile Asp Asp Leu Phe Ser Gly Lys
                85
```

<210> SEQ ID NO 104
<211> LENGTH: 18
<212> TYPE: DNA
<213> ORGANISM: Artificial Sequence
<220> FEATURE:
<223> OTHER INFORMATION: primer

<400> SEQUENCE: 104
cttgaagagg ttgctgat 18

<210> SEQ ID NO 105
<211> LENGTH: 18
<212> TYPE: DNA
<213> ORGANISM: Artificial Sequence
<220> FEATURE:
<223> OTHER INFORMATION: primer

<400> SEQUENCE: 105
aaggatgtga agcagttc 18

<210> SEQ ID NO 106
<211> LENGTH: 31
<212> TYPE: DNA
<213> ORGANISM: Artificial Sequence
<220> FEATURE:
<223> OTHER INFORMATION: oligonucleotide

<400> SEQUENCE: 106
acgtgctagc tttgtcaaca aggaccagat c 31

<210> SEQ ID NO 107
<211> LENGTH: 41
<212> TYPE: DNA
<213> ORGANISM: Artificial Sequence
<220> FEATURE:
<223> OTHER INFORMATION: oligonucleotide

<400> SEQUENCE: 107
acgtggtgac cggtgctgga acccttcccg gagaagaggt c 41

<210> SEQ ID NO 108
<211> LENGTH: 89
<212> TYPE: PRT
<213> ORGANISM: Artificial Sequence
<220> FEATURE:
<223> OTHER INFORMATION: CD81 LEL mutant

<400> SEQUENCE: 108

```
Phe Val Asn Lys Asp Gln Ile Ala Lys Asp Val Lys Gln Phe Tyr Asp
1               5                   10                  15

Gln Ala Leu Arg Glu Cys Cys Asn Thr Phe Asp Ala Asn Asn Ala Cys
            20                  25                  30

Ala Val Val Lys Thr Phe His Glu Thr Leu Asp Cys Cys Gly Ser Ser
        35                  40                  45

Thr Thr His Ser Ser Thr Gly Cys Val Leu Phe Phe Asn Leu Cys Pro
    50                  55                  60

Ser Gly Ser Asn Ile Ile Ser Asn Leu Phe Lys Glu Asp Cys His Gln
65                  70                  75                  80

Lys Ile Asp Asp Leu Phe Ser Gly Lys
                85
```

<210> SEQ ID NO 109
<211> LENGTH: 89

<212> TYPE: PRT
<213> ORGANISM: Artificial Sequence
<220> FEATURE:
<223> OTHER INFORMATION: CD81 LEL mutant

<400> SEQUENCE: 109

```
Phe Val Asn Lys Asp Gln Ile Ala Lys Asp Val Lys Gln Phe Tyr Asp
1               5                   10                  15

Gln Ala Leu Met Ile Cys Cys His Arg His Tyr Ala Asn Asn Ala Cys
            20                  25                  30

Ala Val Val Lys Thr Phe His Glu Thr Leu Asp Cys Cys Gly Ser Ser
        35                  40                  45

Thr Pro Ser Ser Thr Thr Pro Cys Val Leu Gln Asn Asn Leu Cys Pro
    50                  55                  60

Ser Gly Ser Asn Ile Ile Ser Asn Leu Phe Lys Glu Asp Cys His Gln
65                  70                  75                  80

Lys Ile Asp Asp Leu Phe Ser Gly Lys
                85
```

<210> SEQ ID NO 110
<211> LENGTH: 89
<212> TYPE: PRT
<213> ORGANISM: Artificial Sequence
<220> FEATURE:
<223> OTHER INFORMATION: CD81 LEL mutant

<400> SEQUENCE: 110

```
Phe Val Asn Lys Asp Gln Ile Ala Lys Asp Val Lys Gln Phe Tyr Asp
1               5                   10                  15

Gln Ala Leu Val Phe Cys Cys Phe Gly Gly His Ala Asn Asn Ala Cys
            20                  25                  30

Ala Val Val Lys Thr Phe His Glu Thr Leu Asp Cys Cys Gly Ser Ser
        35                  40                  45

Thr His Pro Tyr Lys Thr Lys Cys Val Leu Gln Arg Asn Leu Cys Pro
    50                  55                  60

Ser Gly Ser Asn Ile Ile Ser Asn Leu Phe Lys Glu Asp Cys His Gln
65                  70                  75                  80

Lys Ile Asp Asp Leu Phe Ser Gly Lys
                85
```

<210> SEQ ID NO 111
<211> LENGTH: 89
<212> TYPE: PRT
<213> ORGANISM: Artificial Sequence
<220> FEATURE:
<223> OTHER INFORMATION: CD81 LEL mutant

<400> SEQUENCE: 111

```
Phe Val Asn Lys Asp Gln Ile Ala Lys Asp Val Lys Gln Phe Tyr Asp
1               5                   10                  15

Gln Cys Leu Lys Tyr Ala Cys Lys Gln Gly Asp Trp Glu Asn Ala Lys
            20                  25                  30

Ala Cys Val Lys Thr Phe His Glu Thr Leu Asp Cys Cys Gly Ser Ser
        35                  40                  45

Thr Val Ala Asn Met Thr Arg Cys Val Leu Pro Ala Asn Leu Cys Pro
    50                  55                  60

Ser Gly Ser Asn Ile Ile Ser Asn Leu Phe Lys Glu Asp Cys His Gln
65                  70                  75                  80

Lys Ile Asp Asp Leu Phe Ser Gly Lys
```

85

<210> SEQ ID NO 112
<211> LENGTH: 89
<212> TYPE: PRT
<213> ORGANISM: Artificial Sequence
<220> FEATURE:
<223> OTHER INFORMATION: CD81 LEL mutant

<400> SEQUENCE: 112

Phe Val Asn Lys Asp Gln Ile Ala Lys Asp Val Lys Gln Phe Tyr Asp
1 5 10 15

Gln Cys Leu Leu Trp Ala Cys Ser Lys Arg Tyr Lys Tyr Asn Ala Lys
20 25 30

Ala Cys Val Lys Thr Phe His Glu Thr Leu Asp Cys Cys Gly Ser Ser
35 40 45

Thr Met Gly Asn Leu Thr Glu Cys Val Leu Ile Glu Asn Leu Cys Pro
50 55 60

Ser Gly Ser Asn Ile Ile Ser Asn Leu Phe Lys Glu Asp Cys His Gln
65 70 75 80

Lys Ile Asp Asp Leu Phe Ser Gly Lys
85

<210> SEQ ID NO 113
<211> LENGTH: 89
<212> TYPE: PRT
<213> ORGANISM: Artificial Sequence
<220> FEATURE:
<223> OTHER INFORMATION: CD81 LEL mutant

<400> SEQUENCE: 113

Phe Val Asn Lys Asp Gln Ile Ala Lys Asp Val Lys Gln Phe Tyr Asp
1 5 10 15

Gln Ala Leu Trp Lys Cys Cys Asn Leu Ser Gln Ala Asn Asn Ala Cys
20 25 30

Ala Val Val Lys Thr Phe His Glu Thr Leu Asp Cys Cys Gly Ser Ser
35 40 45

Thr Tyr Leu Cys Ala Thr Tyr Cys Val Leu Trp Pro Asn Leu Cys Pro
50 55 60

Ser Gly Ser Asn Ile Ile Ser Asn Leu Phe Lys Glu Asp Cys His Gln
65 70 75 80

Lys Ile Asp Asp Leu Phe Ser Gly Lys
85

<210> SEQ ID NO 114
<211> LENGTH: 89
<212> TYPE: PRT
<213> ORGANISM: Artificial Sequence
<220> FEATURE:
<223> OTHER INFORMATION: CD81 LEL mutant

<400> SEQUENCE: 114

Phe Val Asn Lys Asp Gln Ile Ala Lys Asp Val Lys Gln Phe Tyr Asp
1 5 10 15

Gln Cys Leu Ser Trp Ala Cys Asn Arg Lys Tyr Glu Pro Asn Ala Lys
20 25 30

Ala Cys Val Lys Thr Phe His Glu Thr Leu Asp Cys Cys Gly Ser Ser
35 40 45

Thr Lys Ala Asn Tyr Thr His Cys Val Leu Glu Met Asn Leu Cys Pro
50 55 60

```
Ser Gly Ser Asn Ile Ile Ser Asn Leu Phe Lys Glu Asp Cys His Gln
65                  70                  75                  80

Lys Ile Asp Asp Leu Phe Ser Gly Lys
                85


<210> SEQ ID NO 115
<211> LENGTH: 89
<212> TYPE: PRT
<213> ORGANISM: Artificial Sequence
<220> FEATURE:
<223> OTHER INFORMATION: CD81 LEL mutant

<400> SEQUENCE: 115

Phe Val Asn Lys Asp Gln Ile Ala Lys Asp Val Lys Gln Phe Tyr Asp
1               5                   10                  15

Gln Cys Leu Arg His Ala Cys Ser Gly Leu Ser Gly Arg Asn Ala Lys
            20                  25                  30

Ala Cys Val Lys Thr Phe His Glu Thr Leu Asp Cys Cys Gly Ser Ser
        35                  40                  45

Thr Ile Lys His Lys Thr Leu Cys Val Leu Ile Lys Asn Leu Cys Pro
    50                  55                  60

Ser Gly Ser Asn Ile Ile Ser Asn Leu Phe Lys Glu Asp Cys His Gln
65                  70                  75                  80

Lys Ile Asp Asp Leu Phe Ser Gly Lys
                85


<210> SEQ ID NO 116
<211> LENGTH: 89
<212> TYPE: PRT
<213> ORGANISM: Artificial Sequence
<220> FEATURE:
<223> OTHER INFORMATION: CD81 LEL mutant

<400> SEQUENCE: 116

Phe Val Asn Lys Asp Gln Ile Ala Lys Asp Val Lys Gln Phe Tyr Asp
1               5                   10                  15

Gln Ala Leu Phe Ile Cys Cys Phe Arg Arg Tyr Ala Asn Asn Ala Cys
            20                  25                  30

Ala Val Val Lys Thr Phe His Glu Thr Leu Asp Cys Cys Gly Ser Ser
        35                  40                  45

Thr Arg Asn Asn Glu Thr Ala Cys Val Leu Ala Lys Asn Leu Cys Pro
    50                  55                  60

Ser Gly Ser Asn Ile Ile Ser Asn Leu Phe Lys Glu Asp Cys His Gln
65                  70                  75                  80

Lys Ile Asp Asp Leu Phe Ser Gly Lys
                85


<210> SEQ ID NO 117
<211> LENGTH: 89
<212> TYPE: PRT
<213> ORGANISM: Artificial Sequence
<220> FEATURE:
<223> OTHER INFORMATION: CD81 LEL mutant

<400> SEQUENCE: 117

Phe Val Asn Lys Asp Gln Ile Ala Lys Asp Val Lys Gln Phe Tyr Asp
1               5                   10                  15

Gln Ala Leu Val Asn Cys Cys Tyr Thr Arg Ala Ala Asn Asn Ala Cys
            20                  25                  30
```

```
Ala Val Val Lys Thr Phe His Glu Thr Leu Asp Cys Cys Gly Ser Ser
        35                  40                  45

Thr His Tyr Val Asp Thr His Cys Val Leu Asn Arg Asn Leu Cys Pro
    50                  55                  60

Ser Gly Ser Asn Ile Ile Ser Asn Leu Phe Lys Glu Asp Cys His Gln
65                  70                  75                  80

Lys Ile Asp Asp Leu Phe Ser Gly Lys
                85


<210> SEQ ID NO 118
<211> LENGTH: 80
<212> TYPE: PRT
<213> ORGANISM: Artificial Sequence
<220> FEATURE:
<223> OTHER INFORMATION: oligonucleotides

<400> SEQUENCE: 118

His Lys Asp Glu Val Ile Lys Glu Val Gln Glu Phe Tyr Lys Asp Thr
1               5                   10                  15

Tyr Asn Lys Leu Lys Thr Lys Asp Glu Pro Gln Arg Glu Thr Leu Lys
            20                  25                  30

Ala Ile His Tyr Ala Leu Asn Cys Cys Gly Leu Ala Gly Gly Val Glu
        35                  40                  45

Gln Phe Ile Ser Asp Ile Cys Pro Lys Lys Asp Val Leu Glu Thr Phe
    50                  55                  60

Thr Val Lys Ser Cys Pro Asp Ala Ile Lys Glu Val Phe Asp Asn Lys
65                  70                  75                  80


<210> SEQ ID NO 119
<211> LENGTH: 31
<212> TYPE: DNA
<213> ORGANISM: Artificial Sequence
<220> FEATURE:
<223> OTHER INFORMATION: oligonucleotides

<400> SEQUENCE: 119

acgtgctagc cacaaggatg aggtgattaa g                                    31


<210> SEQ ID NO 120
<211> LENGTH: 41
<212> TYPE: DNA
<213> ORGANISM: Artificial Sequence
<220> FEATURE:
<223> OTHER INFORMATION: oligonucleotides

<400> SEQUENCE: 120

acgtggtgac cggtgctgga acctttattg tcgaagacct c                         41


<210> SEQ ID NO 121
<211> LENGTH: 33
<212> TYPE: DNA
<213> ORGANISM: Artificial Sequence
<220> FEATURE:
<223> OTHER INFORMATION: oligonucleotides

<400> SEQUENCE: 121

gacacctaca acaagtgcaa aaccaaggat gag                                  33


<210> SEQ ID NO 122
<211> LENGTH: 33
<212> TYPE: DNA
<213> ORGANISM: Artificial Sequence
<220> FEATURE:
```

<223> OTHER INFORMATION: oligonucleotides

<400> SEQUENCE: 122
ctcatccttg gttttgcact tgttgtaggt gtc 33

<210> SEQ ID NO 123
<211> LENGTH: 33
<212> TYPE: DNA
<213> ORGANISM: Artificial Sequence
<220> FEATURE:
<223> OTHER INFORMATION: oligonucleotides

<400> SEQUENCE: 123
aaggatgagc cccagtgtga aacgctgaaa gcc 33

<210> SEQ ID NO 124
<211> LENGTH: 33
<212> TYPE: DNA
<213> ORGANISM: Artificial Sequence
<220> FEATURE:
<223> OTHER INFORMATION: oligonucleotides

<400> SEQUENCE: 124
ggctttcagc gtttcacact ggggctcatc ctt 33

<210> SEQ ID NO 125
<211> LENGTH: 80
<212> TYPE: PRT
<213> ORGANISM: Artificial Sequence
<220> FEATURE:
<223> OTHER INFORMATION: CD9 LEL mutant

<400> SEQUENCE: 125

```
His Lys Asp Glu Val Ile Lys Glu Val Gln Glu Phe Tyr Lys Asp Thr
1               5                   10                  15

Tyr Asn Lys Cys Lys Thr Lys Asp Glu Pro Gln Cys Glu Thr Leu Lys
            20                  25                  30

Ala Ile His Tyr Ala Leu Asn Cys Cys Gly Leu Ala Gly Gly Val Glu
        35                  40                  45

Gln Phe Ile Ser Asp Ile Cys Pro Lys Lys Asp Val Leu Glu Thr Phe
    50                  55                  60

Thr Val Lys Ser Cys Pro Asp Ala Ile Lys Glu Val Phe Asp Asn Lys
65                  70                  75                  80
```

<210> SEQ ID NO 126
<211> LENGTH: 31
<212> TYPE: DNA
<213> ORGANISM: Artificial Sequence
<220> FEATURE:
<223> OTHER INFORMATION: oligonucleotides

<400> SEQUENCE: 126
acgtggatcc cacaaggatg aggtgattaa g 31

<210> SEQ ID NO 127
<211> LENGTH: 32
<212> TYPE: DNA
<213> ORGANISM: Artificial Sequence
<220> FEATURE:
<223> OTHER INFORMATION: oligonucleotides

<400> SEQUENCE: 127
acgtgcggcc gcgctttatt gtcgaagacc tc 32

<210> SEQ ID NO 128
<211> LENGTH: 99
<212> TYPE: DNA
<213> ORGANISM: Artificial Sequence
<220> FEATURE:
<223> OTHER INFORMATION: CD9 LEL mutant
<220> FEATURE:
<221> NAME/KEY: misc_feature
<222> LOCATION: (52)..(53)
<223> OTHER INFORMATION: N is any one of A, C, G, or T
<220> FEATURE:
<221> NAME/KEY: misc_feature
<222> LOCATION: (55)..(56)
<223> OTHER INFORMATION: N is any one of A, C, G, or T
<220> FEATURE:
<221> NAME/KEY: misc_feature
<222> LOCATION: (61)..(62)
<223> OTHER INFORMATION: N is any one of A, C, G, or T
<220> FEATURE:
<221> NAME/KEY: misc_feature
<222> LOCATION: (64)..(65)
<223> OTHER INFORMATION: N is any one of A, C, G, or T
<220> FEATURE:
<221> NAME/KEY: misc_feature
<222> LOCATION: (67)..(68)
<223> OTHER INFORMATION: N is any one of A, C, G, or T
<220> FEATURE:
<221> NAME/KEY: misc_feature
<222> LOCATION: (70)..(71)
<223> OTHER INFORMATION: N is any one of A, C, G, or T
<220> FEATURE:
<221> NAME/KEY: misc_feature
<222> LOCATION: (73)..(74)
<223> OTHER INFORMATION: N is any one of A, C, G, or T
<220> FEATURE:
<221> NAME/KEY: misc_feature
<222> LOCATION: (79)..(80)
<223> OTHER INFORMATION: N is any one of A, C, G, or T

<400> SEQUENCE: 128
cacaaggatg aggtgattaa ggaagtccag gagttttaca aggacaccta cnnknnktgc 60
nnknnknnkn nknnkcccnn ktgtgaaacg ctgaaagcc 99

<210> SEQ ID NO 129
<211> LENGTH: 52
<212> TYPE: DNA
<213> ORGANISM: Artificial Sequence
<220> FEATURE:
<223> OTHER INFORMATION: oligonucleotides

<400> SEQUENCE: 129
cttcgaaggg ccctctagac tcgagcggcc gcgctttatt gtcgaagacc tc 52

<210> SEQ ID NO 130
<211> LENGTH: 22
<212> TYPE: PRT
<213> ORGANISM: Homo sapiens

<400> SEQUENCE: 130

His Asp Pro Gln Thr Thr Asn Leu Leu Tyr Leu Glu Leu Gly Asp Lys
1 5 10 15

Ala Pro Asn Thr Phe Tyr
20

<210> SEQ ID NO 131
<211> LENGTH: 89
<212> TYPE: PRT
<213> ORGANISM: Homo sapiens

<400> SEQUENCE: 131

-continued

Phe Val Asn Lys Asp Gln Ile Ala Lys Asp Val Lys Gln Phe Tyr Asp
1 5 10 15

Gln Ala Leu Gln Gln Ala Val Val Asp Asp Asp Ala Asn Asn Ala Lys
20 25 30

Ala Val Val Lys Thr Phe His Glu Thr Leu Asp Cys Cys Gly Ser Ser
35 40 45

Thr Leu Thr Ala Leu Thr Thr Ser Val Leu Lys Asn Asn Leu Cys Pro
50 55 60

Ser Gly Ser Asn Ile Ile Ser Asn Leu Phe Lys Glu Asp Cys His Gln
65 70 75 80

Lys Ile Asp Asp Leu Phe Ser Gly Lys
85

<210> SEQ ID NO 132
<211> LENGTH: 22
<212> TYPE: PRT
<213> ORGANISM: Homo sapiens

<400> SEQUENCE: 132

Phe Asp Ser Gln Thr Lys Ser Ile Phe Glu Gln Glu Thr Asn Asn Asn
1 5 10 15

Asn Ser Ser Phe Tyr Thr
20

<210> SEQ ID NO 133
<211> LENGTH: 80
<212> TYPE: PRT
<213> ORGANISM: Homo sapiens

<400> SEQUENCE: 133

His Lys Asp Glu Val Ile Lys Glu Val Gln Glu Phe Tyr Lys Asp Thr
1 5 10 15

Tyr Asn Lys Leu Lys Thr Lys Asp Glu Pro Gln Arg Glu Thr Leu Lys
20 25 30

Ala Ile His Tyr Ala Leu Asn Cys Cys Gly Leu Ala Gly Gly Val Glu
35 40 45

Gln Phe Ile Ser Asp Ile Cys Pro Lys Lys Asp Val Leu Glu Thr Phe
50 55 60

Thr Val Lys Ser Cys Pro Asp Ala Ile Lys Glu Val Phe Asp Asn Lys
65 70 75 80

<210> SEQ ID NO 134
<211> LENGTH: 21
<212> TYPE: PRT
<213> ORGANISM: Homo sapiens

<400> SEQUENCE: 134

Leu Leu Ile His Asn Asn Phe Gly Val Leu Phe His Asn Leu Pro Ser
1 5 10 15

Leu Thr Leu Gly Asn
20

<210> SEQ ID NO 135
<211> LENGTH: 78
<212> TYPE: PRT
<213> ORGANISM: Homo sapiens

<400> SEQUENCE: 135

Phe Val Tyr Glu Gln Lys Leu Asn Glu Tyr Val Ala Lys Gly Leu Thr

-continued

```
1               5                   10                  15

Asp Ser Ile His Arg Tyr His Ser Asp Asn Ser Thr Lys Ala Ala Trp
            20                  25                  30

Asp Ser Ile Gln Ser Phe Leu Gln Cys Cys Gly Ile Asn Gly Thr Ser
        35                  40                  45

Asp Trp Thr Ser Gly Pro Pro Ala Ser Cys Pro Ser Asp Arg Lys Val
    50                  55                  60

Glu Gly Cys Tyr Ala Lys Ala Arg Leu Trp Phe His Ser Asn
65                  70                  75


<210> SEQ ID NO 136
<211> LENGTH: 25
<212> TYPE: PRT
<213> ORGANISM: Homo sapiens

<400> SEQUENCE: 136

Thr Tyr Phe Gly Ala His Phe Ala Val Ile Arg Arg Ala Ser Leu Glu
1               5                   10                  15

Lys Asn Pro Tyr Gln Ala Val His Gln
            20                  25


<210> SEQ ID NO 137
<211> LENGTH: 94
<212> TYPE: PRT
<213> ORGANISM: Homo sapiens

<400> SEQUENCE: 137

Phe Trp Arg Leu His Ser Pro Thr Gln Val Glu Asp Ala Met Leu Asp
1               5                   10                  15

Thr Tyr Asp Leu Val Tyr Glu Gln Ala Met Lys Gly Thr Ser His Val
            20                  25                  30

Arg Arg Gln Glu Leu Ala Ala Ile Gln Asp Val Phe Leu Cys Cys Gly
        35                  40                  45

Lys Lys Ser Pro Phe Ser Arg Leu Gly Ser Thr Glu Ala Asp Leu Cys
    50                  55                  60

Gln Gly Glu Glu Ala Ala Arg Glu Asp Cys Leu Gln Gly Ile Arg Ser
65                  70                  75                  80

Phe Leu Arg Thr His Gln Gln Val Ala Ser Ser Leu Thr Ser
                85                  90


<210> SEQ ID NO 138
<211> LENGTH: 24
<212> TYPE: PRT
<213> ORGANISM: Homo sapiens

<400> SEQUENCE: 138

Gly Val Trp Ile Leu Ala Asp Lys Ser Ser Phe Ile Ser Val Leu Gln
1               5                   10                  15

Thr Ser Ser Ser Ser Leu Arg Met
            20


<210> SEQ ID NO 139
<211> LENGTH: 120
<212> TYPE: PRT
<213> ORGANISM: Homo sapiens

<400> SEQUENCE: 139

Phe Asn Met Gly Lys Leu Lys Gln Glu Met Gly Gly Ile Val Thr Glu
1               5                   10                  15
```

Leu Ile Arg Asp Tyr Asn Ser Ser Arg Glu Asp Ser Leu Gln Asp Ala
20 25 30

Trp Asp Tyr Val Gln Ala Gln Val Lys Cys Cys Gly Trp Val Ser Phe
35 40 45

Tyr Asn Trp Thr Asp Asn Ala Glu Leu Met Asn Arg Pro Glu Val Thr
50 55 60

Tyr Pro Cys Ser Cys Glu Val Lys Gly Glu Glu Asp Asn Ser Leu Ser
65 70 75 80

Val Arg Lys Gly Phe Cys Glu Ala Pro Gly Asn Arg Thr Gln Ser Gly
85 90 95

Asn His Pro Glu Asp Trp Pro Val Tyr Gln Glu Gly Cys Met Glu Lys
100 105 110

Val Gln Ala Trp Leu Gln Glu Asn
115 120

<210> SEQ ID NO 140
<211> LENGTH: 20
<212> TYPE: PRT
<213> ORGANISM: Homo sapiens

<400> SEQUENCE: 140

Ala Gln Leu Val Leu Ser Gln Thr Ile Ile Gln Gly Ala Thr Pro Gly
1 5 10 15

Ser Leu Leu Pro
20

<210> SEQ ID NO 141
<211> LENGTH: 96
<212> TYPE: PRT
<213> ORGANISM: Homo sapiens

<400> SEQUENCE: 141

Phe Arg Asp Lys Val Met Ser Glu Phe Asn Asn Asn Phe Arg Gln Gln
1 5 10 15

Met Glu Asn Tyr Pro Lys Asn Asn His Thr Ala Ser Ile Leu Asp Arg
20 25 30

Met Gln Ala Asp Phe Lys Cys Cys Gly Ala Ala Asn Tyr Thr Asp Trp
35 40 45

Glu Lys Ile Pro Ser Met Ser Lys Asn Arg Val Pro Asp Ser Cys Cys
50 55 60

Ile Asn Val Thr Val Gly Cys Gly Ile Asn Phe Asn Glu Lys Ala Ile
65 70 75 80

His Lys Glu Gly Cys Val Glu Lys Ile Gly Gly Trp Leu Arg Lys Asn
85 90 95

<210> SEQ ID NO 142
<211> LENGTH: 21
<212> TYPE: PRT
<213> ORGANISM: Homo sapiens

<400> SEQUENCE: 142

Thr Leu Ala Leu Lys Ser Asp Tyr Ile Ser Leu Leu Ala Ser Gly Thr
1 5 10 15

Tyr Leu Ala Thr Ala
20

<210> SEQ ID NO 143
<211> LENGTH: 110
<212> TYPE: PRT

<213> ORGANISM: Homo sapiens

<400> SEQUENCE: 143

Tyr Ala Tyr Tyr Gln Gln Leu Asn Thr Glu Leu Lys Glu Asn Leu Lys
1 5 10 15

Asp Thr Met Thr Lys Arg Tyr His Gln Pro Gly His Glu Ala Val Thr
20 25 30

Ser Ala Val Asp Gln Leu Gln Gln Glu Phe His Cys Cys Gly Ser Asn
35 40 45

Asn Ser Gln Asp Trp Arg Asp Ser Glu Trp Ile Arg Ser Gln Glu Ala
50 55 60

Gly Gly Arg Val Val Pro Asp Ser Cys Cys Lys Thr Val Val Ala Leu
65 70 75 80

Cys Gly Gln Arg Asp His Ala Ser Asn Ile Tyr Lys Val Glu Gly Gly
85 90 95

Cys Ile Thr Lys Leu Glu Thr Phe Ile Gln Glu His Leu Arg
100 105 110

<210> SEQ ID NO 144
<211> LENGTH: 27
<212> TYPE: PRT
<213> ORGANISM: Homo sapiens

<400> SEQUENCE: 144

Gly Ile Trp Ile Leu Ile Asp Lys Thr Ser Phe Val Ser Phe Val Gly
1 5 10 15

Leu Ala Phe Val Pro Leu Gln Ile Trp Ser Lys
20 25

<210> SEQ ID NO 145
<211> LENGTH: 133
<212> TYPE: PRT
<213> ORGANISM: Homo sapiens

<400> SEQUENCE: 145

Ser Thr Gln Arg Ala Gln Leu Glu Arg Ser Leu Arg Asp Val Val Glu
1 5 10 15

Lys Thr Ile Gln Lys Tyr Gly Thr Asn Pro Glu Glu Thr Ala Ala Glu
20 25 30

Glu Ser Trp Asp Tyr Val Gln Phe Gln Leu Arg Cys Cys Gly Trp His
35 40 45

Tyr Pro Gln Asp Trp Phe Gln Val Leu Ile Leu Arg Gly Asn Gly Ser
50 55 60

Glu Ala His Arg Val Pro Cys Ser Cys Tyr Asn Leu Ser Ala Thr Asn
65 70 75 80

Asp Ser Thr Ile Leu Asp Lys Val Ile Leu Pro Gln Leu Ser Arg Leu
85 90 95

Gly His Leu Ala Arg Ser Arg His Ser Ala Asp Ile Cys Ala Val Pro
100 105 110

Ala Glu Ser His Ile Tyr Arg Glu Gly Cys Ala Gln Gly Leu Gln Lys
115 120 125

Trp Leu His Asn Asn
130

<210> SEQ ID NO 146
<211> LENGTH: 379
<212> TYPE: PRT
<213> ORGANISM: Homo sapiens

<400> SEQUENCE: 146

Met Val Cys Phe Arg Leu Phe Pro Val Pro Gly Ser Gly Leu Val Leu
1               5                   10                  15

Val Cys Leu Val Leu Gly Ala Val Arg Ser Tyr Ala Leu Glu Leu Asn
            20                  25                  30

Leu Thr Asp Ser Glu Asn Ala Thr Cys Leu Tyr Ala Lys Trp Gln Met
        35                  40                  45

Asn Phe Thr Val Arg Tyr Glu Thr Thr Asn Lys Thr Tyr Lys Thr Val
    50                  55                  60

Thr Ile Ser Asp His Gly Thr Val Thr Tyr Asn Gly Ser Ile Cys Gly
65                  70                  75                  80

Asp Asp Gln Asn Gly Pro Lys Ile Ala Val Gln Phe Gly Pro Gly Phe
                85                  90                  95

Ser Trp Ile Ala Asn Phe Thr Lys Ala Ala Ser Thr Tyr Ser Ile Asp
            100                 105                 110

Ser Val Ser Phe Ser Tyr Asn Thr Gly Asp Asn Thr Thr Phe Pro Asp
        115                 120                 125

Ala Glu Asp Lys Gly Ile Leu Thr Val Asp Glu Leu Leu Ala Ile Arg
    130                 135                 140

Ile Pro Leu Asn Asp Leu Phe Arg Cys Asn Ser Leu Ser Thr Leu Glu
145                 150                 155                 160

Lys Asn Asp Val Val Gln His Tyr Trp Asp Val Leu Val Gln Ala Phe
                165                 170                 175

Val Gln Asn Gly Thr Val Ser Thr Asn Glu Phe Leu Cys Asp Lys Asp
            180                 185                 190

Lys Thr Ser Thr Val Ala Pro Thr Ile His Thr Thr Val Pro Ser Pro
        195                 200                 205

Thr Thr Thr Pro Thr Pro Lys Glu Lys Pro Glu Ala Gly Thr Tyr Ser
    210                 215                 220

Val Asn Asn Gly Asn Asp Thr Cys Leu Leu Ala Thr Met Gly Leu Gln
225                 230                 235                 240

Leu Asn Ile Thr Gln Asp Lys Val Ala Ser Val Ile Asn Ile Asn Pro
                245                 250                 255

Asn Thr Thr His Ser Thr Gly Ser Cys Arg Ser His Thr Ala Leu Leu
            260                 265                 270

Arg Leu Asn Ser Ser Thr Ile Lys Tyr Leu Asp Phe Val Phe Ala Val
        275                 280                 285

Lys Asn Glu Asn Arg Phe Tyr Leu Lys Glu Val Asn Ile Ser Met Tyr
    290                 295                 300

Leu Val Asn Gly Ser Val Phe Ser Ile Ala Asn Asn Asn Leu Ser Tyr
305                 310                 315                 320

Trp Asp Ala Pro Leu Gly Ser Ser Tyr Met Cys Asn Lys Glu Gln Thr
                325                 330                 335

Val Ser Val Ser Gly Ala Phe Gln Ile Asn Thr Phe Asp Leu Arg Val
            340                 345                 350

Gln Pro Phe Asn Val Thr Gln Gly Lys Tyr Ser Thr Ala Gln Glu Cys
        355                 360                 365

Ser Leu Asp Asp Asp Thr Ile Leu Ile Pro Ile
    370                 375

<210> SEQ ID NO 147
<211> LENGTH: 21
<212> TYPE: PRT

<213> ORGANISM: Homo sapiens

<400> SEQUENCE: 147

Phe Val Phe Asn Phe Val Phe Trp Leu Ala Gly Gly Val Ile Leu Gly
1 5 10 15

Val Ala Leu Trp Leu
20

<210> SEQ ID NO 148
<211> LENGTH: 19
<212> TYPE: PRT
<213> ORGANISM: Homo sapiens

<400> SEQUENCE: 148

Val Gly Ile Tyr Ile Leu Ile Ala Val Gly Ala Val Met Met Phe Val
1 5 10 15

Gly Phe Leu

<210> SEQ ID NO 149
<211> LENGTH: 21
<212> TYPE: PRT
<213> ORGANISM: Homo sapiens

<400> SEQUENCE: 149

Phe Thr Cys Leu Val Ile Leu Phe Ala Cys Glu Val Ala Ala Gly Ile
1 5 10 15

Trp Gly Phe Val Asn
20

<210> SEQ ID NO 150
<211> LENGTH: 25
<212> TYPE: PRT
<213> ORGANISM: Homo sapiens

<400> SEQUENCE: 150

Leu Tyr Leu Ile Gly Ile Ala Ala Ile Val Val Ala Val Ile Met Ile
1 5 10 15

Phe Glu Met Ile Leu Ser Met Val Leu
20 25

<210> SEQ ID NO 151
<211> LENGTH: 19
<212> TYPE: PRT
<213> ORGANISM: Homo sapiens

<400> SEQUENCE: 151

Phe Asn Phe Ile Phe Trp Leu Ala Gly Ile Ala Val Leu Ala Ile Gly
1 5 10 15

Leu Trp Leu

<210> SEQ ID NO 152
<211> LENGTH: 19
<212> TYPE: PRT
<213> ORGANISM: Homo sapiens

<400> SEQUENCE: 152

Val Tyr Ile Leu Ile Gly Ala Gly Ala Leu Met Met Leu Val Gly Phe
1 5 10 15

Leu Gly Gly

<210> SEQ ID NO 153

<211> LENGTH: 18
<212> TYPE: PRT
<213> ORGANISM: Homo sapiens

<400> SEQUENCE: 153

Leu Phe Phe Gly Phe Leu Leu Val Ile Phe Ala Ile Glu Ile Ala Ala
1 5 10 15

Ala Ile

<210> SEQ ID NO 154
<211> LENGTH: 27
<212> TYPE: PRT
<213> ORGANISM: Homo sapiens

<400> SEQUENCE: 154

Ile Ile Gly Ala Val Gly Ile Gly Ile Ala Val Val Met Ile Phe Gly
1 5 10 15

Met Ile Phe Ser Met Ile Leu Cys Cys Ala Ile
20 25

<210> SEQ ID NO 155
<211> LENGTH: 21
<212> TYPE: PRT
<213> ORGANISM: Homo sapiens

<400> SEQUENCE: 155

Leu Phe Phe Phe Asn Leu Leu Phe Trp Ile Cys Gly Cys Cys Ile Leu
1 5 10 15

Gly Phe Gly Ile Tyr
20

<210> SEQ ID NO 156
<211> LENGTH: 17
<212> TYPE: PRT
<213> ORGANISM: Homo sapiens

<400> SEQUENCE: 156

Asn Val Phe Val Ile Val Gly Ser Ile Ile Met Val Val Ala Phe Leu
1 5 10 15

Gly

<210> SEQ ID NO 157
<211> LENGTH: 27
<212> TYPE: PRT
<213> ORGANISM: Homo sapiens

<400> SEQUENCE: 157

Cys Leu Leu Met Ser Phe Phe Ile Leu Leu Leu Ile Ile Leu Leu Ala
1 5 10 15

Glu Val Thr Leu Ala Ile Leu Leu Phe Val Tyr
20 25

<210> SEQ ID NO 158
<211> LENGTH: 21
<212> TYPE: PRT
<213> ORGANISM: Homo sapiens

<400> SEQUENCE: 158

Phe Leu Tyr Ile Gly Ile Ile Thr Ile Cys Val Cys Val Ile Glu Val
1 5 10 15

Leu Gly Met Ser Phe
20

-continued

<210> SEQ ID NO 159
<211> LENGTH: 23
<212> TYPE: PRT
<213> ORGANISM: Homo sapiens

<400> SEQUENCE: 159

Cys Gln Met Leu Val Thr Cys Phe Phe Ile Leu Leu Leu Gly Leu Ser
1 5 10 15

Val Ala Thr Met Val Thr Leu
20

<210> SEQ ID NO 160
<211> LENGTH: 21
<212> TYPE: PRT
<213> ORGANISM: Homo sapiens

<400> SEQUENCE: 160

Trp Ala Phe Ser Ala Gly Leu Ser Leu Val Gly Leu Leu Thr Leu Gly
1 5 10 15

Ala Val Leu Ser Ala
20

<210> SEQ ID NO 161
<211> LENGTH: 22
<212> TYPE: PRT
<213> ORGANISM: Homo sapiens

<400> SEQUENCE: 161

Gly Leu Met Ala Gly Gly Phe Leu Cys Phe Ser Leu Ala Phe Cys Ala
1 5 10 15

Gln Val Gln Val Val Phe
20

<210> SEQ ID NO 162
<211> LENGTH: 20
<212> TYPE: PRT
<213> ORGANISM: Homo sapiens

<400> SEQUENCE: 162

Ile Gly Leu Ala Leu Thr Val Ser Ala Leu Leu Phe Ser Ser Phe Leu
1 5 10 15

Trp Phe Ala Ile
20

<210> SEQ ID NO 163
<211> LENGTH: 18
<212> TYPE: PRT
<213> ORGANISM: Homo sapiens

<400> SEQUENCE: 163

Leu Phe Leu Phe Asn Leu Ile Phe Phe Ile Leu Gly Ala Val Ile Leu
1 5 10 15

Gly Phe

<210> SEQ ID NO 164
<211> LENGTH: 19
<212> TYPE: PRT
<213> ORGANISM: Homo sapiens

<400> SEQUENCE: 164

Met Gly Ala Tyr Val Phe Ile Gly Val Gly Ala Val Thr Met Leu Met 1 5 10 15

Gly Phe Leu

<210> SEQ ID NO 165
<211> LENGTH: 26
<212> TYPE: PRT
<213> ORGANISM: Homo sapiens

<400> SEQUENCE: 165

Cys Leu Leu Gly Leu Tyr Phe Ala Phe Leu Leu Leu Ile Leu Ile Ala
1 5 10 15

Gln Val Thr Ala Gly Ala Leu Phe Tyr Phe
20 25

<210> SEQ ID NO 166
<211> LENGTH: 24
<212> TYPE: PRT
<213> ORGANISM: Homo sapiens

<400> SEQUENCE: 166

Glu Lys Val Gln Ala Trp Leu Gln Glu Asn Leu Gly Ile Ile Leu Gly
1 5 10 15

Val Gly Val Gly Val Ala Ile Ile
20

<210> SEQ ID NO 167
<211> LENGTH: 22
<212> TYPE: PRT
<213> ORGANISM: Homo sapiens

<400> SEQUENCE: 167

Phe Leu Leu Tyr Val Leu Leu Leu Ala Phe Cys Ala Cys Ala Val Gly
1 5 10 15

Leu Ile Ala Val Gly Val
20

<210> SEQ ID NO 168
<211> LENGTH: 17
<212> TYPE: PRT
<213> ORGANISM: Homo sapiens

<400> SEQUENCE: 168

Val Ile Ile Ala Val Gly Val Phe Leu Phe Leu Val Ala Phe Val Gly
1 5 10 15

Cys

<210> SEQ ID NO 169
<211> LENGTH: 25
<212> TYPE: PRT
<213> ORGANISM: Homo sapiens

<400> SEQUENCE: 169

Met Ile Thr Phe Ala Ile Phe Leu Ser Leu Ile Met Leu Val Glu Val
1 5 10 15

Ala Ala Ala Ile Ala Gly Tyr Val Phe
20 25

<210> SEQ ID NO 170
<211> LENGTH: 26
<212> TYPE: PRT
<213> ORGANISM: Homo sapiens

<400> SEQUENCE: 170

Val Leu Val Val Ala Ala Ala Ala Leu Gly Ile Ala Phe Val Glu Val
1 5 10 15

Leu Gly Ile Val Phe Ala Cys Cys Leu Val
20 25

<210> SEQ ID NO 171
<211> LENGTH: 20
<212> TYPE: PRT
<213> ORGANISM: Homo sapiens

<400> SEQUENCE: 171

Phe Thr Tyr Asn Cys Cys Phe Trp Leu Ala Gly Leu Ala Val Met Ala
1 5 10 15

Val Gly Ile Trp
20

<210> SEQ ID NO 172
<211> LENGTH: 20
<212> TYPE: PRT
<213> ORGANISM: Homo sapiens

<400> SEQUENCE: 172

Tyr Ile Leu Val Val Ala Gly Thr Val Val Met Val Thr Gly Val Leu
1 5 10 15

Gly Cys Cys Ala
20

<210> SEQ ID NO 173
<211> LENGTH: 20
<212> TYPE: PRT
<213> ORGANISM: Homo sapiens

<400> SEQUENCE: 173

Leu Tyr Phe Ile Leu Leu Leu Ile Ile Phe Leu Leu Glu Ile Ile Ala
1 5 10 15

Gly Ile Leu Ala
20

<210> SEQ ID NO 174
<211> LENGTH: 20
<212> TYPE: PRT
<213> ORGANISM: Homo sapiens

<400> SEQUENCE: 174

Val Ile Gly Ala Val Gly Ile Gly Ile Ala Cys Val Gln Val Phe Gly
1 5 10 15

Met Ile Phe Thr
20

<210> SEQ ID NO 175
<211> LENGTH: 18
<212> TYPE: PRT
<213> ORGANISM: Homo sapiens

<400> SEQUENCE: 175

Leu Phe Val Phe Asn Leu Phe Phe Phe Val Leu Gly Ser Leu Ile Phe
1 5 10 15

Cys Phe

<210> SEQ ID NO 176

<211> LENGTH: 20
<212> TYPE: PRT
<213> ORGANISM: Homo sapiens

<400> SEQUENCE: 176

Leu Ala Ile Ser Gly Ile Phe Thr Met Gly Ile Ala Leu Leu Gly Cys
1 5 10 15

Val Gly Ala Leu
20

<210> SEQ ID NO 177
<211> LENGTH: 23
<212> TYPE: PRT
<213> ORGANISM: Homo sapiens

<400> SEQUENCE: 177

Leu Leu Gly Leu Tyr Phe Gly Met Leu Leu Leu Leu Phe Ala Thr Gln
1 5 10 15

Ile Thr Leu Gly Ile Leu Ile
20

<210> SEQ ID NO 178
<211> LENGTH: 24
<212> TYPE: PRT
<213> ORGANISM: Homo sapiens

<400> SEQUENCE: 178

Leu Ile Ser Ile Val Gly Ile Cys Leu Gly Val Gly Leu Leu Glu Leu
1 5 10 15

Gly Phe Met Thr Leu Ser Ile Phe
20

<210> SEQ ID NO 179
<211> LENGTH: 20
<212> TYPE: PRT
<213> ORGANISM: Homo sapiens

<400> SEQUENCE: 179

Ile Val Gly Ala Gly Leu Ser Gly Leu Ile Ile Val Ile Val Ile Ala
1 5 10 15

Tyr Val Ile Gly
20

<210> SEQ ID NO 180
<211> LENGTH: 89
<212> TYPE: PRT
<213> ORGANISM: Artificial Sequence
<220> FEATURE:
<223> OTHER INFORMATION: CD81 LEL mutant

<400> SEQUENCE: 180

Phe Val Asn Lys Asp Gln Ile Ala Lys Asp Val Lys Gln Phe Tyr Asp
1 5 10 15

Gln Cys Leu Gln Gln Ala Cys Val Asp Asp Asp Ala Asn Asn Ala Lys
20 25 30

Ala Cys Val Lys Thr Phe His Glu Thr Leu Asp Cys Cys Gly Ser Ser
35 40 45

Thr Leu Thr Ala Leu Thr Thr Cys Val Leu Lys Asn Asn Leu Cys Pro
50 55 60

Ser Gly Ser Asn Ile Ile Ser Asn Leu Phe Lys Glu Asp Cys His Gln
65 70 75 80

-continued

Lys Ile Asp Asp Leu Phe Ser Gly Lys
85

<210> SEQ ID NO 181
<211> LENGTH: 9
<212> TYPE: PRT
<213> ORGANISM: Artificial Sequence
<220> FEATURE:
<223> OTHER INFORMATION: Binding sequence

<400> SEQUENCE: 181

Pro His His Trp Arg Phe Pro Lys Ala
1 5

<210> SEQ ID NO 182
<211> LENGTH: 25
<212> TYPE: PRT
<213> ORGANISM: Homo sapiens

<400> SEQUENCE: 182

Leu Arg Phe Asp Ser Gln Thr Lys Ser Ile Phe Glu Gln Glu Thr Asn
1 5 10 15

Asn Asn Asn Ser Ser Phe Tyr Thr Gly
20 25

<210> SEQ ID NO 183
<211> LENGTH: 4
<212> TYPE: PRT
<213> ORGANISM: Artificial Sequence
<220> FEATURE:
<223> OTHER INFORMATION: Motif
<220> FEATURE:
<221> NAME/KEY: MISC_FEATURE
<222> LOCATION: (2)..(3)
<223> OTHER INFORMATION: X can be any amino acid

<400> SEQUENCE: 183

Pro Xaa Xaa Cys
1

<210> SEQ ID NO 184
<211> LENGTH: 237
<212> TYPE: PRT
<213> ORGANISM: Homo sapiens

<400> SEQUENCE: 184

Met Ala Gly Val Ser Ala Cys Ile Lys Tyr Ser Met Phe Thr Phe Asn
1 5 10 15

Phe Leu Phe Trp Leu Cys Gly Ile Leu Ile Leu Ala Leu Ala Ile Trp
20 25 30

Val Arg Val Ser Asn Asp Ser Gln Ala Ile Phe Gly Ser Glu Asp Val
35 40 45

Gly Ser Ser Ser Tyr Val Ala Val Asp Ile Leu Ile Ala Val Gly Ala
50 55 60

Ile Ile Met Ile Leu Gly Phe Leu Gly Cys Cys Gly Ala Ile Lys Glu
65 70 75 80

Ser Arg Cys Met Leu Leu Leu Phe Phe Ile Gly Leu Leu Leu Ile Leu
85 90 95

Leu Leu Gln Val Ala Thr Gly Ile Leu Gly Ala Val Phe Lys Ser Lys
100 105 110

Ser Asp Arg Ile Val Asn Glu Thr Leu Tyr Glu Asn Thr Lys Leu Leu
115 120 125

```
Ser Ala Thr Gly Glu Ser Glu Lys Gln Phe Gln Glu Ala Ile Ile Val
    130                 135                 140

Phe Gln Glu Glu Phe Lys Cys Cys Gly Leu Val Asn Gly Ala Ala Asp
145                 150                 155                 160

Trp Gly Asn Asn Phe Gln His Tyr Pro Glu Leu Cys Ala Cys Leu Asp
                165                 170                 175

Lys Gln Arg Pro Cys Gln Ser Tyr Asn Gly Lys Gln Val Tyr Lys Glu
            180                 185                 190

Thr Cys Ile Ser Phe Ile Lys Asp Phe Leu Ala Lys Asn Leu Ile Ile
        195                 200                 205

Val Ile Gly Ile Ser Phe Gly Leu Ala Val Ile Glu Ile Leu Gly Leu
    210                 215                 220

Val Phe Ser Met Val Leu Tyr Cys Gln Ile Gly Asn Lys
225                 230                 235
```

<210> SEQ ID NO 185
<211> LENGTH: 147
<212> TYPE: PRT
<213> ORGANISM: Homo sapiens

<400> SEQUENCE: 185

```
Met His Tyr Tyr Arg Tyr Ser Asn Ala Lys Val Ser Cys Trp Tyr Lys
1               5                   10                  15

Tyr Leu Leu Phe Ser Tyr Asn Ile Ile Phe Trp Asn Gln Cys Cys Gly
            20                  25                  30

Ala Tyr Gly Pro Glu Asp Trp Asp Leu Asn Val Tyr Phe Asn Cys Ser
        35                  40                  45

Gly Ala Ser Tyr Ser Arg Glu Lys Cys Gly Val Pro Phe Ser Cys Cys
    50                  55                  60

Val Pro Asp Pro Ala Gln Lys Val Val Asn Thr Gln Cys Gly Tyr Asp
65                  70                  75                  80

Val Arg Ile Gln Leu Lys Ser Lys Trp Asp Glu Ser Ile Phe Thr Lys
                85                  90                  95

Gly Cys Ile Gln Ala Leu Glu Ser Trp Leu Pro Arg Asn Ile Tyr Ile
            100                 105                 110

Val Ala Gly Val Phe Ile Ala Ile Ser Leu Leu Gln Ile Phe Gly Ile
        115                 120                 125

Phe Leu Ala Arg Thr Leu Ile Ser Asp Ile Glu Ala Val Lys Ala Gly
    130                 135                 140

His His Phe
145
```

<210> SEQ ID NO 186
<211> LENGTH: 249
<212> TYPE: PRT
<213> ORGANISM: Homo sapiens

<400> SEQUENCE: 186

```
Met Ala Ser Arg Arg Met Glu Thr Lys Pro Val Ile Thr Cys Leu Lys
1               5                   10                  15

Thr Leu Leu Ile Ile Tyr Ser Phe Val Phe Trp Ile Thr Gly Val Ile
            20                  25                  30

Leu Leu Ala Val Gly Val Trp Gly Lys Leu Thr Leu Gly Thr Tyr Ile
        35                  40                  45

Ser Leu Ile Ala Glu Asn Ser Thr Asn Ala Pro Tyr Val Leu Ile Gly
    50                  55                  60
```

-continued

Thr Gly Thr Thr Ile Val Val Phe Gly Leu Phe Gly Cys Phe Ala Thr
65 70 75 80

Cys Arg Gly Ser Pro Trp Met Leu Lys Leu Tyr Ala Met Phe Leu Ser
85 90 95

Leu Val Phe Leu Ala Glu Leu Val Ala Gly Ile Ser Gly Phe Val Phe
100 105 110

Arg His Glu Ile Lys Asp Thr Phe Leu Arg Thr Tyr Thr Asp Ala Met
115 120 125

Gln Thr Tyr Asn Gly Asn Asp Glu Arg Ser Arg Ala Val Asp His Val
130 135 140

Gln Arg Ser Leu Ser Cys Cys Gly Val Gln Asn Tyr Thr Asn Trp Ser
145 150 155 160

Thr Ser Pro Tyr Phe Leu Glu His Gly Ile Pro Pro Ser Cys Cys Met
165 170 175

Asn Glu Thr Asp Cys Asn Pro Gln Asp Leu His Asn Leu Thr Val Ala
180 185 190

Ala Thr Lys Val Asn Gln Lys Gly Cys Tyr Asp Leu Val Thr Ser Phe
195 200 205

Met Glu Thr Asn Met Gly Ile Ile Ala Gly Val Ala Phe Gly Ile Ala
210 215 220

Phe Ser Gln Leu Ile Gly Met Leu Leu Ala Cys Cys Leu Ser Arg Phe
225 230 235 240

Ile Thr Ala Asn Gln Tyr Glu Met Val
245

<210> SEQ ID NO 187
<211> LENGTH: 1032
<212> TYPE: PRT
<213> ORGANISM: Homo sapiens

<400> SEQUENCE: 187

Met Ala Trp Glu Ala Arg Arg Glu Pro Gly Pro Arg Arg Ala Ala Val
1 5 10 15

Arg Glu Thr Val Met Leu Leu Leu Cys Leu Gly Val Pro Thr Gly Arg
20 25 30

Pro Tyr Asn Val Asp Thr Glu Ser Ala Leu Leu Tyr Gln Gly Pro His
35 40 45

Asn Thr Leu Phe Gly Tyr Ser Val Val Leu His Ser His Gly Ala Asn
50 55 60

Arg Trp Leu Leu Val Gly Ala Pro Thr Ala Asn Trp Leu Ala Asn Ala
65 70 75 80

Ser Val Ile Asn Pro Gly Ala Ile Tyr Arg Cys Arg Ile Gly Lys Asn
85 90 95

Pro Gly Gln Thr Cys Glu Gln Leu Gln Leu Gly Ser Pro Asn Gly Glu
100 105 110

Pro Cys Gly Lys Thr Cys Leu Glu Glu Arg Asp Asn Gln Trp Leu Gly
115 120 125

Val Thr Leu Ser Arg Gln Pro Gly Glu Asn Gly Ser Ile Val Thr Cys
130 135 140

Gly His Arg Trp Lys Asn Ile Phe Tyr Ile Lys Asn Glu Asn Lys Leu
145 150 155 160

Pro Thr Gly Gly Cys Tyr Gly Val Pro Pro Asp Leu Arg Thr Glu Leu
165 170 175

Ser Lys Arg Ile Ala Pro Cys Tyr Gln Asp Tyr Val Lys Lys Phe Gly
180 185 190

```
Glu Asn Phe Ala Ser Cys Gln Ala Gly Ile Ser Ser Phe Tyr Thr Lys
        195                 200                 205

Asp Leu Ile Val Met Gly Ala Pro Gly Ser Ser Tyr Trp Thr Gly Ser
    210                 215                 220

Leu Phe Val Tyr Asn Ile Thr Thr Asn Lys Tyr Lys Ala Phe Leu Asp
225                 230                 235                 240

Lys Gln Asn Gln Val Lys Phe Gly Ser Tyr Leu Gly Tyr Ser Val Gly
                245                 250                 255

Ala Gly His Phe Arg Ser Gln His Thr Thr Glu Val Val Gly Gly Ala
            260                 265                 270

Pro Gln His Glu Gln Ile Gly Lys Ala Tyr Ile Phe Ser Ile Asp Glu
        275                 280                 285

Lys Glu Leu Asn Ile Leu His Glu Met Lys Gly Lys Lys Leu Gly Ser
    290                 295                 300

Tyr Phe Gly Ala Ser Val Cys Ala Val Asp Leu Asn Ala Asp Gly Phe
305                 310                 315                 320

Ser Asp Leu Leu Val Gly Ala Pro Met Gln Ser Thr Ile Arg Glu Glu
                325                 330                 335

Gly Arg Val Phe Val Tyr Ile Asn Ser Gly Ser Gly Ala Val Met Asn
            340                 345                 350

Ala Met Glu Thr Asn Leu Val Gly Ser Asp Lys Tyr Ala Ala Arg Phe
        355                 360                 365

Gly Glu Ser Ile Val Asn Leu Gly Asp Ile Asp Asn Asp Gly Phe Glu
    370                 375                 380

Asp Val Ala Ile Gly Ala Pro Gln Glu Asp Asp Leu Gln Gly Ala Ile
385                 390                 395                 400

Tyr Ile Tyr Asn Gly Arg Ala Asp Gly Ile Ser Ser Thr Phe Ser Gln
                405                 410                 415

Arg Ile Glu Gly Leu Gln Ile Ser Lys Ser Leu Ser Met Phe Gly Gln
            420                 425                 430

Ser Ile Ser Gly Gln Ile Asp Ala Asp Asn Asn Gly Tyr Val Asp Val
        435                 440                 445

Ala Val Gly Ala Phe Arg Ser Asp Ser Ala Val Leu Leu Arg Thr Arg
    450                 455                 460

Pro Val Val Ile Val Asp Ala Ser Leu Ser His Pro Glu Ser Val Asn
465                 470                 475                 480

Arg Thr Lys Phe Asp Cys Val Glu Asn Gly Trp Pro Ser Val Cys Ile
                485                 490                 495

Asp Leu Thr Leu Cys Phe Ser Tyr Lys Gly Lys Glu Val Pro Gly Tyr
            500                 505                 510

Ile Val Leu Phe Tyr Asn Met Ser Leu Asp Val Asn Arg Lys Ala Glu
        515                 520                 525

Ser Pro Pro Arg Phe Tyr Phe Ser Ser Asn Gly Thr Ser Asp Val Ile
    530                 535                 540

Thr Gly Ser Ile Gln Val Ser Ser Arg Glu Ala Asn Cys Arg Thr His
545                 550                 555                 560

Gln Ala Phe Met Arg Lys Asp Val Arg Asp Ile Leu Thr Pro Ile Gln
                565                 570                 575

Ile Glu Ala Ala Tyr His Leu Gly Pro His Val Ile Ser Lys Arg Ser
            580                 585                 590

Thr Glu Glu Phe Pro Pro Leu Gln Pro Ile Leu Gln Gln Lys Lys Glu
        595                 600                 605
```

-continued

```
Lys Asp Ile Met Lys Lys Thr Ile Asn Phe Ala Arg Phe Cys Ala His
    610                 615                 620

Glu Asn Cys Ser Ala Asp Leu Gln Val Ser Ala Lys Ile Gly Phe Leu
625                 630                 635                 640

Lys Pro His Glu Asn Lys Thr Tyr Leu Ala Val Gly Ser Met Lys Thr
                645                 650                 655

Leu Met Leu Asn Val Ser Leu Phe Asn Ala Gly Asp Asp Ala Tyr Glu
            660                 665                 670

Thr Thr Leu His Val Lys Leu Pro Val Gly Leu Tyr Phe Ile Lys Ile
        675                 680                 685

Leu Glu Leu Glu Glu Lys Gln Ile Asn Cys Glu Val Thr Asp Asn Ser
    690                 695                 700

Gly Val Val Gln Leu Asp Cys Ser Ile Gly Tyr Ile Tyr Val Asp His
705                 710                 715                 720

Leu Ser Arg Ile Asp Ile Ser Phe Leu Leu Asp Val Ser Ser Leu Ser
                725                 730                 735

Arg Ala Glu Glu Asp Leu Ser Ile Thr Val His Ala Thr Cys Glu Asn
            740                 745                 750

Glu Glu Glu Met Asp Asn Leu Lys His Ser Arg Val Thr Val Ala Ile
        755                 760                 765

Pro Leu Lys Tyr Glu Val Lys Leu Thr Val His Gly Phe Val Asn Pro
    770                 775                 780

Thr Ser Phe Val Tyr Gly Ser Asn Asp Glu Asn Glu Pro Glu Thr Cys
785                 790                 795                 800

Met Val Glu Lys Met Asn Leu Thr Phe His Val Ile Asn Thr Gly Asn
                805                 810                 815

Ser Met Ala Pro Asn Val Ser Val Glu Ile Met Val Pro Asn Ser Phe
            820                 825                 830

Ser Pro Gln Thr Asp Lys Leu Phe Asn Ile Leu Asp Val Gln Thr Thr
        835                 840                 845

Thr Gly Glu Cys His Phe Glu Asn Tyr Gln Arg Val Cys Ala Leu Glu
    850                 855                 860

Gln Gln Lys Ser Ala Met Gln Thr Leu Lys Gly Ile Val Arg Phe Leu
865                 870                 875                 880

Ser Lys Thr Asp Lys Arg Leu Leu Tyr Cys Ile Lys Ala Asp Pro His
                885                 890                 895

Cys Leu Asn Phe Leu Cys Asn Phe Gly Lys Met Glu Ser Gly Lys Glu
            900                 905                 910

Ala Ser Val His Ile Gln Leu Glu Gly Arg Pro Ser Ile Leu Glu Met
        915                 920                 925

Asp Glu Thr Ser Ala Leu Lys Phe Glu Ile Arg Ala Thr Gly Phe Pro
    930                 935                 940

Glu Pro Asn Pro Arg Val Ile Glu Leu Asn Lys Asp Glu Asn Val Ala
945                 950                 955                 960

His Val Leu Leu Glu Gly Leu His His Gln Arg Pro Lys Arg Tyr Phe
                965                 970                 975

Thr Ile Val Ile Ile Ser Ser Ser Leu Leu Leu Gly Leu Ile Val Leu
            980                 985                 990

Leu Leu Ile Ser Tyr Val Met Trp  Lys Ala Gly Phe Phe  Lys Arg Gln
        995                 1000                1005

Tyr Lys  Ser Ile Leu Gln Glu  Glu Asn Arg Arg Asp  Ser Trp Ser
    1010                1015                1020

Tyr Ile  Asn Ser Lys Ser Asn  Asp Asp
```

1025 1030

<210> SEQ ID NO 188
<211> LENGTH: 691
<212> TYPE: PRT
<213> ORGANISM: Homo sapiens

<400> SEQUENCE: 188

Met Thr Pro Gln Glu Ile Ala Val Asn Leu Arg Pro Gly Asp Lys Thr
1 5 10 15

Thr Phe Gln Leu Gln Val Arg Gln Val Glu Asp Tyr Pro Val Asp Leu
20 25 30

Tyr Tyr Leu Met Asp Leu Ser Leu Ser Met Lys Asp Asp Leu Asp Asn
35 40 45

Ile Arg Ser Leu Gly Thr Lys Leu Ala Glu Glu Met Arg Lys Leu Thr
50 55 60

Ser Asn Phe Arg Leu Gly Phe Gly Ser Phe Val Asp Lys Asp Ile Ser
65 70 75 80

Pro Phe Ser Tyr Thr Ala Pro Arg Tyr Gln Thr Asn Pro Cys Ile Gly
85 90 95

Tyr Lys Leu Phe Pro Asn Cys Val Pro Ser Phe Gly Phe Arg His Leu
100 105 110

Leu Pro Leu Thr Asp Arg Val Asp Ser Phe Asn Glu Glu Val Arg Lys
115 120 125

Gln Arg Val Ser Arg Asn Arg Asp Ala Pro Glu Gly Gly Phe Asp Ala
130 135 140

Val Leu Gln Ala Ala Val Cys Lys Glu Lys Ile Gly Trp Arg Lys Asp
145 150 155 160

Ala Leu His Leu Leu Val Phe Thr Thr Asp Asp Val Pro His Ile Ala
165 170 175

Leu Asp Gly Lys Leu Gly Gly Leu Val Gln Pro His Asp Gly Gln Cys
180 185 190

His Leu Asn Glu Ala Asn Glu Tyr Thr Ala Ser Asn Gln Met Asp Tyr
195 200 205

Pro Ser Leu Ala Leu Leu Gly Glu Lys Leu Ala Glu Asn Asn Ile Asn
210 215 220

Leu Ile Phe Ala Val Thr Lys Asn His Tyr Met Leu Tyr Lys Asn Phe
225 230 235 240

Thr Ala Leu Ile Pro Gly Thr Thr Val Glu Ile Leu Asp Gly Asp Ser
245 250 255

Lys Asn Ile Ile Gln Leu Ile Ile Asn Ala Tyr Asn Ser Ile Arg Ser
260 265 270

Lys Val Glu Leu Ser Val Trp Asp Gln Pro Glu Asp Leu Asn Leu Phe
275 280 285

Phe Thr Ala Thr Cys Gln Asp Gly Val Ser Tyr Pro Gly Gln Arg Lys
290 295 300

Cys Glu Gly Leu Lys Ile Gly Asp Thr Ala Ser Phe Glu Val Ser Leu
305 310 315 320

Glu Ala Arg Ser Cys Pro Ser Arg His Thr Glu His Val Phe Ala Leu
325 330 335

Arg Pro Val Gly Phe Arg Asp Ser Leu Glu Val Gly Val Thr Tyr Asn
340 345 350

Cys Thr Cys Gly Cys Ser Val Gly Leu Glu Pro Asn Ser Ala Arg Cys
355 360 365

-continued

```
Asn Gly Ser Gly Thr Tyr Val Cys Gly Leu Cys Glu Cys Ser Pro Gly
    370                 375                 380

Tyr Leu Gly Thr Arg Cys Glu Cys Gln Asp Gly Glu Asn Gln Ser Val
385                 390                 395                 400

Tyr Gln Asn Leu Cys Arg Glu Ala Glu Gly Lys Pro Leu Cys Ser Gly
                405                 410                 415

Arg Gly Asp Cys Ser Cys Asn Gln Cys Ser Cys Phe Glu Ser Glu Phe
            420                 425                 430

Gly Lys Ile Tyr Gly Pro Phe Cys Glu Cys Asp Asn Phe Ser Cys Ala
        435                 440                 445

Arg Asn Lys Gly Val Leu Cys Ser Gly His Gly Glu Cys His Cys Gly
    450                 455                 460

Glu Cys Lys Cys His Ala Gly Tyr Ile Gly Asp Asn Cys Asn Cys Ser
465                 470                 475                 480

Thr Asp Ile Ser Thr Cys Arg Gly Arg Asp Gly Gln Ile Cys Ser Glu
                485                 490                 495

Arg Gly His Cys Leu Cys Gly Gln Cys Gln Cys Thr Glu Pro Gly Ala
            500                 505                 510

Phe Gly Glu Met Cys Glu Lys Cys Pro Thr Cys Pro Asp Ala Cys Ser
        515                 520                 525

Thr Lys Arg Asp Cys Val Glu Cys Leu Leu Leu His Ser Gly Lys Pro
    530                 535                 540

Asp Asn Gln Thr Cys His Ser Leu Cys Arg Asp Glu Val Ile Thr Trp
545                 550                 555                 560

Val Asp Thr Ile Val Lys Asp Asp Gln Glu Ala Val Leu Cys Phe Tyr
                565                 570                 575

Lys Thr Ala Lys Asp Cys Val Met Met Phe Thr Tyr Val Glu Leu Pro
            580                 585                 590

Ser Gly Lys Ser Asn Leu Thr Val Leu Arg Glu Pro Glu Cys Gly Asn
        595                 600                 605

Thr Pro Asn Ala Met Thr Ile Leu Leu Ala Val Val Gly Ser Ile Leu
    610                 615                 620

Leu Val Gly Leu Ala Leu Leu Ala Ile Trp Lys Leu Leu Val Thr Ile
625                 630                 635                 640

His Asp Arg Arg Glu Phe Ala Lys Phe Gln Ser Glu Arg Ser Arg Ala
                645                 650                 655

Arg Tyr Glu Met Ala Ser Asn Pro Leu Tyr Arg Lys Pro Ile Ser Thr
            660                 665                 670

His Thr Val Asp Phe Thr Phe Asn Lys Phe Asn Lys Ser Tyr Asn Gly
        675                 680                 685

Thr Val Asp
    690


<210> SEQ ID NO 189
<211> LENGTH: 788
<212> TYPE: PRT
<213> ORGANISM: Homo sapiens

<400> SEQUENCE: 189

Met Gly Ile Glu Leu Leu Cys Leu Phe Phe Leu Phe Leu Gly Arg Asn
1               5                   10                  15

Asp His Val Gln Gly Gly Cys Ala Leu Gly Gly Ala Glu Thr Cys Glu
            20                  25                  30

Asp Cys Leu Leu Ile Gly Pro Gln Cys Ala Trp Cys Ala Gln Glu Asn
        35                  40                  45
```

-continued

```
Phe Thr His Pro Ser Gly Val Gly Glu Arg Cys Asp Thr Pro Ala Asn
    50                  55                  60

Leu Leu Ala Lys Gly Cys Gln Leu Asn Phe Ile Glu Asn Pro Val Ser
65                  70                  75                  80

Gln Val Glu Ile Leu Lys Asn Lys Pro Leu Ser Val Gly Arg Gln Lys
                85                  90                  95

Asn Ser Ser Asp Ile Val Gln Ile Ala Pro Gln Ser Leu Ile Leu Lys
            100                 105                 110

Leu Arg Pro Gly Gly Ala Gln Thr Leu Gln Val His Val Arg Gln Thr
        115                 120                 125

Glu Asp Tyr Pro Val Asp Leu Tyr Tyr Leu Met Asp Leu Ser Ala Ser
    130                 135                 140

Met Asp Asp Asp Leu Asn Thr Ile Lys Glu Leu Gly Ser Arg Leu Ser
145                 150                 155                 160

Lys Glu Met Ser Lys Leu Thr Ser Asn Phe Arg Leu Gly Phe Gly Ser
                165                 170                 175

Phe Val Glu Lys Pro Val Ser Pro Phe Val Lys Thr Thr Pro Glu Glu
            180                 185                 190

Ile Ala Asn Pro Cys Ser Ser Ile Pro Tyr Phe Cys Leu Pro Thr Phe
        195                 200                 205

Gly Phe Lys His Ile Leu Pro Leu Thr Asn Asp Ala Glu Arg Phe Asn
    210                 215                 220

Glu Ile Val Lys Asn Gln Lys Ile Ser Ala Asn Ile Asp Thr Pro Glu
225                 230                 235                 240

Gly Gly Phe Asp Ala Ile Met Gln Ala Ala Val Cys Lys Glu Lys Ile
                245                 250                 255

Gly Trp Arg Asn Asp Ser Leu His Leu Leu Val Phe Val Ser Asp Ala
            260                 265                 270

Asp Ser His Phe Gly Met Asp Ser Lys Leu Ala Gly Ile Val Ile Pro
        275                 280                 285

Asn Asp Gly Leu Cys His Leu Asp Ser Lys Asn Glu Tyr Ser Met Ser
    290                 295                 300

Thr Val Leu Glu Tyr Pro Thr Ile Gly Gln Leu Ile Asp Lys Leu Val
305                 310                 315                 320

Gln Asn Asn Val Leu Leu Ile Phe Ala Val Thr Gln Glu Gln Val His
                325                 330                 335

Leu Tyr Glu Asn Tyr Ala Lys Leu Ile Pro Gly Ala Thr Val Gly Leu
            340                 345                 350

Leu Gln Lys Asp Ser Gly Asn Ile Leu Gln Leu Ile Ile Ser Ala Tyr
        355                 360                 365

Glu Glu Leu Arg Ser Glu Val Glu Leu Glu Val Leu Gly Asp Thr Glu
    370                 375                 380

Gly Leu Asn Leu Ser Phe Thr Ala Ile Cys Asn Asn Gly Thr Leu Phe
385                 390                 395                 400

Gln His Gln Lys Lys Cys Ser His Met Lys Val Gly Asp Thr Ala Ser
                405                 410                 415

Phe Ser Val Thr Val Asn Ile Pro His Cys Glu Arg Arg Ser Arg His
            420                 425                 430

Ile Ile Ile Lys Pro Val Gly Leu Gly Asp Ala Leu Glu Leu Leu Val
        435                 440                 445

Ser Pro Glu Cys Asn Cys Asp Cys Gln Lys Glu Val Glu Val Asn Ser
    450                 455                 460
```

-continued

Ser Lys Cys His His Gly Asn Gly Ser Phe Gln Cys Gly Val Cys Ala
465 470 475 480

Cys His Pro Gly His Met Gly Pro Arg Cys Glu Cys Gly Glu Asp Met
485 490 495

Leu Ser Thr Asp Ser Cys Lys Glu Ala Pro Asp His Pro Ser Cys Ser
500 505 510

Gly Arg Gly Asp Cys Tyr Cys Gly Gln Cys Ile Cys His Leu Ser Pro
515 520 525

Tyr Gly Asn Ile Tyr Gly Pro Tyr Cys Gln Cys Asp Asn Phe Ser Cys
530 535 540

Val Arg His Lys Gly Leu Leu Cys Gly Gly Asn Gly Asp Cys Asp Cys
545 550 555 560

Gly Glu Cys Val Cys Arg Ser Gly Trp Thr Gly Glu Tyr Cys Asn Cys
565 570 575

Thr Thr Ser Thr Asp Ser Cys Val Ser Glu Asp Gly Val Leu Cys Ser
580 585 590

Gly Arg Gly Asp Cys Val Cys Gly Lys Cys Val Cys Thr Asn Pro Gly
595 600 605

Ala Ser Gly Pro Thr Cys Glu Arg Cys Pro Thr Cys Gly Asp Pro Cys
610 615 620

Asn Ser Lys Arg Ser Cys Ile Glu Cys His Leu Ser Ala Ala Gly Gln
625 630 635 640

Ala Arg Glu Glu Cys Val Asp Lys Cys Lys Leu Ala Gly Ala Thr Ile
645 650 655

Ser Glu Glu Glu Asp Phe Ser Lys Asp Gly Ser Val Ser Cys Ser Leu
660 665 670

Gln Gly Glu Asn Glu Cys Leu Ile Thr Phe Leu Ile Thr Thr Asp Asn
675 680 685

Glu Gly Lys Thr Ile Ile His Ser Ile Asn Glu Lys Asp Cys Pro Lys
690 695 700

Pro Pro Asn Ile Pro Met Ile Met Leu Gly Val Ser Leu Ala Ile Leu
705 710 715 720

Leu Ile Gly Val Val Leu Leu Cys Ile Trp Lys Leu Leu Val Ser Phe
725 730 735

His Asp Arg Lys Glu Val Ala Lys Phe Glu Ala Glu Arg Ser Lys Ala
740 745 750

Lys Trp Gln Thr Gly Thr Asn Pro Leu Tyr Arg Gly Ser Thr Ser Thr
755 760 765

Phe Lys Asn Val Thr Tyr Lys His Arg Glu Lys Gln Lys Val Asp Leu
770 775 780

Ser Thr Asp Cys
785

<210> SEQ ID NO 190
<211> LENGTH: 798
<212> TYPE: PRT
<213> ORGANISM: Homo sapiens

<400> SEQUENCE: 190

Met Val Ala Leu Pro Met Val Leu Val Leu Leu Leu Val Leu Ser Arg
1 5 10 15

Gly Glu Ser Glu Leu Asp Ala Lys Ile Pro Ser Thr Gly Asp Ala Thr
20 25 30

Glu Trp Arg Asn Pro His Leu Ser Met Leu Gly Ser Cys Gln Pro Ala
35 40 45

-continued

```
Pro Ser Cys Gln Lys Cys Ile Leu Ser His Pro Ser Cys Ala Trp Cys
    50                  55                  60

Lys Gln Leu Asn Phe Thr Ala Ser Gly Glu Ala Glu Ala Arg Arg Cys
65                  70                  75                  80

Ala Arg Arg Glu Glu Leu Leu Ala Arg Gly Cys Pro Leu Glu Glu Leu
                85                  90                  95

Glu Glu Pro Arg Gly Gln Gln Glu Val Leu Gln Asp Gln Pro Leu Ser
            100                 105                 110

Gln Gly Ala Arg Gly Glu Gly Ala Thr Gln Leu Ala Pro Gln Arg Val
        115                 120                 125

Arg Val Thr Leu Arg Pro Gly Glu Pro Gln Gln Leu Gln Val Arg Phe
    130                 135                 140

Leu Arg Ala Glu Gly Tyr Pro Val Asp Leu Tyr Tyr Leu Met Asp Leu
145                 150                 155                 160

Ser Tyr Ser Met Lys Asp Asp Leu Glu Arg Val Arg Gln Leu Gly His
                165                 170                 175

Ala Leu Leu Val Arg Leu Gln Glu Val Thr His Ser Val Arg Ile Gly
            180                 185                 190

Phe Gly Ser Phe Val Asp Lys Thr Val Leu Pro Phe Val Ser Thr Val
        195                 200                 205

Pro Ser Lys Leu Arg His Pro Cys Pro Thr Arg Leu Glu Arg Cys Gln
    210                 215                 220

Ser Pro Phe Ser Phe His His Val Leu Ser Leu Thr Gly Asp Ala Gln
225                 230                 235                 240

Ala Phe Glu Arg Glu Val Gly Arg Gln Ser Val Ser Gly Asn Leu Asp
                245                 250                 255

Ser Pro Glu Gly Gly Phe Asp Ala Ile Leu Gln Ala Ala Leu Cys Gln
            260                 265                 270

Glu Gln Ile Gly Trp Arg Asn Val Ser Arg Leu Leu Val Phe Thr Ser
        275                 280                 285

Asp Asp Thr Phe His Thr Ala Gly Asp Gly Lys Leu Gly Gly Ile Phe
    290                 295                 300

Met Pro Ser Asp Gly His Cys His Leu Asp Ser Asn Gly Leu Tyr Ser
305                 310                 315                 320

Arg Ser Thr Glu Phe Asp Tyr Pro Ser Val Gly Gln Val Ala Gln Ala
                325                 330                 335

Leu Ser Ala Ala Asn Ile Gln Pro Ile Phe Ala Val Thr Ser Ala Ala
            340                 345                 350

Leu Pro Val Tyr Gln Glu Leu Ser Lys Leu Ile Pro Lys Ser Ala Val
        355                 360                 365

Gly Glu Leu Ser Glu Asp Ser Ser Asn Val Val Gln Leu Ile Met Asp
    370                 375                 380

Ala Tyr Asn Ser Leu Ser Ser Thr Val Thr Leu Glu His Ser Ser Leu
385                 390                 395                 400

Pro Pro Gly Val His Ile Ser Tyr Glu Ser Gln Cys Glu Gly Pro Glu
                405                 410                 415

Lys Arg Glu Gly Lys Ala Glu Asp Arg Gly Gln Cys Asn His Val Arg
            420                 425                 430

Ile Asn Gln Thr Val Thr Phe Trp Val Ser Leu Gln Ala Thr His Cys
        435                 440                 445

Leu Pro Glu Pro His Leu Leu Arg Leu Arg Ala Leu Gly Phe Ser Glu
    450                 455                 460
```

-continued

Glu Leu Ile Val Glu Leu His Thr Leu Cys Asp Cys Asn Cys Ser Asp
465 470 475 480

Thr Gln Pro Gln Ala Pro His Cys Ser Asp Gly Gln Gly His Leu Gln
485 490 495

Cys Gly Val Cys Ser Cys Ala Pro Gly Arg Leu Gly Arg Leu Cys Glu
500 505 510

Cys Ser Val Ala Glu Leu Ser Ser Pro Asp Leu Glu Ser Gly Cys Arg
515 520 525

Ala Pro Asn Gly Thr Gly Pro Leu Cys Ser Gly Lys Gly His Cys Gln
530 535 540

Cys Gly Arg Cys Ser Cys Ser Gly Gln Ser Ser Gly His Leu Cys Glu
545 550 555 560

Cys Asp Asp Ala Ser Cys Glu Arg His Glu Gly Ile Leu Cys Gly Gly
565 570 575

Phe Gly Arg Cys Gln Cys Gly Val Cys His Cys His Ala Asn Arg Thr
580 585 590

Gly Arg Ala Cys Glu Cys Ser Gly Asp Met Asp Ser Cys Ile Ser Pro
595 600 605

Glu Gly Gly Leu Cys Ser Gly His Gly Arg Cys Lys Cys Asn Arg Cys
610 615 620

Gln Cys Leu Asp Gly Tyr Tyr Gly Ala Leu Cys Asp Gln Cys Pro Gly
625 630 635 640

Cys Lys Thr Pro Cys Glu Arg His Arg Asp Cys Ala Glu Cys Gly Ala
645 650 655

Phe Arg Thr Gly Pro Leu Ala Thr Asn Cys Ser Thr Ala Cys Ala His
660 665 670

Thr Asn Val Thr Leu Ala Leu Ala Pro Ile Leu Asp Asp Gly Trp Cys
675 680 685

Lys Glu Arg Thr Leu Asp Asn Gln Leu Phe Phe Phe Leu Val Glu Asp
690 695 700

Asp Ala Arg Gly Thr Val Val Leu Arg Val Arg Pro Gln Glu Lys Gly
705 710 715 720

Ala Asp His Thr Gln Ala Ile Val Leu Gly Cys Val Gly Gly Ile Val
725 730 735

Ala Val Gly Leu Gly Leu Val Leu Ala Tyr Arg Leu Ser Val Glu Ile
740 745 750

Tyr Asp Arg Arg Glu Tyr Ser Arg Phe Glu Lys Glu Gln Gln Gln Leu
755 760 765

Asn Trp Lys Gln Asp Ser Asn Pro Leu Tyr Lys Ser Ala Ile Thr Thr
770 775 780

Thr Ile Asn Pro Arg Phe Gln Glu Ala Asp Ser Pro Thr Leu
785 790 795

<210> SEQ ID NO 191
<211> LENGTH: 760
<212> TYPE: PRT
<213> ORGANISM: Homo sapiens

<400> SEQUENCE: 191

Met Met Asp Gln Ala Arg Ser Ala Phe Ser Asn Leu Phe Gly Gly Glu
1 5 10 15

Pro Leu Ser Tyr Thr Arg Phe Ser Leu Ala Arg Gln Val Asp Gly Asp
20 25 30

Asn Ser His Val Glu Met Lys Leu Ala Val Asp Glu Glu Glu Asn Ala
35 40 45

-continued

```
Asp Asn Asn Thr Lys Ala Asn Val Thr Lys Pro Lys Arg Cys Ser Gly
    50                  55                  60

Ser Ile Cys Tyr Gly Thr Ile Ala Val Ile Val Phe Phe Leu Ile Gly
65                  70                  75                  80

Phe Met Ile Gly Tyr Leu Gly Tyr Cys Lys Gly Val Glu Pro Lys Thr
                85                  90                  95

Glu Cys Glu Arg Leu Ala Gly Thr Glu Ser Pro Val Arg Glu Glu Pro
            100                 105                 110

Gly Glu Asp Phe Pro Ala Ala Arg Arg Leu Tyr Trp Asp Asp Leu Lys
        115                 120                 125

Arg Lys Leu Ser Glu Lys Leu Asp Ser Thr Asp Phe Thr Gly Thr Ile
    130                 135                 140

Lys Leu Leu Asn Glu Asn Ser Tyr Val Pro Arg Glu Ala Gly Ser Gln
145                 150                 155                 160

Lys Asp Glu Asn Leu Ala Leu Tyr Val Glu Asn Gln Phe Arg Glu Phe
                165                 170                 175

Lys Leu Ser Lys Val Trp Arg Asp Gln His Phe Val Lys Ile Gln Val
            180                 185                 190

Lys Asp Ser Ala Gln Asn Ser Val Ile Ile Val Asp Lys Asn Gly Arg
        195                 200                 205

Leu Val Tyr Leu Val Glu Asn Pro Gly Gly Tyr Val Ala Tyr Ser Lys
    210                 215                 220

Ala Ala Thr Val Thr Gly Lys Leu Val His Ala Asn Phe Gly Thr Lys
225                 230                 235                 240

Lys Asp Phe Glu Asp Leu Tyr Thr Pro Val Asn Gly Ser Ile Val Ile
                245                 250                 255

Val Arg Ala Gly Lys Ile Thr Phe Ala Glu Lys Val Ala Asn Ala Glu
            260                 265                 270

Ser Leu Asn Ala Ile Gly Val Leu Ile Tyr Met Asp Gln Thr Lys Phe
        275                 280                 285

Pro Ile Val Asn Ala Glu Leu Ser Phe Phe Gly His Ala His Leu Gly
    290                 295                 300

Thr Gly Asp Pro Tyr Thr Pro Gly Phe Pro Ser Phe Asn His Thr Gln
305                 310                 315                 320

Phe Pro Pro Ser Arg Ser Ser Gly Leu Pro Asn Ile Pro Val Gln Thr
                325                 330                 335

Ile Ser Arg Ala Ala Ala Glu Lys Leu Phe Gly Asn Met Glu Gly Asp
            340                 345                 350

Cys Pro Ser Asp Trp Lys Thr Asp Ser Thr Cys Arg Met Val Thr Ser
        355                 360                 365

Glu Ser Lys Asn Val Lys Leu Thr Val Ser Asn Val Leu Lys Glu Ile
    370                 375                 380

Lys Ile Leu Asn Ile Phe Gly Val Ile Lys Gly Phe Val Glu Pro Asp
385                 390                 395                 400

His Tyr Val Val Val Gly Ala Gln Arg Asp Ala Trp Gly Pro Gly Ala
                405                 410                 415

Ala Lys Ser Gly Val Gly Thr Ala Leu Leu Leu Lys Leu Ala Gln Met
            420                 425                 430

Phe Ser Asp Met Val Leu Lys Asp Gly Phe Gln Pro Ser Arg Ser Ile
        435                 440                 445

Ile Phe Ala Ser Trp Ser Ala Gly Asp Phe Gly Ser Val Gly Ala Thr
    450                 455                 460
```

Glu Trp Leu Glu Gly Tyr Leu Ser Ser Leu His Leu Lys Ala Phe Thr
465 470 475 480

Tyr Ile Asn Leu Asp Lys Ala Val Leu Gly Thr Ser Asn Phe Lys Val
485 490 495

Ser Ala Ser Pro Leu Leu Tyr Thr Leu Ile Glu Lys Thr Met Gln Asn
500 505 510

Val Lys His Pro Val Thr Gly Gln Phe Leu Tyr Gln Asp Ser Asn Trp
515 520 525

Ala Ser Lys Val Glu Lys Leu Thr Leu Asp Asn Ala Ala Phe Pro Phe
530 535 540

Leu Ala Tyr Ser Gly Ile Pro Ala Val Ser Phe Cys Phe Cys Glu Asp
545 550 555 560

Thr Asp Tyr Pro Tyr Leu Gly Thr Thr Met Asp Thr Tyr Lys Glu Leu
565 570 575

Ile Glu Arg Ile Pro Glu Leu Asn Lys Val Ala Arg Ala Ala Ala Glu
580 585 590

Val Ala Gly Gln Phe Val Ile Lys Leu Thr His Asp Val Glu Leu Asn
595 600 605

Leu Asp Tyr Glu Arg Tyr Asn Ser Gln Leu Leu Ser Phe Val Arg Asp
610 615 620

Leu Asn Gln Tyr Arg Ala Asp Ile Lys Glu Met Gly Leu Ser Leu Gln
625 630 635 640

Trp Leu Tyr Ser Ala Arg Gly Asp Phe Phe Arg Ala Thr Ser Arg Leu
645 650 655

Thr Thr Asp Phe Gly Asn Ala Glu Lys Thr Asp Arg Phe Val Met Lys
660 665 670

Lys Leu Asn Asp Arg Val Met Arg Val Glu Tyr His Phe Leu Ser Pro
675 680 685

Tyr Val Ser Pro Lys Glu Ser Pro Phe Arg His Val Phe Trp Gly Ser
690 695 700

Gly Ser His Thr Leu Pro Ala Leu Leu Glu Asn Leu Lys Leu Arg Lys
705 710 715 720

Gln Asn Asn Gly Ala Phe Asn Glu Thr Leu Phe Arg Asn Gln Leu Ala
725 730 735

Leu Ala Thr Trp Thr Ile Gln Gly Ala Ala Asn Ala Leu Ser Gly Asp
740 745 750

Val Trp Asp Ile Asp Asn Glu Phe
755 760

<210> SEQ ID NO 192
<211> LENGTH: 310
<212> TYPE: PRT
<213> ORGANISM: Homo sapiens

<400> SEQUENCE: 192

Met Arg Arg Ala Ala Leu Trp Leu Trp Leu Cys Ala Leu Ala Leu Ser
1 5 10 15

Leu Gln Pro Ala Leu Pro Gln Ile Val Ala Thr Asn Leu Pro Pro Glu
20 25 30

Asp Gln Asp Gly Ser Gly Asp Asp Ser Asp Asn Phe Ser Gly Ser Gly
35 40 45

Ala Gly Ala Leu Gln Asp Ile Thr Leu Ser Gln Gln Thr Pro Ser Thr
50 55 60

Trp Lys Asp Thr Gln Leu Leu Thr Ala Ile Pro Thr Ser Pro Glu Pro
65 70 75 80

Thr Gly Leu Glu Ala Thr Ala Ala Ser Thr Ser Thr Leu Pro Ala Gly
85 90 95

Glu Gly Pro Lys Glu Gly Glu Ala Val Val Leu Pro Glu Val Glu Pro
100 105 110

Gly Leu Thr Ala Arg Glu Gln Glu Ala Thr Pro Arg Pro Arg Glu Thr
115 120 125

Thr Gln Leu Pro Thr Thr His Gln Ala Ser Thr Thr Thr Ala Thr Thr
130 135 140

Ala Gln Glu Pro Ala Thr Ser His Pro His Arg Asp Met Gln Pro Gly
145 150 155 160

His His Glu Thr Ser Thr Pro Ala Gly Pro Ser Gln Ala Asp Leu His
165 170 175

Thr Pro His Thr Glu Asp Gly Gly Pro Ser Ala Thr Glu Arg Ala Ala
180 185 190

Glu Asp Gly Ala Ser Ser Gln Leu Pro Ala Ala Glu Gly Ser Gly Glu
195 200 205

Gln Asp Phe Thr Phe Glu Thr Ser Gly Glu Asn Thr Ala Val Val Ala
210 215 220

Val Glu Pro Asp Arg Arg Asn Gln Ser Pro Val Asp Gln Gly Ala Thr
225 230 235 240

Gly Ala Ser Gln Gly Leu Leu Asp Arg Lys Glu Val Leu Gly Gly Val
245 250 255

Ile Ala Gly Gly Leu Val Gly Leu Ile Phe Ala Val Cys Leu Val Gly
260 265 270

Phe Met Leu Tyr Arg Met Lys Lys Lys Asp Glu Gly Ser Tyr Ser Leu
275 280 285

Glu Glu Pro Lys Gln Ala Asn Gly Gly Ala Tyr Gln Lys Pro Thr Lys
290 295 300

Gln Glu Glu Phe Tyr Ala
305 310

<210> SEQ ID NO 193
<211> LENGTH: 201
<212> TYPE: PRT
<213> ORGANISM: Homo sapiens

<400> SEQUENCE: 193

Met Arg Arg Ala Trp Ile Leu Leu Thr Leu Gly Leu Val Ala Cys Val
1 5 10 15

Ser Ala Glu Ser Arg Ala Glu Leu Thr Ser Asp Lys Asp Met Tyr Leu
20 25 30

Asp Asn Ser Ser Ile Glu Glu Ala Ser Gly Val Tyr Pro Ile Asp Asp
35 40 45

Asp Asp Tyr Ala Ser Ala Ser Gly Ser Gly Ala Asp Glu Asp Val Glu
50 55 60

Ser Pro Glu Leu Thr Thr Ser Arg Pro Leu Pro Lys Ile Leu Leu Thr
65 70 75 80

Ser Ala Ala Pro Lys Val Glu Thr Thr Thr Leu Asn Ile Gln Asn Lys
85 90 95

Ile Pro Ala Gln Thr Lys Ser Pro Glu Glu Thr Asp Lys Glu Lys Val
100 105 110

His Leu Ser Asp Ser Glu Arg Lys Met Asp Pro Ala Glu Glu Asp Thr
115 120 125

Asn Val Tyr Thr Glu Lys His Ser Asp Ser Leu Phe Lys Arg Thr Glu

```
    130                 135                 140

Val Leu Ala Ala Val Ile Ala Gly Gly Val Ile Gly Phe Leu Phe Ala
145                 150                 155                 160

Ile Phe Leu Ile Leu Leu Leu Val Tyr Arg Met Arg Lys Lys Asp Glu
                165                 170                 175

Gly Ser Tyr Asp Leu Gly Glu Arg Lys Pro Ser Ser Ala Ala Tyr Gln
            180                 185                 190

Lys Ala Pro Thr Lys Glu Phe Tyr Ala
        195                 200


<210> SEQ ID NO 194
<211> LENGTH: 442
<212> TYPE: PRT
<213> ORGANISM: Homo sapiens

<400> SEQUENCE: 194

Met Lys Pro Gly Pro Pro His Arg Ala Gly Ala Ala His Gly Ala Gly
1               5                   10                  15

Ala Gly Ala Gly Ala Ala Ala Gly Pro Gly Ala Arg Gly Leu Leu Leu
            20                  25                  30

Pro Pro Leu Leu Leu Leu Leu Leu Ala Gly Arg Ala Ala Gly Ala Gln
        35                  40                  45

Arg Trp Arg Ser Glu Asn Phe Glu Arg Pro Val Asp Leu Glu Gly Ser
    50                  55                  60

Gly Asp Asp Asp Ser Phe Pro Asp Asp Glu Leu Asp Asp Leu Tyr Ser
65                  70                  75                  80

Gly Ser Gly Ser Gly Tyr Phe Glu Gln Glu Ser Gly Ile Glu Thr Ala
                85                  90                  95

Met Arg Phe Ser Pro Asp Val Ala Leu Ala Val Ser Thr Thr Pro Ala
            100                 105                 110

Val Leu Pro Thr Thr Asn Ile Gln Pro Val Gly Thr Pro Phe Glu Glu
        115                 120                 125

Leu Pro Ser Glu Arg Pro Thr Leu Glu Pro Ala Thr Ser Pro Leu Val
    130                 135                 140

Val Thr Glu Val Pro Glu Glu Pro Ser Gln Arg Ala Thr Thr Val Ser
145                 150                 155                 160

Thr Thr Met Ala Thr Thr Ala Ala Thr Ser Thr Gly Asp Pro Thr Val
                165                 170                 175

Ala Thr Val Pro Ala Thr Val Ala Thr Ala Thr Pro Ser Thr Pro Ala
            180                 185                 190

Ala Pro Pro Phe Thr Ala Thr Thr Ala Val Ile Arg Thr Thr Gly Val
        195                 200                 205

Arg Arg Leu Leu Pro Leu Pro Leu Thr Thr Val Ala Thr Ala Arg Ala
    210                 215                 220

Thr Thr Pro Glu Ala Pro Ser Pro Pro Thr Thr Ala Ala Val Leu Asp
225                 230                 235                 240

Thr Glu Ala Pro Thr Pro Arg Leu Val Ser Thr Ala Thr Ser Arg Pro
                245                 250                 255

Arg Ala Leu Pro Arg Pro Ala Thr Thr Gln Glu Pro Asp Ile Pro Glu
            260                 265                 270

Arg Ser Thr Leu Pro Leu Gly Thr Thr Ala Pro Gly Pro Thr Glu Val
        275                 280                 285

Ala Gln Thr Pro Thr Pro Glu Thr Phe Leu Thr Thr Ile Arg Asp Glu
    290                 295                 300
```

-continued

Pro Glu Val Pro Val Ser Gly Gly Pro Ser Gly Asp Phe Glu Leu Pro
305 310 315 320

Glu Glu Glu Thr Thr Gln Pro Asp Thr Ala Asn Glu Val Val Ala Val
325 330 335

Gly Gly Ala Ala Ala Lys Ala Ser Ser Pro Pro Gly Thr Leu Pro Lys
340 345 350

Gly Ala Arg Pro Gly Pro Gly Leu Leu Asp Asn Ala Ile Asp Ser Gly
355 360 365

Ser Ser Ala Ala Gln Leu Pro Gln Lys Ser Ile Leu Glu Arg Lys Glu
370 375 380

Val Leu Val Ala Val Ile Val Gly Gly Val Val Gly Ala Leu Phe Ala
385 390 395 400

Ala Phe Leu Val Thr Leu Leu Ile Tyr Arg Met Lys Lys Lys Asp Glu
405 410 415

Gly Ser Tyr Thr Leu Glu Glu Pro Lys Gln Ala Ser Val Thr Tyr Gln
420 425 430

Lys Pro Asp Lys Gln Glu Glu Phe Tyr Ala
435 440

<210> SEQ ID NO 195
<211> LENGTH: 198
<212> TYPE: PRT
<213> ORGANISM: Homo sapiens

<400> SEQUENCE: 195

Met Ala Pro Ala Arg Leu Phe Ala Leu Leu Leu Phe Phe Val Gly Gly
1 5 10 15

Val Ala Glu Ser Ile Arg Glu Thr Glu Val Ile Asp Pro Gln Asp Leu
20 25 30

Leu Glu Gly Arg Tyr Phe Ser Gly Ala Leu Pro Asp Asp Glu Asp Val
35 40 45

Val Gly Pro Gly Gln Glu Ser Asp Asp Phe Glu Leu Ser Gly Ser Gly
50 55 60

Asp Leu Asp Asp Leu Glu Asp Ser Met Ile Gly Pro Glu Val Val His
65 70 75 80

Pro Leu Val Pro Leu Asp Asn His Ile Pro Glu Arg Ala Gly Ser Gly
85 90 95

Ser Gln Val Pro Thr Glu Pro Lys Lys Leu Glu Glu Asn Glu Val Ile
100 105 110

Pro Lys Arg Ile Ser Pro Val Glu Glu Ser Glu Asp Val Ser Asn Lys
115 120 125

Val Ser Met Ser Ser Thr Val Gln Gly Ser Asn Ile Phe Glu Arg Thr
130 135 140

Glu Val Leu Ala Ala Leu Ile Val Gly Gly Ile Val Gly Ile Leu Phe
145 150 155 160

Ala Val Phe Leu Ile Leu Leu Leu Met Tyr Arg Met Lys Lys Lys Asp
165 170 175

Glu Gly Ser Tyr Asp Leu Gly Lys Lys Pro Ile Tyr Lys Lys Ala Pro
180 185 190

Thr Asn Glu Phe Tyr Ala
195

<210> SEQ ID NO 196
<211> LENGTH: 4392
<212> TYPE: PRT
<213> ORGANISM: Homo sapiens -continued

<400> SEQUENCE: 196

```
Met Gly Trp Arg Ala Ala Gly Ala Leu Leu Leu Ala Leu Leu Leu His
1               5                   10                  15

Gly Arg Leu Leu Ala Val Thr His Gly Leu Arg Ala Tyr Asp Gly Leu
            20                  25                  30

Ser Leu Pro Glu Asp Ile Glu Thr Val Thr Ala Ser Gln Met Arg Trp
        35                  40                  45

Thr His Ser Tyr Leu Ser Asp Asp Glu Asp Met Leu Ala Asp Ser Ile
    50                  55                  60

Ser Gly Asp Asp Leu Gly Ser Gly Asp Leu Gly Ser Gly Asp Phe Gln
65                  70                  75                  80

Met Val Tyr Phe Arg Ala Leu Val Asn Phe Thr Arg Ser Ile Glu Tyr
                85                  90                  95

Ser Pro Gln Leu Glu Asp Ala Gly Ser Arg Glu Phe Arg Glu Val Ser
            100                 105                 110

Glu Ala Val Val Asp Thr Leu Glu Ser Glu Tyr Leu Lys Ile Pro Gly
        115                 120                 125

Asp Gln Val Val Ser Val Val Phe Ile Lys Glu Leu Asp Gly Trp Val
    130                 135                 140

Phe Val Glu Leu Asp Val Gly Ser Glu Gly Asn Ala Asp Gly Ala Gln
145                 150                 155                 160

Ile Gln Glu Met Leu Leu Arg Val Ile Ser Ser Gly Ser Val Ala Ser
                165                 170                 175

Tyr Val Thr Ser Pro Gln Gly Phe Gln Phe Arg Arg Leu Gly Thr Val
            180                 185                 190

Pro Gln Phe Pro Arg Ala Cys Thr Glu Ala Glu Phe Ala Cys His Ser
        195                 200                 205

Tyr Asn Glu Cys Val Ala Leu Glu Tyr Arg Cys Asp Arg Arg Pro Asp
    210                 215                 220

Cys Arg Asp Met Ser Asp Glu Leu Asn Cys Glu Glu Pro Val Leu Gly
225                 230                 235                 240

Ile Ser Pro Thr Phe Ser Leu Leu Val Glu Thr Thr Ser Leu Pro Pro
                245                 250                 255

Arg Pro Glu Thr Thr Ile Met Arg Gln Pro Pro Val Thr His Ala Pro
            260                 265                 270

Gln Pro Leu Leu Pro Gly Ser Val Arg Pro Leu Pro Cys Gly Pro Gln
        275                 280                 285

Glu Ala Ala Cys Arg Asn Gly His Cys Ile Pro Arg Asp Tyr Leu Cys
    290                 295                 300

Asp Gly Gln Glu Asp Cys Glu Asp Gly Ser Asp Glu Leu Asp Cys Gly
305                 310                 315                 320

Pro Pro Pro Pro Cys Glu Pro Asn Glu Phe Pro Cys Gly Asn Gly His
                325                 330                 335

Cys Ala Leu Lys Leu Trp Arg Cys Asp Gly Asp Phe Asp Cys Glu Asp
            340                 345                 350

Arg Thr Asp Glu Ala Asn Cys Pro Thr Lys Arg Pro Glu Glu Val Cys
        355                 360                 365

Gly Pro Thr Gln Phe Arg Cys Val Ser Thr Asn Met Cys Ile Pro Ala
    370                 375                 380

Ser Phe His Cys Asp Glu Glu Ser Asp Cys Pro Asp Arg Ser Asp Glu
385                 390                 395                 400

Phe Gly Cys Met Pro Pro Gln Val Val Thr Pro Pro Arg Glu Ser Ile
```

-continued

```
                405                 410                 415

Gln Ala Ser Arg Gly Gln Thr Val Thr Phe Thr Cys Val Ala Ile Gly
            420                 425                 430

Val Pro Thr Pro Ile Ile Asn Trp Arg Leu Asn Trp Gly His Ile Pro
        435                 440                 445

Ser His Pro Arg Val Thr Val Thr Ser Glu Gly Gly Arg Gly Thr Leu
    450                 455                 460

Ile Ile Arg Asp Val Lys Glu Ser Asp Gln Gly Ala Tyr Thr Cys Glu
465                 470                 475                 480

Ala Met Asn Ala Arg Gly Met Val Phe Gly Ile Pro Asp Gly Val Leu
                485                 490                 495

Glu Leu Val Pro Gln Arg Ala Gly Pro Cys Pro Asp Gly His Phe Tyr
            500                 505                 510

Leu Glu His Ser Ala Ala Cys Leu Pro Cys Phe Cys Phe Gly Ile Thr
        515                 520                 525

Ser Val Cys Gln Ser Thr Arg Arg Phe Arg Asp Gln Ile Arg Leu Arg
    530                 535                 540

Phe Asp Gln Pro Asp Asp Phe Lys Gly Val Asn Val Thr Met Pro Ala
545                 550                 555                 560

Gln Pro Gly Thr Pro Pro Leu Ser Ser Thr Gln Leu Gln Ile Asp Pro
                565                 570                 575

Ser Leu His Glu Phe Gln Leu Val Asp Leu Ser Arg Arg Phe Leu Val
            580                 585                 590

His Asp Ser Phe Trp Ala Leu Pro Glu Gln Phe Leu Gly Asn Lys Val
        595                 600                 605

Asp Ser Tyr Gly Gly Ser Leu Arg Tyr Asn Val Arg Tyr Glu Leu Ala
    610                 615                 620

Arg Gly Met Leu Glu Pro Val Gln Arg Pro Asp Val Val Leu Met Gly
625                 630                 635                 640

Ala Gly Tyr Arg Leu Leu Ser Arg Gly His Thr Pro Thr Gln Pro Gly
                645                 650                 655

Ala Leu Asn Gln Arg Gln Val Gln Phe Ser Glu Glu His Trp Val His
            660                 665                 670

Glu Ser Gly Arg Pro Val Gln Arg Ala Glu Leu Leu Gln Val Leu Gln
        675                 680                 685

Ser Leu Glu Ala Val Leu Ile Gln Thr Val Tyr Asn Thr Lys Met Ala
    690                 695                 700

Ser Val Gly Leu Ser Asp Ile Ala Met Asp Thr Thr Val Thr His Ala
705                 710                 715                 720

Thr Ser His Gly Arg Ala His Ser Val Glu Glu Cys Arg Cys Pro Ile
                725                 730                 735

Gly Tyr Ser Gly Leu Ser Cys Glu Ser Cys Asp Ala His Phe Thr Arg
            740                 745                 750

Val Pro Gly Gly Pro Tyr Leu Gly Thr Cys Ser Gly Cys Asn Cys Asn
        755                 760                 765

Gly His Ala Ser Ser Cys Asp Pro Val Tyr Gly His Cys Leu Asn Cys
    770                 775                 780

Gln His Asn Thr Glu Gly Pro Gln Cys Asn Lys Cys Lys Ala Gly Phe
785                 790                 795                 800

Phe Gly Asp Ala Met Lys Ala Thr Ala Thr Ser Cys Arg Pro Cys Pro
                805                 810                 815

Cys Pro Tyr Ile Asp Ala Ser Arg Arg Phe Ser Asp Thr Cys Phe Leu
            820                 825                 830
```

```
Asp Thr Asp Gly Gln Ala Thr Cys Asp Ala Cys Ala Pro Gly Tyr Thr
        835                 840                 845

Gly Arg Arg Cys Glu Ser Cys Ala Pro Gly Tyr Glu Gly Asn Pro Ile
    850                 855                 860

Gln Pro Gly Gly Lys Cys Arg Pro Val Asn Gln Glu Ile Val Arg Cys
865                 870                 875                 880

Asp Glu Arg Gly Ser Met Gly Thr Ser Gly Glu Ala Cys Arg Cys Lys
                885                 890                 895

Asn Asn Val Val Gly Arg Leu Cys Asn Glu Cys Ala Asp Gly Ser Phe
            900                 905                 910

His Leu Ser Thr Arg Asn Pro Asp Gly Cys Leu Lys Cys Phe Cys Met
        915                 920                 925

Gly Val Ser Arg His Cys Thr Ser Ser Ser Trp Ser Arg Ala Gln Leu
    930                 935                 940

His Gly Ala Ser Glu Glu Pro Gly His Phe Ser Leu Thr Asn Ala Ala
945                 950                 955                 960

Ser Thr His Thr Thr Asn Glu Gly Ile Phe Ser Pro Thr Pro Gly Glu
                965                 970                 975

Leu Gly Phe Ser Ser Phe His Arg Leu Leu Ser Gly Pro Tyr Phe Trp
            980                 985                 990

Ser Leu Pro Ser Arg Phe Leu Gly  Asp Lys Val Thr Ser  Tyr Gly Gly
        995                 1000                1005

Glu Leu  Arg Phe Thr Val Thr  Gln Arg Ser Gln Pro  Gly Ser Thr
    1010                1015                1020

Pro Leu  His Gly Gln Pro Leu  Val Val Leu Gln Gly  Asn Asn Ile
    1025                1030                1035

Ile Leu  Glu His His Val Ala  Gln Glu Pro Ser Pro  Gly Gln Pro
    1040                1045                1050

Ser Thr  Phe Ile Val Pro Phe  Arg Glu Gln Ala Trp  Gln Arg Pro
    1055                1060                1065

Asp Gly  Gln Pro Ala Thr Arg  Glu His Leu Leu Met  Ala Leu Ala
    1070                1075                1080

Gly Ile  Asp Thr Leu Leu Ile  Arg Ala Ser Tyr Ala  Gln Gln Pro
    1085                1090                1095

Ala Glu  Ser Arg Val Ser Gly  Ile Ser Met Asp Val  Ala Val Pro
    1100                1105                1110

Glu Glu  Thr Gly Gln Asp Pro  Ala Leu Glu Val Glu  Gln Cys Ser
    1115                1120                1125

Cys Pro  Pro Gly Tyr Arg Gly  Pro Ser Cys Gln Asp  Cys Asp Thr
    1130                1135                1140

Gly Tyr  Thr Arg Thr Pro Ser  Gly Leu Tyr Leu Gly  Thr Cys Glu
    1145                1150                1155

Arg Cys  Ser Cys His Gly His  Ser Glu Ala Cys Glu  Pro Glu Thr
    1160                1165                1170

Gly Ala  Cys Gln Gly Cys Gln  His His Thr Glu Gly  Pro Arg Cys
    1175                1180                1185

Glu Gln  Cys Gln Pro Gly Tyr  Tyr Gly Asp Ala Gln  Arg Gly Thr
    1190                1195                1200

Pro Gln  Asp Cys Gln Leu Cys  Pro Cys Tyr Gly Asp  Pro Ala Ala
    1205                1210                1215

Gly Gln  Ala Ala His Thr Cys  Phe Leu Asp Thr Asp  Gly His Pro
    1220                1225                1230
```

-continued

```
Thr Cys Asp Ala Cys Ser Pro Gly His Ser Gly Arg His Cys Glu
    1235                1240                1245

Arg Cys Ala Pro Gly Tyr Tyr Gly Asn Pro Ser Gln Gly Gln Pro
    1250                1255                1260

Cys Gln Arg Asp Ser Gln Val Pro Gly Pro Ile Gly Cys Asn Cys
    1265                1270                1275

Asp Pro Gln Gly Ser Val Ser Ser Gln Cys Asp Ala Ala Gly Gln
    1280                1285                1290

Cys Gln Cys Lys Ala Gln Val Glu Gly Leu Thr Cys Ser His Cys
    1295                1300                1305

Arg Pro His His Phe His Leu Ser Ala Ser Asn Pro Asp Gly Cys
    1310                1315                1320

Leu Pro Cys Phe Cys Met Gly Ile Thr Gln Gln Cys Ala Ser Ser
    1325                1330                1335

Ala Tyr Thr Arg His Leu Ile Ser Thr His Phe Ala Pro Gly Asp
    1340                1345                1350

Phe Gln Gly Phe Ala Leu Val Asn Pro Gln Arg Asn Ser Arg Leu
    1355                1360                1365

Thr Gly Glu Phe Thr Val Glu Pro Val Pro Glu Gly Ala Gln Leu
    1370                1375                1380

Ser Phe Gly Asn Phe Ala Gln Leu Gly His Glu Ser Phe Tyr Trp
    1385                1390                1395

Gln Leu Pro Glu Thr Tyr Gln Gly Asp Lys Val Ala Ala Tyr Gly
    1400                1405                1410

Gly Lys Leu Arg Tyr Thr Leu Ser Tyr Thr Ala Gly Pro Gln Gly
    1415                1420                1425

Ser Pro Leu Ser Asp Pro Asp Val Gln Ile Thr Gly Asn Asn Ile
    1430                1435                1440

Met Leu Val Ala Ser Gln Pro Ala Leu Gln Gly Pro Glu Arg Arg
    1445                1450                1455

Ser Tyr Glu Ile Met Phe Arg Glu Glu Phe Trp Arg Arg Pro Asp
    1460                1465                1470

Gly Gln Pro Ala Thr Arg Glu His Leu Leu Met Ala Leu Ala Asp
    1475                1480                1485

Leu Asp Glu Leu Leu Ile Arg Ala Thr Phe Ser Ser Val Pro Leu
    1490                1495                1500

Ala Ala Ser Ile Ser Ala Val Ser Leu Glu Val Ala Gln Pro Gly
    1505                1510                1515

Pro Ser Asn Arg Pro Arg Ala Leu Glu Val Glu Glu Cys Arg Cys
    1520                1525                1530

Pro Pro Gly Tyr Ile Gly Leu Ser Cys Gln Asp Cys Ala Pro Gly
    1535                1540                1545

Tyr Thr Arg Thr Gly Ser Gly Leu Tyr Leu Gly His Cys Glu Leu
    1550                1555                1560

Cys Glu Cys Asn Gly His Ser Asp Leu Cys His Pro Glu Thr Gly
    1565                1570                1575

Ala Cys Ser Gln Cys Gln His Asn Ala Ala Gly Glu Phe Cys Glu
    1580                1585                1590

Leu Cys Ala Pro Gly Tyr Tyr Gly Asp Ala Thr Ala Gly Thr Pro
    1595                1600                1605

Glu Asp Cys Gln Pro Cys Ala Cys Pro Leu Thr Asn Pro Glu Asn
    1610                1615                1620

Met Phe Ser Arg Thr Cys Glu Ser Leu Gly Ala Gly Gly Tyr Arg
```

-continued

```
    1625                1630                1635

Cys Thr  Ala Cys Glu Pro Gly  Tyr Thr Gly Gln Tyr  Cys Glu Gln
    1640                1645                1650

Cys Gly  Pro Gly Tyr Val Gly  Asn Pro Ser Val Gln  Gly Gly Gln
    1655                1660                1665

Cys Leu  Pro Glu Thr Asn Gln  Ala Pro Leu Val Val  Glu Val His
    1670                1675                1680

Pro Ala  Arg Ser Ile Val Pro  Gln Gly Gly Ser His  Ser Leu Arg
    1685                1690                1695

Cys Gln  Val Ser Gly Ser Pro  Pro His Tyr Phe Tyr  Trp Ser Arg
    1700                1705                1710

Glu Asp  Gly Arg Pro Val Pro  Ser Gly Thr Gln Gln  Arg His Gln
    1715                1720                1725

Gly Ser  Glu Leu His Phe Pro  Ser Val Gln Pro Ser  Asp Ala Gly
    1730                1735                1740

Val Tyr  Ile Cys Thr Cys Arg  Asn Leu His Gln Ser  Asn Thr Ser
    1745                1750                1755

Arg Ala  Glu Leu Leu Val Thr  Glu Ala Pro Ser Lys  Pro Ile Thr
    1760                1765                1770

Val Thr  Val Glu Glu Gln Arg  Ser Gln Ser Val Arg  Pro Gly Ala
    1775                1780                1785

Asp Val  Thr Phe Ile Cys Thr  Ala Lys Ser Lys Ser  Pro Ala Tyr
    1790                1795                1800

Thr Leu  Val Trp Thr Arg Leu  His Asn Gly Lys Leu  Pro Thr Arg
    1805                1810                1815

Ala Met  Asp Phe Asn Gly Ile  Leu Thr Ile Arg Asn  Val Gln Leu
    1820                1825                1830

Ser Asp  Ala Gly Thr Tyr Val  Cys Thr Gly Ser Asn  Met Phe Ala
    1835                1840                1845

Met Asp  Gln Gly Thr Ala Thr  Leu His Val Gln Ala  Ser Gly Thr
    1850                1855                1860

Leu Ser  Ala Pro Val Val Ser  Ile His Pro Pro Gln  Leu Thr Val
    1865                1870                1875

Gln Pro  Gly Gln Leu Ala Glu  Phe Arg Cys Ser Ala  Thr Gly Ser
    1880                1885                1890

Pro Thr  Pro Thr Leu Glu Trp  Thr Gly Gly Pro Gly  Gly Gln Leu
    1895                1900                1905

Pro Ala  Lys Ala Gln Ile His  Gly Gly Ile Leu Arg  Leu Pro Ala
    1910                1915                1920

Val Glu  Pro Thr Asp Gln Ala  Gln Tyr Leu Cys Arg  Ala His Ser
    1925                1930                1935

Ser Ala  Gly Gln Gln Val Ala  Arg Ala Val Leu His  Val His Gly
    1940                1945                1950

Gly Gly  Gly Pro Arg Val Gln  Val Ser Pro Glu Arg  Thr Gln Val
    1955                1960                1965

His Ala  Gly Arg Thr Val Arg  Leu Tyr Cys Arg Ala  Ala Gly Val
    1970                1975                1980

Pro Ser  Ala Thr Ile Thr Trp  Arg Lys Glu Gly Gly  Ser Leu Pro
    1985                1990                1995

Pro Gln  Ala Arg Ser Glu Arg  Thr Asp Ile Ala Thr  Leu Leu Ile
    2000                2005                2010

Pro Ala  Ile Thr Thr Ala Asp  Ala Gly Phe Tyr Leu  Cys Val Ala
    2015                2020                2025
```

-continued

```
Thr Ser  Pro Ala Gly Thr Ala  Gln Ala Arg Ile Gln  Val Val Val
    2030                 2035                 2040

Leu Ser  Ala Ser Asp Ala Ser  Pro Pro Pro Val Lys  Ile Glu Ser
    2045                 2050                 2055

Ser Ser  Pro Ser Val Thr Glu  Gly Gln Thr Leu Asp  Leu Asn Cys
    2060                 2065                 2070

Val Val  Ala Gly Ser Ala His  Ala Gln Val Thr Trp  Tyr Arg Arg
    2075                 2080                 2085

Gly Gly  Ser Leu Pro Pro His  Thr Gln Val His Gly  Ser Arg Leu
    2090                 2095                 2100

Arg Leu  Pro Gln Val Ser Pro  Ala Asp Ser Gly Glu  Tyr Val Cys
    2105                 2110                 2115

Arg Val  Glu Asn Gly Ser Gly  Pro Lys Glu Ala Ser  Ile Thr Val
    2120                 2125                 2130

Ser Val  Leu His Gly Thr His  Ser Gly Pro Ser Tyr  Thr Pro Val
    2135                 2140                 2145

Pro Gly  Ser Thr Arg Pro Ile  Arg Ile Glu Pro Ser  Ser Ser His
    2150                 2155                 2160

Val Ala  Glu Gly Gln Thr Leu  Asp Leu Asn Cys Val  Val Pro Gly
    2165                 2170                 2175

Gln Ala  His Ala Gln Val Thr  Trp His Lys Arg Gly  Gly Ser Leu
    2180                 2185                 2190

Pro Ala  Arg His Gln Thr His  Gly Ser Leu Leu Arg  Leu His Gln
    2195                 2200                 2205

Val Thr  Pro Ala Asp Ser Gly  Glu Tyr Val Cys His  Val Val Gly
    2210                 2215                 2220

Thr Ser  Gly Pro Leu Glu Ala  Ser Val Leu Val Thr  Ile Glu Ala
    2225                 2230                 2235

Ser Val  Ile Pro Gly Pro Ile  Pro Pro Val Arg Ile  Glu Ser Ser
    2240                 2245                 2250

Ser Ser  Thr Val Ala Glu Gly  Gln Thr Leu Asp Leu  Ser Cys Val
    2255                 2260                 2265

Val Ala  Gly Gln Ala His Ala  Gln Val Thr Trp Tyr  Lys Arg Gly
    2270                 2275                 2280

Gly Ser  Leu Pro Ala Arg His  Gln Val Arg Gly Ser  Arg Leu Tyr
    2285                 2290                 2295

Ile Phe  Gln Ala Ser Pro Ala  Asp Ala Gly Gln Tyr  Val Cys Arg
    2300                 2305                 2310

Ala Ser  Asn Gly Met Glu Ala  Ser Ile Thr Val Thr  Val Thr Gly
    2315                 2320                 2325

Thr Gln  Gly Ala Asn Leu Ala  Tyr Pro Ala Gly Ser  Thr Gln Pro
    2330                 2335                 2340

Ile Arg  Ile Glu Pro Ser Ser  Ser Gln Val Ala Glu  Gly Gln Thr
    2345                 2350                 2355

Leu Asp  Leu Asn Cys Val Val  Pro Gly Gln Ser His  Ala Gln Val
    2360                 2365                 2370

Thr Trp  His Lys Arg Gly Gly  Ser Leu Pro Val Arg  His Gln Thr
    2375                 2380                 2385

His Gly  Ser Leu Leu Arg Leu  Tyr Gln Ala Ser Pro  Ala Asp Ser
    2390                 2395                 2400

Gly Glu  Tyr Val Cys Arg Val  Leu Gly Ser Ser Val  Pro Leu Glu
    2405                 2410                 2415
```

```
Ala Ser  Val Leu Val Thr Ile  Glu Pro Ala Gly Ser  Val Pro Ala
    2420                 2425                 2430

Leu Gly  Val Thr Pro Thr Val  Arg Ile Glu Ser Ser  Ser Ser Gln
    2435                 2440                 2445

Val Ala  Glu Gly Gln Thr Leu  Asp Leu Asn Cys Leu  Val Ala Gly
    2450                 2455                 2460

Gln Ala  His Ala Gln Val Thr  Trp His Lys Arg Gly  Gly Ser Leu
    2465                 2470                 2475

Pro Ala  Arg His Gln Val His  Gly Ser Arg Leu Arg  Leu Leu Gln
    2480                 2485                 2490

Val Thr  Pro Ala Asp Ser Gly  Glu Tyr Val Cys Arg  Val Val Gly
    2495                 2500                 2505

Ser Ser  Gly Thr Gln Glu Ala  Ser Val Leu Val Thr  Ile Gln Gln
    2510                 2515                 2520

Arg Leu  Ser Gly Ser His Ser  Gln Gly Val Ala Tyr  Pro Val Arg
    2525                 2530                 2535

Ile Glu  Ser Ser Ser Ala Ser  Leu Ala Asn Gly His  Thr Leu Asp
    2540                 2545                 2550

Leu Asn  Cys Leu Val Ala Ser  Gln Ala Pro His Thr  Ile Thr Trp
    2555                 2560                 2565

Tyr Lys  Arg Gly Gly Ser Leu  Pro Ser Arg His Gln  Ile Val Gly
    2570                 2575                 2580

Ser Arg  Leu Arg Ile Pro Gln  Val Thr Pro Ala Asp  Ser Gly Glu
    2585                 2590                 2595

Tyr Val  Cys His Val Ser Asn  Gly Ala Gly Ser Arg  Glu Thr Ser
    2600                 2605                 2610

Leu Ile  Val Thr Ile Gln Gly  Ser Gly Ser Ser His  Val Pro Ser
    2615                 2620                 2625

Val Ser  Pro Pro Ile Arg Ile  Glu Ser Ser Ser Pro  Thr Val Val
    2630                 2635                 2640

Glu Gly  Gln Thr Leu Asp Leu  Asn Cys Val Val Ala  Arg Gln Pro
    2645                 2650                 2655

Gln Ala  Ile Ile Thr Trp Tyr  Lys Arg Gly Gly Ser  Leu Pro Ser
    2660                 2665                 2670

Arg His  Gln Thr His Gly Ser  His Leu Arg Leu His  Gln Met Ser
    2675                 2680                 2685

Val Ala  Asp Ser Gly Glu Tyr  Val Cys Arg Ala Asn  Asn Asn Ile
    2690                 2695                 2700

Asp Ala  Leu Glu Ala Ser Ile  Val Ile Ser Val Ser  Pro Ser Ala
    2705                 2710                 2715

Gly Ser  Pro Ser Ala Pro Gly  Ser Ser Met Pro Ile  Arg Ile Glu
    2720                 2725                 2730

Ser Ser  Ser Ser His Val Ala  Glu Gly Glu Thr Leu  Asp Leu Asn
    2735                 2740                 2745

Cys Val  Val Pro Gly Gln Ala  His Ala Gln Val Thr  Trp His Lys
    2750                 2755                 2760

Arg Gly  Gly Ser Leu Pro Ser  His His Gln Thr Arg  Gly Ser Arg
    2765                 2770                 2775

Leu Arg  Leu His His Val Ser  Pro Ala Asp Ser Gly  Glu Tyr Val
    2780                 2785                 2790

Cys Arg  Val Met Gly Ser Ser  Gly Pro Leu Glu Ala  Ser Val Leu
    2795                 2800                 2805

Val Thr  Ile Glu Ala Ser Gly  Ser Ser Ala Val His  Val Pro Ala
```

```
    2810                2815                2820

Pro Gly Gly Ala Pro Pro Ile Arg Ile Glu Pro Ser Ser Ser Arg
    2825                2830                2835

Val Ala Glu Gly Gln Thr Leu Asp Leu Lys Cys Val Val Pro Gly
    2840                2845                2850

Gln Ala His Ala Gln Val Thr Trp His Lys Arg Gly Gly Asn Leu
    2855                2860                2865

Pro Ala Arg His Gln Val His Gly Pro Leu Leu Arg Leu Asn Gln
    2870                2875                2880

Val Ser Pro Ala Asp Ser Gly Glu Tyr Ser Cys Gln Val Thr Gly
    2885                2890                2895

Ser Ser Gly Thr Leu Glu Ala Ser Val Leu Val Thr Ile Glu Pro
    2900                2905                2910

Ser Ser Pro Gly Pro Ile Pro Ala Pro Gly Leu Ala Gln Pro Ile
    2915                2920                2925

Tyr Ile Glu Ala Ser Ser Ser His Val Thr Glu Gly Gln Thr Leu
    2930                2935                2940

Asp Leu Asn Cys Val Val Pro Gly Gln Ala His Ala Gln Val Thr
    2945                2950                2955

Trp Tyr Lys Arg Gly Gly Ser Leu Pro Ala Arg His Gln Thr His
    2960                2965                2970

Gly Ser Gln Leu Arg Leu His Leu Val Ser Pro Ala Asp Ser Gly
    2975                2980                2985

Glu Tyr Val Cys Arg Ala Ala Ser Gly Pro Gly Pro Glu Gln Glu
    2990                2995                3000

Ala Ser Phe Thr Val Thr Val Pro Pro Ser Glu Gly Ser Ser Tyr
    3005                3010                3015

Arg Leu Arg Ser Pro Val Ile Ser Ile Asp Pro Pro Ser Ser Thr
    3020                3025                3030

Val Gln Gln Gly Gln Asp Ala Ser Phe Lys Cys Leu Ile His Asp
    3035                3040                3045

Gly Ala Ala Pro Ile Ser Leu Glu Trp Lys Thr Arg Asn Gln Glu
    3050                3055                3060

Leu Glu Asp Asn Val His Ile Ser Pro Asn Gly Ser Ile Ile Thr
    3065                3070                3075

Ile Val Gly Thr Arg Pro Ser Asn His Gly Thr Tyr Arg Cys Val
    3080                3085                3090

Ala Ser Asn Ala Tyr Gly Val Ala Gln Ser Val Val Asn Leu Ser
    3095                3100                3105

Val His Gly Pro Pro Thr Val Ser Val Leu Pro Glu Gly Pro Val
    3110                3115                3120

Trp Val Lys Val Gly Lys Ala Val Thr Leu Glu Cys Val Ser Ala
    3125                3130                3135

Gly Glu Pro Arg Ser Ser Ala Arg Trp Thr Arg Ile Ser Ser Thr
    3140                3145                3150

Pro Ala Lys Leu Glu Gln Arg Thr Tyr Gly Leu Met Asp Ser His
    3155                3160                3165

Ala Val Leu Gln Ile Ser Ser Ala Lys Pro Ser Asp Ala Gly Thr
    3170                3175                3180

Tyr Val Cys Leu Ala Gln Asn Ala Leu Gly Thr Ala Gln Lys Gln
    3185                3190                3195

Val Glu Val Ile Val Asp Thr Gly Ala Met Ala Pro Gly Ala Pro
    3200                3205                3210
```

-continued

```
Gln Val Gln Ala Glu Glu Ala Glu Leu Thr Val Glu Ala Gly His
    3215                3220                3225

Thr Ala Thr Leu Arg Cys Ser Ala Thr Gly Ser Pro Ala Pro Thr
    3230                3235                3240

Ile His Trp Ser Lys Leu Arg Ser Pro Leu Pro Trp Gln His Arg
    3245                3250                3255

Leu Glu Gly Asp Thr Leu Ile Ile Pro Arg Val Ala Gln Gln Asp
    3260                3265                3270

Ser Gly Gln Tyr Ile Cys Asn Ala Thr Ser Pro Ala Gly His Ala
    3275                3280                3285

Glu Ala Thr Ile Ile Leu His Val Glu Ser Pro Pro Tyr Ala Thr
    3290                3295                3300

Thr Val Pro Glu His Ala Ser Val Gln Ala Gly Glu Thr Val Gln
    3305                3310                3315

Leu Gln Cys Leu Ala His Gly Thr Pro Pro Leu Thr Phe Gln Trp
    3320                3325                3330

Ser Arg Val Gly Ser Ser Leu Pro Gly Arg Ala Thr Ala Arg Asn
    3335                3340                3345

Glu Leu Leu His Phe Glu Arg Ala Ala Pro Glu Asp Ser Gly Arg
    3350                3355                3360

Tyr Arg Cys Arg Val Thr Asn Lys Val Gly Ser Ala Glu Ala Phe
    3365                3370                3375

Ala Gln Leu Leu Val Gln Gly Pro Pro Gly Ser Leu Pro Ala Thr
    3380                3385                3390

Ser Ile Pro Ala Gly Ser Thr Pro Thr Val Gln Val Thr Pro Gln
    3395                3400                3405

Leu Glu Thr Lys Ser Ile Gly Ala Ser Val Glu Phe His Cys Ala
    3410                3415                3420

Val Pro Ser Asp Arg Gly Thr Gln Leu Arg Trp Phe Lys Glu Gly
    3425                3430                3435

Gly Gln Leu Pro Pro Gly His Ser Val Gln Asp Gly Val Leu Arg
    3440                3445                3450

Ile Gln Asn Leu Asp Gln Ser Cys Gln Gly Thr Tyr Ile Cys Gln
    3455                3460                3465

Ala His Gly Pro Trp Gly Lys Ala Gln Ala Ser Ala Gln Leu Val
    3470                3475                3480

Ile Gln Ala Leu Pro Ser Val Leu Ile Asn Ile Arg Thr Ser Val
    3485                3490                3495

Gln Thr Val Val Val Gly His Ala Val Glu Phe Glu Cys Leu Ala
    3500                3505                3510

Leu Gly Asp Pro Lys Pro Gln Val Thr Trp Ser Lys Val Gly Gly
    3515                3520                3525

His Leu Arg Pro Gly Ile Val Gln Ser Gly Gly Val Val Arg Ile
    3530                3535                3540

Ala His Val Glu Leu Ala Asp Ala Gly Gln Tyr Arg Cys Thr Ala
    3545                3550                3555

Thr Asn Ala Ala Gly Thr Thr Gln Ser His Val Leu Leu Leu Val
    3560                3565                3570

Gln Ala Leu Pro Gln Ile Ser Met Pro Gln Glu Val Arg Val Pro
    3575                3580                3585

Ala Gly Ser Ala Ala Val Phe Pro Cys Ile Ala Ser Gly Tyr Pro
    3590                3595                3600
```

-continued

```
Thr Pro  Asp Ile Ser Trp Ser  Lys Leu Asp Gly Ser  Leu Pro Pro
    3605                 3610                 3615

Asp Ser  Arg Leu Glu Asn Asn  Met Leu Met Leu Pro  Ser Val Arg
    3620                 3625                 3630

Pro Gln  Asp Ala Gly Thr Tyr  Val Cys Thr Ala Thr  Asn Arg Gln
    3635                 3640                 3645

Gly Lys  Val Lys Ala Phe Ala  His Leu Gln Val Pro  Glu Arg Val
    3650                 3655                 3660

Val Pro  Tyr Phe Thr Gln Thr  Pro Tyr Ser Phe Leu  Pro Leu Pro
    3665                 3670                 3675

Thr Ile  Lys Asp Ala Tyr Arg  Lys Phe Glu Ile Lys  Ile Thr Phe
    3680                 3685                 3690

Arg Pro  Asp Ser Ala Asp Gly  Met Leu Leu Tyr Asn  Gly Gln Lys
    3695                 3700                 3705

Arg Val  Pro Gly Ser Pro Thr  Asn Leu Ala Asn Arg  Gln Pro Asp
    3710                 3715                 3720

Phe Ile  Ser Phe Gly Leu Val  Gly Gly Arg Pro Glu  Phe Arg Phe
    3725                 3730                 3735

Asp Ala  Gly Ser Gly Met Ala  Thr Ile Arg His Pro  Thr Pro Leu
    3740                 3745                 3750

Ala Leu  Gly His Phe His Thr  Val Thr Leu Leu Arg  Ser Leu Thr
    3755                 3760                 3765

Gln Gly  Ser Leu Ile Val Gly  Asp Leu Ala Pro Val  Asn Gly Thr
    3770                 3775                 3780

Ser Gln  Gly Lys Phe Gln Gly  Leu Asp Leu Asn Glu  Glu Leu Tyr
    3785                 3790                 3795

Leu Gly  Gly Tyr Pro Asp Tyr  Gly Ala Ile Pro Lys  Ala Gly Leu
    3800                 3805                 3810

Ser Ser  Gly Phe Ile Gly Cys  Val Arg Glu Leu Arg  Ile Gln Gly
    3815                 3820                 3825

Glu Glu  Ile Val Phe His Asp  Leu Asn Leu Thr Ala  His Gly Ile
    3830                 3835                 3840

Ser His  Cys Pro Thr Cys Arg  Asp Arg Pro Cys Gln  Asn Gly Gly
    3845                 3850                 3855

Gln Cys  His Asp Ser Glu Ser  Ser Ser Tyr Val Cys  Val Cys Pro
    3860                 3865                 3870

Ala Gly  Phe Thr Gly Ser Arg  Cys Glu His Ser Gln  Ala Leu His
    3875                 3880                 3885

Cys His  Pro Glu Ala Cys Gly  Pro Asp Ala Thr Cys  Val Asn Arg
    3890                 3895                 3900

Pro Asp  Gly Arg Gly Tyr Thr  Cys Arg Cys His Leu  Gly Arg Ser
    3905                 3910                 3915

Gly Leu  Arg Cys Glu Glu Gly  Val Thr Val Thr Thr  Pro Ser Leu
    3920                 3925                 3930

Ser Gly  Ala Gly Ser Tyr Leu  Ala Leu Pro Ala Leu  Thr Asn Thr
    3935                 3940                 3945

His His  Glu Leu Arg Leu Asp  Val Glu Phe Lys Pro  Leu Ala Pro
    3950                 3955                 3960

Asp Gly  Val Leu Leu Phe Ser  Gly Gly Lys Ser Gly  Pro Val Glu
    3965                 3970                 3975

Asp Phe  Val Ser Leu Ala Met  Val Gly Gly His Leu  Glu Phe Arg
    3980                 3985                 3990

Tyr Glu  Leu Gly Ser Gly Leu  Ala Val Leu Arg Ser  Ala Glu Pro
```

```
    3995                4000                4005

Leu Ala  Leu Gly Arg Trp His  Arg Val Ser Ala Glu  Arg Leu Asn
    4010                4015                4020

Lys Asp  Gly Ser Leu Arg Val  Asn Gly Gly Arg Pro  Val Leu Arg
    4025                4030                4035

Ser Ser  Pro Gly Lys Ser Gln  Gly Leu Asn Leu His  Thr Leu Leu
    4040                4045                4050

Tyr Leu  Gly Gly Val Glu Pro  Ser Val Pro Leu Ser  Pro Ala Thr
    4055                4060                4065

Asn Met  Ser Ala His Phe Arg  Gly Cys Val Gly Glu  Val Ser Val
    4070                4075                4080

Asn Gly  Lys Arg Leu Asp Leu  Thr Tyr Ser Phe Leu  Gly Ser Gln
    4085                4090                4095

Gly Ile  Gly Gln Cys Tyr Asp  Ser Ser Pro Cys Glu  Arg Gln Pro
    4100                4105                4110

Cys Gln  His Gly Ala Thr Cys  Met Pro Ala Gly Glu  Tyr Glu Phe
    4115                4120                4125

Gln Cys  Leu Cys Arg Asp Gly  Phe Lys Gly Asp Leu  Cys Glu His
    4130                4135                4140

Glu Glu  Asn Pro Cys Gln Leu  Arg Glu Pro Cys Leu  His Gly Gly
    4145                4150                4155

Thr Cys  Gln Gly Thr Arg Cys  Leu Cys Leu Pro Gly  Phe Ser Gly
    4160                4165                4170

Pro Arg  Cys Gln Gln Gly Ser  Gly His Gly Ile Ala  Glu Ser Asp
    4175                4180                4185

Trp His  Leu Glu Gly Ser Gly  Gly Asn Asp Ala Pro  Gly Gln Tyr
    4190                4195                4200

Gly Ala  Tyr Phe His Asp Asp  Gly Phe Leu Ala Phe  Pro Gly His
    4205                4210                4215

Val Phe  Ser Arg Ser Leu Pro  Glu Val Pro Glu Thr  Ile Glu Leu
    4220                4225                4230

Glu Val  Arg Thr Ser Thr Ala  Ser Gly Leu Leu Leu  Trp Gln Gly
    4235                4240                4245

Val Glu  Val Gly Glu Ala Gly  Gln Gly Lys Asp Phe  Ile Ser Leu
    4250                4255                4260

Gly Leu  Gln Asp Gly His Leu  Val Phe Arg Tyr Gln  Leu Gly Ser
    4265                4270                4275

Gly Glu  Ala Arg Leu Val Ser  Glu Asp Pro Ile Asn  Asp Gly Glu
    4280                4285                4290

Trp His  Arg Val Thr Ala Leu  Arg Glu Gly Arg Arg  Gly Ser Ile
    4295                4300                4305

Gln Val  Asp Gly Glu Glu Leu  Val Ser Gly Arg Ser  Pro Gly Pro
    4310                4315                4320

Asn Val  Ala Val Asn Ala Lys  Gly Ser Val Tyr Ile  Gly Gly Ala
    4325                4330                4335

Pro Asp  Val Ala Thr Leu Thr  Gly Gly Arg Phe Ser  Ser Gly Ile
    4340                4345                4350

Thr Gly  Cys Val Lys Asn Leu  Val Leu His Ser Ala  Arg Pro Gly
    4355                4360                4365

Ala Pro  Pro Pro Gln Pro Leu  Asp Leu Gln His Arg  Ala Gln Ala
    4370                4375                4380

Gly Ala  Asn Thr Arg Pro Cys  Pro Ser
    4385                4390
```

<210> SEQ ID NO 197
<211> LENGTH: 275
<212> TYPE: PRT
<213> ORGANISM: Homo sapiens

<400> SEQUENCE: 197

Met Ser Ser Phe Gly Tyr Arg Thr Leu Thr Val Ala Leu Phe Thr Leu
1               5                   10                  15

Ile Cys Cys Pro Gly Ser Asp Glu Lys Val Phe Glu Val His Val Arg
            20                  25                  30

Pro Lys Lys Leu Ala Val Glu Pro Lys Gly Ser Leu Glu Val Asn Cys
        35                  40                  45

Ser Thr Thr Cys Asn Gln Pro Glu Val Gly Gly Leu Glu Thr Ser Leu
    50                  55                  60

Asp Lys Ile Leu Leu Asp Glu Gln Ala Gln Trp Lys His Tyr Leu Val
65                  70                  75                  80

Ser Asn Ile Ser His Asp Thr Val Leu Gln Cys His Phe Thr Cys Ser
                85                  90                  95

Gly Lys Gln Glu Ser Met Asn Ser Asn Val Ser Val Tyr Gln Pro Pro
            100                 105                 110

Arg Gln Val Ile Leu Thr Leu Gln Pro Thr Leu Val Ala Val Gly Lys
        115                 120                 125

Ser Phe Thr Ile Glu Cys Arg Val Pro Thr Val Glu Pro Leu Asp Ser
    130                 135                 140

Leu Thr Leu Phe Leu Phe Arg Gly Asn Glu Thr Leu His Tyr Glu Thr
145                 150                 155                 160

Phe Gly Lys Ala Ala Pro Ala Pro Gln Glu Ala Thr Ala Thr Phe Asn
                165                 170                 175

Ser Thr Ala Asp Arg Glu Asp Gly His Arg Asn Phe Ser Cys Leu Ala
            180                 185                 190

Val Leu Asp Leu Met Ser Arg Gly Gly Asn Ile Phe His Lys His Ser
        195                 200                 205

Ala Pro Lys Met Leu Glu Ile Tyr Glu Pro Val Ser Asp Ser Gln Met
    210                 215                 220

Val Ile Ile Val Thr Val Val Ser Val Leu Leu Ser Leu Phe Val Thr
225                 230                 235                 240

Ser Val Leu Leu Cys Phe Ile Phe Gly Gln His Leu Arg Gln Gln Arg
                245                 250                 255

Met Gly Thr Tyr Gly Val Arg Ala Ala Trp Arg Arg Leu Pro Gln Ala
            260                 265                 270

Phe Arg Pro
        275

<210> SEQ ID NO 198
<211> LENGTH: 2555
<212> TYPE: PRT
<213> ORGANISM: Homo sapiens

<400> SEQUENCE: 198

Met Pro Pro Leu Leu Ala Pro Leu Leu Cys Leu Ala Leu Leu Pro Ala
1               5                   10                  15

Leu Ala Ala Arg Gly Pro Arg Cys Ser Gln Pro Gly Glu Thr Cys Leu
            20                  25                  30

Asn Gly Gly Lys Cys Glu Ala Ala Asn Gly Thr Glu Ala Cys Val Cys
        35                  40                  45

-continued

```
Gly Gly Ala Phe Val Gly Pro Arg Cys Gln Asp Pro Asn Pro Cys Leu
    50                  55                  60

Ser Thr Pro Cys Lys Asn Ala Gly Thr Cys His Val Val Asp Arg Arg
65                  70                  75                  80

Gly Val Ala Asp Tyr Ala Cys Ser Cys Ala Leu Gly Phe Ser Gly Pro
                85                  90                  95

Leu Cys Leu Thr Pro Leu Asp Asn Ala Cys Leu Thr Asn Pro Cys Arg
            100                 105                 110

Asn Gly Gly Thr Cys Asp Leu Leu Thr Leu Thr Glu Tyr Lys Cys Arg
        115                 120                 125

Cys Pro Pro Gly Trp Ser Gly Lys Ser Cys Gln Gln Ala Asp Pro Cys
    130                 135                 140

Ala Ser Asn Pro Cys Ala Asn Gly Gly Gln Cys Leu Pro Phe Glu Ala
145                 150                 155                 160

Ser Tyr Ile Cys His Cys Pro Pro Ser Phe His Gly Pro Thr Cys Arg
                165                 170                 175

Gln Asp Val Asn Glu Cys Gly Gln Lys Pro Gly Leu Cys Arg His Gly
            180                 185                 190

Gly Thr Cys His Asn Glu Val Gly Ser Tyr Arg Cys Val Cys Arg Ala
        195                 200                 205

Thr His Thr Gly Pro Asn Cys Glu Arg Pro Tyr Val Pro Cys Ser Pro
    210                 215                 220

Ser Pro Cys Gln Asn Gly Gly Thr Cys Arg Pro Thr Gly Asp Val Thr
225                 230                 235                 240

His Glu Cys Ala Cys Leu Pro Gly Phe Thr Gly Gln Asn Cys Glu Glu
                245                 250                 255

Asn Ile Asp Asp Cys Pro Gly Asn Asn Cys Lys Asn Gly Gly Ala Cys
            260                 265                 270

Val Asp Gly Val Asn Thr Tyr Asn Cys Arg Cys Pro Pro Glu Trp Thr
        275                 280                 285

Gly Gln Tyr Cys Thr Glu Asp Val Asp Glu Cys Gln Leu Met Pro Asn
    290                 295                 300

Ala Cys Gln Asn Gly Gly Thr Cys His Asn Thr His Gly Gly Tyr Asn
305                 310                 315                 320

Cys Val Cys Val Asn Gly Trp Thr Gly Glu Asp Cys Ser Glu Asn Ile
                325                 330                 335

Asp Asp Cys Ala Ser Ala Ala Cys Phe His Gly Ala Thr Cys His Asp
            340                 345                 350

Arg Val Ala Ser Phe Tyr Cys Glu Cys Pro His Gly Arg Thr Gly Leu
        355                 360                 365

Leu Cys His Leu Asn Asp Ala Cys Ile Ser Asn Pro Cys Asn Glu Gly
    370                 375                 380

Ser Asn Cys Asp Thr Asn Pro Val Asn Gly Lys Ala Ile Cys Thr Cys
385                 390                 395                 400

Pro Ser Gly Tyr Thr Gly Pro Ala Cys Ser Gln Asp Val Asp Glu Cys
                405                 410                 415

Ser Leu Gly Ala Asn Pro Cys Glu His Ala Gly Lys Cys Ile Asn Thr
            420                 425                 430

Leu Gly Ser Phe Glu Cys Gln Cys Leu Gln Gly Tyr Thr Gly Pro Arg
        435                 440                 445

Cys Glu Ile Asp Val Asn Glu Cys Val Ser Asn Pro Cys Gln Asn Asp
    450                 455                 460
```

-continued

```
Ala Thr Cys Leu Asp Gln Ile Gly Glu Phe Gln Cys Ile Cys Met Pro
465                 470                 475                 480

Gly Tyr Glu Gly Val His Cys Glu Val Asn Thr Asp Glu Cys Ala Ser
                485                 490                 495

Ser Pro Cys Leu His Asn Gly Arg Cys Leu Asp Lys Ile Asn Glu Phe
            500                 505                 510

Gln Cys Glu Cys Pro Thr Gly Phe Thr Gly His Leu Cys Gln Tyr Asp
        515                 520                 525

Val Asp Glu Cys Ala Ser Thr Pro Cys Lys Asn Gly Ala Lys Cys Leu
    530                 535                 540

Asp Gly Pro Asn Thr Tyr Thr Cys Val Cys Thr Glu Gly Tyr Thr Gly
545                 550                 555                 560

Thr His Cys Glu Val Asp Ile Asp Glu Cys Asp Pro Asp Pro Cys His
                565                 570                 575

Tyr Gly Ser Cys Lys Asp Gly Val Ala Thr Phe Thr Cys Leu Cys Arg
            580                 585                 590

Pro Gly Tyr Thr Gly His His Cys Glu Thr Asn Ile Asn Glu Cys Ser
        595                 600                 605

Ser Gln Pro Cys Arg His Gly Gly Thr Cys Gln Asp Arg Asp Asn Ala
    610                 615                 620

Tyr Leu Cys Phe Cys Leu Lys Gly Thr Thr Gly Pro Asn Cys Glu Ile
625                 630                 635                 640

Asn Leu Asp Asp Cys Ala Ser Ser Pro Cys Asp Ser Gly Thr Cys Leu
                645                 650                 655

Asp Lys Ile Asp Gly Tyr Glu Cys Ala Cys Glu Pro Gly Tyr Thr Gly
            660                 665                 670

Ser Met Cys Asn Ile Asn Ile Asp Glu Cys Ala Gly Asn Pro Cys His
        675                 680                 685

Asn Gly Gly Thr Cys Glu Asp Gly Ile Asn Gly Phe Thr Cys Arg Cys
    690                 695                 700

Pro Glu Gly Tyr His Asp Pro Thr Cys Leu Ser Glu Val Asn Glu Cys
705                 710                 715                 720

Asn Ser Asn Pro Cys Val His Gly Ala Cys Arg Asp Ser Leu Asn Gly
                725                 730                 735

Tyr Lys Cys Asp Cys Asp Pro Gly Trp Ser Gly Thr Asn Cys Asp Ile
            740                 745                 750

Asn Asn Asn Glu Cys Glu Ser Asn Pro Cys Val Asn Gly Gly Thr Cys
        755                 760                 765

Lys Asp Met Thr Ser Gly Tyr Val Cys Thr Cys Arg Glu Gly Phe Ser
    770                 775                 780

Gly Pro Asn Cys Gln Thr Asn Ile Asn Glu Cys Ala Ser Asn Pro Cys
785                 790                 795                 800

Leu Asn Gln Gly Thr Cys Ile Asp Asp Val Ala Gly Tyr Lys Cys Asn
                805                 810                 815

Cys Leu Leu Pro Tyr Thr Gly Ala Thr Cys Glu Val Val Leu Ala Pro
            820                 825                 830

Cys Ala Pro Ser Pro Cys Arg Asn Gly Gly Glu Cys Arg Gln Ser Glu
        835                 840                 845

Asp Tyr Glu Ser Phe Ser Cys Val Cys Pro Thr Gly Trp Gln Gly Gln
    850                 855                 860

Thr Cys Glu Val Asp Ile Asn Glu Cys Val Leu Ser Pro Cys Arg His
865                 870                 875                 880

Gly Ala Ser Cys Gln Asn Thr His Gly Gly Tyr Arg Cys His Cys Gln
```

-continued

```
            885                 890                 895

Ala Gly Tyr Ser Gly Arg Asn Cys Glu Thr Asp Ile Asp Asp Cys Arg
        900                 905                 910

Pro Asn Pro Cys His Asn Gly Gly Ser Cys Thr Asp Gly Ile Asn Thr
    915                 920                 925

Ala Phe Cys Asp Cys Leu Pro Gly Phe Arg Gly Thr Phe Cys Glu Glu
    930                 935                 940

Asp Ile Asn Glu Cys Ala Ser Asp Pro Cys Arg Asn Gly Ala Asn Cys
945                 950                 955                 960

Thr Asp Cys Val Asp Ser Tyr Thr Cys Thr Cys Pro Ala Gly Phe Ser
                965                 970                 975

Gly Ile His Cys Glu Asn Asn Thr Pro Asp Cys Thr Glu Ser Ser Cys
            980                 985                 990

Phe Asn Gly Gly Thr Cys Val Asp  Gly Ile Asn Ser Phe  Thr Cys Leu
        995                 1000                1005

Cys Pro  Pro Gly Phe Thr Gly  Ser Tyr Cys Gln His  Asp Val Asn
    1010                1015                1020

Glu Cys  Asp Ser Gln Pro Cys  Leu His Gly Gly Thr  Cys Gln Asp
    1025                1030                1035

Gly Cys  Gly Ser Tyr Arg Cys  Thr Cys Pro Gln Gly  Tyr Thr Gly
    1040                1045                1050

Pro Asn  Cys Gln Asn Leu Val  His Trp Cys Asp Ser  Ser Pro Cys
    1055                1060                1065

Lys Asn  Gly Gly Lys Cys Trp  Gln Thr His Thr Gln  Tyr Arg Cys
    1070                1075                1080

Glu Cys  Pro Ser Gly Trp Thr  Gly Leu Tyr Cys Asp  Val Pro Ser
    1085                1090                1095

Val Ser  Cys Glu Val Ala Ala  Gln Arg Gln Gly Val  Asp Val Ala
    1100                1105                1110

Arg Leu  Cys Gln His Gly Gly  Leu Cys Val Asp Ala  Gly Asn Thr
    1115                1120                1125

His His  Cys Arg Cys Gln Ala  Gly Tyr Thr Gly Ser  Tyr Cys Glu
    1130                1135                1140

Asp Leu  Val Asp Glu Cys Ser  Pro Ser Pro Cys Gln  Asn Gly Ala
    1145                1150                1155

Thr Cys  Thr Asp Tyr Leu Gly  Gly Tyr Ser Cys Lys  Cys Val Ala
    1160                1165                1170

Gly Tyr  His Gly Val Asn Cys  Ser Glu Glu Ile Asp  Glu Cys Leu
    1175                1180                1185

Ser His  Pro Cys Gln Asn Gly  Gly Thr Cys Leu Asp  Leu Pro Asn
    1190                1195                1200

Thr Tyr  Lys Cys Ser Cys Pro  Arg Gly Thr Gln Gly  Val His Cys
    1205                1210                1215

Glu Ile  Asn Val Asp Asp Cys  Asn Pro Pro Val Asp  Pro Val Ser
    1220                1225                1230

Arg Ser  Pro Lys Cys Phe Asn  Asn Gly Thr Cys Val  Asp Gln Val
    1235                1240                1245

Gly Gly  Tyr Ser Cys Thr Cys  Pro Pro Gly Phe Val  Gly Glu Arg
    1250                1255                1260

Cys Glu  Gly Asp Val Asn Glu  Cys Leu Ser Asn Pro  Cys Asp Ala
    1265                1270                1275

Arg Gly  Thr Gln Asn Cys Val  Gln Arg Val Asn Asp  Phe His Cys
    1280                1285                1290
```

-continued

```
Glu Cys Arg Ala Gly His Thr Gly Arg Arg Cys Glu Ser Val Ile
    1295                1300                1305

Asn Gly Cys Lys Gly Lys Pro Cys Lys Asn Gly Gly Thr Cys Ala
    1310                1315                1320

Val Ala Ser Asn Thr Ala Arg Gly Phe Ile Cys Lys Cys Pro Ala
    1325                1330                1335

Gly Phe Glu Gly Ala Thr Cys Glu Asn Asp Ala Arg Thr Cys Gly
    1340                1345                1350

Ser Leu Arg Cys Leu Asn Gly Gly Thr Cys Ile Ser Gly Pro Arg
    1355                1360                1365

Ser Pro Thr Cys Leu Cys Leu Gly Pro Phe Thr Gly Pro Glu Cys
    1370                1375                1380

Gln Phe Pro Ala Ser Ser Pro Cys Leu Gly Gly Asn Pro Cys Tyr
    1385                1390                1395

Asn Gln Gly Thr Cys Glu Pro Thr Ser Glu Ser Pro Phe Tyr Arg
    1400                1405                1410

Cys Leu Cys Pro Ala Lys Phe Asn Gly Leu Leu Cys His Ile Leu
    1415                1420                1425

Asp Tyr Ser Phe Gly Gly Gly Ala Gly Arg Asp Ile Pro Pro Pro
    1430                1435                1440

Leu Ile Glu Glu Ala Cys Glu Leu Pro Glu Cys Gln Glu Asp Ala
    1445                1450                1455

Gly Asn Lys Val Cys Ser Leu Gln Cys Asn Asn His Ala Cys Gly
    1460                1465                1470

Trp Asp Gly Gly Asp Cys Ser Leu Asn Phe Asn Asp Pro Trp Lys
    1475                1480                1485

Asn Cys Thr Gln Ser Leu Gln Cys Trp Lys Tyr Phe Ser Asp Gly
    1490                1495                1500

His Cys Asp Ser Gln Cys Asn Ser Ala Gly Cys Leu Phe Asp Gly
    1505                1510                1515

Phe Asp Cys Gln Arg Ala Glu Gly Gln Cys Asn Pro Leu Tyr Asp
    1520                1525                1530

Gln Tyr Cys Lys Asp His Phe Ser Asp Gly His Cys Asp Gln Gly
    1535                1540                1545

Cys Asn Ser Ala Glu Cys Glu Trp Asp Gly Leu Asp Cys Ala Glu
    1550                1555                1560

His Val Pro Glu Arg Leu Ala Ala Gly Thr Leu Val Val Val Val
    1565                1570                1575

Leu Met Pro Pro Glu Gln Leu Arg Asn Ser Ser Phe His Phe Leu
    1580                1585                1590

Arg Glu Leu Ser Arg Val Leu His Thr Asn Val Val Phe Lys Arg
    1595                1600                1605

Asp Ala His Gly Gln Gln Met Ile Phe Pro Tyr Tyr Gly Arg Glu
    1610                1615                1620

Glu Glu Leu Arg Lys His Pro Ile Lys Arg Ala Ala Glu Gly Trp
    1625                1630                1635

Ala Ala Pro Asp Ala Leu Leu Gly Gln Val Lys Ala Ser Leu Leu
    1640                1645                1650

Pro Gly Gly Ser Glu Gly Gly Arg Arg Arg Arg Glu Leu Asp Pro
    1655                1660                1665

Met Asp Val Arg Gly Ser Ile Val Tyr Leu Glu Ile Asp Asn Arg
    1670                1675                1680
```

-continued

```
Gln Cys Val Gln Ala Ser Ser Gln Cys Phe Gln Ser Ala Thr Asp
    1685                1690                1695

Val Ala Ala Phe Leu Gly Ala Leu Ala Ser Leu Gly Ser Leu Asn
    1700                1705                1710

Ile Pro Tyr Lys Ile Glu Ala Val Gln Ser Glu Thr Val Glu Pro
    1715                1720                1725

Pro Pro Pro Ala Gln Leu His Phe Met Tyr Val Ala Ala Ala Ala
    1730                1735                1740

Phe Val Leu Leu Phe Phe Val Gly Cys Gly Val Leu Leu Ser Arg
    1745                1750                1755

Lys Arg Arg Arg Gln His Gly Gln Leu Trp Phe Pro Glu Gly Phe
    1760                1765                1770

Lys Val Ser Glu Ala Ser Lys Lys Lys Arg Arg Glu Pro Leu Gly
    1775                1780                1785

Glu Asp Ser Val Gly Leu Lys Pro Leu Lys Asn Ala Ser Asp Gly
    1790                1795                1800

Ala Leu Met Asp Asp Asn Gln Asn Glu Trp Gly Asp Glu Asp Leu
    1805                1810                1815

Glu Thr Lys Lys Phe Arg Phe Glu Glu Pro Val Val Leu Pro Asp
    1820                1825                1830

Leu Asp Asp Gln Thr Asp His Arg Gln Trp Thr Gln Gln His Leu
    1835                1840                1845

Asp Ala Ala Asp Leu Arg Met Ser Ala Met Ala Pro Thr Pro Pro
    1850                1855                1860

Gln Gly Glu Val Asp Ala Asp Cys Met Asp Val Asn Val Arg Gly
    1865                1870                1875

Pro Asp Gly Phe Thr Pro Leu Met Ile Ala Ser Cys Ser Gly Gly
    1880                1885                1890

Gly Leu Glu Thr Gly Asn Ser Glu Glu Glu Glu Asp Ala Pro Ala
    1895                1900                1905

Val Ile Ser Asp Phe Ile Tyr Gln Gly Ala Ser Leu His Asn Gln
    1910                1915                1920

Thr Asp Arg Thr Gly Glu Thr Ala Leu His Leu Ala Ala Arg Tyr
    1925                1930                1935

Ser Arg Ser Asp Ala Ala Lys Arg Leu Leu Glu Ala Ser Ala Asp
    1940                1945                1950

Ala Asn Ile Gln Asp Asn Met Gly Arg Thr Pro Leu His Ala Ala
    1955                1960                1965

Val Ser Ala Asp Ala Gln Gly Val Phe Gln Ile Leu Ile Arg Asn
    1970                1975                1980

Arg Ala Thr Asp Leu Asp Ala Arg Met His Asp Gly Thr Thr Pro
    1985                1990                1995

Leu Ile Leu Ala Ala Arg Leu Ala Val Glu Gly Met Leu Glu Asp
    2000                2005                2010

Leu Ile Asn Ser His Ala Asp Val Asn Ala Val Asp Asp Leu Gly
    2015                2020                2025

Lys Ser Ala Leu His Trp Ala Ala Ala Val Asn Asn Val Asp Ala
    2030                2035                2040

Ala Val Val Leu Leu Lys Asn Gly Ala Asn Lys Asp Met Gln Asn
    2045                2050                2055

Asn Arg Glu Glu Thr Pro Leu Phe Leu Ala Ala Arg Glu Gly Ser
    2060                2065                2070

Tyr Glu Thr Ala Lys Val Leu Leu Asp His Phe Ala Asn Arg Asp
```

```
    2075                2080                2085

Ile Thr  Asp His Met Asp Arg  Leu Pro Arg Asp Ile  Ala Gln Glu
    2090                2095                2100

Arg Met  His His Asp Ile Val  Arg Leu Leu Asp Glu  Tyr Asn Leu
    2105                2110                2115

Val Arg  Ser Pro Gln Leu His  Gly Ala Pro Leu Gly  Gly Thr Pro
    2120                2125                2130

Thr Leu  Ser Pro Pro Leu Cys  Ser Pro Asn Gly Tyr  Leu Gly Ser
    2135                2140                2145

Leu Lys  Pro Gly Val Gln Gly  Lys Lys Val Arg Lys  Pro Ser Ser
    2150                2155                2160

Lys Gly  Leu Ala Cys Gly Ser  Lys Glu Ala Lys Asp  Leu Lys Ala
    2165                2170                2175

Arg Arg  Lys Lys Ser Gln Asp  Gly Lys Gly Cys Leu  Leu Asp Ser
    2180                2185                2190

Ser Gly  Met Leu Ser Pro Val  Asp Ser Leu Glu Ser  Pro His Gly
    2195                2200                2205

Tyr Leu  Ser Asp Val Ala Ser  Pro Pro Leu Leu Pro  Ser Pro Phe
    2210                2215                2220

Gln Gln  Ser Pro Ser Val Pro  Leu Asn His Leu Pro  Gly Met Pro
    2225                2230                2235

Asp Thr  His Leu Gly Ile Gly  His Leu Asn Val Ala  Ala Lys Pro
    2240                2245                2250

Glu Met  Ala Ala Leu Gly Gly  Gly Gly Arg Leu Ala  Phe Glu Thr
    2255                2260                2265

Gly Pro  Pro Arg Leu Ser His  Leu Pro Val Ala Ser  Gly Thr Ser
    2270                2275                2280

Thr Val  Leu Gly Ser Ser Ser  Gly Gly Ala Leu Asn  Phe Thr Val
    2285                2290                2295

Gly Gly  Ser Thr Ser Leu Asn  Gly Gln Cys Glu Trp  Leu Ser Arg
    2300                2305                2310

Leu Gln  Ser Gly Met Val Pro  Asn Gln Tyr Asn Pro  Leu Arg Gly
    2315                2320                2325

Ser Val  Ala Pro Gly Pro Leu  Ser Thr Gln Ala Pro  Ser Leu Gln
    2330                2335                2340

His Gly  Met Val Gly Pro Leu  His Ser Ser Leu Ala  Ala Ser Ala
    2345                2350                2355

Leu Ser  Gln Met Met Ser Tyr  Gln Gly Leu Pro Ser  Thr Arg Leu
    2360                2365                2370

Ala Thr  Gln Pro His Leu Val  Gln Thr Gln Gln Val  Gln Pro Gln
    2375                2380                2385

Asn Leu  Gln Met Gln Gln Gln  Asn Leu Gln Pro Ala  Asn Ile Gln
    2390                2395                2400

Gln Gln  Gln Ser Leu Gln Pro  Pro Pro Pro Pro Pro  Gln Pro His
    2405                2410                2415

Leu Gly  Val Ser Ser Ala Ala  Ser Gly His Leu Gly  Arg Ser Phe
    2420                2425                2430

Leu Ser  Gly Glu Pro Ser Gln  Ala Asp Val Gln Pro  Leu Gly Pro
    2435                2440                2445

Ser Ser  Leu Ala Val His Thr  Ile Leu Pro Gln Glu  Ser Pro Ala
    2450                2455                2460

Leu Pro  Thr Ser Leu Pro Ser  Ser Leu Val Pro Pro  Val Thr Ala
    2465                2470                2475
```

Ala Gln Phe Leu Thr Pro Pro Ser Gln His Ser Tyr Ser Ser Pro
2480 2485 2490

Val Asp Asn Thr Pro Ser His Gln Leu Gln Val Pro Glu His Pro
2495 2500 2505

Phe Leu Thr Pro Ser Pro Glu Ser Pro Asp Gln Trp Ser Ser Ser
2510 2515 2520

Ser Pro His Ser Asn Val Ser Asp Trp Ser Glu Gly Val Ser Ser
2525 2530 2535

Pro Pro Thr Ser Met Gln Ser Gln Ile Ala Arg Ile Pro Glu Ala
2540 2545 2550

Phe Lys
2555

<210> SEQ ID NO 199
<211> LENGTH: 1235
<212> TYPE: PRT
<213> ORGANISM: Homo sapiens

<400> SEQUENCE: 199

Met Pro Ala Leu Arg Pro Ala Leu Leu Trp Ala Leu Leu Ala Leu Trp
1 5 10 15

Leu Cys Cys Ala Ala Pro Ala His Ala Leu Gln Cys Arg Asp Gly Tyr
20 25 30

Glu Pro Cys Val Asn Glu Gly Met Cys Val Thr Tyr His Asn Gly Thr
35 40 45

Gly Tyr Cys Lys Cys Pro Glu Gly Phe Leu Gly Glu Tyr Cys Gln His
50 55 60

Arg Asp Pro Cys Glu Lys Asn Arg Cys Gln Asn Gly Gly Thr Cys Val
65 70 75 80

Ala Gln Ala Met Leu Gly Lys Ala Thr Cys Arg Cys Ala Ser Gly Phe
85 90 95

Thr Gly Glu Asp Cys Gln Tyr Ser Thr Ser His Pro Cys Phe Val Ser
100 105 110

Arg Pro Cys Leu Asn Gly Gly Thr Cys His Met Leu Ser Arg Asp Thr
115 120 125

Tyr Glu Cys Thr Cys Gln Val Gly Phe Thr Gly Lys Glu Cys Gln Trp
130 135 140

Thr Asp Ala Cys Leu Ser His Pro Cys Ala Asn Gly Ser Thr Cys Thr
145 150 155 160

Thr Val Ala Asn Gln Phe Ser Cys Lys Cys Leu Thr Gly Phe Thr Gly
165 170 175

Gln Lys Cys Glu Thr Asp Val Asn Glu Cys Asp Ile Pro Gly His Cys
180 185 190

Gln His Gly Gly Thr Cys Leu Asn Leu Pro Gly Ser Tyr Gln Cys Gln
195 200 205

Cys Pro Gln Gly Phe Thr Gly Gln Tyr Cys Asp Ser Leu Tyr Val Pro
210 215 220

Cys Ala Pro Ser Pro Cys Val Asn Gly Gly Thr Cys Arg Gln Thr Gly
225 230 235 240

Asp Phe Thr Phe Glu Cys Asn Cys Leu Pro Gly Phe Glu Gly Ser Thr
245 250 255

Cys Glu Arg Asn Ile Asp Asp Cys Pro Asn His Arg Cys Gln Asn Gly
260 265 270

Gly Val Cys Val Asp Gly Val Asn Thr Tyr Asn Cys Arg Cys Pro Pro

-continued

```
        275                 280                 285

Gln Trp Thr Gly Gln Phe Cys Thr Glu Asp Val Asp Glu Cys Leu Leu
    290                 295                 300

Gln Pro Asn Ala Cys Gln Asn Gly Gly Thr Cys Ala Asn Arg Asn Gly
305                 310                 315                 320

Gly Tyr Gly Cys Val Cys Val Asn Gly Trp Ser Gly Asp Asp Cys Ser
                325                 330                 335

Glu Asn Ile Asp Asp Cys Ala Phe Ala Ser Cys Thr Pro Gly Ser Thr
            340                 345                 350

Cys Ile Asp Arg Val Ala Ser Phe Ser Cys Met Cys Pro Glu Gly Lys
        355                 360                 365

Ala Gly Leu Leu Cys His Leu Asp Asp Ala Cys Ile Ser Asn Pro Cys
    370                 375                 380

His Lys Gly Ala Leu Cys Asp Thr Asn Pro Leu Asn Gly Gln Tyr Ile
385                 390                 395                 400

Cys Thr Cys Pro Gln Gly Tyr Lys Gly Ala Asp Cys Thr Glu Asp Val
                405                 410                 415

Asp Glu Cys Ala Met Ala Asn Ser Asn Pro Cys Glu His Ala Gly Lys
            420                 425                 430

Cys Val Asn Thr Asp Gly Ala Phe His Cys Glu Cys Leu Lys Gly Tyr
        435                 440                 445

Ala Gly Pro Arg Cys Glu Met Asp Ile Asn Glu Cys His Ser Asp Pro
    450                 455                 460

Cys Gln Asn Asp Ala Thr Cys Leu Asp Lys Ile Gly Gly Phe Thr Cys
465                 470                 475                 480

Leu Cys Met Pro Gly Phe Lys Gly Val His Cys Glu Leu Glu Ile Asn
                485                 490                 495

Glu Cys Gln Ser Asn Pro Cys Val Asn Asn Gly Gln Cys Val Asp Lys
            500                 505                 510

Val Asn Arg Phe Gln Cys Leu Cys Pro Pro Gly Phe Thr Gly Pro Val
        515                 520                 525

Cys Gln Ile Asp Ile Asp Asp Cys Ser Ser Thr Pro Cys Leu Asn Gly
    530                 535                 540

Ala Lys Cys Ile Asp His Pro Asn Gly Tyr Glu Cys Gln Cys Ala Thr
545                 550                 555                 560

Gly Phe Thr Gly Val Leu Cys Glu Glu Asn Ile Asp Asn Cys Asp Pro
                565                 570                 575

Asp Pro Cys His His Gly Gln Cys Gln Asp Gly Ile Asp Ser Tyr Thr
            580                 585                 590

Cys Ile Cys Asn Pro Gly Tyr Met Gly Ala Ile Cys Ser Asp Gln Ile
        595                 600                 605

Asp Glu Cys Tyr Ser Ser Pro Cys Leu Asn Asp Gly Arg Cys Ile Asp
    610                 615                 620

Leu Val Asn Gly Tyr Gln Cys Asn Cys Gln Pro Gly Thr Ser Gly Val
625                 630                 635                 640

Asn Cys Glu Ile Asn Phe Asp Asp Cys Ala Ser Asn Pro Cys Ile His
                645                 650                 655

Gly Ile Cys Met Asp Gly Ile Asn Arg Tyr Ser Cys Val Cys Ser Pro
            660                 665                 670

Gly Phe Thr Gly Gln Arg Cys Asn Ile Asp Ile Asp Glu Cys Ala Ser
        675                 680                 685

Asn Pro Cys Arg Lys Gly Ala Thr Cys Ile Asn Gly Val Asn Gly Phe
    690                 695                 700
```

-continued

Arg Cys Ile Cys Pro Glu Gly Pro His His Pro Ser Cys Tyr Ser Gln
705 710 715 720

Val Asn Glu Cys Leu Ser Asn Pro Cys Ile His Gly Asn Cys Thr Gly
725 730 735

Gly Leu Ser Gly Tyr Lys Cys Leu Cys Asp Ala Gly Trp Val Gly Ile
740 745 750

Asn Cys Glu Val Asp Lys Asn Glu Cys Leu Ser Asn Pro Cys Gln Asn
755 760 765

Gly Gly Thr Cys Asp Asn Leu Val Asn Gly Tyr Arg Cys Thr Cys Lys
770 775 780

Lys Gly Phe Lys Gly Tyr Asn Cys Gln Val Asn Ile Asp Glu Cys Ala
785 790 795 800

Ser Asn Pro Cys Leu Asn Gln Gly Thr Cys Phe Asp Asp Ile Ser Gly
805 810 815

Tyr Thr Cys His Cys Val Leu Pro Tyr Thr Gly Lys Asn Cys Gln Thr
820 825 830

Val Leu Ala Pro Cys Ser Pro Asn Pro Cys Glu Asn Ala Ala Val Cys
835 840 845

Lys Glu Ser Pro Asn Phe Glu Ser Tyr Thr Cys Leu Cys Ala Pro Gly
850 855 860

Trp Gln Gly Gln Arg Cys Thr Ile Asp Ile Asp Glu Cys Ile Ser Lys
865 870 875 880

Pro Cys Met Asn His Gly Leu Cys His Asn Thr Gln Gly Ser Tyr Met
885 890 895

Cys Glu Cys Pro Pro Gly Phe Ser Gly Met Asp Cys Glu Glu Asp Ile
900 905 910

Asp Asp Cys Leu Ala Asn Pro Cys Gln Asn Gly Gly Ser Cys Met Asp
915 920 925

Gly Val Asn Thr Phe Ser Cys Leu Cys Leu Pro Gly Phe Thr Gly Asp
930 935 940

Lys Cys Gln Thr Asp Met Asn Glu Cys Leu Ser Glu Pro Cys Lys Asn
945 950 955 960

Gly Gly Thr Cys Ser Asp Tyr Val Asn Ser Tyr Thr Cys Lys Cys Gln
965 970 975

Ala Gly Phe Asp Gly Val His Cys Glu Asn Asn Ile Asn Glu Cys Thr
980 985 990

Glu Ser Ser Cys Phe Asn Gly Gly Thr Cys Val Asp Gly Ile Asn Ser
995 1000 1005

Phe Ser Cys Leu Cys Pro Val Gly Phe Thr Gly Ser Phe Cys Leu
1010 1015 1020

His Glu Ile Asn Glu Cys Ser Ser His Pro Cys Leu Asn Glu Gly
1025 1030 1035

Thr Cys Val Asp Gly Leu Gly Thr Tyr Arg Cys Ser Cys Pro Leu
1040 1045 1050

Gly Tyr Thr Gly Lys Asn Cys Gln Thr Leu Val Asn Leu Cys Ser
1055 1060 1065

Arg Ser Pro Cys Lys Asn Lys Gly Thr Cys Val Gln Lys Lys Ala
1070 1075 1080

Glu Ser Gln Cys Leu Cys Pro Ser Gly Trp Ala Gly Ala Tyr Cys
1085 1090 1095

Asp Val Pro Asn Val Ser Cys Asp Ile Ala Ala Ser Arg Arg Gly
1100 1105 1110

Val Leu Val Glu His Leu Cys Gln His Ser Gly Val Cys Ile Asn
1115 1120 1125

Ala Gly Asn Thr His Tyr Cys Gln Cys Pro Leu Gly Tyr Thr Gly
1130 1135 1140

Ser Tyr Cys Glu Glu Gln Leu Asp Glu Cys Ala Ser Asn Pro Cys
1145 1150 1155

Gln His Gly Ala Thr Cys Ser Asp Phe Ile Gly Gly Tyr Arg Cys
1160 1165 1170

Glu Cys Val Pro Gly Tyr Gln Gly Val Asn Cys Glu Tyr Glu Val
1175 1180 1185

Asp Glu Cys Gln Asn Gln Pro Cys Gln Asn Gly Gly Thr Cys Ile
1190 1195 1200

Asp Leu Val Asn His Phe Lys Cys Ser Cys Pro Pro Gly Thr Arg
1205 1210 1215

Gly Met Lys Ser Ser Leu Ser Ile Phe His Pro Gly His Cys Leu
1220 1225 1230

Lys Leu
1235

<210> SEQ ID NO 200
<211> LENGTH: 2321
<212> TYPE: PRT
<213> ORGANISM: Homo sapiens

<400> SEQUENCE: 200

Met Gly Pro Gly Ala Arg Gly Arg Arg Arg Arg Arg Arg Pro Met Ser
1 5 10 15

Pro Pro Pro Pro Pro Pro Pro Val Arg Ala Leu Pro Leu Leu Leu Leu
20 25 30

Leu Ala Gly Pro Gly Ala Ala Ala Pro Pro Cys Leu Asp Gly Ser Pro
35 40 45

Cys Ala Asn Gly Gly Arg Cys Thr Gln Leu Pro Ser Arg Glu Ala Ala
50 55 60

Cys Leu Cys Pro Pro Gly Trp Val Gly Glu Arg Cys Gln Leu Glu Asp
65 70 75 80

Pro Cys His Ser Gly Pro Cys Ala Gly Arg Gly Val Cys Gln Ser Ser
85 90 95

Val Val Ala Gly Thr Ala Arg Phe Ser Cys Arg Cys Pro Arg Gly Phe
100 105 110

Arg Gly Pro Asp Cys Ser Leu Pro Asp Pro Cys Leu Ser Ser Pro Cys
115 120 125

Ala His Gly Ala Arg Cys Ser Val Gly Pro Asp Gly Arg Phe Leu Cys
130 135 140

Ser Cys Pro Pro Gly Tyr Gln Gly Arg Ser Cys Arg Ser Asp Val Asp
145 150 155 160

Glu Cys Arg Val Gly Glu Pro Cys Arg His Gly Gly Thr Cys Leu Asn
165 170 175

Thr Pro Gly Ser Phe Arg Cys Gln Cys Pro Ala Gly Tyr Thr Gly Pro
180 185 190

Leu Cys Glu Asn Pro Ala Val Pro Cys Ala Pro Ser Pro Cys Arg Asn
195 200 205

Gly Gly Thr Cys Arg Gln Ser Gly Asp Leu Thr Tyr Asp Cys Ala Cys
210 215 220

Leu Pro Gly Phe Glu Gly Gln Asn Cys Glu Val Asn Val Asp Asp Cys
225 230 235 240

-continued

```
Pro Gly His Arg Cys Leu Asn Gly Gly Thr Cys Val Asp Gly Val Asn
                245                 250                 255

Thr Tyr Asn Cys Gln Cys Pro Pro Glu Trp Thr Gly Gln Phe Cys Thr
            260                 265                 270

Glu Asp Val Asp Glu Cys Gln Leu Gln Pro Asn Ala Cys His Asn Gly
        275                 280                 285

Gly Thr Cys Phe Asn Thr Leu Gly Gly His Ser Cys Val Cys Val Asn
    290                 295                 300

Gly Trp Thr Gly Glu Ser Cys Ser Gln Asn Ile Asp Asp Cys Ala Thr
305                 310                 315                 320

Ala Val Cys Phe His Gly Ala Thr Cys His Asp Arg Val Ala Ser Phe
                325                 330                 335

Tyr Cys Ala Cys Pro Met Gly Lys Thr Gly Leu Leu Cys His Leu Asp
            340                 345                 350

Asp Ala Cys Val Ser Asn Pro Cys His Glu Asp Ala Ile Cys Asp Thr
        355                 360                 365

Asn Pro Val Asn Gly Arg Ala Ile Cys Thr Cys Pro Pro Gly Phe Thr
    370                 375                 380

Gly Gly Ala Cys Asp Gln Asp Val Asp Glu Cys Ser Ile Gly Ala Asn
385                 390                 395                 400

Pro Cys Glu His Leu Gly Arg Cys Val Asn Thr Gln Gly Ser Phe Leu
                405                 410                 415

Cys Gln Cys Gly Arg Gly Tyr Thr Gly Pro Arg Cys Glu Thr Asp Val
            420                 425                 430

Asn Glu Cys Leu Ser Gly Pro Cys Arg Asn Gln Ala Thr Cys Leu Asp
        435                 440                 445

Arg Ile Gly Gln Phe Thr Cys Ile Cys Met Ala Gly Phe Thr Gly Thr
    450                 455                 460

Tyr Cys Glu Val Asp Ile Asp Glu Cys Gln Ser Ser Pro Cys Val Asn
465                 470                 475                 480

Gly Gly Val Cys Lys Asp Arg Val Asn Gly Phe Ser Cys Thr Cys Pro
                485                 490                 495

Ser Gly Phe Ser Gly Ser Thr Cys Gln Leu Asp Val Asp Glu Cys Ala
            500                 505                 510

Ser Thr Pro Cys Arg Asn Gly Ala Lys Cys Val Asp Gln Pro Asp Gly
        515                 520                 525

Tyr Glu Cys Arg Cys Ala Glu Gly Phe Glu Gly Thr Leu Cys Asp Arg
    530                 535                 540

Asn Val Asp Asp Cys Ser Pro Asp Pro Cys His His Gly Arg Cys Val
545                 550                 555                 560

Asp Gly Ile Ala Ser Phe Ser Cys Ala Cys Ala Pro Gly Tyr Thr Gly
                565                 570                 575

Thr Arg Cys Glu Ser Gln Val Asp Glu Cys Arg Ser Gln Pro Cys Arg
            580                 585                 590

His Gly Gly Lys Cys Leu Asp Leu Val Asp Lys Tyr Leu Cys Arg Cys
        595                 600                 605

Pro Ser Gly Thr Thr Gly Val Asn Cys Glu Val Asn Ile Asp Asp Cys
    610                 615                 620

Ala Ser Asn Pro Cys Thr Phe Gly Val Cys Arg Asp Gly Ile Asn Arg
625                 630                 635                 640

Tyr Asp Cys Val Cys Gln Pro Gly Phe Thr Gly Pro Leu Cys Asn Val
                645                 650                 655
```

-continued

```
Glu Ile Asn Glu Cys Ala Ser Ser Pro Cys Gly Glu Gly Gly Ser Cys
            660                 665                 670

Val Asp Gly Glu Asn Gly Phe Arg Cys Leu Cys Pro Pro Gly Ser Leu
        675                 680                 685

Pro Pro Leu Cys Leu Pro Pro Ser His Pro Cys Ala His Glu Pro Cys
    690                 695                 700

Ser His Gly Ile Cys Tyr Asp Ala Pro Gly Gly Phe Arg Cys Val Cys
705                 710                 715                 720

Glu Pro Gly Trp Ser Gly Pro Arg Cys Ser Gln Ser Leu Ala Arg Asp
                725                 730                 735

Ala Cys Glu Ser Gln Pro Cys Arg Ala Gly Gly Thr Cys Ser Ser Asp
            740                 745                 750

Gly Met Gly Phe His Cys Thr Cys Pro Pro Gly Val Gln Gly Arg Gln
        755                 760                 765

Cys Glu Leu Leu Ser Pro Cys Thr Pro Asn Pro Cys Glu His Gly Gly
    770                 775                 780

Arg Cys Glu Ser Ala Pro Gly Gln Leu Pro Val Cys Ser Cys Pro Gln
785                 790                 795                 800

Gly Trp Gln Gly Pro Arg Cys Gln Gln Asp Val Asp Glu Cys Ala Gly
                805                 810                 815

Pro Ala Pro Cys Gly Pro His Gly Ile Cys Thr Asn Leu Ala Gly Ser
            820                 825                 830

Phe Ser Cys Thr Cys His Gly Gly Tyr Thr Gly Pro Ser Cys Asp Gln
        835                 840                 845

Asp Ile Asn Asp Cys Asp Pro Asn Pro Cys Leu Asn Gly Gly Ser Cys
    850                 855                 860

Gln Asp Gly Val Gly Ser Phe Ser Cys Ser Cys Leu Pro Gly Phe Ala
865                 870                 875                 880

Gly Pro Arg Cys Ala Arg Asp Val Asp Glu Cys Leu Ser Asn Pro Cys
                885                 890                 895

Gly Pro Gly Thr Cys Thr Asp His Val Ala Ser Phe Thr Cys Thr Cys
            900                 905                 910

Pro Pro Gly Tyr Gly Gly Phe His Cys Glu Gln Asp Leu Pro Asp Cys
        915                 920                 925

Ser Pro Ser Ser Cys Phe Asn Gly Gly Thr Cys Val Asp Gly Val Asn
    930                 935                 940

Ser Phe Ser Cys Leu Cys Arg Pro Gly Tyr Thr Gly Ala His Cys Gln
945                 950                 955                 960

His Glu Ala Asp Pro Cys Leu Ser Arg Pro Cys Leu His Gly Gly Val
                965                 970                 975

Cys Ser Ala Ala His Pro Gly Phe Arg Cys Thr Cys Leu Glu Ser Phe
            980                 985                 990

Thr Gly Pro Gln Cys Gln Thr Leu  Val Asp Trp Cys Ser  Arg Gln Pro
        995                 1000                1005

Cys Gln  Asn Gly Gly Arg Cys  Val Gln Thr Gly Ala  Tyr Cys Leu
    1010                1015                1020

Cys Pro  Pro Gly Trp Ser Gly  Arg Leu Cys Asp Ile  Arg Ser Leu
    1025                1030                1035

Pro Cys  Arg Glu Ala Ala Ala  Gln Ile Gly Val Arg  Leu Glu Gln
    1040                1045                1050

Leu Cys  Gln Ala Gly Gly Gln  Cys Val Asp Glu Asp  Ser Ser His
    1055                1060                1065

Tyr Cys  Val Cys Pro Glu Gly  Arg Thr Gly Ser His  Cys Glu Gln
```

```
    1070                1075                1080

Glu Val  Asp Pro Cys Leu Ala  Gln Pro Cys Gln His  Gly Gly Thr
    1085                1090                1095

Cys Arg  Gly Tyr Met Gly Gly  Tyr Met Cys Glu Cys  Leu Pro Gly
    1100                1105                1110

Tyr Asn  Gly Asp Asn Cys Glu  Asp Asp Val Asp Glu  Cys Ala Ser
    1115                1120                1125

Gln Pro  Cys Gln His Gly Gly  Ser Cys Ile Asp Leu  Val Ala Arg
    1130                1135                1140

Tyr Leu  Cys Ser Cys Pro Pro  Gly Thr Leu Gly Val  Leu Cys Glu
    1145                1150                1155

Ile Asn  Glu Asp Asp Cys Gly  Pro Gly Pro Pro Leu  Asp Ser Gly
    1160                1165                1170

Pro Arg  Cys Leu His Asn Gly  Thr Cys Val Asp Leu  Val Gly Gly
    1175                1180                1185

Phe Arg  Cys Thr Cys Pro Pro  Gly Tyr Thr Gly Leu  Arg Cys Glu
    1190                1195                1200

Ala Asp  Ile Asn Glu Cys Arg  Ser Gly Ala Cys His  Ala Ala His
    1205                1210                1215

Thr Arg  Asp Cys Leu Gln Asp  Pro Gly Gly Gly Phe  Arg Cys Leu
    1220                1225                1230

Cys His  Ala Gly Phe Ser Gly  Pro Arg Cys Gln Thr  Val Leu Ser
    1235                1240                1245

Pro Cys  Glu Ser Gln Pro Cys  Gln His Gly Gly Gln  Cys Arg Pro
    1250                1255                1260

Ser Pro  Gly Pro Gly Gly Gly  Leu Thr Phe Thr Cys  His Cys Ala
    1265                1270                1275

Gln Pro  Phe Trp Gly Pro Arg  Cys Glu Arg Val Ala  Arg Ser Cys
    1280                1285                1290

Arg Glu  Leu Gln Cys Pro Val  Gly Val Pro Cys Gln  Gln Thr Pro
    1295                1300                1305

Arg Gly  Pro Arg Cys Ala Cys  Pro Pro Gly Leu Ser  Gly Pro Ser
    1310                1315                1320

Cys Arg  Ser Phe Pro Gly Ser  Pro Pro Gly Ala Ser  Asn Ala Ser
    1325                1330                1335

Cys Ala  Ala Ala Pro Cys Leu  His Gly Gly Ser Cys  Arg Pro Ala
    1340                1345                1350

Pro Leu  Ala Pro Phe Phe Arg  Cys Ala Cys Ala Gln  Gly Trp Thr
    1355                1360                1365

Gly Pro  Arg Cys Glu Ala Pro  Ala Ala Ala Pro Glu  Val Ser Glu
    1370                1375                1380

Glu Pro  Arg Cys Pro Arg Ala  Ala Cys Gln Ala Lys  Arg Gly Asp
    1385                1390                1395

Gln Arg  Cys Asp Arg Glu Cys  Asn Ser Pro Gly Cys  Gly Trp Asp
    1400                1405                1410

Gly Gly  Asp Cys Ser Leu Ser  Val Gly Asp Pro Trp  Arg Gln Cys
    1415                1420                1425

Glu Ala  Leu Gln Cys Trp Arg  Leu Phe Asn Asn Ser  Arg Cys Asp
    1430                1435                1440

Pro Ala  Cys Ser Ser Pro Ala  Cys Leu Tyr Asp Asn  Phe Asp Cys
    1445                1450                1455

His Ala  Gly Gly Arg Glu Arg  Thr Cys Asn Pro Val  Tyr Glu Lys
    1460                1465                1470
```

```
Tyr Cys  Ala Asp His Phe Ala  Asp Gly Arg Cys Asp  Gln Gly Cys
    1475                 1480                 1485

Asn Thr  Glu Glu Cys Gly Trp  Asp Gly Leu Asp Cys  Ala Ser Glu
    1490                 1495                 1500

Val Pro  Ala Leu Leu Ala Arg  Gly Val Leu Val Leu  Thr Val Leu
    1505                 1510                 1515

Leu Pro  Pro Glu Glu Leu Leu  Arg Ser Ser Ala Asp  Phe Leu Gln
    1520                 1525                 1530

Arg Leu  Ser Ala Ile Leu Arg  Thr Ser Leu Arg Phe  Arg Leu Asp
    1535                 1540                 1545

Ala His  Gly Gln Ala Met Val  Phe Pro Tyr His Arg  Pro Ser Pro
    1550                 1555                 1560

Gly Ser  Glu Pro Arg Ala Arg  Arg Glu Leu Ala Pro  Glu Val Ile
    1565                 1570                 1575

Gly Ser  Val Val Met Leu Glu  Ile Asp Asn Arg Leu  Cys Leu Gln
    1580                 1585                 1590

Ser Pro  Glu Asn Asp His Cys  Phe Pro Asp Ala Gln  Ser Ala Ala
    1595                 1600                 1605

Asp Tyr  Leu Gly Ala Leu Ser  Ala Val Glu Arg Leu  Asp Phe Pro
    1610                 1615                 1620

Tyr Pro  Leu Arg Asp Val Arg  Gly Glu Pro Leu Glu  Pro Pro Glu
    1625                 1630                 1635

Pro Ser  Val Pro Leu Leu Pro  Leu Leu Val Ala Gly  Ala Val Leu
    1640                 1645                 1650

Leu Leu  Val Ile Leu Val Leu  Gly Val Met Val Ala  Arg Arg Lys
    1655                 1660                 1665

Arg Glu  His Ser Thr Leu Trp  Phe Pro Glu Gly Phe  Ser Leu His
    1670                 1675                 1680

Lys Asp  Val Ala Ser Gly His  Lys Gly Arg Arg Glu  Pro Val Gly
    1685                 1690                 1695

Gln Asp  Ala Leu Gly Met Lys  Asn Met Ala Lys Gly  Glu Ser Leu
    1700                 1705                 1710

Met Gly  Glu Val Ala Thr Asp  Trp Met Asp Thr Glu  Cys Pro Glu
    1715                 1720                 1725

Ala Lys  Arg Leu Lys Val Glu  Glu Pro Gly Met Gly  Ala Glu Glu
    1730                 1735                 1740

Ala Val  Asp Cys Arg Gln Trp  Thr Gln His His Leu  Val Ala Ala
    1745                 1750                 1755

Asp Ile  Arg Val Ala Pro Ala  Met Ala Leu Thr Pro  Pro Gln Gly
    1760                 1765                 1770

Asp Ala  Asp Ala Asp Gly Met  Asp Val Asn Val Arg  Gly Pro Asp
    1775                 1780                 1785

Gly Phe  Thr Pro Leu Met Leu  Ala Ser Phe Cys Gly  Gly Ala Leu
    1790                 1795                 1800

Glu Pro  Met Pro Thr Glu Glu  Asp Glu Ala Asp Asp  Thr Ser Ala
    1805                 1810                 1815

Ser Ile  Ile Ser Asp Leu Ile  Cys Gln Gly Ala Gln  Leu Gly Ala
    1820                 1825                 1830

Arg Thr  Asp Arg Thr Gly Glu  Thr Ala Leu His Leu  Ala Ala Arg
    1835                 1840                 1845

Tyr Ala  Arg Ala Asp Ala Ala  Lys Arg Leu Leu Asp  Ala Gly Ala
    1850                 1855                 1860
```

```
Asp Thr  Asn Ala Gln Asp His  Ser Gly Arg Thr Pro  Leu His Thr
    1865                 1870                 1875

Ala Val  Thr Ala Asp Ala Gln  Gly Val Phe Gln Ile  Leu Ile Arg
    1880                 1885                 1890

Asn Arg  Ser Thr Asp Leu Asp  Ala Arg Met Ala Asp  Gly Ser Thr
    1895                 1900                 1905

Ala Leu  Ile Leu Ala Ala Arg  Leu Ala Val Glu Gly  Met Val Glu
    1910                 1915                 1920

Glu Leu  Ile Ala Ser His Ala  Asp Val Asn Ala Val  Asp Glu Leu
    1925                 1930                 1935

Gly Lys  Ser Ala Leu His Trp  Ala Ala Ala Val Asn  Asn Val Glu
    1940                 1945                 1950

Ala Thr  Leu Ala Leu Leu Lys  Asn Gly Ala Asn Lys  Asp Met Gln
    1955                 1960                 1965

Asp Ser  Lys Glu Glu Thr Pro  Leu Phe Leu Ala Ala  Arg Glu Gly
    1970                 1975                 1980

Ser Tyr  Glu Ala Ala Lys Leu  Leu Leu Asp His Phe  Ala Asn Arg
    1985                 1990                 1995

Glu Ile  Thr Asp His Leu Asp  Arg Leu Pro Arg Asp  Val Ala Gln
    2000                 2005                 2010

Glu Arg  Leu His Gln Asp Ile  Val Arg Leu Leu Asp  Gln Pro Ser
    2015                 2020                 2025

Gly Pro  Arg Ser Pro Pro Gly  Pro His Gly Leu Gly  Pro Leu Leu
    2030                 2035                 2040

Cys Pro  Pro Gly Ala Phe Leu  Pro Gly Leu Lys Ala  Ala Gln Ser
    2045                 2050                 2055

Gly Ser  Lys Lys Ser Arg Arg  Pro Pro Gly Lys Ala  Gly Leu Gly
    2060                 2065                 2070

Pro Gln  Gly Pro Arg Gly Arg  Gly Lys Lys Leu Thr  Leu Ala Cys
    2075                 2080                 2085

Pro Gly  Pro Leu Ala Asp Ser  Ser Val Thr Leu Ser  Pro Val Asp
    2090                 2095                 2100

Ser Leu  Asp Ser Pro Arg Pro  Phe Gly Gly Pro Pro  Ala Ser Pro
    2105                 2110                 2115

Gly Gly  Phe Pro Leu Glu Gly  Pro Tyr Ala Ala Ala  Thr Ala Thr
    2120                 2125                 2130

Ala Val  Ser Leu Ala Gln Leu  Gly Gly Pro Gly Arg  Ala Gly Leu
    2135                 2140                 2145

Gly Arg  Gln Pro Pro Gly Gly  Cys Val Leu Ser Leu  Gly Leu Leu
    2150                 2155                 2160

Asn Pro  Val Ala Val Pro Leu  Asp Trp Ala Arg Leu  Pro Pro Pro
    2165                 2170                 2175

Ala Pro  Pro Gly Pro Ser Phe  Leu Leu Pro Leu Ala  Pro Gly Pro
    2180                 2185                 2190

Gln Leu  Leu Asn Pro Gly Thr  Pro Val Ser Pro Gln  Glu Arg Pro
    2195                 2200                 2205

Pro Pro  Tyr Leu Ala Val Pro  Gly His Gly Glu Glu  Tyr Pro Ala
    2210                 2215                 2220

Ala Gly  Ala His Ser Ser Pro  Pro Lys Ala Arg Phe  Leu Arg Val
    2225                 2230                 2235

Pro Ser  Glu His Pro Tyr Leu  Thr Pro Ser Pro Glu  Ser Pro Glu
    2240                 2245                 2250

His Trp  Ala Ser Pro Ser Pro  Pro Ser Leu Ser Asp  Trp Ser Glu
```

```
    2255                2260                2265

Ser Thr  Pro Ser Pro Ala Thr  Ala Thr Gly Ala Met  Ala Thr Thr
    2270                2275                2280

Thr Gly  Ala Leu Pro Ala Gln  Pro Leu Pro Leu Ser  Val Pro Ser
    2285                2290                2295

Ser Leu  Ala Gln Ala Gln Thr  Gln Leu Gly Pro Gln  Pro Glu Val
    2300                2305                2310

Thr Pro  Lys Arg Gln Val Leu  Ala
    2315                2320


<210> SEQ ID NO 201
<211> LENGTH: 2003
<212> TYPE: PRT
<213> ORGANISM: Homo sapiens

<400> SEQUENCE: 201

Met Gln Pro Pro Ser Leu Leu Leu Leu Leu Leu Leu Leu Leu Leu Leu
1               5                   10                  15

Cys Val Ser Val Val Arg Pro Arg Gly Leu Leu Cys Gly Ser Phe Pro
            20                  25                  30

Glu Pro Cys Ala Asn Gly Gly Thr Cys Leu Ser Leu Ser Leu Gly Gln
        35                  40                  45

Gly Thr Cys Gln Cys Ala Pro Gly Phe Leu Gly Glu Thr Cys Gln Phe
    50                  55                  60

Pro Asp Pro Cys Gln Asn Ala Gln Leu Cys Gln Asn Gly Gly Ser Cys
65                  70                  75                  80

Gln Ala Leu Leu Pro Ala Pro Leu Gly Leu Pro Ser Ser Pro Ser Pro
                85                  90                  95

Leu Thr Pro Ser Phe Leu Cys Thr Cys Leu Pro Gly Phe Thr Gly Glu
            100                 105                 110

Arg Cys Gln Ala Lys Leu Glu Asp Pro Cys Pro Pro Ser Phe Cys Ser
        115                 120                 125

Lys Arg Gly Arg Cys His Ile Gln Ala Ser Gly Arg Pro Gln Cys Ser
    130                 135                 140

Cys Met Pro Gly Trp Thr Gly Glu Gln Cys Gln Leu Arg Asp Phe Cys
145                 150                 155                 160

Ser Ala Asn Pro Cys Val Asn Gly Gly Val Cys Leu Ala Thr Tyr Pro
                165                 170                 175

Gln Ile Gln Cys His Cys Pro Pro Gly Phe Glu Gly His Ala Cys Glu
            180                 185                 190

Arg Asp Val Asn Glu Cys Phe Gln Asp Pro Gly Pro Cys Pro Lys Gly
        195                 200                 205

Thr Ser Cys His Asn Thr Leu Gly Ser Phe Gln Cys Leu Cys Pro Val
    210                 215                 220

Gly Gln Glu Gly Pro Arg Cys Glu Leu Arg Ala Gly Pro Cys Pro Pro
225                 230                 235                 240

Arg Gly Cys Ser Asn Gly Gly Thr Cys Gln Leu Met Pro Glu Lys Asp
                245                 250                 255

Ser Thr Phe His Leu Cys Leu Cys Pro Pro Gly Phe Ile Gly Pro Asp
            260                 265                 270

Cys Glu Val Asn Pro Asp Asn Cys Val Ser His Gln Cys Gln Asn Gly
        275                 280                 285

Gly Thr Cys Gln Asp Gly Leu Asp Thr Tyr Thr Cys Leu Cys Pro Glu
    290                 295                 300
```

-continued

```
Thr Trp Thr Gly Trp Asp Cys Ser Glu Asp Val Asp Glu Cys Glu Thr
305                 310                 315                 320

Gln Gly Pro Pro His Cys Arg Asn Gly Gly Thr Cys Gln Asn Ser Ala
                325                 330                 335

Gly Ser Phe His Cys Val Cys Val Ser Gly Trp Gly Gly Thr Ser Cys
            340                 345                 350

Glu Glu Asn Leu Asp Asp Cys Ile Ala Ala Thr Cys Ala Pro Gly Ser
        355                 360                 365

Thr Cys Ile Asp Arg Val Gly Ser Phe Ser Cys Leu Cys Pro Pro Gly
    370                 375                 380

Arg Thr Gly Leu Leu Cys His Leu Glu Asp Met Cys Leu Ser Gln Pro
385                 390                 395                 400

Cys His Gly Asp Ala Gln Cys Ser Thr Asn Pro Leu Thr Gly Ser Thr
                405                 410                 415

Leu Cys Leu Cys Gln Pro Gly Tyr Ser Gly Pro Thr Cys His Gln Asp
            420                 425                 430

Leu Asp Glu Cys Leu Met Ala Gln Gln Gly Pro Ser Pro Cys Glu His
        435                 440                 445

Gly Gly Ser Cys Leu Asn Thr Pro Gly Ser Phe Asn Cys Leu Cys Pro
    450                 455                 460

Pro Gly Tyr Thr Gly Ser Arg Cys Glu Ala Asp His Asn Glu Cys Leu
465                 470                 475                 480

Ser Gln Pro Cys His Pro Gly Ser Thr Cys Leu Asp Leu Leu Ala Thr
                485                 490                 495

Phe His Cys Leu Cys Pro Pro Gly Leu Glu Gly Gln Leu Cys Glu Val
            500                 505                 510

Glu Thr Asn Glu Cys Ala Ser Ala Pro Cys Leu Asn His Ala Asp Cys
        515                 520                 525

His Asp Leu Leu Asn Gly Phe Gln Cys Ile Cys Leu Pro Gly Phe Ser
    530                 535                 540

Gly Thr Arg Cys Glu Glu Asp Ile Asp Glu Cys Arg Ser Ser Pro Cys
545                 550                 555                 560

Ala Asn Gly Gly Gln Cys Gln Asp Gln Pro Gly Ala Phe His Cys Lys
                565                 570                 575

Cys Leu Pro Gly Phe Glu Gly Pro Arg Cys Gln Thr Glu Val Asp Glu
            580                 585                 590

Cys Leu Ser Asp Pro Cys Pro Val Gly Ala Ser Cys Leu Asp Leu Pro
        595                 600                 605

Gly Ala Phe Phe Cys Leu Cys Pro Ser Gly Phe Thr Gly Gln Leu Cys
    610                 615                 620

Glu Val Pro Leu Cys Ala Pro Asn Leu Cys Gln Pro Lys Gln Ile Cys
625                 630                 635                 640

Lys Asp Gln Lys Asp Lys Ala Asn Cys Leu Cys Pro Asp Gly Ser Pro
                645                 650                 655

Gly Cys Ala Pro Pro Glu Asp Asn Cys Thr Cys His His Gly His Cys
            660                 665                 670

Gln Arg Ser Ser Cys Val Cys Asp Val Gly Trp Thr Gly Pro Glu Cys
        675                 680                 685

Glu Ala Glu Leu Gly Gly Cys Ile Ser Ala Pro Cys Ala His Gly Gly
    690                 695                 700

Thr Cys Tyr Pro Gln Pro Ser Gly Tyr Asn Cys Thr Cys Pro Thr Gly
705                 710                 715                 720

Tyr Thr Gly Pro Thr Cys Ser Glu Glu Met Thr Ala Cys His Ser Gly
```

```
                725                 730                 735

Pro Cys Leu Asn Gly Gly Ser Cys Asn Pro Ser Pro Gly Gly Tyr Tyr
            740                 745                 750

Cys Thr Cys Pro Pro Ser His Thr Gly Pro Gln Cys Gln Thr Ser Thr
        755                 760                 765

Asp Tyr Cys Val Ser Ala Pro Cys Phe Asn Gly Gly Thr Cys Val Asn
    770                 775                 780

Arg Pro Gly Thr Phe Ser Cys Leu Cys Ala Met Gly Phe Gln Gly Pro
785                 790                 795                 800

Arg Cys Glu Gly Lys Leu Arg Pro Ser Cys Ala Asp Ser Pro Cys Arg
                805                 810                 815

Asn Arg Ala Thr Cys Gln Asp Ser Pro Gln Gly Pro Arg Cys Leu Cys
            820                 825                 830

Pro Thr Gly Tyr Thr Gly Gly Ser Cys Gln Thr Leu Met Asp Leu Cys
        835                 840                 845

Ala Gln Lys Pro Cys Pro Arg Asn Ser His Cys Leu Gln Thr Gly Pro
    850                 855                 860

Ser Phe His Cys Leu Cys Leu Gln Gly Trp Thr Gly Pro Leu Cys Asn
865                 870                 875                 880

Leu Pro Leu Ser Ser Cys Gln Lys Ala Ala Leu Ser Gln Gly Ile Asp
                885                 890                 895

Val Ser Ser Leu Cys His Asn Gly Gly Leu Cys Val Asp Ser Gly Pro
            900                 905                 910

Ser Tyr Phe Cys His Cys Pro Pro Gly Phe Gln Gly Ser Leu Cys Gln
        915                 920                 925

Asp His Val Asn Pro Cys Glu Ser Arg Pro Cys Gln Asn Gly Ala Thr
    930                 935                 940

Cys Met Ala Gln Pro Ser Gly Tyr Leu Cys Gln Cys Ala Pro Gly Tyr
945                 950                 955                 960

Asp Gly Gln Asn Cys Ser Lys Glu Leu Asp Ala Cys Gln Ser Gln Pro
                965                 970                 975

Cys His Asn His Gly Thr Cys Thr Pro Lys Pro Gly Gly Phe His Cys
            980                 985                 990

Ala Cys Pro Pro Gly Phe Val Gly  Leu Arg Cys Glu Gly  Asp Val Asp
        995                 1000                1005

Glu Cys  Leu Asp Gln Pro Cys  His Pro Thr Gly Thr  Ala Ala Cys
    1010                1015                1020

His Ser  Leu Ala Asn Ala Phe  Tyr Cys Gln Cys Leu  Pro Gly His
    1025                1030                1035

Thr Gly  Gln Trp Cys Glu Val  Glu Ile Asp Pro Cys  His Ser Gln
    1040                1045                1050

Pro Cys  Phe His Gly Gly Thr  Cys Glu Ala Thr Ala  Gly Ser Pro
    1055                1060                1065

Leu Gly  Phe Ile Cys His Cys  Pro Lys Gly Phe Glu  Gly Pro Thr
    1070                1075                1080

Cys Ser  His Arg Ala Pro Ser  Cys Gly Phe His His  Cys His His
    1085                1090                1095

Gly Gly  Leu Cys Leu Pro Ser  Pro Lys Pro Gly Phe  Pro Pro Arg
    1100                1105                1110

Cys Ala  Cys Leu Ser Gly Tyr  Gly Gly Pro Asp Cys  Leu Thr Pro
    1115                1120                1125

Pro Ala  Pro Lys Gly Cys Gly  Pro Pro Ser Pro Cys  Leu Tyr Asn
    1130                1135                1140
```

-continued

```
Gly Ser  Cys Ser Glu Thr Thr  Gly Leu Gly Gly Pro  Gly Phe Arg
    1145                 1150                 1155

Cys Ser  Cys Pro His Ser Ser  Pro Gly Pro Arg Cys  Gln Lys Pro
    1160                 1165                 1170

Gly Ala  Lys Gly Cys Glu Gly  Arg Ser Gly Asp Gly  Ala Cys Asp
    1175                 1180                 1185

Ala Gly  Cys Ser Gly Pro Gly  Gly Asn Trp Asp Gly  Gly Asp Cys
    1190                 1195                 1200

Ser Leu  Gly Val Pro Asp Pro  Trp Lys Gly Cys Pro  Ser His Ser
    1205                 1210                 1215

Arg Cys  Trp Leu Leu Phe Arg  Asp Gly Gln Cys His  Pro Gln Cys
    1220                 1225                 1230

Asp Ser  Glu Glu Cys Leu Phe  Asp Gly Tyr Asp Cys  Glu Thr Pro
    1235                 1240                 1245

Pro Ala  Cys Thr Pro Ala Tyr  Asp Gln Tyr Cys His  Asp His Phe
    1250                 1255                 1260

His Asn  Gly His Cys Glu Lys  Gly Cys Asn Thr Ala  Glu Cys Gly
    1265                 1270                 1275

Trp Asp  Gly Gly Asp Cys Arg  Pro Glu Asp Gly Asp  Pro Glu Trp
    1280                 1285                 1290

Gly Pro  Ser Leu Ala Leu Leu  Val Val Leu Ser Pro  Pro Ala Leu
    1295                 1300                 1305

Asp Gln  Gln Leu Phe Ala Leu  Ala Arg Val Leu Ser  Leu Thr Leu
    1310                 1315                 1320

Arg Val  Gly Leu Trp Val Arg  Lys Asp Arg Asp Gly  Arg Asp Met
    1325                 1330                 1335

Val Tyr  Pro Tyr Pro Gly Ala  Arg Ala Glu Glu Lys  Leu Gly Gly
    1340                 1345                 1350

Thr Arg  Asp Pro Thr Tyr Gln  Glu Arg Ala Ala Pro  Gln Thr Gln
    1355                 1360                 1365

Pro Leu  Gly Lys Glu Thr Asp  Ser Leu Ser Ala Gly  Phe Val Val
    1370                 1375                 1380

Val Met  Gly Val Asp Leu Ser  Arg Cys Gly Pro Asp  His Pro Ala
    1385                 1390                 1395

Ser Arg  Cys Pro Trp Asp Pro  Gly Leu Leu Leu Arg  Phe Leu Ala
    1400                 1405                 1410

Ala Met  Ala Ala Val Gly Ala  Leu Glu Pro Leu Leu  Pro Gly Pro
    1415                 1420                 1425

Leu Leu  Ala Val His Pro His  Ala Gly Thr Ala Pro  Pro Ala Asn
    1430                 1435                 1440

Gln Leu  Pro Trp Pro Val Leu  Cys Ser Pro Val Ala  Gly Val Ile
    1445                 1450                 1455

Leu Leu  Ala Leu Gly Ala Leu  Leu Val Leu Gln Leu  Ile Arg Arg
    1460                 1465                 1470

Arg Arg  Arg Glu His Gly Ala  Leu Trp Leu Pro Pro  Gly Phe Thr
    1475                 1480                 1485

Arg Arg  Pro Arg Thr Gln Ser  Ala Pro His Arg Arg  Arg Pro Pro
    1490                 1495                 1500

Leu Gly  Glu Asp Ser Ile Gly  Leu Lys Ala Leu Lys  Pro Lys Ala
    1505                 1510                 1515

Glu Val  Asp Glu Asp Gly Val  Val Met Cys Ser Gly  Pro Glu Glu
    1520                 1525                 1530
```

```
Gly Glu  Glu Val Gly Gln Ala  Glu Glu Thr Gly Pro  Pro Ser Thr
    1535                 1540                 1545

Cys Gln  Leu Trp Ser Leu Ser  Gly Gly Cys Gly Ala  Leu Pro Gln
    1550                 1555                 1560

Ala Ala  Met Leu Thr Pro Pro  Gln Glu Ser Glu Met  Glu Ala Pro
    1565                 1570                 1575

Asp Leu  Asp Thr Arg Gly Pro  Asp Gly Val Thr Pro  Leu Met Ser
    1580                 1585                 1590

Ala Val  Cys Cys Gly Glu Val  Gln Ser Gly Thr Phe  Gln Gly Ala
    1595                 1600                 1605

Trp Leu  Gly Cys Pro Glu Pro  Trp Glu Pro Leu Leu  Asp Gly Gly
    1610                 1615                 1620

Ala Cys  Pro Gln Ala His Thr  Val Gly Thr Gly Glu  Thr Pro Leu
    1625                 1630                 1635

His Leu  Ala Ala Arg Phe Ser  Arg Pro Thr Ala Ala  Arg Arg Leu
    1640                 1645                 1650

Leu Glu  Ala Gly Ala Asn Pro  Asn Gln Pro Asp Arg  Ala Gly Arg
    1655                 1660                 1665

Thr Pro  Leu His Ala Ala Val  Ala Ala Asp Ala Arg  Glu Val Cys
    1670                 1675                 1680

Gln Leu  Leu Leu Arg Ser Arg  Gln Thr Ala Val Asp  Ala Arg Thr
    1685                 1690                 1695

Glu Asp  Gly Thr Thr Pro Leu  Met Leu Ala Ala Arg  Leu Ala Val
    1700                 1705                 1710

Glu Asp  Leu Val Glu Glu Leu  Ile Ala Ala Gln Ala  Asp Val Gly
    1715                 1720                 1725

Ala Arg  Asp Lys Trp Gly Lys  Thr Ala Leu His Trp  Ala Ala Ala
    1730                 1735                 1740

Val Asn  Asn Ala Arg Ala Ala  Arg Ser Leu Leu Gln  Ala Gly Ala
    1745                 1750                 1755

Asp Lys  Asp Ala Gln Asp Asn  Arg Glu Gln Thr Pro  Leu Phe Leu
    1760                 1765                 1770

Ala Ala  Arg Glu Gly Ala Val  Glu Val Ala Gln Leu  Leu Leu Gly
    1775                 1780                 1785

Leu Gly  Ala Ala Arg Glu Leu  Arg Asp Gln Ala Gly  Leu Ala Pro
    1790                 1795                 1800

Ala Asp  Val Ala His Gln Arg  Asn His Trp Asp Leu  Leu Thr Leu
    1805                 1810                 1815

Leu Glu  Gly Ala Gly Pro Pro  Glu Ala Arg His Lys  Ala Thr Pro
    1820                 1825                 1830

Gly Arg  Glu Ala Gly Pro Phe  Pro Arg Ala Arg Thr  Val Ser Val
    1835                 1840                 1845

Ser Val  Pro Pro His Gly Gly  Gly Ala Leu Pro Arg  Cys Arg Thr
    1850                 1855                 1860

Leu Ser  Ala Gly Ala Gly Pro  Arg Gly Gly Gly Ala  Cys Leu Gln
    1865                 1870                 1875

Ala Arg  Thr Trp Ser Val Asp  Leu Ala Ala Arg Gly  Gly Gly Ala
    1880                 1885                 1890

Tyr Ser  His Cys Arg Ser Leu  Ser Gly Val Gly Ala  Gly Gly Gly
    1895                 1900                 1905

Pro Thr  Pro Arg Gly Arg Arg  Phe Ser Ala Gly Met  Arg Gly Pro
    1910                 1915                 1920

Arg Pro  Asn Pro Ala Ile Met  Arg Gly Arg Tyr Gly  Val Ala Ala
```

```
    1925                1930                1935

Gly Arg  Gly Gly Arg Val Ser  Thr Asp Asp Trp Pro  Cys Asp Trp
    1940                1945                1950

Val Ala  Leu Gly Ala Cys Gly  Ser Ala Ser Asn Ile  Pro Ile Pro
    1955                1960                1965

Pro Pro  Cys Leu Thr Pro Ser  Pro Glu Arg Gly Ser  Pro Gln Leu
    1970                1975                1980

Asp Cys  Gly Pro Pro Ala Leu  Gln Glu Met Pro Ile  Asn Gln Gly
    1985                1990                1995

Gly Glu  Gly Lys Lys
    2000


<210> SEQ ID NO 202
<211> LENGTH: 723
<212> TYPE: PRT
<213> ORGANISM: Homo sapiens

<400> SEQUENCE: 202

Met Gly Ser Arg Cys Ala Leu Ala Leu Ala Val Leu Ser Ala Leu Leu
1               5                   10                  15

Cys Gln Val Trp Ser Ser Gly Val Phe Glu Leu Lys Leu Gln Glu Phe
            20                  25                  30

Val Asn Lys Lys Gly Leu Leu Gly Asn Arg Asn Cys Cys Arg Gly Gly
        35                  40                  45

Ala Gly Pro Pro Pro Cys Ala Cys Arg Thr Phe Phe Arg Val Cys Leu
    50                  55                  60

Lys His Tyr Gln Ala Ser Val Ser Pro Glu Pro Pro Cys Thr Tyr Gly
65                  70                  75                  80

Ser Ala Val Thr Pro Val Leu Gly Val Asp Ser Phe Ser Leu Pro Asp
                85                  90                  95

Gly Gly Gly Ala Asp Ser Ala Phe Ser Asn Pro Ile Arg Phe Pro Phe
            100                 105                 110

Gly Phe Thr Trp Pro Gly Thr Phe Ser Leu Ile Ile Glu Ala Leu His
        115                 120                 125

Thr Asp Ser Pro Asp Asp Leu Ala Thr Glu Asn Pro Glu Arg Leu Ile
    130                 135                 140

Ser Arg Leu Ala Thr Gln Arg His Leu Thr Val Gly Glu Glu Trp Ser
145                 150                 155                 160

Gln Asp Leu His Ser Ser Gly Arg Thr Asp Leu Lys Tyr Ser Tyr Arg
                165                 170                 175

Phe Val Cys Asp Glu His Tyr Tyr Gly Glu Gly Cys Ser Val Phe Cys
            180                 185                 190

Arg Pro Arg Asp Asp Ala Phe Gly His Phe Thr Cys Gly Glu Arg Gly
        195                 200                 205

Glu Lys Val Cys Asn Pro Gly Trp Lys Gly Pro Tyr Cys Thr Glu Pro
    210                 215                 220

Ile Cys Leu Pro Gly Cys Asp Glu Gln His Gly Phe Cys Asp Lys Pro
225                 230                 235                 240

Gly Glu Cys Lys Cys Arg Val Gly Trp Gln Gly Arg Tyr Cys Asp Glu
                245                 250                 255

Cys Ile Arg Tyr Pro Gly Cys Leu His Gly Thr Cys Gln Gln Pro Trp
            260                 265                 270

Gln Cys Asn Cys Gln Glu Gly Trp Gly Gly Leu Phe Cys Asn Gln Asp
        275                 280                 285
```

-continued

```
Leu Asn Tyr Cys Thr His His Lys Pro Cys Lys Asn Gly Ala Thr Cys
    290                 295                 300

Thr Asn Thr Gly Gln Gly Ser Tyr Thr Cys Ser Cys Arg Pro Gly Tyr
305                 310                 315                 320

Thr Gly Ala Thr Cys Glu Leu Gly Ile Asp Glu Cys Asp Pro Ser Pro
                325                 330                 335

Cys Lys Asn Gly Gly Ser Cys Thr Asp Leu Glu Asn Ser Tyr Ser Cys
            340                 345                 350

Thr Cys Pro Pro Gly Phe Tyr Gly Lys Ile Cys Glu Leu Ser Ala Met
        355                 360                 365

Thr Cys Ala Asp Gly Pro Cys Phe Asn Gly Gly Arg Cys Ser Asp Ser
    370                 375                 380

Pro Asp Gly Gly Tyr Ser Cys Arg Cys Pro Val Gly Tyr Ser Gly Phe
385                 390                 395                 400

Asn Cys Glu Lys Lys Ile Asp Tyr Cys Ser Ser Ser Pro Cys Ser Asn
                405                 410                 415

Gly Ala Lys Cys Val Asp Leu Gly Asp Ala Tyr Leu Cys Arg Cys Gln
            420                 425                 430

Ala Gly Phe Ser Gly Arg His Cys Asp Asp Asn Val Asp Asp Cys Ala
        435                 440                 445

Ser Ser Pro Cys Ala Asn Gly Gly Thr Cys Arg Asp Gly Val Asn Asp
    450                 455                 460

Phe Ser Cys Thr Cys Pro Pro Gly Tyr Thr Gly Arg Asn Cys Ser Ala
465                 470                 475                 480

Pro Val Ser Arg Cys Glu His Ala Pro Cys His Asn Gly Ala Thr Cys
                485                 490                 495

His Glu Arg Gly His Arg Tyr Val Cys Glu Cys Ala Arg Gly Tyr Gly
            500                 505                 510

Gly Pro Asn Cys Gln Phe Leu Leu Pro Glu Leu Pro Pro Gly Pro Ala
        515                 520                 525

Val Val Asp Leu Thr Glu Lys Leu Glu Gly Gln Gly Gly Pro Phe Pro
    530                 535                 540

Trp Val Ala Val Cys Ala Gly Val Ile Leu Val Leu Met Leu Leu Leu
545                 550                 555                 560

Gly Cys Ala Ala Val Val Val Cys Val Arg Leu Arg Leu Gln Lys His
                565                 570                 575

Arg Pro Pro Ala Asp Pro Cys Arg Gly Glu Thr Glu Thr Met Asn Asn
            580                 585                 590

Leu Ala Asn Cys Gln Arg Glu Lys Asp Ile Ser Val Ser Ile Ile Gly
        595                 600                 605

Ala Thr Gln Ile Lys Asn Thr Asn Lys Lys Ala Asp Phe His Gly Asp
    610                 615                 620

His Ser Ala Asp Lys Asn Gly Phe Lys Ala Arg Tyr Pro Ala Val Asp
625                 630                 635                 640

Tyr Asn Leu Val Gln Asp Leu Lys Gly Asp Asp Thr Ala Val Arg Asp
                645                 650                 655

Ala His Ser Lys Arg Asp Thr Lys Cys Gln Pro Gln Gly Ser Ser Gly
            660                 665                 670

Glu Glu Lys Gly Thr Pro Thr Thr Leu Arg Gly Gly Glu Ala Ser Glu
        675                 680                 685

Arg Lys Arg Pro Asp Ser Gly Cys Ser Thr Ser Lys Asp Thr Lys Tyr
    690                 695                 700

Gln Ser Val Tyr Val Ile Ser Glu Glu Lys Asp Glu Cys Val Ile Ala
```

705 710 715 720

Thr Glu Val

<210> SEQ ID NO 203
<211> LENGTH: 685
<212> TYPE: PRT
<213> ORGANISM: Homo sapiens

<400> SEQUENCE: 203

Met Ala Ala Ala Ser Arg Ser Ala Ser Gly Trp Ala Leu Leu Leu Leu
1 5 10 15

Val Ala Leu Trp Gln Gln Arg Ala Ala Gly Ser Gly Val Phe Gln Leu
20 25 30

Gln Leu Gln Glu Phe Ile Asn Glu Arg Gly Val Leu Ala Ser Gly Arg
35 40 45

Pro Cys Glu Pro Gly Cys Arg Thr Phe Phe Arg Val Cys Leu Lys His
50 55 60

Phe Gln Ala Val Val Ser Pro Gly Pro Cys Thr Phe Gly Thr Val Ser
65 70 75 80

Thr Pro Val Leu Gly Thr Asn Ser Phe Ala Val Arg Asp Asp Ser Ser
85 90 95

Gly Gly Gly Arg Asn Pro Leu Gln Leu Pro Phe Asn Phe Thr Trp Pro
100 105 110

Gly Thr Phe Ser Leu Ile Ile Glu Ala Trp His Ala Pro Gly Asp Asp
115 120 125

Leu Arg Pro Glu Ala Leu Pro Pro Asp Ala Leu Ile Ser Lys Ile Ala
130 135 140

Ile Gln Gly Ser Leu Ala Val Gly Gln Asn Trp Leu Leu Asp Glu Gln
145 150 155 160

Thr Ser Thr Leu Thr Arg Leu Arg Tyr Ser Tyr Arg Val Ile Cys Ser
165 170 175

Asp Asn Tyr Tyr Gly Asp Asn Cys Ser Arg Leu Cys Lys Lys Arg Asn
180 185 190

Asp His Phe Gly His Tyr Val Cys Gln Pro Asp Gly Asn Leu Ser Cys
195 200 205

Leu Pro Gly Trp Thr Gly Glu Tyr Cys Gln Gln Pro Ile Cys Leu Ser
210 215 220

Gly Cys His Glu Gln Asn Gly Tyr Cys Ser Lys Pro Ala Glu Cys Leu
225 230 235 240

Cys Arg Pro Gly Trp Gln Gly Arg Leu Cys Asn Glu Cys Ile Pro His
245 250 255

Asn Gly Cys Arg His Gly Thr Cys Ser Thr Pro Trp Gln Cys Thr Cys
260 265 270

Asp Glu Gly Trp Gly Gly Leu Phe Cys Asp Gln Asp Leu Asn Tyr Cys
275 280 285

Thr His His Ser Pro Cys Lys Asn Gly Ala Thr Cys Ser Asn Ser Gly
290 295 300

Gln Arg Ser Tyr Thr Cys Thr Cys Arg Pro Gly Tyr Thr Gly Val Asp
305 310 315 320

Cys Glu Leu Glu Leu Ser Glu Cys Asp Ser Asn Pro Cys Arg Asn Gly
325 330 335

Gly Ser Cys Lys Asp Gln Glu Asp Gly Tyr His Cys Leu Cys Pro Pro
340 345 350

Gly Tyr Tyr Gly Leu His Cys Glu His Ser Thr Leu Ser Cys Ala Asp

```
        355                 360                 365

Ser Pro Cys Phe Asn Gly Gly Ser Cys Arg Glu Arg Asn Gln Gly Ala
    370                 375                 380

Asn Tyr Ala Cys Glu Cys Pro Pro Asn Phe Thr Gly Ser Asn Cys Glu
385                 390                 395                 400

Lys Lys Val Asp Arg Cys Thr Ser Asn Pro Cys Ala Asn Gly Gly Gln
                405                 410                 415

Cys Leu Asn Arg Gly Pro Ser Arg Met Cys Arg Cys Arg Pro Gly Phe
            420                 425                 430

Thr Gly Thr Tyr Cys Glu Leu His Val Ser Asp Cys Ala Arg Asn Pro
        435                 440                 445

Cys Ala His Gly Gly Thr Cys His Asp Leu Glu Asn Gly Leu Met Cys
    450                 455                 460

Thr Cys Pro Ala Gly Phe Ser Gly Arg Arg Cys Glu Val Arg Thr Ser
465                 470                 475                 480

Ile Asp Ala Cys Ala Ser Ser Pro Cys Phe Asn Arg Ala Thr Cys Tyr
                485                 490                 495

Thr Asp Leu Ser Thr Asp Thr Phe Val Cys Asn Cys Pro Tyr Gly Phe
            500                 505                 510

Val Gly Ser Arg Cys Glu Phe Pro Val Gly Leu Pro Pro Ser Phe Pro
        515                 520                 525

Trp Val Ala Val Ser Leu Gly Val Gly Leu Ala Val Leu Leu Val Leu
    530                 535                 540

Leu Gly Met Val Ala Val Ala Val Arg Gln Leu Arg Leu Arg Arg Pro
545                 550                 555                 560

Asp Asp Gly Ser Arg Glu Ala Met Asn Asn Leu Ser Asp Phe Gln Lys
                565                 570                 575

Asp Asn Leu Ile Pro Ala Ala Gln Leu Lys Asn Thr Asn Gln Lys Lys
            580                 585                 590

Glu Leu Glu Val Asp Cys Gly Leu Asp Lys Ser Asn Cys Gly Lys Gln
        595                 600                 605

Gln Asn His Thr Leu Asp Tyr Asn Leu Ala Pro Gly Pro Leu Gly Arg
    610                 615                 620

Gly Thr Met Pro Gly Lys Phe Pro His Ser Asp Lys Ser Leu Gly Glu
625                 630                 635                 640

Lys Ala Pro Leu Arg Leu His Ser Glu Lys Pro Glu Cys Arg Ile Ser
                645                 650                 655

Ala Ile Cys Ser Pro Arg Asp Ser Met Tyr Gln Ser Val Cys Leu Ile
            660                 665                 670

Ser Glu Glu Arg Asn Glu Cys Val Ile Ala Thr Glu Val
        675                 680                 685


<210> SEQ ID NO 204
<211> LENGTH: 1218
<212> TYPE: PRT
<213> ORGANISM: Homo sapiens

<400> SEQUENCE: 204

Met Arg Ser Pro Arg Thr Arg Gly Arg Ser Gly Arg Pro Leu Ser Leu
1               5                   10                  15

Leu Leu Ala Leu Leu Cys Ala Leu Arg Ala Lys Val Cys Gly Ala Ser
            20                  25                  30

Gly Gln Phe Glu Leu Glu Ile Leu Ser Met Gln Asn Val Asn Gly Glu
        35                  40                  45
```

-continued

```
Leu Gln Asn Gly Asn Cys Cys Gly Gly Ala Arg Asn Pro Gly Asp Arg
    50                  55                  60

Lys Cys Thr Arg Asp Glu Cys Asp Thr Tyr Phe Lys Val Cys Leu Lys
65                  70                  75                  80

Glu Tyr Gln Ser Arg Val Thr Ala Gly Gly Pro Cys Ser Phe Gly Ser
                85                  90                  95

Gly Ser Thr Pro Val Ile Gly Gly Asn Thr Phe Asn Leu Lys Ala Ser
            100                 105                 110

Arg Gly Asn Asp Arg Asn Arg Ile Val Leu Pro Phe Ser Phe Ala Trp
        115                 120                 125

Pro Arg Ser Tyr Thr Leu Leu Val Glu Ala Trp Asp Ser Ser Asn Asp
    130                 135                 140

Thr Val Gln Pro Asp Ser Ile Ile Glu Lys Ala Ser His Ser Gly Met
145                 150                 155                 160

Ile Asn Pro Ser Arg Gln Trp Gln Thr Leu Lys Gln Asn Thr Gly Val
                165                 170                 175

Ala His Phe Glu Tyr Gln Ile Arg Val Thr Cys Asp Asp Tyr Tyr Tyr
            180                 185                 190

Gly Phe Gly Cys Asn Lys Phe Cys Arg Pro Arg Asp Asp Phe Phe Gly
        195                 200                 205

His Tyr Ala Cys Asp Gln Asn Gly Asn Lys Thr Cys Met Glu Gly Trp
    210                 215                 220

Met Gly Pro Glu Cys Asn Arg Ala Ile Cys Arg Gln Gly Cys Ser Pro
225                 230                 235                 240

Lys His Gly Ser Cys Lys Leu Pro Gly Asp Cys Arg Cys Gln Tyr Gly
                245                 250                 255

Trp Gln Gly Leu Tyr Cys Asp Lys Cys Ile Pro His Pro Gly Cys Val
            260                 265                 270

His Gly Ile Cys Asn Glu Pro Trp Gln Cys Leu Cys Glu Thr Asn Trp
        275                 280                 285

Gly Gly Gln Leu Cys Asp Lys Asp Leu Asn Tyr Cys Gly Thr His Gln
    290                 295                 300

Pro Cys Leu Asn Gly Gly Thr Cys Ser Asn Thr Gly Pro Asp Lys Tyr
305                 310                 315                 320

Gln Cys Ser Cys Pro Glu Gly Tyr Ser Gly Pro Asn Cys Glu Ile Ala
                325                 330                 335

Glu His Ala Cys Leu Ser Asp Pro Cys His Asn Arg Gly Ser Cys Lys
            340                 345                 350

Glu Thr Ser Leu Gly Phe Glu Cys Glu Cys Ser Pro Gly Trp Thr Gly
        355                 360                 365

Pro Thr Cys Ser Thr Asn Ile Asp Asp Cys Ser Pro Asn Asn Cys Ser
    370                 375                 380

His Gly Gly Thr Cys Gln Asp Leu Val Asn Gly Phe Lys Cys Val Cys
385                 390                 395                 400

Pro Pro Gln Trp Thr Gly Lys Thr Cys Gln Leu Asp Ala Asn Glu Cys
                405                 410                 415

Glu Ala Lys Pro Cys Val Asn Ala Lys Ser Cys Lys Asn Leu Ile Ala
            420                 425                 430

Ser Tyr Tyr Cys Asp Cys Leu Pro Gly Trp Met Gly Gln Asn Cys Asp
        435                 440                 445

Ile Asn Ile Asn Asp Cys Leu Gly Gln Cys Gln Asn Asp Ala Ser Cys
    450                 455                 460

Arg Asp Leu Val Asn Gly Tyr Arg Cys Ile Cys Pro Pro Gly Tyr Ala
```

-continued

```
465                 470                 475                 480

Gly Asp His Cys Glu Arg Asp Ile Asp Glu Cys Ala Ser Asn Pro Cys
                485                 490                 495

Leu Asn Gly Gly His Cys Gln Asn Glu Ile Asn Arg Phe Gln Cys Leu
            500                 505                 510

Cys Pro Thr Gly Phe Ser Gly Asn Leu Cys Gln Leu Asp Ile Asp Tyr
        515                 520                 525

Cys Glu Pro Asn Pro Cys Gln Asn Gly Ala Gln Cys Tyr Asn Arg Ala
    530                 535                 540

Ser Asp Tyr Phe Cys Lys Cys Pro Glu Asp Tyr Glu Gly Lys Asn Cys
545                 550                 555                 560

Ser His Leu Lys Asp His Cys Arg Thr Thr Pro Cys Glu Val Ile Asp
                565                 570                 575

Ser Cys Thr Val Ala Met Ala Ser Asn Asp Thr Pro Glu Gly Val Arg
            580                 585                 590

Tyr Ile Ser Ser Asn Val Cys Gly Pro His Gly Lys Cys Lys Ser Gln
        595                 600                 605

Ser Gly Gly Lys Phe Thr Cys Asp Cys Asn Lys Gly Phe Thr Gly Thr
    610                 615                 620

Tyr Cys His Glu Asn Ile Asn Asp Cys Glu Ser Asn Pro Cys Arg Asn
625                 630                 635                 640

Gly Gly Thr Cys Ile Asp Gly Val Asn Ser Tyr Lys Cys Ile Cys Ser
                645                 650                 655

Asp Gly Trp Glu Gly Ala Tyr Cys Glu Thr Asn Ile Asn Asp Cys Ser
            660                 665                 670

Gln Asn Pro Cys His Asn Gly Gly Thr Cys Arg Asp Leu Val Asn Asp
        675                 680                 685

Phe Tyr Cys Asp Cys Lys Asn Gly Trp Lys Gly Lys Thr Cys His Ser
    690                 695                 700

Arg Asp Ser Gln Cys Asp Glu Ala Thr Cys Asn Asn Gly Gly Thr Cys
705                 710                 715                 720

Tyr Asp Glu Gly Asp Ala Phe Lys Cys Met Cys Pro Gly Gly Trp Glu
                725                 730                 735

Gly Thr Thr Cys Asn Ile Ala Arg Asn Ser Ser Cys Leu Pro Asn Pro
            740                 745                 750

Cys His Asn Gly Gly Thr Cys Val Val Asn Gly Glu Ser Phe Thr Cys
        755                 760                 765

Val Cys Lys Glu Gly Trp Glu Gly Pro Ile Cys Ala Gln Asn Thr Asn
    770                 775                 780

Asp Cys Ser Pro His Pro Cys Tyr Asn Ser Gly Thr Cys Val Asp Gly
785                 790                 795                 800

Asp Asn Trp Tyr Arg Cys Glu Cys Ala Pro Gly Phe Ala Gly Pro Asp
                805                 810                 815

Cys Arg Ile Asn Ile Asn Glu Cys Gln Ser Ser Pro Cys Ala Phe Gly
            820                 825                 830

Ala Thr Cys Val Asp Glu Ile Asn Gly Tyr Arg Cys Val Cys Pro Pro
        835                 840                 845

Gly His Ser Gly Ala Lys Cys Gln Glu Val Ser Gly Arg Pro Cys Ile
    850                 855                 860

Thr Met Gly Ser Val Ile Pro Asp Gly Ala Lys Trp Asp Asp Asp Cys
865                 870                 875                 880

Asn Thr Cys Gln Cys Leu Asn Gly Arg Ile Ala Cys Ser Lys Val Trp
                885                 890                 895
```

```
Cys Gly Pro Arg Pro Cys Leu Leu His Lys Gly His Ser Glu Cys Pro
            900                 905                 910

Ser Gly Gln Ser Cys Ile Pro Ile Leu Asp Asp Gln Cys Phe Val His
        915                 920                 925

Pro Cys Thr Gly Val Gly Glu Cys Arg Ser Ser Ser Leu Gln Pro Val
    930                 935                 940

Lys Thr Lys Cys Thr Ser Asp Ser Tyr Tyr Gln Asp Asn Cys Ala Asn
945                 950                 955                 960

Ile Thr Phe Thr Phe Asn Lys Glu Met Met Ser Pro Gly Leu Thr Thr
                965                 970                 975

Glu His Ile Cys Ser Glu Leu Arg Asn Leu Asn Ile Leu Lys Asn Val
            980                 985                 990

Ser Ala Glu Tyr Ser Ile Tyr Ile  Ala Cys Glu Pro Ser  Pro Ser Ala
        995                 1000                 1005

Asn Asn  Glu Ile His Val Ala  Ile Ser Ala Glu Asp  Ile Arg Asp
    1010                 1015                 1020

Asp Gly  Asn Pro Ile Lys Glu  Ile Thr Asp Lys Ile  Ile Asp Leu
    1025                 1030                 1035

Val Ser  Lys Arg Asp Gly Asn  Ser Ser Leu Ile Ala  Ala Val Ala
    1040                 1045                 1050

Glu Val  Arg Val Gln Arg Arg  Pro Leu Lys Asn Arg  Thr Asp Phe
    1055                 1060                 1065

Leu Val  Pro Leu Leu Ser Ser  Val Leu Thr Val Ala  Trp Ile Cys
    1070                 1075                 1080

Cys Leu  Val Thr Ala Phe Tyr  Trp Cys Leu Arg Lys  Arg Arg Lys
    1085                 1090                 1095

Pro Gly  Ser His Thr His Ser  Ala Ser Glu Asp Asn  Thr Thr Asn
    1100                 1105                 1110

Asn Val  Arg Glu Gln Leu Asn  Gln Ile Lys Asn Pro  Ile Glu Lys
    1115                 1120                 1125

His Gly  Ala Asn Thr Val Pro  Ile Lys Asp Tyr Glu  Asn Lys Asn
    1130                 1135                 1140

Ser Lys  Met Ser Lys Ile Arg  Thr His Asn Ser Glu  Val Glu Glu
    1145                 1150                 1155

Asp Asp  Met Asp Lys His Gln  Gln Lys Ala Arg Phe  Ala Lys Gln
    1160                 1165                 1170

Pro Ala  Tyr Thr Leu Val Asp  Arg Glu Glu Lys Pro  Pro Asn Gly
    1175                 1180                 1185

Thr Pro  Thr Lys His Pro Asn  Trp Thr Asn Lys Gln  Asp Asn Arg
    1190                 1195                 1200

Asp Leu  Glu Ser Ala Gln Ser  Leu Asn Arg Met Glu  Tyr Ile Val
    1205                 1210                 1215
```

<210> SEQ ID NO 205
<211> LENGTH: 1238
<212> TYPE: PRT
<213> ORGANISM: Homo sapiens

<400> SEQUENCE: 205

```
Met Arg Ala Gln Gly Arg Gly Arg Leu Pro Arg Arg Leu Leu Leu Leu
1               5                   10                  15

Leu Ala Leu Trp Val Gln Ala Ala Arg Pro Met Gly Tyr Phe Glu Leu
            20                  25                  30

Gln Leu Ser Ala Leu Arg Asn Val Asn Gly Glu Leu Leu Ser Gly Ala
```

```
        35                  40                  45

Cys Cys Asp Gly Asp Gly Arg Thr Thr Arg Ala Gly Gly Cys Gly His
    50                  55                  60

Asp Glu Cys Asp Thr Tyr Val Arg Val Cys Leu Lys Glu Tyr Gln Ala
65                  70                  75                  80

Lys Val Thr Pro Thr Gly Pro Cys Ser Tyr Gly His Gly Ala Thr Pro
                85                  90                  95

Val Leu Gly Gly Asn Ser Phe Tyr Leu Pro Pro Ala Gly Ala Ala Gly
            100                 105                 110

Asp Arg Ala Arg Ala Arg Ala Arg Ala Gly Gly Asp Gln Asp Pro Gly
        115                 120                 125

Leu Val Val Ile Pro Phe Gln Phe Ala Trp Pro Arg Ser Phe Thr Leu
    130                 135                 140

Ile Val Glu Ala Trp Asp Trp Asp Asn Asp Thr Thr Pro Asn Glu Glu
145                 150                 155                 160

Leu Leu Ile Glu Arg Val Ser His Ala Gly Met Ile Asn Pro Glu Asp
                165                 170                 175

Arg Trp Lys Ser Leu His Phe Ser Gly His Val Ala His Leu Glu Leu
            180                 185                 190

Gln Ile Arg Val Arg Cys Asp Glu Asn Tyr Tyr Ser Ala Thr Cys Asn
        195                 200                 205

Lys Phe Cys Arg Pro Arg Asn Asp Phe Phe Gly His Tyr Thr Cys Asp
    210                 215                 220

Gln Tyr Gly Asn Lys Ala Cys Met Asp Gly Trp Met Gly Lys Glu Cys
225                 230                 235                 240

Lys Glu Ala Val Cys Lys Gln Gly Cys Asn Leu Leu His Gly Gly Cys
                245                 250                 255

Thr Val Pro Gly Glu Cys Arg Cys Ser Tyr Gly Trp Gln Gly Arg Phe
            260                 265                 270

Cys Asp Glu Cys Val Pro Tyr Pro Gly Cys Val His Gly Ser Cys Val
        275                 280                 285

Glu Pro Trp Gln Cys Asn Cys Glu Thr Asn Trp Gly Gly Leu Leu Cys
    290                 295                 300

Asp Lys Asp Leu Asn Tyr Cys Gly Ser His His Pro Cys Thr Asn Gly
305                 310                 315                 320

Gly Thr Cys Ile Asn Ala Glu Pro Asp Gln Tyr Arg Cys Thr Cys Pro
                325                 330                 335

Asp Gly Tyr Ser Gly Arg Asn Cys Glu Lys Ala Glu His Ala Cys Thr
            340                 345                 350

Ser Asn Pro Cys Ala Asn Gly Gly Ser Cys His Glu Val Pro Ser Gly
        355                 360                 365

Phe Glu Cys His Cys Pro Ser Gly Trp Ser Gly Pro Thr Cys Ala Leu
    370                 375                 380

Asp Ile Asp Glu Cys Ala Ser Asn Pro Cys Ala Ala Gly Gly Thr Cys
385                 390                 395                 400

Val Asp Gln Val Asp Gly Phe Glu Cys Ile Cys Pro Glu Gln Trp Val
                405                 410                 415

Gly Ala Thr Cys Gln Leu Asp Ala Asn Glu Cys Glu Gly Lys Pro Cys
            420                 425                 430

Leu Asn Ala Phe Ser Cys Lys Asn Leu Ile Gly Gly Tyr Tyr Cys Asp
        435                 440                 445

Cys Ile Pro Gly Trp Lys Gly Ile Asn Cys His Ile Asn Val Asn Asp
    450                 455                 460
```

-continued

Cys Arg Gly Gln Cys Gln His Gly Gly Thr Cys Lys Asp Leu Val Asn
465 470 475 480

Gly Tyr Gln Cys Val Cys Pro Arg Gly Phe Gly Gly Arg His Cys Glu
485 490 495

Leu Glu Arg Asp Glu Cys Ala Ser Ser Pro Cys His Ser Gly Gly Leu
500 505 510

Cys Glu Asp Leu Ala Asp Gly Phe His Cys His Cys Pro Gln Gly Phe
515 520 525

Ser Gly Pro Leu Cys Glu Val Asp Val Asp Leu Cys Glu Pro Ser Pro
530 535 540

Cys Arg Asn Gly Ala Arg Cys Tyr Asn Leu Glu Gly Asp Tyr Tyr Cys
545 550 555 560

Ala Cys Pro Asp Asp Phe Gly Gly Lys Asn Cys Ser Val Pro Arg Glu
565 570 575

Pro Cys Pro Gly Gly Ala Cys Arg Val Ile Asp Gly Cys Gly Ser Asp
580 585 590

Ala Gly Pro Gly Met Pro Gly Thr Ala Ala Ser Gly Val Cys Gly Pro
595 600 605

His Gly Arg Cys Val Ser Gln Pro Gly Gly Asn Phe Ser Cys Ile Cys
610 615 620

Asp Ser Gly Phe Thr Gly Thr Tyr Cys His Glu Asn Ile Asp Asp Cys
625 630 635 640

Leu Gly Gln Pro Cys Arg Asn Gly Gly Thr Cys Ile Asp Glu Val Asp
645 650 655

Ala Phe Arg Cys Phe Cys Pro Ser Gly Trp Glu Gly Glu Leu Cys Asp
660 665 670

Thr Asn Pro Asn Asp Cys Leu Pro Asp Pro Cys His Ser Arg Gly Arg
675 680 685

Cys Tyr Asp Leu Val Asn Asp Phe Tyr Cys Ala Cys Asp Asp Gly Trp
690 695 700

Lys Gly Lys Thr Cys His Ser Arg Glu Phe Gln Cys Asp Ala Tyr Thr
705 710 715 720

Cys Ser Asn Gly Gly Thr Cys Tyr Asp Ser Gly Asp Thr Phe Arg Cys
725 730 735

Ala Cys Pro Pro Gly Trp Lys Gly Ser Thr Cys Ala Val Ala Lys Asn
740 745 750

Ser Ser Cys Leu Pro Asn Pro Cys Val Asn Gly Gly Thr Cys Val Gly
755 760 765

Ser Gly Ala Ser Phe Ser Cys Ile Cys Arg Asp Gly Trp Glu Gly Arg
770 775 780

Thr Cys Thr His Asn Thr Asn Asp Cys Asn Pro Leu Pro Cys Tyr Asn
785 790 795 800

Gly Gly Ile Cys Val Asp Gly Val Asn Trp Phe Arg Cys Glu Cys Ala
805 810 815

Pro Gly Phe Ala Gly Pro Asp Cys Arg Ile Asn Ile Asp Glu Cys Gln
820 825 830

Ser Ser Pro Cys Ala Tyr Gly Ala Thr Cys Val Asp Glu Ile Asn Gly
835 840 845

Tyr Arg Cys Ser Cys Pro Pro Gly Arg Ala Gly Pro Arg Cys Gln Glu
850 855 860

Val Ile Gly Phe Gly Arg Ser Cys Trp Ser Arg Gly Thr Pro Phe Pro
865 870 875 880

```
His Gly Ser Ser Trp Val Glu Asp Cys Asn Ser Cys Arg Cys Leu Asp
                885                 890                 895

Gly Arg Arg Asp Cys Ser Lys Val Trp Cys Gly Trp Lys Pro Cys Leu
            900                 905                 910

Leu Ala Gly Gln Pro Glu Ala Leu Ser Ala Gln Cys Pro Leu Gly Gln
        915                 920                 925

Arg Cys Leu Glu Lys Ala Pro Gly Gln Cys Leu Arg Pro Pro Cys Glu
    930                 935                 940

Ala Trp Gly Glu Cys Gly Ala Glu Glu Pro Pro Ser Thr Pro Cys Leu
945                 950                 955                 960

Pro Arg Ser Gly His Leu Asp Asn Asn Cys Ala Arg Leu Thr Leu His
                965                 970                 975

Phe Asn Arg Asp His Val Pro Gln Gly Thr Thr Val Gly Ala Ile Cys
            980                 985                 990

Ser Gly Ile Arg Ser Leu Pro Ala  Thr Arg Ala Val Ala  Arg Asp Arg
        995                 1000                1005

Leu Leu  Val Leu Leu Cys Asp  Arg Ala Ser Ser Gly  Ala Ser Ala
    1010                1015                1020

Val Glu  Val Ala Val Ser Phe  Ser Pro Ala Arg Asp  Leu Pro Asp
    1025                1030                1035

Ser Ser  Leu Ile Gln Gly Ala  Ala His Ala Ile Val  Ala Ala Ile
    1040                1045                1050

Thr Gln  Arg Gly Asn Ser Ser  Leu Leu Leu Ala Val  Thr Glu Val
    1055                1060                1065

Lys Val  Glu Thr Val Val Thr  Gly Gly Ser Ser Thr  Gly Leu Leu
    1070                1075                1080

Val Pro  Val Leu Cys Gly Ala  Phe Ser Val Leu Trp  Leu Ala Cys
    1085                1090                1095

Val Val  Leu Cys Val Trp Trp  Thr Arg Lys Arg Arg  Lys Glu Arg
    1100                1105                1110

Glu Arg  Ser Arg Leu Pro Arg  Glu Glu Ser Ala Asn  Asn Gln Trp
    1115                1120                1125

Ala Pro  Leu Asn Pro Ile Arg  Asn Pro Ile Glu Arg  Pro Gly Gly
    1130                1135                1140

His Lys  Asp Val Leu Tyr Gln  Cys Lys Asn Phe Thr  Pro Pro Pro
    1145                1150                1155

Arg Arg  Ala Asp Glu Ala Leu  Pro Gly Pro Ala Gly  His Ala Ala
    1160                1165                1170

Val Arg  Glu Asp Glu Glu Asp  Glu Asp Leu Gly Arg  Gly Glu Glu
    1175                1180                1185

Asp Ser  Leu Glu Ala Glu Lys  Phe Leu Ser His Lys  Phe Thr Lys
    1190                1195                1200

Asp Pro  Gly Arg Ser Pro Gly  Arg Pro Ala His Trp  Ala Ser Gly
    1205                1210                1215

Pro Lys  Val Asp Asn Arg Ala  Val Arg Ser Ile Asn  Glu Ala Arg
    1220                1225                1230

Tyr Ala  Gly Lys Glu
    1235
```

<210> SEQ ID NO 206
<211> LENGTH: 1074
<212> TYPE: PRT
<213> ORGANISM: Homo sapiens

<400> SEQUENCE: 206

-continued

```
Met Thr Leu Ala Thr Asp Pro Thr Asp Gly Ser Ile Leu Ala Cys Asp
1               5                   10                  15

Pro Gly Leu Ser Arg Thr Cys Asp Gln Asn Thr Tyr Leu Ser Gly Leu
            20                  25                  30

Cys Tyr Leu Phe Arg Gln Asn Leu Gln Gly Pro Met Leu Gln Gly Arg
        35                  40                  45

Pro Gly Phe Gln Glu Cys Ile Lys Gly Asn Val Asp Leu Val Phe Leu
    50                  55                  60

Phe Asp Gly Ser Met Ser Leu Gln Pro Asp Glu Phe Gln Lys Ile Leu
65                  70                  75                  80

Asp Phe Met Lys Asp Val Met Lys Lys Leu Ser Asn Thr Ser Tyr Gln
                85                  90                  95

Phe Ala Ala Val Gln Phe Ser Thr Ser Tyr Lys Thr Glu Phe Asp Phe
            100                 105                 110

Ser Asp Tyr Val Lys Arg Lys Asp Pro Asp Ala Leu Leu Lys His Val
        115                 120                 125

Lys His Met Leu Leu Leu Thr Asn Thr Phe Gly Ala Ile Asn Tyr Val
    130                 135                 140

Ala Thr Glu Val Phe Arg Glu Glu Leu Gly Ala Arg Pro Asp Ala Thr
145                 150                 155                 160

Lys Val Leu Ile Ile Ile Thr Asp Gly Glu Ala Thr Asp Ser Gly Asn
                165                 170                 175

Ile Asp Ala Ala Lys Asp Ile Ile Arg Tyr Ile Ile Gly Ile Gly Lys
            180                 185                 190

His Phe Gln Thr Lys Glu Ser Gln Glu Thr Leu His Lys Phe Ala Ser
        195                 200                 205

Lys Pro Ala Ser Glu Phe Val Lys Ile Leu Asp Thr Phe Glu Lys Leu
    210                 215                 220

Lys Asp Leu Phe Thr Glu Leu Gln Lys Lys Ile Tyr Val Ile Glu Gly
225                 230                 235                 240

Thr Ser Lys Gln Asp Leu Thr Ser Phe Asn Met Glu Leu Ser Ser Ser
                245                 250                 255

Gly Ile Ser Ala Asp Leu Ser Arg Gly His Ala Val Val Gly Ala Val
            260                 265                 270

Gly Ala Lys Asp Trp Ala Gly Gly Phe Leu Asp Leu Lys Ala Asp Leu
        275                 280                 285

Gln Asp Asp Thr Phe Ile Gly Asn Glu Pro Leu Thr Pro Glu Val Arg
    290                 295                 300

Ala Gly Tyr Leu Gly Tyr Thr Val Thr Trp Leu Pro Ser Arg Gln Lys
305                 310                 315                 320

Thr Ser Leu Leu Ala Ser Gly Ala Pro Arg Tyr Gln His Met Gly Arg
                325                 330                 335

Val Leu Leu Phe Gln Glu Pro Gln Gly Gly Gly His Trp Ser Gln Val
            340                 345                 350

Gln Thr Ile His Gly Thr Gln Ile Gly Ser Tyr Phe Gly Gly Glu Leu
        355                 360                 365

Cys Gly Val Asp Val Asp Gln Asp Gly Glu Thr Glu Leu Leu Leu Ile
    370                 375                 380

Gly Ala Pro Leu Phe Tyr Gly Glu Gln Arg Gly Gly Arg Val Phe Ile
385                 390                 395                 400

Tyr Gln Arg Arg Gln Leu Gly Phe Glu Glu Val Ser Glu Leu Gln Gly
                405                 410                 415
```

Asp Pro Gly Tyr Pro Leu Gly Arg Phe Gly Glu Ala Ile Thr Ala Leu
420 425 430

Thr Asp Ile Asn Gly Asp Gly Leu Val Asp Val Ala Val Gly Ala Pro
435 440 445

Leu Glu Glu Gln Gly Ala Val Tyr Ile Phe Asn Gly Arg His Gly Gly
450 455 460

Leu Ser Pro Gln Pro Ser Gln Arg Ile Glu Gly Thr Gln Val Leu Ser
465 470 475 480

Gly Ile Gln Trp Phe Gly Arg Ser Ile His Gly Val Lys Asp Leu Glu
485 490 495

Gly Asp Gly Leu Ala Asp Val Ala Val Gly Ala Glu Ser Gln Met Ile
500 505 510

Val Leu Ser Ser Arg Pro Val Val Asp Met Val Thr Leu Met Ser Phe
515 520 525

Ser Pro Ala Glu Ile Pro Val His Glu Val Glu Cys Ser Tyr Ser Thr
530 535 540

Ser Asn Lys Met Lys Glu Gly Val Asn Ile Thr Ile Cys Phe Gln Ile
545 550 555 560

Lys Ser Leu Ile Pro Gln Phe Gln Gly Arg Leu Val Ala Asn Leu Thr
565 570 575

Tyr Thr Leu Gln Leu Asp Gly His Arg Thr Arg Arg Arg Gly Leu Phe
580 585 590

Pro Gly Gly Arg His Glu Leu Arg Arg Asn Ile Ala Val Thr Thr Ser
595 600 605

Met Ser Cys Thr Asp Phe Ser Phe His Phe Pro Val Cys Val Gln Asp
610 615 620

Leu Ile Ser Pro Ile Asn Val Ser Leu Asn Phe Ser Leu Trp Glu Glu
625 630 635 640

Glu Gly Thr Pro Arg Asp Gln Arg Ala Gln Gly Lys Asp Ile Pro Pro
645 650 655

Ile Leu Arg Pro Ser Leu His Ser Glu Thr Trp Glu Ile Pro Phe Glu
660 665 670

Lys Asn Cys Gly Glu Asp Lys Lys Cys Glu Ala Asn Leu Arg Val Ser
675 680 685

Phe Ser Pro Ala Arg Ser Arg Ala Leu Arg Leu Thr Ala Phe Ala Ser
690 695 700

Leu Ser Val Glu Leu Ser Leu Ser Asn Leu Glu Glu Asp Ala Tyr Trp
705 710 715 720

Val Gln Leu Asp Leu His Phe Pro Pro Gly Leu Ser Phe Arg Lys Val
725 730 735

Glu Met Leu Lys Pro His Ser Gln Ile Pro Val Ser Cys Glu Glu Leu
740 745 750

Pro Glu Glu Ser Arg Leu Leu Ser Arg Ala Leu Ser Cys Asn Val Ser
755 760 765

Ser Pro Ile Phe Lys Ala Gly His Ser Val Ala Leu Gln Met Met Phe
770 775 780

Asn Thr Leu Val Asn Ser Ser Trp Gly Asp Ser Val Glu Leu His Ala
785 790 795 800

Asn Val Thr Cys Asn Asn Glu Asp Ser Asp Leu Leu Glu Asp Asn Ser
805 810 815

Ala Thr Thr Ile Ile Pro Ile Leu Tyr Pro Ile Asn Ile Leu Ile Gln
820 825 830

Asp Gln Glu Asp Ser Thr Leu Tyr Val Ser Phe Thr Pro Lys Gly Pro 835 840 845

Lys Ile His Gln Val Lys His Met Tyr Gln Val Arg Ile Gln Pro Ser
850 855 860

Ile His Asp His Asn Ile Pro Thr Leu Glu Ala Val Val Gly Val Pro
865 870 875 880

Gln Pro Pro Ser Glu Gly Pro Ile Thr His Gln Trp Ser Val Gln Met
885 890 895

Glu Pro Pro Val Pro Cys His Tyr Glu Asp Leu Glu Arg Leu Pro Asp
900 905 910

Ala Ala Glu Pro Cys Leu Pro Gly Ala Leu Phe Arg Cys Pro Val Val
915 920 925

Phe Arg Gln Glu Ile Leu Val Gln Val Ile Gly Thr Leu Glu Leu Val
930 935 940

Gly Glu Ile Glu Ala Ser Ser Met Phe Ser Leu Cys Ser Ser Leu Ser
945 950 955 960

Ile Ser Phe Asn Ser Ser Lys His Phe His Leu Tyr Gly Ser Asn Ala
965 970 975

Ser Leu Ala Gln Val Val Met Lys Val Asp Val Val Tyr Glu Lys Gln
980 985 990

Met Leu Tyr Leu Tyr Val Leu Ser Gly Ile Gly Gly Leu Leu Leu Leu
995 1000 1005

Leu Leu Ile Phe Ile Val Leu Tyr Lys Val Gly Phe Phe Lys Arg
1010 1015 1020

Asn Leu Lys Glu Lys Met Glu Ala Gly Arg Gly Val Pro Asn Gly
1025 1030 1035

Ile Pro Ala Glu Asp Ser Glu Gln Leu Ala Ser Gly Gln Glu Ala
1040 1045 1050

Gly Asp Pro Gly Cys Leu Lys Pro Leu His Glu Lys Asp Ser Glu
1055 1060 1065

Ser Gly Gly Gly Lys Asp
1070

<210> SEQ ID NO 207
<211> LENGTH: 1153
<212> TYPE: PRT
<213> ORGANISM: Homo sapiens

<400> SEQUENCE: 207

Met Ala Leu Arg Val Leu Leu Leu Thr Ala Leu Thr Leu Cys His Gly
1 5 10 15

Phe Asn Leu Asp Thr Glu Asn Ala Met Thr Phe Gln Glu Asn Ala Arg
20 25 30

Gly Phe Gly Gln Ser Val Val Gln Leu Gln Gly Ser Arg Val Val Val
35 40 45

Gly Ala Pro Gln Glu Ile Val Ala Ala Asn Gln Arg Gly Ser Leu Tyr
50 55 60

Gln Cys Asp Tyr Ser Thr Gly Ser Cys Glu Pro Ile Arg Leu Gln Val
65 70 75 80

Pro Val Glu Ala Val Asn Met Ser Leu Gly Leu Ser Leu Ala Ala Thr
85 90 95

Thr Ser Pro Pro Gln Leu Leu Ala Cys Gly Pro Thr Val His Gln Thr
100 105 110

Cys Ser Glu Asn Thr Tyr Val Lys Gly Leu Cys Phe Leu Phe Gly Ser
115 120 125

-continued

```
Asn Leu Arg Gln Gln Pro Gln Lys Phe Pro Glu Ala Leu Arg Gly Cys
    130                 135                 140

Pro Gln Glu Asp Ser Asp Ile Ala Phe Leu Ile Asp Gly Ser Gly Ser
145                 150                 155                 160

Ile Ile Pro His Asp Phe Arg Arg Met Lys Glu Phe Val Ser Thr Val
                165                 170                 175

Met Glu Gln Leu Lys Lys Ser Lys Thr Leu Phe Ser Leu Met Gln Tyr
            180                 185                 190

Ser Glu Glu Phe Arg Ile His Phe Thr Phe Lys Glu Phe Gln Asn Asn
        195                 200                 205

Pro Asn Pro Arg Ser Leu Val Lys Pro Ile Thr Gln Leu Leu Gly Arg
    210                 215                 220

Thr His Thr Ala Thr Gly Ile Arg Lys Val Val Arg Glu Leu Phe Asn
225                 230                 235                 240

Ile Thr Asn Gly Ala Arg Lys Asn Ala Phe Lys Ile Leu Val Val Ile
                245                 250                 255

Thr Asp Gly Glu Lys Phe Gly Asp Pro Leu Gly Tyr Glu Asp Val Ile
            260                 265                 270

Pro Glu Ala Asp Arg Glu Gly Val Ile Arg Tyr Val Ile Gly Val Gly
        275                 280                 285

Asp Ala Phe Arg Ser Glu Lys Ser Arg Gln Glu Leu Asn Thr Ile Ala
    290                 295                 300

Ser Lys Pro Pro Arg Asp His Val Phe Gln Val Asn Asn Phe Glu Ala
305                 310                 315                 320

Leu Lys Thr Ile Gln Asn Gln Leu Arg Glu Lys Ile Phe Ala Ile Glu
                325                 330                 335

Gly Thr Gln Thr Gly Ser Ser Ser Ser Phe Glu His Glu Met Ser Gln
            340                 345                 350

Glu Gly Phe Ser Ala Ala Ile Thr Ser Asn Gly Pro Leu Leu Ser Thr
        355                 360                 365

Val Gly Ser Tyr Asp Trp Ala Gly Gly Val Phe Leu Tyr Thr Ser Lys
    370                 375                 380

Glu Lys Ser Thr Phe Ile Asn Met Thr Arg Val Asp Ser Asp Met Asn
385                 390                 395                 400

Asp Ala Tyr Leu Gly Tyr Ala Ala Ala Ile Ile Leu Arg Asn Arg Val
                405                 410                 415

Gln Ser Leu Val Leu Gly Ala Pro Arg Tyr Gln His Ile Gly Leu Val
            420                 425                 430

Ala Met Phe Arg Gln Asn Thr Gly Met Trp Glu Ser Asn Ala Asn Val
        435                 440                 445

Lys Gly Thr Gln Ile Gly Ala Tyr Phe Gly Ala Ser Leu Cys Ser Val
    450                 455                 460

Asp Val Asp Ser Asn Gly Ser Thr Asp Leu Val Leu Ile Gly Ala Pro
465                 470                 475                 480

His Tyr Tyr Glu Gln Thr Arg Gly Gly Gln Val Ser Val Cys Pro Leu
                485                 490                 495

Pro Arg Gly Gln Arg Ala Arg Trp Gln Cys Asp Ala Val Leu Tyr Gly
            500                 505                 510

Glu Gln Gly Gln Pro Trp Gly Arg Phe Gly Ala Ala Leu Thr Val Leu
        515                 520                 525

Gly Asp Val Asn Gly Asp Lys Leu Thr Asp Val Ala Ile Gly Ala Pro
    530                 535                 540

Gly Glu Glu Asp Asn Arg Gly Ala Val Tyr Leu Phe His Gly Thr Ser
```

545 550 555 560

Gly Ser Gly Ile Ser Pro Ser His Ser Gln Arg Ile Ala Gly Ser Lys
565 570 575

Leu Ser Pro Arg Leu Gln Tyr Phe Gly Gln Ser Leu Ser Gly Gly Gln
580 585 590

Asp Leu Thr Met Asp Gly Leu Val Asp Leu Thr Val Gly Ala Gln Gly
595 600 605

His Val Leu Leu Leu Arg Ser Gln Pro Val Leu Arg Val Lys Ala Ile
610 615 620

Met Glu Phe Asn Pro Arg Glu Val Ala Arg Asn Val Phe Glu Cys Asn
625 630 635 640

Asp Gln Val Val Lys Gly Lys Glu Ala Gly Glu Val Arg Val Cys Leu
645 650 655

His Val Gln Lys Ser Thr Arg Asp Arg Leu Arg Glu Gly Gln Ile Gln
660 665 670

Ser Val Val Thr Tyr Asp Leu Ala Leu Asp Ser Gly Arg Pro His Ser
675 680 685

Arg Ala Val Phe Asn Glu Thr Lys Asn Ser Thr Arg Arg Gln Thr Gln
690 695 700

Val Leu Gly Leu Thr Gln Thr Cys Glu Thr Leu Lys Leu Gln Leu Pro
705 710 715 720

Asn Cys Ile Glu Asp Pro Val Ser Pro Ile Val Leu Arg Leu Asn Phe
725 730 735

Ser Leu Val Gly Thr Pro Leu Ser Ala Phe Gly Asn Leu Arg Pro Val
740 745 750

Leu Ala Glu Asp Ala Gln Arg Leu Phe Thr Ala Leu Phe Pro Phe Glu
755 760 765

Lys Asn Cys Gly Asn Asp Asn Ile Cys Gln Asp Asp Leu Ser Ile Thr
770 775 780

Phe Ser Phe Met Ser Leu Asp Cys Leu Val Val Gly Gly Pro Arg Glu
785 790 795 800

Phe Asn Val Thr Val Thr Val Arg Asn Asp Gly Glu Asp Ser Tyr Arg
805 810 815

Thr Gln Val Thr Phe Phe Phe Pro Leu Asp Leu Ser Tyr Arg Lys Val
820 825 830

Ser Thr Leu Gln Asn Gln Arg Ser Gln Arg Ser Trp Arg Leu Ala Cys
835 840 845

Glu Ser Ala Ser Ser Thr Glu Val Ser Gly Ala Leu Lys Ser Thr Ser
850 855 860

Cys Ser Ile Asn His Pro Ile Phe Pro Glu Asn Ser Glu Val Thr Phe
865 870 875 880

Asn Ile Thr Phe Asp Val Asp Ser Lys Ala Ser Leu Gly Asn Lys Leu
885 890 895

Leu Leu Lys Ala Asn Val Thr Ser Glu Asn Asn Met Pro Arg Thr Asn
900 905 910

Lys Thr Glu Phe Gln Leu Glu Leu Pro Val Lys Tyr Ala Val Tyr Met
915 920 925

Val Val Thr Ser His Gly Val Ser Thr Lys Tyr Leu Asn Phe Thr Ala
930 935 940

Ser Glu Asn Thr Ser Arg Val Met Gln His Gln Tyr Gln Val Ser Asn
945 950 955 960

Leu Gly Gln Arg Ser Leu Pro Ile Ser Leu Val Phe Leu Val Pro Val
965 970 975

```
Arg Leu Asn Gln Thr Val Ile Trp Asp Arg Pro Gln Val Thr Phe Ser
            980                 985                 990

Glu Asn Leu Ser Ser Thr Cys His  Thr Lys Glu Arg Leu  Pro Ser His
        995                 1000                 1005

Ser Asp  Phe Leu Ala Glu Leu  Arg Lys Ala Pro Val  Val Asn Cys
    1010                 1015                 1020

Ser Ile  Ala Val Cys Gln Arg  Ile Gln Cys Asp Ile  Pro Phe Phe
    1025                 1030                 1035

Gly Ile  Gln Glu Glu Phe Asn  Ala Thr Leu Lys Gly  Asn Leu Ser
    1040                 1045                 1050

Phe Asp  Trp Tyr Ile Lys Thr  Ser His Asn His Leu  Leu Ile Val
    1055                 1060                 1065

Ser Thr  Ala Glu Ile Leu Phe  Asn Asp Ser Val Phe  Thr Leu Leu
    1070                 1075                 1080

Pro Gly  Gln Gly Ala Phe Val  Arg Ser Gln Thr Glu  Thr Lys Val
    1085                 1090                 1095

Glu Pro  Phe Glu Val Pro Asn  Pro Leu Pro Leu Ile  Val Gly Ser
    1100                 1105                 1110

Ser Val  Gly Gly Leu Leu Leu  Leu Ala Leu Ile Thr  Ala Ala Leu
    1115                 1120                 1125

Tyr Lys  Leu Gly Phe Phe Lys  Arg Gln Tyr Lys Asp  Met Met Ser
    1130                 1135                 1140

Glu Gly  Gly Pro Pro Gly Ala  Glu Pro Gln
    1145                 1150


<210> SEQ ID NO 208
<211> LENGTH: 1153
<212> TYPE: PRT
<213> ORGANISM: Homo sapiens

<400> SEQUENCE: 208

Met Ala Leu Arg Val Leu Leu Leu Thr Ala Leu Thr Leu Cys His Gly
1               5                   10                  15

Phe Asn Leu Asp Thr Glu Asn Ala Met Thr Phe Gln Glu Asn Ala Arg
            20                  25                  30

Gly Phe Gly Gln Ser Val Val Gln Leu Gln Gly Ser Arg Val Val Val
        35                  40                  45

Gly Ala Pro Gln Glu Ile Val Ala Ala Asn Gln Arg Gly Ser Leu Tyr
    50                  55                  60

Gln Cys Asp Tyr Ser Thr Gly Ser Cys Glu Pro Ile Arg Leu Gln Val
65                  70                  75                  80

Pro Val Glu Ala Val Asn Met Ser Leu Gly Leu Ser Leu Ala Ala Thr
                85                  90                  95

Thr Ser Pro Pro Gln Leu Leu Ala Cys Gly Pro Thr Val His Gln Thr
            100                 105                 110

Cys Ser Glu Asn Thr Tyr Val Lys Gly Leu Cys Phe Leu Phe Gly Ser
        115                 120                 125

Asn Leu Arg Gln Gln Pro Gln Lys Phe Pro Glu Ala Leu Arg Gly Cys
    130                 135                 140

Pro Gln Glu Asp Ser Asp Ile Ala Phe Leu Ile Asp Gly Ser Gly Ser
145                 150                 155                 160

Ile Ile Pro His Asp Phe Arg Arg Met Lys Glu Phe Val Ser Thr Val
                165                 170                 175

Met Glu Gln Leu Lys Lys Ser Lys Thr Leu Phe Ser Leu Met Gln Tyr
```

```
            180                 185                 190

Ser Glu Glu Phe Arg Ile His Phe Thr Phe Lys Glu Phe Gln Asn Asn
        195                 200                 205

Pro Asn Pro Arg Ser Leu Val Lys Pro Ile Thr Gln Leu Leu Gly Arg
    210                 215                 220

Thr His Thr Ala Thr Gly Ile Arg Lys Val Val Arg Glu Leu Phe Asn
225                 230                 235                 240

Ile Thr Asn Gly Ala Arg Lys Asn Ala Phe Lys Ile Leu Val Val Ile
                245                 250                 255

Thr Asp Gly Glu Lys Phe Gly Asp Pro Leu Gly Tyr Glu Asp Val Ile
            260                 265                 270

Pro Glu Ala Asp Arg Glu Gly Val Ile Arg Tyr Val Ile Gly Val Gly
        275                 280                 285

Asp Ala Phe Arg Ser Glu Lys Ser Arg Gln Glu Leu Asn Thr Ile Ala
    290                 295                 300

Ser Lys Pro Pro Arg Asp His Val Phe Gln Val Asn Asn Phe Glu Ala
305                 310                 315                 320

Leu Lys Thr Ile Gln Asn Gln Leu Arg Glu Lys Ile Phe Ala Ile Glu
                325                 330                 335

Gly Thr Gln Thr Gly Ser Ser Ser Ser Phe Glu His Glu Met Ser Gln
            340                 345                 350

Glu Gly Phe Ser Ala Ala Ile Thr Ser Asn Gly Pro Leu Leu Ser Thr
        355                 360                 365

Val Gly Ser Tyr Asp Trp Ala Gly Gly Val Phe Leu Tyr Thr Ser Lys
    370                 375                 380

Glu Lys Ser Thr Phe Ile Asn Met Thr Arg Val Asp Ser Asp Met Asn
385                 390                 395                 400

Asp Ala Tyr Leu Gly Tyr Ala Ala Ala Ile Ile Leu Arg Asn Arg Val
                405                 410                 415

Gln Ser Leu Val Leu Gly Ala Pro Arg Tyr Gln His Ile Gly Leu Val
            420                 425                 430

Ala Met Phe Arg Gln Asn Thr Gly Met Trp Glu Ser Asn Ala Asn Val
        435                 440                 445

Lys Gly Thr Gln Ile Gly Ala Tyr Phe Gly Ala Ser Leu Cys Ser Val
    450                 455                 460

Asp Val Asp Ser Asn Gly Ser Thr Asp Leu Val Leu Ile Gly Ala Pro
465                 470                 475                 480

His Tyr Tyr Glu Gln Thr Arg Gly Gly Gln Val Ser Val Cys Pro Leu
                485                 490                 495

Pro Arg Gly Gln Arg Ala Arg Trp Gln Cys Asp Ala Val Leu Tyr Gly
            500                 505                 510

Glu Gln Gly Gln Pro Trp Gly Arg Phe Gly Ala Ala Leu Thr Val Leu
        515                 520                 525

Gly Asp Val Asn Gly Asp Lys Leu Thr Asp Val Ala Ile Gly Ala Pro
    530                 535                 540

Gly Glu Glu Asp Asn Arg Gly Ala Val Tyr Leu Phe His Gly Thr Ser
545                 550                 555                 560

Gly Ser Gly Ile Ser Pro Ser His Ser Gln Arg Ile Ala Gly Ser Lys
                565                 570                 575

Leu Ser Pro Arg Leu Gln Tyr Phe Gly Gln Ser Leu Ser Gly Gly Gln
            580                 585                 590

Asp Leu Thr Met Asp Gly Leu Val Asp Leu Thr Val Gly Ala Gln Gly
        595                 600                 605
```

-continued

His Val Leu Leu Leu Arg Ser Gln Pro Val Leu Arg Val Lys Ala Ile
    610                 615                 620

Met Glu Phe Asn Pro Arg Glu Val Ala Arg Asn Val Phe Glu Cys Asn
625                 630                 635                 640

Asp Gln Val Val Lys Gly Lys Glu Ala Gly Glu Val Arg Val Cys Leu
                645                 650                 655

His Val Gln Lys Ser Thr Arg Asp Arg Leu Arg Glu Gly Gln Ile Gln
            660                 665                 670

Ser Val Val Thr Tyr Asp Leu Ala Leu Asp Ser Gly Arg Pro His Ser
        675                 680                 685

Arg Ala Val Phe Asn Glu Thr Lys Asn Ser Thr Arg Arg Gln Thr Gln
    690                 695                 700

Val Leu Gly Leu Thr Gln Thr Cys Glu Thr Leu Lys Leu Gln Leu Pro
705                 710                 715                 720

Asn Cys Ile Glu Asp Pro Val Ser Pro Ile Val Leu Arg Leu Asn Phe
                725                 730                 735

Ser Leu Val Gly Thr Pro Leu Ser Ala Phe Gly Asn Leu Arg Pro Val
            740                 745                 750

Leu Ala Glu Asp Ala Gln Arg Leu Phe Thr Ala Leu Phe Pro Phe Glu
        755                 760                 765

Lys Asn Cys Gly Asn Asp Asn Ile Cys Gln Asp Asp Leu Ser Ile Thr
    770                 775                 780

Phe Ser Phe Met Ser Leu Asp Cys Leu Val Val Gly Gly Pro Arg Glu
785                 790                 795                 800

Phe Asn Val Thr Val Thr Val Arg Asn Asp Gly Glu Asp Ser Tyr Arg
                805                 810                 815

Thr Gln Val Thr Phe Phe Phe Pro Leu Asp Leu Ser Tyr Arg Lys Val
            820                 825                 830

Ser Thr Leu Gln Asn Gln Arg Ser Gln Arg Ser Trp Arg Leu Ala Cys
        835                 840                 845

Glu Ser Ala Ser Ser Thr Glu Val Ser Gly Ala Leu Lys Ser Thr Ser
    850                 855                 860

Cys Ser Ile Asn His Pro Ile Phe Pro Glu Asn Ser Glu Val Thr Phe
865                 870                 875                 880

Asn Ile Thr Phe Asp Val Asp Ser Lys Ala Ser Leu Gly Asn Lys Leu
                885                 890                 895

Leu Leu Lys Ala Asn Val Thr Ser Glu Asn Asn Met Pro Arg Thr Asn
            900                 905                 910

Lys Thr Glu Phe Gln Leu Glu Leu Pro Val Lys Tyr Ala Val Tyr Met
        915                 920                 925

Val Val Thr Ser His Gly Val Ser Thr Lys Tyr Leu Asn Phe Thr Ala
    930                 935                 940

Ser Glu Asn Thr Ser Arg Val Met Gln His Gln Tyr Gln Val Ser Asn
945                 950                 955                 960

Leu Gly Gln Arg Ser Leu Pro Ile Ser Leu Val Phe Leu Val Pro Val
                965                 970                 975

Arg Leu Asn Gln Thr Val Ile Trp Asp Arg Pro Gln Val Thr Phe Ser
            980                 985                 990

Glu Asn Leu Ser Ser Thr Cys His  Thr Lys Glu Arg Leu  Pro Ser His
        995                 1000                1005

Ser Asp  Phe Leu Ala Glu Leu  Arg Lys Ala Pro Val  Val Asn Cys
    1010                1015                1020

```
Ser Ile  Ala Val Cys Gln Arg  Ile Gln Cys Asp Ile  Pro Phe Phe
    1025                 1030                 1035

Gly Ile  Gln Glu Glu Phe Asn  Ala Thr Leu Lys Gly  Asn Leu Ser
    1040                 1045                 1050

Phe Asp  Trp Tyr Ile Lys Thr  Ser His Asn His Leu  Leu Ile Val
    1055                 1060                 1065

Ser Thr  Ala Glu Ile Leu Phe  Asn Asp Ser Val Phe  Thr Leu Leu
    1070                 1075                 1080

Pro Gly  Gln Gly Ala Phe Val  Arg Ser Gln Thr Glu  Thr Lys Val
    1085                 1090                 1095

Glu Pro  Phe Glu Val Pro Asn  Pro Leu Pro Leu Ile  Val Gly Ser
    1100                 1105                 1110

Ser Val  Gly Gly Leu Leu Leu  Leu Ala Leu Ile Thr  Ala Ala Leu
    1115                 1120                 1125

Tyr Lys  Leu Gly Phe Phe Lys  Arg Gln Tyr Lys Asp  Met Met Ser
    1130                 1135                 1140

Glu Gly  Gly Pro Pro Gly Ala  Glu Pro Gln
    1145                 1150


<210> SEQ ID NO 209
<211> LENGTH: 769
<212> TYPE: PRT
<213> ORGANISM: Homo sapiens

<400> SEQUENCE: 209

Met Leu Gly Leu Arg Pro Pro Leu Leu Ala Leu Val Gly Leu Leu Ser
1               5                   10                  15

Leu Gly Cys Val Leu Ser Gln Glu Cys Thr Lys Phe Lys Val Ser Ser
            20                  25                  30

Cys Arg Glu Cys Ile Glu Ser Gly Pro Gly Cys Thr Trp Cys Gln Lys
        35                  40                  45

Leu Asn Phe Thr Gly Pro Gly Asp Pro Asp Ser Ile Arg Cys Asp Thr
    50                  55                  60

Arg Pro Gln Leu Leu Met Arg Gly Cys Ala Ala Asp Asp Ile Met Asp
65                  70                  75                  80

Pro Thr Ser Leu Ala Glu Thr Gln Glu Asp His Asn Gly Gly Gln Lys
                85                  90                  95

Gln Leu Ser Pro Gln Lys Val Thr Leu Tyr Leu Arg Pro Gly Gln Ala
            100                 105                 110

Ala Ala Phe Asn Val Thr Phe Arg Arg Ala Lys Gly Tyr Pro Ile Asp
        115                 120                 125

Leu Tyr Tyr Leu Met Asp Leu Ser Tyr Ser Met Leu Asp Asp Leu Arg
    130                 135                 140

Asn Val Lys Lys Leu Gly Gly Asp Leu Leu Arg Ala Leu Asn Glu Ile
145                 150                 155                 160

Thr Glu Ser Gly Arg Ile Gly Phe Gly Ser Phe Val Asp Lys Thr Val
                165                 170                 175

Leu Pro Phe Val Asn Thr His Pro Asp Lys Leu Arg Asn Pro Cys Pro
            180                 185                 190

Asn Lys Glu Lys Glu Cys Gln Pro Pro Phe Ala Phe Arg His Val Leu
        195                 200                 205

Lys Leu Thr Asn Asn Ser Asn Gln Phe Gln Thr Glu Val Gly Lys Gln
    210                 215                 220

Leu Ile Ser Gly Asn Leu Asp Ala Pro Glu Gly Gly Leu Asp Ala Met
225                 230                 235                 240
```

-continued

```
Met Gln Val Ala Ala Cys Pro Glu Glu Ile Gly Trp Arg Asn Val Thr
                245                 250                 255

Arg Leu Leu Val Phe Ala Thr Asp Asp Gly Phe His Phe Ala Gly Asp
            260                 265                 270

Gly Lys Leu Gly Ala Ile Leu Thr Pro Asn Asp Gly Arg Cys His Leu
        275                 280                 285

Glu Asp Asn Leu Tyr Lys Arg Ser Asn Glu Phe Asp Tyr Pro Ser Val
    290                 295                 300

Gly Gln Leu Ala His Lys Leu Ala Glu Asn Asn Ile Gln Pro Ile Phe
305                 310                 315                 320

Ala Val Thr Ser Arg Met Val Lys Thr Tyr Glu Lys Leu Thr Glu Ile
                325                 330                 335

Ile Pro Lys Ser Ala Val Gly Glu Leu Ser Glu Asp Ser Ser Asn Val
            340                 345                 350

Val His Leu Ile Lys Asn Ala Tyr Asn Lys Leu Ser Ser Arg Val Phe
        355                 360                 365

Leu Asp His Asn Ala Leu Pro Asp Thr Leu Lys Val Thr Tyr Asp Ser
    370                 375                 380

Phe Cys Ser Asn Gly Val Thr His Arg Asn Gln Pro Arg Gly Asp Cys
385                 390                 395                 400

Asp Gly Val Gln Ile Asn Val Pro Ile Thr Phe Gln Val Lys Val Thr
                405                 410                 415

Ala Thr Glu Cys Ile Gln Glu Gln Ser Phe Val Ile Arg Ala Leu Gly
            420                 425                 430

Phe Thr Asp Ile Val Thr Val Gln Val Leu Pro Gln Cys Glu Cys Arg
        435                 440                 445

Cys Arg Asp Gln Ser Arg Asp Arg Ser Leu Cys His Gly Lys Gly Phe
    450                 455                 460

Leu Glu Cys Gly Ile Cys Arg Cys Asp Thr Gly Tyr Ile Gly Lys Asn
465                 470                 475                 480

Cys Glu Cys Gln Thr Gln Gly Arg Ser Ser Gln Glu Leu Glu Gly Ser
                485                 490                 495

Cys Arg Lys Asp Asn Asn Ser Ile Ile Cys Ser Gly Leu Gly Asp Cys
            500                 505                 510

Val Cys Gly Gln Cys Leu Cys His Thr Ser Asp Val Pro Gly Lys Leu
        515                 520                 525

Ile Tyr Gly Gln Tyr Cys Glu Cys Asp Thr Ile Asn Cys Glu Arg Tyr
    530                 535                 540

Asn Gly Gln Val Cys Gly Gly Pro Gly Arg Gly Leu Cys Phe Cys Gly
545                 550                 555                 560

Lys Cys Arg Cys His Pro Gly Phe Glu Gly Ser Ala Cys Gln Cys Glu
                565                 570                 575

Arg Thr Thr Glu Gly Cys Leu Asn Pro Arg Arg Val Glu Cys Ser Gly
            580                 585                 590

Arg Gly Arg Cys Arg Cys Asn Val Cys Glu Cys His Ser Gly Tyr Gln
        595                 600                 605

Leu Pro Leu Cys Gln Glu Cys Pro Gly Cys Pro Ser Pro Cys Gly Lys
    610                 615                 620

Tyr Ile Ser Cys Ala Glu Cys Leu Lys Phe Glu Lys Gly Pro Phe Gly
625                 630                 635                 640

Lys Asn Cys Ser Ala Ala Cys Pro Gly Leu Gln Leu Ser Asn Asn Pro
                645                 650                 655
```

Val Lys Gly Arg Thr Cys Lys Glu Arg Asp Ser Glu Gly Cys Trp Val
660 665 670

Ala Tyr Thr Leu Glu Gln Gln Asp Gly Met Asp Arg Tyr Leu Ile Tyr
675 680 685

Val Asp Glu Ser Arg Glu Cys Val Ala Gly Pro Asn Ile Ala Ala Ile
690 695 700

Val Gly Gly Thr Val Ala Gly Ile Val Leu Ile Gly Ile Leu Leu Leu
705 710 715 720

Val Ile Trp Lys Ala Leu Ile His Leu Ser Asp Leu Arg Glu Tyr Arg
725 730 735

Arg Phe Glu Lys Glu Lys Leu Lys Ser Gln Trp Asn Asn Asp Asn Pro
740 745 750

Leu Phe Lys Ser Ala Thr Thr Thr Val Met Asn Pro Lys Phe Ala Glu
755 760 765

Ser

<210> SEQ ID NO 210
<211> LENGTH: 1039
<212> TYPE: PRT
<213> ORGANISM: Homo sapiens

<400> SEQUENCE: 210

Met Ala Arg Ala Leu Cys Pro Leu Gln Ala Leu Trp Leu Leu Glu Trp
1 5 10 15

Val Leu Leu Leu Leu Gly Pro Cys Ala Ala Pro Pro Ala Trp Ala Leu
20 25 30

Asn Leu Asp Pro Val Gln Leu Thr Phe Tyr Ala Gly Pro Asn Gly Ser
35 40 45

Gln Phe Gly Phe Ser Leu Asp Phe His Lys Asp Ser His Gly Arg Val
50 55 60

Ala Ile Val Val Gly Ala Pro Arg Thr Leu Gly Pro Ser Gln Glu Glu
65 70 75 80

Thr Gly Gly Val Phe Leu Cys Pro Trp Arg Ala Glu Gly Gly Gln Cys
85 90 95

Pro Ser Leu Leu Phe Asp Leu Arg Asp Glu Thr Arg Asn Val Gly Ser
100 105 110

Gln Thr Leu Gln Thr Phe Lys Ala Arg Gln Gly Leu Gly Ala Ser Val
115 120 125

Val Ser Trp Ser Asp Val Ile Val Ala Cys Ala Pro Trp Gln His Trp
130 135 140

Asn Val Leu Glu Lys Thr Glu Glu Ala Glu Lys Thr Pro Val Gly Ser
145 150 155 160

Cys Phe Leu Ala Gln Pro Glu Ser Gly Arg Arg Ala Glu Tyr Ser Pro
165 170 175

Cys Arg Gly Asn Thr Leu Ser Arg Ile Tyr Val Glu Asn Asp Phe Ser
180 185 190

Trp Asp Lys Arg Tyr Cys Glu Ala Gly Phe Ser Ser Val Val Thr Gln
195 200 205

Ala Gly Glu Leu Val Leu Gly Ala Pro Gly Gly Tyr Tyr Phe Leu Gly
210 215 220

Leu Leu Ala Gln Ala Pro Val Ala Asp Ile Phe Ser Ser Tyr Arg Pro
225 230 235 240

Gly Ile Leu Leu Trp His Val Ser Ser Gln Ser Leu Ser Phe Asp Ser
245 250 255

-continued

Ser Asn Pro Glu Tyr Phe Asp Gly Tyr Trp Gly Tyr Ser Val Ala Val
260 265 270

Gly Glu Phe Asp Gly Asp Leu Asn Thr Thr Glu Tyr Val Val Gly Ala
275 280 285

Pro Thr Trp Ser Trp Thr Leu Gly Ala Val Glu Ile Leu Asp Ser Tyr
290 295 300

Tyr Gln Arg Leu His Arg Leu Arg Gly Glu Gln Met Ala Ser Tyr Phe
305 310 315 320

Gly His Ser Val Ala Val Thr Asp Val Asn Gly Asp Gly Arg His Asp
325 330 335

Leu Leu Val Gly Ala Pro Leu Tyr Met Glu Ser Arg Ala Asp Arg Lys
340 345 350

Leu Ala Glu Val Gly Arg Val Tyr Leu Phe Leu Gln Pro Arg Gly Pro
355 360 365

His Ala Leu Gly Ala Pro Ser Leu Leu Leu Thr Gly Thr Gln Leu Tyr
370 375 380

Gly Arg Phe Gly Ser Ala Ile Ala Pro Leu Gly Asp Leu Asp Arg Asp
385 390 395 400

Gly Tyr Asn Asp Ile Ala Val Ala Ala Pro Tyr Gly Gly Pro Ser Gly
405 410 415

Arg Gly Gln Val Leu Val Phe Leu Gly Gln Ser Glu Gly Leu Arg Ser
420 425 430

Arg Pro Ser Gln Val Leu Asp Ser Pro Phe Pro Thr Gly Ser Ala Phe
435 440 445

Gly Phe Ser Leu Arg Gly Ala Val Asp Ile Asp Asp Asn Gly Tyr Pro
450 455 460

Asp Leu Ile Val Gly Ala Tyr Gly Ala Asn Gln Val Ala Val Tyr Arg
465 470 475 480

Ala Gln Pro Val Val Lys Ala Ser Val Gln Leu Leu Val Gln Asp Ser
485 490 495

Leu Asn Pro Ala Val Lys Ser Cys Val Leu Pro Gln Thr Lys Thr Pro
500 505 510

Val Ser Cys Phe Asn Ile Gln Met Cys Val Gly Ala Thr Gly His Asn
515 520 525

Ile Pro Gln Lys Leu Ser Leu Asn Ala Glu Leu Gln Leu Asp Arg Gln
530 535 540

Lys Pro Arg Gln Gly Arg Arg Val Leu Leu Leu Gly Ser Gln Gln Ala
545 550 555 560

Gly Thr Thr Leu Asn Leu Asp Leu Gly Gly Lys His Ser Pro Ile Cys
565 570 575

His Thr Thr Met Ala Phe Leu Arg Asp Glu Ala Asp Phe Arg Asp Lys
580 585 590

Leu Ser Pro Ile Val Leu Ser Leu Asn Val Ser Leu Pro Pro Thr Glu
595 600 605

Ala Gly Met Ala Pro Ala Val Val Leu His Gly Asp Thr His Val Gln
610 615 620

Glu Gln Thr Arg Ile Val Leu Asp Cys Gly Glu Asp Asp Val Cys Val
625 630 635 640

Pro Gln Leu Gln Leu Thr Ala Ser Val Thr Gly Ser Pro Leu Leu Val
645 650 655

Gly Ala Asp Asn Val Leu Glu Leu Gln Met Asp Ala Ala Asn Glu Gly
660 665 670

Glu Gly Ala Tyr Glu Ala Glu Leu Ala Val His Leu Pro Gln Gly Ala

```
        675                 680                 685

His Tyr Met Arg Ala Leu Ser Asn Val Glu Gly Phe Glu Arg Leu Ile
    690                 695                 700

Cys Asn Gln Lys Lys Glu Asn Glu Thr Arg Val Val Leu Cys Glu Leu
705                 710                 715                 720

Gly Asn Pro Met Lys Lys Asn Ala Gln Ile Gly Ile Ala Met Leu Val
                725                 730                 735

Ser Val Gly Asn Leu Glu Glu Ala Gly Glu Ser Val Ser Phe Gln Leu
            740                 745                 750

Gln Ile Arg Ser Lys Asn Ser Gln Asn Pro Asn Ser Lys Ile Val Leu
        755                 760                 765

Leu Asp Val Pro Val Arg Ala Glu Ala Gln Val Glu Leu Arg Gly Asn
    770                 775                 780

Ser Phe Pro Ala Ser Leu Val Val Ala Ala Glu Glu Gly Glu Arg Glu
785                 790                 795                 800

Gln Asn Ser Leu Asp Ser Trp Gly Pro Lys Val Glu His Thr Tyr Glu
                805                 810                 815

Leu His Asn Asn Gly Pro Gly Thr Val Asn Gly Leu His Leu Ser Ile
            820                 825                 830

His Leu Pro Gly Gln Ser Gln Pro Ser Asp Leu Leu Tyr Ile Leu Asp
        835                 840                 845

Ile Gln Pro Gln Gly Gly Leu Gln Cys Phe Pro Gln Pro Pro Val Asn
    850                 855                 860

Pro Leu Lys Val Asp Trp Gly Leu Pro Ile Pro Ser Pro Ser Pro Ile
865                 870                 875                 880

His Pro Ala His His Lys Arg Asp Arg Arg Gln Ile Phe Leu Pro Glu
                885                 890                 895

Pro Glu Gln Pro Ser Arg Leu Gln Asp Pro Val Leu Val Ser Cys Asp
            900                 905                 910

Ser Ala Pro Cys Thr Val Val Gln Cys Asp Leu Gln Glu Met Ala Arg
        915                 920                 925

Gly Gln Arg Ala Met Val Thr Val Leu Ala Phe Leu Trp Leu Pro Ser
    930                 935                 940

Leu Tyr Gln Arg Pro Leu Asp Gln Phe Val Leu Gln Ser His Ala Trp
945                 950                 955                 960

Phe Asn Val Ser Ser Leu Pro Tyr Ala Val Pro Pro Leu Ser Leu Pro
                965                 970                 975

Arg Gly Glu Ala Gln Val Trp Thr Gln Leu Leu Arg Ala Leu Glu Glu
            980                 985                 990

Arg Ala Ile Pro Ile Trp Trp Val  Leu Val Gly Val Leu  Gly Gly Leu
        995                 1000                1005

Leu Leu  Leu Thr Ile Leu Val  Leu Ala Met Trp Lys  Val Gly Phe
    1010                1015                1020

Phe Lys  Arg Asn Arg Pro Pro  Leu Glu Glu Asp Asp  Glu Glu Gly
    1025                1030                1035

Glu
```

```
<210> SEQ ID NO 211
<211> LENGTH: 1012
<212> TYPE: PRT
<213> ORGANISM: Homo sapiens

<400> SEQUENCE: 211

Met Ala Phe Pro Pro Arg Arg Arg Leu Arg Leu Gly Pro Arg Gly Leu
```

-continued

```
1               5                   10                  15

Pro Leu Leu Leu Ser Gly Leu Leu Leu Pro Leu Cys Arg Ala Phe Asn
            20                  25                  30

Leu Asp Val Asp Ser Pro Ala Glu Tyr Ser Gly Pro Glu Gly Ser Tyr
        35                  40                  45

Phe Gly Phe Ala Val Asp Phe Phe Val Pro Ser Ala Ser Ser Arg Met
    50                  55                  60

Phe Leu Leu Val Gly Ala Pro Lys Ala Asn Thr Thr Gln Pro Gly Ile
65                  70                  75                  80

Val Glu Gly Gly Gln Val Leu Lys Cys Asp Trp Ser Ser Thr Arg Arg
                85                  90                  95

Cys Gln Pro Ile Glu Phe Asp Ala Thr Gly Asn Arg Asp Tyr Ala Lys
            100                 105                 110

Asp Asp Pro Leu Glu Phe Lys Ser His Gln Trp Phe Gly Ala Ser Val
        115                 120                 125

Arg Ser Lys Gln Asp Lys Ile Leu Ala Cys Ala Pro Leu Tyr His Trp
    130                 135                 140

Arg Thr Glu Met Lys Gln Glu Arg Glu Pro Val Gly Thr Cys Phe Leu
145                 150                 155                 160

Gln Asp Gly Thr Lys Thr Val Glu Tyr Ala Pro Cys Arg Ser Arg Gln
                165                 170                 175

Leu Ile Ser Asp Gln Val Ala Glu Ile Val Ser Lys Tyr Asp Pro Asn
            180                 185                 190

Val Tyr Ser Ile Lys Tyr Asn Asn Gln Leu Ala Thr Arg Thr Ala Gln
        195                 200                 205

Ala Ile Phe Asp Asp Ser Tyr Leu Gly Tyr Ser Val Ala Val Gly Asp
    210                 215                 220

Phe Asn Gly Asp Gly Ile Asp Asp Phe Val Ser Gly Val Pro Arg Ala
225                 230                 235                 240

Ala Arg Thr Leu Gly Met Val Tyr Ile Tyr Asp Gly Lys Asn Met Ser
                245                 250                 255

Ser Leu Tyr Asn Phe Thr Gly Glu Gln Met Ala Ala Tyr Phe Gly Phe
            260                 265                 270

Ser Val Ala Ala Thr Asp Ile Asn Gly Asp Asp Tyr Ala Asp Val Phe
        275                 280                 285

Ile Gly Ala Pro Leu Phe Met Asp Arg Gly Ser Asp Gly Lys Leu Gln
    290                 295                 300

Glu Val Gly Gln Val Ser Val Ser Leu Gln Arg Ala Ser Gly Asp Phe
305                 310                 315                 320

Gln Thr Thr Lys Leu Asn Gly Phe Glu Val Phe Ala Arg Phe Gly Ser
                325                 330                 335

Ala Ile Ala Pro Leu Gly Asp Leu Asp Gln Asp Gly Phe Asn Asp Ile
            340                 345                 350

Ala Ile Ala Ala Pro Tyr Gly Gly Glu Asp Lys Lys Gly Ile Val Tyr
        355                 360                 365

Ile Phe Asn Gly Arg Ser Thr Gly Leu Asn Ala Val Pro Ser Gln Ile
    370                 375                 380

Leu Glu Gly Gln Trp Ala Ala Arg Ser Met Pro Pro Ser Phe Gly Tyr
385                 390                 395                 400

Ser Met Lys Gly Ala Thr Asp Ile Asp Lys Asn Gly Tyr Pro Asp Leu
                405                 410                 415

Ile Val Gly Ala Phe Gly Val Asp Arg Ala Ile Leu Tyr Arg Ala Arg
            420                 425                 430
```

-continued

```
Pro Val Ile Thr Val Asn Ala Gly Leu Glu Val Tyr Pro Ser Ile Leu
        435                 440                 445

Asn Gln Asp Asn Lys Thr Cys Ser Leu Pro Gly Thr Ala Leu Lys Val
    450                 455                 460

Ser Cys Phe Asn Val Arg Phe Cys Leu Lys Ala Asp Gly Lys Gly Val
465                 470                 475                 480

Leu Pro Arg Lys Leu Asn Phe Gln Val Glu Leu Leu Leu Asp Lys Leu
                485                 490                 495

Lys Gln Lys Gly Ala Ile Arg Arg Ala Leu Phe Leu Tyr Ser Arg Ser
            500                 505                 510

Pro Ser His Ser Lys Asn Met Thr Ile Ser Arg Gly Gly Leu Met Gln
        515                 520                 525

Cys Glu Glu Leu Ile Ala Tyr Leu Arg Asp Glu Ser Glu Phe Arg Asp
    530                 535                 540

Lys Leu Thr Pro Ile Thr Ile Phe Met Glu Tyr Arg Leu Asp Tyr Arg
545                 550                 555                 560

Thr Ala Ala Asp Thr Thr Gly Leu Gln Pro Ile Leu Asn Gln Phe Thr
                565                 570                 575

Pro Ala Asn Ile Ser Arg Gln Ala His Ile Leu Leu Asp Cys Gly Glu
            580                 585                 590

Asp Asn Val Cys Lys Pro Lys Leu Glu Val Ser Val Asp Ser Asp Gln
        595                 600                 605

Lys Lys Ile Tyr Ile Gly Asp Asp Asn Pro Leu Thr Leu Ile Val Lys
    610                 615                 620

Ala Gln Asn Gln Gly Glu Gly Ala Tyr Glu Ala Glu Leu Ile Val Ser
625                 630                 635                 640

Ile Pro Leu Gln Ala Asp Phe Ile Gly Val Val Arg Asn Asn Glu Ala
                645                 650                 655

Leu Ala Arg Leu Ser Cys Ala Phe Lys Thr Glu Asn Gln Thr Arg Gln
            660                 665                 670

Val Val Cys Asp Leu Gly Asn Pro Met Lys Ala Gly Thr Gln Leu Leu
        675                 680                 685

Ala Gly Leu Arg Phe Ser Val His Gln Gln Ser Glu Met Asp Thr Ser
    690                 695                 700

Val Lys Phe Asp Leu Gln Ile Gln Ser Ser Asn Leu Phe Asp Lys Val
705                 710                 715                 720

Ser Pro Val Val Ser His Lys Val Asp Leu Ala Val Leu Ala Ala Val
                725                 730                 735

Glu Ile Arg Gly Val Ser Ser Pro Asp His Ile Phe Leu Pro Ile Pro
            740                 745                 750

Asn Trp Glu His Lys Glu Asn Pro Glu Thr Glu Glu Asp Val Gly Pro
        755                 760                 765

Val Val Gln His Ile Tyr Glu Leu Arg Asn Asn Gly Pro Ser Ser Phe
    770                 775                 780

Ser Lys Ala Met Leu His Leu Gln Trp Pro Tyr Lys Tyr Asn Asn Asn
785                 790                 795                 800

Thr Leu Leu Tyr Ile Leu His Tyr Asp Ile Asp Gly Pro Met Asn Cys
                805                 810                 815

Thr Ser Asp Met Glu Ile Asn Pro Leu Arg Ile Lys Ile Ser Ser Leu
            820                 825                 830

Gln Thr Thr Glu Lys Asn Asp Thr Val Ala Gly Gln Gly Glu Arg Asp
        835                 840                 845
```

-continued

```
His Leu Ile Thr Lys Arg Asp Leu Ala Leu Ser Glu Gly Asp Ile His
    850                 855                 860

Thr Leu Gly Cys Gly Val Ala Gln Cys Leu Lys Ile Val Cys Gln Val
865                 870                 875                 880

Gly Arg Leu Asp Arg Gly Lys Ser Ala Ile Leu Tyr Val Lys Ser Leu
                885                 890                 895

Leu Trp Thr Glu Thr Phe Met Asn Lys Glu Asn Gln Asn His Ser Tyr
            900                 905                 910

Ser Leu Lys Ser Ser Ala Ser Phe Asn Val Ile Glu Phe Pro Tyr Lys
        915                 920                 925

Asn Leu Pro Ile Glu Asp Ile Thr Asn Ser Thr Leu Val Thr Thr Asn
    930                 935                 940

Val Thr Trp Gly Ile Gln Pro Ala Pro Met Pro Val Pro Val Trp Val
945                 950                 955                 960

Ile Ile Leu Ala Val Leu Ala Gly Leu Leu Leu Leu Ala Val Leu Val
                965                 970                 975

Phe Val Met Tyr Arg Met Gly Phe Phe Lys Arg Val Arg Pro Pro Gln
            980                 985                 990

Glu Glu Gln Glu Arg Glu Gln Leu  Gln Pro His Glu Asn  Gly Glu Gly
        995                 1000                1005

Asn Ser  Glu Thr
    1010


<210> SEQ ID NO 212
<211> LENGTH: 788
<212> TYPE: PRT
<213> ORGANISM: Homo sapiens

<400> SEQUENCE: 212

Met Arg Ala Arg Pro Arg Pro Arg Pro Leu Trp Ala Thr Val Leu Ala
1               5                   10                  15

Leu Gly Ala Leu Ala Gly Val Gly Val Gly Gly Pro Asn Ile Cys Thr
            20                  25                  30

Thr Arg Gly Val Ser Ser Cys Gln Gln Cys Leu Ala Val Ser Pro Met
        35                  40                  45

Cys Ala Trp Cys Ser Asp Glu Ala Leu Pro Leu Gly Ser Pro Arg Cys
    50                  55                  60

Asp Leu Lys Glu Asn Leu Leu Lys Asp Asn Cys Ala Pro Glu Ser Ile
65                  70                  75                  80

Glu Phe Pro Val Ser Glu Ala Arg Val Leu Glu Asp Arg Pro Leu Ser
                85                  90                  95

Asp Lys Gly Ser Gly Asp Ser Ser Gln Val Thr Gln Val Ser Pro Gln
            100                 105                 110

Arg Ile Ala Leu Arg Leu Arg Pro Asp Asp Ser Lys Asn Phe Ser Ile
        115                 120                 125

Gln Val Arg Gln Val Glu Asp Tyr Pro Val Asp Ile Tyr Tyr Leu Met
    130                 135                 140

Asp Leu Ser Tyr Ser Met Lys Asp Asp Leu Trp Ser Ile Gln Asn Leu
145                 150                 155                 160

Gly Thr Lys Leu Ala Thr Gln Met Arg Lys Leu Thr Ser Asn Leu Arg
                165                 170                 175

Ile Gly Phe Gly Ala Phe Val Asp Lys Pro Val Ser Pro Tyr Met Tyr
            180                 185                 190

Ile Ser Pro Pro Glu Ala Leu Glu Asn Pro Cys Tyr Asp Met Lys Thr
        195                 200                 205
```

-continued

```
Thr Cys Leu Pro Met Phe Gly Tyr Lys His Val Leu Thr Leu Thr Asp
    210                 215                 220

Gln Val Thr Arg Phe Asn Glu Glu Val Lys Lys Gln Ser Val Ser Arg
225                 230                 235                 240

Asn Arg Asp Ala Pro Glu Gly Gly Phe Asp Ala Ile Met Gln Ala Thr
                245                 250                 255

Val Cys Asp Glu Lys Ile Gly Trp Arg Asn Asp Ala Ser His Leu Leu
            260                 265                 270

Val Phe Thr Thr Asp Ala Lys Thr His Ile Ala Leu Asp Gly Arg Leu
        275                 280                 285

Ala Gly Ile Val Gln Pro Asn Asp Gly Gln Cys His Val Gly Ser Asp
    290                 295                 300

Asn His Tyr Ser Ala Ser Thr Thr Met Asp Tyr Pro Ser Leu Gly Leu
305                 310                 315                 320

Met Thr Glu Lys Leu Ser Gln Lys Asn Ile Asn Leu Ile Phe Ala Val
                325                 330                 335

Thr Glu Asn Val Val Asn Leu Tyr Gln Asn Tyr Ser Glu Leu Ile Pro
            340                 345                 350

Gly Thr Thr Val Gly Val Leu Ser Met Asp Ser Ser Asn Val Leu Gln
        355                 360                 365

Leu Ile Val Asp Ala Tyr Gly Lys Ile Arg Ser Lys Val Glu Leu Glu
    370                 375                 380

Val Arg Asp Leu Pro Glu Glu Leu Ser Leu Ser Phe Asn Ala Thr Cys
385                 390                 395                 400

Leu Asn Asn Glu Val Ile Pro Gly Leu Lys Ser Cys Met Gly Leu Lys
                405                 410                 415

Ile Gly Asp Thr Val Ser Phe Ser Ile Glu Ala Lys Val Arg Gly Cys
            420                 425                 430

Pro Gln Glu Lys Glu Lys Ser Phe Thr Ile Lys Pro Val Gly Phe Lys
        435                 440                 445

Asp Ser Leu Ile Val Gln Val Thr Phe Asp Cys Asp Cys Ala Cys Gln
    450                 455                 460

Ala Gln Ala Glu Pro Asn Ser His Arg Cys Asn Asn Gly Asn Gly Thr
465                 470                 475                 480

Phe Glu Cys Gly Val Cys Arg Cys Gly Pro Gly Trp Leu Gly Ser Gln
                485                 490                 495

Cys Glu Cys Ser Glu Glu Asp Tyr Arg Pro Ser Gln Gln Asp Glu Cys
            500                 505                 510

Ser Pro Arg Glu Gly Gln Pro Val Cys Ser Gln Arg Gly Glu Cys Leu
        515                 520                 525

Cys Gly Gln Cys Val Cys His Ser Ser Asp Phe Gly Lys Ile Thr Gly
    530                 535                 540

Lys Tyr Cys Glu Cys Asp Asp Phe Ser Cys Val Arg Tyr Lys Gly Glu
545                 550                 555                 560

Met Cys Ser Gly His Gly Gln Cys Ser Cys Gly Asp Cys Leu Cys Asp
                565                 570                 575

Ser Asp Trp Thr Gly Tyr Tyr Cys Asn Cys Thr Thr Arg Thr Asp Thr
            580                 585                 590

Cys Met Ser Ser Asn Gly Leu Leu Cys Ser Gly Arg Gly Lys Cys Glu
        595                 600                 605

Cys Gly Ser Cys Val Cys Ile Gln Pro Gly Ser Tyr Gly Asp Thr Cys
    610                 615                 620
```

Glu Lys Cys Pro Thr Cys Pro Asp Ala Cys Thr Phe Lys Lys Glu Cys
625 630 635 640

Val Glu Cys Lys Lys Phe Asp Arg Gly Ala Leu His Asp Glu Asn Thr
645 650 655

Cys Asn Arg Tyr Cys Arg Asp Glu Ile Glu Ser Val Lys Glu Leu Lys
660 665 670

Asp Thr Gly Lys Asp Ala Val Asn Cys Thr Tyr Lys Asn Glu Asp Asp
675 680 685

Cys Val Val Arg Phe Gln Tyr Tyr Glu Asp Ser Ser Gly Lys Ser Ile
690 695 700

Leu Tyr Val Val Glu Glu Pro Glu Cys Pro Lys Gly Pro Asp Ile Leu
705 710 715 720

Val Val Leu Leu Ser Val Met Gly Ala Ile Leu Leu Ile Gly Leu Ala
725 730 735

Ala Leu Leu Ile Trp Lys Leu Leu Ile Thr Ile His Asp Arg Lys Glu
740 745 750

Phe Ala Lys Phe Glu Glu Glu Arg Ala Arg Ala Lys Trp Asp Thr Ala
755 760 765

Asn Asn Pro Leu Tyr Lys Glu Ala Thr Ser Thr Phe Thr Asn Ile Thr
770 775 780

Tyr Arg Gly Thr
785

<210> SEQ ID NO 213
<211> LENGTH: 1752
<212> TYPE: PRT
<213> ORGANISM: Homo sapiens

<400> SEQUENCE: 213

Met Ala Gly Pro Arg Pro Ser Pro Trp Ala Arg Leu Leu Leu Ala Ala
1 5 10 15

Leu Ile Ser Val Ser Leu Ser Gly Thr Leu Ala Asn Arg Cys Lys Lys
20 25 30

Ala Pro Val Lys Ser Cys Thr Glu Cys Val Arg Val Asp Lys Asp Cys
35 40 45

Ala Tyr Cys Thr Asp Glu Met Phe Arg Asp Arg Arg Cys Asn Thr Gln
50 55 60

Ala Glu Leu Leu Ala Ala Gly Cys Gln Arg Glu Ser Ile Val Val Met
65 70 75 80

Glu Ser Ser Phe Gln Ile Thr Glu Glu Thr Gln Ile Asp Thr Thr Leu
85 90 95

Arg Arg Ser Gln Met Ser Pro Gln Gly Leu Arg Val Arg Leu Arg Pro
100 105 110

Gly Glu Glu Arg His Phe Glu Leu Glu Val Phe Glu Pro Leu Glu Ser
115 120 125

Pro Val Asp Leu Tyr Ile Leu Met Asp Phe Ser Asn Ser Met Ser Asp
130 135 140

Asp Leu Asp Asn Leu Lys Lys Met Gly Gln Asn Leu Ala Arg Val Leu
145 150 155 160

Ser Gln Leu Thr Ser Asp Tyr Thr Ile Gly Phe Gly Lys Phe Val Asp
165 170 175

Lys Val Ser Val Pro Gln Thr Asp Met Arg Pro Glu Lys Leu Lys Glu
180 185 190

Pro Trp Pro Asn Ser Asp Pro Pro Phe Ser Phe Lys Asn Val Ile Ser
195 200 205

-continued

```
Leu Thr Glu Asp Val Asp Glu Phe Arg Asn Lys Leu Gln Gly Glu Arg
    210                 215                 220

Ile Ser Gly Asn Leu Asp Ala Pro Glu Gly Gly Phe Asp Ala Ile Leu
225                 230                 235                 240

Gln Thr Ala Val Cys Thr Arg Asp Ile Gly Trp Arg Pro Asp Ser Thr
                245                 250                 255

His Leu Leu Val Phe Ser Thr Glu Ser Ala Phe His Tyr Glu Ala Asp
            260                 265                 270

Gly Ala Asn Val Leu Ala Gly Ile Met Ser Arg Asn Asp Glu Arg Cys
        275                 280                 285

His Leu Asp Thr Thr Gly Thr Tyr Thr Gln Tyr Arg Thr Gln Asp Tyr
    290                 295                 300

Pro Ser Val Pro Thr Leu Val Arg Leu Leu Ala Lys His Asn Ile Ile
305                 310                 315                 320

Pro Ile Phe Ala Val Thr Asn Tyr Ser Tyr Ser Tyr Tyr Glu Lys Leu
                325                 330                 335

His Thr Tyr Phe Pro Val Ser Ser Leu Gly Val Leu Gln Glu Asp Ser
            340                 345                 350

Ser Asn Ile Val Glu Leu Leu Glu Glu Ala Phe Asn Arg Ile Arg Ser
        355                 360                 365

Asn Leu Asp Ile Arg Ala Leu Asp Ser Pro Arg Gly Leu Arg Thr Glu
    370                 375                 380

Val Thr Ser Lys Met Phe Gln Lys Thr Arg Thr Gly Ser Phe His Ile
385                 390                 395                 400

Arg Arg Gly Glu Val Gly Ile Tyr Gln Val Gln Leu Arg Ala Leu Glu
                405                 410                 415

His Val Asp Gly Thr His Val Cys Gln Leu Pro Glu Asp Gln Lys Gly
            420                 425                 430

Asn Ile His Leu Lys Pro Ser Phe Ser Asp Gly Leu Lys Met Asp Ala
        435                 440                 445

Gly Ile Ile Cys Asp Val Cys Thr Cys Glu Leu Gln Lys Glu Val Arg
    450                 455                 460

Ser Ala Arg Cys Ser Phe Asn Gly Asp Phe Val Cys Gly Gln Cys Val
465                 470                 475                 480

Cys Ser Glu Gly Trp Ser Gly Gln Thr Cys Asn Cys Ser Thr Gly Ser
                485                 490                 495

Leu Ser Asp Ile Gln Pro Cys Leu Arg Glu Gly Glu Asp Lys Pro Cys
            500                 505                 510

Ser Gly Arg Gly Glu Cys Gln Cys Gly His Cys Val Cys Tyr Gly Glu
        515                 520                 525

Gly Arg Tyr Glu Gly Gln Phe Cys Glu Tyr Asp Asn Phe Gln Cys Pro
    530                 535                 540

Arg Thr Ser Gly Phe Leu Cys Asn Asp Arg Gly Arg Cys Ser Met Gly
545                 550                 555                 560

Gln Cys Val Cys Glu Pro Gly Trp Thr Gly Pro Ser Cys Asp Cys Pro
                565                 570                 575

Leu Ser Asn Ala Thr Cys Ile Asp Ser Asn Gly Gly Ile Cys Asn Gly
            580                 585                 590

Arg Gly His Cys Glu Cys Gly Arg Cys His Cys His Gln Gln Ser Leu
        595                 600                 605

Tyr Thr Asp Thr Ile Cys Glu Ile Asn Tyr Ser Ala Ile His Pro Gly
    610                 615                 620
```

-continued

Leu Cys Glu Asp Leu Arg Ser Cys Val Gln Cys Gln Ala Trp Gly Thr
625 630 635 640

Gly Glu Lys Lys Gly Arg Thr Cys Glu Glu Cys Asn Phe Lys Val Lys
645 650 655

Met Val Asp Glu Leu Lys Arg Ala Glu Glu Val Val Val Arg Cys Ser
660 665 670

Phe Arg Asp Glu Asp Asp Asp Cys Thr Tyr Ser Tyr Thr Met Glu Gly
675 680 685

Asp Gly Ala Pro Gly Pro Asn Ser Thr Val Leu Val His Lys Lys Lys
690 695 700

Asp Cys Pro Pro Gly Ser Phe Trp Trp Leu Ile Pro Leu Leu Leu Leu
705 710 715 720

Leu Leu Pro Leu Leu Ala Leu Leu Leu Leu Leu Cys Trp Lys Tyr Cys
725 730 735

Ala Cys Cys Lys Ala Cys Leu Ala Leu Leu Pro Cys Cys Asn Arg Gly
740 745 750

His Met Val Gly Phe Lys Glu Asp His Tyr Met Leu Arg Glu Asn Leu
755 760 765

Met Ala Ser Asp His Leu Asp Thr Pro Met Leu Arg Ser Gly Asn Leu
770 775 780

Lys Gly Arg Asp Val Val Arg Trp Lys Val Thr Asn Asn Met Gln Arg
785 790 795 800

Pro Gly Phe Ala Thr His Ala Ala Ser Ile Asn Pro Thr Glu Leu Val
805 810 815

Pro Tyr Gly Leu Ser Leu Arg Leu Ala Arg Leu Cys Thr Glu Asn Leu
820 825 830

Leu Lys Pro Asp Thr Arg Glu Cys Ala Gln Leu Arg Gln Glu Val Glu
835 840 845

Glu Asn Leu Asn Glu Val Tyr Arg Gln Ile Ser Gly Val His Lys Leu
850 855 860

Gln Gln Thr Lys Phe Arg Gln Gln Pro Asn Ala Gly Lys Lys Gln Asp
865 870 875 880

His Thr Ile Val Asp Thr Val Leu Met Ala Pro Arg Ser Ala Lys Pro
885 890 895

Ala Leu Leu Lys Leu Thr Glu Lys Gln Val Glu Gln Arg Ala Phe His
900 905 910

Asp Leu Lys Val Ala Pro Gly Tyr Tyr Thr Leu Thr Ala Asp Gln Asp
915 920 925

Ala Arg Gly Met Val Glu Phe Gln Glu Gly Val Glu Leu Val Asp Val
930 935 940

Arg Val Pro Leu Phe Ile Arg Pro Glu Asp Asp Asp Glu Lys Gln Leu
945 950 955 960

Leu Val Glu Ala Ile Asp Val Pro Ala Gly Thr Ala Thr Leu Gly Arg
965 970 975

Arg Leu Val Asn Ile Thr Ile Ile Lys Glu Gln Ala Arg Asp Val Val
980 985 990

Ser Phe Glu Gln Pro Glu Phe Ser Val Ser Arg Gly Asp Gln Val Ala
995 1000 1005

Arg Ile Pro Val Ile Arg Arg Val Leu Asp Gly Gly Lys Ser Gln
1010 1015 1020

Val Ser Tyr Arg Thr Gln Asp Gly Thr Ala Gln Gly Asn Arg Asp
1025 1030 1035

Tyr Ile Pro Val Glu Gly Glu Leu Leu Phe Gln Pro Gly Glu Ala

-continued

```
    1040                1045                1050

Trp Lys  Glu Leu Gln Val Lys  Leu Leu Glu Leu Gln  Glu Val Asp
    1055                1060                1065

Ser Leu  Leu Arg Gly Arg Gln  Val Arg Arg Phe His  Val Gln Leu
    1070                1075                1080

Ser Asn  Pro Lys Phe Gly Ala  His Leu Gly Gln Pro  His Ser Thr
    1085                1090                1095

Thr Ile  Ile Ile Arg Asp Pro  Asp Glu Leu Asp Arg  Ser Phe Thr
    1100                1105                1110

Ser Gln  Met Leu Ser Ser Gln  Pro Pro Pro His Gly  Asp Leu Gly
    1115                1120                1125

Ala Pro  Gln Asn Pro Asn Ala  Lys Ala Ala Gly Ser  Arg Lys Ile
    1130                1135                1140

His Phe  Asn Trp Leu Pro Pro  Ser Gly Lys Pro Met  Gly Tyr Arg
    1145                1150                1155

Val Lys  Tyr Trp Ile Gln Gly  Asp Ser Glu Ser Glu  Ala His Leu
    1160                1165                1170

Leu Asp  Ser Lys Val Pro Ser  Val Glu Leu Thr Asn  Leu Tyr Pro
    1175                1180                1185

Tyr Cys  Asp Tyr Glu Met Lys  Val Cys Ala Tyr Gly  Ala Gln Gly
    1190                1195                1200

Glu Gly  Pro Tyr Ser Ser Leu  Val Ser Cys Arg Thr  His Gln Glu
    1205                1210                1215

Val Pro  Ser Glu Pro Gly Arg  Leu Ala Phe Asn Val  Val Ser Ser
    1220                1225                1230

Thr Val  Thr Gln Leu Ser Trp  Ala Glu Pro Ala Glu  Thr Asn Gly
    1235                1240                1245

Glu Ile  Thr Ala Tyr Glu Val  Cys Tyr Gly Leu Val  Asn Asp Asp
    1250                1255                1260

Asn Arg  Pro Ile Gly Pro Met  Lys Lys Val Leu Val  Asp Asn Pro
    1265                1270                1275

Lys Asn  Arg Met Leu Leu Ile  Glu Asn Leu Arg Glu  Ser Gln Pro
    1280                1285                1290

Tyr Arg  Tyr Thr Val Lys Ala  Arg Asn Gly Ala Gly  Trp Gly Pro
    1295                1300                1305

Glu Arg  Glu Ala Ile Ile Asn  Leu Ala Thr Gln Pro  Lys Arg Pro
    1310                1315                1320

Met Ser  Ile Pro Ile Ile Pro  Asp Ile Pro Ile Val  Asp Ala Gln
    1325                1330                1335

Ser Gly  Glu Asp Tyr Asp Ser  Phe Leu Met Tyr Ser  Asp Asp Val
    1340                1345                1350

Leu Arg  Ser Pro Ser Gly Ser  Gln Arg Pro Ser Val  Ser Asp Asp
    1355                1360                1365

Thr Glu  His Leu Val Asn Gly  Arg Met Asp Phe Ala  Phe Pro Gly
    1370                1375                1380

Ser Thr  Asn Ser Leu His Arg  Met Thr Thr Thr Ser  Ala Ala Ala
    1385                1390                1395

Tyr Gly  Thr His Leu Ser Pro  His Val Pro His Arg  Val Leu Ser
    1400                1405                1410

Thr Ser  Ser Thr Leu Thr Arg  Asp Tyr Asn Ser Leu  Thr Arg Ser
    1415                1420                1425

Glu His  Ser His Ser Thr Thr  Leu Pro Arg Asp Tyr  Ser Thr Leu
    1430                1435                1440
```

Thr Ser Val Ser Ser His Asp Ser Arg Leu Thr Ala Gly Val Pro
1445 1450 1455

Asp Thr Pro Thr Arg Leu Val Phe Ser Ala Leu Gly Pro Thr Ser
1460 1465 1470

Leu Arg Val Ser Trp Gln Glu Pro Arg Cys Glu Arg Pro Leu Gln
1475 1480 1485

Gly Tyr Ser Val Glu Tyr Gln Leu Leu Asn Gly Gly Glu Leu His
1490 1495 1500

Arg Leu Asn Ile Pro Asn Pro Ala Gln Thr Ser Val Val Val Glu
1505 1510 1515

Asp Leu Leu Pro Asn His Ser Tyr Val Phe Arg Val Arg Ala Gln
1520 1525 1530

Ser Gln Glu Gly Trp Gly Arg Glu Arg Glu Gly Val Ile Thr Ile
1535 1540 1545

Glu Ser Gln Val His Pro Gln Ser Pro Leu Cys Pro Leu Pro Gly
1550 1555 1560

Ser Ala Phe Thr Leu Ser Thr Pro Ser Ala Pro Gly Pro Leu Val
1565 1570 1575

Phe Thr Ala Leu Ser Pro Asp Ser Leu Gln Leu Ser Trp Glu Arg
1580 1585 1590

Pro Arg Arg Pro Asn Gly Asp Ile Val Gly Tyr Leu Val Thr Cys
1595 1600 1605

Glu Met Ala Gln Gly Gly Gly Pro Ala Thr Ala Phe Arg Val Asp
1610 1615 1620

Gly Asp Ser Pro Glu Ser Arg Leu Thr Val Pro Gly Leu Ser Glu
1625 1630 1635

Asn Val Pro Tyr Lys Phe Lys Val Gln Ala Arg Thr Thr Glu Gly
1640 1645 1650

Phe Gly Pro Glu Arg Glu Gly Ile Ile Thr Ile Glu Ser Gln Asp
1655 1660 1665

Gly Gly Pro Phe Pro Gln Leu Gly Ser Arg Ala Gly Leu Phe Gln
1670 1675 1680

His Pro Leu Gln Ser Glu Tyr Ser Ser Ile Thr Thr Thr His Thr
1685 1690 1695

Ser Ala Thr Glu Pro Phe Leu Val Asp Gly Leu Thr Leu Gly Ala
1700 1705 1710

Gln His Leu Glu Ala Gly Gly Ser Leu Thr Arg His Val Thr Gln
1715 1720 1725

Glu Phe Val Ser Arg Thr Leu Thr Thr Ser Gly Thr Leu Ser Thr
1730 1735 1740

His Met Asp Gln Gln Phe Phe Gln Thr
1745 1750

<210> SEQ ID NO 214
<211> LENGTH: 967
<212> TYPE: PRT
<213> ORGANISM: Homo sapiens

<400> SEQUENCE: 214

Met Ala Lys Gly Phe Tyr Ile Ser Lys Ser Leu Gly Ile Leu Gly Ile
1 5 10 15

Leu Leu Gly Val Ala Ala Val Cys Thr Ile Ile Ala Leu Ser Val Val
20 25 30

Tyr Ser Gln Glu Lys Asn Lys Asn Ala Asn Ser Ser Pro Val Ala Ser

-continued

```
        35                  40                  45

Thr Thr Pro Ser Ala Ser Ala Thr Thr Asn Pro Ala Ser Ala Thr Thr
    50                  55                  60

Leu Asp Gln Ser Lys Ala Trp Asn Arg Tyr Arg Leu Pro Asn Thr Leu
65                  70                  75                  80

Lys Pro Asp Ser Tyr Arg Val Thr Leu Arg Pro Tyr Leu Thr Pro Asn
                85                  90                  95

Asp Arg Gly Leu Tyr Val Phe Lys Gly Ser Ser Thr Val Arg Phe Thr
            100                 105                 110

Cys Lys Glu Ala Thr Asp Val Ile Ile Ile His Ser Lys Lys Leu Asn
        115                 120                 125

Tyr Thr Leu Ser Gln Gly His Arg Val Val Leu Arg Gly Val Gly Gly
    130                 135                 140

Ser Gln Pro Pro Asp Ile Asp Lys Thr Glu Leu Val Glu Pro Thr Glu
145                 150                 155                 160

Tyr Leu Val Val His Leu Lys Gly Ser Leu Val Lys Asp Ser Gln Tyr
                165                 170                 175

Glu Met Asp Ser Glu Phe Glu Gly Glu Leu Ala Asp Asp Leu Ala Gly
            180                 185                 190

Phe Tyr Arg Ser Glu Tyr Met Glu Gly Asn Val Arg Lys Val Val Ala
        195                 200                 205

Thr Thr Gln Met Gln Ala Ala Asp Ala Arg Lys Ser Phe Pro Cys Phe
    210                 215                 220

Asp Glu Pro Ala Met Lys Ala Glu Phe Asn Ile Thr Leu Ile His Pro
225                 230                 235                 240

Lys Asp Leu Thr Ala Leu Ser Asn Met Leu Pro Lys Gly Pro Ser Thr
                245                 250                 255

Pro Leu Pro Glu Asp Pro Asn Trp Asn Val Thr Glu Phe His Thr Thr
            260                 265                 270

Pro Lys Met Ser Thr Tyr Leu Leu Ala Phe Ile Val Ser Glu Phe Asp
        275                 280                 285

Tyr Val Glu Lys Gln Ala Ser Asn Gly Val Leu Ile Arg Ile Trp Ala
    290                 295                 300

Arg Pro Ser Ala Ile Ala Ala Gly His Gly Asp Tyr Ala Leu Asn Val
305                 310                 315                 320

Thr Gly Pro Ile Leu Asn Phe Phe Ala Gly His Tyr Asp Thr Pro Tyr
                325                 330                 335

Pro Leu Pro Lys Ser Asp Gln Ile Gly Leu Pro Asp Phe Asn Ala Gly
            340                 345                 350

Ala Met Glu Asn Trp Gly Leu Val Thr Tyr Arg Glu Asn Ser Leu Leu
        355                 360                 365

Phe Asp Pro Leu Ser Ser Ser Ser Ser Asn Lys Glu Arg Val Val Thr
    370                 375                 380

Val Ile Ala His Glu Leu Ala His Gln Trp Phe Gly Asn Leu Val Thr
385                 390                 395                 400

Ile Glu Trp Trp Asn Asp Leu Trp Leu Asn Glu Gly Phe Ala Ser Tyr
                405                 410                 415

Val Glu Tyr Leu Gly Ala Asp Tyr Ala Glu Pro Thr Trp Asn Leu Lys
            420                 425                 430

Asp Leu Met Val Leu Asn Asp Val Tyr Arg Val Met Ala Val Asp Ala
        435                 440                 445

Leu Ala Ser Ser His Pro Leu Ser Thr Pro Ala Ser Glu Ile Asn Thr
    450                 455                 460
```

-continued

Pro Ala Gln Ile Ser Glu Leu Phe Asp Ala Ile Ser Tyr Ser Lys Gly
465 470 475 480

Ala Ser Val Leu Arg Met Leu Ser Ser Phe Leu Ser Glu Asp Val Phe
485 490 495

Lys Gln Gly Leu Ala Ser Tyr Leu His Thr Phe Ala Tyr Gln Asn Thr
500 505 510

Ile Tyr Leu Asn Leu Trp Asp His Leu Gln Glu Ala Val Asn Asn Arg
515 520 525

Ser Ile Gln Leu Pro Thr Thr Val Arg Asp Ile Met Asn Arg Trp Thr
530 535 540

Leu Gln Met Gly Phe Pro Val Ile Thr Val Asp Thr Ser Thr Gly Thr
545 550 555 560

Leu Ser Gln Glu His Phe Leu Leu Asp Pro Asp Ser Asn Val Thr Arg
565 570 575

Pro Ser Glu Phe Asn Tyr Val Trp Ile Val Pro Ile Thr Ser Ile Arg
580 585 590

Asp Gly Arg Gln Gln Gln Asp Tyr Trp Leu Ile Asp Val Arg Ala Gln
595 600 605

Asn Asp Leu Phe Ser Thr Ser Gly Asn Glu Trp Val Leu Leu Asn Leu
610 615 620

Asn Val Thr Gly Tyr Tyr Arg Val Asn Tyr Asp Glu Glu Asn Trp Arg
625 630 635 640

Lys Ile Gln Thr Gln Leu Gln Arg Asp His Ser Ala Ile Pro Val Ile
645 650 655

Asn Arg Ala Gln Ile Ile Asn Asp Ala Phe Asn Leu Ala Ser Ala His
660 665 670

Lys Val Pro Val Thr Leu Ala Leu Asn Asn Thr Leu Phe Leu Ile Glu
675 680 685

Glu Arg Gln Tyr Met Pro Trp Glu Ala Ala Leu Ser Ser Leu Ser Tyr
690 695 700

Phe Lys Leu Met Phe Asp Arg Ser Glu Val Tyr Gly Pro Met Lys Asn
705 710 715 720

Tyr Leu Lys Lys Gln Val Thr Pro Leu Phe Ile His Phe Arg Asn Asn
725 730 735

Thr Asn Asn Trp Arg Glu Ile Pro Glu Asn Leu Met Asp Gln Tyr Ser
740 745 750

Glu Val Asn Ala Ile Ser Thr Ala Cys Ser Asn Gly Val Pro Glu Cys
755 760 765

Glu Glu Met Val Ser Gly Leu Phe Lys Gln Trp Met Glu Asn Pro Asn
770 775 780

Asn Asn Pro Ile His Pro Asn Leu Arg Ser Thr Val Tyr Cys Asn Ala
785 790 795 800

Ile Ala Gln Gly Gly Glu Glu Glu Trp Asp Phe Ala Trp Glu Gln Phe
805 810 815

Arg Asn Ala Thr Leu Val Asn Glu Ala Asp Lys Leu Arg Ala Ala Leu
820 825 830

Ala Cys Ser Lys Glu Leu Trp Ile Leu Asn Arg Tyr Leu Ser Tyr Thr
835 840 845

Leu Asn Pro Asp Leu Ile Arg Lys Gln Asp Ala Thr Ser Thr Ile Ile
850 855 860

Ser Ile Thr Asn Asn Val Ile Gly Gln Gly Leu Val Trp Asp Phe Val
865 870 875 880

```
Gln Ser Asn Trp Lys Lys Leu Phe Asn Asp Tyr Gly Gly Gly Ser Phe
                885                 890                 895

Ser Phe Ser Asn Leu Ile Gln Ala Val Thr Arg Arg Phe Ser Thr Glu
            900                 905                 910

Tyr Glu Leu Gln Gln Leu Glu Gln Phe Lys Lys Asp Asn Glu Glu Thr
        915                 920                 925

Gly Phe Gly Ser Gly Thr Arg Ala Leu Glu Gln Ala Leu Glu Lys Thr
    930                 935                 940

Lys Ala Asn Ile Lys Trp Val Lys Glu Asn Lys Glu Val Val Leu Gln
945                 950                 955                 960

Trp Phe Thr Glu Asn Ser Lys
                965


<210> SEQ ID NO 215
<211> LENGTH: 351
<212> TYPE: PRT
<213> ORGANISM: Homo sapiens

<400> SEQUENCE: 215

Met Ser Phe Pro Cys Lys Phe Val Ala Ser Phe Leu Leu Ile Phe Asn
1               5                   10                  15

Val Ser Ser Lys Gly Ala Val Ser Lys Glu Ile Thr Asn Ala Leu Glu
            20                  25                  30

Thr Trp Gly Ala Leu Gly Gln Asp Ile Asn Leu Asp Ile Pro Ser Phe
        35                  40                  45

Gln Met Ser Asp Asp Ile Asp Asp Ile Lys Trp Glu Lys Thr Ser Asp
    50                  55                  60

Lys Lys Lys Ile Ala Gln Phe Arg Lys Glu Lys Glu Thr Phe Lys Glu
65                  70                  75                  80

Lys Asp Thr Tyr Lys Leu Phe Lys Asn Gly Thr Leu Lys Ile Lys His
                85                  90                  95

Leu Lys Thr Asp Asp Gln Asp Ile Tyr Lys Val Ser Ile Tyr Asp Thr
            100                 105                 110

Lys Gly Lys Asn Val Leu Glu Lys Ile Phe Asp Leu Lys Ile Gln Glu
        115                 120                 125

Arg Val Ser Lys Pro Lys Ile Ser Trp Thr Cys Ile Asn Thr Thr Leu
    130                 135                 140

Thr Cys Glu Val Met Asn Gly Thr Asp Pro Glu Leu Asn Leu Tyr Gln
145                 150                 155                 160

Asp Gly Lys His Leu Lys Leu Ser Gln Arg Val Ile Thr His Lys Trp
                165                 170                 175

Thr Thr Ser Leu Ser Ala Lys Phe Lys Cys Thr Ala Gly Asn Lys Val
            180                 185                 190

Ser Lys Glu Ser Ser Val Glu Pro Val Ser Cys Pro Glu Lys Gly Leu
        195                 200                 205

Asp Ile Tyr Leu Ile Ile Gly Ile Cys Gly Gly Gly Ser Leu Leu Met
    210                 215                 220

Val Phe Val Ala Leu Leu Val Phe Tyr Ile Thr Lys Arg Lys Lys Gln
225                 230                 235                 240

Arg Ser Arg Arg Asn Asp Glu Glu Leu Glu Thr Arg Ala His Arg Val
                245                 250                 255

Ala Thr Glu Glu Arg Gly Arg Lys Pro His Gln Ile Pro Ala Ser Thr
            260                 265                 270

Pro Gln Asn Pro Ala Thr Ser Gln His Pro Pro Pro Pro Pro Gly His
        275                 280                 285
```

Arg Ser Gln Ala Pro Ser His Arg Pro Pro Pro Pro Gly His Arg Val
    290                 295                 300

Gln His Gln Pro Gln Lys Arg Pro Pro Ala Pro Ser Gly Thr Gln Val
305                 310                 315                 320

His Gln Gln Lys Gly Pro Pro Leu Pro Arg Pro Arg Val Gln Pro Lys
                325                 330                 335

Pro Pro His Gly Ala Ala Glu Asn Ser Leu Ser Pro Ser Ser Asn
            340                 345                 350

<210> SEQ ID NO 216
<211> LENGTH: 207
<212> TYPE: PRT
<213> ORGANISM: Homo sapiens

<400> SEQUENCE: 216

Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Val Met
        115                 120                 125

Ser Val Ala Thr Ile Val Ile Val Asp Ile Cys Ile Thr Gly Gly Leu
    130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Pro Val Pro Asn Pro Asp Tyr Glu Pro Ile Arg
            180                 185                 190

Lys Gly Gln Arg Asp Leu Tyr Ser Gly Leu Asn Gln Arg Arg Ile
        195                 200                 205

<210> SEQ ID NO 217
<211> LENGTH: 164
<212> TYPE: PRT
<213> ORGANISM: Homo sapiens

<400> SEQUENCE: 217

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
    50                  55                  60

Gln Gln Gly Gln Asn Gln Leu Tyr Asn Glu Leu Asn Leu Gly Arg Arg
65 70 75 80

Glu Glu Tyr Asp Val Leu Asp Lys Arg Arg Gly Arg Asp Pro Glu Met
85 90 95

Gly Gly Lys Pro Gln Arg Arg Lys Asn Pro Gln Glu Gly Leu Tyr Asn
100 105 110

Glu Leu Gln Lys Asp Lys Met Ala Glu Ala Tyr Ser Glu Ile Gly Met
115 120 125

Lys Gly Glu Arg Arg Arg Gly Lys Gly His Asp Gly Leu Tyr Gln Gly
130 135 140

Leu Ser Thr Ala Thr Lys Asp Thr Tyr Asp Ala Leu His Met Gln Ala
145 150 155 160

Leu Pro Pro Arg

<210> SEQ ID NO 218
<211> LENGTH: 769
<212> TYPE: PRT
<213> ORGANISM: Homo sapiens

<400> SEQUENCE: 218

Met Leu Gly Leu Arg Pro Pro Leu Leu Ala Leu Val Gly Leu Leu Ser
1 5 10 15

Leu Gly Cys Val Leu Ser Gln Glu Cys Thr Lys Phe Lys Val Ser Ser
20 25 30

Cys Arg Glu Cys Ile Glu Ser Gly Pro Gly Cys Thr Trp Cys Gln Lys
35 40 45

Leu Asn Phe Thr Gly Pro Gly Asp Pro Asp Ser Ile Arg Cys Asp Thr
50 55 60

Arg Pro Gln Leu Leu Met Arg Gly Cys Ala Ala Asp Asp Ile Met Asp
65 70 75 80

Pro Thr Ser Leu Ala Glu Thr Gln Glu Asp His Asn Gly Gly Gln Lys
85 90 95

Gln Leu Ser Pro Gln Lys Val Thr Leu Tyr Leu Arg Pro Gly Gln Ala
100 105 110

Ala Ala Phe Asn Val Thr Phe Arg Arg Ala Lys Gly Tyr Pro Ile Asp
115 120 125

Leu Tyr Tyr Leu Met Asp Leu Ser Tyr Ser Met Leu Asp Asp Leu Arg
130 135 140

Asn Val Lys Lys Leu Gly Gly Asp Leu Leu Arg Ala Leu Asn Glu Ile
145 150 155 160

Thr Glu Ser Gly Arg Ile Gly Phe Gly Ser Phe Val Asp Lys Thr Val
165 170 175

Leu Pro Phe Val Asn Thr His Pro Asp Lys Leu Arg Asn Pro Cys Pro
180 185 190

Asn Lys Glu Lys Glu Cys Gln Pro Pro Phe Ala Phe Arg His Val Leu
195 200 205

Lys Leu Thr Asn Asn Ser Asn Gln Phe Gln Thr Glu Val Gly Lys Gln
210 215 220

Leu Ile Ser Gly Asn Leu Asp Ala Pro Glu Gly Gly Leu Asp Ala Met
225 230 235 240

Met Gln Val Ala Ala Cys Pro Glu Glu Ile Gly Trp Arg Asn Val Thr
245 250 255

Arg Leu Leu Val Phe Ala Thr Asp Asp Gly Phe His Phe Ala Gly Asp
260 265 270

-continued

```
Gly Lys Leu Gly Ala Ile Leu Thr Pro Asn Asp Gly Arg Cys His Leu
        275                 280                 285

Glu Asp Asn Leu Tyr Lys Arg Ser Asn Glu Phe Asp Tyr Pro Ser Val
    290                 295                 300

Gly Gln Leu Ala His Lys Leu Ala Glu Asn Asn Ile Gln Pro Ile Phe
305                 310                 315                 320

Ala Val Thr Ser Arg Met Val Lys Thr Tyr Glu Lys Leu Thr Glu Ile
                325                 330                 335

Ile Pro Lys Ser Ala Val Gly Glu Leu Ser Glu Asp Ser Ser Asn Val
            340                 345                 350

Val His Leu Ile Lys Asn Ala Tyr Asn Lys Leu Ser Ser Arg Val Phe
        355                 360                 365

Leu Asp His Asn Ala Leu Pro Asp Thr Leu Lys Val Thr Tyr Asp Ser
    370                 375                 380

Phe Cys Ser Asn Gly Val Thr His Arg Asn Gln Pro Arg Gly Asp Cys
385                 390                 395                 400

Asp Gly Val Gln Ile Asn Val Pro Ile Thr Phe Gln Val Lys Val Thr
                405                 410                 415

Ala Thr Glu Cys Ile Gln Glu Gln Ser Phe Val Ile Arg Ala Leu Gly
            420                 425                 430

Phe Thr Asp Ile Val Thr Val Gln Val Leu Pro Gln Cys Glu Cys Arg
        435                 440                 445

Cys Arg Asp Gln Ser Arg Asp Arg Ser Leu Cys His Gly Lys Gly Phe
    450                 455                 460

Leu Glu Cys Gly Ile Cys Arg Cys Asp Thr Gly Tyr Ile Gly Lys Asn
465                 470                 475                 480

Cys Glu Cys Gln Thr Gln Gly Arg Ser Ser Gln Glu Leu Glu Gly Ser
                485                 490                 495

Cys Arg Lys Asp Asn Asn Ser Ile Ile Cys Ser Gly Leu Gly Asp Cys
            500                 505                 510

Val Cys Gly Gln Cys Leu Cys His Thr Ser Asp Val Pro Gly Lys Leu
        515                 520                 525

Ile Tyr Gly Gln Tyr Cys Glu Cys Asp Thr Ile Asn Cys Glu Arg Tyr
    530                 535                 540

Asn Gly Gln Val Cys Gly Gly Pro Gly Arg Gly Leu Cys Phe Cys Gly
545                 550                 555                 560

Lys Cys Arg Cys His Pro Gly Phe Glu Gly Ser Ala Cys Gln Cys Glu
                565                 570                 575

Arg Thr Thr Glu Gly Cys Leu Asn Pro Arg Arg Val Glu Cys Ser Gly
            580                 585                 590

Arg Gly Arg Cys Arg Cys Asn Val Cys Glu Cys His Ser Gly Tyr Gln
        595                 600                 605

Leu Pro Leu Cys Gln Glu Cys Pro Gly Cys Pro Ser Pro Cys Gly Lys
    610                 615                 620

Tyr Ile Ser Cys Ala Glu Cys Leu Lys Phe Glu Lys Gly Pro Phe Gly
625                 630                 635                 640

Lys Asn Cys Ser Ala Ala Cys Pro Gly Leu Gln Leu Ser Asn Asn Pro
                645                 650                 655

Val Lys Gly Arg Thr Cys Lys Glu Arg Asp Ser Glu Gly Cys Trp Val
            660                 665                 670

Ala Tyr Thr Leu Glu Gln Gln Asp Gly Met Asp Arg Tyr Leu Ile Tyr
        675                 680                 685
```

-continued

```
Val Asp Glu Ser Arg Glu Cys Val Ala Gly Pro Asn Ile Ala Ala Ile
    690                 695                 700

Val Gly Gly Thr Val Ala Gly Ile Val Leu Ile Gly Ile Leu Leu Leu
705                 710                 715                 720

Val Ile Trp Lys Ala Leu Ile His Leu Ser Asp Leu Arg Glu Tyr Arg
                725                 730                 735

Arg Phe Glu Lys Glu Lys Leu Lys Ser Gln Trp Asn Asn Asp Asn Pro
            740                 745                 750

Leu Phe Lys Ser Ala Thr Thr Thr Val Met Asn Pro Lys Phe Ala Glu
        755                 760                 765

Ser


<210> SEQ ID NO 219
<211> LENGTH: 556
<212> TYPE: PRT
<213> ORGANISM: Homo sapiens

<400> SEQUENCE: 219

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
    50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
        275                 280                 285
```

```
Gly Trp Lys Val Ser Ala Val Thr Leu Ala Tyr Leu Ile Phe Cys Leu
    290                 295                 300

Cys Ser Leu Val Gly Ile Leu His Leu Gln Arg Ala Leu Val Leu Arg
305                 310                 315                 320

Arg Lys Arg Lys Arg Met Thr Asp Pro Thr Arg Arg Phe Phe Lys Val
                325                 330                 335

Thr Pro Pro Pro Gly Ser Gly Pro Gln Asn Gln Tyr Gly Asn Val Leu
            340                 345                 350

Ser Leu Pro Thr Pro Thr Ser Gly Leu Gly Arg Ala Gln Arg Trp Ala
        355                 360                 365

Ala Gly Leu Gly Gly Thr Ala Pro Ser Tyr Gly Asn Pro Ser Ser Asp
    370                 375                 380

Val Gln Ala Asp Gly Ala Leu Gly Ser Arg Ser Pro Pro Gly Val Gly
385                 390                 395                 400

Pro Glu Glu Glu Glu Gly Glu Gly Tyr Glu Glu Pro Asp Ser Glu Glu
                405                 410                 415

Asp Ser Glu Phe Tyr Glu Asn Asp Ser Asn Leu Gly Gln Asp Gln Leu
            420                 425                 430

Ser Gln Asp Gly Ser Gly Tyr Glu Asn Pro Glu Asp Glu Pro Leu Gly
        435                 440                 445

Pro Glu Asp Glu Asp Ser Phe Ser Asn Ala Glu Ser Tyr Glu Asn Glu
    450                 455                 460

Asp Glu Glu Leu Thr Gln Pro Val Ala Arg Thr Met Asp Phe Leu Ser
465                 470                 475                 480

Pro His Gly Ser Ala Trp Asp Pro Ser Arg Glu Ala Thr Ser Leu Gly
                485                 490                 495

Ser Gln Ser Tyr Glu Asp Met Arg Gly Ile Leu Tyr Ala Ala Pro Gln
            500                 505                 510

Leu Arg Ser Ile Arg Gly Gln Pro Gly Pro Asn His Glu Glu Asp Ala
        515                 520                 525

Asp Ser Tyr Glu Asn Met Asp Asn Pro Asp Gly Pro Asp Pro Ala Trp
    530                 535                 540

Gly Gly Gly Gly Arg Met Gly Thr Trp Ser Thr Arg
545                 550                 555


<210> SEQ ID NO 220
<211> LENGTH: 483
<212> TYPE: PRT
<213> ORGANISM: Homo sapiens

<400> SEQUENCE: 220

Met Phe Cys Ser Thr Ser Ala Val Asn Ser Cys Ala Arg Cys Phe Phe
1               5                   10                  15

His Ser Val Cys Pro Ala Gly Met Ile Val Lys Phe Pro Gly Thr Ala
            20                  25                  30

Gln Lys Asn Thr Val Cys Glu Pro Ala Ser Pro Gly Val Ser Pro Ala
        35                  40                  45

Cys Ala Ser Pro Glu Asn Cys Lys Glu Pro Ser Ser Gly Thr Ile Pro
    50                  55                  60

Gln Ala Lys Pro Thr Pro Val Ser Pro Ala Thr Ser Ser Ala Ser Thr
65                  70                  75                  80

Met Pro Val Arg Gly Gly Thr Arg Leu Ala Gln Glu Ala Ala Ser Lys
                85                  90                  95

Leu Thr Arg Ala Pro Asp Ser Pro Ser Ser Val Gly Arg Pro Ser Ser
            100                 105                 110
```

```
Asp Pro Gly Leu Ser Pro Thr Gln Pro Cys Pro Glu Gly Ser Gly Asp
        115                 120                 125

Cys Arg Lys Gln Cys Glu Pro Asp Tyr Tyr Leu Asp Glu Ala Gly Arg
    130                 135                 140

Cys Thr Ala Cys Val Ser Cys Ser Arg Asp Asp Leu Val Glu Lys Thr
145                 150                 155                 160

Pro Cys Ala Trp Asn Ser Ser Arg Thr Cys Glu Cys Arg Pro Gly Met
                165                 170                 175

Ile Cys Ala Thr Ser Ala Thr Asn Ser Cys Ala Arg Cys Val Pro Tyr
            180                 185                 190

Pro Ile Cys Ala Ala Glu Thr Val Thr Lys Pro Gln Asp Met Ala Glu
        195                 200                 205

Lys Asp Thr Thr Phe Glu Ala Pro Pro Leu Gly Thr Gln Pro Asp Cys
    210                 215                 220

Asn Pro Thr Pro Glu Asn Gly Glu Ala Pro Ala Ser Thr Ser Pro Thr
225                 230                 235                 240

Gln Ser Leu Leu Val Asp Ser Gln Ala Ser Lys Thr Leu Pro Ile Pro
                245                 250                 255

Thr Ser Ala Pro Val Ala Leu Ser Ser Thr Gly Lys Pro Val Leu Asp
            260                 265                 270

Ala Gly Pro Val Leu Phe Trp Val Ile Leu Val Leu Val Val Val Val
        275                 280                 285

Gly Ser Ser Ala Phe Leu Leu Cys His Arg Arg Ala Cys Arg Lys Arg
    290                 295                 300

Ile Arg Gln Lys Leu His Leu Cys Tyr Pro Val Gln Thr Ser Gln Pro
305                 310                 315                 320

Lys Leu Glu Leu Val Asp Ser Arg Pro Arg Arg Ser Ser Thr Leu Arg
                325                 330                 335

Ser Gly Ala Ser Val Thr Glu Pro Val Ala Glu Glu Arg Gly Leu Met
            340                 345                 350

Ser Gln Pro Leu Met Glu Thr Cys His Ser Val Gly Ala Ala Tyr Leu
        355                 360                 365

Glu Ser Leu Pro Leu Gln Asp Ala Ser Pro Ala Gly Gly Pro Ser Ser
    370                 375                 380

Pro Arg Asp Leu Pro Glu Pro Arg Val Ser Thr Glu His Thr Asn Asn
385                 390                 395                 400

Lys Ile Glu Lys Ile Tyr Ile Met Lys Ala Asp Thr Val Ile Val Gly
                405                 410                 415

Thr Val Lys Ala Glu Leu Pro Glu Gly Arg Gly Leu Ala Gly Pro Ala
            420                 425                 430

Glu Pro Glu Leu Glu Glu Glu Leu Glu Ala Asp His Thr Pro His Tyr
        435                 440                 445

Pro Glu Gln Glu Thr Glu Pro Pro Leu Gly Ser Cys Ser Asp Val Met
    450                 455                 460

Leu Ser Val Glu Glu Glu Gly Lys Glu Asp Pro Leu Pro Thr Ala Ala
465                 470                 475                 480

Ser Gly Lys
```

<210> SEQ ID NO 221
<211> LENGTH: 328
<212> TYPE: PRT
<213> ORGANISM: Homo sapiens

<400> SEQUENCE: 221

```
Met Leu Val Arg Arg Gly Ala Arg Ala Gly Pro Arg Met Pro Arg Gly
1               5                   10                  15

Trp Thr Ala Leu Cys Leu Leu Ser Leu Leu Pro Ser Gly Phe Met Ser
            20                  25                  30

Leu Asp Asn Asn Gly Thr Ala Thr Pro Glu Leu Pro Thr Gln Gly Thr
        35                  40                  45

Phe Ser Asn Val Ser Thr Asn Val Ser Tyr Gln Glu Thr Thr Thr Pro
    50                  55                  60

Ser Thr Leu Gly Ser Thr Ser Leu His Pro Val Ser Gln His Gly Asn
65                  70                  75                  80

Glu Ala Thr Thr Asn Ile Thr Glu Thr Thr Val Lys Phe Thr Ser Thr
                85                  90                  95

Ser Val Ile Thr Ser Val Tyr Gly Asn Thr Asn Ser Ser Val Gln Ser
            100                 105                 110

Gln Thr Ser Val Ile Ser Thr Val Phe Thr Thr Pro Ala Asn Val Ser
        115                 120                 125

Thr Pro Glu Thr Thr Leu Lys Pro Ser Leu Ser Pro Gly Asn Val Ser
    130                 135                 140

Asp Leu Ser Thr Thr Ser Thr Ser Leu Ala Thr Ser Pro Thr Lys Pro
145                 150                 155                 160

Tyr Thr Ser Ser Ser Pro Ile Leu Ser Asp Ile Lys Ala Glu Ile Lys
                165                 170                 175

Cys Ser Gly Ile Arg Glu Val Lys Leu Thr Gln Gly Ile Cys Leu Glu
            180                 185                 190

Gln Asn Lys Thr Ser Ser Cys Ala Glu Phe Lys Lys Asp Arg Gly Glu
        195                 200                 205

Gly Leu Ala Arg Val Leu Cys Gly Glu Glu Gln Ala Asp Ala Asp Ala
    210                 215                 220

Gly Ala Gln Val Cys Ser Leu Leu Leu Ala Gln Ser Glu Val Arg Pro
225                 230                 235                 240

Gln Cys Leu Leu Leu Val Leu Ala Asn Arg Thr Glu Ile Ser Ser Lys
                245                 250                 255

Leu Gln Leu Met Lys Lys His Gln Ser Asp Leu Lys Lys Leu Gly Ile
            260                 265                 270

Leu Asp Phe Thr Glu Gln Asp Val Ala Ser His Gln Ser Tyr Ser Gln
        275                 280                 285

Lys Thr Leu Ile Ala Leu Val Thr Ser Gly Ala Leu Leu Ala Val Leu
    290                 295                 300

Gly Ile Thr Gly Tyr Phe Leu Met Asn Arg Arg Ser Trp Ser Pro Thr
305                 310                 315                 320

Gly Glu Arg Leu Glu Leu Glu Pro
                325
```

<210> SEQ ID NO 222
<211> LENGTH: 472
<212> TYPE: PRT
<213> ORGANISM: Homo sapiens

<400> SEQUENCE: 222

```
Met Gly Cys Asp Arg Asn Cys Gly Leu Ile Ala Gly Ala Val Ile Gly
1               5                   10                  15

Ala Val Leu Ala Val Phe Gly Gly Ile Leu Met Pro Val Gly Asp Leu
            20                  25                  30

Leu Ile Gln Lys Thr Ile Lys Lys Gln Val Val Leu Glu Glu Gly Thr
```

```
        35                  40                  45

Ile Ala Phe Lys Asn Trp Val Lys Thr Gly Thr Glu Val Tyr Arg Gln
    50                  55                  60

Phe Trp Ile Phe Asp Val Gln Asn Pro Gln Glu Val Met Met Asn Ser
65                  70                  75                  80

Ser Asn Ile Gln Val Lys Gln Arg Gly Pro Tyr Thr Tyr Arg Val Arg
                85                  90                  95

Phe Leu Ala Lys Glu Asn Val Thr Gln Asp Ala Glu Asp Asn Thr Val
            100                 105                 110

Ser Phe Leu Gln Pro Asn Gly Ala Ile Phe Glu Pro Ser Leu Ser Val
        115                 120                 125

Gly Thr Glu Ala Asp Asn Phe Thr Val Leu Asn Leu Ala Val Ala Ala
    130                 135                 140

Ala Ser His Ile Tyr Gln Asn Gln Phe Val Gln Met Ile Leu Asn Ser
145                 150                 155                 160

Leu Ile Asn Lys Ser Lys Ser Ser Met Phe Gln Val Arg Thr Leu Arg
                165                 170                 175

Glu Leu Leu Trp Gly Tyr Arg Asp Pro Phe Leu Ser Leu Val Pro Tyr
            180                 185                 190

Pro Val Thr Thr Thr Val Gly Leu Phe Tyr Pro Tyr Asn Asn Thr Ala
        195                 200                 205

Asp Gly Val Tyr Lys Val Phe Asn Gly Lys Asp Asn Ile Ser Lys Val
    210                 215                 220

Ala Ile Ile Asp Thr Tyr Lys Gly Lys Arg Asn Leu Ser Tyr Trp Glu
225                 230                 235                 240

Ser His Cys Asp Met Ile Asn Gly Thr Asp Ala Ala Ser Phe Pro Pro
                245                 250                 255

Phe Val Glu Lys Ser Gln Val Leu Gln Phe Phe Ser Ser Asp Ile Cys
            260                 265                 270

Arg Ser Ile Tyr Ala Val Phe Glu Ser Asp Val Asn Leu Lys Gly Ile
        275                 280                 285

Pro Val Tyr Arg Phe Val Leu Pro Ser Lys Ala Phe Ala Ser Pro Val
    290                 295                 300

Glu Asn Pro Asp Asn Tyr Cys Phe Cys Thr Glu Lys Ile Ile Ser Lys
305                 310                 315                 320

Asn Cys Thr Ser Tyr Gly Val Leu Asp Ile Ser Lys Cys Lys Glu Gly
                325                 330                 335

Arg Pro Val Tyr Ile Ser Leu Pro His Phe Leu Tyr Ala Ser Pro Asp
            340                 345                 350

Val Ser Glu Pro Ile Asp Gly Leu Asn Pro Asn Glu Glu Glu His Arg
        355                 360                 365

Thr Tyr Leu Asp Ile Glu Pro Ile Thr Gly Phe Thr Leu Gln Phe Ala
    370                 375                 380

Lys Arg Leu Gln Val Asn Leu Leu Val Lys Pro Ser Glu Lys Ile Gln
385                 390                 395                 400

Val Leu Lys Asn Leu Lys Arg Asn Tyr Ile Val Pro Ile Leu Trp Leu
                405                 410                 415

Asn Glu Thr Gly Thr Ile Gly Asp Glu Lys Ala Asn Met Phe Arg Ser
            420                 425                 430

Gln Val Thr Gly Lys Ile Asn Leu Leu Gly Leu Ile Glu Met Ile Leu
        435                 440                 445

Leu Ser Val Gly Val Val Met Phe Val Ala Phe Met Ile Ser Tyr Cys
    450                 455                 460
```

```
Ala Cys Arg Ser Lys Thr Ile Lys
465                 470


<210> SEQ ID NO 223
<211> LENGTH: 237
<212> TYPE: PRT
<213> ORGANISM: Homo sapiens

<400> SEQUENCE: 223

Met Val Arg Leu Pro Leu Gln Cys Val Leu Trp Gly Cys Leu Leu Thr
1               5                   10                  15

Ala Val His Pro Glu Pro Pro Thr Ala Cys Arg Glu Lys Gln Tyr Leu
            20                  25                  30

Ile Asn Ser Gln Cys Cys Ser Leu Cys Gln Pro Gly Gln Lys Leu Val
        35                  40                  45

Ser Asp Cys Thr Glu Phe Thr Glu Thr Glu Cys Leu Pro Cys Gly Glu
    50                  55                  60

Ser Glu Phe Leu Asp Thr Trp Asn Arg Glu Thr His Cys His Gln His
65                  70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
        115                 120                 125

Phe Gly Val Lys Gln Ile Ala Thr Gly Val Ser Asp Thr Ile Cys Glu
    130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Glu Ser Trp Thr Met
            180                 185                 190

Gly Pro Gly Glu Ser Leu Gly Arg Ser Pro Gly Ser Ala Glu Ser Pro
        195                 200                 205

Gly Gly Asp Pro His His Leu Arg Asp Pro Val Cys His Pro Leu Gly
    210                 215                 220

Ala Gly Leu Tyr Gln Lys Gly Gly Gln Glu Ala Asn Gln
225                 230                 235


<210> SEQ ID NO 224
<211> LENGTH: 261
<212> TYPE: PRT
<213> ORGANISM: Homo sapiens

<400> SEQUENCE: 224

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80
```

Leu Leu Asn Cys Glu Glu Ile Lys Ser Gln Phe Glu Gly Phe Val Lys
85 90 95

Asp Ile Met Leu Asn Lys Glu Glu Thr Lys Lys Glu Asn Ser Phe Glu
100 105 110

Met Gln Lys Gly Asp Gln Asn Pro Gln Ile Ala Ala His Val Ile Ser
115 120 125

Glu Ala Ser Ser Lys Thr Thr Ser Val Leu Gln Trp Ala Glu Lys Gly
130 135 140

Tyr Tyr Thr Met Ser Asn Asn Leu Val Thr Leu Glu Asn Gly Lys Gln
145 150 155 160

Leu Thr Val Lys Arg Gln Gly Leu Tyr Tyr Ile Tyr Ala Gln Val Thr
165 170 175

Phe Cys Ser Asn Arg Glu Ala Ser Ser Gln Ala Pro Phe Ile Ala Ser
180 185 190

Leu Cys Leu Lys Ser Pro Gly Arg Phe Glu Arg Ile Leu Leu Arg Ala
195 200 205

Ala Asn Thr His Ser Ser Ala Lys Pro Cys Gly Gln Gln Ser Ile His
210 215 220

Leu Gly Gly Val Phe Glu Leu Gln Pro Gly Ala Ser Val Phe Val Asn
225 230 235 240

Val Thr Asp Pro Ser Gln Val Ser His Gly Thr Gly Phe Thr Ser Phe
245 250 255

Gly Leu Leu Lys Leu
260

<210> SEQ ID NO 225
<211> LENGTH: 361
<212> TYPE: PRT
<213> ORGANISM: Homo sapiens

<400> SEQUENCE: 225

Met Asp Lys Phe Trp Trp His Ala Ala Trp Gly Leu Cys Leu Val Pro
1 5 10 15

Leu Ser Leu Ala Gln Ile Asp Leu Asn Ile Thr Cys Arg Phe Ala Gly
20 25 30

Val Phe His Val Glu Lys Asn Gly Arg Tyr Ser Ile Ser Arg Thr Glu
35 40 45

Ala Ala Asp Leu Cys Lys Ala Phe Asn Ser Thr Leu Pro Thr Met Ala
50 55 60

Gln Met Glu Lys Ala Leu Ser Ile Gly Phe Glu Thr Cys Arg Tyr Gly
65 70 75 80

Phe Ile Glu Gly His Val Val Ile Pro Arg Ile His Pro Asn Ser Ile
85 90 95

Cys Ala Ala Asn Asn Thr Gly Val Tyr Ile Leu Thr Ser Asn Thr Ser
100 105 110

Gln Tyr Asp Thr Tyr Cys Phe Asn Ala Ser Ala Pro Pro Glu Glu Asp
115 120 125

Cys Thr Ser Val Thr Asp Leu Pro Asn Ala Phe Asp Gly Pro Ile Thr
130 135 140

Ile Thr Ile Val Asn Arg Asp Gly Thr Arg Tyr Val Gln Lys Gly Glu
145 150 155 160

Tyr Arg Thr Asn Pro Glu Asp Ile Tyr Pro Ser Asn Pro Thr Asp Asp
165 170 175

Asp Val Ser Ser Gly Ser Ser Ser Glu Arg Ser Ser Thr Ser Gly Gly 180 185 190

Tyr Ile Phe Tyr Thr Phe Ser Thr Val His Pro Ile Pro Asp Glu Asp
195 200 205

Ser Pro Trp Ile Thr Asp Ser Thr Asp Arg Ile Pro Ala Thr Arg Asp
210 215 220

Gln Asp Thr Phe His Pro Ser Gly Gly Ser His Thr Thr His Gly Ser
225 230 235 240

Glu Ser Asp Gly His Ser His Gly Ser Gln Glu Gly Gly Ala Asn Thr
245 250 255

Thr Ser Gly Pro Ile Arg Thr Pro Gln Ile Pro Glu Trp Leu Ile Ile
260 265 270

Leu Ala Ser Leu Leu Ala Leu Ala Leu Ile Leu Ala Val Cys Ile Ala
275 280 285

Val Asn Ser Arg Arg Arg Cys Gly Gln Lys Lys Lys Leu Val Ile Asn
290 295 300

Ser Gly Asn Gly Ala Val Glu Asp Arg Lys Pro Ser Gly Leu Asn Gly
305 310 315 320

Glu Ala Ser Lys Ser Gln Glu Met Val His Leu Val Asn Lys Glu Ser
325 330 335

Ser Glu Thr Pro Asp Gln Phe Met Thr Ala Asp Glu Thr Arg Asn Leu
340 345 350

Gln Asn Val Asp Met Lys Ile Gly Val
355 360

<210> SEQ ID NO 226
<211> LENGTH: 87
<212> TYPE: PRT
<213> ORGANISM: Homo sapiens

<400> SEQUENCE: 226

Met Thr Met Tyr Leu Trp Leu Lys Leu Leu Ala Phe Gly Phe Ala Phe
1 5 10 15

Leu Asp Thr Glu Val Phe Val Thr Gly Gln Ser Pro Thr Pro Ser Pro
20 25 30

Thr Gly His Leu Gln Ala Glu Glu Gln Gly Ser Gln Ser Lys Ser Pro
35 40 45

Asn Leu Lys Ser Arg Glu Ala Asp Ser Ser Ala Phe Ser Trp Trp Pro
50 55 60

Lys Ala Arg Glu Pro Leu Thr Asn His Trp Ser Lys Ser Lys Ser Pro
65 70 75 80

Lys Ala Glu Glu Leu Gly Val
85

<210> SEQ ID NO 227
<211> LENGTH: 323
<212> TYPE: PRT
<213> ORGANISM: Homo sapiens

<400> SEQUENCE: 227

Met Trp Pro Leu Val Ala Ala Leu Leu Leu Gly Ser Ala Cys Cys Gly
1 5 10 15

Ser Ala Gln Leu Leu Phe Asn Lys Thr Lys Ser Val Glu Phe Thr Phe
20 25 30

Cys Asn Asp Thr Val Val Ile Pro Cys Phe Val Thr Asn Met Glu Ala
35 40 45

Gln Asn Thr Thr Glu Val Tyr Val Lys Trp Lys Phe Lys Gly Arg Asp

```
    50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Tyr Arg Val Val Ser Trp Phe Ser Pro Asn Glu Asn Ile Leu
    130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
            180                 185                 190

Gly Ala Ile Leu Phe Val Pro Gly Glu Tyr Ser Leu Lys Asn Ala Thr
        195                 200                 205

Gly Leu Gly Leu Ile Val Thr Ser Thr Gly Ile Leu Ile Leu Leu His
    210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
            260                 265                 270

Ser Gly Leu Ser Ile Leu Ala Leu Ala Gln Leu Leu Gly Leu Val Tyr
        275                 280                 285

Met Lys Phe Val Ala Ser Asn Gln Lys Thr Ile Gln Pro Pro Arg Lys
    290                 295                 300

Ala Val Glu Glu Pro Leu Asn Ala Phe Lys Glu Ser Lys Gly Met Met
305                 310                 315                 320

Asn Asp Glu


<210> SEQ ID NO 228
<211> LENGTH: 329
<212> TYPE: PRT
<213> ORGANISM: Homo sapiens

<400> SEQUENCE: 228

Met Asp Pro Gln Cys Thr Met Gly Leu Ser Asn Ile Leu Phe Val Met
1               5                   10                  15

Ala Phe Leu Leu Ser Gly Ala Ala Pro Leu Lys Ile Gln Ala Tyr Phe
            20                  25                  30

Asn Glu Thr Ala Asp Leu Pro Cys Gln Phe Ala Asn Ser Gln Asn Gln
        35                  40                  45

Ser Leu Ser Glu Leu Val Val Phe Trp Gln Asp Gln Glu Asn Leu Val
    50                  55                  60

Leu Asn Glu Val Tyr Leu Gly Lys Glu Lys Phe Asp Ser Val His Ser
65                  70                  75                  80

Lys Tyr Met Gly Arg Thr Ser Phe Asp Ser Asp Ser Trp Thr Leu Arg
                85                  90                  95

Leu His Asn Leu Gln Ile Lys Asp Lys Gly Leu Tyr Gln Cys Ile Ile
```

```
            100                 105                 110

His His Lys Lys Pro Thr Gly Met Ile Arg Ile His Gln Met Asn Ser
        115                 120                 125

Glu Leu Ser Val Leu Ala Asn Phe Ser Gln Pro Glu Ile Val Pro Ile
    130                 135                 140

Ser Asn Ile Thr Glu Asn Val Tyr Ile Asn Leu Thr Cys Ser Ser Ile
145                 150                 155                 160

His Gly Tyr Pro Glu Pro Lys Lys Met Ser Val Leu Leu Arg Thr Lys
                165                 170                 175

Asn Ser Thr Ile Glu Tyr Asp Gly Val Met Gln Lys Ser Gln Asp Asn
            180                 185                 190

Val Thr Glu Leu Tyr Asp Val Ser Ile Ser Leu Ser Val Ser Phe Pro
        195                 200                 205

Asp Val Thr Ser Asn Met Thr Ile Phe Cys Ile Leu Glu Thr Asp Lys
    210                 215                 220

Thr Arg Leu Leu Ser Ser Pro Phe Ser Ile Glu Leu Glu Asp Pro Gln
225                 230                 235                 240

Pro Pro Pro Asp His Ile Pro Trp Ile Thr Ala Val Leu Pro Thr Val
                245                 250                 255

Ile Ile Cys Val Met Val Phe Cys Leu Ile Leu Trp Lys Trp Lys Lys
            260                 265                 270

Lys Lys Arg Pro Arg Asn Ser Tyr Lys Cys Gly Thr Asn Thr Met Glu
        275                 280                 285

Arg Glu Glu Ser Glu Gln Thr Lys Lys Arg Glu Lys Ile His Ile Pro
    290                 295                 300

Glu Arg Ser Asp Glu Ala Gln Arg Val Phe Lys Ser Ser Lys Thr Ser
305                 310                 315                 320

Ser Cys Asp Lys Ser Asp Thr Cys Phe
                325


<210> SEQ ID NO 229
<211> LENGTH: 635
<212> TYPE: PRT
<213> ORGANISM: Homo sapiens

<400> SEQUENCE: 229

Met Pro Ser Trp Ala Leu Phe Met Val Thr Ser Cys Leu Leu Leu Ala
1               5                   10                  15

Pro Gln Asn Leu Ala Gln Val Ser Ser Gln Asp Val Ser Leu Leu Ala
            20                  25                  30

Ser Asp Ser Glu Pro Leu Lys Cys Phe Ser Arg Thr Phe Glu Asp Leu
        35                  40                  45

Thr Cys Phe Trp Asp Glu Glu Glu Ala Ala Pro Ser Gly Thr Tyr Gln
    50                  55                  60

Leu Leu Tyr Ala Tyr Pro Arg Glu Lys Pro Arg Ala Cys Pro Leu Ser
65                  70                  75                  80

Ser Gln Ser Met Pro His Phe Gly Thr Arg Tyr Val Cys Gln Phe Pro
                85                  90                  95

Asp Gln Glu Glu Val Arg Leu Phe Phe Pro Leu His Leu Trp Val Lys
            100                 105                 110

Asn Val Phe Leu Asn Gln Thr Arg Thr Gln Arg Val Leu Phe Val Asp
        115                 120                 125

Ser Val Gly Leu Pro Ala Pro Pro Ser Ile Ile Lys Ala Met Gly Gly
    130                 135                 140
```

-continued

```
Ser Gln Pro Gly Glu Leu Gln Ile Ser Trp Glu Glu Pro Ala Pro Glu
145                 150                 155                 160

Ile Ser Asp Phe Leu Arg Tyr Glu Leu Arg Tyr Gly Pro Arg Asp Pro
                165                 170                 175

Lys Asn Ser Thr Gly Pro Thr Val Ile Gln Leu Ile Ala Thr Glu Thr
            180                 185                 190

Cys Cys Pro Ala Leu Gln Arg Pro His Ser Ala Ser Ala Leu Asp Gln
        195                 200                 205

Ser Pro Cys Ala Gln Pro Thr Met Pro Trp Gln Asp Gly Pro Lys Gln
    210                 215                 220

Thr Ser Pro Ser Arg Glu Ala Ser Ala Leu Thr Ala Glu Gly Gly Ser
225                 230                 235                 240

Cys Leu Ile Ser Gly Leu Gln Pro Gly Asn Ser Tyr Trp Leu Gln Leu
                245                 250                 255

Arg Ser Glu Pro Asp Gly Ile Ser Leu Gly Gly Ser Trp Gly Ser Trp
            260                 265                 270

Ser Leu Pro Val Thr Val Asp Leu Pro Gly Asp Ala Val Ala Leu Gly
        275                 280                 285

Leu Gln Cys Phe Thr Leu Asp Leu Lys Asn Val Thr Cys Gln Trp Gln
    290                 295                 300

Gln Gln Asp His Ala Ser Ser Gln Gly Phe Phe Tyr His Ser Arg Ala
305                 310                 315                 320

Arg Cys Cys Pro Arg Asp Arg Tyr Pro Ile Trp Glu Asn Cys Glu Glu
                325                 330                 335

Glu Glu Lys Thr Asn Pro Gly Leu Gln Thr Pro Gln Phe Ser Arg Cys
            340                 345                 350

His Phe Lys Ser Arg Asn Asp Ser Ile Ile His Ile Leu Val Glu Val
        355                 360                 365

Thr Thr Ala Pro Gly Thr Val His Ser Tyr Leu Gly Ser Pro Phe Trp
    370                 375                 380

Ile His Gln Ala Val Arg Leu Pro Thr Pro Asn Leu His Trp Arg Glu
385                 390                 395                 400

Ile Ser Ser Gly His Leu Glu Leu Glu Trp Gln His Pro Ser Ser Trp
                405                 410                 415

Ala Ala Gln Glu Thr Cys Tyr Gln Leu Arg Tyr Thr Gly Glu Gly His
            420                 425                 430

Gln Asp Trp Lys Val Leu Glu Pro Pro Leu Gly Ala Arg Gly Gly Thr
        435                 440                 445

Leu Glu Leu Arg Pro Arg Ser Arg Tyr Arg Leu Gln Leu Arg Ala Arg
    450                 455                 460

Leu Asn Gly Pro Thr Tyr Gln Gly Pro Trp Ser Ser Trp Ser Asp Pro
465                 470                 475                 480

Thr Arg Val Glu Thr Ala Thr Glu Thr Ala Trp Ile Ser Leu Val Thr
                485                 490                 495

Ala Leu His Leu Val Leu Gly Leu Ser Ala Val Leu Gly Leu Leu Leu
            500                 505                 510

Leu Arg Trp Gln Phe Pro Ala His Tyr Arg Arg Leu Arg His Ala Leu
        515                 520                 525

Trp Pro Ser Leu Pro Asp Leu His Arg Val Leu Gly Gln Tyr Leu Arg
    530                 535                 540

Asp Thr Ala Ala Leu Ser Pro Pro Lys Ala Thr Val Ser Asp Thr Cys
545                 550                 555                 560

Glu Glu Val Glu Pro Ser Leu Leu Glu Ile Leu Pro Lys Ser Ser Glu
```

```
                565                 570                 575

Arg Thr Pro Leu Pro Leu Cys Ser Ser Gln Ala Gln Met Asp Tyr Arg
            580                 585                 590

Arg Leu Gln Pro Ser Cys Leu Gly Thr Met Pro Leu Ser Val Cys Pro
        595                 600                 605

Pro Met Ala Glu Ser Gly Ser Cys Cys Thr Thr His Ile Ala Asn His
    610                 615                 620

Ser Tyr Leu Pro Leu Ser Tyr Trp Gln Gln Pro
625                 630                 635


<210> SEQ ID NO 230
<211> LENGTH: 352
<212> TYPE: PRT
<213> ORGANISM: Homo sapiens

<400> SEQUENCE: 230

Met Ala Arg Met Gly Leu Ala Gly Ala Ala Gly Arg Trp Trp Gly Leu
1               5                   10                  15

Ala Leu Gly Leu Thr Ala Phe Phe Leu Pro Gly Val His Ser Gln Val
            20                  25                  30

Val Gln Val Asn Asp Ser Met Tyr Gly Phe Ile Gly Thr Asp Val Val
        35                  40                  45

Leu His Cys Ser Phe Ala Asn Pro Leu Pro Ser Val Lys Ile Thr Gln
    50                  55                  60

Val Thr Trp Gln Lys Ser Thr Asn Gly Ser Lys Gln Asn Val Ala Ile
65                  70                  75                  80

Tyr Asn Pro Ser Met Gly Val Ser Val Leu Ala Pro Tyr Arg Glu Arg
                85                  90                  95

Val Glu Phe Leu Arg Pro Ser Phe Thr Asp Gly Thr Ile Arg Leu Ser
            100                 105                 110

Arg Leu Glu Leu Glu Asp Glu Gly Val Tyr Ile Cys Glu Phe Ala Thr
        115                 120                 125

Phe Pro Thr Gly Asn Arg Glu Ser Gln Leu Asn Leu Thr Val Met Ala
    130                 135                 140

Lys Pro Thr Asn Trp Ile Glu Gly Thr Gln Ala Val Leu Arg Ala Lys
145                 150                 155                 160

Lys Gly Gln Asp Asp Lys Val Leu Val Ala Thr Cys Thr Ser Ala Asn
                165                 170                 175

Gly Lys Pro Pro Ser Val Val Ser Trp Glu Thr Arg Leu Lys Gly Glu
            180                 185                 190

Ala Glu Tyr Gln Glu Ile Arg Asn Pro Asn Gly Thr Val Thr Val Ile
        195                 200                 205

Ser Arg Tyr Arg Leu Val Pro Ser Arg Glu Ala His Gln Gln Ser Leu
    210                 215                 220

Ala Cys Ile Val Asn Tyr His Met Asp Arg Phe Lys Glu Ser Leu Thr
225                 230                 235                 240

Leu Asn Val Gln Tyr Glu Pro Glu Val Thr Ile Glu Gly Phe Asp Gly
                245                 250                 255

Asn Trp Tyr Leu Gln Arg Met Asp Val Lys Leu Thr Cys Lys Ala Asp
            260                 265                 270

Ala Asn Pro Pro Ala Thr Glu Tyr His Trp Thr Thr Leu Asn Gly Ser
        275                 280                 285

Leu Pro Lys Gly Val Glu Ala Gln Asn Arg Thr Leu Phe Phe Lys Gly
    290                 295                 300
```

```
Pro Ile Asn Tyr Ser Leu Ala Gly Thr Tyr Ile Cys Glu Ala Thr Asn
305                 310                 315                 320

Pro Ile Gly Thr Arg Ser Gly Gln Val Glu Val Asn Ile Thr Ala Phe
                325                 330                 335

Cys Gln Leu Ile Tyr Pro Gly Lys Gly Arg Thr Arg Ala Arg Met Phe
            340                 345                 350


<210> SEQ ID NO 231
<211> LENGTH: 972
<212> TYPE: PRT
<213> ORGANISM: Homo sapiens

<400> SEQUENCE: 231

Met Gly Pro Gly Val Leu Leu Leu Leu Leu Val Ala Thr Ala Trp His
1               5                   10                  15

Gly Gln Gly Ile Pro Val Ile Glu Pro Ser Val Pro Glu Leu Val Val
            20                  25                  30

Lys Pro Gly Ala Thr Val Thr Leu Arg Cys Val Gly Asn Gly Ser Val
        35                  40                  45

Glu Trp Asp Gly Pro Pro Ser Pro His Trp Thr Leu Tyr Ser Asp Gly
    50                  55                  60

Ser Ser Ser Ile Leu Ser Thr Asn Asn Ala Thr Phe Gln Asn Thr Gly
65                  70                  75                  80

Thr Tyr Arg Cys Thr Glu Pro Gly Asp Pro Leu Gly Gly Ser Ala Ala
                85                  90                  95

Ile His Leu Tyr Val Lys Asp Pro Ala Arg Pro Trp Asn Val Leu Ala
            100                 105                 110

Gln Glu Val Val Val Phe Glu Asp Gln Asp Ala Leu Leu Pro Cys Leu
        115                 120                 125

Leu Thr Asp Pro Val Leu Glu Ala Gly Val Ser Leu Val Arg Val Arg
    130                 135                 140

Gly Arg Pro Leu Met Arg His Thr Asn Tyr Ser Phe Ser Pro Trp His
145                 150                 155                 160

Gly Phe Thr Ile His Arg Ala Lys Phe Ile Gln Ser Gln Asp Tyr Gln
                165                 170                 175

Cys Ser Ala Leu Met Gly Gly Arg Lys Val Met Ser Ile Ser Ile Arg
            180                 185                 190

Leu Lys Val Gln Lys Val Ile Pro Gly Pro Pro Ala Leu Thr Leu Val
        195                 200                 205

Pro Ala Glu Leu Val Arg Ile Arg Gly Glu Ala Ala Gln Ile Val Cys
    210                 215                 220

Ser Ala Ser Ser Val Asp Val Asn Phe Asp Val Phe Leu Gln His Asn
225                 230                 235                 240

Asn Thr Lys Leu Ala Ile Pro Gln Gln Ser Asp Phe His Asn Asn Arg
                245                 250                 255

Tyr Gln Lys Val Leu Thr Leu Asn Leu Asp Gln Val Asp Phe Gln His
            260                 265                 270

Ala Gly Asn Tyr Ser Cys Val Ala Ser Asn Val Gln Gly Lys His Ser
        275                 280                 285

Thr Ser Met Phe Phe Arg Val Val Glu Ser Ala Tyr Leu Asn Leu Ser
    290                 295                 300

Ser Glu Gln Asn Leu Ile Gln Glu Val Thr Val Gly Glu Gly Leu Asn
305                 310                 315                 320

Leu Lys Val Met Val Glu Ala Tyr Pro Gly Leu Gln Gly Phe Asn Trp
                325                 330                 335
```

-continued

```
Thr Tyr Leu Gly Pro Phe Ser Asp His Gln Pro Glu Pro Lys Leu Ala
            340                 345                 350

Asn Ala Thr Thr Lys Asp Thr Tyr Arg His Thr Phe Thr Leu Ser Leu
        355                 360                 365

Pro Arg Leu Lys Pro Ser Glu Ala Gly Arg Tyr Ser Phe Leu Ala Arg
    370                 375                 380

Asn Pro Gly Gly Trp Arg Ala Leu Thr Phe Glu Leu Thr Leu Arg Tyr
385                 390                 395                 400

Pro Pro Glu Val Ser Val Ile Trp Thr Phe Ile Asn Gly Ser Gly Thr
                405                 410                 415

Leu Leu Cys Ala Ala Ser Gly Tyr Pro Gln Pro Asn Val Thr Trp Leu
            420                 425                 430

Gln Cys Ser Gly His Thr Asp Arg Cys Asp Glu Ala Gln Val Leu Gln
        435                 440                 445

Val Trp Asp Asp Pro Tyr Pro Glu Val Leu Ser Gln Glu Pro Phe His
    450                 455                 460

Lys Val Thr Val Gln Ser Leu Leu Thr Val Glu Thr Leu Glu His Asn
465                 470                 475                 480

Gln Thr Tyr Glu Cys Arg Ala His Asn Ser Val Gly Ser Gly Ser Trp
                485                 490                 495

Ala Phe Ile Pro Ile Ser Ala Gly Ala His Thr His Pro Pro Asp Glu
            500                 505                 510

Phe Leu Phe Thr Pro Val Val Val Ala Cys Met Ser Ile Met Ala Leu
        515                 520                 525

Leu Leu Leu Leu Leu Leu Leu Leu Leu Tyr Lys Tyr Lys Gln Lys Pro
    530                 535                 540

Lys Tyr Gln Val Arg Trp Lys Ile Ile Glu Ser Tyr Glu Gly Asn Ser
545                 550                 555                 560

Tyr Thr Phe Ile Asp Pro Thr Gln Leu Pro Tyr Asn Glu Lys Trp Glu
                565                 570                 575

Phe Pro Arg Asn Asn Leu Gln Phe Gly Lys Thr Leu Gly Ala Gly Ala
            580                 585                 590

Phe Gly Lys Val Val Glu Ala Thr Ala Phe Gly Leu Gly Lys Glu Asp
        595                 600                 605

Ala Val Leu Lys Val Ala Val Lys Met Leu Lys Ser Thr Ala His Ala
    610                 615                 620

Asp Glu Lys Glu Ala Leu Met Ser Glu Leu Lys Ile Met Ser His Leu
625                 630                 635                 640

Gly Gln His Glu Asn Ile Val Asn Leu Leu Gly Ala Cys Thr His Gly
                645                 650                 655

Gly Pro Val Leu Val Ile Thr Glu Tyr Cys Cys Tyr Gly Asp Leu Leu
            660                 665                 670

Asn Phe Leu Arg Arg Lys Ala Glu Ala Met Leu Gly Pro Ser Leu Ser
        675                 680                 685

Pro Gly Gln Asp Pro Glu Gly Gly Val Asp Tyr Lys Asn Ile His Leu
    690                 695                 700

Glu Lys Lys Tyr Val Arg Arg Asp Ser Gly Phe Ser Ser Gln Gly Val
705                 710                 715                 720

Asp Thr Tyr Val Glu Met Arg Pro Val Ser Thr Ser Ser Asn Asp Ser
                725                 730                 735

Phe Ser Glu Gln Asp Leu Asp Lys Glu Asp Gly Arg Pro Leu Glu Leu
            740                 745                 750
```

```
Arg Asp Leu Leu His Phe Ser Ser Gln Val Ala Gln Gly Met Ala Phe
        755                 760                 765

Leu Ala Ser Lys Asn Cys Ile His Arg Asp Val Ala Ala Arg Asn Val
    770                 775                 780

Leu Leu Thr Asn Gly His Val Ala Lys Ile Gly Asp Phe Gly Leu Ala
785                 790                 795                 800

Arg Asp Ile Met Asn Asp Ser Asn Tyr Ile Val Lys Gly Asn Ala Arg
                805                 810                 815

Leu Pro Val Lys Trp Met Ala Pro Glu Ser Ile Phe Asp Cys Val Tyr
            820                 825                 830

Thr Val Gln Ser Asp Val Trp Ser Tyr Gly Ile Leu Leu Trp Glu Ile
        835                 840                 845

Phe Ser Leu Gly Leu Asn Pro Tyr Pro Gly Ile Leu Val Asn Ser Lys
    850                 855                 860

Phe Tyr Lys Leu Val Lys Asp Gly Tyr Gln Met Ala Gln Pro Ala Phe
865                 870                 875                 880

Ala Pro Lys Asn Ile Tyr Ser Ile Met Gln Ala Cys Trp Ala Leu Glu
                885                 890                 895

Pro Thr His Arg Pro Thr Phe Gln Gln Ile Cys Ser Phe Leu Gln Glu
            900                 905                 910

Gln Ala Gln Glu Asp Arg Arg Glu Arg Asp Tyr Thr Asn Leu Pro Ser
        915                 920                 925

Ser Ser Arg Ser Gly Gly Ser Gly Ser Ser Ser Ser Glu Leu Glu Glu
    930                 935                 940

Glu Ser Ser Ser Glu His Leu Thr Cys Cys Glu Gln Gly Asp Ile Ala
945                 950                 955                 960

Gln Pro Leu Leu Gln Pro Asn Asn Tyr Gln Phe Cys
                965                 970


<210> SEQ ID NO 232
<211> LENGTH: 975
<212> TYPE: PRT
<213> ORGANISM: Homo sapiens

<400> SEQUENCE: 232

Met Arg Gly Ala Arg Gly Ala Trp Asp Phe Leu Cys Val Leu Leu Leu
1               5                   10                  15

Leu Leu Arg Val Gln Thr Gly Ser Ser Gln Pro Ser Val Ser Pro Gly
            20                  25                  30

Glu Pro Ser Pro Pro Ser Ile His Pro Gly Lys Ser Asp Leu Ile Val
        35                  40                  45

Arg Val Gly Asp Glu Ile Arg Leu Leu Cys Thr Asp Pro Gly Phe Val
    50                  55                  60

Lys Trp Thr Phe Glu Ile Leu Asp Glu Thr Asn Glu Asn Lys Gln Asn
65                  70                  75                  80

Glu Trp Ile Thr Glu Lys Ala Glu Ala Thr Asn Thr Gly Lys Tyr Thr
                85                  90                  95

Cys Thr Asn Lys His Gly Leu Ser Asn Ser Ile Tyr Val Phe Val Arg
            100                 105                 110

Asp Pro Ala Lys Leu Phe Leu Val Asp Arg Ser Leu Tyr Gly Lys Glu
        115                 120                 125

Asp Asn Asp Thr Leu Val Arg Cys Pro Leu Thr Asp Pro Glu Val Thr
    130                 135                 140

Asn Tyr Ser Leu Lys Gly Cys Gln Gly Lys Pro Leu Pro Lys Asp Leu
145                 150                 155                 160
```

```
Arg Phe Ile Pro Asp Pro Lys Ala Gly Ile Met Ile Lys Ser Val Lys
                165                 170                 175

Arg Ala Tyr His Arg Leu Cys Leu His Cys Ser Val Asp Gln Glu Gly
            180                 185                 190

Lys Ser Val Leu Ser Glu Lys Phe Ile Leu Lys Val Arg Pro Ala Phe
        195                 200                 205

Lys Ala Val Pro Val Val Ser Val Ser Lys Ala Ser Tyr Leu Leu Arg
    210                 215                 220

Glu Gly Glu Glu Phe Thr Val Thr Cys Thr Ile Lys Asp Val Ser Ser
225                 230                 235                 240

Ser Val Tyr Ser Thr Trp Lys Arg Glu Asn Ser Gln Thr Lys Leu Gln
                245                 250                 255

Glu Lys Tyr Asn Ser Trp His His Gly Asp Phe Asn Tyr Glu Arg Gln
            260                 265                 270

Ala Thr Leu Thr Ile Ser Ser Ala Arg Val Asn Asp Ser Gly Val Phe
        275                 280                 285

Met Cys Tyr Ala Asn Asn Thr Phe Gly Ser Ala Asn Val Thr Thr Thr
    290                 295                 300

Leu Glu Val Val Asp Lys Gly Phe Ile Asn Ile Phe Pro Met Ile Asn
305                 310                 315                 320

Thr Thr Val Phe Val Asn Asp Gly Glu Asn Val Asp Leu Ile Val Glu
                325                 330                 335

Tyr Glu Ala Phe Pro Lys Pro Glu His Gln Gln Trp Ile Tyr Met Asn
            340                 345                 350

Arg Thr Phe Thr Asp Lys Trp Glu Asp Tyr Pro Lys Ser Glu Asn Glu
        355                 360                 365

Ser Asn Ile Arg Tyr Val Ser Glu Leu His Leu Thr Arg Leu Lys Gly
    370                 375                 380

Thr Glu Gly Gly Thr Tyr Thr Phe Leu Val Ser Asn Ser Asp Val Asn
385                 390                 395                 400

Ala Ala Ile Ala Phe Asn Val Tyr Val Asn Thr Lys Pro Glu Ile Leu
                405                 410                 415

Thr Tyr Asp Arg Leu Val Asn Gly Met Leu Gln Cys Val Ala Ala Gly
            420                 425                 430

Phe Pro Glu Pro Thr Ile Asp Trp Tyr Phe Cys Pro Gly Thr Glu Gln
        435                 440                 445

Arg Cys Ser Ala Ser Val Leu Pro Val Asp Val Gln Thr Leu Asn Ser
    450                 455                 460

Ser Gly Pro Pro Phe Gly Lys Leu Val Val Gln Ser Ser Ile Asp Ser
465                 470                 475                 480

Ser Ala Phe Lys His Asn Gly Thr Val Glu Cys Lys Ala Tyr Asn Asp
                485                 490                 495

Val Gly Lys Thr Ser Ala Tyr Phe Asn Phe Ala Phe Lys Gly Asn Asn
            500                 505                 510

Lys Glu Gln Ile His Pro His Thr Leu Phe Thr Pro Leu Leu Ile Gly
        515                 520                 525

Phe Val Ile Val Ala Gly Met Met Cys Ile Ile Val Met Ile Leu Thr
    530                 535                 540

Tyr Lys Tyr Leu Gln Lys Pro Met Tyr Glu Val Gln Trp Lys Val Val
545                 550                 555                 560

Glu Glu Ile Asn Gly Asn Asn Tyr Val Tyr Ile Asp Pro Thr Gln Leu
                565                 570                 575
```

Pro Tyr Asp His Lys Trp Glu Phe Pro Arg Asn Arg Leu Ser Phe Gly
580 585 590

Lys Thr Leu Gly Ala Gly Ala Phe Gly Lys Val Val Glu Ala Thr Ala
595 600 605

Tyr Gly Leu Ile Lys Ser Asp Ala Ala Met Thr Val Ala Val Lys Met
610 615 620

Leu Lys Pro Ser Ala His Leu Thr Glu Arg Glu Ala Leu Met Ser Glu
625 630 635 640

Leu Lys Val Leu Ser Tyr Leu Gly Asn His Met Asn Ile Val Asn Leu
645 650 655

Leu Gly Ala Cys Thr Ile Gly Gly Pro Thr Leu Val Ile Thr Glu Tyr
660 665 670

Cys Cys Tyr Gly Asp Leu Leu Asn Phe Leu Arg Arg Lys Arg Asp Ser
675 680 685

Phe Ile Cys Ser Lys Gln Glu Asp His Ala Glu Ala Ala Leu Tyr Lys
690 695 700

Asn Leu Leu His Ser Lys Glu Ser Ser Cys Asp Ser Thr Asn Glu Tyr
705 710 715 720

Met Asp Met Lys Pro Gly Val Ser Tyr Val Val Pro Thr Lys Ala Asp
725 730 735

Lys Arg Arg Ser Val Arg Ile Gly Ser Tyr Ile Glu Arg Asp Val Thr
740 745 750

Pro Ala Ile Met Glu Asp Asp Glu Leu Ala Leu Asp Leu Glu Asp Leu
755 760 765

Leu Ser Phe Ser Tyr Gln Val Ala Lys Gly Met Ala Phe Leu Ala Ser
770 775 780

Lys Asn Cys Ile His Arg Asp Leu Ala Ala Arg Asn Ile Leu Leu Thr
785 790 795 800

His Gly Arg Ile Thr Lys Ile Cys Asp Phe Gly Leu Ala Arg Asp Ile
805 810 815

Lys Asn Asp Ser Asn Tyr Val Val Lys Gly Asn Ala Arg Leu Pro Val
820 825 830

Lys Trp Met Ala Pro Glu Ser Ile Phe Asn Cys Val Tyr Thr Phe Glu
835 840 845

Ser Asp Val Trp Ser Tyr Gly Ile Phe Leu Trp Glu Leu Phe Ser Leu
850 855 860

Gly Ser Ser Pro Tyr Pro Gly Met Pro Val Asp Ser Lys Phe Tyr Lys
865 870 875 880

Met Ile Lys Glu Gly Phe Arg Met Leu Ser Pro Glu His Ala Pro Ala
885 890 895

Glu Met Tyr Asp Ile Met Lys Thr Cys Trp Asp Ala Asp Pro Leu Lys
900 905 910

Arg Pro Thr Phe Lys Gln Ile Val Gln Leu Ile Glu Lys Gln Ile Ser
915 920 925

Glu Ser Thr Asn His Ile Tyr Ser Asn Leu Ala Asn Cys Ser Pro Asn
930 935 940

Arg Gln Lys Pro Val Val Asp His Ser Val Arg Ile Asn Ser Val Gly
945 950 955 960

Ser Thr Ala Ser Ser Ser Gln Pro Leu Leu Val His Asp Asp Val
965 970 975

<210> SEQ ID NO 233
<211> LENGTH: 439
<212> TYPE: PRT

<213> ORGANISM: Homo sapiens

<400> SEQUENCE: 233

Met Ile Ile Val Ala His Val Leu Leu Ile Leu Leu Gly Ala Thr Glu
1 5 10 15

Ile Leu Gln Ala Asp Leu Leu Pro Asp Glu Lys Ile Ser Leu Leu Pro
20 25 30

Pro Val Asn Phe Thr Ile Lys Val Thr Gly Leu Ala Gln Val Leu Leu
35 40 45

Gln Trp Lys Pro Asn Pro Asp Gln Glu Gln Arg Asn Val Asn Leu Glu
50 55 60

Tyr Gln Val Lys Ile Asn Ala Pro Lys Glu Asp Asp Tyr Glu Thr Arg
65 70 75 80

Ile Thr Glu Ser Lys Cys Val Thr Ile Leu His Lys Gly Phe Ser Ala
85 90 95

Ser Val Arg Thr Ile Leu Gln Asn Asp His Ser Leu Leu Ala Ser Ser
100 105 110

Trp Ala Ser Ala Glu Leu His Ala Pro Pro Gly Ser Pro Gly Thr Ser
115 120 125

Ile Val Asn Leu Thr Cys Thr Thr Asn Thr Thr Glu Asp Asn Tyr Ser
130 135 140

Arg Leu Arg Ser Tyr Gln Val Ser Leu His Cys Thr Trp Leu Val Gly
145 150 155 160

Thr Asp Ala Pro Glu Asp Thr Gln Tyr Phe Leu Tyr Tyr Arg Tyr Gly
165 170 175

Ser Trp Thr Glu Glu Cys Gln Glu Tyr Ser Lys Asp Thr Leu Gly Arg
180 185 190

Asn Ile Ala Cys Trp Phe Pro Arg Thr Phe Ile Leu Ser Lys Gly Arg
195 200 205

Asp Trp Leu Ala Val Leu Val Asn Gly Ser Ser Lys His Ser Ala Ile
210 215 220

Arg Pro Phe Asp Gln Leu Phe Ala Leu His Ala Ile Asp Gln Ile Asn
225 230 235 240

Pro Pro Leu Asn Val Thr Ala Glu Ile Glu Gly Thr Arg Leu Ser Ile
245 250 255

Gln Trp Glu Lys Pro Val Ser Ala Phe Pro Ile His Cys Phe Asp Tyr
260 265 270

Glu Val Lys Ile His Asn Thr Arg Asn Gly Tyr Leu Gln Ile Glu Lys
275 280 285

Leu Met Thr Asn Ala Phe Ile Ser Ile Ile Asp Asp Leu Ser Lys Tyr
290 295 300

Asp Val Gln Val Arg Ala Ala Val Ser Ser Met Cys Arg Glu Ala Gly
305 310 315 320

Leu Trp Ser Glu Trp Ser Gln Pro Ile Tyr Val Gly Asn Asp Glu His
325 330 335

Lys Pro Leu Arg Glu Trp Phe Val Ile Val Ile Met Ala Thr Ile Cys
340 345 350

Phe Ile Leu Leu Ile Leu Ser Leu Ile Cys Lys Ile Cys His Leu Trp
355 360 365

Ile Lys Leu Phe Pro Pro Ile Pro Ala Pro Lys Ser Asn Ile Lys Asp
370 375 380

Leu Phe Val Thr Thr Asn Tyr Glu Val Leu Cys Ile Phe Ile Tyr Ile
385 390 395 400

Leu Asp Ser Ala Asp Asn Phe Leu Gln Lys Lys Lys Ala Gly Ser Ser
405 410 415

Glu Thr Glu Ile Glu Val Ile Cys Tyr Ile Glu Lys Pro Gly Val Glu
420 425 430

Thr Leu Glu Asp Ser Val Phe
435

<210> SEQ ID NO 234
<211> LENGTH: 818
<212> TYPE: PRT
<213> ORGANISM: Homo sapiens

<400> SEQUENCE: 234

Met Glu Asn Gln Asp Ala Leu Val Cys Ile Ser Glu Ser Val Pro Glu
1 5 10 15

Pro Ile Val Glu Trp Val Leu Cys Asp Ser Gln Gly Glu Ser Cys Lys
20 25 30

Glu Glu Ser Pro Ala Val Val Lys Lys Glu Glu Lys Val Leu His Glu
35 40 45

Leu Phe Gly Thr Asp Ile Arg Cys Cys Ala Arg Asn Glu Leu Gly Arg
50 55 60

Glu Cys Thr Arg Leu Phe Thr Ile Asp Leu Asn Gln Thr Pro Gln Thr
65 70 75 80

Thr Leu Pro Gln Leu Phe Leu Lys Val Gly Glu Pro Leu Trp Ile Arg
85 90 95

Cys Lys Ala Val His Val Asn His Gly Phe Gly Leu Thr Trp Glu Leu
100 105 110

Glu Asn Lys Ala Leu Glu Glu Gly Asn Tyr Phe Glu Met Ser Thr Tyr
115 120 125

Ser Thr Asn Arg Thr Met Ile Arg Ile Leu Phe Ala Phe Val Ser Ser
130 135 140

Val Ala Arg Asn Asp Thr Gly Tyr Tyr Thr Cys Ser Ser Ser Lys His
145 150 155 160

Pro Ser Gln Ser Ala Leu Val Thr Ile Val Glu Lys Gly Phe Ile Asn
165 170 175

Ala Thr Asn Ser Ser Glu Asp Tyr Glu Ile Asp Gln Tyr Glu Glu Phe
180 185 190

Cys Phe Ser Val Arg Phe Lys Ala Tyr Pro Gln Ile Arg Cys Thr Trp
195 200 205

Thr Phe Ser Arg Lys Ser Phe Pro Cys Glu Gln Lys Gly Leu Asp Asn
210 215 220

Gly Tyr Ser Ile Ser Lys Phe Cys Asn His Lys His Gln Pro Gly Glu
225 230 235 240

Tyr Ile Phe His Ala Glu Asn Asp Asp Ala Gln Phe Thr Lys Met Phe
245 250 255

Thr Leu Asn Ile Arg Arg Lys Pro Gln Val Leu Ala Glu Ala Ser Ala
260 265 270

Ser Gln Ala Ser Cys Phe Ser Asp Gly Tyr Pro Leu Pro Ser Trp Thr
275 280 285

Trp Lys Lys Cys Ser Asp Lys Ser Pro Asn Cys Thr Glu Glu Ile Thr
290 295 300

Glu Gly Val Trp Asn Arg Lys Ala Asn Arg Lys Val Phe Gly Gln Trp
305 310 315 320

Val Ser Ser Ser Thr Leu Asn Met Ser Glu Ala Ile Lys Gly Phe Leu
325 330 335

-continued

```
Val Lys Cys Cys Ala Tyr Asn Ser Leu Gly Thr Ser Cys Glu Thr Ile
            340                 345                 350

Leu Leu Asn Ser Pro Gly Pro Phe Pro Phe Ile Gln Asp Asn Ile Ser
        355                 360                 365

Phe Tyr Ala Thr Ile Gly Val Cys Leu Leu Phe Ile Val Val Leu Thr
    370                 375                 380

Leu Leu Ile Cys His Lys Tyr Lys Lys Gln Phe Arg Tyr Glu Ser Gln
385                 390                 395                 400

Leu Gln Met Val Gln Val Thr Gly Ser Ser Asp Asn Glu Tyr Phe Tyr
                405                 410                 415

Val Asp Phe Arg Glu Tyr Glu Tyr Asp Leu Lys Trp Glu Phe Pro Arg
            420                 425                 430

Glu Asn Leu Glu Phe Gly Lys Val Leu Gly Ser Gly Ala Phe Gly Lys
        435                 440                 445

Val Met Asn Ala Thr Ala Tyr Gly Ile Ser Lys Thr Gly Val Ser Ile
    450                 455                 460

Gln Val Ala Val Lys Met Leu Lys Glu Lys Ala Asp Ser Ser Glu Arg
465                 470                 475                 480

Glu Ala Leu Met Ser Glu Leu Lys Met Met Thr Gln Leu Gly Ser His
                485                 490                 495

Glu Asn Ile Val Asn Leu Leu Gly Ala Cys Thr Leu Ser Gly Pro Ile
            500                 505                 510

Tyr Leu Ile Phe Glu Tyr Cys Cys Tyr Gly Asp Leu Leu Asn Tyr Leu
        515                 520                 525

Arg Ser Lys Arg Glu Lys Phe His Arg Thr Trp Thr Glu Ile Phe Lys
    530                 535                 540

Glu His Asn Phe Ser Phe Tyr Pro Thr Phe Gln Ser His Pro Asn Ser
545                 550                 555                 560

Ser Met Pro Gly Ser Arg Glu Val Gln Ile His Pro Asp Ser Asp Gln
                565                 570                 575

Ile Ser Gly Leu His Gly Asn Ser Phe His Ser Glu Asp Glu Ile Glu
            580                 585                 590

Tyr Glu Asn Gln Lys Arg Leu Glu Glu Glu Glu Asp Leu Asn Val Leu
        595                 600                 605

Thr Phe Glu Asp Leu Leu Cys Phe Ala Tyr Gln Val Ala Lys Gly Met
    610                 615                 620

Glu Phe Leu Glu Phe Lys Ser Cys Val His Arg Asp Leu Ala Ala Arg
625                 630                 635                 640

Asn Val Leu Val Thr His Gly Lys Val Val Lys Ile Cys Asp Phe Gly
                645                 650                 655

Leu Ala Arg Asp Ile Met Ser Asp Ser Asn Tyr Val Val Arg Gly Asn
            660                 665                 670

Ala Arg Leu Pro Val Lys Trp Met Ala Pro Glu Ser Leu Phe Glu Gly
        675                 680                 685

Ile Tyr Thr Ile Lys Ser Asp Val Trp Ser Tyr Gly Ile Leu Leu Trp
    690                 695                 700

Glu Ile Phe Ser Leu Gly Val Asn Pro Tyr Pro Gly Ile Pro Val Asp
705                 710                 715                 720

Ala Asn Phe Tyr Lys Leu Ile Gln Asn Gly Phe Lys Met Asp Gln Pro
                725                 730                 735

Phe Tyr Ala Thr Glu Glu Ile Tyr Ile Ile Met Gln Ser Cys Trp Ala
            740                 745                 750
```

-continued

```
Phe Asp Ser Arg Lys Arg Pro Ser Phe Pro Asn Leu Thr Ser Phe Leu
        755                 760                 765

Gly Cys Gln Leu Ala Asp Ala Glu Glu Ala Met Tyr Gln Asn Val Asp
    770                 775                 780

Gly Arg Val Ser Glu Cys Pro His Thr Tyr Gln Asn Arg Arg Pro Phe
785                 790                 795                 800

Ser Arg Glu Met Asp Leu Gly Leu Leu Ser Pro Gln Ala Gln Val Glu
                805                 810                 815

Asp Ser


<210> SEQ ID NO 235
<211> LENGTH: 423
<212> TYPE: PRT
<213> ORGANISM: Homo sapiens

<400> SEQUENCE: 235

Met Glu Gly Ile Ser Glu Asn Ala Pro Leu Pro Asn Val Pro Asn Ala
1               5                   10                  15

Pro Ser Asp Lys His Glu Asp Gly Lys Arg Pro Thr His Arg Arg Ser
            20                  25                  30

Ala Arg Leu Gly Glu Glu Val Pro Phe Val His Phe Leu Thr Leu Pro
        35                  40                  45

Pro Asn Ile Pro Gln Ala Pro Lys Gly Leu Arg Phe Lys Thr Ala Phe
    50                  55                  60

Ser Leu Pro Thr Thr Ser Cys Leu Lys Pro Arg Met Ile Tyr Thr Ser
65                  70                  75                  80

Asp Asn Tyr Thr Glu Glu Met Gly Ser Gly Asp Tyr Asp Ser Met Lys
                85                  90                  95

Glu Pro Cys Phe Arg Glu Glu Asn Ala Asn Phe Asn Lys Ile Phe Leu
            100                 105                 110

Pro Thr Ile Tyr Ser Ile Ile Phe Leu Thr Gly Ile Val Gly Asn Gly
        115                 120                 125

Leu Val Ile Leu Val Met Gly Tyr Gln Lys Lys Leu Arg Ser Met Thr
    130                 135                 140

Asp Lys Tyr Arg Leu His Leu Ser Val Ala Asp Leu Leu Phe Val Ile
145                 150                 155                 160

Thr Leu Pro Phe Trp Ala Val Asp Ala Val Ala Asn Trp Tyr Phe Gly
                165                 170                 175

Asn Phe Leu Cys Lys Ala Val His Val Ile Tyr Thr Val Asn Leu Tyr
            180                 185                 190

Ser Ser Val Leu Ile Leu Ala Phe Ile Ser Leu Asp Arg Tyr Leu Ala
        195                 200                 205

Ile Val His Ala Thr Asn Ser Gln Arg Pro Arg Lys Leu Leu Ala Glu
    210                 215                 220

Lys Val Val Tyr Val Gly Val Trp Ile Pro Ala Leu Leu Leu Thr Ile
225                 230                 235                 240

Pro Asp Phe Ile Phe Ala Asn Val Ser Glu Ala Asp Asp Arg Tyr Ile
                245                 250                 255

Cys Asp Arg Phe Tyr Pro Asn Asp Leu Trp Val Val Val Phe Gln Phe
            260                 265                 270

Gln His Ile Met Val Gly Leu Ile Leu Pro Gly Ile Val Ile Leu Ser
        275                 280                 285

Cys Tyr Cys Ile Ile Ile Ser Lys Leu Ser His Ser Lys Gly His Gln
    290                 295                 300
```

Lys Arg Lys Ala Leu Lys Thr Thr Val Ile Leu Ile Leu Ala Phe Phe
305 310 315 320

Ala Cys Trp Leu Pro Tyr Tyr Ile Gly Ile Ser Ile Asp Ser Phe Ile
325 330 335

Leu Leu Glu Ile Ile Lys Gln Gly Cys Glu Phe Glu Asn Thr Val His
340 345 350

Lys Trp Ile Ser Ile Thr Glu Ala Leu Ala Phe Phe His Cys Cys Leu
355 360 365

Asn Pro Ile Leu Tyr Ala Phe Leu Gly Ala Lys Phe Lys Thr Ser Ala
370 375 380

Gln His Ala Leu Thr Ser Val Ser Arg Gly Ser Ser Leu Lys Ile Leu
385 390 395 400

Ser Lys Gly Lys Arg Gly Gly His Ser Ser Val Ser Thr Glu Ser Glu
405 410 415

Ser Ser Ser Phe His Ser Ser
420

<210> SEQ ID NO 236
<211> LENGTH: 278
<212> TYPE: PRT
<213> ORGANISM: Homo sapiens

<400> SEQUENCE: 236

Met Glu Arg Leu Val Ile Arg Met Pro Phe Ser His Leu Ser Thr Tyr
1 5 10 15

Ser Leu Val Trp Val Met Ala Ala Val Val Leu Cys Thr Ala Gln Val
20 25 30

Gln Val Val Thr Gln Asp Glu Arg Glu Gln Leu Tyr Thr Pro Ala Ser
35 40 45

Leu Lys Cys Ser Leu Gln Asn Ala Gln Glu Ala Leu Ile Val Thr Trp
50 55 60

Gln Lys Lys Lys Ala Val Ser Pro Glu Asn Met Val Thr Phe Ser Glu
65 70 75 80

Asn His Gly Val Val Ile Gln Pro Ala Tyr Lys Asp Lys Ile Asn Ile
85 90 95

Thr Gln Leu Gly Leu Gln Asn Ser Thr Ile Thr Phe Trp Asn Ile Thr
100 105 110

Leu Glu Asp Glu Gly Cys Tyr Met Cys Leu Phe Asn Thr Phe Gly Phe
115 120 125

Gly Lys Ile Ser Gly Thr Ala Cys Leu Thr Val Tyr Val Gln Pro Ile
130 135 140

Val Ser Leu His Tyr Lys Phe Ser Glu Asp His Leu Asn Ile Thr Cys
145 150 155 160

Ser Ala Thr Ala Arg Pro Ala Pro Met Val Phe Trp Lys Val Pro Arg
165 170 175

Ser Gly Ile Glu Asn Ser Thr Val Thr Leu Ser His Pro Asn Gly Thr
180 185 190

Thr Ser Val Thr Ser Ile Leu His Ile Lys Asp Pro Lys Asn Gln Val
195 200 205

Gly Lys Glu Val Ile Cys Gln Val Leu His Leu Gly Thr Val Thr Asp
210 215 220

Phe Lys Gln Thr Val Asn Lys Gly Tyr Trp Phe Ser Val Pro Leu Leu
225 230 235 240

Leu Ser Ile Val Ser Leu Val Ile Leu Leu Val Leu Ile Ser Ile Leu
245 250 255

Leu Tyr Trp Lys Arg His Arg Asn Gln Asp Arg Gly Glu Leu Ser Gln
260 265 270

Gly Val Gln Lys Met Thr
275

<210> SEQ ID NO 237
<211> LENGTH: 288
<212> TYPE: PRT
<213> ORGANISM: Homo sapiens

<400> SEQUENCE: 237

Met Gln Ile Pro Gln Ala Pro Trp Pro Val Val Trp Ala Val Leu Gln
1 5 10 15

Leu Gly Trp Arg Pro Gly Trp Phe Leu Asp Ser Pro Asp Arg Pro Trp
20 25 30

Asn Pro Pro Thr Phe Ser Pro Ala Leu Leu Val Val Thr Glu Gly Asp
35 40 45

Asn Ala Thr Phe Thr Cys Ser Phe Ser Asn Thr Ser Glu Ser Phe Val
50 55 60

Leu Asn Trp Tyr Arg Met Ser Pro Ser Asn Gln Thr Asp Lys Leu Ala
65 70 75 80

Ala Phe Pro Glu Asp Arg Ser Gln Pro Gly Gln Asp Cys Arg Phe Arg
85 90 95

Val Thr Gln Leu Pro Asn Gly Arg Asp Phe His Met Ser Val Val Arg
100 105 110

Ala Arg Arg Asn Asp Ser Gly Thr Tyr Leu Cys Gly Ala Ile Ser Leu
115 120 125

Ala Pro Lys Ala Gln Ile Lys Glu Ser Leu Arg Ala Glu Leu Arg Val
130 135 140

Thr Glu Arg Arg Ala Glu Val Pro Thr Ala His Pro Ser Pro Ser Pro
145 150 155 160

Arg Pro Ala Gly Gln Phe Gln Thr Leu Val Val Gly Val Val Gly Gly
165 170 175

Leu Leu Gly Ser Leu Val Leu Leu Val Trp Val Leu Ala Val Ile Cys
180 185 190

Ser Arg Ala Ala Arg Gly Thr Ile Gly Ala Arg Arg Thr Gly Gln Pro
195 200 205

Leu Lys Glu Asp Pro Ser Ala Val Pro Val Phe Ser Val Asp Tyr Gly
210 215 220

Glu Leu Asp Phe Gln Trp Arg Glu Lys Thr Pro Glu Pro Pro Val Pro
225 230 235 240

Cys Val Pro Glu Gln Thr Glu Tyr Ala Thr Ile Val Phe Pro Ser Gly
245 250 255

Met Gly Thr Ser Ser Pro Ala Arg Arg Gly Ser Ala Asp Gly Pro Arg
260 265 270

Ser Ala Gln Pro Leu Arg Pro Glu Asp Gly His Cys Ser Trp Pro Leu
275 280 285

<210> SEQ ID NO 238
<211> LENGTH: 273
<212> TYPE: PRT
<213> ORGANISM: Homo sapiens

<400> SEQUENCE: 238

Met Ile Phe Leu Leu Leu Met Leu Ser Leu Glu Leu Gln Leu His Gln
1 5 10 15

Ile Ala Ala Leu Phe Thr Val Thr Val Pro Lys Glu Leu Tyr Ile Ile
20 25 30

Glu His Gly Ser Asn Val Thr Leu Glu Cys Asn Phe Asp Thr Gly Ser
35 40 45

His Val Asn Leu Gly Ala Ile Thr Ala Ser Leu Gln Lys Val Glu Asn
50 55 60

Asp Thr Ser Pro His Arg Glu Arg Ala Thr Leu Leu Glu Glu Gln Leu
65 70 75 80

Pro Leu Gly Lys Ala Ser Phe His Ile Pro Gln Val Gln Val Arg Asp
85 90 95

Glu Gly Gln Tyr Gln Cys Ile Ile Ile Tyr Gly Val Ala Trp Asp Tyr
100 105 110

Lys Tyr Leu Thr Leu Lys Val Lys Ala Ser Tyr Arg Lys Ile Asn Thr
115 120 125

His Ile Leu Lys Val Pro Glu Thr Asp Glu Val Glu Leu Thr Cys Gln
130 135 140

Ala Thr Gly Tyr Pro Leu Ala Glu Val Ser Trp Pro Asn Val Ser Val
145 150 155 160

Pro Ala Asn Thr Ser His Ser Arg Thr Pro Glu Gly Leu Tyr Gln Val
165 170 175

Thr Ser Val Leu Arg Leu Lys Pro Pro Pro Gly Arg Asn Phe Ser Cys
180 185 190

Val Phe Trp Asn Thr His Val Arg Glu Leu Thr Leu Ala Ser Ile Asp
195 200 205

Leu Gln Ser Gln Met Glu Pro Arg Thr His Pro Thr Trp Leu Leu His
210 215 220

Ile Phe Ile Pro Phe Cys Ile Ile Ala Phe Ile Phe Ile Ala Thr Val
225 230 235 240

Ile Ala Leu Arg Lys Gln Leu Cys Gln Lys Leu Tyr Ser Ser Lys Asp
245 250 255

Thr Thr Lys Arg Pro Val Thr Thr Thr Lys Arg Glu Val Asn Ser Ala
260 265 270

Ile

<210> SEQ ID NO 239
<211> LENGTH: 290
<212> TYPE: PRT
<213> ORGANISM: Homo sapiens

<400> SEQUENCE: 239

Met Arg Ile Phe Ala Val Phe Ile Phe Met Thr Tyr Trp His Leu Leu
1 5 10 15

Asn Ala Phe Thr Val Thr Val Pro Lys Asp Leu Tyr Val Val Glu Tyr
20 25 30

Gly Ser Asn Met Thr Ile Glu Cys Lys Phe Pro Val Glu Lys Gln Leu
35 40 45

Asp Leu Ala Ala Leu Ile Val Tyr Trp Glu Met Glu Asp Lys Asn Ile
50 55 60

Ile Gln Phe Val His Gly Glu Glu Asp Leu Lys Val Gln His Ser Ser
65 70 75 80

Tyr Arg Gln Arg Ala Arg Leu Leu Lys Asp Gln Leu Ser Leu Gly Asn
85 90 95

Ala Ala Leu Gln Ile Thr Asp Val Lys Leu Gln Asp Ala Gly Val Tyr
100 105 110

Arg Cys Met Ile Ser Tyr Gly Gly Ala Asp Tyr Lys Arg Ile Thr Val
115 120 125

Lys Val Asn Ala Pro Tyr Asn Lys Ile Asn Gln Arg Ile Leu Val Val
130 135 140

Asp Pro Val Thr Ser Glu His Glu Leu Thr Cys Gln Ala Glu Gly Tyr
145 150 155 160

Pro Lys Ala Glu Val Ile Trp Thr Ser Ser Asp His Gln Val Leu Ser
165 170 175

Gly Lys Thr Thr Thr Thr Asn Ser Lys Arg Glu Glu Lys Leu Phe Asn
180 185 190

Val Thr Ser Thr Leu Arg Ile Asn Thr Thr Thr Asn Glu Ile Phe Tyr
195 200 205

Cys Thr Phe Arg Arg Leu Asp Pro Glu Glu Asn His Thr Ala Glu Leu
210 215 220

Val Ile Pro Glu Leu Pro Leu Ala His Pro Pro Asn Glu Arg Thr His
225 230 235 240

Leu Val Ile Leu Gly Ala Ile Leu Leu Cys Leu Gly Val Ala Leu Thr
245 250 255

Phe Ile Phe Arg Leu Arg Lys Gly Arg Met Met Asp Val Lys Lys Cys
260 265 270

Gly Ile Gln Asp Thr Asn Ser Lys Lys Gln Ser Asp Thr His Leu Glu
275 280 285

Glu Thr
290

<210> SEQ ID NO 240
<211> LENGTH: 705
<212> TYPE: PRT
<213> ORGANISM: Homo sapiens

<400> SEQUENCE: 240

Met Arg Pro Ser Gly Thr Ala Gly Ala Ala Leu Leu Ala Leu Leu Ala
1 5 10 15

Ala Leu Cys Pro Ala Ser Arg Ala Leu Glu Glu Lys Lys Val Cys Gln
20 25 30

Gly Thr Ser Asn Lys Leu Thr Gln Leu Gly Thr Phe Glu Asp His Phe
35 40 45

Leu Ser Leu Gln Arg Met Phe Asn Asn Cys Glu Val Val Leu Gly Asn
50 55 60

Leu Glu Ile Thr Tyr Val Gln Arg Asn Tyr Asp Leu Ser Phe Leu Lys
65 70 75 80

Thr Ile Gln Glu Val Ala Gly Tyr Val Leu Ile Ala Leu Asn Thr Val
85 90 95

Glu Arg Ile Pro Leu Glu Asn Leu Gln Ile Ile Arg Gly Asn Met Tyr
100 105 110

Tyr Glu Asn Ser Tyr Ala Leu Ala Val Leu Ser Asn Tyr Asp Ala Asn
115 120 125

Lys Thr Gly Leu Lys Glu Leu Pro Met Arg Asn Leu Gln Glu Ile Leu
130 135 140

His Gly Ala Val Arg Phe Ser Asn Asn Pro Ala Leu Cys Asn Val Glu
145 150 155 160

Ser Ile Gln Trp Arg Asp Ile Val Ser Ser Asp Phe Leu Ser Asn Met
165 170 175

Ser Met Asp Phe Gln Asn His Leu Gly Ser Cys Gln Lys Cys Asp Pro

-continued

```
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Asn Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605
```

Lys Tyr Ala Asp Ala Gly His Val Cys His Leu Cys His Pro Asn Cys
    610                 615                 620

Thr Tyr Gly Pro Gly Asn Glu Ser Leu Lys Ala Met Leu Phe Cys Leu
625                 630                 635                 640

Phe Lys Leu Ser Ser Cys Asn Gln Ser Asn Asp Gly Ser Val Ser His
                645                 650                 655

Gln Ser Gly Ser Pro Ala Ala Gln Glu Ser Cys Leu Gly Trp Ile Pro
            660                 665                 670

Ser Leu Leu Pro Ser Glu Phe Gln Leu Gly Trp Gly Gly Cys Ser His
        675                 680                 685

Leu His Ala Trp Pro Ser Ala Ser Val Ile Ile Thr Ala Ser Ser Cys
    690                 695                 700

His
705

<210> SEQ ID NO 241
<211> LENGTH: 1248
<212> TYPE: PRT
<213> ORGANISM: Homo sapiens

<400> SEQUENCE: 241

Met Val Val Ala Leu Arg Tyr Val Trp Pro Leu Leu Leu Cys Ser Pro
1               5                   10                  15

Cys Leu Leu Ile Gln Ile Pro Glu Glu Leu Met Glu Pro Pro Val Ile
            20                  25                  30

Thr Glu Gln Ser Pro Arg Arg Leu Val Val Phe Pro Thr Asp Asp Ile
        35                  40                  45

Ser Leu Lys Cys Glu Ala Ser Gly Lys Pro Glu Val Gln Phe Arg Trp
    50                  55                  60

Thr Arg Asp Gly Val His Phe Lys Pro Lys Glu Glu Leu Gly Val Thr
65                  70                  75                  80

Val Tyr Gln Ser Pro His Ser Gly Ser Phe Thr Ile Thr Gly Asn Asn
                85                  90                  95

Ser Asn Phe Ala Gln Arg Phe Gln Gly Ile Tyr Arg Cys Phe Ala Ser
            100                 105                 110

Asn Lys Leu Gly Thr Ala Met Ser His Glu Ile Arg Leu Met Ala Glu
        115                 120                 125

Gly Ala Pro Lys Trp Pro Lys Glu Thr Val Lys Pro Val Glu Val Glu
    130                 135                 140

Glu Gly Glu Ser Val Val Leu Pro Cys Asn Pro Pro Pro Ser Ala Glu
145                 150                 155                 160

Pro Leu Arg Ile Tyr Trp Met Asn Ser Lys Ile Leu His Ile Lys Gln
                165                 170                 175

Asp Glu Arg Val Thr Met Gly Gln Asn Gly Asn Leu Tyr Phe Ala Asn
            180                 185                 190

Val Leu Thr Ser Asp Asn His Ser Asp Tyr Ile Cys His Ala His Phe
        195                 200                 205

Pro Gly Thr Arg Thr Ile Ile Gln Lys Glu Pro Ile Asp Leu Arg Val
    210                 215                 220

Lys Ala Thr Asn Ser Met Ile Asp Arg Lys Pro Arg Leu Leu Phe Pro
225                 230                 235                 240

Thr Asn Ser Ser Ser His Leu Val Ala Leu Gln Gly Gln Pro Leu Val
                245                 250                 255

Leu Glu Cys Ile Ala Glu Gly Phe Pro Thr Pro Thr Ile Lys Trp Leu

```
            260                 265                 270

Arg Pro Ser Gly Pro Met Pro Ala Asp Arg Val Thr Tyr Gln Asn His
        275                 280                 285

Asn Lys Thr Leu Gln Leu Leu Lys Val Gly Glu Glu Asp Asp Gly Glu
    290                 295                 300

Tyr Arg Cys Leu Ala Glu Asn Ser Leu Gly Ser Ala Arg His Ala Tyr
305                 310                 315                 320

Tyr Val Thr Val Glu Ala Ala Pro Tyr Trp Leu His Lys Pro Gln Ser
                325                 330                 335

His Leu Tyr Gly Pro Gly Glu Thr Ala Arg Leu Asp Cys Gln Val Gln
            340                 345                 350

Gly Arg Pro Gln Pro Glu Val Thr Trp Arg Ile Asn Gly Ile Pro Val
        355                 360                 365

Glu Glu Leu Ala Lys Asp Gln Lys Tyr Arg Ile Gln Arg Gly Ala Leu
    370                 375                 380

Ile Leu Ser Asn Val Gln Pro Ser Asp Thr Met Val Thr Gln Cys Glu
385                 390                 395                 400

Ala Arg Asn Arg His Gly Leu Leu Leu Ala Asn Ala Tyr Ile Tyr Val
                405                 410                 415

Val Gln Leu Pro Ala Lys Ile Leu Thr Ala Asp Asn Gln Thr Tyr Met
            420                 425                 430

Ala Val Gln Gly Ser Thr Ala Tyr Leu Leu Cys Lys Ala Phe Gly Ala
        435                 440                 445

Pro Val Pro Ser Val Gln Trp Leu Asp Glu Asp Gly Thr Thr Val Leu
    450                 455                 460

Gln Asp Glu Arg Phe Phe Pro Tyr Ala Asn Gly Thr Leu Gly Ile Arg
465                 470                 475                 480

Asp Leu Gln Ala Asn Asp Thr Gly Arg Tyr Phe Cys Leu Ala Ala Asn
                485                 490                 495

Asp Gln Asn Asn Val Thr Ile Met Ala Asn Leu Lys Val Lys Asp Ala
            500                 505                 510

Thr Gln Ile Thr Gln Gly Pro Arg Ser Thr Ile Glu Lys Lys Gly Ser
        515                 520                 525

Arg Val Thr Phe Thr Cys Gln Ala Ser Phe Asp Pro Ser Leu Gln Pro
    530                 535                 540

Ser Ile Thr Trp Arg Gly Asp Gly Arg Asp Leu Gln Glu Leu Gly Asp
545                 550                 555                 560

Ser Asp Lys Tyr Phe Ile Glu Asp Gly Arg Leu Val Ile His Ser Leu
                565                 570                 575

Asp Tyr Ser Asp Gln Gly Asn Tyr Ser Cys Val Ala Ser Thr Glu Leu
            580                 585                 590

Asp Val Val Glu Ser Arg Ala Gln Leu Leu Val Val Gly Ser Pro Gly
        595                 600                 605

Pro Val Pro Arg Leu Val Leu Ser Asp Leu His Leu Leu Thr Gln Ser
    610                 615                 620

Gln Val Arg Val Ser Trp Ser Pro Ala Glu Asp His Asn Ala Pro Ile
625                 630                 635                 640

Glu Lys Tyr Asp Ile Glu Phe Glu Asp Lys Glu Met Ala Pro Glu Lys
                645                 650                 655

Trp Tyr Ser Leu Gly Lys Val Pro Gly Asn Gln Thr Ser Thr Thr Leu
            660                 665                 670

Lys Leu Ser Pro Tyr Val His Tyr Thr Phe Arg Val Thr Ala Ile Asn
        675                 680                 685
```

```
Lys Tyr Gly Pro Gly Glu Pro Ser Pro Val Ser Glu Thr Val Val Thr
    690                 695                 700

Pro Glu Ala Ala Pro Glu Lys Asn Pro Val Asp Val Lys Gly Glu Gly
705                 710                 715                 720

Asn Glu Thr Thr Asn Met Val Ile Thr Trp Lys Pro Leu Arg Trp Met
                725                 730                 735

Asp Trp Asn Ala Pro Gln Val Gln Tyr Arg Val Gln Trp Arg Pro Gln
            740                 745                 750

Gly Thr Arg Gly Pro Trp Gln Glu Gln Ile Val Ser Asp Pro Phe Leu
        755                 760                 765

Val Val Ser Asn Thr Ser Thr Phe Val Pro Tyr Glu Ile Lys Val Gln
    770                 775                 780

Ala Val Asn Ser Gln Gly Lys Gly Pro Glu Pro Gln Val Thr Ile Gly
785                 790                 795                 800

Tyr Ser Gly Glu Asp Tyr Pro Gln Ala Ile Pro Glu Leu Glu Gly Ile
                805                 810                 815

Glu Ile Leu Asn Ser Ser Ala Val Leu Val Lys Trp Arg Pro Val Asp
            820                 825                 830

Leu Ala Gln Val Lys Gly His Leu Arg Gly Tyr Asn Val Thr Tyr Trp
        835                 840                 845

Arg Glu Gly Ser Gln Arg Lys His Ser Lys Arg His Ile His Lys Asp
    850                 855                 860

His Val Val Val Pro Ala Asn Thr Thr Ser Val Ile Leu Ser Gly Leu
865                 870                 875                 880

Arg Pro Tyr Ser Ser Tyr His Leu Glu Val Gln Ala Phe Asn Gly Arg
                885                 890                 895

Gly Ser Gly Pro Ala Ser Glu Phe Thr Phe Ser Thr Pro Glu Gly Val
            900                 905                 910

Pro Gly His Pro Glu Ala Leu His Leu Glu Cys Gln Ser Asn Thr Ser
        915                 920                 925

Leu Leu Leu Arg Trp Gln Pro Pro Leu Ser His Asn Gly Val Leu Thr
    930                 935                 940

Gly Tyr Val Leu Ser Tyr His Pro Leu Asp Glu Gly Gly Lys Gly Gln
945                 950                 955                 960

Leu Ser Phe Asn Leu Arg Asp Pro Glu Leu Arg Thr His Asn Leu Thr
                965                 970                 975

Asp Leu Ser Pro His Leu Arg Tyr Arg Phe Gln Leu Gln Ala Thr Thr
            980                 985                 990

Lys Glu Gly Pro Gly Glu Ala Ile  Val Arg Glu Gly Gly  Thr Met Ala
        995                 1000                1005

Leu Ser  Gly Ile Ser Asp Phe  Gly Asn Ile Ser Ala  Thr Ala Gly
    1010                1015                1020

Glu Asn  Tyr Ser Val Val Ser  Trp Val Pro Lys Glu  Gly Gln Cys
    1025                1030                1035

Asn Phe  Arg Phe His Ile Leu  Phe Lys Ala Leu Gly  Glu Glu Lys
    1040                1045                1050

Gly Gly  Ala Ser Leu Ser Pro  Gln Tyr Val Ser Tyr  Asn Gln Ser
    1055                1060                1065

Ser Tyr  Thr Gln Trp Asp Leu  Gln Pro Asp Thr Asp  Tyr Glu Ile
    1070                1075                1080

His Leu  Phe Lys Glu Arg Met  Phe Arg His Gln Met  Ala Val Lys
    1085                1090                1095
```

```
Thr Asn  Gly Thr Gly Arg Val  Arg Leu Pro Pro Ala  Gly Phe Ala
    1100                 1105                 1110

Thr Glu  Gly Trp Phe Ile Gly  Phe Val Ser Ala Ile  Ile Leu Leu
    1115                 1120                 1125

Leu Leu  Val Leu Leu Ile Leu  Cys Phe Ile Lys Arg  Ser Lys Gly
    1130                 1135                 1140

Gly Lys  Tyr Ser Val Lys Asp  Lys Glu Asp Thr Gln  Val Asp Ser
    1145                 1150                 1155

Glu Ala  Arg Pro Met Lys Asp  Glu Thr Phe Gly Glu  Tyr Ser Asp
    1160                 1165                 1170

Asn Glu  Glu Lys Ala Phe Gly  Ser Ser Gln Pro Ser  Leu Asn Gly
    1175                 1180                 1185

Asp Ile  Lys Pro Leu Gly Ser  Asp Asp Ser Leu Ala  Asp Tyr Gly
    1190                 1195                 1200

Gly Ser  Val Asp Val Gln Phe  Asn Glu Asp Gly Ser  Phe Ile Gly
    1205                 1210                 1215

Gln Tyr  Ser Gly Lys Lys Glu  Lys Glu Ala Ala Gly  Gly Asn Asp
    1220                 1225                 1230

Ser Ser  Gly Ala Thr Ser Pro  Ile Asn Pro Ala Val  Ala Leu Glu
    1235                 1240                 1245


<210> SEQ ID NO 242
<211> LENGTH: 769
<212> TYPE: PRT
<213> ORGANISM: Homo sapiens

<400> SEQUENCE: 242

Met Leu Gly Leu Arg Pro Pro Leu Leu Ala Leu Val Gly Leu Leu Ser
1               5                   10                  15

Leu Gly Cys Val Leu Ser Gln Glu Cys Thr Lys Phe Lys Val Ser Ser
            20                  25                  30

Cys Arg Glu Cys Ile Glu Ser Gly Pro Gly Cys Thr Trp Cys Gln Lys
        35                  40                  45

Leu Asn Phe Thr Gly Pro Gly Asp Pro Asp Ser Ile Arg Cys Asp Thr
    50                  55                  60

Arg Pro Gln Leu Leu Met Arg Gly Cys Ala Ala Asp Asp Ile Met Asp
65                  70                  75                  80

Pro Thr Ser Leu Ala Glu Thr Gln Glu Asp His Asn Gly Gly Gln Lys
                85                  90                  95

Gln Leu Ser Pro Gln Lys Val Thr Leu Tyr Leu Arg Pro Gly Gln Ala
            100                 105                 110

Ala Ala Phe Asn Val Thr Phe Arg Arg Ala Lys Gly Tyr Pro Ile Asp
        115                 120                 125

Leu Tyr Tyr Leu Met Asp Leu Ser Tyr Ser Met Leu Asp Asp Leu Arg
    130                 135                 140

Asn Val Lys Lys Leu Gly Gly Asp Leu Leu Arg Ala Leu Asn Glu Ile
145                 150                 155                 160

Thr Glu Ser Gly Arg Ile Gly Phe Gly Ser Phe Val Asp Lys Thr Val
                165                 170                 175

Leu Pro Phe Val Asn Thr His Pro Asp Lys Leu Arg Asn Pro Cys Pro
            180                 185                 190

Asn Lys Glu Lys Glu Cys Gln Pro Pro Phe Ala Phe Arg His Val Leu
        195                 200                 205

Lys Leu Thr Asn Asn Ser Asn Gln Phe Gln Thr Glu Val Gly Lys Gln
    210                 215                 220
```

```
Leu Ile Ser Gly Asn Leu Asp Ala Pro Glu Gly Gly Leu Asp Ala Met
225                 230                 235                 240

Met Gln Val Ala Ala Cys Pro Glu Glu Ile Gly Trp Arg Asn Val Thr
                245                 250                 255

Arg Leu Leu Val Phe Ala Thr Asp Asp Gly Phe His Phe Ala Gly Asp
            260                 265                 270

Gly Lys Leu Gly Ala Ile Leu Thr Pro Asn Asp Gly Arg Cys His Leu
        275                 280                 285

Glu Asp Asn Leu Tyr Lys Arg Ser Asn Glu Phe Asp Tyr Pro Ser Val
    290                 295                 300

Gly Gln Leu Ala His Lys Leu Ala Glu Asn Asn Ile Gln Pro Ile Phe
305                 310                 315                 320

Ala Val Thr Ser Arg Met Val Lys Thr Tyr Glu Lys Leu Thr Glu Ile
                325                 330                 335

Ile Pro Lys Ser Ala Val Gly Glu Leu Ser Glu Asp Ser Ser Asn Val
            340                 345                 350

Val His Leu Ile Lys Asn Ala Tyr Asn Lys Leu Ser Ser Arg Val Phe
        355                 360                 365

Leu Asp His Asn Ala Leu Pro Asp Thr Leu Lys Val Thr Tyr Asp Ser
    370                 375                 380

Phe Cys Ser Asn Gly Val Thr His Arg Asn Gln Pro Arg Gly Asp Cys
385                 390                 395                 400

Asp Gly Val Gln Ile Asn Val Pro Ile Thr Phe Gln Val Lys Val Thr
                405                 410                 415

Ala Thr Glu Cys Ile Gln Glu Gln Ser Phe Val Ile Arg Ala Leu Gly
            420                 425                 430

Phe Thr Asp Ile Val Thr Val Gln Val Leu Pro Gln Cys Glu Cys Arg
        435                 440                 445

Cys Arg Asp Gln Ser Arg Asp Arg Ser Leu Cys His Gly Lys Gly Phe
    450                 455                 460

Leu Glu Cys Gly Ile Cys Arg Cys Asp Thr Gly Tyr Ile Gly Lys Asn
465                 470                 475                 480

Cys Glu Cys Gln Thr Gln Gly Arg Ser Ser Gln Glu Leu Glu Gly Ser
                485                 490                 495

Cys Arg Lys Asp Asn Asn Ser Ile Ile Cys Ser Gly Leu Gly Asp Cys
            500                 505                 510

Val Cys Gly Gln Cys Leu Cys His Thr Ser Asp Val Pro Gly Lys Leu
        515                 520                 525

Ile Tyr Gly Gln Tyr Cys Glu Cys Asp Thr Ile Asn Cys Glu Arg Tyr
    530                 535                 540

Asn Gly Gln Val Cys Gly Gly Pro Gly Arg Gly Leu Cys Phe Cys Gly
545                 550                 555                 560

Lys Cys Arg Cys His Pro Gly Phe Glu Gly Ser Ala Cys Gln Cys Glu
                565                 570                 575

Arg Thr Thr Glu Gly Cys Leu Asn Pro Arg Arg Val Glu Cys Ser Gly
            580                 585                 590

Arg Gly Arg Cys Arg Cys Asn Val Cys Glu Cys His Ser Gly Tyr Gln
        595                 600                 605

Leu Pro Leu Cys Gln Glu Cys Pro Gly Cys Pro Ser Pro Cys Gly Lys
    610                 615                 620

Tyr Ile Ser Cys Ala Glu Cys Leu Lys Phe Glu Lys Gly Pro Phe Gly
625                 630                 635                 640
```

```
Lys Asn Cys Ser Ala Ala Cys Pro Gly Leu Gln Leu Ser Asn Asn Pro
                645                 650                 655

Val Lys Gly Arg Thr Cys Lys Glu Arg Asp Ser Glu Gly Cys Trp Val
            660                 665                 670

Ala Tyr Thr Leu Glu Gln Gln Asp Gly Met Asp Arg Tyr Leu Ile Tyr
        675                 680                 685

Val Asp Glu Ser Arg Glu Cys Val Ala Gly Pro Asn Ile Ala Ala Ile
    690                 695                 700

Val Gly Gly Thr Val Ala Gly Ile Val Leu Ile Gly Ile Leu Leu Leu
705                 710                 715                 720

Val Ile Trp Lys Ala Leu Ile His Leu Ser Asp Leu Arg Glu Tyr Arg
                725                 730                 735

Arg Phe Glu Lys Glu Lys Leu Lys Ser Gln Trp Asn Asn Asp Asn Pro
            740                 745                 750

Leu Phe Lys Ser Ala Thr Thr Thr Val Met Asn Pro Lys Phe Ala Glu
        755                 760                 765

Ser


<210> SEQ ID NO 243
<211> LENGTH: 585
<212> TYPE: PRT
<213> ORGANISM: Homo sapiens

<400> SEQUENCE: 243

Met Thr Pro Pro Arg Leu Phe Trp Val Trp Leu Leu Val Ala Gly Thr
1               5                   10                  15

Gln Gly Val Asn Asp Gly Asp Met Arg Leu Ala Asp Gly Gly Ala Thr
            20                  25                  30

Asn Gln Gly Arg Val Glu Ile Phe Tyr Arg Gly Gln Trp Gly Thr Val
        35                  40                  45

Cys Asp Asn Leu Trp Asp Leu Thr Asp Ala Ser Val Val Cys Arg Ala
    50                  55                  60

Leu Gly Phe Glu Asn Ala Thr Gln Ala Leu Gly Arg Ala Ala Phe Gly
65                  70                  75                  80

Gln Gly Ser Gly Pro Ile Met Leu Asp Glu Val Gln Cys Thr Gly Thr
                85                  90                  95

Glu Ala Ser Leu Ala Asp Cys Lys Ser Leu Gly Trp Leu Lys Ser Asn
            100                 105                 110

Cys Arg His Glu Arg Asp Ala Gly Val Val Cys Thr Asn Glu Thr Arg
        115                 120                 125

Ser Thr His Thr Leu Asp Leu Ser Arg Glu Leu Ser Glu Ala Leu Gly
    130                 135                 140

Gln Ile Phe Asp Ser Gln Arg Gly Cys Asp Leu Ser Ile Ser Val Asn
145                 150                 155                 160

Val Gln Gly Glu Asp Ala Leu Gly Phe Cys Gly His Thr Val Ile Leu
                165                 170                 175

Thr Ala Asn Leu Glu Ala Gln Ala Leu Trp Lys Glu Pro Gly Ser Asn
            180                 185                 190

Val Thr Met Ser Val Asp Ala Glu Cys Val Pro Met Val Arg Asp Leu
        195                 200                 205

Leu Arg Tyr Phe Tyr Ser Arg Arg Ile Asp Ile Thr Leu Ser Ser Val
    210                 215                 220

Lys Cys Phe His Lys Leu Ala Ser Ala Tyr Gly Ala Arg Gln Leu Gln
225                 230                 235                 240
```

Gly Tyr Cys Ala Ser Leu Phe Ala Ile Leu Leu Pro Gln Asp Pro Ser
245 250 255

Phe Gln Met Pro Leu Asp Leu Tyr Ala Tyr Ala Val Ala Thr Gly Asp
260 265 270

Ala Leu Leu Glu Lys Leu Cys Leu Gln Phe Leu Ala Trp Asn Phe Glu
275 280 285

Ala Leu Thr Gln Ala Glu Ala Trp Pro Ser Val Pro Thr Asp Leu Leu
290 295 300

Gln Leu Leu Leu Pro Arg Ser Asp Leu Ala Val Pro Ser Glu Leu Ala
305 310 315 320

Leu Leu Lys Ala Val Asp Thr Trp Ser Trp Gly Glu Arg Ala Ser His
325 330 335

Glu Glu Val Glu Gly Leu Val Glu Lys Ile Arg Phe Pro Met Met Leu
340 345 350

Pro Glu Glu Leu Phe Glu Leu Gln Phe Asn Leu Ser Leu Tyr Trp Ser
355 360 365

His Glu Ala Leu Phe Gln Lys Lys Thr Leu Gln Ala Leu Glu Phe His
370 375 380

Thr Val Pro Phe Gln Leu Leu Ala Arg Tyr Lys Gly Leu Asn Leu Thr
385 390 395 400

Glu Asp Thr Tyr Lys Pro Arg Ile Tyr Thr Ser Pro Thr Trp Ser Ala
405 410 415

Phe Val Thr Asp Ser Ser Trp Ser Ala Arg Lys Ser Gln Leu Val Tyr
420 425 430

Gln Ser Arg Arg Gly Pro Leu Val Lys Tyr Ser Ser Asp Tyr Phe Gln
435 440 445

Ala Pro Ser Asp Tyr Arg Tyr Tyr Pro Tyr Gln Ser Phe Gln Thr Pro
450 455 460

Gln His Pro Ser Phe Leu Phe Gln Asp Lys Arg Val Ser Trp Ser Leu
465 470 475 480

Val Tyr Leu Pro Thr Ile Gln Ser Cys Trp Asn Tyr Gly Phe Ser Cys
485 490 495

Ser Ser Asp Glu Leu Pro Val Leu Gly Leu Thr Lys Ser Gly Gly Ser
500 505 510

Asp Arg Thr Ile Ala Tyr Glu Asn Lys Ala Leu Met Leu Cys Glu Gly
515 520 525

Leu Phe Val Ala Asp Val Thr Asp Phe Glu Gly Trp Lys Ala Ala Ile
530 535 540

Pro Ser Ala Leu Asp Thr Asn Ser Ser Lys Ser Thr Ser Ser Phe Pro
545 550 555 560

Cys Pro Ala Gly His Phe Asn Gly Phe Arg Thr Val Ile Arg Pro Phe
565 570 575

Tyr Leu Thr Asn Ser Ser Gly Val Asp
580 585

<210> SEQ ID NO 244
<211> LENGTH: 343
<212> TYPE: PRT
<213> ORGANISM: Homo sapiens

<400> SEQUENCE: 244

Met Pro Arg Pro Arg Leu Leu Ala Ala Leu Cys Gly Ala Leu Leu Cys
1 5 10 15

Ala Pro Ser Leu Leu Val Ala Leu Glu Cys Val Glu Pro Leu Gly Leu
20 25 30

-continued

```
Glu Asn Gly Asn Ile Ala Asn Ser Gln Ile Ala Ala Ser Ser Val Arg
        35                  40                  45

Val Thr Phe Leu Gly Leu Gln His Trp Val Pro Glu Leu Ala Arg Leu
    50                  55                  60

Asn Arg Ala Gly Met Val Asn Ala Trp Thr Pro Ser Ser Asn Asp Asp
65                  70                  75                  80

Asn Pro Trp Ile Gln Val Asn Leu Leu Arg Arg Met Trp Val Thr Gly
                85                  90                  95

Val Val Thr Gln Gly Ala Ser Arg Leu Ala Ser His Glu Tyr Leu Lys
            100                 105                 110

Ala Phe Lys Val Ala Tyr Ser Leu Asn Gly His Glu Phe Asp Phe Ile
        115                 120                 125

His Asp Val Asn Lys Lys His Lys Glu Phe Val Gly Asn Trp Asn Lys
    130                 135                 140

Asn Ala Val His Val Asn Leu Phe Glu Thr Pro Val Glu Ala Gln Tyr
145                 150                 155                 160

Val Arg Leu Tyr Pro Thr Ser Cys His Thr Ala Cys Thr Leu Arg Phe
                165                 170                 175

Glu Leu Leu Gly Cys Glu Leu Asn Gly Cys Ala Asn Pro Leu Gly Leu
            180                 185                 190

Lys Asn Asn Ser Ile Pro Asp Lys Gln Ile Thr Ala Ser Ser Ser Tyr
        195                 200                 205

Lys Thr Trp Gly Leu His Leu Phe Ser Trp Asn Pro Ser Tyr Ala Arg
    210                 215                 220

Leu Asp Lys Gln Gly Asn Phe Asn Ala Trp Val Ala Gly Ser Tyr Gly
225                 230                 235                 240

Asn Asp Gln Trp Leu Gln Val Asp Leu Gly Ser Ser Lys Glu Val Thr
                245                 250                 255

Gly Ile Ile Thr Gln Gly Ala Arg Asn Phe Gly Ser Val Gln Phe Val
            260                 265                 270

Ala Ser Tyr Lys Val Ala Tyr Ser Asn Asp Ser Ala Asn Trp Thr Glu
        275                 280                 285

Tyr Gln Asp Pro Arg Thr Gly Ser Ser Lys Ile Phe Pro Gly Asn Trp
    290                 295                 300

Asp Asn His Ser His Lys Lys Asn Leu Phe Glu Thr Pro Ile Leu Ala
305                 310                 315                 320

Arg Tyr Val Arg Ile Leu Pro Val Ala Trp His Asn Arg Ile Ala Leu
                325                 330                 335

Arg Leu Glu Leu Leu Gly Cys
            340
```

<210> SEQ ID NO 245
<211> LENGTH: 1525
<212> TYPE: PRT
<213> ORGANISM: Homo sapiens

<400> SEQUENCE: 245

```
Met Arg Gly Val Gly Trp Gln Met Leu Ser Leu Ser Leu Gly Leu Val
1               5                   10                  15

Leu Ala Ile Leu Asn Lys Val Ala Pro Gln Ala Cys Pro Ala Gln Cys
            20                  25                  30

Ser Cys Ser Gly Ser Thr Val Asp Cys His Gly Leu Ala Leu Arg Ser
        35                  40                  45

Val Pro Arg Asn Ile Pro Arg Asn Thr Glu Arg Leu Asp Leu Asn Gly
```

-continued

```
    50                  55                  60

Asn Asn Ile Thr Arg Ile Thr Lys Thr Asp Phe Ala Gly Leu Arg His
65                  70                  75                  80

Leu Arg Val Leu Gln Leu Met Glu Asn Lys Ile Ser Thr Ile Glu Arg
                85                  90                  95

Gly Ala Phe Gln Asp Leu Lys Glu Leu Glu Arg Leu Arg Leu Asn Arg
            100                 105                 110

Asn His Leu Gln Leu Phe Pro Glu Leu Leu Phe Leu Gly Thr Ala Lys
        115                 120                 125

Leu Tyr Arg Leu Asp Leu Ser Glu Asn Gln Ile Gln Ala Ile Pro Arg
    130                 135                 140

Lys Ala Phe Arg Gly Ala Val Asp Ile Lys Asn Leu Gln Leu Asp Tyr
145                 150                 155                 160

Asn Gln Ile Ser Cys Ile Glu Asp Gly Ala Phe Arg Ala Leu Arg Asp
                165                 170                 175

Leu Glu Val Leu Thr Leu Asn Asn Asn Asn Ile Thr Arg Leu Ser Val
            180                 185                 190

Ala Ser Phe Asn His Met Pro Lys Leu Arg Thr Phe Arg Leu His Ser
        195                 200                 205

Asn Asn Leu Tyr Cys Asp Cys His Leu Ala Trp Leu Ser Asp Trp Leu
    210                 215                 220

Arg Gln Arg Pro Arg Val Gly Leu Tyr Thr Gln Cys Met Gly Pro Ser
225                 230                 235                 240

His Leu Arg Gly His Asn Val Ala Glu Val Gln Lys Arg Glu Phe Val
                245                 250                 255

Cys Ser Asp Glu Glu Glu Gly His Gln Ser Phe Met Ala Pro Ser Cys
            260                 265                 270

Ser Val Leu His Cys Pro Ala Ala Cys Thr Cys Ser Asn Asn Ile Val
        275                 280                 285

Asp Cys Arg Gly Lys Gly Leu Thr Glu Ile Pro Thr Asn Leu Pro Glu
    290                 295                 300

Thr Ile Thr Glu Ile Arg Leu Glu Gln Asn Thr Ile Lys Val Ile Pro
305                 310                 315                 320

Pro Gly Ala Phe Ser Pro Tyr Lys Lys Leu Arg Arg Ile Asp Leu Ser
                325                 330                 335

Asn Asn Gln Ile Ser Glu Leu Ala Pro Asp Ala Phe Gln Gly Leu Arg
            340                 345                 350

Ser Leu Asn Ser Leu Val Leu Tyr Gly Asn Lys Ile Thr Glu Leu Pro
        355                 360                 365

Lys Ser Leu Phe Glu Gly Leu Phe Ser Leu Gln Leu Leu Leu Leu Asn
    370                 375                 380

Ala Asn Lys Ile Asn Cys Leu Arg Val Asp Ala Phe Gln Asp Leu His
385                 390                 395                 400

Asn Leu Asn Leu Leu Ser Leu Tyr Asp Asn Lys Leu Gln Thr Ile Ala
                405                 410                 415

Lys Gly Thr Phe Ser Pro Leu Arg Ala Ile Gln Thr Met His Leu Ala
            420                 425                 430

Gln Asn Pro Phe Ile Cys Asp Cys His Leu Lys Trp Leu Ala Asp Tyr
        435                 440                 445

Leu His Thr Asn Pro Ile Glu Thr Ser Gly Ala Arg Cys Thr Ser Pro
    450                 455                 460

Arg Arg Leu Ala Asn Lys Arg Ile Gly Gln Ile Lys Ser Lys Lys Phe
465                 470                 475                 480
```

-continued

```
Arg Cys Ser Gly Thr Glu Asp Tyr Arg Ser Lys Leu Ser Gly Asp Cys
                485                 490                 495

Phe Ala Asp Leu Ala Cys Pro Glu Lys Cys Arg Cys Glu Gly Thr Thr
            500                 505                 510

Val Asp Cys Ser Asn Gln Lys Leu Asn Lys Ile Pro Glu His Ile Pro
        515                 520                 525

Gln Tyr Thr Ala Glu Leu Arg Leu Asn Asn Asn Glu Phe Thr Val Leu
    530                 535                 540

Glu Ala Thr Gly Ile Phe Lys Lys Leu Pro Gln Leu Arg Lys Ile Asn
545                 550                 555                 560

Phe Ser Asn Asn Lys Ile Thr Asp Ile Glu Glu Gly Ala Phe Glu Gly
                565                 570                 575

Ala Ser Gly Val Asn Glu Ile Leu Leu Thr Ser Asn Arg Leu Glu Asn
            580                 585                 590

Val Gln His Lys Met Phe Lys Gly Leu Glu Ser Leu Lys Thr Leu Met
        595                 600                 605

Leu Arg Ser Asn Arg Ile Thr Cys Val Gly Asn Asp Ser Phe Ile Gly
    610                 615                 620

Leu Ser Ser Val Arg Leu Leu Ser Leu Tyr Asp Asn Gln Ile Thr Thr
625                 630                 635                 640

Val Ala Pro Gly Ala Phe Asp Thr Leu His Ser Leu Ser Thr Leu Asn
                645                 650                 655

Leu Leu Ala Asn Pro Phe Asn Cys Asn Cys Tyr Leu Ala Trp Leu Gly
            660                 665                 670

Glu Trp Leu Arg Lys Lys Arg Ile Val Thr Gly Asn Pro Arg Cys Gln
        675                 680                 685

Lys Pro Tyr Phe Leu Lys Glu Ile Pro Ile Gln Asp Val Ala Ile Gln
    690                 695                 700

Asp Phe Thr Cys Asp Asp Gly Asn Asp Asp Asn Ser Cys Ser Pro Leu
705                 710                 715                 720

Ser Arg Cys Pro Thr Glu Cys Thr Cys Leu Asp Thr Val Val Arg Cys
                725                 730                 735

Ser Asn Lys Gly Leu Lys Val Leu Pro Lys Gly Ile Pro Arg Asp Val
            740                 745                 750

Thr Glu Leu Tyr Leu Asp Gly Asn Gln Phe Thr Leu Val Pro Lys Glu
        755                 760                 765

Leu Ser Asn Tyr Lys His Leu Thr Leu Ile Asp Leu Ser Asn Asn Arg
    770                 775                 780

Ile Ser Thr Leu Ser Asn Gln Ser Phe Ser Asn Met Thr Gln Leu Leu
785                 790                 795                 800

Thr Leu Ile Leu Ser Tyr Asn Arg Leu Arg Cys Ile Pro Pro Arg Thr
                805                 810                 815

Phe Asp Gly Leu Lys Ser Leu Arg Leu Leu Ser Leu His Gly Asn Asp
            820                 825                 830

Ile Ser Val Val Pro Glu Gly Ala Phe Asn Asp Leu Ser Ala Leu Ser
        835                 840                 845

His Leu Ala Ile Gly Ala Asn Pro Leu Tyr Cys Asp Cys Asn Met Gln
    850                 855                 860

Trp Leu Ser Asp Trp Val Lys Ser Glu Tyr Lys Glu Pro Gly Ile Ala
865                 870                 875                 880

Arg Cys Ala Gly Pro Gly Glu Met Ala Asp Lys Leu Leu Leu Thr Thr
                885                 890                 895
```

-continued

```
Pro Ser Lys Lys Phe Thr Cys Gln Gly Pro Val Asp Val Asn Ile Leu
            900                 905                 910

Ala Lys Cys Asn Pro Cys Leu Ser Asn Pro Cys Lys Asn Asp Gly Thr
        915                 920                 925

Cys Asn Ser Asp Pro Val Asp Phe Tyr Arg Cys Thr Cys Pro Tyr Gly
    930                 935                 940

Phe Lys Gly Gln Asp Cys Asp Val Pro Ile His Ala Cys Ile Ser Asn
945                 950                 955                 960

Pro Cys Lys His Gly Gly Thr Cys His Leu Lys Glu Gly Glu Glu Asp
                965                 970                 975

Gly Phe Trp Cys Ile Cys Ala Asp Gly Phe Glu Gly Glu Asn Cys Glu
            980                 985                 990

Val Asn Val Asp Asp Cys Glu Asp  Asn Asp Cys Glu Asn  Asn Ser Thr
        995                 1000                1005

Cys Val  Asp Gly Ile Asn Asn  Tyr Thr Cys Leu Cys  Pro Pro Glu
    1010                1015                1020

Tyr Thr  Gly Glu Leu Cys Glu  Glu Lys Leu Asp Phe  Cys Ala Gln
    1025                1030                1035

Asp Leu  Asn Pro Cys Gln His  Asp Ser Lys Cys Ile  Leu Thr Pro
    1040                1045                1050

Lys Gly  Phe Lys Cys Asp Cys  Thr Pro Gly Tyr Val  Gly Glu His
    1055                1060                1065

Cys Asp  Ile Asp Phe Asp Asp  Cys Gln Asp Asn Lys  Cys Lys Asn
    1070                1075                1080

Gly Ala  His Cys Thr Asp Ala  Val Asn Gly Tyr Thr  Cys Ile Cys
    1085                1090                1095

Pro Glu  Gly Tyr Ser Gly Leu  Phe Cys Glu Phe Ser  Pro Pro Met
    1100                1105                1110

Val Leu  Pro Arg Thr Ser Pro  Cys Asp Asn Phe Asp  Cys Gln Asn
    1115                1120                1125

Gly Ala  Gln Cys Ile Val Arg  Ile Asn Glu Pro Ile  Cys Gln Cys
    1130                1135                1140

Leu Pro  Gly Tyr Gln Gly Glu  Lys Cys Glu Lys Leu  Val Ser Val
    1145                1150                1155

Asn Phe  Ile Asn Lys Glu Ser  Tyr Leu Gln Ile Pro  Ser Ala Lys
    1160                1165                1170

Val Arg  Pro Gln Thr Asn Ile  Thr Leu Gln Ile Ala  Thr Asp Glu
    1175                1180                1185

Asp Ser  Gly Ile Leu Leu Tyr  Lys Gly Asp Lys Asp  His Ile Ala
    1190                1195                1200

Val Glu  Leu Tyr Arg Gly Arg  Val Arg Ala Ser Tyr  Asp Thr Gly
    1205                1210                1215

Ser His  Pro Ala Ser Ala Ile  Tyr Ser Val Glu Thr  Ile Asn Asp
    1220                1225                1230

Gly Asn  Phe His Ile Val Glu  Leu Leu Ala Leu Asp  Gln Ser Leu
    1235                1240                1245

Ser Leu  Ser Val Asp Gly Gly  Asn Pro Lys Ile Ile  Thr Asn Leu
    1250                1255                1260

Ser Lys  Gln Ser Thr Leu Asn  Phe Asp Ser Pro Leu  Tyr Val Gly
    1265                1270                1275

Gly Met  Pro Gly Lys Ser Asn  Val Ala Ser Leu Arg  Gln Ala Pro
    1280                1285                1290

Gly Gln  Asn Gly Thr Ser Phe  His Gly Cys Ile Arg  Asn Leu Tyr
```

```
    1295                1300                1305

Ile Asn  Ser Glu Leu Gln Asp  Phe Gln Lys Val Pro  Met Gln Thr
    1310                1315                1320

Gly Ile  Leu Pro Gly Cys Glu  Pro Cys His Lys Lys  Val Cys Ala
    1325                1330                1335

His Gly  Thr Cys Gln Pro Ser  Ser Gln Ala Gly Phe  Thr Cys Glu
    1340                1345                1350

Cys Gln  Glu Gly Trp Met Gly  Pro Leu Cys Asp Gln  Arg Thr Asn
    1355                1360                1365

Asp Pro  Cys Leu Gly Asn Lys  Cys Val His Gly Thr  Cys Leu Pro
    1370                1375                1380

Ile Asn  Ala Phe Ser Tyr Ser  Cys Lys Cys Leu Glu  Gly His Gly
    1385                1390                1395

Gly Val  Leu Cys Asp Glu Glu  Glu Asp Leu Phe Asn  Pro Cys Gln
    1400                1405                1410

Ala Ile  Lys Cys Lys His Gly  Lys Cys Arg Leu Ser  Gly Leu Gly
    1415                1420                1425

Gln Pro  Tyr Cys Glu Cys Ser  Ser Gly Tyr Thr Gly  Asp Ser Cys
    1430                1435                1440

Asp Arg  Glu Ile Ser Cys Arg  Gly Glu Arg Ile Arg  Asp Tyr Tyr
    1445                1450                1455

Gln Lys  Gln Gln Gly Tyr Ala  Ala Cys Gln Thr Thr  Lys Lys Val
    1460                1465                1470

Ser Arg  Leu Glu Cys Arg Gly  Gly Cys Ala Gly Gly  Gln Cys Cys
    1475                1480                1485

Gly Pro  Leu Arg Ser Lys Arg  Arg Lys Tyr Ser Phe  Glu Cys Thr
    1490                1495                1500

Asp Gly  Ser Ser Phe Val Asp  Glu Val Glu Lys Val  Val Lys Cys
    1505                1510                1515

Gly Cys  Thr Arg Cys Val Ser
    1520                1525


<210> SEQ ID NO 246
<211> LENGTH: 289
<212> TYPE: PRT
<213> ORGANISM: Homo sapiens

<400> SEQUENCE: 246

Met Lys Asp Arg Leu Glu Gln Leu Lys Ala Lys Gln Leu Thr Gln Asp
1               5                   10                  15

Asp Asp Thr Asp Ala Val Glu Ile Ala Ile Asp Asn Thr Ala Phe Met
            20                  25                  30

Asp Glu Phe Phe Ser Glu Ile Glu Glu Thr Arg Leu Asn Ile Asp Lys
        35                  40                  45

Ile Ser Glu His Val Glu Glu Ala Lys Lys Leu Tyr Ser Ile Ile Leu
    50                  55                  60

Ser Ala Pro Ile Pro Glu Pro Lys Thr Lys Asp Asp Leu Glu Gln Leu
65                  70                  75                  80

Thr Thr Glu Ile Lys Lys Arg Ala Asn Asn Val Arg Asn Lys Leu Lys
                85                  90                  95

Ser Met Glu Lys His Ile Glu Glu Asp Glu Val Arg Ser Ser Ala Asp
            100                 105                 110

Leu Arg Ile Arg Lys Ser Gln His Ser Val Leu Ser Arg Lys Phe Val
        115                 120                 125
```

```
Glu Val Met Thr Lys Tyr Asn Glu Ala Gln Val Asp Phe Arg Glu Arg
    130                 135                 140

Ser Lys Gly Arg Ile Gln Arg Gln Leu Glu Ile Thr Gly Lys Lys Thr
145                 150                 155                 160

Thr Asp Glu Glu Leu Glu Glu Met Leu Glu Ser Gly Asn Pro Ala Ile
                165                 170                 175

Phe Thr Ser Gly Ile Ile Asp Ser Gln Ile Ser Lys Gln Ala Leu Ser
            180                 185                 190

Glu Ile Glu Gly Arg His Lys Asp Ile Val Arg Leu Glu Ser Ser Ile
        195                 200                 205

Lys Glu Leu His Asp Met Phe Met Asp Ile Ala Met Leu Val Glu Asn
    210                 215                 220

Gln Gly Glu Met Leu Asp Asn Ile Glu Leu Asn Val Met His Thr Val
225                 230                 235                 240

Asp His Val Glu Lys Ala Arg Asp Glu Thr Lys Lys Ala Val Lys Tyr
                245                 250                 255

Gln Ser Gln Ala Arg Lys Lys Leu Ile Ile Ile Ile Val Leu Val Val
            260                 265                 270

Val Leu Leu Gly Ile Leu Ala Leu Ile Ile Gly Leu Ser Val Gly Leu
        275                 280                 285

Asn


<210> SEQ ID NO 247
<211> LENGTH: 524
<212> TYPE: PRT
<213> ORGANISM: Homo sapiens

<400> SEQUENCE: 247

Met Cys Pro Arg Ala Ala Arg Ala Pro Ala Thr Leu Leu Leu Ala Leu
1               5                   10                  15

Gly Ala Val Leu Trp Pro Ala Ala Gly Ala Trp Glu Leu Thr Ile Leu
            20                  25                  30

His Thr Asn Asp Val His Ser Arg Leu Glu Gln Thr Ser Glu Asp Ser
        35                  40                  45

Ser Lys Cys Val Asn Ala Ser Arg Cys Met Gly Gly Val Ala Arg Leu
    50                  55                  60

Phe Thr Lys Val Gln Gln Ile Arg Arg Ala Glu Pro Asn Val Leu Leu
65                  70                  75                  80

Leu Asp Ala Gly Asp Gln Tyr Gln Gly Thr Ile Trp Phe Thr Val Tyr
                85                  90                  95

Lys Gly Ala Glu Val Ala His Phe Met Asn Ala Leu Arg Tyr Asp Ala
            100                 105                 110

Met Ala Leu Gly Asn His Glu Phe Asp Asn Gly Val Glu Gly Leu Ile
        115                 120                 125

Glu Pro Leu Leu Lys Glu Ala Lys Phe Pro Ile Leu Ser Ala Asn Ile
    130                 135                 140

Lys Ala Lys Gly Pro Leu Ala Ser Gln Ile Ser Gly Leu Tyr Leu Pro
145                 150                 155                 160

Tyr Lys Val Leu Pro Val Gly Asp Glu Val Val Gly Ile Val Gly Tyr
                165                 170                 175

Thr Ser Lys Glu Thr Pro Phe Leu Ser Asn Pro Gly Thr Asn Leu Val
            180                 185                 190

Phe Glu Asp Glu Ile Thr Ala Leu Gln Pro Glu Val Asp Lys Leu Lys
        195                 200                 205
```

-continued

```
Thr Leu Asn Val Asn Lys Ile Ile Ala Leu Gly His Ser Gly Phe Glu
    210                 215                 220

Met Asp Lys Leu Ile Ala Gln Lys Val Arg Gly Val Asp Val Val Val
225                 230                 235                 240

Gly Gly His Ser Asn Thr Phe Leu Tyr Thr Gly Asn Pro Pro Ser Lys
                245                 250                 255

Glu Val Pro Ala Gly Lys Tyr Pro Phe Ile Val Thr Ser Asp Asp Gly
            260                 265                 270

Arg Lys Val Pro Val Val Gln Ala Tyr Ala Phe Gly Lys Tyr Leu Gly
        275                 280                 285

Tyr Leu Lys Ile Glu Phe Asp Glu Arg Gly Asn Val Ile Ser Ser His
    290                 295                 300

Gly Asn Pro Ile Leu Leu Asn Ser Ser Ile Pro Glu Asp Pro Ser Ile
305                 310                 315                 320

Lys Ala Asp Ile Asn Lys Trp Arg Ile Lys Leu Asp Asn Tyr Ser Thr
                325                 330                 335

Gln Glu Leu Gly Lys Thr Ile Val Tyr Leu Asp Gly Ser Ser Gln Ser
            340                 345                 350

Cys Arg Phe Arg Glu Cys Asn Met Gly Asn Leu Ile Cys Asp Ala Met
        355                 360                 365

Ile Asn Asn Asn Leu Arg His Thr Asp Glu Met Phe Trp Asn His Val
    370                 375                 380

Ser Met Cys Ile Leu Asn Gly Gly Gly Ile Arg Ser Pro Ile Asp Glu
385                 390                 395                 400

Arg Asn Asn Gly Ile His Val Val Tyr Asp Leu Ser Arg Lys Pro Gly
                405                 410                 415

Asp Arg Val Val Lys Leu Asp Val Leu Cys Thr Lys Cys Arg Val Pro
            420                 425                 430

Ser Tyr Asp Pro Leu Lys Met Asp Glu Val Tyr Lys Val Ile Leu Pro
        435                 440                 445

Asn Phe Leu Ala Asn Gly Gly Asp Gly Phe Gln Met Ile Lys Asp Glu
    450                 455                 460

Leu Leu Arg His Asp Ser Gly Asp Gln Asp Ile Asn Val Val Ser Thr
465                 470                 475                 480

Tyr Ile Ser Lys Met Lys Val Ile Tyr Pro Ala Val Glu Gly Arg Ile
                485                 490                 495

Lys Phe Ser Thr Gly Ser His Cys His Gly Ser Phe Ser Leu Ile Phe
            500                 505                 510

Leu Ser Leu Trp Ala Val Ile Phe Val Leu Tyr Gln
        515                 520
```

<210> SEQ ID NO 248
<211> LENGTH: 161
<212> TYPE: PRT
<213> ORGANISM: Homo sapiens

<400> SEQUENCE: 248

```
Met Asn Leu Ala Ile Ser Ile Ala Leu Leu Leu Thr Val Leu Gln Val
1               5                   10                  15

Ser Arg Gly Gln Lys Val Thr Ser Leu Thr Ala Cys Leu Val Asp Gln
            20                  25                  30

Ser Leu Arg Leu Asp Cys Arg His Glu Asn Thr Ser Ser Ser Pro Ile
        35                  40                  45

Gln Tyr Glu Phe Ser Leu Thr Arg Glu Thr Lys Lys His Val Leu Phe
    50                  55                  60
```

```
Gly Thr Val Gly Val Pro Glu His Thr Tyr Arg Ser Arg Thr Asn Phe
65                  70                  75                  80

Thr Ser Lys Tyr Asn Met Lys Val Leu Tyr Leu Ser Ala Phe Thr Ser
                85                  90                  95

Lys Asp Glu Gly Thr Tyr Thr Cys Ala Leu His His Ser Gly His Ser
            100                 105                 110

Pro Pro Ile Ser Ser Gln Asn Val Thr Val Leu Arg Asp Lys Leu Val
        115                 120                 125

Lys Cys Glu Gly Ile Ser Leu Leu Ala Gln Asn Thr Ser Trp Leu Leu
    130                 135                 140

Leu Leu Leu Leu Ser Leu Ser Leu Leu Gln Ala Thr Asp Phe Met Ser
145                 150                 155                 160

Leu


<210> SEQ ID NO 249
<211> LENGTH: 798
<212> TYPE: PRT
<213> ORGANISM: Homo sapiens

<400> SEQUENCE: 249

Met Asn Leu Gln Pro Ile Phe Trp Ile Gly Leu Ile Ser Ser Val Cys
1               5                   10                  15

Cys Val Phe Ala Gln Thr Asp Glu Asn Arg Cys Leu Lys Ala Asn Ala
            20                  25                  30

Lys Ser Cys Gly Glu Cys Ile Gln Ala Gly Pro Asn Cys Gly Trp Cys
        35                  40                  45

Thr Asn Ser Thr Phe Leu Gln Glu Gly Met Pro Thr Ser Ala Arg Cys
    50                  55                  60

Asp Asp Leu Glu Ala Leu Lys Lys Lys Gly Cys Pro Pro Asp Asp Ile
65                  70                  75                  80

Glu Asn Pro Arg Gly Ser Lys Asp Ile Lys Lys Asn Lys Asn Val Thr
                85                  90                  95

Asn Arg Ser Lys Gly Thr Ala Glu Lys Leu Lys Pro Glu Asp Ile Thr
            100                 105                 110

Gln Ile Gln Pro Gln Gln Leu Val Leu Arg Leu Arg Ser Gly Glu Pro
        115                 120                 125

Gln Thr Phe Thr Leu Lys Phe Lys Arg Ala Glu Asp Tyr Pro Ile Asp
    130                 135                 140

Leu Tyr Tyr Leu Met Asp Leu Ser Tyr Ser Met Lys Asp Asp Leu Glu
145                 150                 155                 160

Asn Val Lys Ser Leu Gly Thr Asp Leu Met Asn Glu Met Arg Arg Ile
                165                 170                 175

Thr Ser Asp Phe Arg Ile Gly Phe Gly Ser Phe Val Glu Lys Thr Val
            180                 185                 190

Met Pro Tyr Ile Ser Thr Thr Pro Ala Lys Leu Arg Asn Pro Cys Thr
        195                 200                 205

Ser Glu Gln Asn Cys Thr Ser Pro Phe Ser Tyr Lys Asn Val Leu Ser
    210                 215                 220

Leu Thr Asn Lys Gly Glu Val Phe Asn Glu Leu Val Gly Lys Gln Arg
225                 230                 235                 240

Ile Ser Gly Asn Leu Asp Ser Pro Glu Gly Gly Phe Asp Ala Ile Met
                245                 250                 255

Gln Val Ala Val Cys Gly Ser Leu Ile Gly Trp Arg Asn Val Thr Arg
            260                 265                 270
```

-continued

```
Leu Leu Val Phe Ser Thr Asp Ala Gly Phe His Phe Ala Gly Asp Gly
        275                 280                 285

Lys Leu Gly Gly Ile Val Leu Pro Asn Asp Gly Gln Cys His Leu Glu
    290                 295                 300

Asn Asn Met Tyr Thr Met Ser His Tyr Tyr Asp Tyr Pro Ser Ile Ala
305                 310                 315                 320

His Leu Val Gln Lys Leu Ser Glu Asn Asn Ile Gln Thr Ile Phe Ala
                325                 330                 335

Val Thr Glu Glu Phe Gln Pro Val Tyr Lys Glu Leu Lys Asn Leu Ile
            340                 345                 350

Pro Lys Ser Ala Val Gly Thr Leu Ser Ala Asn Ser Ser Asn Val Ile
        355                 360                 365

Gln Leu Ile Ile Asp Ala Tyr Asn Ser Leu Ser Ser Glu Val Ile Leu
    370                 375                 380

Glu Asn Gly Lys Leu Ser Glu Gly Val Thr Ile Ser Tyr Lys Ser Tyr
385                 390                 395                 400

Cys Lys Asn Gly Val Asn Gly Thr Gly Glu Asn Gly Arg Lys Cys Ser
                405                 410                 415

Asn Ile Ser Ile Gly Asp Glu Val Gln Phe Glu Ile Ser Ile Thr Ser
            420                 425                 430

Asn Lys Cys Pro Lys Lys Asp Ser Asp Ser Phe Lys Ile Arg Pro Leu
        435                 440                 445

Gly Phe Thr Glu Glu Val Glu Val Ile Leu Gln Tyr Ile Cys Glu Cys
    450                 455                 460

Glu Cys Gln Ser Glu Gly Ile Pro Glu Ser Pro Lys Cys His Glu Gly
465                 470                 475                 480

Asn Gly Thr Phe Glu Cys Gly Ala Cys Arg Cys Asn Glu Gly Arg Val
                485                 490                 495

Gly Arg His Cys Glu Cys Ser Thr Asp Glu Val Asn Ser Glu Asp Met
            500                 505                 510

Asp Ala Tyr Cys Arg Lys Glu Asn Ser Ser Glu Ile Cys Ser Asn Asn
        515                 520                 525

Gly Glu Cys Val Cys Gly Gln Cys Val Cys Arg Lys Arg Asp Asn Thr
    530                 535                 540

Asn Glu Ile Tyr Ser Gly Lys Phe Cys Glu Cys Asp Asn Phe Asn Cys
545                 550                 555                 560

Asp Arg Ser Asn Gly Leu Ile Cys Gly Gly Asn Gly Val Cys Lys Cys
                565                 570                 575

Arg Val Cys Glu Cys Asn Pro Asn Tyr Thr Gly Ser Ala Cys Asp Cys
            580                 585                 590

Ser Leu Asp Thr Ser Thr Cys Glu Ala Ser Asn Gly Gln Ile Cys Asn
        595                 600                 605

Gly Arg Gly Ile Cys Glu Cys Gly Val Cys Lys Cys Thr Asp Pro Lys
    610                 615                 620

Phe Gln Gly Gln Thr Cys Glu Met Cys Gln Thr Cys Leu Gly Val Cys
625                 630                 635                 640

Ala Glu His Lys Glu Cys Val Gln Cys Arg Ala Phe Asn Lys Gly Glu
                645                 650                 655

Lys Lys Asp Thr Cys Thr Gln Glu Cys Ser Tyr Phe Asn Ile Thr Lys
            660                 665                 670

Val Glu Ser Arg Asp Lys Leu Pro Gln Pro Val Gln Pro Asp Pro Val
        675                 680                 685
```

-continued

```
Ser His Cys Lys Glu Lys Asp Val Asp Asp Cys Trp Phe Tyr Phe Thr
    690                 695                 700

Tyr Ser Val Asn Gly Asn Asn Glu Val Met Val His Val Val Glu Asn
705                 710                 715                 720

Pro Glu Cys Pro Thr Gly Pro Asp Ile Ile Pro Ile Val Ala Gly Val
                725                 730                 735

Val Ala Gly Ile Val Leu Ile Gly Leu Ala Leu Leu Leu Ile Trp Lys
            740                 745                 750

Leu Leu Met Ile Ile His Asp Arg Arg Glu Phe Ala Lys Phe Glu Lys
        755                 760                 765

Glu Lys Met Asn Ala Lys Trp Asp Thr Gly Glu Asn Pro Ile Tyr Lys
    770                 775                 780

Ser Ala Val Thr Thr Val Val Asn Pro Lys Tyr Glu Gly Lys
785                 790                 795
```

<210> SEQ ID NO 250
<211> LENGTH: 476
<212> TYPE: PRT
<213> ORGANISM: Homo sapiens

<400> SEQUENCE: 250

```
Met Leu Glu Ala Ser Gln Asp Met Gly Arg Thr Leu Glu Trp Arg Pro
1               5                   10                  15

Arg Thr Pro Ala Leu Val Arg Gly Cys His Leu Glu Gly Val Ala Gly
            20                  25                  30

His Lys Glu Ala His Ile Leu Arg Val Leu Pro Gly His Ser Ala Gly
        35                  40                  45

Pro Arg Thr Val Thr Val Lys Val Glu Leu Ser Cys Ala Pro Gly Asp
    50                  55                  60

Leu Asp Ala Val Leu Ile Leu Gln Gly Pro Pro Tyr Val Ser Trp Leu
65                  70                  75                  80

Ile Asp Ala Asn His Asn Met Gln Ile Trp Thr Thr Gly Glu Tyr Ser
                85                  90                  95

Phe Lys Ile Phe Pro Glu Lys Asn Ile Arg Gly Phe Lys Leu Pro Asp
            100                 105                 110

Thr Pro Gln Gly Leu Leu Gly Glu Ala Arg Met Leu Asn Ala Ser Ile
        115                 120                 125

Val Ala Ser Phe Val Glu Leu Pro Leu Ala Ser Ile Val Ser Leu His
    130                 135                 140

Ala Ser Ser Cys Gly Gly Arg Leu Gln Thr Ser Pro Ala Pro Ile Gln
145                 150                 155                 160

Thr Thr Pro Pro Lys Asp Thr Cys Ser Pro Glu Leu Leu Met Ser Leu
                165                 170                 175

Ile Gln Thr Lys Cys Ala Asp Asp Ala Met Thr Leu Val Leu Lys Lys
            180                 185                 190

Glu Leu Val Ala His Leu Lys Cys Thr Ile Thr Gly Leu Thr Phe Trp
        195                 200                 205

Asp Pro Ser Cys Glu Ala Glu Asp Arg Gly Asp Lys Phe Val Leu Arg
    210                 215                 220

Ser Ala Tyr Ser Ser Cys Gly Met Gln Val Ser Ala Ser Met Ile Ser
225                 230                 235                 240

Asn Glu Ala Val Val Asn Ile Leu Ser Ser Ser Ser Pro Gln Arg Lys
                245                 250                 255

Lys Val His Cys Leu Asn Met Asp Ser Leu Ser Phe Gln Leu Gly Leu
            260                 265                 270
```

Tyr Leu Ser Pro His Phe Leu Gln Ala Ser Asn Thr Ile Glu Pro Gly
275 280 285

Gln Gln Ser Phe Val Gln Val Arg Val Ser Pro Ser Val Ser Glu Phe
290 295 300

Leu Leu Gln Leu Asp Ser Cys His Leu Asp Leu Gly Pro Glu Gly Gly
305 310 315 320

Thr Val Glu Leu Ile Gln Gly Arg Ala Ala Lys Gly Asn Cys Val Ser
325 330 335

Leu Leu Ser Pro Ser Pro Glu Gly Asp Pro Arg Phe Ser Phe Leu Leu
340 345 350

His Phe Tyr Thr Val Pro Ile Pro Lys Thr Gly Thr Leu Ser Cys Thr
355 360 365

Val Ala Leu Arg Pro Lys Thr Gly Ser Gln Asp Gln Glu Val His Arg
370 375 380

Thr Val Phe Met Arg Leu Asn Ile Ile Ser Pro Asp Leu Ser Gly Cys
385 390 395 400

Thr Ser Lys Gly Leu Val Leu Pro Ala Val Leu Gly Ile Thr Phe Gly
405 410 415

Ala Phe Leu Ile Gly Ala Leu Leu Thr Ala Ala Leu Trp Tyr Ile Tyr
420 425 430

Ser His Thr Arg Ser Pro Ser Lys Arg Glu Pro Val Val Ala Val Ala
435 440 445

Ala Pro Ala Ser Ser Glu Ser Ser Ser Thr Asn His Ser Ile Gly Ser
450 455 460

Thr Gln Ser Thr Pro Cys Ser Thr Ser Ser Met Ala
465 470 475

<210> SEQ ID NO 251
<211> LENGTH: 739
<212> TYPE: PRT
<213> ORGANISM: Homo sapiens

<400> SEQUENCE: 251

Met Pro Gly Lys Met Val Val Ile Leu Gly Ala Ser Asn Ile Leu Trp
1 5 10 15

Ile Met Phe Ala Ala Ser Gln Ala Phe Lys Ile Glu Thr Thr Pro Glu
20 25 30

Ser Arg Tyr Leu Ala Gln Ile Gly Asp Ser Val Ser Leu Thr Cys Ser
35 40 45

Thr Thr Gly Cys Glu Ser Pro Phe Phe Ser Trp Arg Thr Gln Ile Asp
50 55 60

Ser Pro Leu Asn Gly Lys Val Thr Asn Glu Gly Thr Thr Ser Thr Leu
65 70 75 80

Thr Met Asn Pro Val Ser Phe Gly Asn Glu His Ser Tyr Leu Cys Thr
85 90 95

Ala Thr Cys Glu Ser Arg Lys Leu Glu Lys Gly Ile Gln Val Glu Ile
100 105 110

Tyr Ser Phe Pro Lys Asp Pro Glu Ile His Leu Ser Gly Pro Leu Glu
115 120 125

Ala Gly Lys Pro Ile Thr Val Lys Cys Ser Val Ala Asp Val Tyr Pro
130 135 140

Phe Asp Arg Leu Glu Ile Asp Leu Leu Lys Gly Asp His Leu Met Lys
145 150 155 160

Ser Gln Glu Phe Leu Glu Asp Ala Asp Arg Lys Ser Leu Glu Thr Lys

-continued

```
                165                 170                 175

Ser Leu Glu Val Thr Phe Thr Pro Val Ile Glu Asp Ile Gly Lys Val
            180                 185                 190

Leu Val Cys Arg Ala Lys Leu His Ile Asp Glu Met Asp Ser Val Pro
        195                 200                 205

Thr Val Arg Gln Ala Val Lys Glu Leu Gln Val Tyr Ile Ser Pro Lys
    210                 215                 220

Asn Thr Val Ile Ser Val Asn Pro Ser Thr Lys Leu Gln Glu Gly Gly
225                 230                 235                 240

Ser Val Thr Met Thr Cys Ser Ser Glu Gly Leu Pro Ala Pro Glu Ile
                245                 250                 255

Phe Trp Ser Lys Lys Leu Asp Asn Gly Asn Leu Gln His Leu Ser Gly
            260                 265                 270

Asn Ala Thr Leu Thr Leu Ile Ala Met Arg Met Glu Asp Ser Gly Ile
        275                 280                 285

Tyr Val Cys Glu Gly Val Asn Leu Ile Gly Lys Asn Arg Lys Glu Val
    290                 295                 300

Glu Leu Ile Val Gln Glu Lys Pro Phe Thr Val Glu Ile Ser Pro Gly
305                 310                 315                 320

Pro Arg Ile Ala Ala Gln Ile Gly Asp Ser Val Met Leu Thr Cys Ser
                325                 330                 335

Val Met Gly Cys Glu Ser Pro Ser Phe Ser Trp Arg Thr Gln Ile Asp
            340                 345                 350

Ser Pro Leu Ser Gly Lys Val Arg Ser Glu Gly Thr Asn Ser Thr Leu
        355                 360                 365

Thr Leu Ser Pro Val Ser Phe Glu Asn Glu His Ser Tyr Leu Cys Thr
    370                 375                 380

Val Thr Cys Gly His Lys Lys Leu Glu Lys Gly Ile Gln Val Glu Leu
385                 390                 395                 400

Tyr Ser Phe Pro Arg Asp Pro Glu Ile Glu Met Ser Gly Gly Leu Val
                405                 410                 415

Asn Gly Ser Ser Val Thr Val Ser Cys Lys Val Pro Ser Val Tyr Pro
            420                 425                 430

Leu Asp Arg Leu Glu Ile Glu Leu Leu Lys Gly Glu Thr Ile Leu Glu
        435                 440                 445

Asn Ile Glu Phe Leu Glu Asp Thr Asp Met Lys Ser Leu Glu Asn Lys
    450                 455                 460

Ser Leu Glu Met Thr Phe Ile Pro Thr Ile Glu Asp Thr Gly Lys Ala
465                 470                 475                 480

Leu Val Cys Gln Ala Lys Leu His Ile Asp Asp Met Glu Phe Glu Pro
                485                 490                 495

Lys Gln Arg Gln Ser Thr Gln Thr Leu Tyr Val Asn Val Ala Pro Arg
            500                 505                 510

Asp Thr Thr Val Leu Val Ser Pro Ser Ser Ile Leu Glu Glu Gly Ser
        515                 520                 525

Ser Val Asn Met Thr Cys Leu Ser Gln Gly Phe Pro Ala Pro Lys Ile
    530                 535                 540

Leu Trp Ser Arg Gln Leu Pro Asn Gly Glu Leu Gln Pro Leu Ser Glu
545                 550                 555                 560

Asn Ala Thr Leu Thr Leu Ile Ser Thr Lys Met Glu Asp Ser Gly Val
                565                 570                 575

Tyr Leu Cys Glu Gly Ile Asn Gln Ala Gly Arg Ser Arg Lys Glu Val
            580                 585                 590
```

```
Glu Leu Ile Ile Gln Val Thr Pro Lys Asp Ile Lys Leu Thr Ala Phe
        595                 600                 605

Pro Ser Glu Ser Val Lys Glu Gly Asp Thr Val Ile Ile Ser Cys Thr
    610                 615                 620

Cys Gly Asn Val Pro Glu Thr Trp Ile Ile Leu Lys Lys Lys Ala Glu
625                 630                 635                 640

Thr Gly Asp Thr Val Leu Lys Ser Ile Asp Gly Ala Tyr Thr Ile Arg
                645                 650                 655

Lys Ala Gln Leu Lys Asp Ala Gly Val Tyr Glu Cys Glu Ser Lys Asn
            660                 665                 670

Lys Val Gly Ser Gln Leu Arg Ser Leu Thr Leu Asp Val Gln Gly Arg
        675                 680                 685

Glu Asn Asn Lys Asp Tyr Phe Ser Pro Glu Leu Leu Val Leu Tyr Phe
    690                 695                 700

Ala Ser Ser Leu Ile Ile Pro Ala Ile Gly Met Ile Ile Tyr Phe Ala
705                 710                 715                 720

Arg Lys Ala Asn Met Lys Gly Ser Tyr Ser Leu Val Glu Ala Gln Lys
                725                 730                 735

Ser Lys Val


<210> SEQ ID NO 252
<211> LENGTH: 646
<212> TYPE: PRT
<213> ORGANISM: Homo sapiens

<400> SEQUENCE: 252

Met Gly Leu Pro Arg Leu Val Cys Ala Phe Leu Leu Ala Ala Cys Cys
1               5                   10                  15

Cys Cys Pro Arg Val Ala Gly Val Pro Gly Glu Ala Glu Gln Pro Ala
            20                  25                  30

Pro Glu Leu Val Glu Val Glu Val Gly Ser Thr Ala Leu Leu Lys Cys
        35                  40                  45

Gly Leu Ser Gln Ser Gln Gly Asn Leu Ser His Val Asp Trp Phe Ser
    50                  55                  60

Val His Lys Glu Lys Arg Thr Leu Ile Phe Arg Val Arg Gln Gly Gln
65                  70                  75                  80

Gly Gln Ser Glu Pro Gly Glu Tyr Glu Gln Arg Leu Ser Leu Gln Asp
                85                  90                  95

Arg Gly Ala Thr Leu Ala Leu Thr Gln Val Thr Pro Gln Asp Glu Arg
            100                 105                 110

Ile Phe Leu Cys Gln Gly Lys Arg Pro Arg Ser Gln Glu Tyr Arg Ile
        115                 120                 125

Gln Leu Arg Val Tyr Lys Ala Pro Glu Glu Pro Asn Ile Gln Val Asn
    130                 135                 140

Pro Leu Gly Ile Pro Val Asn Ser Lys Glu Pro Glu Glu Val Ala Thr
145                 150                 155                 160

Cys Val Gly Arg Asn Gly Tyr Pro Ile Pro Gln Val Ile Trp Tyr Lys
                165                 170                 175

Asn Gly Arg Pro Leu Lys Glu Glu Lys Asn Arg Val His Ile Gln Ser
            180                 185                 190

Ser Gln Thr Val Glu Ser Ser Gly Leu Tyr Thr Leu Gln Ser Ile Leu
        195                 200                 205

Lys Ala Gln Leu Val Lys Glu Asp Lys Asp Ala Gln Phe Tyr Cys Glu
    210                 215                 220
```

-continued

```
Leu Asn Tyr Arg Leu Pro Ser Gly Asn His Met Lys Glu Ser Arg Glu
225                 230                 235                 240

Val Thr Val Pro Val Phe Tyr Pro Thr Glu Lys Val Trp Leu Glu Val
                245                 250                 255

Glu Pro Val Gly Met Leu Lys Glu Gly Asp Arg Val Glu Ile Arg Cys
            260                 265                 270

Leu Ala Asp Gly Asn Pro Pro Pro His Phe Ser Ile Ser Lys Gln Asn
        275                 280                 285

Pro Ser Thr Arg Glu Ala Glu Glu Glu Thr Thr Asn Asp Asn Gly Val
    290                 295                 300

Leu Val Leu Glu Pro Ala Arg Lys Glu His Ser Gly Arg Tyr Glu Cys
305                 310                 315                 320

Gln Gly Leu Asp Leu Asp Thr Met Ile Ser Leu Leu Ser Glu Pro Gln
                325                 330                 335

Glu Leu Leu Val Asn Tyr Val Ser Asp Val Arg Val Ser Pro Ala Ala
            340                 345                 350

Pro Glu Arg Gln Glu Gly Ser Ser Leu Thr Leu Thr Cys Glu Ala Glu
        355                 360                 365

Ser Ser Gln Asp Leu Glu Phe Gln Trp Leu Arg Glu Glu Thr Gly Gln
    370                 375                 380

Val Leu Glu Arg Gly Pro Val Leu Gln Leu His Asp Leu Lys Arg Glu
385                 390                 395                 400

Ala Gly Gly Gly Tyr Arg Cys Val Ala Ser Val Pro Ser Ile Pro Gly
                405                 410                 415

Leu Asn Arg Thr Gln Leu Val Asn Val Ala Ile Phe Gly Pro Pro Trp
            420                 425                 430

Met Ala Phe Lys Glu Arg Lys Val Trp Val Lys Glu Asn Met Val Leu
        435                 440                 445

Asn Leu Ser Cys Glu Ala Ser Gly His Pro Arg Pro Thr Ile Ser Trp
    450                 455                 460

Asn Val Asn Gly Thr Ala Ser Glu Gln Asp Gln Asp Pro Gln Arg Val
465                 470                 475                 480

Leu Ser Thr Leu Asn Val Leu Val Thr Pro Glu Leu Leu Glu Thr Gly
                485                 490                 495

Val Glu Cys Thr Ala Ser Asn Asp Leu Gly Lys Asn Thr Ser Ile Leu
            500                 505                 510

Phe Leu Glu Leu Val Asn Leu Thr Thr Leu Thr Pro Asp Ser Asn Thr
        515                 520                 525

Thr Thr Gly Leu Ser Thr Ser Thr Ala Ser Pro His Thr Arg Ala Asn
    530                 535                 540

Ser Thr Ser Thr Glu Arg Lys Leu Pro Glu Pro Glu Ser Arg Gly Val
545                 550                 555                 560

Val Ile Val Ala Val Ile Val Cys Ile Leu Val Leu Ala Val Leu Gly
                565                 570                 575

Ala Val Leu Tyr Phe Leu Tyr Lys Lys Gly Lys Leu Pro Cys Arg Arg
            580                 585                 590

Ser Gly Lys Gln Glu Ile Thr Leu Pro Pro Ser Arg Lys Ser Glu Leu
        595                 600                 605

Val Val Glu Val Lys Ser Asp Lys Leu Pro Glu Glu Met Gly Leu Leu
    610                 615                 620

Gln Gly Ser Ser Gly Asp Lys Arg Ala Pro Gly Asp Gln Gly Glu Lys
625                 630                 635                 640
```

Tyr Ile Asp Leu Arg His
645

<210> SEQ ID NO 253
<211> LENGTH: 178
<212> TYPE: PRT
<213> ORGANISM: Homo sapiens

<400> SEQUENCE: 253

Met Ser Arg Leu Ser Arg Ser Leu Leu Trp Ala Ala Thr Cys Leu Gly
1 5 10 15

Val Leu Cys Val Leu Ser Ala Asp Lys Asn Thr Thr Gln His Pro Asn
20 25 30

Val Thr Thr Leu Ala Pro Ile Ser Asn Val Thr Ser Ala Pro Val Thr
35 40 45

Ser Leu Pro Leu Val Thr Thr Pro Ala Pro Glu Thr Cys Glu Gly Arg
50 55 60

Asn Ser Cys Val Ser Cys Phe Asn Val Ser Val Val Asn Thr Thr Cys
65 70 75 80

Phe Trp Ile Glu Cys Lys Asp Glu Ser Tyr Cys Ser His Asn Ser Thr
85 90 95

Val Ser Asp Cys Gln Val Gly Asn Thr Thr Asp Phe Cys Ser Val Ser
100 105 110

Thr Ala Thr Pro Val Pro Thr Ala Asn Ser Thr Gly Thr Thr Asn Asn
115 120 125

Thr Val Thr Pro Thr Ser Gln Pro Val Arg Lys Ser Thr Phe Asp Ala
130 135 140

Ala Ser Phe Ile Gly Gly Ile Val Leu Val Leu Gly Val Gln Ala Val
145 150 155 160

Ile Phe Phe Leu Tyr Lys Phe Cys Lys Ser Lys Glu Arg Asn Tyr His
165 170 175

Thr Leu

<210> SEQ ID NO 254
<211> LENGTH: 583
<212> TYPE: PRT
<213> ORGANISM: Homo sapiens

<400> SEQUENCE: 254

Met Glu Ser Lys Gly Ala Ser Ser Cys Arg Leu Leu Phe Cys Leu Leu
1 5 10 15

Ile Ser Ala Thr Val Phe Arg Pro Gly Leu Gly Trp Tyr Thr Val Asn
20 25 30

Ser Ala Tyr Gly Asp Thr Ile Ile Ile Pro Cys Arg Leu Asp Val Pro
35 40 45

Gln Asn Leu Met Phe Gly Lys Trp Lys Tyr Glu Lys Pro Asp Gly Ser
50 55 60

Pro Val Phe Ile Ala Phe Arg Ser Ser Thr Lys Lys Ser Val Gln Tyr
65 70 75 80

Asp Asp Val Pro Glu Tyr Lys Asp Arg Leu Asn Leu Ser Glu Asn Tyr
85 90 95

Thr Leu Ser Ile Ser Asn Ala Arg Ile Ser Asp Glu Lys Arg Phe Val
100 105 110

Cys Met Leu Val Thr Glu Asp Asn Val Phe Glu Ala Pro Thr Ile Val
115 120 125

Lys Val Phe Lys Gln Pro Ser Lys Pro Glu Ile Val Ser Lys Ala Leu

-continued

```
    130                 135                 140

Phe Leu Glu Thr Glu Gln Leu Lys Lys Leu Gly Asp Cys Ile Ser Glu
145                 150                 155                 160

Asp Ser Tyr Pro Asp Gly Asn Ile Thr Trp Tyr Arg Asn Gly Lys Val
                165                 170                 175

Leu His Pro Leu Glu Gly Ala Val Val Ile Ile Phe Lys Lys Glu Met
            180                 185                 190

Asp Pro Val Thr Gln Leu Tyr Thr Met Thr Ser Thr Leu Glu Tyr Lys
        195                 200                 205

Thr Thr Lys Ala Asp Ile Gln Met Pro Phe Thr Cys Ser Val Thr Tyr
    210                 215                 220

Tyr Gly Pro Ser Gly Gln Lys Thr Ile His Ser Glu Gln Ala Val Phe
225                 230                 235                 240

Asp Ile Tyr Tyr Pro Thr Glu Gln Val Thr Ile Gln Val Leu Pro Pro
                245                 250                 255

Lys Asn Ala Ile Lys Glu Gly Asp Asn Ile Thr Leu Lys Cys Leu Gly
            260                 265                 270

Asn Gly Asn Pro Pro Pro Glu Glu Phe Leu Phe Tyr Leu Pro Gly Gln
        275                 280                 285

Pro Glu Gly Ile Arg Ser Ser Asn Thr Tyr Thr Leu Thr Asp Val Arg
    290                 295                 300

Arg Asn Ala Thr Gly Asp Tyr Lys Cys Ser Leu Ile Asp Lys Lys Ser
305                 310                 315                 320

Met Ile Ala Ser Thr Ala Ile Thr Val His Tyr Leu Asp Leu Ser Leu
                325                 330                 335

Asn Pro Ser Gly Glu Val Thr Arg Gln Ile Gly Asp Ala Leu Pro Val
            340                 345                 350

Ser Cys Thr Ile Ser Ala Ser Arg Asn Ala Thr Val Val Trp Met Lys
        355                 360                 365

Asp Asn Ile Arg Leu Arg Ser Ser Pro Ser Phe Ser Ser Leu His Tyr
    370                 375                 380

Gln Asp Ala Gly Asn Tyr Val Cys Glu Thr Ala Leu Gln Glu Val Glu
385                 390                 395                 400

Gly Leu Lys Lys Arg Glu Ser Leu Thr Leu Ile Val Glu Gly Lys Pro
                405                 410                 415

Gln Ile Lys Met Thr Lys Lys Thr Asp Pro Ser Gly Leu Ser Lys Thr
            420                 425                 430

Ile Ile Cys His Val Glu Gly Phe Pro Lys Pro Ala Ile Gln Trp Thr
        435                 440                 445

Ile Thr Gly Ser Gly Ser Val Ile Asn Gln Thr Glu Glu Ser Pro Tyr
    450                 455                 460

Ile Asn Gly Arg Tyr Tyr Ser Lys Ile Ile Ile Ser Pro Glu Glu Asn
465                 470                 475                 480

Val Thr Leu Thr Cys Thr Ala Glu Asn Gln Leu Glu Arg Thr Val Asn
                485                 490                 495

Ser Leu Asn Val Ser Ala Ile Ser Ile Pro Glu His Asp Glu Ala Asp
            500                 505                 510

Glu Ile Ser Asp Glu Asn Arg Glu Lys Val Asn Asp Gln Ala Lys Leu
        515                 520                 525

Ile Val Gly Ile Val Val Gly Leu Leu Leu Ala Ala Leu Val Ala Gly
    530                 535                 540

Val Val Tyr Trp Leu Tyr Met Lys Lys Ser Lys Thr Ala Ser Lys His
545                 550                 555                 560
```

```
Val Asn Lys Asp Leu Gly Asn Met Glu Glu Asn Lys Lys Leu Glu Glu
                565                 570                 575

Asn Asn His Lys Thr Glu Ala
            580


<210> SEQ ID NO 255
<211> LENGTH: 317
<212> TYPE: PRT
<213> ORGANISM: Homo sapiens

<400> SEQUENCE: 255

Met Lys Thr Ala Leu Ile Leu Leu Ser Ile Leu Gly Met Ala Cys Ala
1               5                   10                  15

Phe Ser Met Lys Asn Leu His Arg Arg Val Lys Ile Glu Asp Ser Glu
            20                  25                  30

Glu Asn Gly Val Phe Lys Tyr Arg Pro Arg Tyr Tyr Leu Tyr Lys His
        35                  40                  45

Ala Tyr Phe Tyr Pro His Leu Lys Arg Phe Pro Val Gln Gly Ser Ser
    50                  55                  60

Asp Ser Ser Glu Glu Asn Gly Asp Asp Ser Ser Glu Glu Glu Glu Glu
65                  70                  75                  80

Glu Glu Glu Thr Ser Asn Glu Gly Glu Asn Asn Glu Glu Ser Asn Glu
                85                  90                  95

Asp Glu Asp Ser Glu Ala Glu Asn Thr Thr Leu Ser Ala Thr Thr Leu
            100                 105                 110

Gly Tyr Gly Glu Asp Ala Thr Pro Gly Thr Gly Tyr Thr Gly Leu Ala
        115                 120                 125

Ala Ile Gln Leu Pro Lys Lys Ala Gly Asp Ile Thr Asn Lys Ala Thr
    130                 135                 140

Lys Glu Lys Glu Ser Asp Glu Glu Glu Glu Glu Glu Glu Glu Gly Asn
145                 150                 155                 160

Glu Asn Glu Glu Ser Glu Ala Glu Val Asp Glu Asn Glu Gln Gly Ile
                165                 170                 175

Asn Gly Thr Ser Thr Asn Ser Thr Glu Ala Glu Asn Gly Asn Gly Ser
            180                 185                 190

Ser Gly Gly Asp Asn Gly Glu Glu Gly Glu Glu Glu Ser Val Thr Gly
        195                 200                 205

Ala Asn Ala Glu Asp Thr Thr Glu Thr Gly Arg Gln Gly Lys Gly Thr
    210                 215                 220

Ser Lys Thr Thr Thr Ser Pro Asn Gly Gly Phe Glu Pro Thr Thr Pro
225                 230                 235                 240

Pro Gln Val Tyr Arg Thr Thr Ser Pro Pro Phe Gly Lys Thr Thr Thr
                245                 250                 255

Val Glu Tyr Glu Gly Glu Tyr Glu Tyr Thr Gly Ala Asn Glu Tyr Asp
            260                 265                 270

Asn Gly Tyr Glu Ile Tyr Glu Ser Glu Asn Gly Glu Pro Arg Gly Asp
        275                 280                 285

Asn Tyr Arg Ala Tyr Glu Asp Glu Tyr Ser Tyr Phe Lys Gly Gln Gly
    290                 295                 300

Tyr Asp Gly Tyr Asp Gly Gln Asn Tyr Tyr His His Gln
305                 310                 315


<210> SEQ ID NO 256
<211> LENGTH: 532
<212> TYPE: PRT
```

<213> ORGANISM: Homo sapiens

<400> SEQUENCE: 256

Met Ala Pro Ser Ser Pro Arg Pro Ala Leu Pro Ala Leu Leu Val Leu
1               5                   10                  15

Leu Gly Ala Leu Phe Pro Gly Pro Gly Asn Ala Gln Thr Ser Val Ser
            20                  25                  30

Pro Ser Lys Val Ile Leu Pro Arg Gly Gly Ser Val Leu Val Thr Cys
        35                  40                  45

Ser Thr Ser Cys Asp Gln Pro Lys Leu Leu Gly Ile Glu Thr Pro Leu
    50                  55                  60

Pro Lys Lys Glu Leu Leu Leu Pro Gly Asn Asn Arg Lys Val Tyr Glu
65                  70                  75                  80

Leu Ser Asn Val Gln Glu Asp Ser Gln Pro Met Cys Tyr Ser Asn Cys
                85                  90                  95

Pro Asp Gly Gln Ser Thr Ala Lys Thr Phe Leu Thr Val Tyr Trp Thr
            100                 105                 110

Pro Glu Arg Val Glu Leu Ala Pro Leu Pro Ser Trp Gln Pro Val Gly
        115                 120                 125

Lys Asn Leu Thr Leu Arg Cys Gln Val Glu Gly Gly Ala Pro Arg Ala
    130                 135                 140

Asn Leu Thr Val Val Leu Leu Arg Gly Glu Lys Glu Leu Lys Arg Glu
145                 150                 155                 160

Pro Ala Val Gly Glu Pro Ala Glu Val Thr Thr Thr Val Leu Val Arg
                165                 170                 175

Arg Asp His His Gly Ala Asn Phe Ser Cys Arg Thr Glu Leu Asp Leu
            180                 185                 190

Arg Pro Gln Gly Leu Glu Leu Phe Glu Asn Thr Ser Ala Pro Tyr Gln
        195                 200                 205

Leu Gln Thr Phe Val Leu Pro Ala Thr Pro Pro Gln Leu Val Ser Pro
    210                 215                 220

Arg Val Leu Glu Val Asp Thr Gln Gly Thr Val Val Cys Ser Leu Asp
225                 230                 235                 240

Gly Leu Phe Pro Val Ser Glu Ala Gln Val His Leu Ala Leu Gly Asp
                245                 250                 255

Gln Arg Leu Asn Pro Thr Val Thr Tyr Gly Asn Asp Ser Phe Ser Ala
            260                 265                 270

Lys Ala Ser Val Ser Val Thr Ala Glu Asp Glu Gly Thr Gln Arg Leu
        275                 280                 285

Thr Cys Ala Val Ile Leu Gly Asn Gln Ser Gln Glu Thr Leu Gln Thr
    290                 295                 300

Val Thr Ile Tyr Ser Phe Pro Ala Pro Asn Val Ile Leu Thr Lys Pro
305                 310                 315                 320

Glu Val Ser Glu Gly Thr Glu Val Thr Val Lys Cys Glu Ala His Pro
                325                 330                 335

Arg Ala Lys Val Thr Leu Asn Gly Val Pro Ala Gln Pro Leu Gly Pro
            340                 345                 350

Arg Ala Gln Leu Leu Leu Lys Ala Thr Pro Glu Asp Asn Gly Arg Ser
        355                 360                 365

Phe Ser Cys Ser Ala Thr Leu Glu Val Ala Gly Gln Leu Ile His Lys
    370                 375                 380

Asn Gln Thr Arg Glu Leu Arg Val Leu Tyr Gly Pro Arg Leu Asp Glu
385                 390                 395                 400

```
Arg Asp Cys Pro Gly Asn Trp Thr Trp Pro Glu Asn Ser Gln Gln Thr
                405                 410                 415

Pro Met Cys Gln Ala Trp Gly Asn Pro Leu Pro Glu Leu Lys Cys Leu
            420                 425                 430

Lys Asp Gly Thr Phe Pro Leu Pro Ile Gly Glu Ser Val Thr Val Thr
        435                 440                 445

Arg Asp Leu Glu Gly Thr Tyr Leu Cys Arg Ala Arg Ser Thr Gln Gly
    450                 455                 460

Glu Val Thr Arg Lys Val Thr Val Asn Val Leu Ser Pro Arg Tyr Glu
465                 470                 475                 480

Ile Val Ile Ile Thr Val Val Ala Ala Ala Val Ile Met Gly Thr Ala
                485                 490                 495

Gly Leu Ser Thr Tyr Leu Tyr Asn Arg Gln Arg Lys Ile Lys Lys Tyr
            500                 505                 510

Arg Leu Gln Gln Ala Gln Lys Gly Thr Pro Met Lys Pro Asn Thr Gln
        515                 520                 525

Ala Thr Pro Pro
    530


<210> SEQ ID NO 257
<211> LENGTH: 137
<212> TYPE: PRT
<213> ORGANISM: Homo sapiens

<400> SEQUENCE: 257

Met Tyr Gly Lys Ile Ile Phe Val Leu Leu Leu Ser Glu Ile Val Ser
1               5                   10                  15

Ile Ser Ala Leu Ser Thr Thr Glu Val Ala Met His Thr Ser Thr Ser
            20                  25                  30

Ser Ser Val Thr Lys Ser Tyr Ile Ser Ser Gln Thr Asn Asp Thr His
        35                  40                  45

Lys Arg Asp Thr Tyr Ala Ala Thr Pro Arg Ala His Glu Val Ser Glu
    50                  55                  60

Ile Ser Val Arg Thr Val Tyr Pro Pro Glu Glu Glu Thr Glu Ile Thr
65                  70                  75                  80

Leu Ile Ile Phe Gly Val Met Ala Gly Val Ile Gly Thr Ile Leu Leu
                85                  90                  95

Ile Ser Tyr Gly Ile Arg Arg Leu Ile Lys Lys Ser Pro Ser Asp Val
            100                 105                 110

Lys Pro Leu Pro Ser Pro Asp Thr Asp Val Pro Leu Ser Ser Val Glu
        115                 120                 125

Ile Glu Asn Pro Glu Thr Ser Asp Gln
    130                 135


<210> SEQ ID NO 258
<211> LENGTH: 883
<212> TYPE: PRT
<213> ORGANISM: Homo sapiens

<400> SEQUENCE: 258

Met Gln Lys Ile Met His Ile Ser Val Leu Leu Ser Pro Val Leu Trp
1               5                   10                  15

Gly Leu Ile Phe Gly Val Ser Ser Asn Ser Ile Gln Ile Gly Gly Leu
            20                  25                  30

Phe Pro Arg Gly Ala Asp Gln Glu Tyr Ser Ala Phe Arg Val Gly Met
        35                  40                  45
```

-continued

```
Val Gln Phe Ser Thr Ser Glu Phe Arg Leu Thr Pro His Ile Asp Asn
    50                  55                  60

Leu Glu Val Ala Asn Ser Phe Ala Val Thr Asn Ala Phe Cys Ser Gln
65                  70                  75                  80

Phe Ser Arg Gly Val Tyr Ala Ile Phe Gly Phe Tyr Asp Lys Lys Ser
                85                  90                  95

Val Asn Thr Ile Thr Ser Phe Cys Gly Thr Leu His Val Ser Phe Ile
            100                 105                 110

Thr Pro Ser Phe Pro Thr Asp Gly Thr His Pro Phe Val Ile Gln Met
        115                 120                 125

Arg Pro Asp Leu Lys Gly Ala Leu Leu Ser Leu Ile Glu Tyr Tyr Gln
    130                 135                 140

Trp Asp Lys Phe Ala Tyr Leu Tyr Asp Ser Asp Arg Gly Leu Ser Thr
145                 150                 155                 160

Leu Gln Ala Val Leu Asp Ser Ala Ala Glu Lys Lys Trp Gln Val Thr
                165                 170                 175

Ala Ile Asn Val Gly Asn Ile Asn Asn Asp Lys Lys Asp Glu Met Tyr
            180                 185                 190

Arg Ser Leu Phe Gln Asp Leu Glu Leu Lys Lys Glu Arg Arg Val Ile
        195                 200                 205

Leu Asp Cys Glu Arg Asp Lys Val Asn Asp Ile Val Asp Gln Val Ile
    210                 215                 220

Thr Ile Gly Lys His Val Lys Gly Tyr His Tyr Ile Ile Ala Asn Leu
225                 230                 235                 240

Gly Phe Thr Asp Gly Asp Leu Leu Lys Ile Gln Phe Gly Gly Ala Asn
                245                 250                 255

Val Ser Gly Phe Gln Ile Val Asp Tyr Asp Asp Ser Leu Val Ser Lys
            260                 265                 270

Phe Ile Glu Arg Trp Ser Thr Leu Glu Glu Lys Glu Tyr Pro Gly Ala
        275                 280                 285

His Thr Thr Thr Ile Lys Tyr Thr Ser Ala Leu Thr Tyr Asp Ala Val
    290                 295                 300

Gln Val Met Thr Glu Ala Phe Arg Asn Leu Arg Lys Gln Arg Ile Glu
305                 310                 315                 320

Ile Ser Arg Arg Gly Asn Ala Gly Asp Cys Leu Ala Asn Pro Ala Val
                325                 330                 335

Pro Trp Gly Gln Gly Val Glu Ile Glu Arg Ala Leu Lys Gln Val Gln
            340                 345                 350

Val Glu Gly Leu Ser Gly Asn Ile Lys Phe Asp Gln Asn Gly Lys Arg
        355                 360                 365

Ile Asn Tyr Thr Ile Asn Ile Met Glu Leu Lys Thr Asn Gly Pro Arg
    370                 375                 380

Lys Ile Gly Tyr Trp Ser Glu Val Asp Lys Met Val Val Thr Leu Thr
385                 390                 395                 400

Glu Leu Pro Ser Gly Asn Asp Thr Ser Gly Leu Glu Asn Lys Thr Val
                405                 410                 415

Val Val Thr Thr Ile Leu Glu Ser Pro Tyr Val Met Met Lys Lys Asn
            420                 425                 430

His Glu Met Leu Glu Gly Asn Glu Arg Tyr Glu Gly Tyr Cys Val Asp
        435                 440                 445

Leu Ala Ala Glu Ile Ala Lys His Cys Gly Phe Lys Tyr Lys Leu Thr
    450                 455                 460

Ile Val Gly Asp Gly Lys Tyr Gly Ala Arg Asp Ala Asp Thr Lys Ile
```

-continued

```
465                 470                 475                 480

Trp Asn Gly Met Val Gly Glu Leu Val Tyr Gly Lys Ala Asp Ile Ala
                485                 490                 495

Ile Ala Pro Leu Thr Ile Thr Leu Val Arg Glu Glu Val Ile Asp Phe
            500                 505                 510

Ser Lys Pro Phe Met Ser Leu Gly Ile Ser Ile Met Ile Lys Lys Pro
        515                 520                 525

Gln Lys Ser Lys Pro Gly Val Phe Ser Phe Leu Asp Pro Leu Ala Tyr
    530                 535                 540

Glu Ile Trp Met Cys Ile Val Phe Ala Tyr Ile Gly Val Ser Val Val
545                 550                 555                 560

Leu Phe Leu Val Ser Arg Phe Ser Pro Tyr Glu Trp His Thr Glu Glu
                565                 570                 575

Phe Glu Asp Gly Arg Glu Thr Gln Ser Ser Glu Ser Thr Asn Glu Phe
            580                 585                 590

Gly Ile Phe Asn Ser Leu Trp Phe Ser Leu Gly Ala Phe Met Gln Gln
        595                 600                 605

Gly Cys Asp Ile Ser Pro Arg Ser Leu Ser Gly Arg Ile Val Gly Gly
    610                 615                 620

Val Trp Trp Phe Phe Thr Leu Ile Ile Ile Ser Ser Tyr Thr Ala Asn
625                 630                 635                 640

Leu Ala Ala Phe Leu Thr Val Glu Arg Met Val Ser Pro Ile Glu Ser
                645                 650                 655

Ala Glu Asp Leu Ser Lys Gln Thr Glu Ile Ala Tyr Gly Thr Leu Asp
            660                 665                 670

Ser Gly Ser Thr Lys Glu Phe Phe Arg Arg Ser Lys Ile Ala Val Phe
        675                 680                 685

Asp Lys Met Trp Thr Tyr Met Arg Ser Ala Glu Pro Ser Val Phe Val
    690                 695                 700

Arg Thr Thr Ala Glu Gly Val Ala Arg Val Arg Lys Ser Lys Gly Lys
705                 710                 715                 720

Tyr Ala Tyr Leu Leu Glu Ser Thr Met Asn Glu Tyr Ile Glu Gln Arg
                725                 730                 735

Lys Pro Cys Asp Thr Met Lys Val Gly Gly Asn Leu Asp Ser Lys Gly
            740                 745                 750

Tyr Gly Ile Ala Thr Pro Lys Gly Ser Ser Leu Arg Thr Pro Val Asn
        755                 760                 765

Leu Ala Val Leu Lys Leu Ser Glu Gln Gly Val Leu Asp Lys Leu Lys
    770                 775                 780

Asn Lys Trp Trp Tyr Asp Lys Gly Glu Cys Gly Ala Lys Asp Ser Gly
785                 790                 795                 800

Ser Lys Glu Lys Thr Ser Ala Leu Ser Leu Ser Asn Val Ala Gly Val
                805                 810                 815

Phe Tyr Ile Leu Val Gly Gly Leu Gly Leu Ala Met Leu Val Ala Leu
            820                 825                 830

Ile Glu Phe Cys Tyr Lys Ser Arg Ala Glu Ala Lys Arg Met Lys Val
        835                 840                 845

Ala Lys Asn Ala Gln Asn Ile Asn Pro Ser Ser Ser Gln Asn Ser Gln
    850                 855                 860

Asn Phe Ala Thr Tyr Lys Glu Gly Tyr Asn Val Tyr Gly Ile Glu Ser
865                 870                 875                 880

Val Lys Ile
```

<210> SEQ ID NO 259
<211> LENGTH: 894
<212> TYPE: PRT
<213> ORGANISM: Homo sapiens

<400> SEQUENCE: 259

```
Met Ala Arg Gln Lys Lys Met Gly Gln Ser Val Leu Arg Ala Val Phe
1               5                   10                  15

Phe Leu Val Leu Gly Leu Leu Gly His Ser His Gly Gly Phe Pro Asn
            20                  25                  30

Thr Ile Ser Ile Gly Gly Leu Phe Met Arg Asn Thr Val Gln Glu His
        35                  40                  45

Ser Ala Phe Arg Phe Ala Val Gln Leu Tyr Asn Thr Asn Gln Asn Thr
    50                  55                  60

Thr Glu Lys Pro Phe His Leu Asn Tyr His Val Asp His Leu Asp Ser
65                  70                  75                  80

Ser Asn Ser Phe Ser Val Thr Asn Ala Phe Cys Ser Gln Phe Ser Arg
                85                  90                  95

Gly Val Tyr Ala Ile Phe Gly Phe Tyr Asp Gln Met Ser Met Asn Thr
            100                 105                 110

Leu Thr Ser Phe Cys Gly Ala Leu His Thr Ser Phe Val Thr Pro Ser
        115                 120                 125

Phe Pro Thr Asp Ala Asp Val Gln Phe Val Ile Gln Met Arg Pro Ala
    130                 135                 140

Leu Lys Gly Ala Ile Leu Ser Leu Leu Gly His Tyr Lys Trp Glu Lys
145                 150                 155                 160

Phe Val Tyr Leu Tyr Asp Thr Glu Arg Gly Phe Ser Ile Leu Gln Ala
                165                 170                 175

Ile Met Glu Ala Ala Val Gln Asn Asn Trp Gln Val Thr Ala Arg Ser
            180                 185                 190

Val Gly Asn Ile Lys Asp Val Gln Glu Phe Arg Arg Ile Ile Glu Glu
        195                 200                 205

Met Asp Arg Arg Gln Glu Lys Arg Tyr Leu Ile Asp Cys Glu Val Glu
    210                 215                 220

Arg Ile Asn Thr Ile Leu Glu Gln Val Val Ile Leu Gly Lys His Ser
225                 230                 235                 240

Arg Gly Tyr His Tyr Met Leu Ala Asn Leu Gly Phe Thr Asp Ile Leu
                245                 250                 255

Leu Glu Arg Val Met His Gly Gly Ala Asn Ile Thr Gly Phe Gln Ile
            260                 265                 270

Val Asn Asn Glu Asn Pro Met Val Gln Gln Phe Ile Gln Arg Trp Val
        275                 280                 285

Arg Leu Asp Glu Arg Glu Phe Pro Glu Ala Lys Asn Ala Pro Leu Lys
    290                 295                 300

Tyr Thr Ser Ala Leu Thr His Asp Ala Ile Leu Val Ile Ala Glu Ala
305                 310                 315                 320

Phe Arg Tyr Leu Arg Arg Gln Arg Val Asp Val Ser Arg Arg Gly Ser
                325                 330                 335

Ala Gly Asp Cys Leu Ala Asn Pro Ala Val Pro Trp Ser Gln Gly Ile
            340                 345                 350

Asp Ile Glu Arg Ala Leu Lys Met Val Gln Val Gln Gly Met Thr Gly
        355                 360                 365

Asn Ile Gln Phe Asp Thr Tyr Gly Arg Arg Thr Asn Tyr Thr Ile Asp
    370                 375                 380
```

-continued

```
Val Tyr Glu Met Lys Val Ser Gly Ser Arg Lys Ala Gly Tyr Trp Asn
385                 390                 395                 400

Glu Tyr Glu Arg Phe Val Pro Phe Ser Asp Gln Gln Ile Ser Asn Asp
                405                 410                 415

Ser Ala Ser Ser Glu Asn Arg Thr Ile Val Val Thr Thr Ile Leu Glu
            420                 425                 430

Ser Pro Tyr Val Met Tyr Lys Lys Asn His Glu Gln Leu Glu Gly Asn
        435                 440                 445

Glu Arg Tyr Glu Gly Tyr Cys Val Asp Leu Ala Tyr Glu Ile Ala Lys
    450                 455                 460

His Val Arg Ile Lys Tyr Lys Leu Ser Ile Val Gly Asp Gly Lys Tyr
465                 470                 475                 480

Gly Ala Arg Asp Pro Glu Thr Lys Ile Trp Asn Gly Met Val Gly Glu
                485                 490                 495

Leu Val Tyr Gly Arg Ala Asp Ile Ala Val Ala Pro Leu Thr Ile Thr
            500                 505                 510

Leu Val Arg Glu Glu Val Ile Asp Phe Ser Lys Pro Phe Met Ser Leu
        515                 520                 525

Gly Ile Ser Ile Met Ile Lys Lys Pro Gln Lys Ser Lys Pro Gly Val
    530                 535                 540

Phe Ser Phe Leu Asp Pro Leu Ala Tyr Glu Ile Trp Met Cys Ile Val
545                 550                 555                 560

Phe Ala Tyr Ile Gly Val Ser Val Val Leu Phe Leu Val Ser Arg Phe
                565                 570                 575

Ser Pro Tyr Glu Trp His Leu Glu Asp Asn Asn Glu Glu Pro Arg Asp
            580                 585                 590

Pro Gln Ser Pro Pro Asp Pro Pro Asn Glu Phe Gly Ile Phe Asn Ser
        595                 600                 605

Leu Trp Phe Ser Leu Gly Ala Phe Met Gln Gln Gly Cys Asp Ile Ser
    610                 615                 620

Pro Arg Ser Leu Ser Gly Arg Ile Val Gly Gly Val Trp Trp Phe Phe
625                 630                 635                 640

Thr Leu Ile Ile Ile Ser Ser Tyr Thr Ala Asn Leu Ala Ala Phe Leu
                645                 650                 655

Thr Val Glu Arg Met Val Ser Pro Ile Glu Ser Ala Glu Asp Leu Ala
            660                 665                 670

Lys Gln Thr Glu Ile Ala Tyr Gly Thr Leu Asp Ser Gly Ser Thr Lys
        675                 680                 685

Glu Phe Phe Arg Arg Ser Lys Ile Ala Val Tyr Glu Lys Met Trp Ser
    690                 695                 700

Tyr Met Lys Ser Ala Glu Pro Ser Val Phe Thr Lys Thr Thr Ala Asp
705                 710                 715                 720

Gly Val Ala Arg Val Arg Lys Ser Lys Gly Lys Phe Ala Phe Leu Leu
                725                 730                 735

Glu Ser Thr Met Asn Glu Tyr Ile Glu Gln Arg Lys Pro Cys Asp Thr
            740                 745                 750

Met Lys Val Gly Gly Asn Leu Asp Ser Lys Gly Tyr Gly Val Ala Thr
        755                 760                 765

Pro Lys Gly Ser Ala Leu Gly Asn Ala Val Asn Leu Ala Val Leu Lys
    770                 775                 780

Leu Asn Glu Gln Gly Leu Leu Asp Lys Leu Lys Asn Lys Trp Trp Tyr
785                 790                 795                 800
```

Asp Lys Gly Glu Cys Gly Ser Gly Gly Gly Asp Ser Lys Asp Lys Thr
805 810 815

Ser Ala Leu Ser Leu Ser Asn Val Ala Gly Val Phe Tyr Ile Leu Val
820 825 830

Gly Gly Leu Gly Leu Ala Met Met Val Ala Leu Ile Glu Phe Cys Tyr
835 840 845

Lys Ser Arg Ala Glu Ser Lys Arg Met Lys Leu Thr Lys Asn Thr Gln
850 855 860

Asn Phe Lys Pro Ala Pro Ala Thr Asn Thr Gln Asn Tyr Ala Thr Tyr
865 870 875 880

Arg Glu Gly Tyr Asn Val Tyr Gly Thr Glu Ser Val Lys Ile
885 890

<210> SEQ ID NO 260
<211> LENGTH: 261
<212> TYPE: PRT
<213> ORGANISM: Homo sapiens

<400> SEQUENCE: 260

Met Gly His Glu Gln Asn Gln Gly Ala Ala Leu Leu Gln Met Leu Pro
1 5 10 15

Leu Leu Trp Leu Leu Pro His Ser Trp Ala Val Pro Glu Ala Pro Thr
20 25 30

Pro Met Trp Pro Asp Asp Leu Gln Asn His Thr Phe Leu His Thr Val
35 40 45

Tyr Cys Gln Asp Gly Ser Pro Ser Val Gly Leu Ser Glu Ala Tyr Asp
50 55 60

Glu Asp Gln Leu Phe Phe Phe Asp Phe Ser Gln Asn Thr Arg Val Pro
65 70 75 80

Arg Leu Pro Glu Phe Ala Asp Trp Ala Gln Glu Gln Gly Asp Ala Pro
85 90 95

Ala Ile Leu Phe Asp Lys Glu Phe Cys Glu Trp Met Ile Gln Gln Ile
100 105 110

Gly Pro Lys Leu Asp Gly Lys Ile Pro Val Ser Arg Gly Phe Pro Ile
115 120 125

Ala Glu Val Phe Thr Leu Lys Pro Leu Glu Phe Gly Lys Pro Asn Thr
130 135 140

Leu Val Cys Phe Val Ser Asn Leu Phe Pro Pro Met Leu Thr Val Asn
145 150 155 160

Trp Gln His His Ser Val Pro Val Glu Gly Phe Gly Pro Thr Phe Val
165 170 175

Ser Ala Val Asp Gly Leu Ser Phe Gln Ala Phe Ser Tyr Leu Asn Phe
180 185 190

Thr Pro Glu Pro Ser Asp Ile Phe Ser Cys Ile Val Thr His Glu Ile
195 200 205

Asp Arg Tyr Thr Ala Ile Ala Tyr Trp Val Pro Arg Asn Ala Leu Pro
210 215 220

Ser Asp Leu Leu Glu Asn Val Leu Cys Gly Val Ala Phe Gly Leu Gly
225 230 235 240

Val Leu Gly Ile Ile Val Gly Ile Val Leu Ile Ile Tyr Phe Arg Lys
245 250 255

Pro Cys Ser Gly Asp
260

<210> SEQ ID NO 261

<211> LENGTH: 428
<212> TYPE: PRT
<213> ORGANISM: Homo sapiens

<400> SEQUENCE: 261

```
Met Gly Asn Cys His Thr Val Gly Pro Asn Glu Ala Leu Val Val Ser
1               5                   10                  15

Gly Gly Cys Cys Gly Ser Asp Tyr Lys Gln Tyr Val Phe Gly Gly Trp
            20                  25                  30

Ala Trp Ala Trp Trp Cys Ile Ser Asp Thr Gln Arg Ile Ser Leu Glu
        35                  40                  45

Ile Met Thr Leu Gln Pro Arg Cys Glu Asp Val Glu Thr Ala Glu Gly
    50                  55                  60

Val Ala Leu Thr Val Thr Gly Val Ala Gln Val Lys Ile Met Thr Glu
65                  70                  75                  80

Lys Glu Leu Leu Ala Val Ala Cys Glu Gln Phe Leu Gly Lys Asn Val
                85                  90                  95

Gln Asp Ile Lys Asn Val Val Leu Gln Thr Leu Glu Gly His Leu Arg
            100                 105                 110

Ser Ile Leu Gly Thr Leu Thr Val Glu Gln Ile Tyr Gln Asp Arg Asp
        115                 120                 125

Gln Phe Ala Lys Leu Val Arg Glu Val Ala Ala Pro Asp Val Gly Arg
    130                 135                 140

Met Gly Ile Glu Ile Leu Ser Phe Thr Ile Lys Asp Val Tyr Asp Lys
145                 150                 155                 160

Val Asp Tyr Leu Ser Ser Leu Gly Lys Thr Gln Thr Ala Val Val Gln
                165                 170                 175

Arg Asp Ala Asp Ile Gly Val Ala Glu Ala Glu Arg Asp Ala Gly Ile
            180                 185                 190

Arg Glu Ala Glu Cys Lys Lys Glu Met Leu Asp Val Lys Phe Met Ala
        195                 200                 205

Asp Thr Lys Ile Ala Asp Ser Lys Arg Ala Phe Glu Leu Gln Lys Ser
    210                 215                 220

Ala Phe Ser Glu Glu Val Asn Ile Lys Thr Ala Glu Ala Gln Leu Ala
225                 230                 235                 240

Tyr Glu Leu Gln Gly Ala Arg Glu Gln Gln Lys Ile Arg Gln Glu Glu
                245                 250                 255

Ile Glu Ile Glu Val Val Gln Arg Lys Lys Gln Ile Ala Val Glu Ala
            260                 265                 270

Gln Glu Ile Leu Arg Thr Asp Lys Glu Leu Ile Ala Thr Val Arg Arg
        275                 280                 285

Pro Ala Glu Ala Glu Ala His Arg Ile Gln Gln Ile Ala Glu Gly Glu
    290                 295                 300

Lys Val Lys Gln Val Leu Leu Ala Gln Ala Glu Ala Glu Lys Ile Arg
305                 310                 315                 320

Lys Ile Gly Glu Ala Glu Ala Ala Val Ile Glu Ala Met Gly Lys Ala
                325                 330                 335

Glu Ala Glu Arg Met Lys Leu Lys Ala Glu Ala Tyr Gln Lys Tyr Gly
            340                 345                 350

Asp Ala Ala Lys Met Ala Leu Val Leu Glu Ala Leu Pro Gln Ile Ala
        355                 360                 365

Ala Lys Ile Ala Ala Pro Leu Thr Lys Val Asp Glu Ile Val Val Leu
    370                 375                 380

Ser Gly Asp Asn Ser Lys Val Thr Ser Glu Val Asn Arg Leu Leu Ala
```

```
385                 390                 395                 400

Glu Leu Pro Ala Ser Val His Ala Leu Thr Gly Val Asp Leu Ser Lys
                405                 410                 415

Ile Pro Leu Ile Lys Lys Ala Thr Gly Val Gln Val
            420                 425


<210> SEQ ID NO 262
<211> LENGTH: 865
<212> TYPE: PRT
<213> ORGANISM: Homo sapiens

<400> SEQUENCE: 262

Met Ala Leu Val Leu Gly Ser Leu Leu Leu Leu Gly Leu Cys Gly Asn
1               5                   10                  15

Ser Phe Ser Gly Gly Gln Pro Ser Ser Thr Asp Ala Pro Lys Ala Trp
            20                  25                  30

Asn Tyr Glu Leu Pro Ala Thr Asn Tyr Glu Thr Gln Asp Ser His Lys
        35                  40                  45

Ala Gly Pro Ile Gly Ile Leu Phe Glu Leu Val His Ile Phe Leu Tyr
    50                  55                  60

Val Val Gln Pro Arg Asp Phe Pro Glu Asp Thr Leu Arg Lys Phe Leu
65                  70                  75                  80

Gln Lys Ala Tyr Glu Ser Lys Ile Asp Tyr Asp Lys Pro Glu Thr Val
                85                  90                  95

Ile Leu Gly Leu Lys Ile Val Tyr Tyr Glu Ala Gly Ile Ile Leu Cys
            100                 105                 110

Cys Val Leu Gly Leu Leu Phe Ile Ile Leu Met Pro Leu Val Gly Tyr
        115                 120                 125

Phe Phe Cys Met Cys Arg Cys Cys Asn Lys Cys Gly Gly Glu Met His
    130                 135                 140

Gln Arg Gln Lys Glu Asn Gly Pro Phe Leu Arg Lys Cys Phe Ala Ile
145                 150                 155                 160

Ser Leu Leu Val Ile Cys Ile Ile Ile Ser Ile Gly Ile Phe Tyr Gly
                165                 170                 175

Phe Val Ala Asn His Gln Val Arg Thr Arg Ile Lys Arg Ser Arg Lys
            180                 185                 190

Leu Ala Asp Ser Asn Phe Lys Asp Leu Arg Thr Leu Leu Asn Glu Thr
        195                 200                 205

Pro Glu Gln Ile Lys Tyr Ile Leu Ala Gln Tyr Asn Thr Thr Lys Asp
    210                 215                 220

Lys Ala Phe Thr Asp Leu Asn Ser Ile Asn Ser Val Leu Gly Gly Gly
225                 230                 235                 240

Ile Leu Asp Arg Leu Arg Pro Asn Ile Ile Pro Val Leu Asp Glu Ile
                245                 250                 255

Lys Ser Met Ala Thr Ala Ile Lys Glu Thr Lys Glu Ala Leu Glu Asn
            260                 265                 270

Met Asn Ser Thr Leu Lys Ser Leu His Gln Gln Ser Thr Gln Leu Ser
        275                 280                 285

Ser Ser Leu Thr Ser Val Lys Thr Ser Leu Arg Ser Ser Leu Asn Asp
    290                 295                 300

Pro Leu Cys Leu Val His Pro Ser Ser Glu Thr Cys Asn Ser Ile Arg
305                 310                 315                 320

Leu Ser Leu Ser Gln Leu Asn Ser Asn Pro Glu Leu Arg Gln Leu Pro
                325                 330                 335
```

-continued

```
Pro Val Asp Ala Glu Leu Asp Asn Val Asn Asn Val Leu Arg Thr Asp
            340                 345                 350

Leu Asp Gly Leu Val Gln Gln Gly Tyr Gln Ser Leu Asn Asp Ile Pro
        355                 360                 365

Asp Arg Val Gln Arg Gln Thr Thr Thr Val Val Ala Gly Ile Lys Arg
    370                 375                 380

Val Leu Asn Ser Ile Gly Ser Asp Ile Asp Asn Val Thr Gln Arg Leu
385                 390                 395                 400

Pro Ile Gln Asp Ile Leu Ser Ala Phe Ser Val Tyr Val Asn Asn Thr
                405                 410                 415

Glu Ser Tyr Ile His Arg Asn Leu Pro Thr Leu Glu Glu Tyr Asp Ser
            420                 425                 430

Tyr Trp Trp Leu Gly Gly Leu Val Ile Cys Ser Leu Leu Thr Leu Ile
        435                 440                 445

Val Ile Phe Tyr Tyr Leu Gly Leu Leu Cys Gly Val Cys Gly Tyr Asp
    450                 455                 460

Arg His Ala Thr Pro Thr Thr Arg Gly Cys Val Ser Asn Thr Gly Gly
465                 470                 475                 480

Val Phe Leu Met Val Gly Val Gly Leu Ser Phe Leu Phe Cys Trp Ile
                485                 490                 495

Leu Met Ile Ile Val Val Leu Thr Phe Val Phe Gly Ala Asn Val Glu
            500                 505                 510

Lys Leu Ile Cys Glu Pro Tyr Thr Ser Lys Glu Leu Phe Arg Val Leu
        515                 520                 525

Asp Thr Pro Tyr Leu Leu Asn Glu Asp Trp Glu Tyr Tyr Leu Ser Gly
    530                 535                 540

Lys Leu Phe Asn Lys Ser Lys Met Lys Leu Thr Phe Glu Gln Val Tyr
545                 550                 555                 560

Ser Asp Cys Lys Lys Asn Arg Gly Thr Tyr Gly Thr Leu His Leu Gln
                565                 570                 575

Asn Ser Phe Asn Ile Ser Glu His Leu Asn Ile Asn Glu His Thr Gly
            580                 585                 590

Ser Ile Ser Ser Glu Leu Glu Ser Leu Lys Val Asn Leu Asn Ile Phe
        595                 600                 605

Leu Leu Gly Ala Ala Gly Arg Lys Asn Leu Gln Asp Phe Ala Ala Cys
    610                 615                 620

Gly Ile Asp Arg Met Asn Tyr Asp Ser Tyr Leu Ala Gln Thr Gly Lys
625                 630                 635                 640

Ser Pro Ala Gly Val Asn Leu Leu Ser Phe Ala Tyr Asp Leu Glu Ala
                645                 650                 655

Lys Ala Asn Ser Leu Pro Pro Gly Asn Leu Arg Asn Ser Leu Lys Arg
            660                 665                 670

Asp Ala Gln Thr Ile Lys Thr Ile His Gln Gln Arg Val Leu Pro Ile
        675                 680                 685

Glu Gln Ser Leu Ser Thr Leu Tyr Gln Ser Val Lys Ile Leu Gln Arg
    690                 695                 700

Thr Gly Asn Gly Leu Leu Glu Arg Val Thr Arg Ile Leu Ala Ser Leu
705                 710                 715                 720

Asp Phe Ala Gln Asn Phe Ile Thr Asn Asn Thr Ser Ser Val Ile Ile
                725                 730                 735

Glu Glu Thr Lys Lys Tyr Gly Arg Thr Ile Ile Gly Tyr Phe Glu His
            740                 745                 750

Tyr Leu Gln Trp Ile Glu Phe Ser Ile Ser Glu Lys Val Ala Ser Cys
```

755 760 765

Lys Pro Val Ala Thr Ala Leu Asp Thr Ala Val Asp Val Phe Leu Cys
770 775 780

Ser Tyr Ile Ile Asp Pro Leu Asn Leu Phe Trp Phe Gly Ile Gly Lys
785 790 795 800

Ala Thr Val Phe Leu Leu Pro Ala Leu Ile Phe Ala Val Lys Leu Ala
805 810 815

Lys Tyr Tyr Arg Arg Met Asp Ser Glu Asp Val Tyr Asp Asp Val Glu
820 825 830

Thr Ile Pro Met Lys Asn Met Glu Asn Gly Asn Asn Gly Tyr His Lys
835 840 845

Asp His Val Tyr Gly Ile His Asn Pro Val Met Thr Ser Pro Ser Gln
850 855 860

His
865

<210> SEQ ID NO 263
<211> LENGTH: 451
<212> TYPE: PRT
<213> ORGANISM: Homo sapiens

<400> SEQUENCE: 263

Met Ala Thr Met Val Pro Ser Val Leu Trp Pro Arg Ala Cys Trp Thr
1 5 10 15

Leu Leu Val Cys Cys Leu Leu Thr Pro Gly Val Gln Gly Gln Glu Phe
20 25 30

Leu Leu Arg Val Glu Pro Gln Asn Pro Val Leu Ser Ala Gly Gly Ser
35 40 45

Leu Phe Val Asn Cys Ser Thr Asp Cys Pro Ser Ser Glu Lys Ile Ala
50 55 60

Leu Glu Thr Ser Leu Ser Lys Glu Leu Val Ala Ser Gly Met Gly Trp
65 70 75 80

Ala Ala Phe Asn Leu Ser Asn Val Thr Gly Asn Ser Arg Ile Leu Cys
85 90 95

Ser Val Tyr Cys Asn Gly Ser Gln Ile Thr Gly Ser Ser Asn Ile Thr
100 105 110

Val Tyr Arg Leu Pro Glu Arg Val Glu Leu Ala Pro Leu Pro Pro Trp
115 120 125

Gln Pro Val Gly Gln Asn Phe Thr Leu Arg Cys Gln Val Glu Asp Gly
130 135 140

Ser Pro Arg Thr Ser Leu Thr Val Val Leu Leu Arg Trp Glu Glu Glu
145 150 155 160

Leu Ser Arg Gln Pro Ala Val Glu Glu Pro Ala Glu Val Thr Ala Thr
165 170 175

Val Leu Ala Ser Arg Asp Asp His Gly Ala Pro Phe Ser Cys Arg Thr
180 185 190

Glu Leu Asp Met Gln Pro Gln Gly Leu Gly Leu Phe Val Asn Thr Ser
195 200 205

Ala Pro Arg Gln Leu Arg Thr Phe Gly Phe Leu Gly Pro Ile Val Asn
210 215 220

Leu Ser Glu Pro Thr Ala His Glu Gly Ser Thr Val Thr Val Ser Cys
225 230 235 240

Met Ala Gly Ala Arg Val Gln Val Thr Leu Asp Gly Val Pro Ala Ala
245 250 255

-continued

```
Ala Pro Gly Gln Pro Ala Gln Leu Gln Leu Asn Ala Thr Glu Ser Asp
            260                 265                 270

Asp Gly Arg Ser Phe Phe Cys Ser Ala Thr Leu Glu Val Asp Gly Glu
        275                 280                 285

Phe Leu His Arg Asn Ser Ser Val Gln Leu Arg Val Leu Tyr Gly Pro
    290                 295                 300

Lys Ile Asp Arg Ala Thr Cys Pro Gln His Leu Lys Trp Lys Asp Lys
305                 310                 315                 320

Thr Arg His Val Leu Gln Cys Gln Ala Arg Gly Asn Pro Tyr Pro Glu
                325                 330                 335

Leu Arg Cys Leu Lys Glu Gly Ser Ser Arg Glu Val Pro Val Gly Ile
            340                 345                 350

Pro Phe Phe Val Asn Val Thr His Asn Gly Thr Tyr Gln Cys Gln Ala
        355                 360                 365

Ser Ser Ser Arg Gly Lys Tyr Thr Leu Val Val Val Met Asp Ile Glu
    370                 375                 380

Ala Gly Ser Ser His Phe Val Pro Val Phe Val Ala Val Leu Leu Thr
385                 390                 395                 400

Leu Gly Val Val Thr Ile Val Leu Ala Leu Met Tyr Val Phe Arg Glu
                405                 410                 415

His Gln Arg Ser Gly Ser Tyr His Val Arg Glu Glu Ser Thr Tyr Leu
            420                 425                 430

Pro Leu Thr Ser Met Gln Pro Thr Glu Ala Met Gly Glu Glu Pro Ser
        435                 440                 445

Arg Ala Glu
    450
```